(12) United States Patent
Takayama et al.

(10) Patent No.: US 7,601,746 B2
(45) Date of Patent: Oct. 13, 2009

(54) COMPOUNDS EXHIBITING THROMBOPOIETIN RECEPTOR AGONISM

(75) Inventors: Masami Takayama, Osaka (JP); Yutaka Yoshida, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 26 days.

(21) Appl. No.: 10/567,993

(22) PCT Filed: Aug. 10, 2004

(86) PCT No.: PCT/JP2004/011453

§ 371 (c)(1),
(2), (4) Date: Sep. 1, 2006

(87) PCT Pub. No.: WO2005/014561

PCT Pub. Date: Feb. 17, 2005

(65) Prior Publication Data

US 2007/0043087 A1 Feb. 22, 2007

(30) Foreign Application Priority Data

Aug. 12, 2003 (JP) .............................. 2003-292080

(51) Int. Cl.
*A61K 31/427* (2006.01)
*C07D 277/38* (2006.01)
(52) U.S. Cl. ...................................... 514/370; 548/190
(58) Field of Classification Search ................. 548/190; 514/370
See application file for complete search history.

(56) References Cited

U.S. PATENT DOCUMENTS

| | | | |
|---|---|---|---|
| 5,112,867 A | 5/1992 | Kinoshita et al. | |
| 5,413,997 A | 5/1995 | Kinoshita et al. | |
| 5,607,952 A | 3/1997 | Badorc et al. | |
| 5,654,322 A | 8/1997 | Hirata et al. | |
| 5,654,622 A | 8/1997 | Toya et al. | |
| 5,869,451 A | 2/1999 | Dower et al. | |
| 6,140,330 A | 10/2000 | Mori et al. | |
| 6,225,323 B1 | 5/2001 | Yatscoff et al. | |
| 6,306,871 B1 | 10/2001 | Yatscoff et al. | |
| 6,555,519 B2 | 4/2003 | Washburn | |
| 6,670,387 B1 | 12/2003 | Luengo et al. | |
| 6,737,382 B1 | 5/2004 | Iwataki et al. | |
| 2003/0195231 A1 | 10/2003 | Takemoto et al. | |
| 2004/0063764 A1 | 4/2004 | Takemoto et al. | |
| 2004/0082626 A1 | 4/2004 | Takemoto et al. | |
| 2005/0153977 A1 | 7/2005 | Sugasawa et al. | |

FOREIGN PATENT DOCUMENTS

| EP | 0 295 656 B1 | 11/1992 |
|---|---|---|
| EP | 0 656 355 A1 | 6/1995 |
| EP | 0 719 775 B1 | 7/1996 |
| EP | 1 207 155 | 5/2002 |
| EP | 1 253 142 | 10/2002 |
| EP | 1253142 A1 * | 10/2002 |
| EP | 1 466 912 | 10/2004 |
| JP | 07-112975 | 5/1995 |
| JP | 10-072492 | 3/1998 |
| JP | 10-287634 | 10/1998 |
| JP | 11-001477 | 1/1999 |
| JP | 11-152276 | 6/1999 |
| WO | WO 94/04516 | 3/1994 |
| WO | WO 96/40750 | 12/1996 |
| WO | WO 00/35446 | 6/2000 |
| WO | WO 01/07423 | 2/2001 |
| WO | WO 01/53267 | 7/2001 |
| WO | WO 02/059099 | 8/2002 |
| WO | WO 02/059100 | 8/2002 |
| WO | WO 03/062233 | 7/2003 |

OTHER PUBLICATIONS

Vigon et al., "Molecular Cloning and Characterization of MPL, the Human Homolog of the v-mpl Oncogene: Identification of a Member of the Hematopoietic Growth Factor Receptor Superfamily", Proc. Natl. Acad. Sci. USA, vol. 89, Cell Biology, pp. 5640-5644, (1992).

* cited by examiner

*Primary Examiner*—Rei-Tsang Shiao
*Assistant Examiner*—Janet L Coppins
(74) *Attorney, Agent, or Firm*—Finnegan, Henderson, Farabow, Garrett & Dunner, LLP

(57) ABSTRACT

A compound represented by the general formula (I):

wherein $R^1$ is a hydrogen atom, a halogen atom, or the like; $R^2$, $R^3$, and $R^4$ are each independently a hydrogen atom, a halogen atom, C1-C15 alkyl optionally substituted with one or more C1-C12 alkyloxy or the like, or the like; $R^5$ is a hydrogen atom or the like; $R^6$ and $R^7$ are a hydrogen atom or the like; $R^8$ is C1-C3 alkyl or the like; $R^9$ is a hydrogen atom or the like), a prodrug, a pharmaceutically acceptable salt, or solvate thereof.

24 Claims, No Drawings

COMPOUNDS EXHIBITING THROMBOPOIETIN RECEPTOR AGONISM

TECHNICAL FIELD

The present invention relates to compounds exhibiting thrombopoietin receptor agonism.

BACKGROUND ART

Thrombopoietin, polypeptide cytokine composed of 332 amino acids, activates the production of platelets by stimulating the differentiation and proliferation of megakaryocytes through the receptor and is expected as a medicine for hemopathy accompanied with the unusual number of platelets, for example, thrombocytopenia and the like. DNA sequences encoding the thrombopoietin receptor have been described in Non-Patent 1. Low molecular peptides having an affinity for the thrombopoietin receptor is also known in Patent 1 and Patent 2, but these peptide derivatives are not generally practical for oral administration.

As a low molecule compound having an affinity to the thrombopoietin receptor, 1,4-benzodiazepine derivatives are described in Patent 3 and Patent 4,1-azonaphthalene derivatives are described in Patent 5, N-(4-phenyl-1,3-thiazol-2-yl) carboxamide derivatives are described in Patent 6, Patent 7, Patent 8, Patent 9, and Patent 10.

Patent 1: JP98/72492
Patent 2: WO96/40750
Patent 3: JP99/1477
Patent 4: JP99/152276
Patent 5: WO00/35446
Patent 6: WO01/07423
Patent 7: WO01/53267
Patent 8: WO02/059099
Patent 9: WO02/059100
Patent 10: JP98/287634
Non-Patent 1: Proc. Natl. Acad. Sci., 89, 5640-5644 (1992)

DISCLOSURE OF INVENTION

The object of the present invention is to prepare pharmaceutical compositions exhibiting thrombopoietin receptor agonism and provide orally administrable platelet production modifiers.

In the above situation, the inventors of the present invention have found that the following compounds exhibit strong thrombopoietin receptor agonism.

The present invention relates to:
1) A compound represented by the general formula (I):

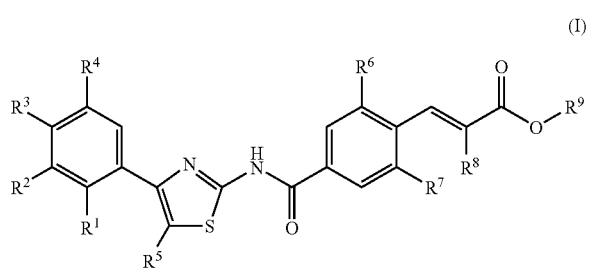

(I)

wherein $R^1$ is a hydrogen atom, a halogen atom, C1-C6 alkyl, or C1-C12 alkyloxy;

$R^2$, $R^3$, and $R^4$ are each independently a hydrogen atom, a halogen atom, C1-C15 alkyl optionally substituted with one or two substituent(s) selected from substituent group A, C2-C15 alkenyl optionally substituted with one or two substituent(s) selected from substituent group A, C2-C15 alkynyl optionally substituted with one or two substituent(s) selected from substituent group A, C3-C8 cycloalkyl, C1-C15 alkyloxy optionally substituted with one or two substituent(s) selected from substituent group A, or phenyl optionally substituted with one or two substituent(s) selected from substituent group A;

$R^5$ is a hydrogen atom, a halogen atom, C1-C3 alkyl, C1-C3 alkyloxy, or morpholono;

$R^6$ is a hydrogen atom, a halogen atom, or C1-C3 alkyl;

$R^7$ is a halogen atom or C1-C3 alkyl;

$R^8$ is a halogen atom, C1-C3 alkyl, or C1-C3 alkyloxy;

configuration of double bond substituted with $R^8$ is E configuration or Z configuration;

$R^9$ is a hydrogen atom or C1-C6 alkyl; or $R^1$ and $R^5$ are taken together with the adjacent carbon atoms may form a 5 to 8 membered ring which may contain a heteroatom(s) and/or an unsaturated bond(s), wherein the ring may be substituted with one or two C1-C8 alkyl;

provided that when $R^2$ and $R^3$ are a chlorine atom, $R^6$ is not a hydrogen atom;

substituent group A consists of a halogen atom, C3-C8 cycloalkyl, C3-C8 cycloalkenyl, phenyl, naphthyl, pyridyl, oxolanyl, cyano, C1-C12 alkyloxy, C2-C12 alkenyloxy, C2-C12 alkynyloxy, C3-C8 cycloalkyl-C1-C8 alkyloxy, phenyl-C1-C8 alkyloxy, naphthyl-C1-C8 alkyloxy, C1-C8 alkyloxy-C1-C8 alkyloxy, (C1-C8 alkyloxy-C1-C8 alkyloxy)C1-C8 alkyloxy, di(C1-C8 alkyloxy)C1-C8 alkyloxy, oxolanyl-C1-C8 alkyloxy, haloC1-C8 alkyloxy, C3-C8 cycloalkyloxy, amino optionally substituted with C1-C8 alkyl, C1-C8 alkylthio, and C1-C8 alkylthio-C1-C8 alkyloxy;

a pharmaceutically acceptable salt, or solvate thereof,

2) A compound of 1), wherein both of $R^6$ and $R^7$ are a fluorine atom or a chlorine atom, a pharmaceutically acceptable salt, or solvate thereof, 3) A compound of 1) or 2), wherein $R^5$ is a hydrogen atom or C1-C3 alkyloxy, a pharmaceutically acceptable salt, or solvate thereof, 4) A compound of any one of 1) to 3), wherein $R^8$ is methyl or methyloxy, a pharmaceutically acceptable salt, or solvate thereof, 5) A compound of any one of 1) to 4), wherein $R^2$ is C1-C15 alkyl optionally substituted with one or two substituent(s) selected from substituent group A, C2-C15 alkynyl optionally substituted with one or two substituent(s) selected from substituent group A, or C1-C15 alkyloxy optionally substituted with one or two substituent(s) selected from substituent group A, a pharmaceutically acceptable salt, or solvate thereof, 6) A compound of any one of 1) to 4), wherein $R^2$ is C1-C12 alkyl optionally substituted with one or two C1-C8 alkyloxy, and both of $R^3$ and $R^4$ are a hydrogen atom, a pharmaceutically acceptable salt, or solvate thereof, 7) A compound represented by the general formula (II):

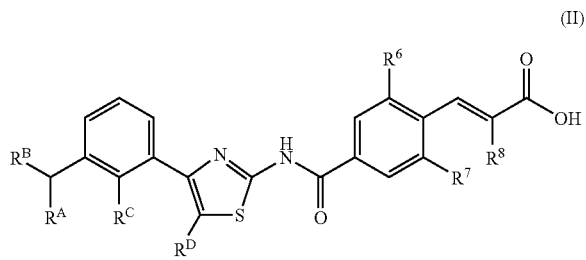

(II)

wherein $R^A$ is a hydrogen atom, C1-C12 alkyloxy, C1-C8 alkyloxy-C1-C8 alkyloxy or (C1-C8 alkyloxy-C1-C8 alkyloxy)C1-C8 alkyloxy;

$R^B$ is C1-C14 alkyl optionally substituted with one or two substituent(s) selected from substituent group B, C2-C14 alkynyl optionally substituted with one or two substituent(s) selected from substituent group B, C3-C8 cycloalkyl, C1-C14 alkyloxy optionally substituted with one or two substituent(s) selected from substituent group B, phenyl, or naphthyl;

$R^C$ is a hydrogen atom, a halogen atom, C1-C6 alkyl, or C1-C12 alkyloxy;

$R^D$ is a hydrogen atom, a halogen atom, C1-C3 alkyl, C1-C3 alkyloxy, or morpholino;

$R^6$ and $R^7$ are each independently a halogen atom or C1-C3 alkyl;

$R^8$ is a halogen atom, C1-C3 alkyl, or C1-C3 alkyloxy;

configuration of double bond substituted with $R^8$ is E configuration or Z configuration;

substituent group B consists of a halogen atom, C3-C8 cycloalkyl, C3-C8 cycloalkenyl, phenyl, naphthyl, pyridyl, oxolanyl, cyano, C1-C8 alkyloxy, C2-C8 alkenyloxy, C2-C8 alkynyloxy, C3-C8 cycloalkyl-C1-C8 alkyloxy, phenyl-C1-C8 alkyloxy, naphthyl-C1-C8 alkyloxy, C1-C8 alkyloxy-C1-C8 alkyloxy, (C1-C8 alkyloxy-C1-C8 alkyloxy)C1-C8 alkyloxy, di(C1-C8 alkyloxy)C1-C8 alkyloxy, oxolanyl-C1-C8 alkyloxy, haloC1-C8 alkyloxy, C3-C8 cycloalkyloxy, amino optionally substituted with C1-C8 alkyl, C1-C8 alkylthio, and C1-C8 alkylthio-C1-C8 alkyloxy;

a pharmaceutically acceptable salt, or solvate thereof,

8) A compound of 7), wherein both of $R^6$ and $R^7$ are a fluorine atom or a chlorine atom, a pharmaceutically acceptable salt, or solvate thereof, 9) A compound of 7) or 8), wherein $R^8$ is methyl or methyloxy, a pharmaceutically acceptable salt, or solvate thereof, 10) A compound of any one of 7) to 9), wherein $R^C$ is a fluorine atom or C1-C3 alkyloxy, a pharmaceutically acceptable salt, or solvate thereof, 11) A compound of any one of 7) to 10), wherein $R^A$ is C1-C8 alkyloxy; $R^B$ is C1-C11 alkyl optionally substituted with one or two substituent(s) selected from substituent group B, C2-C11 alkynyl optionally substituted with one or two substituent(s) selected from substituent group B, a pharmaceutically acceptable salt, or solvate thereof, 12) A compound of 7), wherein $R^C$ is a fluorine atom or C1-C3 alkyloxy, $R^D$ is a hydrogen atom or C1-C3 alkyloxy, both of $R^6$ and $R^7$ are a fluorine atom or a chlorine atom, $R^8$ is methyl or methyloxy, $R^A$ is C1-C3 alkyloxy, $R^B$ is C8-C12 alkyl optionally substituted with one or two substituent(s) selected from substituent group B, a pharmaceutically acceptable salt, or solvate thereof, 13) A compound represented by the general formula (III):

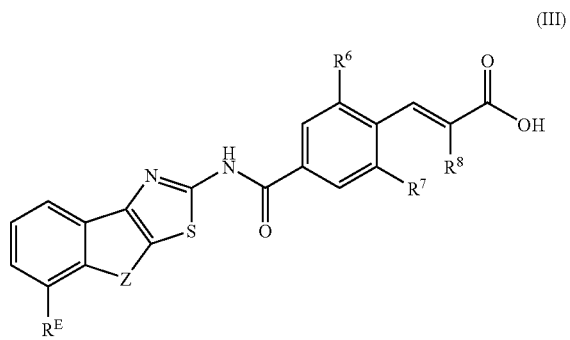

(III)

wherein $R^E$ is C1-C15 alkyl optionally substituted with one or two substituent(s) selected from substituent group C, C2-C15 alkynyl optionally substituted with one or two substituent(s) selected from substituent group C, or C1-C15 alkyloxy optionally substituted with one or two substituent(s) selected from substituent group C;

Z is straight-chain C1-C4 alkylene optionally substituted with C1-C8 alkyl, which may contain an optionally substituted a heteroatom(s) or straight-chain C2-C4 alkenylene optionally substituted with C1-C8 alkyl, which may contain an optionally substituted heteroatom(s);

$R^6$ and $R^7$ are each independently a halogen atom or C1-C3 alkyl;

$R^8$ is a halogen atom, C1-C3 alkyl, or C1-C3 alkyloxy;

configuration of double bond substituted with $R^8$ is E configuration or Z configuration;

substituent group C consists of a halogen atom, C3-C8 cycloalkyl, C3-C8 cycloalkenyl, phenyl, naphthyl, pyridyl, oxolanyl, cyano, C1-C8 alkyloxy, C2-C8 alkenyloxy, C2-C8 alkynyloxy, C3-C8 cycloalkyl-C1-C8 alkyloxy, phenyl-C1-C8 alkyloxy, naphthyl-C1-C8 alkyloxy, C1-C8 alkyloxy-C1-C8 alkyloxy, (C1-C8 alkyloxy-C1-C8 alkyloxy)C1-C8 alkyloxy, di(C1-C8 alkyloxy)C1-C8 alkyloxy, oxolanyl-C1-C8 alkyloxy, haloC1-C8 alkyloxy, C3-C8 cycloalkyloxy, amino optionally substituted with C1-C8 alkyl, C1-C8 alkylthio, and C1-C8 alkylthio-C1-C8 alkyloxy;

a pharmaceutically acceptable salt, or solvate thereof,

14) A compound of 13), wherein both of $R^6$ and $R^7$ are a fluorine atom or a chlorine atom, a pharmaceutically acceptable salt, or solvate thereof, 15) A compound of 13) or 14), wherein $R^8$ is methyl or methyloxy, a pharmaceutically acceptable salt, or solvate thereof, 16) A compound of any one of 13) to 15), wherein Z is C1-C14 alkylene, —O—(C1-C3 alkylene)-, or —(C1-C3 alkylene)-O—, a pharmaceutically acceptable salt, or solvate thereof, 17) A compound of any one of 13) to 16), wherein $R^E$ is C1-C10 alkyl optionally substituted with one or two substituent(s) selected from substituent group C, C2-C10 alkynyl optionally substituted with one or two substituent(s) selected from substituent group C, or C1-C10 alkyloxy optionally substituted with one or two substituent(s) selected from substituent group C, a pharmaceutically acceptable salt, or solvate thereof, 18) A compound of 13), wherein both of $R^6$ and $R^7$ are a fluorine atom or a chlorine atom, $R^8$ is methyl or methyloxy, $R^E$ is C1-C8 alkyl optionally substituted with one or two C1-C6 alkyloxy, Z is C1-C2 alkylene, a pharmaceutically acceptable salt, or solvate thereof, 19) A compound represented by the general formula (II-A):

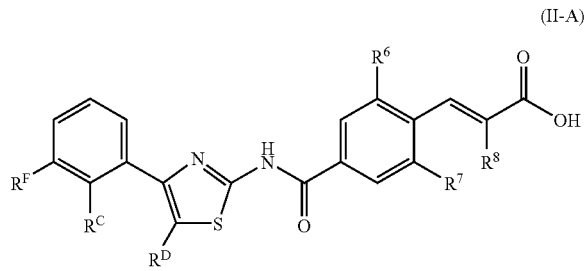

(II-A)

wherein $R^C$ is a hydrogen atom, a halogen atom, C1-C6 alkyl, or C1-C12 alkyloxy;

$R^D$ is a hydrogen atom, a halogen atom, C1-C3 alkyl, C1-C3 alkyloxy, or morpholino;

$R^F$ is C1-C14 alkyl optionally substituted with one or two substituent(s) selected from substituent group D, C2-C14 alkenyl optionally substituted with one or two substituent(s) selected from substituent group D, C2-C14 alkynyl optionally substituted with one or two substituent(s) selected from substituent group D, C1-C14 alkyloxy optionally substituted with one or two substituent(s) selected from substituent group C, C3-C8 cycloalkyl, or phenyl optionally substituted with one or two substituent(s) selected from substituent group D;

$R^6$ and $R^7$ are each independently a halogen atom or C1-C3 alkyl;

$R^8$ is a halogen atom, C1-C3 alkyl, or C1-C3 alkyloxy;

substituent group D consists of a halogen atom, C3-C8 cycloalkyl, C3-C8 cycloalkenyl, phenyl, naphthyl, pyridyl, oxolanyl, cyano, C1-C8 alkyloxy, C2-C8 alkenyloxy, C2-C8 alkynyloxy, C3-C8 cycloalkyl-C1-C8 alkyloxy, phenyl-C1-C8 alkyloxy, naphthyl-C1-C8 alkyloxy, C1-C8 alkyloxy-C1-C8 alkyloxy, (C1-C8 alkyloxy-C1-C8 alkyloxy)C1-C8 alkyloxy, di(C1-C8 alkyloxy)C1-C8 alkyloxy, oxolanyl-C1-C8 alkyloxy, haloC1-C8 alkyloxy, C3-C8 cycloalkyloxy, amino optionally substituted with C1-C8 alkyl, C1-C8 alkylthio, and C1-C8 alkylthio-C1-C8 alkyloxy;

a pharmaceutically acceptable salt, or solvate thereof,

20) A compound of 19), wherein both of $R^6$ and $R^7$ are a fluorine atom or a chlorine atom, a pharmaceutically acceptable salt, or solvate thereof, 21) A compound of claim 19), wherein $R^8$ is methyl or methyloxy, a pharmaceutically acceptable salt, or solvate thereof, 22) A compound of 19), wherein $R^C$ is a fluorine atom or C1-C3 alkyloxy, a pharmaceutically acceptable salt, or solvate thereof, 23) A compound of any one of 19) to 22), wherein $R^E$ is C1-C14 alkyl optionally substituted with one or two substituent(s) selected from substituent group D, C2-C14 alkynyl optionally substituted with one or two substituent(s) selected from substituent group D, or C1-C14 alkyloxy optionally substituted with one or two substituent(s) selected from substituent group D, a pharmaceutically acceptable salt, or solvate thereof, 24) A pharmaceutical composition containing a compound as an active ingredient, a pharmaceutically acceptable salt, or solvate thereof of any one of 1) to 23), 25) A pharmaceutical composition containing a compound as an active ingredient, a pharmaceutically acceptable salt, or solvate thereof of any one of 1) to 23), which is exhibiting thrombopoietin receptor agonism, 26) A platelet production modifier which contains a compound as an active ingredient, a pharmaceutically acceptable salt, or solvate thereof of any one of 1) to 23), 27) Use of a compound, a pharmaceutically acceptable salt, or solvate thereof of any one of 1) to 23) for preparation of a pharmaceutical composition for modifiering a platelet production, 28) A method for modifiering a platelet production of a mammal, including a human, which comprises administration to said mammal of a compound, a pharmaceutically acceptable salt, or solvate thereof of any one of 1) to 23) in a pharmaceutically effective amount.

In the present specification, the term "halogen atom" means fluorine atom (fluoro), chlorine atom (chloro), bromine atom (bromo), and iodine atom (iodo).

In the present specification, nitrogen atom, oxygen atom, sulfur atom, and the like are exemplified as "heteroatom".

In the present specification, the term "alkyl" employed alone or in combination with other term includes a straight- or branched chain alkyl having contains forward-mentioned number of carbon. Methyl, ethyl, n-propyl, isopropyl, n-butyl, isobutyl, sec-butyl, tert-butyl, n-pentyl, isopentyl, neopentyl, n-hexyl, isohexyl, n-heptyl, n-octyl, n-nonyl, n-decyl, n-undecyl, n-dodecyl, n-tridecyl, n-tetradecyl, n-pentadecyl, and the like are exemplified as "alkyl".

In the present specification, the term "alkenyl" employed alone or in combination with other term includes a straight- or branched chain alkenyl having forward-mentioned number of carbon. Ethenyl, 2-propen-1-yl, 3-butene-1-yl, 14-pentadecen-1-yl, and tke like are exemplified as "alkenyl".

In the present specification, the term "alkynyl" employed alone or in combination with other term includes a straight- or branched chain alkynyl having forward-mentioned number of carbon. Ethynyl, 1-propyn-1-yl, 1-butyn-1-yl, 1-pentyn-1-yl, 1-hexyn-1-yl, 1-heptyn-1-yl, 1-decyn-1-yl, 1-pentadecyn-1-yl, and the like are exemplified as "alkynyl".

In the present specification, the term "cycloalkyl" employed alone or in combination with other term includes a mono-carbocyclic group having forward-mentioned number of carbon. Cyclopropyl, cyclobutyl, cyclopentyl, cyclohexyl, cycloheptyl, cyclooctyl, and the like are exemplified as "cycloalkyl".

In the present specification, the term "cycloalkenyl" employed alone or in combination with other term includes a mono-carbocyclic group having forward-mentioned number of carbon and one or more double bond(s). Cyclopropenyl, 1-cyclobuten-1-yl, 1-cyclopenten-1-yl, 1-cyclohexen-1-yl, 1-cyclohepten-1-yl, 1-cycloocten-1-yl, and the like are exemplified as "cycloalkenyl".

In the present specification, the term "naphthyl" means 1-naphthyl or 2-naphthyl.

In the present specification, the term "pyridyl" means 2-pyridyl, 3-pyridyl or 4-pyridyl.

In the present specification, the term "oxolanyl" means 2-oxolanyl or 3-oxolanyl.

In the present specification, the term "alkyloxy" employed alone or in combination with other term includes alkyloxy having forward-mentioned number of carbon. Methyloxy, ethyloxy, n-propyloxy, isopropyloxy, n-butyloxy, isobutyloxy, sec-butyloxy, tert-butyloxy, n-pentyloxy, isopentyloxy, neo-pentyloxy, n-hexyloxy, isohexyloxy, n-heptyloxy, n-octyloxy, n-nonyloxy, n-decyloxy, n-undecyloxy, n-dodecyloxy, n-pentadecyloxy, and the like are exemplified as "alkyloxy".

In the present specification, the term "haloalkyloxy" employed alone or in combination with other term includes the above-mentioned "alkyloxy" substituted with one or more halogen atom(s). Chloromethyloxy, difluoromethyloxy, 2,2,2-trifluoroethyloxy, 3-chloropropyloxy, 4-fluorobutyloxy, and the like are exemplified as "haloalkyloxy".

In the present specification, the term "alkenyloxy" employed alone or in combination with other term includes the above-mentioned "alkenyl" substituted with one or more hydroxy. 2-Propenyloxy, 3-butenyloxy, 4-octenyloxy, and the like are exemplified as "alkenyloxy".

In the present specification, the term "alkynyloxy" employed alone or in combination with other term includes the above-mentioned "alkynyl" substituted with one or more hydroxy. 2-Propynnyloxy, 3-butynyloxy, 4-octynyloxy, and the like are exemplified as "alkynyloxy".

In the present specification, cylopropylmethyloxy, 2-cylopropylethyloxy, 2-cylobutylethyloxy, 3-cylopentylpropyloxy, cylohexylmethyloxy, 4-cylohexylbutyloxy, 8-cylooctyloctyloxy, and the like are exemplified as "C3-C8 cycloalkyl-C1-C8 alkyloxy".

In the present specification, phenylmethyloxy, 2-phenylethyloxy, 3-phenylpropyloxy, 4-phenylbutyloxy, 8-phenyloctyloxy, and the like are exemplified as "phenyl-C1-C8 alkyloxy".

In the present specification, 1-naphthylmethyloxy, 2-naphthylmethyloxy, 2-(1-naphthyl)ethyloxy, 3-(2-naphthyl)propyloxy, 4-(1-naphthyl)butyloxy, 8-(2-naphthyl)octyloxy, and the like are exemplified as "naphthyl-C1-C8 alkyloxy".

In the present specification, 2-methyloxyethyloxy, 2-ethyloxyethyloxy, 3-methyloxypropyloxy, 4-ethyloxybutyloxy, and the like are exemplified as "C1-C4 alkyloxy-C2-C4 alkyloxy".

In the present specification, methyloxymethyloxy, 2-methyloxyethyloxy, 2-ethyloxyethyloxy, 3-methyloxypropyloxy, 4-ethyloxybutyloxy, 6-butyloxyhexyloxy, 8-octyloxyoctyloxy, and the like are exemplified as "C1-C8 alkyloxy-C1-C8 alkyloxy".

In the present specification, 2-(methyloxymethyloxy)ethyloxy, 2-(2-ethyloxyethyloxy)ethyloxy, 3-(2-methyloxyethyloxy)propyloxy, 4-(2-ethyloxyethyloxy)butyloxy, and the like are exemplified as "(C1-C4 alkyloxy-C2-C4 alkyloxy) C2-C4 alkyloxy".

In the present specification, 2-(2-methyloxyethyloxy)ethyloxy, 2-(2-ethyloxyethyloxy)ethyloxy, 3-(2-methyloxyethyloxy)propyloxy, 4-(2-ethyloxyethyloxy)butyloxy, 8-(2-butyloxyethyloxy)octyloxy, and the like are exemplified as "(C1-C8alkyloxy-C1-C8 alkyloxy)C1-C8 alkyloxy".

In the present specification, 1,3-di(methyloxy)-2-propyloxy, 1,3-di(ethyloxy)-2-propyloxy, 1-ethyloxy-3-methyloxy-2-propyloxy, and the like are exemplified as "di(C1-C8alkyloxy)C1-C8 alkyloxy".

In the present specification, "oxolanyl-C1-C8 alkyloxy" means the above-mentioned "C1-C8 alkyloxy" substituted with oxolanyl. Examples of oxolanyl-C1-C8 alkyloxy includes 2-oxolanyletyloxy, 3-oxolanylpropyloxy, 4-oxolanylbutyloxy, 8-oxolanyloctyloxy, and the like.

In the present specification, the term "cycloalkyloxy" employed alone or in combination with other term includes an oxygen atom substituted with a mono-carbocyclic group having forward-mentioned number of carbon. Cycloalkyloxy include cyclopropyloxy, cyclobutyloxy, cyclopentyloxy, cyclohexyloxy, cyclooctynyloxy, and the like are exemplified as "cycloalkyloxy".

In the present specification, the term "alkylthio" employed alone or in combination with other term includes a straight- or branched chain alkylthio having forward-mentioned number of carbon. Alkylthio include methylthio, ethylthio, n-propylthio, isopropylthio, n-butylthio, isobutylthio, sec-butylthio, tert-butylthio, n-pentylthio, isopentylthio, neo-pentylthio, n-hexylthio, isohexylthio, n-heptylthio, n-octylthio, and the like are exemplified as "alkylthio".

In the present specification, 2-methylthioethyloxy, 2-ethylthioethyloxy, 3-methylthiopropyloxy, 4-ethylthiobutyloxy, 8-butylthiooctyloxy, and the like are exemplified as "C1-C8 alkylthio-C1-C8 alkyloxy".

In the present specification, the term "C1-C2 alkylene" means methylene and ethylene.

In the present specification, the term "straight-chain C1-C4 alkylene" means straight-chain alkylene having one to four carbon atom(s). Methylene, ethylene, trimethylene, and teteramethylene are exemplified as "straight-chain C1-C4 alkylene".

In the present specification, the term "C1-C3 alkylene" means straight-chain alkylene having one to three carbon atom(s). Methylene, ethylene, and trimethylene are exemplified as "C1-C3 alkylene".

In the present specification, the term "straight-chain C1-C4 alkylene optionally substituted with C1-C8 alkyl, which may contain optionally substituted a heteroatom(s)" means straight-chain alkylene having one to four carbon atom(s) which may contain optionally substituted one to three heteroatom(s) optionally substituted with C1-C8 alkyl and the alkylene may be optionally substituted with C1-C8 alkyl. Examples are —$CH_2$—, —$CH_2CH_2$—, —$CH(n-C_4H_9)CH_2$—, —$CH(n-C_6H_{13})CH_2$—, —$CH(n-C_7H_{15})CH_2$—, —$CH_2CH_2CH_2$—, —$CH_2CH_2CH_2CH_2$—, —$CH_2O$—, —$OCH_2$—, —$SCH_2$—, —$OCH_2O$—, —$OCH_2CH_2O$—, —$CH_2CH_2OCH_2CH_2$—, and the like.

In the present specification, the term "straight-chain C2-C4 alkenylene optionally substituted with C1-C8 alkyl, which may contain optionally substituted a heteroatom(s)" means straight-chain alkenylene having two to four carbon atom(s) which may contain optionally substituted one to three heteroatom(s) optionally substituted with C1-C8 alkyl and the alkenylne may be optionally substituted with C1-C8 alkyl. Examples are —CH=CH—, —O—CH=CH—, —S—CH=CH—, —O—CH=CH—O—, and the like.

In the present specification, C1-C8 alkyl is exemplified as "optionally substituted heteroatom".

In the present specification, cyclopentadiene, benzene, cyclohexadiene, cycloheptadiene, furan, thiophen, pyran, and the like are exemplified as "5 to 8 membered ring taken together with the adjacent carbon atoms which may contain a heteroatom(s) and/or an unsaturated bond(s)".

In the present specification, the term "amino optionally substituted with C1-C8 alkyl" means non-substituted amino and amino substituted with one or two C1-C8 alkyl. Examples are amino, monomethylamino, dimethylamino, ethylamino, diethylamino, and the like.

Preferable are a fluorine atom and a chlorine atom as "halogen atom" for $R^1$, $R^2$, $R^3$, $R^4$, $R^5$, $R^C$, and $R^D$. Especially, a fluorine atom is preferable.

Preferable are a fluorine atom and a chlorine atom as "halogen atom" for $R^6$, $R^7$, and $R^8$.

Preferable are C1-C4 alkyl as "C1-C6 alkyl" for $R^1$, $R^9$, and $R^C$. Especially, methyl or ethyl is preferable.

Preferable is methyl as "C1-C3 alkyl" for $R^5$, $R^6$, $R^7$, $R^8$, and $R^D$.

Preferable are C1-C8 alkyloxy as "C1-C12 alkyloxy" for $R^1$ and $R^C$. Especially, methyloxy or ethyloxy is preferable.

Preferable is methyloxy as "C1-C3 alkyloxy" for $R^5$, $R^8$, and $R^D$.

Preferable is C1-C12 alkyl as "C1-C15 alkyl" of "C1-C15 alkyl optionally substituted with substituent(s) selected from substituent group A" for $R^2$, $R^3$, and $R^4$. Preferable are C5-C6 cycloalkyl, C1-C8 alkyloxy, C1-C4 alkyloxy-C2-C4alkyloxy, (C1-C4 alkyloxy-C2-C4alkyloxy)C2-C4 alkyloxy, or methylthio as "substituent(s) selected from substituent group A". Preferable is one or two as "number(s) of substituent(s)".

Preferable is a 5 to 6 membered ring which may contain a heteroatom(s) and/or an unsaturated bond(s) as "$R^1$ and $R^5$ taken together with the adjacent carbon atoms may form a 5 to 8 membered ring which may contain a heteroatom(s) and/or an unsaturated bond(s)". Preferable are an oxygen atom, a sulfur atom, or a nitrogen atom as heteroatom. Preferable is one as a number of heteroatom. Preferable is a double bond as an unsaturated bond. Preferable is one as a number of double bond.

Preferable is C1-C8 alkyloxy as "C1-C12 alkyloxy" for $R^A$.

Preferable is C1-C4 alkyloxy-C2-C4 alkyloxy as "C1-C8 alkyloxy-C1-C8alkyloxy" for $R^A$.

Preferable is (C1-C4 alkyloxy-C2-C4 alkyloxy)C2-C4 alkyloxy as "(C1-C8 alkyloxy-C1-C8alkyloxy)C1-C8 alkyloxy" for $R^A$.

Preferable is C1-C12 alkyl as "C1-C14 alkyl" of "straght- or branched chain C1-C14 alkyl optionally substituted with substituent(s) selected from substituent group B" for $R^B$. Preferable are C5-C6 cycloalkyl, C1-C8 alkyloxy, C1-C4 alkyloxy-C2-C4alkyloxy, (C1-C4 alkyloxy-C2-C4alkyloxy) C2-C4 alkyloxy, or methylthio as "substituent(s) selected from substituent group B". Preferable is one as "number of substituent(s)".

Preferable is C1-C10 alkyl as "C1-C15 alkyl" of "straght- or branched chain C1-C15 alkyl optionally substituted with substituent(s) selected from substituent group C" for $R^E$. Especially, C1-C8 alkyl is preferable. Preferable are C5-C6 cycloalkyl, C1-C8 alkyloxy, C1-C4 alkyloxy-C2-C4alkyloxy, (C1-C4 alkyloxy-C2-C4alkyloxy)C2-C4 alkyloxy, or methylthio as "substituent(s) selected from substituent group C". Especially, C1-C6 alkyloxy is preferable. Preferable is one or two as "number of substituent(s)".

Preferable are C1-C4 alkylene, —O—(C1-C3 alkylene), (C1-C3 alkylene)-O— as "straght-chain C1-C4 alkylene optionally substituted with C1-C8 alkyl, which may contain optionally substituted heteroatom" for Z. Especially, C1-C2 alkylene or —OCH$_2$O— is preferable.

Substituents groups (Ia) to (Io) are shown as preferable substituent(s) groups for $R^1$ to $R^9$ of the compound represented by general formula (I)

For $R^1$, (Ia) a hydrogen atom, a halogen atom, or C1-C6 alkyloxy, (Ib) halogen atom or C1-C6 alkyloxy.

For $R^2$, (Ic) C1-C15 alkyl substituted with one or same or different two substituent(s) selected from substituent group consists of (C5-C6 cycloalkyl, C1-C8 alkyloxy, C1-C4 alkyloxy-C2-C4 alkyloxy, (C1-C4 alkyloxy-C2-C4 alkyloxy)C2-C4 alkyloxy, and methylthio), C2-C15 alkynyl substituted with one or same or different two substituent(s) selected from substituent group consists of (C5-C6 cycloalkyl, C1-C8 alkyloxy, C1-C4 alkyloxy-C2-C4 alkyloxy, (C1-C4 alkyloxy-C2-C4 alkyloxy)C2-C4 alkyloxy, and methylthio) or C1-C15 alkyloxy substituted with one or same or different two substituent(s) selected from substituent group consists of (C5-C6 cycloalkyl, C1-C8 alkyloxy, C1-C4 alkyloxy-C2-C4 alkyloxy, (C1-C4 alkyloxy-C2-C4 alkyloxy)C2-C4 alkyloxy, and methylthio), (Id) C1-C15 alkyl substituted with one substituent selected from substituent group consists of (C1-C8 alkyloxy and C1-C4 alkyloxy-C2-C4 alkyloxy), C2-C15 alkynyl substituted with one substituent selected from substituent group consists of (C1-C8 alkyloxy and C1-C4 alkyloxy-C2-C4 alkyloxy), or C1-C15 alkyloxy substituted with one substituent selected from substituent group consists of (C1-C8 alkyloxy and C1-C4 alkyloxy-C2-C4 alkyloxy), (Ie) C1-C15 alkyl substituted with one C1-C8 alkyloxy, C2-C15 alkynyl substituted with one C1-C8 alkyloxy, or C1-C15 alkyloxy substituted with one C1-C8 alkyloxy.

For $R^3$, $R^4$, and $R^5$, (If) each independently a hydrogen atom or C1-C3 alkyloxy.

For $R^G$ and $R^7$, (Ig) each independently a halogen atom.

For $R^8$, (Ih) a halogen atom, C1-C3 alkyl, or C1-C3 alkyloxy, (Ii) C1-C3 alkyl or C1-C3 alkyloxy, (Ij) C1-C3 alkyl.

For $R^9$, (Ik) a hydrogen atom.

Or, $R^1$ and $R^5$ may form a (Il) 5 to 6 membered ring taken together with the adjacent carbon atoms which may contain an oxygen atom, (Im) 6 membered carbocylic ring taken together with the adjacent carbon atoms, (In) 6 membered ring taken together with the adjacent carbon atoms which contains one oxygen atom.

Examples of preferable group of the compound represented by general formula (I) contains [$R^1$, $R^2$, $R^3$, $R^4$, $R^5$, $R^6$, $R^7$, $R^8$, $R^9$]=[Ia, Ic, If, If, If, Ig, Ig, Ih, Ik], [Ia, Ic, If, If, If, Ig, Ig, Ii, Ik], [Ia, Ic, If, If, If, Ig, Ig, Ij, Ik], [Ia, Id, If, If, If, Ig, Ig, Ih, Ik], [Ia, Id, If, If, If, Ig, Ig, Ii, Ik], [Ia, Id, If, If, If, Ig, Ig, Ij, Ik], [Ia, Ie, If, If, If, Ig, Ig, Ih, Ik], [Ia, Ie, If, If, If, Ig, Ig, Ii, Ik], [Ia, Ie, If, If, If, Ig, Ig, Ij, Ik], [Ib, Ic, If, If, If, Ig, Ig, Ih, Ik], [Ib, Ic, If, If, If, Ig, Ig, Ii, Ik], [Ib, Ic, If, If, If, Ig, Ig, Ij, Ik], [Ib, Id, If, If, If, Ig, Ig, Ih, Ik], [Ib, Id, If, If, If, Ig, Ig, Ii, Ik], [Ib, Id, If, If, If, Ig, Ig, Ij, Ik], [Ib, Ie, If, If, If, Ig, Ig, Ih, Ik], [Ib, Ie, If, If, If, Ig, Ig, Ii, Ik], [Ib, Ie, If, If, If, Ig, Ig, Ij, Ik], or [$R^1$-$R^5$, $R^2$, $R^3$, $R^4$, $R^6$, $R^7$, $R^8$, $R^9$]=[Il, Ic, If, If, Ig, Ig, Ih, Ik], [Il, Ic, If, If, Ig, Ig, Ii, Ik], [Il, Ic, If, If, Ig, Ig, Ij, Ik], [Il, Id, If, If, Ig, Ig, Ih, Ik], [Il, Id, If, If, Ig, Ig, Ii, Ik], [Il, Id, If, If, Ig, Ig, Ij, Ik], [Il, Ie, If, If, Ig, Ig, Ih, Ik], [Il, Ie, If, If, Ig, Ig, Ii, Ik], [Il, Ie, If, If, Ig, Ig, Ij, Ik], [Im, Ic, It If, Ig, Ig, Ih, Ik], [Im, Ic, If, If, Ig, Ig, Ii, Ik], [Im, Ic, If If, Ig, Ig, Ij, Ik], [Im, Id, If, If, Ig, Ig, Ih, Ik], [Im, Id, If, If, Ig, Ig, Ii, Ik], [Im, Id, If, If, Ig, Ig, Ij, Ik], [Im, Ie, If, If, Ig, Ig, Ih, Ik], [Im, Ie, If, If, Ig, Ig, Ii, Ik], [Im, Ie, If, If, Ig, Ig, Ij, Ik], [In, Ic, If If, Ig, Ig, Ih, Ik], [In, Ic, If If, Ig, Ig, Ii, Ik], [In, Ic, If, If, Ig, Ig, Ij, Ik], [In, Id, If, If, Ig, Ig, Ih, Ik], [In, Id, If, If, Ig, Ig, Ii, Ik], [In, Id, If, If, Ig, Ig, Ij, Ik], [In, Ie, If, If, Ig, Ig, Ih, Ik], [In, Ie, If, If, Ig, Ig, Ii, Ik], [In, Ie, If, If, Ig, Ig, Ij, Ik].

Substituents groups (IIa) to (IIn) are shown as preferable substituent(s) groups for $R^6$ to $R^8$ and $R^A$ to $R^D$ of the compound represented by general formula (II)

For $R^6$ and $R^7$, (IIa) each independently a halogen atom.

For $R^8$, (IIb) a halogen atom, C1-C3 alkyl, or C1-C3 alkyloxy, (IIc) C1-C3 alkyl or C1-C3 alkyloxy, (IId) C1-C3 alkyl.

For $R^A$, (IIe) a hydrogen atom, C1-C8 alkyloxy, or C1-C4 alkyloxy-C2-C4 alkyloxy, (IIf) C1-C8 alkyloxy, (IIg) C1-C4 alkyloxy-C2-C4 alkyloxy.

For $R^B$, (IIh) C1-C14 alkyl substituted with one substituent selected from substituent group consists of (a hydrogen atom, C1-C8 alkyloxy, and C1-C4 alkyloxy-C2-C4 alkyloxy), C2-C14 alkynyl substituted with one substituent selected from substituent group consists of (a hydrogen atom, C1-C8 alkyloxy, and C1-C4 alkyloxy-C2-C4 alkyloxy), or C1-C14 alkyloxy substituted with one substituent selected from substituent group consists of (a hydrogen atom, C1-C8 alkyloxy, and C1-C4 alkyloxy-C2-C4 alkyloxy), (IIi) C1-C14 alkyl, (IIj) C1-C14 alkyl substituted with one C1-C8 alkyloxy, C2-C14 alkynyl substituted with one C1-C8 alkyloxy, or C1-C14 alkyloxy substituted with one C1-C8 alkyloxy, (IIk) C1-C14 alkyl substituted with one C1-C4 alkyloxy-C2-C4 alkyloxy, C2-C14 alkynyl substituted with one C1-C4 alkyloxy-C2-C4 alkyloxy, or C1-C14 alkyloxy substituted with one C1-C4 alkyloxy-C2-C4 alkyloxy.

For $R^C$, (III) a hydrogen atom, a halogen atom, or C1-C6 alkyloxy, (IIm) halogen atom or C1-C6 alkyloxy.

For $R^D$, (IIn) a hydrogen atom or C1-C3 alkyloxy.

Examples of preferable group of the compound represented by general formula (II) contains [$R^6$, $R^7$, $R^8$, $R^A$, $R^B$, $R^C$, $R^D$]=[IIa, IIa, IIb, IIe, IIh, III, IIn], [IIa, IIa, IIb, IIe, IIh, IIm, IIn], [IIa, IIa, IIb, IIe, IIi, III, IIn], [IIa, IIa, IIb, IIe, IIi, IIm, IIn], [IIa, IIa, IIb, IIe, IIj, III, IIn], [IIa, IIa, IIb, IIe, IIj, IIm, IIn], [IIa, IIa, IIb, IIe, IIk, III, IIn], [IIa, IIa, IIb, IIe, IIk, IIm, IIn], [IIa, IIa, IIb, IIf, IIh, III, IIn], [IIa, IIa, IIb, IIf, IIh, IIm, IIn], [IIa, IIa, IIb, IIf, IIi, III, IIn], [IIa, IIa, IIb, IIf, IIi, IIm, IIn], [IIa, IIa, IIb, IIf, IIj, III, IIn], [IIa, IIa, IIb, IIf, IIj, IIm, IIn], [IIa, IIa, IIb, IIf, IIk, III, IIn], [IIa, IIa, IIb, IIf, IIk, IIm, IIn], [IIa, Ia, IIb, IIg, IIh, III, IIn], [IIa, IIa, IIb, IIg, IIh, IIm, IIn], [IIa, IIa, IIb, IIg, IIi, III, IIn], [IIa, IIa, IIb, IIg, IIi, IIm, IIn], [IIa, IIa, IIb, IIg, IIj, III, IIn], [IIa, IIa, IIb, IIg, IIj, IIm, IIn], [IIa, IIa, IIb, IIg, IIk, III, IIn], [IIa, IIa, IIb, IIg, IIk, IIm, IIn], [IIa, Iha, IIc, IIe, IIh, III, IIn], [IIa, IIa, IIc, IIe, IIh, IIm, IIn], [IIa, IIa, IIc, IIe, IIi, III, IIn], [IIa, IIa, IIc, IIe, IIi, IIm, IIn], [IIa, IIa, IIc, IIe, IIj, III, IIn], [IIa, IIa, IIc, IIe, IIj, IIm, IIn], [IIa, IIa, IIc, IIe, IIk, III, IIn], [IIa, IIa, IIc, IIe, IIk, IIm, IIn], [IIa, IIa, IIc, IIf, IIh, III, IIn], [IIa, IIa, IIc, IIf, IIh, IIm, IIn], [IIa, IIa, IIc, IIf, IIi, III, IIn], [IIa, IIa, IIc, IIf, IIi, IIm, IIn], [IIa, IIa, IIc, IIf, IIj, III, IIn], [IIa, IIa, IIc, IIf, IIj, IIm, IIn], [IIa, IIa, IIc, IIf, IIk, III, IIn], [IIa, IIa, IIc, IIf, IIk, IIm, IIn], [IIa, IIa, IIc, IIg, IIh, III, IIn], [IIa, IIa, IIc, IIg, IIh, IIm, IIn], [IIa, IIa, IIc, IIg, IIi, III, IIn], [IIa, IIa, IIc, IIg, IIi, IIm, IIn], [IIa, IIa, IIc, IIg, IIj, III, IIn], [IIa, IIa, IIc, IIg, IIj, IIm, IIn], [IIa, IIa, IIc, IIg, IIk, III, IIn], [IIa, IIa, IIc, IIg, IIk, IIm, IIn], [IIa, IIa, IId, IIe, IIh, III, IIn], [IIa, IIa, IId, IIe, IIh, IIm, IIn], [IIa, IIa, IId, IIe, IIi, III, IIn], [IIa, IIa, IId, IIe, IIi, IIm, IIn], [IIa, IIa, IId, IIe, IIj, III, IIn], [IIa, IIa, IId, IIe, IIj, IIm, IIn], [IIa, IIa, IId, IIe, IIk, III, IIn], [IIa, IIa, IId, IIe, IIk, IIm, IIn], [IIa, IIa, IId, IIf, IIh, III, IIn], [IIa, IIa, IId, IIf, IIh, IIm, IIn], [IIa, IIa, IId, IIf, IIi, III, IIn], [IIa, IIa, IId, IIf, IIi, IIm, IIn], [IIa, IIa, IId, IIf, IIj, III, IIn], [IIa, IIa, IId, IIf, IIj, IIm, IIn], [IIa, IIa, IId, IIf, IIk, III, IIn], [IIa, IIa, IId, IIf, IIk, IIm, IIn], [IIa, IIa, IId, IIg, IIh, III, IIn], [IIa, IIa, IId, IIg, IIh, IIm, IIn], [IIa, IIa, IId, IIg, IIi, III, IIn], [IIa, IIa, IId, IIg, IIi, IIm, IIn], [IIa, IIa, IId, IIg, IIj, III, IIn], [IIa, IIa, IId, IIg, IIj, IIm, IIn], [IIa, IIa, IId, IIg, IIk, III, IIn], [IIa, IIa, IId, IIg, IIk, IIm, IIn].

Substituents groups (IIIa) to (IIIn) are shown as preferable substituent(s) groups for $R^6$ to $R^8$, $R^E$, and Z of the compound represented by general formula (III)

For $R^6$ and $R^7$, (IIIa) each independently a halogen atom.

For $R^8$, (IIIb) a halogen atom, C1-C3 alkyl, or C1-C3 alkyloxy, (IIIc) C1-C3 alkyl or C1-C3 alkyloxy, (IIId) C1-C3 alkyl.

For $R^E$, (IIIe) C1-C15 alkyl substituted with one substituent selected from substituent group consists of (C1-C8 alkyloxy and C1-C4 alkyloxy-C2-C4 alkyloxy), C2-C15 alkynyl substituted with one substituent selected from substituent group consists of (C1-C8 alkyloxy and C1-C4 alkyloxy-C2-C4 alkyloxy), or C1-C15 alkyloxy substituted with one substituent selected from substituent group consists of (C1-C8 alkyloxy and C1-C4 alkyloxy-C2-C4 alkyloxy), (IIIf) C1-C15 alkyl substituted with one C1-C8 alkyloxy, C2-C15 alkynyl substituted with one C1-C8 alkyloxy, or C1-C15 alkyloxy substituted with one C1-C8 alkyloxy, (IIIg) C1-C15 alkyl substituted with one C1-C4 alkyloxy-C2-C4 alkyloxy, C2-C15 alkynyl substituted with one C1-C4 alkyloxy-C2-C4 alkyloxy, or C1-C15 alkyloxy substituted with one C1-C4 alkyloxy-C2-C4 alkyloxy.

For Z, (IIIh) ethylene or oxymethylene, (IIIi) ethylene.

Examples of preferable group of the compound represented by general formula (III) contains [$R^6$, $R^7$, $R^8$, $R^E$, Z]=[IIIa, IIIa, IIIb, IIIe, IIIh], [IIIa, IIIa, IIIb, IIIe, IIIi], [IIIa, IIIa, IIIb, IIIf, IIIh], [IIIa, IIIa, IIIb, IIIf, IIIi], [IIIa, IIIa, IIIb, IIIg, IIIh], [IIIa, IIIa, IIIb, IIIg, IIIi], [IIIa, IIIa, IIIc, IIIe, IIIh], [IIIa, IIIa, IIIc, IIIe, IIIi], [IIIa, IIIa, IIIc, IIIf, IIIh], [IIIa, IIIa, IIIc, IIIf, IIIi], [IIIa, IIIa, IIIc, IIIg, IIIh], [IIIa, IIIa, IIIc, IIIg, IIIi], [IIIa, IIIa, IIId, IIIe, IIIh], [IIIa, IIIa, IIId, IIIe, IIIi], [IIIa, IIIa, IIId, IIIf, IIIh], [IIIa, IIIa, IIId, IIIf, IIIi], [IIIa, IIIa, IIId, IIIg, IIIh], [IIIa, IIIa, IIId, IIIg, IIIi].

Substituents groups (II-Aa) to (II-Al) are shown as preferable substituent(s) groups for $R^6$ to $R^8$, $R^C$, $R^D$, and $R^F$ of the compound represented by general formula (II-A)

For $R^6$ and $R^7$, (II-Aa) each independently a halogen atom.

For $R^8$, (II-Ab) a halogen atom, C1-C3 alkyl, or C1-C3 alkyloxy, (III-Ac) C1-C3 alkyl or C1-C3 alkyloxy, (II-Ad) C1-C3 alkyl.

For $R^C$, (II-Ae) a halogen atom or C1-C6 alkyloxy, (III-Af) halogen atom, (II-Ag) C1-C6 alkyloxy.

For $R^D$, (II-Ah) a hydrogen atom or C1-C3 alkyloxy, (II-Ai) a hydrogen atom.

For $R^F$, (II-Aj) C1-C14 alkyl substituted with one substituent selected from substituent group consists of (C1-C8 alkyloxy and C1-C4 alkyloxy-C2-C4 alkyloxy), C2-C14 alkynyl substituted with one substituent selected from substituent group consists of (C1-C8 alkyloxy and C1-C4 alkyloxy-C2-C4 alkyloxy), or C1-C 14 alkyloxy substituted with one substituent selected from substituent group consists of (C1-C8 alkyloxy and C1-C4 alkyloxy-C2-C4 alkyloxy), (II-Ak) C1-C14 alkyl substituted with one C1-C8 alkyloxy, C2-C14 alkynyl substituted with one C1-C8 alkyloxy, or C1-C14 alkyloxy substituted with one C1-C8 alkyloxy, (II-Al) C1-C14 alkyl substituted with one C1-C4 alkyloxy-C2-C4 alkyloxy, C2-C14 alkynyl substituted with one C1-C4 alkyloxy-C2-C4 alkyloxy, or C1-C14 alkyloxy substituted with one C1-C4 alkyloxy-C2-C4 alkyloxy.

Examples of preferable group of the compound represented by general formula (II-A) contains [$R^6$, $R^7$, $R^8$, $R^C$, $R^D$, $R^F$]=[II-Aa, II-Aa, II-Ab, II-Ae, II-Ah, II-Aj], [II-Aa, II-Aa, II-Ab, II-Ae, II-Ah, II-Ak], [II-Aa, II-Aa, II-Ab, II-Ae, II-Ah, II-Al], [II-Aa, II-Aa, II-Ab, II-Ae, II-Ai, II-Aj], [II-Aa, II-Aa, II-Ab, II-Ae, II-Ai, II-Ak], [II-Aa, II-Aa, II-Ab, II-Ae, II-Ai, II-Al], [II-Aa, II-Aa, II-Ab, II-Af, II-Ah, II-Aj], [II-Aa, II-Aa, II-Ab, II-Af, II-Ah, II-Ak], [II-Aa, II-Aa, II-Ab, II-Af, II-Ah, II-Al], [II-Aa, II-Aa, II-Ab, II-Af, II-Ai, II-Aj], [II-Aa, II-Aa, II-Ab, II-Af, II-Ai, II-Ak], [II-Aa, II-Aa, II-Ab, II-Af, II-Ai, II-Al], [II-Aa, II-Aa, II-Ab, II-Ag, II-Ah, II-Aj], [II-Aa, II-Aa, II-Ab, II-Ag, II-Ah, II-Ak], [II-Aa, II-Aa, II-Ab, II-Ag, II-Ah, II-Al], [II-Aa, II-Aa, II-Ab, II-Ag, II-Ai, II-Ak], [II-Aa, II-Aa, II-Ab, II-Ag, II-Aj, II-Al], [II-Aa, II-Aa, II-Ac, II-Ae, II-Ah, II-Aj], [II-Aa, II-Aa, II-Ac, II-Ae, II-Ah, II-Ak], [II-Aa, II-Aa, II-Ac, II-Ae, II-Ah, II-Al], [II-Aa, II-Aa, II-Ac, II-Ae, II-Ai, II-Aj], [II-Aa, II-Aa, II-Ac, II-Ae, II-Ai, II-Ak], [II-Aa, II-Aa, II-Ac, II-Ae, II-Ai, II-Al], [II-Aa, II-Aa, II-Ac, II-Af, II-Ah, II-Aj], [II-Aa, II-Aa, II-Ac, II-Af, II-Ah, II-Ak], [II-Aa, II-Aa, II-Ac, II-Af, II-Ah, II-Al], [II-Aa, II-Aa, II-Ac, II-Af, II-Aj, II-Aj], [II-Aa, II-Aa, II-Ac, II-Af, II-Aj, II-Ak], [II-Aa, II-Aa, II-Ac, II-Af, II-Aj, II-Al], [II-Aa, II-Aa, II-Ac, II-Ag, II-Ah, II-Aj], [II-Aa, II-Aa, II-Ac, II-Ag, II-Ah, II-Ak], [II-Aa, II-Aa, II-Ac, II-Ag, II-Ah, II-Al], [II-Aa, II-Aa, II-Ac, II-Ag, II-Ai, II-Aj], [II-Aa, II-Aa, II-Ac, II-Ag, II-Ai, II-Ak], [II-Aa, II-Aa, II-Ac, II-Ag, II-Ai, II-Al], [II-Aa, II-Aa, II-Ad, II-Ae, II-Ah, II-Aj], [II-Aa, II-Aa, II-Ad, II-Ae, II-Ah, II-Ak], [II-Aa, II-Aa, II-Ad, II-Ae, II-Ah, II-Al], [II-Aa, II-Aa, II-Ad, II-Ae, II-Ai, II-Aj], [II-Aa, II-Aa, II-Ad, II-Ae, II-Ai, II-Ak], [II-Aa, II-Aa, II-Ad, II-Ae, II-Ai, II-Al],

[II-Aa, II-Aa, II-Ad, II-Af, II-Ah, II-Aj], [II-Aa, II-Aa, II-Ad, II-Af, II-Ah, II-Ak], [II-Aa, II-Aa, II-Ad, I-Af, II-Ah, II-Al], [II-Aa, II-Aa, II-Ad, II-Af, II-AJ, II-Aj], [II-Aa, II-Aa, II-Ad, II-Af, II-Aj, I-Ak], [II-Aa, II-Aa, II-Ad, II-Af, II-Aj, II-Al], [II-Aa, II-Aa, II-Ad, II-Ag, II-Ah, II-Aj], [II-Aa, II-Aa, II-Ad, II-Ag, II-Ah, II-Ak], [II-Aa, II-Aa, II-Ad, II-Ag, II-Ah, II-Al], [II-Aa, II-Aa, II-Ad, II-Ag, II-Ai, II-Aj], [II-Aa, II-Aa, II-Ad, II-Ag, II-Ai, II-Ak], [II-Aa, II-Aa, II-Ad, II-Ag, II-Ai, II-Al], [II-Aa, II-Aa, II-Ad, II-Ag, II-Ai, II-Al].

In the present specification, the term "platelet production modifier" means pharmaceutical composition for hemopathy accompanied with the unusual number of platelet. For example the hemopathy is thrombocytopenia (thrombocytopenia after bone marrow transplantation, chemotherapy-indeuced thrombocytopenia, Aplastic anemia, myelodysplasia syndrome, acquired thrombopenia such as idiopathic thrombopoietinic purpura, congenital amegakaryocytic thrombocytopenia such as thrombopoietin deficiency), and the like. For example this medicine can be used as treating agent in the case of decreacing number of platelet by administrating antitumor agent, or as protecting agent in the case of expecting the decreace of number of platelet by administrating antitumor agent.

In the present specification, the term "modifiering a platelet production" means 1) increasing a number of platelet decreased by administrating antitumor agent and the like. 2) maintaining a number of platelet which may be decreased by administrating antitumor agent and the like. 3) reducing the ratio of the platelet number of decrease caused by administrating antitumor agent and the like.

BEST MODE FOR CARRYING OUT THE INVENTION

Compounds (I) of the invention can be synthesized by the following methods A to B and the similar process.

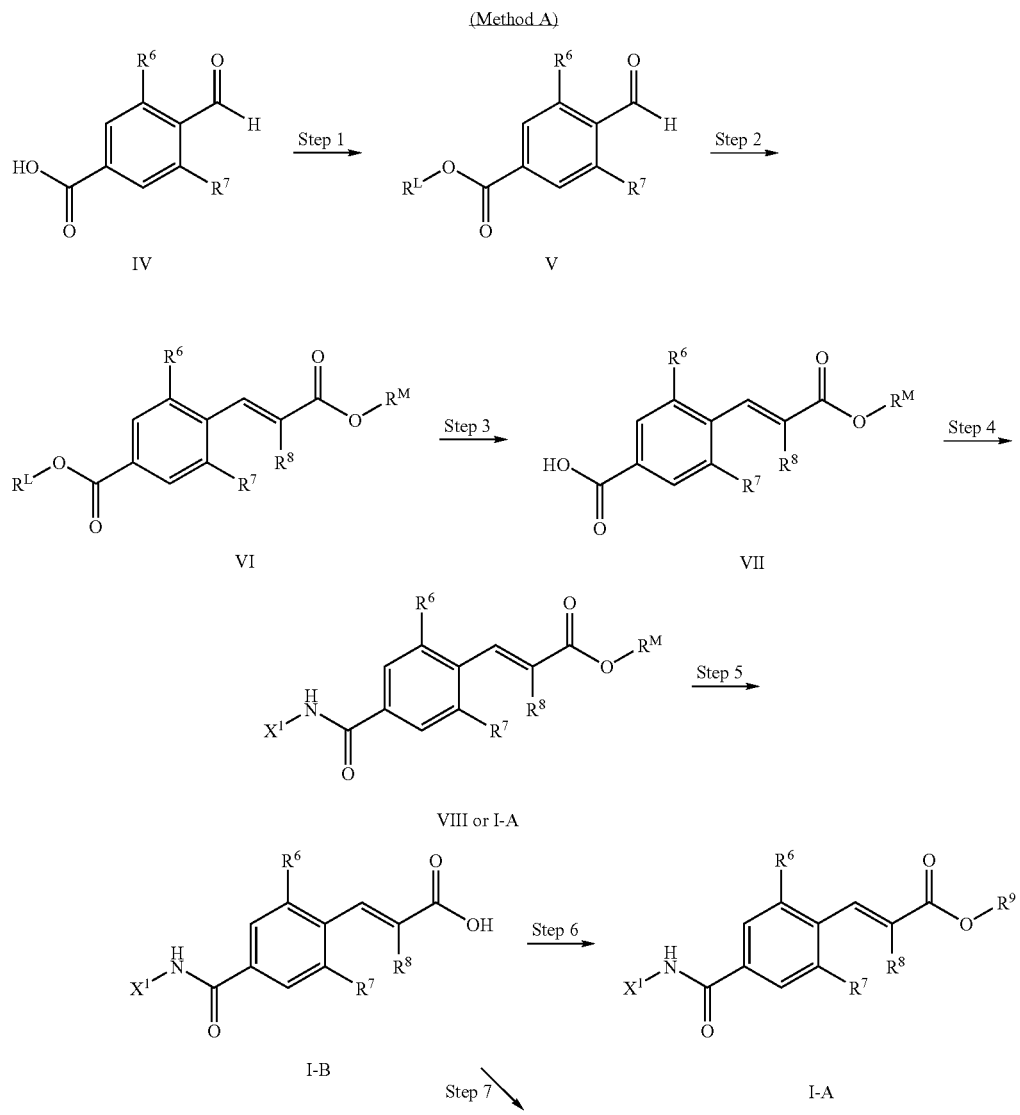

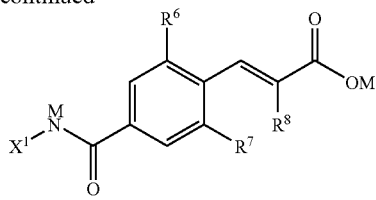

I-C wherein $R^6$, $R^7$, $R^8$, and $R^9$ are as defined above mentioned; $R^L$ and $R^M$ are a protecting group; $X^1$ is a group represented by the formula (IX), M is alkali metal.

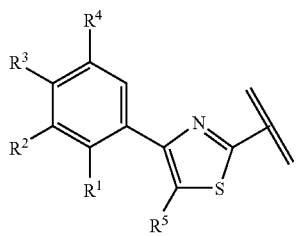

wherein $R^1$, $R^2$, $R^3$, $R^4$, and $R^5$ are as defined above mentioned.

(Step 1)

This step is a process of preparing the compound (V) by protecting of a carboxyl group of 4-formylbenzoic acid derivatives (IV) by $R^L$. In step 3 conbination of $R^L$ and $R^M$ is important in order to remove selectively protecting groups of two carboxylic acid. In the case of $R^L$ is a protecting group such as methyl and ethyl, which can be removed by basic condition, it is necessary that a protecting group of $R^M$ can be removed by another condition except basic condition. Examples of $R^M$ are allyl (removed by palladium (0) complex), tert-butyl, p-methyloxybenzyl, triphenylmethyl, diphenylmethyl (removed by acidic condition), trimethylsilylethyl, trimethylsilylethoxymethyl, tert-butyldimethylsilyl (removed by fluoride ion) and the like.

Esterification condition can be used the method of reacting with considerable halocompound in the presence of suitable base. And it can be synthesized by condensation reaction using an alcohol derivative as starting material.

(Step 2)

This step is a process of preparing the compound (VI) by converting an aldehyde group of the compound (V) to olefin. For examples, the olefin can be syntesized by the reaction using phosphineylide such as Wittig reaction, Horner-Emmons reaction, or by dehydrated condensation reaction such as Knoevenagel reaction.

(Step 3)

This step is a process of preparing the compound (VII) removing the protecting group $R^L$ of the compound (VI). The removal of protecting group $R^L$ is carried out under suitable reaction condition as described in Protective Groups in Organic Synthesis, Theodora W Green (John Wiley & Sons).

(Step 4)

This step is a process of preparing amide the compound (VIII) or the compound (I-A wherein $R^M$ is C1-C4 alkyl) from the compound (VII) and an amine derivative ($X^1$—$NH_2$) by the method such as active esterification, acid chloride, mixed acid anhydride. This step is reacted in the solvent such as tetrahydrofuran, dioxane, dichloromethane, toluene, benzene. At active esterification method it can be carried out by using 1-hydroxybenzotriazole, hydroxysuccinimide, dimethylaminopyridine, and the like and dicyclohexylcarbodiimide, 1-ethyl-3-(3-dimethylaminopropyl)carbodiimide hydrochloride salt, and the like as condensation reagent. At acid halide method it can be carried out by converting free carboxylic acid which is reacted with thionyl chloride or oxalyl chloride to acid chloride. At mixed acid anhydride method it can be carried out by converting carboxylic acid which is reacted with ethylchloroformate, isobutylchloroformate or the like to mixed acid anhydride. Triethylamine, pyridine or the like are used as base in these reaction according to be necessary.

(Step 5)

This step is a process of preparing the compound (I-B) by removing a protecting group $R^M$ of the compound (VIII) or the compound (I-A). The protecting group $R^M$ is removed under suitable reaction condition by using the method as described in Protective Groups in Organic Synthesis, Theodora W Green (John Wiley & Sons).

(Step 6)

This step is a process of preparing the compound (I-A) by alkylating the compound (I-B). This step is reacted in the solvent such as tetrahydrofuran, dioxane, dichloromethane, toluene, N,N-dimethylformamide. At alkylation method it can be carried out by condensation with C1-C6 alkyl halide in the presence of base such as potassium carbonate, sodium hydride. At acid chloride method it can be carried out by converting free carboxylic acid which is reacted with thionyl chloride or oxalyl chloride to acid chloride, and then was reacted with C1-C6 alcohol. Triethylamine, pyridine or the like are used as base in these reaction according to be necessary.

(Step 7)

This step is a process of preparing the compound (I-C) by treating the compound (I-B) with alkali metal such as sodium, potassium or alkali metal hydroxide. This step is reacted in the solvent such as tetrahydrofuran, dioxane, dichloromethane, toluene, N,N-dimethylformamide, alcohol such as methanol, ethanol, and the like in the presence of base such as alkali metal such as sodium, potassium or alkali metal hydroxide.

(Method B)

This method is another method for preparing the compound (VIII) or the compound (I-A) as described method A.

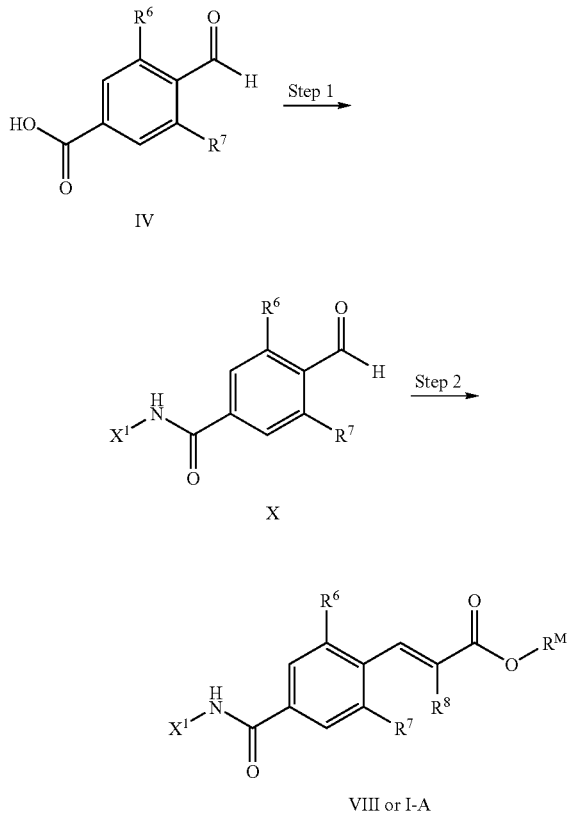

wherein $R^6$, $R^7$, $R^8$, $R^M$, and $X^1$ are as defined above mentioned.

(Step 1)

This step is a process of preparing the compound (X) in a manner similar to Step 4 of Method A.

(Step 2)

This step is a process of preparing the compound (VIII) or the compound (I-A) by converting an aldehyde group of the compound (X) to olefin in a manner similar to Step 2 of Method A.

(Method C)

This method is another method for preparing the compound (VIII) or the compound (I-A) as described method A.

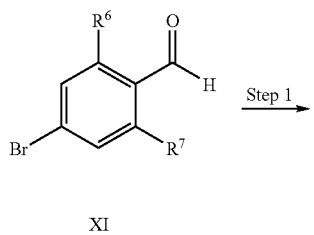

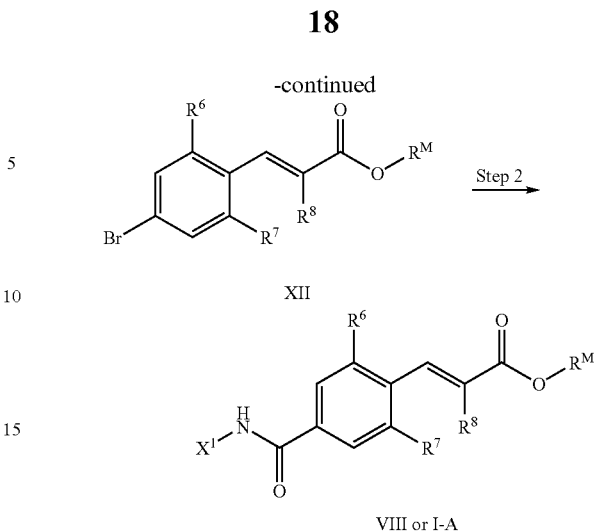

wherein $R^6$, $R^7$, $R^8$ $R^M$, and $X^1$ are as defined above mentioned.

(Step 1)

This step is a process of preparing the compound (XII) by converting an aldehyde group of the compound (XI) to olefin group in a manner similar to Step 2 of Method A.

(Step 2)

This step is a process of preparing the compound (VIII) or the compound (I-A) by substituting a bromo group of the compound (XII). At this step it can be carried out by adding carbon monoxide to a DMF solution of the compound (XII) and $X^1NH_2$ in the presence of dichlorobistriphenylphosphinepalladium and base such as triethylamine. The reaction temperature is used 20° C. to 120° C., preferably 50° C. to 100° C. The reaction time is used 1 h to 48 h, preferably 4 h to 24 h.

The term "solvate" includes, for example, solvates with organic solvents, hydrates, and the like.

The term "compound of the present invention" herein used includes a pharmaceutically acceptable salt or solvate thereof. The salt is exemplified by a salt with alkali metals (e.g., lithium, sodium, potassium, and the like), alkaline earth metals (e.g., magnesium, calcium, and the like), ammonium, organic bases, amino acids, mineral acids (e.g., hydrochloric acid, hydrobromic acid, phosphoric acid, sulfuric acid, and the like), or organic acids (e.g., acetic acid, citric acid, maleic acid, fumaric acid, benzenesulfonic acid, p-toluenesulfonic acid, and the like). These salts can be formed by the usual method. These hydrates can coordinate with any water molecules when hydrates are formed.

Prodrug is a derivative of the compound having a group which can be decomposed chemically or metabolically, and such prodrug is a compound according to the present invention which becomes pharmaceutically active by means of solvolysis or by placing the compound in vivo under a physiological condition. The method of both selection and manufacture of appropriate prodrug derivatives is described in, for example. Design of Prodrugs, Elsevier, Amsterdam, 1985). For instance, prodrugs such as an ester derivative which is prepared by reacting a basal acid compound with a suitable alcohol, or an amide derivative which is prepared by reacting a basal acid compound with a suitable amine are exemplified when the compounds according to present invention have a carboxylic group. Particularly preferred esters as prodrugs are methyl ester, ethyl ester, n-propyl ester, isopropyl ester, n-butyl ester, isobutyl ester, tert-butyl ester, morpholinoethyl ester, and N,N-diethylglycolamido ester, and the like. For instance, when the compounds according to present invention have a hydroxy group, prodrugs such as an acyloxy derivative which is prepared by reacting with a suitable acyl halide or a suitable acid anhydride. Particularly preferred acyloxy derivatives as prodrugs —OCOC$_2$H$_5$, —OCO(t-Bu), —OCOC$_{15}$H$_{31}$, —OCO(m-COONa-Ph), —COCH$_2$CH$_2$COONa, —OCOCH(NH$_2$)CH$_3$, —OCOCH$_2$N(CH$_3$)$_2$, and the like. For instance, when the compounds according to present invention have an amino group, prodrugs such as an amide derivative which is prepared by reacting with a suitable acid halide or a suitable acid anhydride. Particularly preferred amide as prodrugs are —NHCO(CH$_2$)$_{20}$CH$_3$, —NHCOCH(NH$_2$)CH$_3$, and the like.

The compound of the present invention is not restricted to any particular isomers but includes all possible isomers and racemic modifications.

The present invention compounds show excellent thrombopoietin receptor agonism as described in examples mentioned later, and may be used as a pharmaceutical composition (platelet production modifier) for hemopathy accompanied with the unusual number of platelet, for example thrombocytopenia (e.g., thrombocytopenia after bone marrow transplantation, chemocherapy-indeuced thrombocytopenia, Aplastic anemia, myelodysplastic syndrome, acquired thrombocytopenia such as idiopathic thrombocytopenic purpura, congenital amegakaryocytic thrombocytopenia such as thrombopoietin deficiency), and the like. And the present compound may be used as treating and/or preventing agent for the unusual number of platelet accompanied with administering antitumor agent.

When the compound of the present invention is administered to a person for the treatment of the above diseases, it can be administered orally as powder, granules, tablets, capsules, pilulae, and liquid medicines, or parenterally as injections, suppositories, percutaneous formulations, insufflation, or the like. An effective dose of the compound is formulated by being mixed with appropriate medicinal admixtures such as excipient, binder, penetrant, disintegrators, lubricant, and the like if necessary. Parenteral injections are prepared by sterilizing the compound together with an appropriate carrier.

The dosage varies with the conditions of the patients, administration route, their age, and body weight. In the case of oral administration, the dosage can generally be between 0.1 to 100 mg/kg/day, and preferably 1 to 20 mg/kg/day for adult.

The following examples are provided to further illustrate the present invention and are not to be constructed as limiting the scope thereof.

Abbreviations described below are used in the following examples.

Me: methyl
Et: ethyl
n-Bu: n-butyl
Ph: phenyl
Tf: trifluoromethanesulfonyl
DMF: N,N-dimethylformamide
THF: tetrahydrofuran

EXAMPLES

Example 1

Synthesis of Compound (A1)

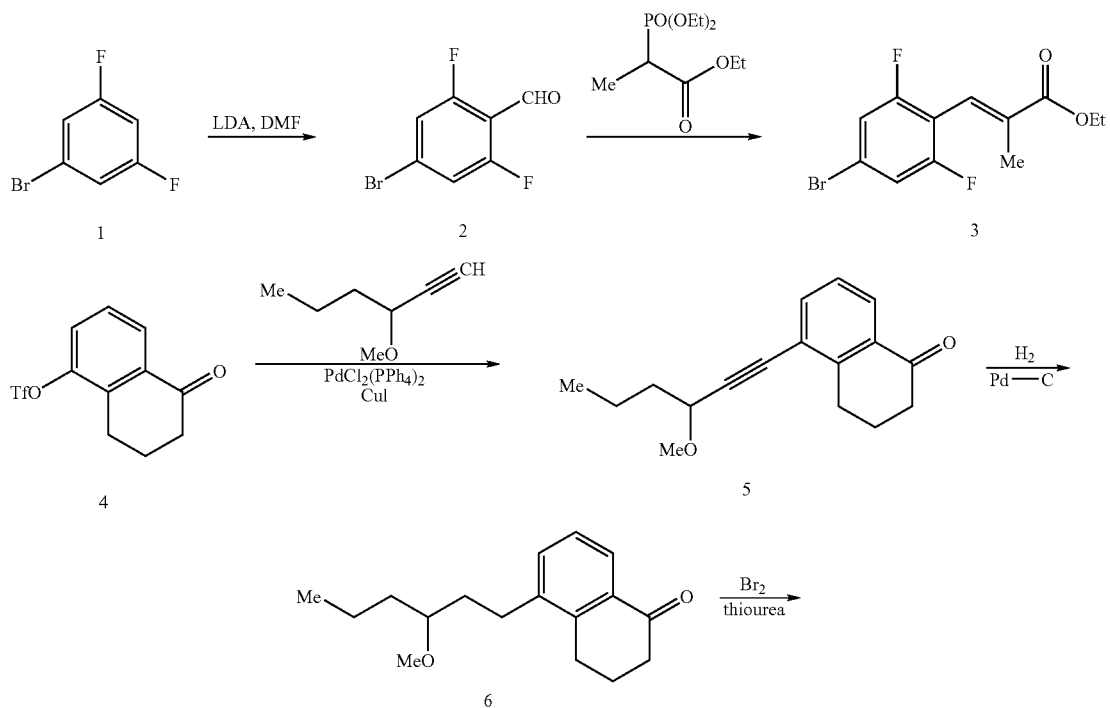

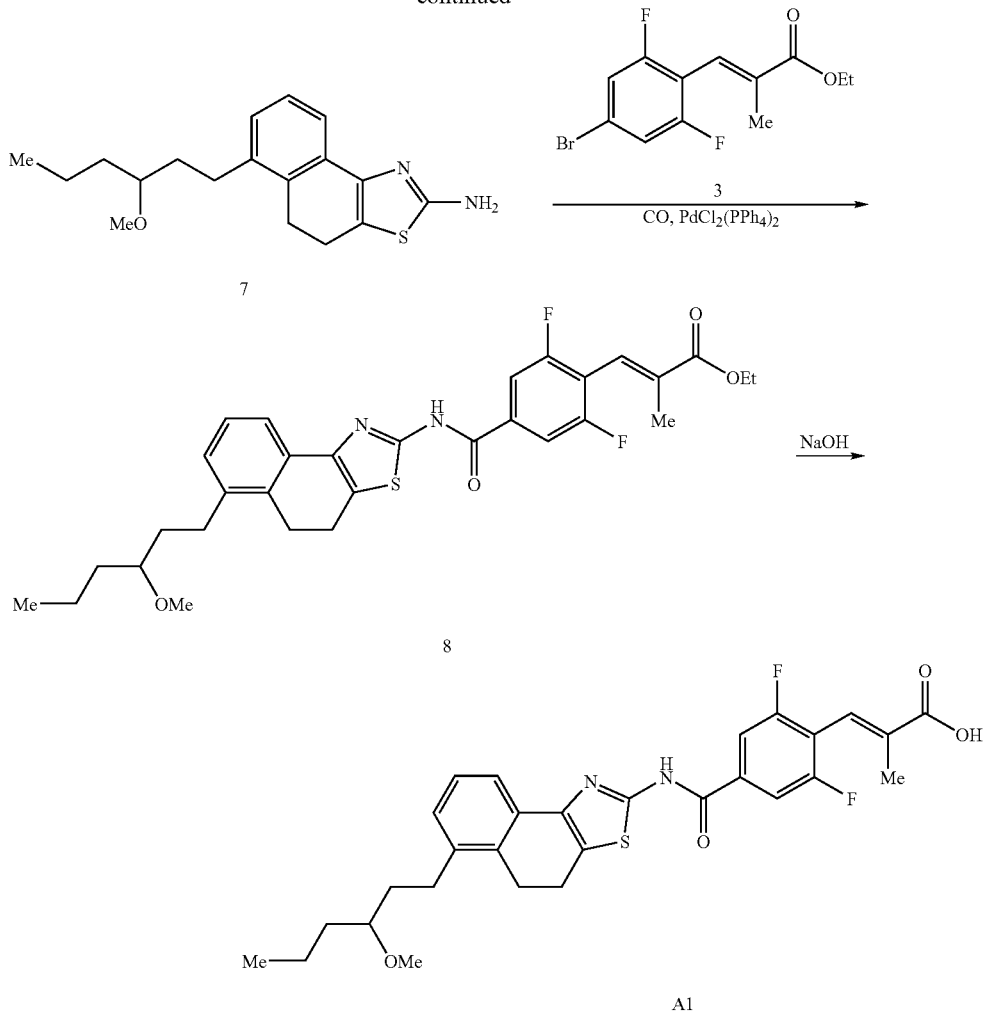

1) Synethesis of 4-bromo-2,6-difluorobenzaldehyde (2)

To a THF (250 mL) solution of diisopropylamine (53 mL) was added 2.44 M hexane solution of butyl lithium at −78° C., and the reaction mixture was stirred for 30 miniute. To the reaction mixture was added a THF solution of 3,5-difluoro-bromobenzene (1) (36 g), and then the reaction mixture was stirred for 1 h. To the reaction mixture was added DMF 146 mL, and the reaction mixture was stirred for additional 1 h. To the reaction mixture was added a saturated ammonium chloride aqueous solution, and the reaction mixture was extracted with ethyl acetate. The organic layer was washed with water, and brine, dried over magnesium sulfate, and evaporated. The obtained residue was purified by column chromatography (hexane:ethyl acetate=20:1) to obtain the compoumd (2) 23.2 g.

$^1$H-NMR(CDCl$_3$) 10.29(s, 1H), 7.19-7.25(m, 2H).

2) Synthesis of ethyl 3-(4-bromo-2,6-difluorophenyl)-2-methylacrylate (3)

To a THF (100 mL) solution of triethyl-2-phosphonopropionic acid (33.8 mL) was added sodium hydride (8.4 g) under ice-cooling. After the reaction mixture was stirred for 1 h, to the reaction mixture was added a THF solution of 4-bromo-2,6-difluorobenzaldehyde (2) (23.2 g) dropwise under ice-cooling. After the reaction mixture was stirred under ice-cooling for 2 h, to the reaction mixture were added ice-water, 2N hydrochloric acid, and the reaction mixture was extracted with ethyl acetate. The organic layer was washed with water, and brine, dried over magnesium sulfate, and evaporated. The obtained residue was purified by column chromatography (hexane:ethyl acetate=15:1) to obtain the compoumd (3) 32.08 g.

$^1$H-NMR(CDCl$_3$) 7.32(d, 1H, J=1.5 Hz), 7.11-7.17(m, 2H), 4.28(q, 2H, J=7.2 Hz), 1.86(d, 3H, J=1.5 Hz), 1.35(t, 3H, J=7.2 Hz).

3) Synthesis of 5-(3-methyloxyhexyn-1-yl)tetralone (5)

To a DMF (100 mL) solution of 5-hydroxytetralone trifluoromethanesulfonic acid ester (4) (13.5 g), 3-methyloxy-1-hexyne (10.3 g), dichlorobistriphenylphosphinepalladium (0.9 g), and copper iodide (0.5 g) was added triethylamine (10 mL), and then the reaction mixture was stirred at 80° C. for 64 h. To the reaction mixture were added water, and the reaction mixture was extracted with ethyl acetate. The organic layer was washed with water, and brine, dried over magnesium sulfate, and evaporated. The obtained residue was purified by column chromatography (hexane:ethyl acetate=4:1) to obtain the compoumd (5) 11 g.

$^1$H-NMR(CDCl$_3$) 8.01(d, 1H, J=7.8 Hz), 7.62(dd, 1H, J=7.4 Hz, 1.4 Hz), 7.27(t, 1H, J=7.7 Hz), 4.23(t, 1H, J=6.6 Hz), 3.50(s, 3H), 3.11(t, 2H, J=6.1 Hz), 2.64-2.69(m, 2H), 2.14-2.21(m, 2H), 1.77-1.84(m, 2H), 1.52-1.60(m, 2H), 0.99 (t, 3H, J=7.4 Hz),

4) Synthesis of 5-(3-methyloxyhexyl)tetralone (6)

To a THF (60 mL) solution of 5-(3-methyloxyhexyn-1-yl) tetralone (5) (11 g) was added 10% palladium-carbon (0.9 g), and the reaction mixture was stirred under a hydrogen gas atmosphere for 5 h. The reaction mixture filtered off, and the filtrate was evaporated. The obtained residue was purified by column chromatography (hexane:ethyl acetate=9:1) to obtain the compoumd (6) 9.0 g.

$^1$H-NMR(CDCl$_3$) 7.94(dd, 1H, J=7.8 Hz, 1.4 Hz), 7.36(dd, 1H, J=7.4 Hz, 1.4 Hz), 7.25(t, 1H, J=7.7 Hz), 3.37(s, 3H), 3.23-3.24(m, 1H), 2.91-2.96(m, 2H), 2.63-2.83(m, 4H), 2.05-2.17(m, 2H), 1.71-1.77(m, 2H), 1.26-1.59(m, 4H), 0.94(t, 3H, J=7.2 Hz).

5) Synthesis n of 4,5-dihydro-6-(3-methyloxyhexyl) naphtho[1,2-d]thiazol-2-ylamine (7)

To a 10% methanol-chloroform (60 mL) solution of 5-(3-methyloxyhexyl)tetralone (6) (9.0 g) was added bromine (5.5 g), and the reaction mixture was stirred for 1 h. After the solvent was evaoprated, the residue was dissolved in ethanol (60 mL), and to the residue was added thiourea (2.65 g). After the mixture was heated at reflux for 7 h, the reaction solvent was evported. To the residue was added a saturated sodium hydrogencarbonate aqueous solution, and the mixture was extracted with ethyl acetate. The organic layer was dried over magnesium sulfate, and evaporated. The obtained residue was purified by column chromatography (hexane:ethyl acetate=4:1) to obtain the compoumd (7) 4.6 g.

$^1$H-NMR(CDCl$_3$) 7.59(d, 1H, J=7.5 Hz), 7.17(t, 1H, J=7.7 Hz), 7.05(d, 1H, J=7.7 Hz), 4.93(bs, 2H), 3.36(s, 3H), 3.21(t, 1H, J=5.8 Hz), 2.99-3.05(m, 2H), 2.63-2.87(m, 4H), 1.68-1.76(m, 4H), 1.35-1.56(m, 4H), 0.93(t, 3H, J=7.2 Hz).

6) Synthesis of ethyl 3-{2,6-difluoro-4-[4,5-dihydro-6-(3-methyloxyhexyl)naphtho[1,2-d]thiazol-2-ylcarbamoyl]phenyl}-2-methylacrylate (8)

To a DMF (25 mL) solution of 4,5-dihydro-6-(3-methyloxyhexyl)naphtho[1,2-d]thiazol-2-ylamine (7) (4.5 g), 3-(4-bromo-2,6-difluorophenyl)-2-methylacrylic acid ethyl ester (3) (4.35 g), and dichlorobistriphenylphosphinepalladium (0.8 g) was added triethylamine (10 mL), and the reaction mixture was stirred under carbon monoxide atomosphere at 85° C. for 16 h. To the reaction mixture was added water, and the reaction mixture was extracted with ethyl acetate. The organic layer was washed with water, and brine, dried over magnesium sulfate, and evaporated. The obtained residue was purified by column chromatography (hexane:ethyl acetate=4:1) to obtain the compoumd (8) 7.1 g.

$^1$H-NMR(CDCl$_3$) 7.36-7.38(m, 3H), 7.25(bs, 1H), 7.00(d, 2H, J=2.3 Hz), 4.29(q, 2H, J=7.2 Hz), 3.38(s, 3H), 3.22(t, 1H, J=5.5 Hz), 3.01-3.05(m, 4H), 2.60-2.80(m, 2H), 1.80(s, 3H), 1.67-1.75(m, 2H), 1.24-1.60(m, 7H), 0.94(t, 3H, J=7.2 Hz).

7) Synthesis of 3-{2,6-difluoro-4-[4,5-dihydro-6-(3-methyloxyhexyl)naphtho[1,2-d]thiazol-2-ylcarbamoyl]phenyl}-2-methylacrylic acid (A1)

A mixture of THF (40 mL), methanol (40 mL), and 2N sodium hydroxide aqueous solution (40 mL) of 3-{2,6-difluoro-4-[4,5-dihydro-6-(3-methyloxyhexyl)naphtho[1,2-d]thiazol-2-ylcarbamoyl]phenyl}-2-methylacrylic acid ethyl ester (8) (7.0 g), was stirred at room temperature for 3 h. The reaction mixture was acidified with hydrochloric acid, and extracted with ethyl acetate. The organic layer was washed with water, and brine, dried over magnesium sulfate, and evaporated. The residue was recrystallized from ethyl acetate to obtain the compound (A1) 5.5 g.

$^1$H-NMR(DMSO-d$_6$) 12.93(bs, 2H), 7.95(d, 2H, J=8.3 Hz), 7.64(d, 1H, J=7.5 Hz), 7.33(s, 3H), 7.09(d, 1H, J=6.7 Hz), 3.27(s, 3H), 3.21(t, 1H, J=6.3 Hz), 2.99(s, 4H), 2.60-2.80(m, 2H), 1.80(d, 3H, J=1.6 Hz), 1.64-1.66(m, 2H), 1.45-1.47(m, 2H), 1.31-1.33(m, 2H), 0.89(t, 3H, J=7.0 Hz).

Example 2

Synthesis of Compound (A1307)

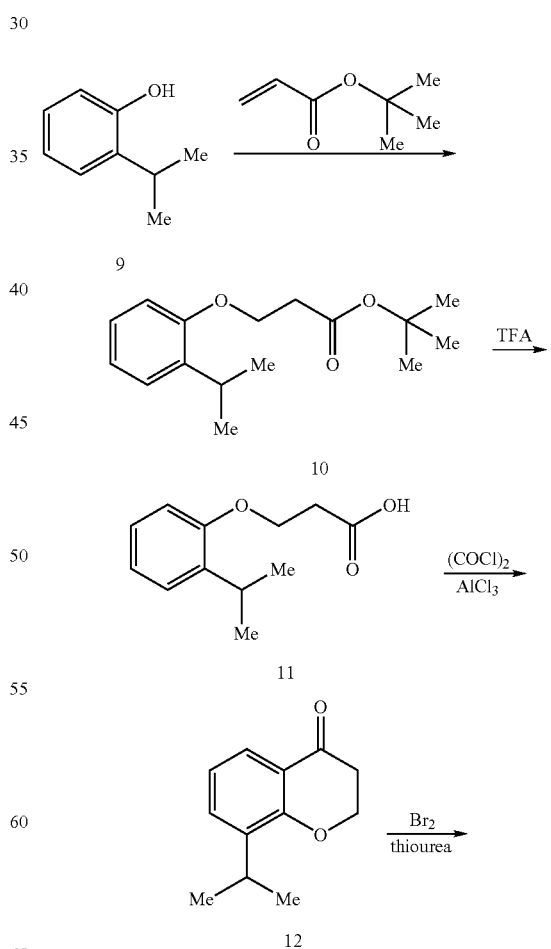

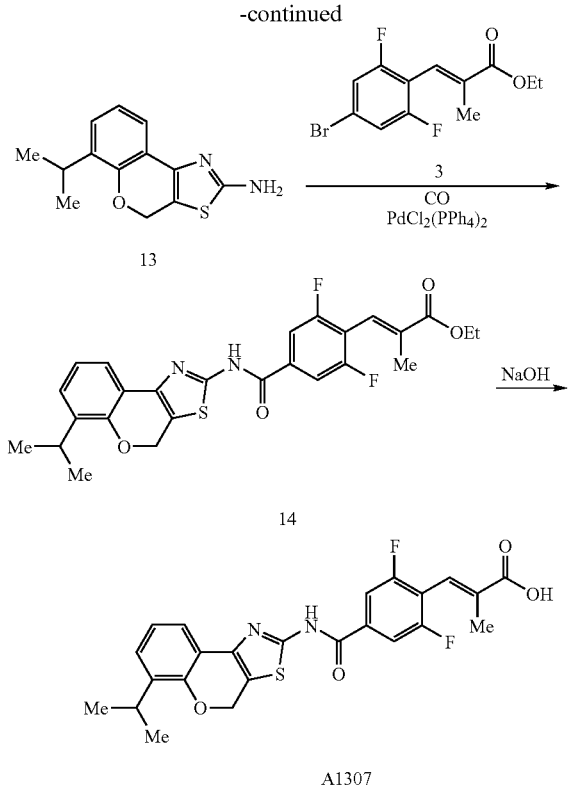

A1307

1) Synthesis of tert-butyl 3-(2-isopropylphenoxy)propionate (10)

2-Isopropylphenol (6 g) was dissolved in acrylic acid tert-butyl ester (6.2 g), and to the mixture was added potassium tert-butyloxide (0.3 g). The reaction mixture was stirred at 130° C. for 6 h. To the reaction mixture was added water, the reaction mixture extracted with ethyl acetate. The organic layer was washed with brine, dried over magnesium sulfate, and evaporated. The obtained residue was purified by column chromatography (hexane:ethyl acetate=9:1) to obtain the compound (10) 4.3 g.

$^1$H-NMR(CDCl3) 7.20(dd, 1H, J=7.5, 1.7 Hz), 7.14(dt, 1H, J=7.5, 1.7Hz), 6.92(dd, 1H, J=7.5, 1.7 Hz), 6.86(dt, 1H, J=7.5, 1.7 Hz), 4.21(t, 2H, J=6.3 Hz), 3.30(sext, 1H, J=7.0 Hz), 2.72(t, 2H, J=6.3 Hz), 1.45(s, 9H), 1.15(d, 6H, J=7.0 Hz).

2) Synthesis of 3-(2-isopropylphenoxy)propionic acid (11)

3-(2-Isopropylphenoxy)propionic acid tert-butyl ester (10) (4.3 g) was dissolved in dichloromethane (40 mL), and to the mixture was added trifluoroacetic acid (4 mL). The reaction mixture was stirred at room temperature for 3 h, and evaporated. The obtained residue was purified by column chromatography (hexane:ethyl acetate=4:1) to obtain the compound (11) 3.14 g.

$^1$H-NMR(CDCl3) 7.23(dd, 1H, J=7.5, 1.7 Hz), 7.17(dt, 1H, J=7.5, 1.7 Hz), 6.95(dd, 1H, J=7.5, 1.7 Hz), 6.89(dt, 1H, J=7.5, 1.7 Hz), 4.26(t, 2H, J=6.3 Hz), 3.30(sext, 1H, J=7.0 Hz), 2.78(t, 2H, J=6.3 Hz), 1.19(d, 6H, J=7.0 Hz).

3) Synthesis of 8-isopropylchroman-4-one (12)

3-(2-Isopropylphenoxy)propionic acid (11) was dissolved in dichloromethane (30 mL), and to the mixture were added oxalyl chloride (2.1 g) and DMF (5 mL) under ice-cooling. The reaction mixture was stirred for 30 minutes and cooled at −20° C. To the reaction mixture was added aluminium chloride (4 g), and the reaction mixture was stirred at −20° C. for 2 h. To the reaction mixture was added 2N hydrochloric acid, and the reaction mixture was extracted with dicloromethane. The organic layer was washed with brine, dried over magnesium sulfate, and evaporated. The obtained residue was purified by column chromatography (hexane:ethyl acetate=4:1) to obtain the compound (12) 2.3 g.

$^1$H-NMR(CDCl3) 7.73(d, 1H, J=7.5 Hz), 7.37(d, 1H, J=7.5 Hz), 6.93(t, 1H, J=7.5 Hz), 4.56(t, 2H, J=6.3 Hz), 3.25(sext, 1H, J=7.0 Hz), 2.78(t, 2H, J=6.3 Hz), 1.24(d, 6H, J=7.0 Hz).

4) Synthesis of 6-isopropyl-4H-chromeno[4,3-d]thiazol-2-ylamine (13)

8-Isopropylchroman-4-one (12) (2.3 g) was dissolved with 10% methanol-chloroform (20 mL), and to the mixture was added bromine (1.93 g). After the reaction mixture was stirred for 1 h, and evaporated. The residue was dissolved in ethanol (30 mL), and to the reaction mixture was added thiourea (0.92 g). The reaction mixture was heated at reflux, and evaporated. The residue was extracted with ethyl acetate, and a saturated sodium hydrogencarbonate aqueous solution, and the organic layer was dried over magnesium sulfate, and evaporated. The residue was purified by column chromatography (hexane:ethyl acetate=4:1) to obtain the compound (13) 0.7 g.

1H-NMR(CDCl3) 7.43(d, 1H, J=7.5 Hz), 7.10(d, 1H, J=7.5 Hz), 6.95(t, 1H, J=7.5 Hz), 5.29(s, 2H), 5.20(bs, 2H), 3.25(sext, 1H, J=7.0 Hz), 1.24(d, 6H, J=7.0 Hz)

5) (E)-3-[2,6-difluoro-4-(6-isopropyl-4H-chromeno[4,3-d]thiazol-2-ylcarbamoyl)phenyl]-2-methylacrylic acid ethyl ester(14)

6-Isopropyl-4H-chromeno[4,3-d]thiazol-2-ylamine (13) (360 mg), (Z)-3-(4-bromo-2,6-difluorophenyl)-2-methylacrylic acid ethyl ester (460 mg), and dichlorobistriphenylphosphinepalladium (150 mg) were dissolved in DMF (6 mL). To the mixture was poured triethylamine (0.84 mL), and the reaction mixture was stirred under carbon monoxide atmosphere at 85° C. for 16 h. The reaction mixture was added into water, and extracted with ethyl acetate. The organic layer was washed with water, and brine, and dried over magnesium sulfate, and evaporated. The residue was purified by column chromatography (hexane:ethyl acetate=4:1) to obtain the compound (14) 620 mg.

1H-NMR(CDCl3) 7.44(s, 1H), 7.42(s, 1H), 7.28-7.33(m, 1H), 7.10(d, 1H, J=7.6 Hz), 6.85(t, 1H, J=7.6 Hz), 5.49(s, 2H), 4.27(q, 2H, J=7.0 Hz), 3.25(sext, 1H, J=7.0 Hz), 1.79(s, 3H), 1.25(t, 3H, J=7.0 Hz), 1.20(d, 6H, J=7.0 Hz).

6) (E)-3-[2,6-difluoro-4-(6-isopropyl-4H-chromeno[4,3-d]thiazol-2-ylcarbamoyl)phenyl]-2-methylacrylic acid (A1309)

(E)-3-[2,6-difluoro-4-(6-isopropyl-4H-chromeno[4,3-d]thiazol-2-ylcarbamoyl)phenyl]-2-methylacrylic acid ethyl ester (620 mg) was dissolved in THF (2 mL), methanol (2 ml), and 2N sodium hydroxide aqueous solution (2 mL), and the reaction mixture was stirred at room temperature for 3 h. The reaction mixture was acidified with hydrochloric acid and extracted with ethyl acetate. The organic layer was washed with water, and brine, dried over magnesium sulfate, and evaporated. The residue was recrystallized from ethyl acetate to obtain the compound (A1309) 460 mg.

1H-NMR(DMSO-d6) 12.93(bs, 1H), 7.98(s, 1H), 7.97(s, 1H), 7.48(d, 1H, J=7.6 Hz), 7.33(s, 1H), 7.11(d, 1H, J=7.6 Hz), 7.01(t, 1H, J=7.6 Hz ), 5.49(s, 2H), 3.20-3.30(m, 1H), 1.79(s, 3H), 1.04(d, 6H, J=6.0 Hz).

A2-A12, A339, A341, A346, A347, A349, A351, A401, A423, A430, A440, A450, A500, A601, A928, A930, A936, A937, A939, A941, A944, A954, A993, A1003, A1016, A1018, A1033, A1123, A1295-A1308, and A1310-A1332 were synthesized by similar method described above.

Example 3

Synthesis of 3-[2,6-difluoro-4-(4,5-dihydro-6-pentyl-naphtho[1,2-d]thiazol-2-ylcabamoyl)phenyl]-2-methylacrylic acid (A2)

1H-NMR(DMSO-d6) 12.92(bs, 2H), 7.91-7.98(m, 2H), 7.62-7.65(m, 1H), 7.33(s, 1H), 7.18-7.23(m, 1H), 7.06-7.10(m, 1H), 2.97(s, 4H), 2.63(t, 2H, J=7.6 Hz), 1.80(s, 3H), 1.52(t, 2H, J=6.9 Hz), 1.32-1.35(m, 4H), 0.88(t, 3H, J=6.0 Hz).

Example 4

Synthesis of 3-{2,6-difluoro-4-[4,5-dihydro-6-(3,3-dimethylbutyl)naphtho[1,2-d]thiazol-2-ylcabamoyl)phenyl]-2-methylacrylic acid (A3)

1H-NMR(DMSO-d6) 12.96(bs, 2H), 7.92(d, 2H, J=8.1 Hz), 7.60(d, 1H, J=7.5 Hz), 7.30(s, 1H), 7.17(d, 1H, J=7.5 Hz), 7.03-7.06(m, 1H), 2.94(s, 4H), 2.53-2.59(m, 2H), 1.77 (s, 3H), 1.31-1.37(m, 2H), 0.91(s, 9H).

Example 5

Synthesis of 3-{2,6-difluoro-4-[4,5-dihydro-6-(3-methyloxy-4,4-dimethylpentyl)naphtho[1,2-d]thiazol-2-ylcabamoyl]phenyl}-2-methylacrylic acid (A4)

1H-NMR(DMSO-d6) 12.91(bs, 1H), 7.95(d, 2H, J=7.6 Hz), 7.63(d, 1H, J=7.6 Hz), 7.33(d, 1H, J=1.3 Hz), 7.21(t, 1H, J=7.6 Hz), 7.09(d, 1H, J=7.6 Hz), 3.33(s, 3H), 3.21-3.26(m, 1H), 2.95-2.99(m, 4H), 2.65-2.70(m, 2H), 1.80(d, 3H, J=1.3 Hz), 1.70-1.80(m, 2H), 0.88(s, 9H).

Example 6

Synthesis of 3-{4-[6-(3-n-butyloxypropyl)-4,5-dihydronaphto[1,2-d]thiazol-2-ylcabamoyl]-2,6-difluorophenyl}-2-methylacrylic acid (A5)

1H-NMR(DMSO-d6) 12.94(bs, 1H), 7.94(d, 2H, J=7.6 Hz), 7.64(d, 1H, J=7.6 Hz), 7.33(d, 1H, J=1.3 Hz), 7.21(t, 1H, J=7.6 Hz), 7.05(d, 1H, J=7.6 Hz), 3.33-3.40(m, 4H), 2.95-2.99(m, 4H), 2.65(t, 2H, J=7.6 Hz), 1.88(d, 3H, J=1.3 Hz), 1.70-1.80(m, 2H), 1.45-1.53(m, 2H), 1.31-1.40(m, 2H), 0.89(t, 3H, J=7.4 Hz).

Example 7

Synthesis of 3-(2,6-difluoro-4-{4,5-dihydro-6-[3-(2,2-dimethylpropyloxy)propyl]naphtho[1,2-d]thiazol-2-ylcabamoyl}phenyl)-2-methylacrylic acid (A6)

1H-NMR(DMSO-d6) 12.93(bs, 1H), 7.95(d, 2H, J=7.6 Hz), 7.65(d, 1H, J=7.6 Hz), 7.33 (d, 1H, J=1.3 Hz), 7.21(t, 1H, J=7.6 Hz), 7.09(d, 1H, J=7.6 Hz), 3.40(t, 2H. J=6.4 Hz), 3.05(s, 2H), 2.95-2.99(m, 4H), 2.71(t, 2H, J=7.4 Hz), 1.84(d, 3H, J=1.3 Hz), 1.70-1.80(m, 2H), 0.91(s, 9H).

Example 8

Synthesis of 3-{2,6-difluoro-4-[4,5-dihydro-6-(3-isopropyloxypropyl)naphtho[1,2-d]thiazol-2-ylcabamoyl]phenyl}-2-methylacrylic acid (A7)

1H-NMR(DMSO-d6) 12.94(bs, 1H), 7.95(d, 2H, J=7.3 Hz), 7.65(d, 1H, J=7.3 Hz), 7.33(d, 1H, J=1.3 Hz), 7.21(t, 1H, J=7.3 Hz), 7.09(d, 1H, J=7.3 Hz), 3.53(hept, 1H, J=6.1 Hz), 3.40(t, 2H, J=6.4 Hz), 2.95-2.99(m, 4H), 2.69(t, 2H, J=7.0 Hz), 1.84(d, 3H, J=1.3 Hz), 1.75-1.80(m, 2H), 1.11(d, 6H, J=6.1 Hz).

Example 9

Synthesis of 3-{2,6-difluoro-4,5-dihydro-4-[6-(3-ethyloxypropyl)naphtho[1,2-d]thiazol-2-ylcabamoyl]phenyl}-2-methylacrylic acid (A8)

1H-NMR(DMSO-d6) 12.92(bs, 1H), 7.95(d, 2H, J=7.6 Hz), 7.64(d, 1H, J=7.6 Hz), 7.34(d, 1H, J=1.3 Hz), 7.21(t, 1H, J=7.6 Hz), 7.09(d, 1H, J=7.6 Hz), 3.33-3.40(m, 4H), 2.95-2.99(m, 4H), 2.71(t, 2H, J=7.0 Hz), 1.80(d, 3H, J=1.3 Hz), 1.70-1.80(m, 2H), 1.12(t, 3H, J=7.4 Hz).

Example 10

Synthesis of 3-{2,6-difluoro-4-[4,5-dihydro-6-(3-n-propyloxypropyl)naphtho[1,2-d]thiazol-2-ylcabamoyl]phenyl}-2-methylacrylic acid (A9)

1H-NMR(DMSO-d6) 12.91(bs, 1H), 7.95(d, 2H, J=7.6 Hz), 7.65(d, 1H, J=7.6 Hz), 7.33 (d, 1H, J=1.3 Hz), 7.21(t, 1H, J=7.6 Hz), 7.09(d, 1H, J=7.6 Hz), 3.33-3.40(m, 4H), 2.95-2.99(m, 4H), 2.70(t, 2H, J=7.0 Hz), 1.80(d, 3H, J=1.3 Hz), 1.70-180(m, 2H), 1.45-1.53(m, 2H), 0.89(t, 3H, J=7.4 Hz).

Example 11

Synthesis of 3-{2,6-dichloro-4-[4,5-dihydro-6-(3-ethyloxypropyl)naphtho[1,2-d]thiazol-2-ylcabamoyl]phenyl}-2-methylacrylic acid (A10)

1H-NMR(DMSO-d6) 12.92(bs, 1H), 8.28(s, 2H), 7.64(d, 1H, J=7.6 Hz), 7.4(d, 1H, J=1.3 Hz), 7.21(t, 1H, J=7.6 Hz), 7.09(d, 1H, J=7.6 Hz), 3.33-3.40(m, 4H), 2.95-2.99(m, 4H), 2.71(t, 2H, J=7.0 Hz), 1.75-1.80(m, 2H), 1.70(d, 3H, J=1.3 Hz), 1.12(t, 3H, J=7.0 Hz).

Example 12

Synthesis of 3-{4-[6-(3-n-butyloxypropyl)-4,5-dihydronaphtho[1,2-d]thiazol-2-ylcabamoyl]-2,6-dichlorophenyl}-2-methylacrylic acid (A11)

1H-NMR(DMSO-d6) 12.91(bs, 1H), 8.27(s, 2H), 7.64(d, 1H, J=7.6 Hz), 7.40(d, 1H, J=1.3 Hz), 7.21(t, 1H, J=7.6 Hz), 7.09(d, 1H, J=7.6 Hz), 3.33-3.40(m, 4H), 2.95-2.99(m, 4H), 2.70(t, 2H, J=7.0 Hz), 1.75-1.80(m, 2H), 1.70(d, 3H, J=1.3 Hz), 1.52-1.58(m, 2H), 1.31-1.40(m, 2H), 0.89(t, 3H, J=7.0 Hz).

Example 13

Synthesis of 3-{2,6-difluoro-4-[4,5-dihydro-6-(3-methyloxyhexyl)naphtho[1,2-d]thiazol-2-ylcabamoyl]phenyl}-2-methylacrylic acid (A12)

1H-NMR(DMSO-d6) 12.97(bs, 1H), 8.27(s, 2H), 7.64(d, 1H, J=7.6 Hz), 7.40(d, 1H, J=1.3 Hz), 7.24(t, 1H, J=7.6 Hz), 7.09(d, 1H, J=7.6 Hz), 3.33(s, 3H), 3.21-3.26(m, 1H), 2.95-2.99(m, 4H), 2.65-2.70(m, 2H), 1.70(d, 3H, J=1.3 Hz), 1.65-1.70(m, 2H), 1.52-1.58(m, 2H), 1.31-1.40(m, 2H), 0.89(t, 3H, J=7.0 Hz).

Example 14

Synthesis of (E)-3-{2,6-difluoro-4-[6-(3-methyloxypentyl)-4,5-dihydronaphtho[1,2-d]thiazol-2-ylcabamoyl]phenyl}-2-methylacrylic acid (A339)

1H-NMR(DMSO-d6) 12.91(bs, 1H), 7.96(s, 1H), 7.93(s, 1H), 7.65(d, 1H, J=7.6 Hz), 7.33(s, 1H), 7.21(t, 1H, J=7.6 Hz), 7.09(d, 1H, J=7.6 Hz), 3.27(s, 3H), 3.10-3.16(m, 1H), 2.95-2.99(m, 4H), 2.65-2.80(m, 2H), 1.80(s, 3H), 1.60-1.70(m, 2H), 1.45-1.60(m, 2H), 0.86(t, 3H, J=7.6 Hz).

Example 15

Synthesis of (E)-3-{2,6-difluoro-4-[6-(3-methyloxyheptyl)-4,5-dihydronaphtho[1,2-d]thiazol-2-ylcabamoyl]phenyl}-2-methylacrylic acid (A341)

1H-NMR(DMSO-d6) 12.91(bs, 1H), 7.96(s, 1H), 7.93(s, 1H), 7.65(d, 1H, J=7.6 Hz), 7.33(s, 1H), 7.21(t, 1H, J=7.6 Hz), 7.09(d, 1H, J=7.6 Hz), 3.25(s, 3H), 3.14-3.22(m, 1H), 2.95-2.99(m, 4H), 2.50-2.65(m, 2H), 1.79(s, 3H), 1.60-1.69(m, 2H), 1.45-1.55(m, 2H), 1.22-1.34(m, 4H), 0.90-094(m, 3H).

Example 16

Synthesis of (E)-3-{4-[6-(3-ethyloxypentyl)-4,5-dihydronaphtho[1,2-d]thiazol-2-ylcabamoyl]-2,6-difluorophenyl}-2-methylacrylic acid (A346)

1H-NMR(DMSO-d6) 12.91(bs, 1H), 7.96(s, 1H), 7.94(s, 1H), 7.64(d, 1H, J=7.6 Hz), 7.33(s, 1H), 7.18(t, 1H, J=7.6 Hz), 7.09(d, 1H, J=7.6 Hz), 3.45(q, 2H, J=7.0 Hz), 3.20-3.26(m, 1H), 2.95-2.99(m, 4H), 2.60-2.80(m, 2H), 1.79(s, 3H), 1.60-1.69(m, 2H), 1.45-1.55(m, 2H), 1.13(t, 3H, J=7.0 Hz), 0.86(t, 3H, J=7.6 Hz).

Example 17

Synthesis of (E)-3-{4-[6-(3-ethyloxyhexyl)-4,5-dihydronaphtho[1,2-d]thiazol-2-ylcabamoyl]-2,6-difluorophenyl}-2-methylacrylic acid (A347)

1H-NMR(DMSO-d6) 12.91(bs, 1H), 7.96(s, 1H), 7.94(s, 1H), 7.64(d, 1H, J=7.6 Hz), 7.33(s, 1H), 7.20(t, 1H, J=7.6 Hz), 7.09(d, 1H, J=7.6 Hz), 3.45(q, 2H, J=7.0 Hz), 3.20-3.26(m, 1H), 2.95-2.99(m, 4H), 2.60-2.80(m, 2H), 1.79(s, 3H), 1.60-1.69(m, 2H), 1.45-1.55(m, 2H), 1.30-1.40(m, 2H), 1.13(t, 3H, J=7.0 Hz), 0.86(t, 3H, J=7.6 Hz).

Example 18

Synthesis of (E)-3-{4-[6-(3-ethyloxyheptyl)-4,5-dihydronaphtho[1,2-d]thiazol-2-ylcabamoyl]-2,6-difluorophenyl}-2-methylacrylic acid (A349)

1H-NMR(DMSO-d6) 12.91(bs, 1H), 7.96(s, 1H), 7.94(s, 1H), 7.64(d, 1H, J=7.6 Hz), 7.33(s, 1H), 7.20(t, 1H, J=7.6 Hz), 7.09(d, 1H, J=7.6 Hz), 3.48(q, 2H, J=7.0 Hz), 3.20-3.26(m, 1H), 2.95-2.99(m, 4H,), 2.60-2.80(m, 2H), 1.79(s, 3H), 1.60-1.69(m, 2H), 1.45-1.55(m, 2H), 1.30-1.40(m, 4H), 1.13(t, 3H, J=7.0 Hz), 0.86-0.89(m, 3H).

Example 19

Synthesis of (E)-3-{4-[6-(3-ethyloxy-4,4-dimethylpentyl)-4,5-dihydronaphtho[1,2-d]thiazol-2-ylcabamoyl]-2,6-difluorophenyl}-2-methylacrylic acid (A351)

1H-NMR(DMSO-d6) 12.95(bs, 1H), 7.96(s, 1H), 7.93(s, 1H), 7.65(d, 1H, J=7.6 Hz), 7.33 (s, 1H), 7.23(t, 1H, J=7.6 Hz), 7.09(d, 1H, J=7.6 Hz), 3.50-3.65(m, 2H), 2.95-2.99(m, 4H), 2.80-2.90(m, 2H), 2.59-2.65(m, 1H), 1.80(s, 3H), 1.60-1.70(m, 1H), 1.45-1.5 (m, 1H), 1.17(t, 3H, J=7.0 Hz), 0.90(s, 9H).

Example 20

Synthesis of (E)-3-{2,6-difluoro-4-[6-(3-pentyloxypropyl)-4,5-dihydronaphtho[1,2-d]thiazol-2-ylcabamoyl]phenyl}-2-methylacrylic acid (A401)

1H-NMR(DMSO-d6) 12.91(bs, 1H), 7.96(s, 1H), 7.93(s, 1H), 7.65(d, 1H, J=7.6 Hz), 7.33(s, 1H), 7.21(t, 1H, J=7.6 Hz), 7.09(d, 1H, J=7.6 Hz), 3.36(t, 2H, J=6.4 Hz), 3.28(t, 2H, J=7.0 Hz), 2.95-2.99(m, 4H), 2.74(t, 2H, J=7.0 Hz), 1.78(s, 3H), 1.69-1.75(m, 2H), 1.48-1.55(m, 2H), 1.22-1.34(m, 4H), 0.90-0.94(m, 3H).

Example 21

Synthesis of (Z)-3-{2,6-difluoro-4-[6-(3-methyloxyhexyl)-4,5-dihydronaphtho[1,2-d]thiazol-2-ylcabamoyl]phenyl}-2-methyloxyacrylic acid (A423)

1H-NMR(DMSO-d6) 12.92(bs, 1H), 7.91(s, 1H), 7.89(s, 1H), 7.65(d, 1H, J=7.6 Hz), 7.20(t, 1H, J=7.6 Hz), 7.09(d, 1H, J=7.6 Hz), 6.65(s, 1H), 3.7 (s, 3H), 3.22(s, 3H), 3.14-3.22(m, 1H), 2.95-2.99(m, 4H), 2.55-2.70(m, 2H), 1.60-1.69(m, 2H), 1.45-1.55(m, 2H), 1.22-1.34(m, 2H), 0.90-094(m, 3H).

Example 22

Synthesis of (Z)-3-{4-[6-(3-ethyloxypropyl)-4,5-dihydronaphtho[1,2-d]thiazol-2-ylcabamoyl]-2,6-difluorophenyl}-2-methyloxyacrylic acid (A430)

1H-NMR(DMSO-d6) 12.92(bs, 1H), 7.91(s, 1H), 7.89(s, 1H), 7.64(d, 1H, J=7.6 Hz), 7.21(t, 1H, J=7.6 Hz), 7.06(d, 1H, J=7.6 Hz), 6.61(s, 1H), 3.71(s, 3H), 3.33-3.40(m, 4H), 2.95-2.99(m, 4H), 2.71(t, 2H, J=7.0 Hz), 1.70-1.80(m, 2H), 1.13(t, 3H, J=7.0 Hz).

Example 23

Synthesis of (Z)-3-{2,6-difluoro-4-[6-(3-propyloxypropyl)-4,5-dihydronaphtho[1,2-d]thiazol-2-ylcabamoyl]phenyl}-2-methyloxyacrylic acid (A440)

1H-NMR(DMSO-d6) 12.92(bs, 1H), 7.92(s, 1H), 7.89(s, 1H), 7.64(d, 1H, J=7.6 Hz), 7.21(t, 1H, J=7.6 Hz), 7.06(d, 1H, J=7.6 Hz), 6.62(s, 1H), 3.71(s, 3H), 3.33-3.40(m, 4H), 2.95-2.99(m, 4H), 2.71(t, 2H, J=7.0 Hz), 1.70-1.80(m, 2H), 1.45-1.55(m, 2H), 0.89 (t, 3H, J=7.0 Hz).

Example 24

Synthesis of (Z)-3-{2,6-difluoro-4-[6-(3-isopropyloxypropyl)-4,5-dihydronaphtho[1,2-d]thiazol-2-ylcabamoyl]phenyl}-2-methyloxyacrylic acid (A450)

1H-NMR(DMSO-d6) 12.92(bs, 1H), 7.91(s, 1H), 7.89(s, 1H), 7.64(d, 1H, J=7.6 Hz), 7.20(t, 1H, J=7.6 Hz), 7.04(d, 1H, J=7.6 Hz), 6.66(s, 1H), 3.71(s, 3H), 3.50-3.60(m, 1H), 3.38(t, 2H, J=7.0 Hz), 2.95-2.99(m, 4H), 2.69(t, 2H, J=7.0 Hz), 1.70-1.80(m, 2H), 1.11(d, 6H, J=6.0 Hz).

Example 25

Synthesis of (Z)-3-(4-{6-[3-(2,2-dimethylpropyloxy)propyl]-4,5-dihydronaphtho[1,2-d]thiazol-2-ylcabamoyl]-2,6-difluorophenyl}-2-methyloxyacrylic acid (A500)

1H-NMR(DMSO-d6) 12.92(bs, 1H), 7.90(s, 1H), 7.88(s, 1H), 7.64(d, 1H, J=7.6 Hz), 7.20(t, 1H, J=7.6 Hz), 7.04(d, 1H, J=7.6 Hz), 6.65(s, 1H), 3.71(s, 3H), 3.40(t, 2H, J=7.0 Hz), 3.07(s, 2H), 2.95-2.99(m, 4H), 2.69(t, 2H, J=7.0 Hz), 1.70-1.80(m, 2H), 0.90(s, 9H).

Example 26

Synthesis of (E)-3-{2,6-dichloro-4-[6-(3,3-dimethylbutyl)-4,5-dihydronaphtho[1,2-d]thiazol-2-ylcabamoyl]phenyl}-2-methylacrylic acid (A601)

1H-NMR(DMSO-d6) 12.99(bs, 2H), 8.28(s, 2H), 7.61-7.64(m, 1H), 7.40(d, 1H, J=1.3 Hz), 7.18-7.23(m, 1H), 7.07-7.10(m, 1H), 2.98(s, 4H), 2.49-2.64(m, 2H), 1.69(s, 3H), 1.35-1.41(m, 2H), 0.98(s, 9H).

Example 27

Synthesis of (E)-3-{2,6-dichloro-4-[6-(3-methyloxypentyl)-4,5-dihydronaphtho[1,2-d]thiazol-2-ylcabamoyl]phenyl}-2-methylacrylic acid (A928)

1H-NMR(DMSO-d6) 12.95(bs, 1H), 8.28(s, 2H), 7.64(d, 1H, J=7.6 Hz), 7.40(s, 1H), 7.21(t, 1H, J=7.6 Hz), 7.09(d, 1H, J=7.6 Hz), 3.27(s, 3H), 3.10-3.16(m, 1H), 2.95-2.99(m, 4H), 2.65-2.80(m, 2H), 1.68(s, 3H), 1.60-1.69(m, 2H), 1.45-1.55(m, 2H), 0.86(t, 3H, J=7.6 Hz).

Example 28

Synthesis of (E)-3-{2,6-dichloro-4-[6-(3-methyloxyheptyl)-4,5-dihydronaphtho[1,2-d]thiazol-2-ylcabamoyl]phenyl}-2-methylacrylic acid (A930)

1H-NMR(DMSO-d6) 12.95(bs, 1H), 8.28(s, 2H), 7.64(d, 1H, J=7.6 Hz), 7.40(s, 1H), 7.21(t, 1H, J=7.6 Hz), 7.09(d, 1H, J=7.6Hz), 3.27(s, 3H), 3.14-3.22(m, 1H), 2.95-2.99(m, 4H), 2.55-2.65(m, 2H), 1.68(s, 3H), 1.66-1.69(m, 2H), 1.45-1.55(m, 2H), 1.22-1.34(m, 4H), 0.90-094(m, 3H).

Example 29

Synthesis of (E)-3-{2,6-dichloro-4-[6-(3-methyloxy-4,4-dimethylpentyl)-4,5-dihydronaphtho[1,2-d]thiazol-2-ylcabamoyl]phenyl}-2-methylacrylic acid (A932)

1H-NMR(DMSO-d6) 12.95(bs, 1H), 8.28(s, 2H), 7.64(d, 1H, J=7.6 Hz), 7.40(d, 1H), J=1.3 Hz), 7.21(t, 1H, J=7.6 Hz), 7.09(d, 1H, J=7.6 Hz), 3.44(s, 3H), 2.95-2.99(m, 4H), 2.65-2.70(m, 2H), 1.68(s, 3H), 1.45-1.55(m, 2H), 0.90(s, 9H).

Example 30

Synthesis of (E)-3-{2,6-dichloro-4-[6-(3-ethyloxypentyl)-4,5-dihydronaphtho[1,2-d]thiazol-2-ylcabamoyl]phenyl}-2-methylacrylic acid (A936)

1H-NMR(DMSO-d6) 12.95(bs, 1H), 8.28(s, 2H), 7.64(d, 1H, J=7.6 Hz), 7.40(s, 1H), 7.21(t, 1H, J=7.6 Hz), 7.09(d, 1H, J=7.6 Hz), 3.45(q, 2H, J=7.0 Hz), 3.20-3.26(m, 1H), 2.95-2.99(m, 4H), 2.65-2.80(m, 2H), 1.68(s, 3H), 1.60-1.69(m, 2H), 1.45-1.55(m, 2H), 1.13 (t, 3H, J=7.0 Hz), 0.86(t, 3H, J=7.6 Hz).

Example 31

Synthesis of (E)-3-{2,6-dichloro-4-[6-(3-ethyloxyhexyl)-4,5-dihydronaphtho[1,2-d]thiazol-2-ylcabamoyl]phenyl}-2-methylacrylic acid (A937)

1H-NMR(DMSO-d6) 12.95(bs, 1H), 8.28(s, 2H), 7.63(d, 1H, J=7.6 Hz), 7.40(s, 1H), 7.21(t, 1H, J=7.6 Hz), 7.07(d, 1H, J=7.6 Hz), 3.47(q, 2H, J=7.0 Hz), 3.20-3.26(m, 1H), 2.95-2.99(m, 4H), 2.65-2.80(m, 2H), 1.68(s, 3H), 1.60-1.69(m, 2H), 1.45-1.55(m, 2H), 1.30-1.40(m, 2H), 1.13(t, 3H, J=7.0 Hz), 0.86(t, 3H, J=7.6 Hz),

Example 32

Synthesis of (E)-3-{2,6-dichloro-4-[6-(3-ethyloxy-heptyl)-4,5-dihydronaphtho[1,2-d]thiazol-2-yl-cabamoyl]phenyl}-2-methylacrylic acid (A939)

1H-NMR(DMSO-d6) 12.95(bs, 1H), 8.23(s, 2H), 7.63(d, 1H, J=7.6 Hz), 7.40(s, 1H), 7.21(t, 1H, J=7.6 Hz), 7.10(d, 1H, J=7.6 Hz), 3.47(q, 2H, J=7.0 Hz), 3.20-3.26(m, 1H), 2.95-2.99(m, 4H), 2.65-2.80(m, 2H), 1.68(s, 3H), 1.60-1.69(m, 2H), 1.45-1.55(m, 2H), 1.30-1.40(m, 4H), 1.13(t, 3H, J=7.0 Hz), 0.86-0.89(m, 3H).

Example 33

Synthesis of (E)-3-{2,6-dichloro-4-[6-(3-ethyloxy-4,4-dimethylpentyl)-4,5-dihydronaphtho[1,2-d]thiazol-2-ylcabamoyl]phenyl}-2-methylacrylic acid (A941)

1H-NMR(DMSO-d6) 12.95(bs, 1H), 8.28(s, 2H), 7.64(d, 1H, J=7.6 Hz), 7.40(s, 1H), 7.21(t, 1H, J=7.6 Hz), 7.12(d, 1H, J=7.6 Hz), 3.50-3.65(m, 2H), 2.95-2.99(m, 4H), 2.80-2.90(m, 2H), 2.59-2.65(m, 1H), 1.68(s, 3H), 1.60-1.70(m, 1H), 1.45-1.50(m, 1H), 1.17(t, 3H, J=7.0 Hz), 0.90(s, 9H).

Example 34

Synthesis of (E)-3-{2,6-dichloro-4-[6-(3-propyloxypropyl)-4,5-dihydronaphtho[1,2-d]thiazol-2-yl-cabamoyl]phenyl}-2-methylacrylic acid (A944)

1H-NMR(DMSO-d6) 12.92(bs, 1H), 8.28(s, 2H), 7.64(d, 1H, J=7.6 Hz), 7.40(d, 1H, J=1.3 Hz), 7.2(t, 1H, J=7.6 Hz), 7.09(d, 1H, J=7.6 Hz), 3.33-3.40(m, 4H), 2.95-2.99(m, 4H), 2.70(t, 2H, J=7.0 Hz), 1.70-1.80(m, 2H), 1.66(s, 3H), 1.45-1.53(m, 2H), 0.88(t, 3H, J=7.4 Hz).

Example 35

Synthesis of (E)-3-{2,6-dichloro-4-[6-(3-isopropyloxypropyl)-4,5-dihydronaphtho[1,2-d]thiazol-2-ylcabamoyl]phenyl}-2-methylacrylic acid (A954)

1H-NMR(DMSO-d6) 12.9(bs, 1H), 8.28(s, 2H), 7.64(d, 1H, J=7.6 Hz), 7.40(d, 1H, J=1.3 Hz), 7.21(t, 1H, J=7.6 Hz), 7.09(d, 1H, J=7.6 Hz), 3.50-3.58(m, 1H), 3.38(t, 2H, J=7.0), 2.95-2.99(m, 4H), 2.70(t, 2H, J=7.0 Hz), 1.70-1.80(m, 2H). 1.66(s, 3H), 1.10(d, 6H, J=6.0 Hz).

Example 36

Synthesis of (E)-3-{2,6-dichloro-4-[6-(3-pentyloxypropyl)-4,5-dihydronaphtho[1,2-d]thiazol-2-ylcabamoyl]phenyl}-2-methylacrylic acid (A993)

1H-NMR(DMSO-d6) 12.95(bs, 1H), 8.24(s, 2H), 7.64(d, 1H, J=7.6 Hz), 7.40(s, 1H), 7.21 (t, 1H, J=7.6 Hz), 7.09(d, 1H, J=7.6 Hz), 3.36(t, 2H, J=6.4 Hz), 3.28(t, 2H, J=7.0 Hz), 2.95-2.99(m, 4H), 2.70(t, 2H, J=7.0 Hz), 1.69-1.75(m, 2H), 1.68(s, 3H), 1.48-1.55(m, 2H), 1.22-1.34(m, 4H), 0.90-0.94(m, 3H).

Example 37

Synthesis of (E)-3-(2,6-dichloro-4-{6-[3-(2,2-dimethylpropyloxy)propyl]-4,5-dihydronaphtho[1,2-d]thiazol-2-ylcabamoyl}phenyl)-2-methylacrylic acid (A1003)

1H-NMR(DMSO-d6) 12.95(bs, 1H), 8.27(s, 2H), 7.64(d, 1H, J=7.6 Hz), 7.40(d, 1H, J=1.3 Hz), 7.21(t, 1H, J=7.6 Hz), 7.09(d, 1H, J=7.6 Hz), 3.38(t, 2H, J=7.0 Hz), 3.07(s, 2H), 2.95-2.99(m, 4H), 2.70(t, 2H, J=7.0 Hz), 1.70-1.80(m, 2H), 1.68(s, 3H), 0.90(s, 9H).

Example 38

Synthesis of (Z)-3-{2,6-dichloro-4-[6-(3-methyloxyhexyl)-4,5-dihydronaphtho[1,2-d]thiazol-2-ylcabamoyl]phenyl}-2-methyloxyacrylic acid (A1016)

1H-NMR(DMSO-d6) 12.92(bs, 1H), 8.23(s, 2H), 7.64(d, 1H, J=7.6 Hz), 7.21(t, 1H, J=7.6 Hz), 7.09(d, 1H, J=7.6 Hz), 6.76(s, 1H), 3.60(s, 3H), 3.27(s, 3H), 3.14-3.22(m, 1H), 2.95-2.99(m, 4H), 2.55-2.75(m, 2H), 1.60-1.69(m, 2H), 1.45-1.55(m, 2H), 1.22-1.34(m, 2H), 0.90-094(m, 3H).

Example 39

Synthesis of (Z)-3-{2,6-dichloro-4-[6-(3-methyloxyheptyl)-4,5-dihydronaphtho[1,2-d]thiazol-2-ylcabamoyl]phenyl}-2-methyloxyacrylic acid (A1018)

1H-NMR(DMSO-d6) 12.95(bs, 1H), 8.27(s, 2H), 7.64(d, 1H, J=7.6 Hz ), 7.21(t, 1H, J=7.6 Hz), 7.09(d, 1H, J=7.6 Hz ), 6.73(s, 1H), 3.61(s, 3H), 3.27(s, 3H), 3.14-3.22(m, 1H), 2.95-2.99(m, 4H), 2.55-2.65(m, 2H), 1.62-1.69(m, 2H), 1.45-1.55(m, 2H), 1.22-1.34(m, 2H), 0.90-094(m, 3H).

Example 40

Synthesis of (Z)-3-{2,6-dichloro-4-[6-(3-propyloxypropyl)-4,5-dihydronaphtho[1,2-d]thiazol-2-ylcabamoyl]phenyl}-2-methyloxyacrylic acid (A1033)

1H-NMR(DMSO-d6) 12.95(bs, 1H), 8.23(s, 2H), 7.62(d, 1H, J=7.6 Hz), 7.21(t, 1H, J=7.6 Hz), 7.09(d, 1H, J=7.6 Hz), 6.73(s, 1H), 3.61(s, 3H), 3.33-3.40(m, 4H), 2.95-2.99(m, 4H), 2.70(t, 2H, J=7.0 Hz), 1.70-1.80(m, 2H), 1.45-1.53 (m, 2H), 0.89(t, 3H, J=7.0 Hz).

Example 41

Synthesis of (E)-3-{2,6-dichloro-4-[6-(3-propyloxypropyl)-4H-chromeno[4,3-d]thiazol-2-ylcabamoyl]phenyl}-2-methylacrylic acid (A1123)

1H-NMR(DMSO-d6) 12.9 (bs, 1H), 8.28(s, 2H), 7.49(d, 1H, J=7.6 Hz), 7.38(s, 1H), 7.09(d, 1H, J=7.6 Hz), 6.97(t, 1H, J=7.6 Hz), 5.49(s, 2H), 3.33-3.40(m, 4H), 2.63(t, 2H, J=7.0 Hz), 1.70-1.80(m, 2H), 1.68(s, 3H), 1.45-1.53(m, 2H), 0.89(t, 3H), J=7.4 Hz).

Example 42

Synthesis of (E)-3-{2,6-difluoro-4-[6-(3-methyloxy-3-methylbutyl)-4,5-dihydronaphto[1,2-d]thiazol-2-ylcabamoyl]phenyl}-2-methylacrylic acid (A1295)

1H-NMR(DMSO-d6) 13.02(bs, 1H), 7.96(s, 1H), 7.93(s, 1H), 7.65(d, 1H, J=7.5 Hz), 7.33(s, 1H), 7.21(t, 2H, J=7.5 Hz), 7.11(d, 1H, J=7.5 Hz), 3.18(s, 3H), 2.60-2.65(m, 2H), 1.79(s, 3H), 1.60-1.69(m, 2H), 1.18(s, 6H).

Example 43

Synthesis of (E)-3-(4-{6-[3-(2-ethyloxy-1-ethyloxymethylethyloxy)propyl]-4,5-dihydronaphtho[1,2-d]thiazol-2-ylcabamoyl]-2,6-difluorophenyl}-2-methylacrylic acid (A1296)

1H-NMR(DMSO-d6) 13.02(bs, 1H), 7.97(s, 1H), 7.94(s, 1H), 7.65(d, 1H, J=7.5 Hz), 7.33(s, 1H), 7.21(t, 2H, J=7.5 Hz), 7.10(d, 1H, J=7.5 Hz), 3.56-3.60(m, 4H), 3.40-3.50(m, 7H), 2.95-2.99 (m, 4H), 2.69(t, 2H, J=7.3 Hz), 1.79(s, 3H), 1.67-1.73(m, 2H), 1.10(t, 6H, J=7.3 Hz).

Example 44

Synthesis of (E)-3-(2,6-difluoro-4-{6-[3-(2-isopropyloxyethyloxy)propyl]-4,5-dihydronaphtho[1,2-d]thiazol-2-ylcabamoyl}phenyl)-2-methylacrylic acid (A1297)

1H-NMR(DMSO-d6) 13.02(bs, 1H), 7.97(s, 1H), 7.94(s, 1H), 7.65(d, 1H, J=7.5 Hz), 7.33(s, 1H), 7.21(t, 2H, J=7.5 Hz), 7.11(d, 1H, J=7.5 Hz), 3.56-3.60(m, 4H), 2.95-2.99 (m, 4H), 2.70 (t, 2H, J=7.4 Hz), 1.78 (s, 3H), 1.65-1.70 (m, 2H), 1.10 (d, 6H, J=6.0 Hz),

Example 45

Synthesis of (E)-3-(2,6-difluoro-4-{6-[3-(2-ethyloxy-1-ethyloxymethylethyloxy)propyl]-4,5-dihydronaphtho[1,2-d]thiazol-2-ylcabamoyl}phenyl)-2-methylacrylic acid (A1298)

1H-NMR(DMSO-d6) 12.97(bs, 1H), 8.27(s, 2H), 7.66(d, 1H, J=7.6 Hz), 7.39(s, 1H), 7.20(t, 1H, J=7.6 Hz), 7.09(d, 1H, J=7.6 Hz), 3.56-3.60(m, 4H), 3.40-3.50(m, 7H), 2.95-2.99 (m, 4H), 2.69(t, 2H, J=7.2 Hz), 1.65-1.78(m, 2H), 1.69(s, 3H), 1.02(t, 6H, J=7.2 Hz).

Example 46

Synthesis of (E)-3-(2,6-dichloro-4-{6-[3-(2-methyloxyethyloxy)propyl]-4,5-dihydronaphtho[1,2-d]thiazol-2-ylcabamoyl}phenyl)-2-methylacrylic acid (A1299)

1H-NMR(DMSO-d6) 12.92(bs, 1H,), 8.28(s, 2H,), 7.64(d, 1H, J=7.6 Hz), 7.40(d, 1H, J=1.3 Hz), 7.21(t, 1H, J=7.6 Hz), 7.09(d, 1H, J=7.6 Hz), 3.40-3.50(m, 6H), 3.18(s, 3H), 2.95-2.99(m, 4H), 2.68(t, 2H, J=7.4 Hz), 1.68-1.78(m, 2H), 1.68(s, 3H).

Example 47

Synthesis of (E)-3-(2,6-difluoro-4-{6-[3-(2-methyloxyethyloxy)propyl]-4,5dihydronaphtho[1,2-d]thiazol-2-ylcabamoyl}phenyl)-2-methylacrylic acid (A1300)

1H-NMR(DMSO-d6) 12.91(bs, 1H), 7.96(s, 1H), 7.93(s, 1H), 7.65(d, 1H, J=7.6 Hz), 7.33 (d, 1H, J=1.3 Hz), 7.21(t, 1H, J=7.6 Hz), 7.09(d, 1H, J=7.6 Hz), 3.40-3.50(m, 6H), 3.18(s, 3H), 2.95-2.99(m, 4H), 2.68(t, 2H, J=7.4 Hz), 1.80-1.88(m, 2H), 1.78(s, 3H),

Example 48

Synthesis of (E)-3-[2,6-difluoro-4-(6-hexyloxy-4,5-dihydronaphtho[1,2-d]thiazol-2-ylcabamoyl)phenyl]-2-methylacrylic acid (A1301)

1H-NMR(DMSO-d6) 12.91(bs, 1H), 7.96(s, 1H), 7.94(s, 1H), 7.37(d, 1H, J=7.6 Hz), 7.33(s, 1H), 7.24(t, 1H, J=7.6 Hz), 6.92(d, 1H, J=7.6 Hz), 4.00(t, 2H, J=7.0 Hz), 2.95-2.99 (m, 4H), 1.80(s, 3H), 1.70-1.80(m, 2H), 1.45-1.55(m, 2H), 1.30-1.40(m, 4H), 0.89-0.91(m, 3H).

Example 49

Synthesis of (E)-3-[2,6-dichloro-4-(6-hexyloxy-4,5-dihydronaphtho[1,2-d]thiazol-2-ylcabamoyl)phenyl]-2-methylacrylic acid (A1302)

1H-NMR(DMSO-d6) 12.92(bs, 1H), 8.28(s, 2H), 7.39(s, 1H), 7.37(d, 1H, J=7.6 Hz), 7.24(t, 1H, J=7.6 Hz), 6.91(d, 1H, J=7.6 Hz), 4.00(t, 2H, J=7.0 Hz), 2.95-2.99(m, 4H), 1.70-1.80(m, 2H), 1.68(s, 3H), 1.45-1.55(m, 2H), 1.30-1.40(m, 4H), 0.89-0.91(m, 3H).

Example 50

Synthesis of (E)-3-[2,6-dichloro-4-(6-isobutyloxy-4,5-dihydronaphtho[1,2-d]thiazol-2-ylcabamoyl)phenyl]-2-methylacrylic acid (A1303)

1H-NMR(DMSO-d6) 12.92(bs, 1H), 8.28(s, 2H), 7.39(s, 1H), 7.37(d, 1H, J=7.6 Hz), 7.24(t, 1H, J=7.6 Hz), 6.89(d, 1H, J=7.6 Hz), 3.79(d, 2H, J=6.6 Hz), 2.95-2.99(m, 4H), 2.05-2.15(m, 1H), 1.68(s, 3H), 1.02(d, 6H, J=6.0 Hz).

Example 51

Synthesis of (E)-3-[2,6-difluoro-4-(6-isobutyloxy-4,5-dihydronaphtho[1,2-d]thiazol-2-ylcabamoyl)phenyl]-2-methylacrylic acid (A1304)

1H-NMR(DMSO-d6) 12.93(bs, 1H), 7.96(s, 1H), 7.94(s, 1H), 7.37(d, 1H, J=7.6 Hz), 7.33(s, 1H), 7.24(t, 1H, J=7.6 Hz), 6.92(d, 1H, J=7.6.Hz), 3.79(d, 2H, J=6.6 Hz), 2.95-2.99 (m, 4H), 2.05-2.15(m, 1H), 1.78(s, 3H), 1.02(d, 6H, J=6.0 Hz).

Example 52

Synthesis of (E)-3-{4-[6-(2-ethyloxyethyloxy)-4,5-dihydronaphtho[1,2-d]thiazol-2-ylcabamoyl]-2,6-difluorophenyl}-2-methylacrylic acid (A1305)

1H-NMR(DMSO-d6) 12.93(bs, 1H), 7.96(s, 1H), 7.94(s, 1H), 7.40(d, 1H, J=7.6 Hz), 7.33(s, 1H), 7.24(t, 1H, J=7.6 Hz), 6.95(d, 1H, J=7.6 Hz ), 4.13(t, 2H, J=5.0 Hz), 3.73(t, 2H, J=5.0 Hz), 3.54(q, 2H, J=7.0 Hz), 2.95-2.99(m, 4H,), 1.78(s, 3H), 1.15(t, 3H, J=7.0 Hz).

Example 53

Synthesis of (E)-3-{2,6-dichloro-4-[6-(2-ethyloxyethyloxy)-4,5-dihydronaphtho[1,2-d]thiazol-2-ylcabamoyl]phenyl}-2-methylacrylic acid (A1306)

1H-NMR(DMSO-d6) 12.92(bs, 1H), 8.28(s, 2H), 7.39(s, 1H), 7.37(d, 1H, J=7.6 Hz), 7.24(t, 1H, J=7.6 Hz), 6.95(d, 1H, J=7.6 Hz ), 4.13(t, 2H, J=5.0 Hz), 3.73(t, 2H, J=5.0 Hz), 3.54(q, 2H, J=7.0 Hz), 2.95-2.99(m, 4H), 1.68(s, 3H), 1.14(t, 3H, J=7.0 Hz).

Example 54

Synthesis of (E)-3-[4-(6-ethyl-4H-chromeno[4,3-d]thiazol-2-ylcabamoyl]-2,6-difluorophenyl}-2-methylacrylic acid (A1307)

1H-NMR(DMSO-d6) 12.93(bs, 1H), 7.96(s, 1H), 7.94(s, 1H), 7.48(d, 1H, J=7.6 Hz), 7.33(s, 1H), 7.11 d, 1H, J=7.6 Hz), 6.97(d, 1H, J=7.6 Hz), 5.49(s, 2H), 2.60(q, 2H, J=7.0 Hz), 1.79(s, 3H), 1.14(t, 3H, J=7.0 Hz).

Example 55

Synthesis of (E)-3-[2,6-difluoro-4-(6-propyl-4H-chromeno[4,3-d]thiazol-2-ylcabamoyl)phenyl]-2-methylacrylic acid (A1308)

1H-NMR(DMSO-d6) 12.93(bs, 1H), 7.96(s, 1H), 7.94(s, 1H), 7.49(d, 1H, J=7.6 Hz), 7.33(s, 1H), 7.07(d, 1H, J=7.6 Hz), 6.97(t, 1H, J=7.6 Hz ), 5.47(s, 2H), 2.53(t, 2H, J=7.0 Hz), 1.79(s, 3H), 1.49-1.59(m, 2H), 0.94(t, 3H, J=7.0 Hz).

Example 56

Synthesis of (E)-3-[2,6-dichloro-4-(6-ethyl-4H-chromeno[4,3-d]thiazol-2-ylcabamoyl)phenyl]-2-methylacrylic acid (A1310)

1H-NMR(DMSO-d6) 12.92(bs, 1H), 8.26(s, 2H), 7.47(d, 1H, J=7.6 Hz), 7.38(s, 1H), 7.09(d 1H, J=7.6 Hz), 6.95(t, 1H, J=7.6 Hz), 5.49(s, 2H), 2.55(q, 2H), J=7.0 Hz), 1.69(s, 3H), 1.14 t, 3H, J=7.0 Hz).

Example 57

Synthesis of (E)-3-[2,6-dichloro-4-(6-propyl-4H-chromeno[4,3-d]thiazol-2-ylcabamoyl)phenyl]-2-methylacrylic acid (A1311)

1H-NMR(DMSO-d6) 12.92(bs, 1H), 8.27(s, 2H), 7.47(d, 1H, J=7.6 Hz), 7.38(s, 1H), 7.09(d, 1H, J=7.6 Hz), 6.95(t, 1H, J=7.6 Hz), 5.49(s, 2H), 2.53(t, 2H, J=7.0 Hz), 1.66(s, 3H), 1.49-1.59(m, 2H), 0.94(t, 3H, J=7.0 Hz).

Example 58

Synthesis of (E)-3-[2,6-dichloro-4-(6-isopropyl-4H-chromeno[4,3-d]thiazol-2-ylcabamoyl)phenyl]-2-methylacrylic acid (A1312)

1H-NMR(DMSO-d6) 12.92(bs, 1H), 8.27(s, 2H), 7.49(d, 1H, J=7.6 Hz), 7.38(s, 1H), 7.13(d, 1H, J=7.6 Hz), 7.01(t, 1H, J=7.6 Hz), 5.49(s, 2H), 3.20-3.30(m, 2H), 1.69(s, 3H), 1.04 (d, 6H, J=6.0 Hz).

Example 59

Synthesis of (E)-3-{2,6-difluoro-4-[6-(3-propyloxypropyl)-4H-chromeno[4,3-d]thiazol-2-ylcabamoyl]phenyl}-2-methylacrylic acid (A1313)

1H-NMR(DMSO-d6) 12.93(bs, 1H), 7.96(s, 1H), 7.94(s, 1H), 7.49(d, 1H, J=7.6 Hz), 7.33(s, 1H), 7.10(d, 1H, J=7.6 Hz), 6.95(t, 1H, J=7.6 Hz), 5.49(s, 2H), 3.33-3.40(m, 4H), 2.63(t, 2H, J=7.0 Hz), 1.80(s, 3H), 1.70-1.80(m, 2H), 1.45-1.53(m, 2H), 0.89(t, 3H, J=7.4 Hz).

Example 60

Synthesis of (E)-3-[2,6-difluoro-4-(6-hexyl-4H-chromeno[4,3-d]thiazol-2-ylcabamoyl)phenyl]-2-methylacrylic acid (A1314)

1H-NMR(DMSO-d6) 12.93(bs, 1H), 7.96(s, 1H), 7.94(s, 1H), 7.49(d, 1H, J=7.6 Hz), 7.33(s, 1H), 7.10(d, 1H, J=7.6 Hz), 6.97(t, 1H, J=7.6 Hz), 5.47(s, 2H), 2.53(t, 2H, J=7.0 Hz), 1.80(s, 3H), 1.49-1.59(m, 2H), 1.25-1.36(m, 6H), 0.94(t, 3H, J=7.0 Hz).

Example 61

Synthesis of (E)-3-{4-[6-(3,3-dimethylbutyl)-4H-chromeno[4,3-d]thiazol-2-ylcabamoyl]-2,6-difluorophenyl}-2-methylacrylic acid (A1315)

1H-NMR(DMSO-d6) 12.93(bs, 1H), 7.96(s, 1H), 7.94(s, 1H), 7.4 (d, 1H, J=7.6 Hz), 7.33(s, 1H), 7.10(d, 1H, J=7.6 Hz), 6.97(t, 1H, J=7.6 Hz), 5.47(s, 2H), 2.50-2.60(m, 2H), 1.80(s, 3H), 1.39-1.45(m, 2H), 0.95(s, 9H).

Example 62

Synthesis of (E)-3-[2,6-dichloro-4-(6-hexyl-4H-chromeno[4,3-d]thiazol-2-ylcabamoyl)phenyl]-2-methylacrylic acid (A1316)

1H-NMR(DMSO-d6) 12.92(bs, 1H), 8.27(s, 2H), 7.48(d, 1H, J=7.6 Hz), 7.3 (s, 1H), 7.09(d, 1H, J=7.6 Hz), 6.97(t, 1H, J=7.6 Hz), 5.49(s, 2H), 2.56(t, 2H, J=7.0 Hz), 1.68(s, 3H), 1.49-1.59(m, 2H), 1.25-1.36(m, 6H), 0.86(t, 3H, J=7.0 Hz).

Example 63

Synthesis of (E)-3-{2,6-dichloro-4-[6-(3,3-dimethylbutyl)-4H-chromeno[4,3-d]thiazol-2-ylcabamoyl]phenyl}-2-methylacrylic acid (A1317)

1H-NMR(DMSO-d6) 12.92(bs, 1H), 8.28(s, 2H), 7.50(d, 1H, J=7.6 Hz), 7.40(s, 1H), 7.09(d, 1H, J=7.6 Hz), 6.96(t, 1H, J=7.6 Hz), 5.49(s, 2H), 2.50-2.60(m, 2H), 1.68(s, 3H), 1.39-1.45(m, 2H), 0.95(s, 9H).

Example 64

Synthesis of (Z)-3-{2,6-dichloro-4-[6-(3,3-dimethyl-butyl)-4,5-dihydronaphtho[1,2-d]thiazol-2-ylcabamoyl]phenyl}-2-methyloxyacrylic acid (A1318)

1H-NMR(DMSO-d6) 12.90 (bs, 2H), 8.23 (s, 2H), 7.63 (d, 1H, J=7.5 Hz), 7.20 (t, 1H, J=7.5 Hz), 7.08 (d, 1H, J=7.7 Hz), 6.73 (s, 1H), 3.61 (s, 3H), 2.98 (s, 4H), 2.49-2.64 (m, 2H), 1.35-1.41 (m, 2H), 0.98 (s, 9H).

Example 65

Synthesis of (Z)-3-{4-[6-(3,3-dimethylbutyl)-4,5-dihydronaphtho[1,2-d]thiazol-2-ylcabamoyl]-2,6-difluorophenyl}-2-methyloxyacrylic acid (A1319)

1H-NMR(DMSO-d6) 12.87 (bs, 2H), 7.88-7.91 (m, 2H), 7.62-7.65 (m, 1H), 7.20 (t, 1H, J=7.5 Hz), 7.07-7.09 (m, 1H), 6.65 (s, 1H), 3.71 (s, 3H), 2.98 (s, 4H), 2.49-2.64 (m, 2H), 1.35-1.41 (m, 2H), 0.98 (s, 9H).

Example 66

Synthesis of (E)-3-[2,6-difluoro-4-(5-pentyl-4,5-dihydronaphtho[1,2-d]thiazol-2-ylcabamoyl)phenyl]-2-methylacrylic acid (A1320)

1H-NMR(DMSO-d6) 12.91(bs, 1H), 7.96(s, 1H), 7.93(s, 1H), 7.73(d, 1H, J=7.6 Hz), 7.39(s, 1H), 7.22-7.35(m, 3H), 2.94-3.16(m, 3H), 1.80(s, 3H), 1.40-1.55(m, 2H), 1.20-1.30(m, 6H), 0.86 (t, 3H, J=7.0 Hz).

Example 67

Synthesis of (E)-3-[2,6-dichloro-4-(5-pentyl-4,5-dihydronaphtho[1,2-d]thiazol-2-ylcabamoyl)phenyl]-2-methylacrylic acid (A1321)

1H-NMR(DMSO-d6) 12.91(bs, 1H), 8.28(s, 2H), 7.73(d, 1H, J=7.6 Hz), 7.39(s, 1H), 7.22-7.35(m, 3H), 2.94-3.16(m, 3H), 1.69(s, 3H), 1.40-1.55(m, 2H), 1.20-1.30(m, 6H), 0.86 (t, 3H, J=7.0 Hz).

Example 68

Synthesis of (E)-3-[2,6-difluoro-4-(5-heptyl-4,5-dihydronaphtho[1,2-d]thiazol-2-ylcabamoyl)phenyl]-2-methylacrylic acid (A1322)

1H-NMR(DMSO-d6) 12.91(bs, 1H), 7.96(s, 1H), 7.93(s, 1H), 7.73(d, 1H, J=7.6 Hz), 7.39(s, 1H), 7.22-7.35(m, 3H), 2.94-3.16(m, 3H), 1.80(s, 3H), 1.40-1.55(m, 2H), 1.20-1.30 (m, 10H), 0.86(t, 3H, J=7.0 Hz).

Example 69

Synthesis of (E)-3-[2,6-difluoro-4-(5-pent-1-ynyl-4,5-dihydronaphtho[1,2-d]thiazol-2-ylcabamoyl)phenyl]-2-methylacrylic acid (A1323)

1H-NMR(DMSO-d6) 12.97(bs, 2H), 7.91-7.99(m, 2H), 7.70-7.73(m, 1H), 7.33(s, 1H), 7.24-7.30(m, 2H), 3.18(t, 2H, J=7.5 Hz), 3.01(t, 2H, J=7.8 Hz), 2.42-2.54(m, 2H), 1.80(s, 3H), 1.55-1.66(m, 2H), 1.04(t, 3H, J=7.5 Hz).

Example 70

Synthesis of (E)-3-[2,6-difluoro-4-(6-hept-1-ynyl-4,5-dihydronaphtho[1,2-d]thiazol-2-ylcabamoyl)phenyl]-2-methylacrylic acid (A1324)

1H-NMR(DMSO-d6) 12.97(bs, 2H), 7.92-8.00(m, 2H), 7.71(t, 1H, J=3.9 Hz), 7.34(s, 1H), 7.28(d, 2H, J=3.6 Hz), 3.17(t, 2H, J=7.8 Hz), 3.01(t, 2H, J=8.1 Hz), 1.81(s, 3H), 1.55-1.64(m, 2H), 1.29-1.49(m, 4H), 0.91(t, 3H, J=7.2 Hz).

Example 71

Synthesis of (E)-3-[4-(6-dec-1-ynyl-4,5-dihydronaphtho[1,2-d]thiazol-2-ylcabamoyl)-2,6-difluorophenyl]-2-methylacrylic acid (A1325)

1H-NMR(DMSO-d6) 12.99(bs, 2H), 7.95(d, 2H, J=7.8 Hz), 7.71(t, 1H, J=4.8 Hz), 7.27-7.34(m, 3H), 3.17(t, 2H, J=8.1 Hz), 3.01(t, 2H, J=8.1 Hz), 1.81(s, 3H), 1.20-1.60(m, 12H), 0.84-0.88(m, 3H).

Example 72

Synthesis of (E)-3-{2,6-difluoro-4-[6-(4-methylpent-1-ynyl-4,5-dihydronaphtho[1,2-d]thiazol-2-ylcabamoyl)phenyl]-2-methylacrylic acid (A1326)

1H-NMR(DMSO-d6) 12.97(bs, 2H), 7.96(d, 2H, J=8.4 Hz), 7.70-7.73(m, 1H), 7.23-7.34(m, 3H), 3.18(t, 2H, J=8.4 Hz), 3.02(t, 2H, J=8.1 Hz), 2.40(d, 2H, J=6.3 Hz), 1.85-1.94(m, 1H), 1.81(s, 3H), 2.07(d, 6H, J=6.6 Hz).

Example 73

Synthesis of (E)-3-[2,6-dichloro-4-(5-heptyl-4,5-dihydronaphtho[1,2-d]thiazol-2-ylcabamoyl)phenyl]-2-methylacrylic acid (A1327)

1H-NMR(DMSO-d6) 12.91(bs, 1H), 8.26(s, 2H), 7.73(d, 1H, J=7.6 Hz), 7.39(s, 1H), 7.22-7.35(m, 3H), 2.94-3.16(m, 3H), 1.69(s, 3H), 1.40-1.55(m, 2H), 1.20-1.30(m, 10H), 0.86 (t, 3H, J=7.0 Hz).

Example 74

Synthesis of (E)-3-[4-(5-butyl-4,5-dihydronaphtho[1,2-d]thiazol-2-ylcabamoyl)-2,6-difluorophenyl]-2-methylacrylic acid (A1328)

1H-NMR(DMSO-d6) 12.91(bs, 1H), 7.96(s, 1H), 7.93(s, 1H), 7.73(d, 1H, J=7.6 Hz), 7.39(s, 1H), 7.22-7.35(m, 3H), 2.94-3.16(m, 3H), 1.80(s, 3H), 1.40-1.55(m, 2H), 1.20-1.30 (m, 4H), 0.86(t, 3H, J=7.0 Hz).

Example 75

Synthesis of (E)-3-[4-(5-butyl-4,5-dihydronaphtho[1,2-d]thiazol-2-ylcabamoyl)-2,6-dichlorophenyl]-2-methylacrylic acid (A1329)

1H-NMR(DMSO-d6) 12.91(bs, 1H), 8.27(s, 2H), 7.70(d, 1H, J=7.6 Hz), 7.39(s, 1H), 7.22-7.35(m, 3H), 2.94-3.16(m, 3H), 1.69(s, 3H), 1.40-1.55(m, 2H), 1.20-1.30(m, 4H), 0.86 (t, 3H, J=7.0 Hz).

Example 76

Synthesis of (E)-3-[4-(6-cyclohexy-1-enylethynyl-4,5-dihydronaphtho[1,2-d]thiazol-2-ylcabamoyl)-2,6-difluorophenyl]-2-methylacrylic acid (A1330)

1H-NMR(DMSO-d6) 12.97(bs, 2H), 7.92-8.00(m, 2H), 7.72-7.75(m, 1H), 7.29-7.38(m, 3H), 6.20-6.28(m, 1H), 3.17 (t, 2H, J=7.5 Hz), 3.02(t, 2H, J=7.5 Hz), 2.06-2.26(m, 4H), 1.81(s, 3H), 1.54-1.70(m, 4H).

Example 77

Synthesis of (E)-3-{2,6-difluoro-4-[6-(3-methyloxyprop-1-ynyl)-4,5-dihydronaphtho[1,2-d]thiazol-2-ylcabamoyl)phenyl]-2-methylacrylic acid (A1331)

1H-NMR(DMSO-d6) 12.98(bs, 2H), 7.92-8.00(m, 2H), 7.75-7.80(m, 1H), 7.29-7.38(m, 3H), 4.40(s, 2H), 3.37(s, 3H), 3.20(t, 2H, J=6.6 Hz), 3.03(t, 2H, J=6.6 Hz), 1.80(s, 3H).

Example 78

Synthesis of (E)-3-{2,6-dichloro-4-[6-(3-ethyloxypentyl)-4,5-dihydronaphtho[1,2-d]thiazol-2-ylcabamoyl)phenyl]-2-methylacrylic acid (A1332)

1H-NMR(CDCl3) 7.72(s, 2H), 7.25(s, 2H), 6.99(d, 1H, J=7.6 Hz), 6.94(t, 1H, J=7.6 Hz), 4.27(q, 2H, J=7.0 Hz), 3.49-3.56(m,2H), 3.20-3.25(m, 1H), 2.95-3.11(m,4H), 2.60-2.80(m, 2H), 1.60-1.69(m, 2H), 1.61(s, 3H), 1.45-1.55(m, 2H), 1.48 (t, 3H, J=7.0 Hz), 1.28 (t, 3H, J=7.0 Hz), 0.86(t, 3H, J=7.2 Hz).

The compounds described below can be synthesized by similar method described above.

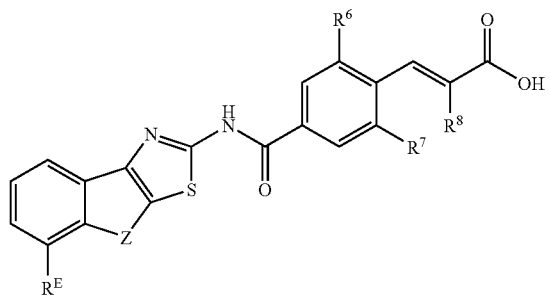

wherein $R^6$, $R^7$, and $R^8$ are independently fluoro, chloro, or methyl;

$R^E$ is n-pentyl, 3,3-dimethylbuthyl, 1-methyloxyethyl, 1-methyloxypropyl, 1-methyloxybutyl, 1-methyloxy-2-methylpropyl, 1-methyloxypentyl, 1-methyloxy-3-methylbutyl, 1-methyloxy-2,2-dimethylpropyl, 1-methyloxyhexyl, 1-methyloxy-3,3-dimethylbutyl, 1-ethyloxyethyl, 1-ethyloxypropyl, 1-ethyloxybutyl, 1-ethyloxy-2-methylpropyl, 1-ethyloxypentyl, 1-ethyloxy-3-methylbutyl, 1-ethyloxy-2,2-dimethylpropyl, 1-ethyloxyhexyl, 1-ethyloxy-3,3-dimethylbutyl, 1-n-propyloxyethyl, 1-n-propyloxypropyl, 1-n-propyloxybutyl, 1-n-propyloxy-2-methylpropyl, 1-n-propyloxypentyl, 1-n-propyloxy-3-methylbutyl, 1-n-propyloxy-2,2-dimethylpropyl, 1-n-propyloxyhexyl, 1-n-propyloxy-3,3-dimethylbutyl, 1-isopropyloxyethyl, 1-isopropyloxypropyl, 1-isopropyloxybutyl, 1-isopropyloxy-2-methylpropyl, 1-isopropyloxypentyl, 1-isopropyloxy-3-methylbutyl, 1-isopropyloxy-2,2-dimethylpropyl, 1-isopropyloxyhexyl, 1-isopropyloxy-3,3-dimethylbutyl, 1-n-butyloxyethyl, 1-n-butyloxypropyl, 1-n-butyloxybutyl, 1-n-butyloxy-2-methylpropyl, 1-n-butyloxypentyl, 1-n-butyloxy-3-methylbutyl, 1-n-butyloxy-2,2-dimethylpropyl, 1-isobutyloxyhexyl, 1-isobutyloxy-3,3-dimethylbutyl, 1-isobutyloxyethyl, 1-isobutyloxypropyl, 1-isobutyloxybutyl, 1-isobutyloxy-2-methylpropyl, 1-isobutyloxypentyl, 1-isobutyloxy-3-methylbutyl, 1-isobutyloxy-2,2-dimethylpropyl, 1-isobutyloxyhexyl, 1-isobutyloxy-3,3-dimethylbutyl, 1-t-butyloxyethyl, 1-t-butyloxypropyl, 1-t-butyloxybutyl, 1-t-butyloxy-2-methylpropyl, 1-t-butyloxypentyl, 1-t-butyloxy-3-methylbutyl, 1-t-butyloxy-2,2-dimethylpropyl, 1-t-butyloxyhexyl, 1-t-butyloxy-3,3-dimethylbutyl, 1-n-pentyloxyethyl, 1-n-pentyloxypropyl, 1-n-pentyloxybutyl, 1-n-pentyloxy-2-methylpropyl, 1-n-pentylloxypentyl, 1-n-pentyloxy-3-methylbutyl, 1-n-pentyloxy-2,2-dimethylpropyl, 1-n-pentyloxyhexyl, 1-n-pentyloxy-3,3-dimethylbutyl, 1-neopentyloxyethyl, 1-neopentyloxypropyl, 1-neopentyloxybutyl, 1-neopentyloxy-2-methylpropyl, 1-neopentyloxypentyl, 1-neopentyloxy-3-methylbutyl, 1-neopentyloxy-2,2-dimethylpropyl, 1-neopentyloxyhexyl, 1-neopentyloxy-3,3-dimethylbutyl, 3-methyloxypropyl, 3-methyloxybutyl, 3-methyloxypentyl, 3-methyloxyhexyl, 3-methyloxy-4-methylpentyl, 3-methyloxyheptyl, 3-methyloxy-5-methylhexyl, 3-methyloxy-4,4-dimethylpentyl, 3-methyloxyoctyl, 3-methyloxy-5,5-dimethylhexyl, 3-ethyloxypropyl, 3-ethyloxybutyl, 3-ethyloxypentyl, 3-ethyloxyhexyl, 3-ethyloxy-4-methylpentyl, 3-ethyloxyheptyl, 3-ethyloxy-5-methylhexyl, 3-ethyloxy-4,4-dimethylpentyl, 3-ethyloxyoctyl, 3-ethyloxy-5,5-dimethylhexyl, 3-n-propyloxypropyl, 3-n-propyloxybutyl, 3-n-propyloxypentyl, 3-n-propyloxyhexyl, 3-n-propyloxy-4-methylpentyl, 3-n-propyloxyheptyl, 3-n-propyloxy-5-methylhexyl, 3-n-propyloxy-4,4-dimethylpentyl, 3-n-propyloxyoctyl, 3-n-propyloxy-5,5-dimethylhexyl, 3-isopropyloxypropyl, 3-isopropyloxybutyl, 3-isopropyloxypentyl, 3-isopropyloxyhexyl, 3-isopropyloxy-4-methylpentyl, 3-isopropyloxyheptyl, 3-isopropyloxy-5-methylhexyl, 3-isopropyloxy-4,4-dimethylpentyl, 3-isopropyloxyoctyl, 3-isopropyloxy-5,5-dimethylhexyl, 3-n-butyloxypropyl, 3-n-butyloxybutyl, 3-n-butyloxypentyl, 3-n-butyloxyhexyl, 3-n-butyloxy-4-methylpentyl, 3-n-butyloxyheptyl, 3-n-butyloxy-5-methylhexyl, 3-n-butyloxy-4,4-dimethylpentyl, 3-n-butyloxyoctyl, 3-n-butyloxy-5,5-dimethylhexyl, 3-isobutyloxypropyl, 3-isobutyloxybutyl, 3-isobutyloxypentyl, 3-isobutyloxyhexyl, 3-isobutyloxy-4-methylpentyl, 3-isobutyloxyheptyl, 3-isobutyloxy-5-methylhexyl, 3-isobutyloxy-4,4-dimethylpentyl, 3-isobutyloxyoctyl, 3-isobutyloxy-5,5-dimethylhexyl, 3-t-butyloxypropyl, 3-t-butyloxybutyl, 3-t-butyloxypentyl, 3-t-butyloxyhexyl, 3-t-butyloxy-4-methylpentyl, 3-t-butyloxyheptyl, 3-t-butyloxy-5-methylhexyl, 3-t-butyloxy-4,4-dimethylpentyl, 3-t-butyloxyoctyl, 3-t-butyloxy-5,5-dimethylhexyl, 3-n-pentyloxypropyl, 3-n-pentyloxybutyl, 3-n-pentyloxypentyl, 3-n-pentylxyhexyl, 3-n-pentyloxy-4-methylpentyl, 3-n-pentyloxyheptyl, 3-n-pentyloxy-5-methylhexyl, 3-n-pentyloxy-4,4-dimethylpentyl, 3-n-pentyloxyoctyl, or 3-n-pentyloxy-5,5-dimethylhexyl;

Z is ethylene or oxymethylene.

(Compound No., $R^6$, $R^7$, $R^8$, $R^E$, Z)=(A13, F, F, Me, 1-methyloxyethyl, CH2CH2), (A14, F, F, Me, 1-methyloxypropyl, CH2CH2), (A15, F, F,. Me, 1-methyloxybutyl, CH2CH2), (A16, F, F, Me, 1-methyloxy-2-methylpropyl, CH2CH2), (A17, F, F, Me, 1-methyloxypentyl, CH2CH2), (A18, F, F, Me, 1-methyloxy-3-methylbutyl, CH2CH2), (A19, F, F, Me, 1-methyloxy-2,2-dimethylpropyl, CH2CH2), (A20, F, F, Me, 1-methyloxyhexyl, CH2CH2), (A21, F, F, Me, 1-methyloxy- 3,3-dimethylbutyl, CH2CH2), (A22, F, F, Me, 1-ethyloxyethyl, CH2CH2), (A23, F, F, Me, 1-ethyloxypropyl, CH2CH2), (A24, F, F, Me, 1-ethyloxybutyl, CH2CH2), (A25, F, F, Me, 1-ethyloxy-2-methylpropyl, CH2CH2), (A26, F, F, Me, 1-ethyloxypentyl, CH2CH2), (A27, F, F, Me, 1-ethyloxy-3-methylbutyl, CH2CH2), (A28, F, F, Me, 1-ethyloxy-2,2-dimethylpropyl, CH2CH2), (A29, F, F, Me, 1-ethyloxyhexyl, CH2CH2), (A30, F, F, Me, 1-ethyloxy-3,3-dimethylbutyl, CH2CH2), (A31, F, F, Me, 1-n-propyloxyethyl, CH2CH2), (A32, F, F, Me, 1-n-propyloxypropyl, CH2CH2), (A33, F, F, Me, 1-n-propyloxybutyl, CH2CH2), (A34, F, F, Me, 1-n-propyloxy-2-methylpropyl, CH2CH2), (A35, F, F, Me, 1-n-propyloxypentyl, CH2CH2), (A36, F, F, Me, 1-n-propyloxy-3-methylbutyl, CH2CH2), (A37, F, F, Me, 1-n-propyloxy-2,2-dimethylpropyl, CH2CH2), (A38, F, F, Me, 1-n-propyloxyhexyl, CH2CH2), (A39, F, F, Me, 1-n-propyloxy-3,3-dimethylbutyl, CH2CH2), (A40, F, F, Me, 1-isopropyloxyethyl, CH2CH2), (A41, F, F, Me, 1-isopropyloxypropyl, CH2CH2), (A42, F, F, Me, 1-isopropyloxybutyl, CH2CH2), (A43, F, F, Me, 1-isopropyloxy-2-methylpropyl, CH2CH2), (A44, F, F, Me, 1-isopropyloxypentyl, CH2CH2), (A45, F, F, Me, 1-isopropyloxy-3-methylbutyl, CH2CH2), (A46, F, F, Me, 1-isopropyloxy-2,2-dimethylpropyl, CH2CH2), (A47, F, F, Me, 1-isopropyloxyhexyl, CH2CH2), (A48, F, F, Me, 1-isopropyloxy-3,3-dimethylbutyl, CH2CH2), (A49, F, F, Me, 1-n-butyloxyethyl, CH2CH2), (A50, F, F, Me, 1-n-butyloxypropyl, CH2CH2), (A51, F, F, Me, 1-n-butyloxybutyl, CH2CH2), (A52, F, F, Me, 1-n-butyloxy-2-methylpropyl, CH2CH2), (A53, F, F, Me, 1-n-butyloxypentyl, CH2CH2), (A54, F, F, Me, 1-n-butyloxy-3-methylbutyl, CH2CH2), (A55, F, F, Me, 1-n-butyloxy-2,2-dimethylpropyl, CH2CH2), (A56, F, F, Me, 1-n-butyloxyhexyl, CH2CH2), (A57, F, F, Me, 1-n-butyloxy-3,3-dimethylbutyl, CH2CH2), (A58, F, F, Me, 1-isobutyloxyethyl, CH2CH2), (A59, F, F, Me, 1-isobutyloxypropyl, CH2CH2), (A60, F, F, Me, 1-isobutyloxybutyl, CH2CH2), (A61, F, F, Me, 1-isobutyloxy-2-methylpropyl, CH2CH2), (A62, F, F, Me, 1-isobutyloxypentyl, CH2CH2), (A63, F, F, Me, 1-isobutyloxy-3-methylbutyl, CH2CH2), (A64, F, F, Me, 1-isobutyloxy-2,2-dimethylpropyl, CH2CH2), (A65, F, F, Me, 1-isobutyloxyhexyl, CH2CH2), (A66, F, F, Me, 1-isobutyloxy-3,3-dimethylbutyl, CH2CH2), (A67, F, F, Me, 1-t-butyloxyethyl, CH2CH2), (A68, F, F, Me, 1-t-butyloxypropyl, CH2CH2), (A69, F, F, Me, 1-t-butyloxybutyl, CH2CH2), (A70, F, F, Me, 1-t-butyloxy-2-methylpropyl, CH2CH2), (A71, F, F, Me, 1-t-butyloxypentyl, CH2CH2), (A72, F, F, Me, 1-t-butyloxy-3-methylbutyl, CH2CH2), (A73, F, F, Me, 1-t-butyloxy-2,2-dimethylpropyl, CH2CH2), (A74, F, F, Me, 1-t-butyloxyhexyl, CH2CH2), (A75, F. F, Me, 1-t-butyloxy-3,3-dimethylbutyl, CH2CH2), (A76, F, F, Me, 1-n-pentyloxyethyl, CH2CH2), (A77, F, F, Me, 1-n-pentyloxypropyl, CH2CH2), (A78, F, F, Me, 1-n-pentyloxybutyl, CH2CH2), (A79, F, F, Me, 1-n-pentyloxy-2-methylpropyl, CH2CH2), (A80, F, F, Me, 1-n-pentyloxypentyl, CH2CH2), (A81, F, F, Me, 1-n-pentyloxy-3-methylbutyl, CH2CH2), (A82, F, F, Me, 1-n-pentyloxy-2,2-dimethylpropyl, CH2CH2), (A83, F, F, Me, 1-n-pentyloxyhexyl, CH2CH2), (A84, F, F, Me, 1-n-pentyloxy-3,3-dimethylbutyl, CH2CH2), (A85, F, F, Me, 1-neopentyloxyethyl, CH2CH2), (A86, F, F, Me, 1-neopentyloxypropyl, CH2CH2), (A87, F, F, Me, 1-neopentyloxybutyl, CH2CH2), (A88, F, F, Me, 1-neopentyloxy-2-methylpropyl, CH2CH2), (A89, F, F, Me, 1-neopentyloxypentyl, C142CH2), (A90, F, F, Me, 1-neopentyloxy-3-methylbutyl, CH2CH2), (A91, F, F, Me, 1-neopentyloxy-2,2-dimethylpropyl, CH2CH2), (A92, F, F, Me, 1-neopentyloxyhexyl, CH2CH2), (A93, F, F, Me, 1-neopentyloxy-3,3-dimethylbutyl, CH2CH2), (A94, F, F, OMe, 1-methyloxyethyl, CH2CH2), (A95, F, F, OMe, 1-methyloxypropyl, CH2CH2), (A96, F, F, OMe, 1-methyloxybutyl, CH2CH2), (A97, F, F, OMe, 1-methyloxy-2-methylpropyl, CH2CH2), (A98, F, F, OMe, 1-methyloxypentyl, CH2CH2), (A99, F, F, OMe, 1-methyloxy-3-methylbutyl, CH2CH2), (A100, F, F, OMe, 1-methyloxy-2,2-dimethylpropyl, CH2CH2), (A101, F, F, OMe, 1-methyloxyhexyl, CH2CH2), (A102, F, F, OMe, 1-methyloxy-3,3-dimethylbutyl, CH2CH2), (A103, F, F, OMe, 1-ethyloxyethyl, CH2CH2), (A104, F, F, OMe, 1-ethyloxypropyl, CH2CH2), (A105, F, F, OMe, 1-ethyloxybutyl, CH2CH2), (A106, F, F, OMe, 1-ethyloxy-2-methylpropyl, CH2CH2), (A107, F, F, OMe, 1-ethyloxypentyl, CH2CH2), (A108, F, F, OMe, 1-ethyloxy-3-methylbutyl, CH2CH2), (A109, F, F, OMe, 1-ethyloxy-2,2-dimethylpropyl, CH2CH2), (AL110, F, F, OMe, 1-ethyloxyhexyl, CH2CH2), (A111, F, F, OMe, 1-ethyloxy-3,3-dimethylbutyl, CH2CH2), (A112, F, F, OMe, 1-n-propyloxyethyl, CH2CH2), (A113, F, F, OMe, 1-n-propyloxypropyl, CH2CH2), (A114, F, F, OMe, 1-n-propyloxybutyl, CH2CH2), (A115, F, F, OMe, 1-n-propyloxy-2-methylpropyl, CH2CH2), (A116, F, F, OMe, 1-n-propyloxypentyl, CH2CH2), (A117, F, F, OMe, 1-n-propyloxy-3-methylbutyl, CH2CH2), (A118, F, F, OMe, 1-n-propyloxy-2,2-dimethylpropyl, CH2CH2), (A119, F, F, OMe, 1-n-propyloxyhexyl, CH2CH2), (A120, F, F, OMe, 1-n-propyloxy-3,3-dimethylbutyl, CH2CH2), (A121, F, F, OMe, 1-isopropyloxyethyl, CH2CH2), (A122, F, F, OMe, 1-isopropyloxypropyl, CH2CH2), (A123, F, F, OMe, 1-isopropyloxybutyl, CH2CH2), (A124, F, F,. OMe, 1-isopropyloxy-2-methylpropyl, CH2CH2), (A125, F, F, OMe, 1-isopropyloxypentyl, CH2CH2), (A126, F, F, OMe, 1-isopropyloxy-3-methylbutyl, CH2CH2), (A127, F, F, OMe, 1-isopropyloxy-2,2-dimethylpropyl, CH2CH2), (A128, F, F, OMe, 1-isopropyloxyhexyl, CH2CH2), (A129, F, F, OMe, 1-isopropyloxy-3,3-dimethylbutyl, CH2CH2), (A130, F, F, OMe, 1-n-butyloxyethyl, CH2CH2), (A131, F, F, OMe, 1-n-butyloxypropyl, CH2CH2), (A132, F, F, OMe, 1-n-butyloxybutyl, CH2CH2), (A133, F, F, OMe, 1-n-butyloxy-2-methylpropyl, CH2CH2), (A134, F, F, OMe, 1-n-butyloxypentyl, CH2CH2), (A135, F, F, OMe, 1-n-butyloxy-3-methylbutyl, CH2CH2), (A136, F, F, OMe, 1-n-butyloxy-2,2-dimethylpropyl, CH2CH2), (A137, F, F, OMe, 1-n-butyloxyhexyl, CH2CH2), (A138, F, F, OMe, 1-n-butyloxy-3,3-dimethylbutyl, CH2CH2), (A139, F, F, OMe, 1-isobutyloxyethyl, CH2CH2), (A140, F, F, OMe, 1-isobutyloxypropyl, CH2CH2), (A141, F, F, OMe, 1-isobutyloxybutyl, CH2CH2), (A142, F, F, OMe, 1-isobutyloxy-2-methylpropyl, CH2CH2), (A143, F, F, OMe, 1-isobutyloxypentyl, CH2CH2), (A144, F, F, OMe, 1-isobutyloxy-3-methylbutyl, CH2CH2), (A145, F, F, OMe, 1-isobutyloxy-2,2-dimethylpropyl, CH2CH2), (A146, F, F, OMe, 1-isobutyloxyhexyl, CH2CH2), (A147, F, F, OMe, 1-isobutyloxy-3,3-dimethylbutyl, CH2CH2), (A148, F, F, OMe, 1-t-butyloxyethyl, CH2CH2), (A149, F, F, OMe, 1-t-butyloxypropyl, CH2CH2), (A150, F, F, OMe, 1-t-butyloxybutyl, CH2CH2), (A151, F, F, OMe, 1-t-butyloxy-2-methylpropyl, CH2CH2), (A152, F, F, OMe, 1-t-butyloxypentyl, CH2CH2), (A153, F, F, OMe, 1-t-butyloxy-3-methylbutyl, CH2CH2), (A154, F, F, OMe, 1-t-butyloxy-2,2-dimethylpropyl, CH2CH2), (A155, F, F, OMe, 1-t-butyloxyhexyl, CH2CH2), (A156, F, F, OMe, 1-t-butyloxy-3,3-dimethylbutyl, CH2CH2), (A157, F, F, OMe, 1-n-pentyloxyethyl, CH2CH2), (A158, F, F, OMe, 1-n-pentyloxypropyl, CH2CH2), (A159, F, F, OMe, 1-n-pentyloxybutyl, CH2CH2), (A160, F, F, OMe, 1-n-pentyloxy-2-methylpropyl, CH2CH2), (A161, F, F, OMe, 1-n-pentyloxypentyl, CH2CH2), (A162, F, F, OMe, 1-n-pentyloxy-3-methylbutyl, CH2CH2), (A163, F, F, OMe, 1-n-pentyloxy-2,2-dimethylpropyl, CH2CH2), (A164, F, F, OMe, 1-n-pentyloxyhexyl, CH2CH2), (A165, F, F, OMe, 1-n-pentyloxy-3,3-dimethylbutyl, CH2CH2), (A166, F, F, OMe, 1-neopentyloxyethyl, CH2CH2), (A167, F, F, OMe, 1-neopentyloxypropyl, CH2CH2), (A168, F, F, OMe, 1-neopentyloxybutyl, CH2CH2), (A169, F, F, OMe, 1-neopentyloxy-2-methylpropyl, CH2CH2), (A170, F, F, OMe, 1-neopentyloxypentyl, CH2CH2), (A171, F, F, OMe, 1-neopentyloxy-3-methylbutyl, CH2CH2), (A172, F, F, OMe, 1-neopentyloxy-2,2-dimethylpropyl, CH2CH2), (A173, F, F, OMe, 1-neopentyloxyhexyl, CH2CH2), (A174, F, F, OMe, 1-neopentyloxy-3,3-dimethylbutyl, CH2CH2), (A175, F, F, Me, 1-methyloxyethyl, OCH2), (A176, F, F, Me, 1-methyloxypropyl, OCH2), (A177, F, F, Me, 1-methyloxybutyl, OCH2), (A178, F, F, Me, 1-methyloxy-2-methylpropyl, OCH2), (A179, F, F, Me, 1-methyloxypentyl, OCH2), (A180, F, F, Me, 1-methyloxy-3-methylbutyl, OCH2), (A181, F, F, Me, 1-methyloxy-2,2-dimethylpropyl, OCH2), (A182, F, F, Me, 1-methyloxyhexyl, OCH2), (A183, F, F, Me, 1-methyloxy-3,3-dimethylbutyl, OCH2), (A184, F, F, Me, 1-ethyloxyethyl, OCH2), (A185, F, F, Me, 1-ethyloxypropyl, OCH2), (A186, F, F, Me, 1-ethyloxybutyl, OCH2), (A187, F, F, Me, 1-ethyloxy-2-methylpropyl, OCH2), (A188, F, F, Me, 1-ethyloxypentyl, OCH2), (A189, F, F, Me, 1-ethyloxy-3-methylbutyl, OCH2), (A190, F, F, Me, 1-ethyloxy-2,2-dimethylpropyl, OCH2), (A191, F, F, Me, 1-ethyloxyhexyl, OCH2), (A192, F, F, Me, 1-ethyloxy-3,3-dimethylbutyl, OCH2), (A193, F, F, Me, 1-n-propyloxyethyl, OCH2), (A194, F, F, Me, 1-n-propyloxypropyl, OCH2), (A195, F, F, Me, 1-n-propyloxybutyl, OCH2), (A196, F, F, Me, 1-n-propyloxy-2-methylpropyl, OCH2), (A197, F, F, Me, 1-n-propyloxypentyl, OCH2), (A198, F, F, Me, 1-n-propyloxy-3-methylbutyl, OCH2), (A199, F, F, Me, 1-n-propyloxy-2,2-dimethylpropyl, OCH2), (A200, F, F, Me, 1-n-propyloxyhexyl, OCH2), (A201, F, F, Me, 1-n-propyloxy-3,3-dimethylbutyl, OCH2), (A202, F, F, Me, 1-isopropyloxyethyl, OCH2), (A203, F, F, Me, 1-isopropyloxypropyl, OCH2), (A204, F, F, Me, 1-isopropyloxybutyl, OCH2), (A205, F, F, Me, 1-isopropyloxy-2-methylpropyl, OCH2), (A206, F, F, Me, 1-isopropyloxypentyl, OCH2), (A207, F, F, Me, 1-isopropyloxy-3-methylbutyl, OCH2), (A208, F, F, Me, 1-isopropyloxy-2,2-dimethylpropyl, OCH2), (A209, F, F, Me, 1-isopropyloxyhexyl, OCH2), (A210, F, F, Me, 1-isopropyloxy-3,3-dimethylbutyl, OCH2), (A211, F, F, Me, 1-n-butyloxyethyl, OCH2), (A212, F, F, Me, 1-n-butyloxypropyl, OCH2), (A213, F, F, Me, 1-n-butyloxybutyl, OCH2), (A214, F, F, Me, 1-n-butyloxy-2-methylpropyl, OCH2), (A215, F, F, Me, 1-n-butyloxypentyl, OCH2), (A216, F, F, Me, 1-n-butyloxy-3-methylbutyl, OCH2), (A217, F, F, Me, 1-n-butyloxy-2,2-dimethylpropyl, OCH2), (A218, F, F, Me, 1-n-butyloxyhexyl, OCH2), (A219, F, F, Me, 1-n-butyloxy-3,3-dimethylbutyl, OCH2), (A220, F, F, Me, 1-isobutyloxyethyl, OCH2), (A221, F, F, Me, 1-isobutyloxypropyl, OCH2), (A222, F, F, Me, 1-isobutyloxybutyl, OCH2), (A223, F, F, Me, 1-isobutyloxy-2-methylpropyl, OCH2), (A224, F, F, Me, 1-isobutyloxypentyl, OCH2), (A225, F, F, Me, 1-isobutyloxy-3-methylbutyl, OCH2), (A226, F, F, Me, 1-isobutyloxy-2,2-dimethylpropyl, OCH2), (A227, F, F, Me, 1-isobutyloxyhexyl, OCH2), (A228, F, F, Me, 1-isobutyloxy-3,3-dimethylbutyl, OCH2), (A229, F, F, Me, 1-t-butyloxyethyl, OCH2), (A230, F, F, Me, 1-t-butyloxypropyl, OCH2), (A231, F, F, Me, 1-t-butyloxybutyl, OCH2), (A232, F, F, Me, 1-t-butyloxy-2-methylpropyl, OCH2), (A233, F, F, Me, 1-t-butyloxypentyl, OCH2), (A234, F, F, Me, 1-t-butyloxy-3-methylbutyl, OCH2), (A235, F, F, Me, 1-t-butyloxy-2,2-dimethylpropyl, OCH2), (A236, F, F, Me, 1-t-butyloxyhexyl, OCH2), (A237, F, F, Me, 1-t-butyloxy-3,3-dimethylbutyl, OCH2), (A238, F, F, Me, 1-n-pentyloxyethyl, OCH2), (A239, F, F, Me, 1-n-pentyloxypropyl, OCH2), (A240, F, F, Me, 1-n-pentyloxybutyl, OCH2), (A241, F, F, Me, 1-n-pentyloxy-2-methylpropyl, OCH2), (A242, F, F, Me, 1-n-pentyloxypentyl, OCH2), (A243, F, F, Me, 1-n-pentyloxy-3-methylbutyl, OCH2), (A244, F, F, Me, 1-n-pentyloxy-2,2-dimethylpropyl, OCH2), (A245, F, F, Me, 1-n-pentyloxyhexyl, OCH2), (A246, F, F, Me, 1-n-pentyloxy-3,3-dimethylbutyl, OCH2), (A247, F, F, Me, 1-neopentyloxyethyl, OCH2), (A248, F, F, Me, 1-neopentyloxypropyl, OCH2), (A249, F, F, Me, 1-neopentyloxybutyl, OCH2), (A250, F, F, Me, 1-neopentyloxy-2-methylpropyl, OCH2), (A251, F, F, Me, 1-neopentyloxypentyl, OCH2), (A252, F, F, Me, 1-neopentyloxy-3-methylbutyl, OCH2), (A253, F, F, Me, 1-neopentyloxy-2,2-dimethylpropyl, OCH2), (A254, F, F, Me, 1-neopentyloxyhexyl, OCH2), (A255, F, F, Me, 1-neopentyloxy-3,3-dimethylbutyl, OCH2), (A256, F, F, OMe, 1-methyloxyethyl, OCH2), (A257, F, F, OMe, 1-methyloxypropyl, OCH2), (A258, F, F, OMe, 1-methyloxybutyl, OCH2), (A259, F, F, OMe, 1-methyloxy-2-methylpropyl, OCH2), (A260, F, F, OMe, 1-methyloxypentyl, OCH2), (A261, F, F, OMe, 1-methyloxy-3-methylbutyl, OCH2), (A262, F, F, OMe, 1-methyloxy-2,2-dimethylpropyl, OCH2), (A263, F, F, OMe, 1-methyloxyhexyl, OCH2), (A264, F, F, OMe, 1-methyloxy-3,3-dimethylbutyl, OCH2), (A265, F, F, OMe, 1-ethyloxyethyl, OCH2), (A266, F, F, OMe, 1-ethyloxypropyl, OCH2), (A267, F, F, OMe, 1-ethyloxybutyl, OCH2), (A268, F, F, OMe, 1-ethyloxy-2-methylpropyl, OCH2), (A269, F, F, OMe, 1-ethyloxypentyl, OCH2), (A270, F, F, OMe, 1-ethyloxy-3-methylbutyl, OCH2), (A271, F, F, OMe, 1-ethyloxy-2,2-dimethylpropyl, OCH2), (A272, F, F, OMe, 1-ethyloxyhexyl, OCH2), (A273, F, F, OMe, 1-ethyloxy-3,3-dimethylbutyl, OCH2), (A274, F, F, OMe, 1-n-propyloxyethyl, OCH2), (A275, F, F, OMe, 1-n-propyloxypropyl, OCH2), (A276, F, F, OMe, 1-n-propyloxybutyl, OCH2), (A277, F, F, OMe, 1-n-propyloxy-2-methylpropyl, OCH2), (A278, F, F, OMe, 1-n-propyloxypentyl, OCH2), (A279, F, F, OMe, 1-n-propyloxy-3-methylbutyl, OCH2), (A280, F, F, OMe, 1-n-propyloxy-2,2-dimethylpropyl, OCH2), (A281, F, F, OMe, 1-n-propyloxyhexyl, OCH2), (A282, F, F, OMe, 1-n-propyloxy-3,3-dimethylbutyl, OCH2), (A283, F, F, OMe, 1-isopropyloxyethyl, OCH2), (A284, F, F, OMe, 1-isopropyloxypropyl, OCH2), (A285, F, F, OMe, 1-isopropyloxybutyl, OCH2), (A286, F, F, OMe, 1-isopropyloxy-2-methylpropyl, OCH2), (A287, F, F, OMe, 1-isopropyloxypentyl, OCH2), (A288, F, F, OMe, 1-isopropyloxy-3-methylbutyl, OCH2), (A289, F, F, OMe, 1-isopropyloxy-2,2-dimethylpropyl, OCH2), (A290, F, F, OMe, 1-isopropyloxyhexyl, OCH2), (A291, F, F, OMe, 1-isopropyloxy-3,3-dimethylbutyl, OCH2), (A292, F, F, OMe, 1-n-butyloxyethyl, OCH2), (A293, F, F, OMe, 1-n-butyloxypropyl, OCH2), (A294, F, F, OMe, 1-n-butyloxybutyl, OCH2), (A295, F, F, OMe, 1-n-butyloxy-2-methylpropyl, OCH2), (A296, F, F, OMe, 1-n-butyloxypentyl, OCH2), (A297, F, F, OMe, 1-n-butyloxy-3-methylbutyl, OCH2), (A298, F, F, OMe, 1-n-butyloxy-2,2-dimethylpropyl, OCH2), (A299, F, F, OMe, 1-n-butyloxyhexyl, OCH2), (A300, F, F, OMe, 1-n-butyloxy-3,3-dimethylbutyl, OCH2), (A301, F, F, OMe, 1-isobutyloxyethyl, OCH2), (A302, F, F, OMe, 1-isobutyloxypropyl, OCH2), (A303, F, F, OMe, 1-isobutyloxybutyl, OCH2), (A304, F, F, OMe, 1-isobutyloxy-2-methylpropyl, OCH2), (A305, F, F, OMe, 1-isobutyloxypentyl, OCH2), (A306, F, F, OMe, 1-isobutyloxy-3-methylbutyl, OCH2), (A307, F, F, OMe, 1-isobutyloxy-2,2-dimethylpropyl, OCH2), (A308, F, F, OMe, 1-isobutyloxyhexyl, OCH2), (A309, F, F, OMe, 1-isobutyloxy-3,3-dimethylbutyl, OCH2), (A310, F, F, OMe, 1-t-butyloxyethyl, OCH2), (A311, F, F, OMe, 1-t-butyloxypropyl, OCH2), (A312, F, F, OMe, 1-t-butyloxybutyl, OCH2), (A313, F, F, OMe, 1-t-butyloxy-2-methylpropyl, OCH2), (A314, F, F, OMe, 1-t-butyloxypentyl, OCH2), (A315, F, F, OMe, 1-t-butyloxy-3-methylbutyl, OCH2), (A316, F, F, OMe, 1-t-butyloxy-2,2-dimethylpropyl, OCH2), (A317, F, F, OMe, 1-t-butyloxyhexyl, OCH2), (A318, F, F, OMe, 1-t-butyloxy-3,3-dimethylbutyl, OCH2), (A319, F, F, OMe, 1-n-pentyloxyethyl, OCH2), (A320, F, F, OMe, 1-n-pentyloxypropyl, OCH2), (A321, F, F, OMe, 1-n-pentyloxybutyl, OCH2), (A322, F, F, OMe, 1-n-pentyloxy-2-methylpropyl, OCH2), (A323, F, F, OMe, 1-n-pentyloxypentyl, OCH2), (A324, F, F, OMe, 1-n-pentyloxy-3-methylbutyl, OCH2), (A325, F, F, OMe, 1-n-pentyloxy-2,2-dimethylpropyl, OCH2), (A326, F, F, OMe, 1-n-pentyloxyhexyl, OCH2), (A327, F, F, OMe, 1-n-pentyloxy-3,3-dimethylbutyl, OCH2), (A328, F, F, OMe, 1-neopentyloxyethyl, OCH2), (A329, F, F, OMe, 1-neopentyloxypropyl, OCH2), (A330, F, F, OMe, 1-neopentyloxybutyl, OCH2), (A331, F, F, OMe, 1-neopentyloxy-2-methylpropyl, OCH2), (A332, F, F, OMe, 1-neopentyloxypentyl, OCH2), (A333, F, F, OMe, 1-neopentyloxy-3-methylbutyl, OCH2), (A334, F, F, OMe, 1-neopentyloxy-2,2-dimethylpropyl, OCH2), (A335, F, F, OMe, 1-neopentyloxyhexyl, OCH2), (A336, F, F, OMe, 1-neopentyloxy-3,3-dimethylbutyl, OCH2), (A337, F, F, Me, 3-methyloxypropyl, CH2CH2), (A338, F, F, Me, 3-methyloxybutyl, CH2CH2), (A340, F, F, Me, 3-methyloxy-4-methylpentyl, CH2CH2), (A342, F, F, Me, 3-methyloxy-5-methylhexyl, CH2CH2), (A343, F, F, Me, 3-methyloxyoctyl, CH2CH2), (A344, F, F, Me, 3-methyloxy-5,5-dimethylhexyl, CH2CH2), (A345, F, F, Me, 3-ethyloxybutyl, CH2CH2), (A348, F, F, Me, 3-ethyloxy-4-methylpentyl, CH2CH2), (A350, F, F, Me, 3-ethyloxy-5-methylhexyl, CH2CH2), (A352, F, F, Me, 3-ethyloxyoctyl, CH2CH2), (A353, F, F, Me, 3-ethyloxy-5,5-dimethylhexyl, CH2CH2), (A354, F, F, Me, 3-n-propyloxybutyl, CH2CH2), (A355, F, F, Me, 3-n-propyloxypentyl, CH2CH2), (A356, F, F, Me, 3-n-propyloxyhexyl, CH2CH2), (A357, F, F, Me, 3-n-propyloxy-4-methylpentyl, CH2CH2), (A358, F, F, Me, 3-n-propyloxyheptyl, CH2CH2), (A359, F, F, Me, 3-n-propyloxy-5-methylhexyl, CH2CH2), (A360, F, F, Me, 3-n-propyloxy-4,4-dimethylpentyl, CH2CH2), (A361, F, F, Me, 3-n-propyloxyoctyl, CH2CH2), (A362, F, F, Me, 3-n-propyloxy-5,5-dimethylhexyl, CH2CH2), (A363, F, F, Me, 3-isopropyloxybutyl, CH2CH2), (A364, F, F, Me, 3-isopropyloxypentyl, CH2CH2), (A365, F, F, Me, 3-isopropyloxyhexyl, CH2CH2), (A366, F, F, Me, 3-isopropyloxy-4-methylpentyl, CH2CH2), (A367, F, F, Me, 3-isopropyloxyheptyl, CH2CH2), (A368, F, F, Me, 3-isopropyloxy-5-methylhexyl, CH2CH2), (A369, F, F, Me, 3-isopropyloxy-4,4-dimethylpentyl, CH2CH2), (A370, F, F, Me, 3-isopropyloxyoctyl, CH2CH2), (A371, F, F, Me, 3-isopropyloxy-5,5-dimethylhexyl, CH2CH2), (A372, F, F, Me, 3-n-butyloxybutyl, CH2CH2), (A373, F, F, Me, 3-n-butyloxypentyl, CH2CH2), (A374, F, F, Me, 3-n-butyloxyhexyl, CH2CH2), (A375, F, F, Me, 3-n-butyloxy-4-methylpentyl, CH2CH2), (A376, F, F, Me, 3-n-butyloxyheptyl, CH2CH2), (A377, F, F, Me, 3-n-butyloxy-5-methylhexyl, CH2CH2), (A378, F, F, Me, 3-n-butyloxy-4,4-dimethylpentyl, CH2CH2), (A379, F, F, Me, 3-n-butyloxyoctyl, CH2CH2), (A380, F, F, Me, 3-n-butyloxy-5,5-dimethylhexyl, CH2CH2), (A381, F, F, Me, 3-isobutyloxypropyl, CH2CH2), (A382, F, F, Me, 3-isobutyloxybutyl, CH2CH2), (A383, F, F, Me, 3-isobutyloxypentyl, CH2CH2), (A384, F, F, Me, 3-isobutyloxyhexyl, CH2CH2), (A385, F, F, Me, 3-isobutyloxy-4-methylpentyl, CH2CH2), (A386, F, F, Me, 3-isobutyloxyheptyl, CH2CH2), (A387, F, F, Me, 3-isobutyloxy-5-methylhexyl, CH2CH2), (A388, F, F, Me, 3-isobutyloxy-4,4-dimethylpentyl, CH2CH2), (A389, F, F, Me, 3-isobutyloxyoctyl, CH2CH2), (A390, F, F, Me, 3-isobutyloxy-5,5-dimethylhexyl, CH2CH2), (A391, F, F, Me, 3-t-butyloxypropyl, CH2CH2), (A392, F, F, Me, 3-t-butyloxybutyl, CH2CH2), (A393, F, F, Me, 3-t-butyloxypentyl, CH2CH2), (A394, F, F, Me, 3-t-butyloxyhexyl, CH2CH2), (A395, F, F, Me, 3-t-butyloxy-4-methylpentyl, CH2CH2), (A396, F, F, Me, 3-t-butyloxyheptyl, CH2CH2), (A397, F, F, Me, 3-t-butyloxy-5-methylhexyl, CH2CH2), (A398, F, F, Me, 3-t-butyloxy-4,4-dimethylpentyl, CH2CH2), (A399, F, F, Me, 3-t-butyloxyoctyl, CH2CH2), (A400, F, F, Me, 3-t-butyloxy-5,5-dimethylhexyl, CH2CH2), (A402, F, F, Me, 3-n-pentyloxybutyl, CH2CH2), (A403, F, F, Me, 3-n-pentyloxypentyl, CH2CH2), (A404, F, F, Me, 3-n-pentyloxyhexyl, CH2CH2), (A405, F, F, Me, 3-n-pentyloxy-4-methylpentyl, CH2CH2), (A406, F, F, Me, 3-n-pentyloxyheptyl, CH2CH2), (A407, F, F, Me, 3-n-pentyloxy-5-methylhexyl, CH2CH2), (A408, F, F, Me, 3-n-pentyloxy-4,4-dimethylpentyl, CH2CH2), (A409, F, F, Me, 3-n-pentyloxyoctyl, CH2CH2), (A410, F, F, Me, 3-n-pentyloxy-5,5-dimethylhexyl, CH2CH2), (A411, F, F, Me, 3-neopentyloxybutyl, CH2CH2), (A412, F, F, Me, 3-neopentyloxypentyl, CH2CH2), (A413, F, F, Me, 3-neopentyloxyhexyl, CH2CH2), (A414, F, F, Me, 3-neopentyloxy-4-methylpentyl, CH2CH2), (A415, F, F, Me, 3-neopentyloxyheptyl, CH2CH2), (A416, F, F, Me, 3-neopentyloxy-5-methylhexyl, CH2CH2), (A417, F, F, Me, 3-neopentyloxy-4,4-dimethylpentyl, CH2CH2), (A418, F, F, Me, 3-neopentyloxyoctyl, CH2CH2), (A419, F, F, Me, 3-neopentyloxy-5,5-dimethylhexyl, CH2CH2), (A420, F, F, OMe, 3-methyloxypropyl, CH2CH2), (A421, F, F, OMe, 3-methyloxybutyl, CH2CH2), (A422, F, F, OMe, 3-methyloxypentyl, CH2CH2), (A424, F, F, OMe, 3-methyloxy-4-methylpentyl, CH2CH2), (A425, F, F, OMe, 3-methyloxyheptyl, CH2CH2), (A426, F, F, OMe, 3-methyloxy-5-methylhexyl, CH2CH2), (A427, F, F, OMe, 3-metoxy-4,4-dimethylpentyl, CH2CH2), (A428, F, F, OMe, 3-methyloxyoctyl, CH2CH2), (A429, F, F, OMe, 3-methyloxy-5,5-dimethylhexyl, CH2CH2), (A431, F, F, OMe, 3-ethyloxybutyl, CH2CH2), (A432, F, F, OMe, 3-ethyloxypentyl, CH2CH2), (A433, F, F, OMe, 3-ethyloxyhexyl, CH2CH2), (A434, F, F, OMe, 3-ethyloxy-4-methylpentyl, CH2CH2), (A435, F, F, OMe, 3-ethyloxyheptyl, CH2CH2), (A436, F, F, OMe, 3-ethyloxy-5-methylhexyl, CH2CH2), (A437, F, F, OMe, 3-ethyloxy-4,4-dimethylpentyl, CH2CH2), (A438, F, F, OMe, 3-ethyloxyoctyl, CH2CH2), (A439, F, F, OMe, 3-ethyloxy-5,5-dimethylhexyl, CH2CH2), (A441, F, F, OMe, 3-n-propyloxybutyl, CH2CH2), (A442, F, F, OMe, 3-n-propyloxypentyl, CH2CH2), (A443, F, F, OMe, 3-n-propyloxyhexyl, CH2CH2), (A444, F, F, OMe, 3-n-propyloxy-4-methylpentyl, CH2CH2), (A445, F, F, OMe, 3-n-propyloxyheptyl, CH2CH2), (A446, F, F, OMe, 3-n-propyloxy-5-methylhexyl, CH2CH2), (A447, F, F, OMe, 3-n-propyloxy-4,4-dimethylpentyl, CH2CH2), (A448, F, F, OMe, 3-n-propyloxyoctyl, CH2CH2), (A449, F, F, OMe, 3-n-propyloxy-5,5-dimethylhexyl, CH2CH2), (A451, F, F, OMe, 3-isopropyloxybutyl, CH2CH2), (A452, F, F, OMe, 3-isopropyloxypentyl, CH2CH2), (A453, F, F, OMe, 3-isopropyloxyhexyl, CH2CH2), (A454, F, F, OMe, 3-isopropyloxy-4-methylpentyl, CH2CH2), (A455, F, F, OMe, 3-isopropyloxyheptyl, CH2CH2), (A456, F, F, OMe, 3-isopropyloxy-5-methylhexyl, CH2CH2), (A457, F, F, OMe, 3-isopropyloxy-4,4-dimethylpentyl, CH2CH2), (A458, F, F, OMe, 3-isopropyloxyoctyl, CH2CH2), (A459, F, F, OMe, 3-isopropyloxy-5,5-dimethylhexyl, CH2CH2), (A460, F, F, OMe, 3-n-butyloxypropyl, CH2CH2), (A461, F, F, OMe, 3-n-butyloxybutyl, CH2CH2), (A462, F, F, OMe, 3-n-butyloxypentyl, CH2CH2), (A463, F, F, OMe, 3-n-butyloxyhexyl, CH2CH2), (A464, F, F, OMe, 3-n-butyloxy-4-methylpentyl, CH2CH2), (A465, F, F, OMe, 3-n-butyloxyheptyl, CH2CH2), (A466, F, F, OMe, 3-n-butyloxy-5-methylhexyl, CH2CH2), (A467, F, F, OMe, 3-n-butyloxy-4,4-dimethylpentyl, CH2CH2), (A468, F, F, OMe, 3-n-butyloxyoctyl, CH2CH2), (A469, F, F, OMe, 3-n-butyloxy-5,5-dimethylhexyl, CH2CH2), (A470, F, F, OMe, 3-isobutyloxypropyl, CH2CH2), (A471, F, F, OMe, 3-isobutyloxybutyl, CH2CH2), (A472, F, F, OMe, 3-isobutyloxypentyl, CH2CH2), (A473, F, F, OMe, 3-isobutyloxyhexyl, CH2CH2), (A474, F, F, OMe, 3-isobutyloxy-4-methylpentyl, CH2CH2), (A475, F, F, OMe, 3-isobutyloxyheptyl, CH2CH2), (A476, F, F. OMe, 3-isobutyloxy-5-methylhexyl, CH2CH2), (A477, F, F, OMe, 3-isobutyloxy-4,4-dimethylpentyl, CH2CH2), (A478, F, F, OMe, 3-isobutyloxyoctyl, CH2CH2), (A479, F, F, OMe, 3-isobutyloxy-5,5-dimethylhexyl, CH2CH2), (A480, F, F, OMe, 3-t-butyloxypropyl, CH2CH2), (A481, F, F, OMe, 3-t-butyloxybutyl, CH2CH2), (A482, F, F, OMe, 3-t-butyloxypentyl, CH2CH2), (A483, F, F, OMe, 3-t-butyloxyhexyl, CH2CH2), (A484, F, F, OMe, 3-t-butyloxy-4-methylpentyl, CH2CH2), (A485, F, F, OMe, 3-t-butyloxyheptyl, CH2CH2), (A486, F, F, OMe, 3-t-butyloxy-5-methylhexyl, CH2CH2), (A487, F, F, OMe, 3-t-butyloxy-4,4-dimethylpentyl, CH2CH2), (A488, F, F, OMe, 3-t-butyloxyoctyl, CH2CH2), (A489, F, F, OMe, 3-t-butyloxy-5,5-dimethylhexyl, CH2CH2), (A490, F, F, OMe, 3-n-pentyloxypropyl, CH2CH2), (A491, F, F, OMe, 3-n-pentyloxybutyl, CH2CH2), (A492, F, F, OMe, 3-n-pentyloxypentyl, CH2CH2), (A493, F, F, OMe, 3-n-pentyloxyhexyl, CH2CH2), (A494, F, F, OMe, 3-n-pentyloxy-4-methylpentyl, CH2CH2), (A495, F, F, OMe, 3-n-pentyloxyheptyl, CH2CH2), (A496, F, F, OMe, 3-n-pentyloxy-5-methylhexyl, CH2CH2), (A497, F, F, OMe, 3-n-pentyloxy-4,4-dimethylpentyl, CH2CH2), (A498, F, F, OMe, 3-n-pentyloxyoctyl, CH2CH2), (A499, F, F, OMe, 3-n-pentyloxy-5,5-dimethylhexyl, CH2CH2), (A501, F, F, OMe, 3-neopentyloxybutyl, CH2CH2), (A502, F, F, OMe, 3-neopentyloxypentyl, CH2CH2), (A503, F, F, OMe, 3-neopentyloxyhexyl, CH2CH2), (A504, F, F, OMe, 3-neopentyloxy-4-methylpentyl, CH2CH2), (A505, F, F, OMe, 3-neopentyloxyheptyl, CH2CH2), (A506, F, F, OMe, 3-neopentyloxy-5-methylhexyl, CH2CH2), (A507, F, F, OMe, 3-neopentyloxy-4,4-dimethylpentyl, CH2CH2), (A508, F, F, OMe, 3-neopentyloxyoctyl, CH2CH2), (A509, F, F, OMe, 3-neopentyloxy-5,5-dimethylhexyl, CH2CH2), (A510, F, F, OMe, 3-methyloxypropyl, OCH2), (A511, F, F, OMe, 3-methyloxybutyl, OCH2), (A512, F, F, OMe, 3-methyloxypentyl, OCH2), (A513, F, F, OMe, 3-methyloxyhexyl, OCH2), (A514, F, F, OMe, 3-methyloxy-4-methylpentyl, OCH2), (A515, F, F, OMe, 3-methyloxyheptyl, OCH2), (A516, F, F, OMe, 3-methyloxy-5-methylhexyl, OCH2), (A517, F, F, OMe, 3-metoxy-4,4-dimethylpentyl, OCH2), (A518, F, F, OMe, 3-methyloxyoctyl, OCH2), (A519, F, F, OMe, 3-methyloxy-5,5-dimethylhexyl, OCH2), (A520, F, F, OMe, 3-ethyloxypropyl, OCH2), (A521, F, F, OMe, 3-ethyloxybutyl, OCH2), (A522, F, F, OMe, 3-ethyloxypentyl, OCH2), (A523, F, F, OMe, 3-ethyloxyhexyl, OCH2), (A524, F, F, OMe, 3-ethyloxy-4-methylpentyl, OCH2), (A525, F, F, OMe, 3-ethyloxyheptyl, OCH2), (A526, F, F, OMe, 3-ethyloxy-5-methylhexyl, OCH2), (A527, F, F, OMe, 3-ethyloxy-4,4-dimethylpentyl, OCH2), (A528, F, F, OMe, 3-ethyloxyoctyl, OCH2), (A529, F, F, OMe, 3-ethyloxy-5,5-dimethylhexyl, OCH2), (A530, F, F, OMe, 3-n-propyloxypropyl, OCH2), (A531, F, F, OMe, 3-n-propyloxybutyl, OCH2), (A532, F, F, OMe, 3-n-propyloxypentyl, OCH2), (A533, F, F, OMe, 3-n-propyloxyhexyl, OCH2), (A534, F, F, OMe, 3-n-propyloxy-4-methylpentyl, OCH2), (A535, F, F, OMe, 3-n-propyloxyheptyl, OCH2), (A536, F, F, OMe, 3-n-propyloxy-5-methylhexyl, OCH2), (A537, F, F, OMe, 3-n-propyloxy-4,4-dimethylpentyl, OCH2), (A538, F, F, OMe, 3-n-propyloxyoctyl, OCH2), (A539, F, F, OMe, 3-n-propyloxy-5,5-dimethylhexyl, OCH2), (A540, F, F, OMe, 3-isopropyloxypropyl, OCH2), (A541, F, F, OMe, 3-isopropyloxybutyl, OCH2), (A542, F, F, OMe, 3-isopropyloxypentyl, OCH2), (A543, F, F, OMe, 3-isopropyloxyhexyl, OCH2), (A544, F, F, OMe, 3-isopropyloxy-4-methylpentyl, OCH2), (A545, F, F, OMe, 3-isopropyloxyheptyl, OCH2), (A546, F, F, OMe, 3-isopropyloxy-5-methylhexyl, OCH2), (A547, F, F, OMe, 3-isopropyloxy-4,4-dimethylpentyl, OCH2), (A548, F, F, OMe, 3-isopropyloxyoctyl, OCH2), (A549, F, F, OMe, 3-isopropyloxy-5,5-dimethylhexyl, OCH2), (A550, F, F, OMe, 3-n-butyloxypropyl, OCH2), (A551, F, F, OMe, 3-n-butyloxybutyl, OCH2), (A552, F, F, OMe, 3-n-butyloxypentyl, OCH2), (A553, F, F, OMe, 3-n-butyloxyhexyl, OCH2), (A554, F, F, OMe, 3-n-butyloxy-4-methylpentyl, OCH2), (A555, F, F, OMe, 3-n-butyloxyheptyl, OCH2), (A556, F, F, OMe, 3-n-butyloxy-5-methylhexyl, OCH2), (A557, F, F, OMe, 3-n-butyloxy-4,4-dimethylpentyl, OCH2), (A558, F, F, OMe, 3-n-butyloxyoctyl, OCH2), (A559, F, F, OMe, 3-n-butyloxy-5,5-dimethylhexyl, OCH2), (A560, F, F, OMe, 3-isobutyloxypropyl, OCH2), (A561, F, F, OMe, 3-isobutyloxybutyl, OCH2), (A562, F, F, OMe, 3-isobutyloxypentyl, OCH2), (A563, F, F, OMe, 3-isobutyloxyhexyl, OCH2), (A564, F, F, OMe, 3-isobutyloxy-4-methylpentyl, OCH2), (A565, F, F, OMe, 3-isobutyloxyheptyl, OCH2), (A566, F, F, OMe, 3-isobutyloxy-5-methylhexyl, OCH2), (A567, F, F, OMe, 3-isobutyloxy-4,4-dimethylpentyl, OCH2), (A568, F, F, OMe, 3-isobutyloxyoctyl, OCH2), (A569, F, F, OMe, 3-isobutyloxy-5,5-dimethylhexyl, OCH2), (A570, F, F, OMe, 3-t-butyloxypropyl, OCH2), (A571, F, F, OMe, 3-t-butyloxybutyl, OCH2), (A572, F, F. OMe, 3-t-butyloxypentyl, OCH2), (A573, F, F, OMe, 3-t-butyloxyhexyl, OCH2), (A574, F, F, OMe, 3-t-butyloxy-4-methylpentyl, OCH2), (A575, F, F, OMe, 3-t-butyloxyheptyl, OCH2), (A576, F, F, OMe, 3-t-butyloxy-5-methylhexyl, OCH2), (A577, F, F, OMe, 3-t-butyloxy-4,4-dimethylpentyl, OCH2), (A578, F, F, OMe, 3-t-butyloxyoctyl, OCH2), (A579, F, F, OMe, 3-t-butyloxy-5,5-dimethylhexyl, OCH2), (A580, F, F, OMe, 3-n-pentyloxypropyl, OCH2), (A581, F, F, OMe, 3-n-pentyloxybutyl, OCH2), (A582, F, F, OMe, 3-n-pentyloxypentyl, OCH2), (A583, F, F, OMe, 3-n-pentyloxyhexyl, OCH2), (A584, F, F, OMe, 3-n-pentyloxy-4-methylpentyl, OCH2), (A585, F, F, OMe, 3-n-pentyloxyheptyl, OCH2), (A586, F, F, OMe, 3-n-pentyloxy-5-methylhexyl, OCH2), (A587, F, F, OMe, 3-n-pentyloxy-4,4-dimethylpentyl, OCH2), (A588, F, F, OMe, 3-n-pentyloxyoctyl, OCH2), (A589, F, F, OMe, 3-n-pentyloxy-5,5-dimethylhexyl: OCH2), (A590, F, F, OMe, 3-neopentyloxypropyl, OCH2), (A591, F, F, OMe, 3-neopentyloxybutyl, OCH4), (A592, F, F, OMe, 3-neopentyloxypentyl, OCH2), (A593, F, F, OMe, 3-neopentyloxyhexyl, OCH2), (A594, F, F, OMe, 3-neopentyloxy-4-methylpentyl, OCH2), (A595, F, F, OMe, 3-neopentyloxyheptyl, OCH2), (A596, F, F, OMe, 3-neopentyloxy-5-methylhexyl, OCH2), (A597, F, F, OMe, 3-neopentyloxy-4,4-dimethylpentyl, OCH2), (A598, F, F, OMe, 3-neopentyloxyoctyl, OCH2), (A599, F, F, OMe, 3-neopentyloxy-5,5-dimethylhexyl, OCH2), (A600, Cl, Cl, Me, n-pentyl, CH2CH2), (A602, Cl, Cl, Me, 1-methyloxyethyl, CH2CH2), (A603, Cl, Cl, Me, 1-methyloxypropyl, CH2CH2), (A604, Cl, Cl, Me, 1-methyloxybutyl, CH2CH2), (A605, Cl, Cl, Me, 1-methyloxy-2-methylpropyl, CH2CH2), (A606, Cl, Cl, Me, 1-methyloxypentyl, CH2CH2), (A607, Cl, Cl, Me, 1-methyloxy-3-methylbutyl, CH2CH2), (A608, Cl, Cl, Me, 1-methyloxy-2,2-dimethylpropyl, CH2CH2), (A609, Cl, Cl, Me, 1-methyloxyhexyl, CH2CH2), (A610, Cl, Cl, Me, 1-methyloxy-3,3-dimethylbutyl, CH2CH2), (A611, Cl, Cl, Me, 1-ethyloxyethyl, CH2CH2), (A612, Cl, Cl, Me, 1-ethyloxypropyl, CH2CH2), (A613, Cl, Cl, Me, 1-ethyloxybutyl, CH2CH2), (A614, Cl, Cl, Me, 1-ethyloxy-2-methylpropyl, CH2CH2), (A615, Cl, Cl, Me, 1-ethyloxypentyl, CH2CH2), (A616, Cl, Cl, Me, 1-ethyloxy-3-methylbutyl, CH2CH2), (A617, Cl, Cl, Me, 1-ethyloxy-2,2-dimethylpropyl, CH2CH2), (A618, Cl, Cl, Me, 1-ethyloxyhexyl, CH2CH2), (A619, Cl, Cl, Me, 1-ethyloxy-3,3-dimethylbutyl, CH2CH2), (A620, Cl, Cl, Me, 1-n-propyloxyethyl, CH2CH2), (A621, Cl, Cl, Me, 1-n-propyloxypropyl, CH2CH2), (A622, Cl, Cl, Me, 1-n-propyloxybutyl, CH2CH2), (A623, Cl, Cl, Me, 1-n-propyloxy-2-methylpropyl, CH2CH2), (A624, Cl, Cl, Me, 1-n-propyloxypentyl, CH2CH2), (A625, Cl, Cl, Me, 1-n-propyloxy-3-methylbutyl, CH2CH2), (A626, Cl, Cl, Me, 1-n-propyloxy-2,2-dimethylpropyl, CH2CH2), (A627, Cl, Cl, Me, 1-n-propyloxy-n-hexyl, CH2CH2), (A628, Cl, Cl, Me, 1-n-propyloxy-3,3-dimethylbutyl, CH2CH2), (A629, Cl, Cl, Me, 1-isopropyloxyethyl, CH2CH2), (A630, Cl, Cl, Me, 1-isopropyloxypropyl, CH2CH2), (A631, Cl, Cl, Me, 1-isopropyloxybutyl, CH2CH2), (A632, Cl, Cl, Me, 1-isopropyloxy-2-methylpropyl, CH2CH2), (A633, Cl, Cl, Me, 1-isopropyloxypentyl, CH2CH2), (A634, Cl, Cl, Me, 1-isopropyloxy-3-methylbutyl, CH2CH2), (A635, Cl, Cl, Me, 1-isopropyloxy-2,2-dimethylpropyl, CH2CH2), (A636, Cl, Cl, Me, 1-isopropyloxyhexyl, CH2CH2), (A637, Cl, Cl, Me, 1-isopropyloxy-3,3-dimethylbutyl, CH2CH2), (A638, Cl, Cl, Me, 1-n-butyloxyethyl, CH2CH2), (A639, Cl, Cl, Me, 1-n-butyloxypropyl, CH2CH2), (A640, Cl, Cl, Me, 1-n-butyloxybutyl, CH2CH2), (A641, Cl, Cl, Me, 1-n-butyloxy-2-methylpropyl, CH2CH2), (A642, Cl, Cl, Me, 1-n-butyloxypentyl, CH2CH2), (A643, Cl, Cl, Me, 1-n-butyloxy-3-methylbutyl, CH2CH2), (A644, Cl, Cl, Me, 1-n-butyloxy-2,2-dimethylpropyl, CH2CH2), (A645, Cl, Cl, Me, 1-n-butyloxyhexyl, CH2CH2), (A646, Cl, Cl, Me, 1-n-butyloxy-3,3-dimethylbutyl, CH2CH2), (A647, Cl, Cl, Me, 1-isobutyloxyethyl, CH2CH2), (A648, Cl, Cl, Me, 1-isobutyloxypropyl, CH2CH2), (A649, Cl, Cl, Me, 1-isobutyloxybutyl, CH2CH2), (A650, Cl, Cl, Me, 1-isobutyloxy-2-methylpropyl, CH2CH2), (A651, Cl, Cl, Me, 1-isobutyloxypentyl, CH2CH2), (A652, Cl, Cl, Me, 1-isobutyloxy-3-methylbutyl, CH2CH2), (A653, Cl, Cl, Me, 1-isobutyloxy-2,2-dimethylpropyl, CH2CH2), (A654, Cl, Cl, Me, 1-isobutyloxyhexyl, CH2CH2), (A655, Cl, Cl, Me, 1-isobutyloxy-3,3-dimethylbutyl, CH2CH2), (A656, Cl, Cl, Me, 1-t-butyloxyethyl, CH2CH2), (A657, Cl, Cl, Me, 1-t-butyloxypropyl, CH2CH2), (A658, Cl, Cl, Me, 1-t-butyloxybutyl, CH2CH2), (A659, Cl, Cl, Me, 1-t-butyloxy-2-methylpropyl, CH2CH2), (A660, Cl, Cl, Me, 1-t-butyloxypentyl, CH2CH2), (A661, Cl, Cl, Me, 1-t-butyloxy-3-methylbutyl, CH2CH2), (A662, Cl, Cl, Me, 1-t-butyloxy-2,2-dimethylpropyl, CH2CH2), (A663, Cl, Cl, Me, 1-t-butyloxyhexyl, CH2CH2), (A664, Cl, Cl, Me, 1-t-butyloxy-3,3-dimethylbutyl, CH2CH2), (A665, Cl, Cl, Me, 1-n-pentyloxyethyl, CH2CH2), (A666, Cl, Cl, Me, 1-n-pentyloxypropyl, CH2CH2), (A667, Cl, Cl, Me, 1-n-pentyloxybutyl, CH2CH2), (A668, Cl, Cl, Me, 1-n-pentyloxy-2-methylpropyl, CH2CH2), (A669, Cl, Cl, Me, 1-n-pentyloxypentyl, CH2CH2), (A670, Cl, Cl, Me, 1-n-pentyloxy-3-methylbutyl, CH2CH2), (A671, Cl, Cl, Me, 1-n-pentyloxy-2,2-dimethylpropyl, CH2CH2), (A672, Cl, Cl, Me, 1-n-pentyloxyhexyl, CH2CH2), (A673, Cl, Cl, Me, 1-n-pentyloxy-3,3-dimethylbutyl, CH2CH2), (A674, Cl, Cl, Me, 1-neopentyloxyethyl, CH2CH2), (A675, Cl, Cl, Me, 1-neopentyloxypropyl, CH2CH2), (A676, Cl, Cl, Me, 1-neopentyloxybutyl, CH2CH2), (A677, Cl, Cl, Me, 1-neopentyloxy-2-methylpropyl, CH2CH2), (A678, Cl, Cl, Me, 1-neopentyloxypentyl, CH2CH2), (A679, Cl, Cl, Me, 1-neopentyloxy-3-methylbutyl, CH2CH2), (A680, Cl, Cl, Me, 1-neopentyloxy-2,2-dimethylpropyl, CH2CH2), (A681, Cl, Cl, Me, 1-neopentyloxyhexyl, CH2CH2), (A682, Cl, Cl, Me, 1-neopentyloxy-3,3-dimethylbutyl, CH2CH2), (A683, Cl, Cl, OMe, 1-methyloxyethyl, CH2CH2), (A684, Cl, Cl, OMe, 1-methyloxypropyl, CH2CH2), (A685, Cl, Cl, OMe, 1-methyloxybutyl, CH2CH2), (A686, Cl, Cl, OMe, 1-methyloxy-2-methylpropyl, CH2CH2), (A687, Cl, Cl, OMe, 1-methyloxypentyl, CH2CH2), (A688, Cl, Cl, OMe, 1-methyloxy-3-methylbutyl, CH2CH2), (A689, Cl, Cl, OMe, 1-methyloxy-2,2-dimethylpropyl, CH2CH2), (A690, Cl, Cl, OMe, 1-methyloxyhexyl, CH2CH2), (A691, Cl, Cl, OMe, 1-methyloxy-3,3-dimethylbutyl, CH2CH2), (A692, Cl, Cl, OMe, 1-ethyloxyethyl, CH2CH2), (A693, Cl, Cl, OMe, 1-ethyloxypropyl, CH2CH2), (A694, Cl, Cl, OMe, 1-ethyloxybutyl, CH2CH2), (A695, Cl, Cl, OMe, 1-ethyloxy-2-methylpropyl, CH2CH2), (A696, Cl, Cl, OMe, 1-ethyloxypentyl, CH2CH2), (A697, Cl, Cl, OMe, 1-ethyloxy-3-methylbutyl, CH2CH2), (A698, Cl, Cl, OMe, 1-ethyloxy-2,2-dimethylpropyl, CH2CH2), (A699, Cl, Cl, OMe, 1-ethyloxyhexyl, CH2CH2), (A700, Cl, Cl, OMe, 1-ethyloxy-3,3-dimethylbutyl, CH2CH2), (A701, Cl, Cl, OMe, 1-n-propyloxyethyl, CH2CH2), (A702, Cl, Cl, OMe, 1-n-propyloxypropyl, CH2CH2), (A703, Cl, Cl, OMe, 1-n-propyloxybutyl, CH2CH2), (A704, Cl, Cl, OMe, 1-n-propyloxy-2-methylpropyl, CH2CH2), (A705, Cl, Cl, OMe, 1-n-propyloxypentyl, CH2CH2), (A706, Cl, Cl, OMe, 1-n-propyloxy-3-methylbutyl, CH2CH2), (A707, Cl, Cl, OMe, 1-n-propyloxy-2,2-dimethylpropyl, CH2CH2), (A708, Cl, Cl, OMe, 1-n-propyloxy-n-hexyl, CH2CH2), (A709, Cl, Cl, OMe, 1-n-propyloxy-3,3-dimethylbutyl, CH2CH2), (A710, Cl, Cl, OMe, 1-isopropyloxyethyl, CH2CH2), (A711, Cl, Cl, OMe, 1-isopropyloxypropyl, CH2CH2), (A712, Cl, Cl, OMe, 1-isopropyloxybutyl, CH2CH2), (A713, Cl, Cl, OMe, 1-isopropyloxy-2-methylpropyl, CH2CH2), (A714, Cl, Cl, OMe, 1-isopropyloxypentyl, CH2CH2), (A715, Cl, Cl, OMe, 1-isopropyloxy-3-methylbutyl, CH2CH2), (A716, Cl, Cl, OMe, 1-isopropyloxy-2,2-dimethylpropyl, CH2CH2), (A717, Cl, Cl, OMe, 1-isopropyloxyhexyl, CH2CH2), (A718, Cl, Cl, OMe, 1-isopropyloxy-3,3-dimethylbutyl, CH2CH2), (A719, Cl, Cl, OMe, 1-n-butyloxyethyl, CH2CH2), (A720, Cl, Cl, OMe, 1-n-butyloxypropyl, CH2CH2), (A721, Cl, Cl, OMe, 1-n-butyloxybutyl, CH2CH2), (A722, Cl, Cl, OMe, 1-n-butyloxy-2-methylpropyl, CH2CH2), (A723, Cl, Cl, OMe, 1-n-butyloxypentyl, CH2CH2), (A724, Cl, Cl, OMe, 1-n-butyloxy-3-methylbutyl, CH2CH2), (A725, Cl, Cl, OMe, 1-n-butyloxy-2,2-dimethylpropyl, CH2CH2), (A726, Cl, Cl, OMe, 1-n-butyloxyhexyl, CH2CH2), (A727, Cl, Cl, OMe, 1-n-butyloxy-3,3-dimethylbutyl, CH2CH2), (A728, Cl, Cl, OMe, 1-isobutyloxyethyl, CH2CH2), (A729, Cl, Cl, OMe, 1-isobutyloxypropyl, CH2CH2), (A730, Cl, Cl, OMe, 1-isobutyloxybutyl, CH2CH2), (A731, Cl, Cl, OMe, 1-isobutyloxy-2-methylpropyl, CH2CH2), (A732, Cl, Cl, OMe, 1-isobutyloxypentyl, CH2CH2), (A733, Cl, Cl, OMe, 1-isobutyloxy-3-methylbutyl, CH2CH2), (A734, Cl, Cl, OMe, 1-isobutyloxy-2,2-dimethylpropyl, CH2CH2), (A735, Cl, Cl, OMe, 1-isobutyloxyhexyl, CH2CH2), (A736, Cl, Cl, OMe, 1-isobutyloxy-3,3-dimethylbutyl, CH2CH2), (A737, Cl, Cl, OMe, 1-t-butyloxyethyl, CH2CH2), (A738; Cl, Cl, OMe, 1-t-butyloxypropyl, CH2CH2), (A739, Cl, Cl, OMe, 1-t-butyloxybutyl, CH2CH2), (A740, Cl, Cl, OMe, 1-t-butyloxy-2-methylpropyl, CH2CH2), (A741, Cl, Cl, OMe, 1-t-butyloxypentyl, CH2CH2), (A742, Cl, Cl, OMe, 1-t-butyloxy-3-methylbutyl, CH2CH2), (A743, Cl, Cl, OMe, 1-t-butyloxy-2,2-dimethylpropyl, CH2CH2), (A744, Cl, Cl, OMe, 1-t-butyloxyhexyl, CH2CH2), (A745, Cl, Cl, OMe, 1-t-butyloxy-3,3-dimethylbutyl, CH2CH2), (A746, Cl, Cl, OMe, 1-n-pentyloxyethyl, CH2CH2), (A747, Cl, Cl, OMe, 1-n-pentyloxypropyl, CH2CH2), (A748, Cl, Cl, OMe, 1-n-pentyloxybutyl, CH2CH2), (A749, Cl, Cl, OMe, 1-n-pentyloxy-2-methylpropyl, CH2CH2), (A750, Cl, Cl, OMe, 1-n-pentyloxypentyl, CH2CH2), (A751, Cl, Cl, OMe, 1-n-pentyloxy-3-methylbutyl, CH2CH2), (A752, Cl, Cl, OMe, 1-n-pentyloxy-2,2-dimethylpropyl, CH2CH2), (A753, Cl, Cl, OMe, 1-n-pentyloxyhexyl, CH2CH2), (A754, Cl, Cl, OMe, 1-n-pentyloxy-3,3-dimethylbutyl, CH2CH2), (A755, Cl, Cl, OMe, 1-neopentyloxyethyl, CH2CH2), (A756, Cl, Cl, OMe, 1-neopentyloxypropyl, CH2CH2), (A757, Cl, Cl, OMe, 1-neopentyloxybutyl, CH2CH2), (A758, Cl, Cl, OMe, 1-neopentyloxy-2-methylpropyl, CH2CH2), (A759, Cl, Cl, OMe, 1-neopentyloxypentyl, CH2CH2), (A760, Cl, Cl, OMe, 1-neopentyloxy-3-methylbutyl, CH2CH2), (A761, Cl, Cl, OMe, 1-neopentyloxy-2,2-dimethylpropyl, CH2CH2), (A762, Cl, Cl, OMe, 1-neopentyloxyhexyl, CH2CH2), (A763, Cl, Cl, OMe, 1-neopentyloxy-3,3-dimethylbutyl, CH2CH2), (A764, Cl, Cl, Me, 1-methyloxyethyl, OCH2), (A765, Cl, Cl, Me, 1-methyloxypropyl, OCH2), (A766, Cl, Cl, Me, 1-methyloxybutyl, OCH2), (A767, Cl, Cl, Me, 1-methyloxy-2-methylpropyl, OCH2), (A768, Cl, Cl, Me, 1-methyloxypentyl, OCH2), (A769, Cl, Cl, Me, 1-methyloxy-3-methylbutyl, OCH2), (A770, Cl, Cl, Me, 1-methyloxy-2,2-dimethylpropyl, OCH2), (A771, Cl, Cl, Me, 1-methyloxyhexyl, OCH2), (A772, Cl, Cl, Me, 1-methyloxy-3,3-dimethylbutyl, OCH2), (A773, Cl, Cl, Me, 1-ethyloxyethyl, OCH2), (A774, Cl, Cl, Me, 1-ethyloxypropyl, OCH2), (A775, Cl, Cl, Me, 1-ethyloxybutyl, OCH2), (A776, Cl, Cl, Me, 1-ethyloxy-2-methylpropyl, OCH2), (A777, Cl, Cl, Me, 1-ethyloxypentyl, OCH2), (A778, Cl, Cl, Me, 1-ethyloxy-3-methylbutyl, OCH2), (A779, Cl, Cl, Me, 1-ethyloxy-2,2-dimethylpropyl, OCH2), (A780, Cl, Cl, Me, 1-ethyloxyhexyl, OCH2), (A781, Cl, Cl, Me, 1-ethyloxy-3,3-dimethylbutyl, OCH2), (A782, Cl, Cl, Me, 1-n-propyloxyethyl, OCH2), (A783, Cl, Cl, Me, 1-n-propyloxypropyl, OCH2), (A784, Cl, Cl, Me, 1-n-propyloxybutyl, OCH2), (A785, Cl, Cl, Me, 1-n-propyloxy-2-methylpropyl, OCH2), (A786, Cl, Cl, Me, 1-n-propyloxypentyl, OCH2), (A787, Cl, Cl, Me, 1-n-propyloxy-3-methylbutyl, OCH2), (A788, Cl, Cl, Me, 1-n-propyloxy-2,2-dimethylpropyl, OCH2), (A789, Cl, Cl, Me, 1-n-propyloxyhexyl, OCH2), (A790, Cl, Cl, Me, 1-n-propyloxy-3,3-dimethylbutyl, OCH2), (A791, Cl, Cl, Me, 1-isopropyloxyethyl, OCH2), (A792, Cl, Cl, Me, 1-isopropyloxypropyl, OCH2), (A793, Cl, Cl, Me, 1-isopropyloxybutyl, OCH2), (A794, Cl, Cl, Me, 1-isopropyloxy-2-methylpropyl, OCH2), (A795, Cl, Cl, Me, 1-isopropyloxypentyl, OCH2), (A796, Cl, Cl, Me, 1-isopropyloxy-3-methylbutyl, OCH2), (A797, Cl, Cl, Me, 1-isopropyloxy-2,2-dimethylpropyl, OCH2), (A798, Cl, Cl, Me, 1-isopropyloxyhexyl, OCH2), (A799, Cl, Cl, Me, 1-isopropyloxy-3,3-dimethylbutyl, OCH2), (A800, Cl, Cl, Me, 1-n-butyloxyethyl, OCH2), (A801, Cl, Cl, Me, 1-n-butyloxypropyl, OCH2), (A802, Cl, Cl, Me, 1-n-butyloxybutyl, OCH2), (A803, Cl, Cl, Me, 1-n-butyloxy-2-methylpropyl, OCH2), (A804, Cl, Cl, Me, 1-n-butyloxypentyl, OCH2), (A805, Cl, Cl, Me, 1-n-butyloxy-3-methylbutyl, OCH2), (A806, Cl, Cl, Me, 1-n-butyloxy-2,2-dimethylpropyl, OCH2), (A807, Cl, Cl, Me, 1-n-butyloxyhexyl, OCH2), (A808, Cl, Cl, Me, 1-n-butyloxy-3,3-dimethylbutyl, OCH2), (A809, Cl, Cl, Me, 1-isobutyloxyethyl, OCH2), (A810, Cl, Cl, Me, 1-isobutyloxypropyl, OCH2), (A811, Cl, Cl, Me, 1-isobutyloxybutyl, OCH2), (A812, Cl, Cl, Me, 1-isobutyloxy-2-methylpropyl, OCH2), (A813, Cl, Cl, Me, 1-isobutyloxypentyl, OCH2), (A814, Cl, Cl, Me, 1-isobutyloxy-3-methylbutyl, OCH2), (A815, Cl, Cl, Me, 1-isobutyloxy-2,2-dimethylpropyl, OCH2), (A816, Cl, Cl, Me, 1-isobutyloxyhexyl, OCH2), (A817, Cl, Cl, Me, 1-isobutyloxy-3,3-dimethylbutyl, OCH2), (A818, Cl, Cl, Me, 1-t-butyloxyethyl, OCH2), (A819, Cl, Cl, Me, 1-t-butyloxypropyl, OCH2), (A820, Cl, Cl, Me, 1-t-butyloxybutyl, OCH2), (A821, Cl, Cl, Me, 1-t-butyloxy-2-methylpropyl, OCH2), (A822, Cl, Cl, Me, 1-t-butyloxypentyl, OCH2), (A823, Cl, Cl, Me, 1-t-butyloxy-3-methylbutyl, OCH2), (A824, Cl, Cl, Me, 1-t-butyloxy-2,2-dimethylpropyl, OCH2), (A825, Cl, Cl, Me, 1-t-butyloxyhexyl, OCH2), (A826, Cl, Cl, Me, 1-t-butyloxy-3,3-dimethylbutyl, OCH2), (A827, Cl, Cl, Me, 1-n-pentyloxyethyl, OCH2), (A828, Cl, Cl, Me, 1-n-pentyloxypropyl, OCH2), (A829, Cl, Cl, Me, 1-n-pentyloxybutyl, OCH2), (A830, Cl, Cl, Me, 1-n-pentyloxy-2-methylpropyl, OCH2), (A831, Cl, Cl, Me, 1-n-pentyloxypentyl, OCH2), (A832, Cl, Cl, Me, 1-n-pentyloxy-3-methylbutyl, OCH2), (A833, Cl, Cl, Me, 1-n-pentyloxy-2,2-dimethylpropyl, OCH2), (A834, Cl, Cl, Me, 1-n-pentyloxyhexyl, OCH2), (A835, Cl, Cl, Me, 1-n-pentyloxy-3,3-dimethylbutyl, OCH2), (A836, Cl, Cl, Me, 1-neopentyloxyethyl, OCH2), (A837, Cl, Cl, Me, 1-neopentyloxypropyl, OCH2), (A838, Cl, Cl, Me, 1-neopentyloxybutyl, OCH2), (A839, Cl, Cl, Me, 1-neopentyloxy-2-methylpropyl, OCH2), (A840, Cl, Cl, Me, 1-neopentyloxypentyl, OCH2), (A841, Cl, Cl, Me, 1-neopentyloxy-3-methylbutyl, OCH2), (A842, Cl, Cl, Me, 1-neopentyloxy-2,2-dimethylpropyl, OCH2), (A843, Cl, Cl, Me, 1-neopentyloxyhexyl, OCH2), (A844, Cl, Cl, Me, 1-neopentyloxy-3,3-dimethylbutyl, OCH2), (A845, Cl, Cl, OMe, 1-methyloxyethyl, OCH2), (A846, Cl, Cl, OMe, 1-methyloxypropyl, OCH2), (A847, Cl, Cl, OMe, 1-methyloxybutyl, OCH2), (A848, Cl, Cl, OMe, 1-methyloxy-2-methylpropyl, OCH2), (A849, Cl, Cl, OMe, 1-methyloxypentyl, OCH2), (A850, Cl, Cl, OMe, 1-methyloxy-3-methylbutyl, OCH2), (A851, Cl, Cl, OMe, 1-methyloxy-2,2-dimethylpropyl, OCH2), (A852, Cl, Cl, OMe, 1-methyloxyhexyl, OCH2), (A853, Cl, Cl, OMe, 1-methyloxy-3,3-dimethylbutyl, OCH2), (A854, Cl, Cl, OMe, 1-ethyloxyethyl, OCH2), (A855, Cl, Cl, OMe, 1-ethyloxypropyl, OCH2), (A856, Cl, Cl, OMe, 1-ethyloxybutyl, OCH2), (A857, Cl, Cl, OMe, 1-ethyloxy-2-methylpropyl, OCH2), (A858, Cl, Cl, OMe, 1-ethyloxypentyl, OCH2), (A859, Cl, Cl, OMe, 1-ethyloxy-3-methylbutyl, OCH2), (A860, Cl, Cl, OMe, 1-ethyloxy-2,2-dimethylpropyl, OCH2), (A861, Cl, Cl, OMe, 1-ethyloxyhexyl, OCH2), (A862, Cl, Cl, OMe, 1-ethyloxy-3,3-dimethylbutyl, OCH2), (A863, Cl, Cl, OMe, 1-n-propyloxyethyl, OCH2), (A864, Cl, Cl, OMe, 1-n-propyloxypropyl, OCH2), (A865, Cl, Cl, OMe, 1-n-propyloxybutyl, OCH2), (A866, Cl, Cl, OMe, 1-n-propyloxy-2-methylpropyl, OCH2), (A867, Cl, Cl, OMe, 1-n-propyloxypentyl, OCH2), (A868, Cl, Cl, OMe, 1-n-propyloxy-3-methylbutyl, OCH2), (A869, Cl, Cl, OMe, 1-n-propyloxy-2,2-dimethylpropyl, OCH2), (A870, Cl, Cl, OMe, 1-n-propyloxyhexyl, OCH2), (A871, Cl, Cl, OMe, 1-n-propyloxy-3,3-dimethylbutyl, OCH2), (A872, Cl, Cl, OMe, 1-isopropyloxyethyl, OCH2), (A873, Cl, Cl, OMe, 1-isopropyloxypropyl, OCH2), (A874, Cl, Cl, OMe, 1-isopropyloxybutyl, OCH2), (A875, Cl, Cl, OMe, 1-isopropyloxy-2-methylpropyl, OCH2), (A876, Cl, Cl, OMe, 1-isopropyloxypentyl, OCH2), (A877, Cl, Cl, OMe, 1-isopropyloxy-3-methylbutyl, OCH2), (A878, Cl, Cl, OMe, 1-isopropyloxy-2,2-dimethylpropyl, OCH2), (A879, Cl, Cl, OMe, 1-isopropyloxyhexyl, OCH2), (A880, Cl, Cl, OMe, 1-isopropyloxy-3,3-dimethylbutyl, OCH2), (A881, Cl, Cl, OMe, 1-n-butyloxyethyl, OCH2), (A882, Cl, Cl, OMe, 1-n-butyloxypropyl, OCH2), (A883, Cl, Cl, OMe, 1-n-butyloxybutyl, OCH2), (A884, Cl, Cl, OMe, 1-n-butyloxy-2-methylpropyl, OCH2), (A885, Cl, Cl, OMe, 1-n-butyloxypentyl, OCH2), (A886, Cl, Cl, OMe, 1-n-butyloxy-3-methylbutyl, OCH2), (A887, Cl, Cl, OMe, 1-n-butyloxy-2,2-dimethylpropyl, OCH2), (A888, Cl, Cl, OMe, 1-n-butyloxyhexyl, OCH2), (A889, Cl, Cl, OMe, 1-n-butyloxy-3,3-dimethylbutyl, OCH2), (A890, Cl, Cl, OMe, 1-isobutyloxyethyl, OCH2), (A891, Cl, Cl, OMe, 1-isobutyloxypropyl, OCH2), (A892, Cl, Cl, OMe, 1-isobutyloxybutyl, OCH2), (A893, Cl, Cl, OMe, 1-isobutyloxy-2-methylpropyl, OCH2), (A894, Cl, Cl, OMe, 1-isobutyloxypentyl, OCH2), (A895, Cl, Cl, OMe, 1-isobutyloxy-3-methylbutyl, OCH2), (A896, Cl, Cl, OMe, 1-isobutyloxy-2,2-dimethylpropyl, OCH2), (A897, Cl, Cl, OMe, 1-isobutyloxyhexyl, OCH2), (A898, Cl, Cl, OMe, 1-isobutyloxy-3,3-dimethylbutyl, OCH2), (A899, Cl, Cl, OMe, .1-t-butyloxyethyl, OCH2), (A900, Cl, Cl, OMe, 1-t-butyloxypropyl, OCH2), (A901, Cl, Cl, OMe, 1-t-butyloxybutyl, OCH2), (A902, Cl, Cl, OMe, 1-t-butyloxy-2-methylpropyl, OCH2), (A903, Cl, Cl, OMe, 1-t-butyloxypentyl, OCH2), (A904, Cl, Cl, OMe, 1-t-butyloxy-3-methylbutyl, OCH2), (A905, Cl, Cl, OMe, 1-t-butyloxy-2,2-dimethylpropyl, OCH2), (A906, Cl, Cl, OMe, 1-t-butyloxyhexyl, OCH2), (A907, Cl, Cl, OMe, 1-t-butyloxy-3,3-dimethylbutyl, OCH2), (A908, Cl, Cl, OMe, 1-n-pentyloxyethyl, OCH2), (A909, Cl, Cl, OMe, 1-n-pentyloxypropyl, OCH2), (A910, Cl, Cl, OMe, 1-n-pentyloxybutyl, OCH2), (A911, Cl, Cl, OMe, 1-n-pentyloxy-2-methylpropyl, OCH2), (A912, Cl, Cl, OMe, 1-n-pentyloxypentyl, OCH2), (A913, Cl, Cl, OMe, 1-n-pentyloxy-3-methylbutyl, OCH2), (A914, Cl, Cl, OMe, 1-n-pentyloxy-2,2-dimethylpropyl, OCH2), (A915, Cl, Cl, OMe, 1-n-pentyloxyhexyl, OCH2), (A916, Cl, Cl, OMe, 1-n-pentyloxy-3,3-dimethylbutyl, OCH2), (A917, Cl, Cl, OMe, 1-neopentyloxyethyl, OCH2), (A918, Cl, Cl, OMe, 1-neopentyloxypropyl, OCH2), (A919, Cl, Cl, OMe, 1-neopentyloxybutyl, OCH2), (A920, Cl, Cl, OMe, 1-neopentyloxy-2-methylpropyl, OCH2), (A921, Cl, Cl, OMe, 1-neopentyloxypentyl, OCH2), (A922, Cl, Cl, OMe, 1-neopentyloxy-3-methylbutyl, OCH2), (A923, Cl, Cl, OMe, 1-neopentyloxy-2,2-dimethylpropyl, OCH2), (A924, Cl, Cl, OMe, 1-neopentyloxyhexyl, OCH2), (A925, Cl, Cl, OMe, 1-neopentyloxy-3,3-dimethylbutyl, OCH2), (A926, Cl, Cl, Me, 3-methyloxypropyl, CH2CH2), (A927, Cl, Cl, Me, 3-methyloxybutyl, CH2CH2), (A929, Cl, Cl, Me, 3-methyloxy-4-methylpentyl, CH2CH2), (A931, Cl, Cl, Me, 3-methyloxy-5-methylhexyl, CH2CH2), (A933, Cl, Cl, Me, 3-methyloxyoctyl, CH2CH2), (A934, Cl, Cl, Me, 3-methyloxy-5,5-dimethylhexyl, CH2CH2), (A935, Cl, Cl, Me, 3-ethyloxybutyl, CH2CH2), (A938, Cl, Cl, Me, 3-ethyloxy-4-methylpentyl, CH2CH2), (A940, Cl, Cl, Me, 3-ethyloxy-5-methylhexyl, CH2CH2), (A942, Cl, Cl, Me, 3-ethyloxyoctyl, CH2CH2), (A943, Cl, Cl, Me, 3-ethyloxy-5,5-dimethylhexyl, CH2CH2), (A945, Cl, Cl, Me, 3-n-propyloxybutyl, CH2CH2), (A946, Cl, Cl, Me, 3-n-propyloxypentyl, CH2CH2), (A947, Cl, Cl, Me, 3-n-propyloxyhexyl, CH2CH2), (A948, Cl, Cl, Me, 3-n-propyloxy-4-methylpentyl, CH2CH2), (A949, Cl, Cl, Me, 3-n-propyloxyheptyl, CH2CH2), (A950, Cl, Cl, Me, 3-n-propyloxy-5-methylhexyl, CH2CH2), (A951, Cl, Cl, Me, 3-n-propyloxy-4,4-dimethylpentyl, CH2CH2), (A952, Cl, Cl, Me, 3-n-propyloxyoctyl, CH2CH2), (A953, Cl, Cl, Me, 3-n-propyloxy-5,5-dimethylhexyl, CH2CH2), (A955, Cl, Cl, Me, 3-isopropyloxybutyl, CH2CH2), (A956, Cl, Cl, Me, 3-isopropyloxypentyl, CH2CH2), (A957, Cl, Cl, Me, 3-isopropyloxyhexyl, CH2CH2), (A958, Cl, Cl, Me, 3-isopropyloxy-4-methylpentyl, CH2CH2), (A959, Cl, Cl, Me, 3-isopropyloxyheptyl, CH2CH2), (A960, Cl, Cl, Me, 3-isopropyloxy-5-methylhexyl, CH2CH2), (A961, Cl, Cl, Me, 3-isopropyloxy-4,4-dimethylpentyl, CH2CH2), (A962, Cl, Cl, Me, 3-isopropyloxyoctyl, CH2CH2), (A963, Cl, Cl, Me, 3-isopropyloxy-5,5-dimethylhexyl, CH2CH2), (A964, Cl, Cl, Me, 3-n-butyloxybutyl, CH2CH2), (A965, Cl, Cl, Me, 3-n-butyloxypentyl, CH2CH2), (A966, Cl, Cl, Me, 3-n-butyloxyhexyl, CH2CH2), (A967, Cl, Cl, Me, 3-n-butyloxy-4-methylpentyl, CH2CH2), (A968, Cl, Cl, Me, 3-n-butyloxyheptyl, CH2CH2), (A969, Cl, Cl, Me, 3-n-butyloxy-5-methylhexyl, CH2CH2), (A970, Cl, Cl, Me, 3-n-butyloxy-4,4-dimethylpentyl, CH2CH2), (A971, Cl, Cl, Me, 3-n-butyloxyoctyl, CH2CH2), (A972, Cl, Cl, Me, 3-n-butyloxy-5,5-dimethylhexyl, CH2CH2), (A973, Cl, Cl, Me, 3-isobutyloxypropyl, CH2CH2), (A974, Cl, Cl, Me, 3-isobutyloxybutyl, CH2CH2), (A975, Cl, Cl, Me, 3-isobutyloxypentyl, CH2CH2), (A976, Cl, Cl, Me, 3-isobutyloxyhexyl, CH2CH2), (A977, Cl, Cl, Me, 3-isobutyloxy-4-methylpentyl, CH2CH2), (A978, Cl, Cl, Me, 3-isobutyloxyheptyl, CH2CH2), (A979, Cl, Cl, Me, 3-isobutyloxy-5-methylhexyl, CH2CH2), (A980, Cl, Cl, Me, 3-isobutyloxy-4,4-dimethylpentyl, CH2CH2), (A981, Cl, Cl, Me, 3-isobutyloxyoctyl, CH2CH2), (A982, Cl, Cl, Me, 3-isobutyloxy-5,5-dimethylhexyl, CH2CH2), (A983, Cl, Cl, Me, 3-t-butyloxypropyl, CH2CH2), (A984, Cl, Cl, Me, 3-t-butyloxybutyl, CH2CH2), (A985, Cl, Cl, Me, 3-t-butyloxypentyl, CH2CH2), (A986, Cl, Cl, Me, 3-t-butyloxyhexyl, CH2CH2), (A987, Cl, Cl, Me, 3-t-butyloxy-4-methylpentyl, CH2CH2), (A988, Cl, Cl, Me, 3-t-butyloxyheptyl, CH2CH2), (A989, Cl, Cl, Me, 3-t-butyloxy-5-methylhexyl, CH2CH2), (A990, Cl, Cl, Me, 3-t-butyloxy-4,4-dimethylpentyl, CH2CH2), (A991, Cl, Cl, Me, 3-t-butyloxyoctyl, CH2CH2), (A992, Cl, Cl, Me, 3-t-butyloxy-5,5-dimethylhexyl, CH2CH2), (A994, Cl, Cl, Me, 3-n-pentyloxybutyl, CH2CH2), (A995, Cl, Cl, Me, 3-n-pentyloxypentyl, CH2CH2), (A996, Cl, Cl, Me, 3-n-pentyloxyhexyl, CH2CH2), (A997, Cl, Cl, Me, 3-n-pentyloxy-4-methylpentyl, CH2CH2), (A998, Cl, Cl; Me, 3-n-pentyloxyheptyl, CH2CH2), (A999, Cl, Cl, Me, 3-n-pentyloxy-5-methylhexyl, CH2CH2), (A1000, Cl, Cl, Me, 3-n-pentyloxy-4,4-dimethylpentyl, CH2CH2), (A1001, Cl, Cl, Me, 3-n-pentyloxyoctyl, CH2CH2), (A1002, Cl, Cl, Me, 3-n-pentyloxy-5,5-dimethylhexyl, CH2CH2), (A1004, Cl, Cl, Me, 3-neopentyloxybutyl, CH2CH2), (A1005, Cl, Cl, Me, 3-neopentyloxypentyl, CH2CH2), (A1006, Cl, Cl, Me, 3-neopentyloxyhexyl, CH2CH2), (A1007, Cl, Cl, Me, 3-neopentyloxy-4-methylpentyl, CH2CH2), (A1008, Cl, Cl, Me, 3-neopentyloxyheptyl, CH2CH2), (A1009, Cl, Cl, Me, 3-neopentyloxy-5-methylhexyl, CH2CH2), (A1010, Cl, Cl, Me, 3-neopentyloxy-4,4-dimethylpentyl, CH2CH2), (A1011, Cl, Cl, Me, 3-neopentyloxyoctyl, CH2CH2), (A1012, Cl, Cl, Me, 3-neopentyloxy-5,5-dimethylhexyl, CH2CH2), (A1013, Cl, Cl, OMe, 3-methyloxypropyl, CH2CH2), (A1014, Cl, Cl, OMe, 3-methyloxybutyl, CH2CH2), (A1015, Cl, Cl, OMe, 3-methyloxypentyl, CH2CH2), (A1017, Cl, Cl, OMe, 3-methyloxy-4-methylpentyl, CH2CH2), (A1019, Cl, Cl, OMe, 3-methyloxy-5-methylhexyl, CH2CH2), (A1020, Cl, Cl, OMe, 3-metoxy-4,4-dimethylpentyl, CH2CH2), (A1021, Cl, Cl, OMe, 3-methyloxyoctyl, CH2CH2), (A1022, Cl, Cl, OMe, 3-methyloxy-5,5-dimethylhexyl, CH2CH2), (A1023, Cl, Cl, OMe, 3-ethyloxypropyl, CH2CH2), (A1024, Cl, Cl, OMe, 3-ethyloxybutyl, CH2CH2), (A1025, Cl, Cl, OMe, 3-ethyloxypentyl, CH2CH2), (A1026, Cl, Cl, OMe, 3-ethyloxyhexyl, CH2CH2), (A1027, Cl, Cl, OMe, 3-ethyloxy-4-methylpentyl, CH2CH2), (A1028, Cl, Cl, OMe, 3-ethyloxyheptyl, CH2CH2), (A1029, Cl, Cl, OMe, 3-ethyloxy-5-methylhexyl, CH2CH2), (A1030, Cl, Cl, OMe, 3-etoxy-4,4-dimethylpentyl, CH2CH2), (A1031, Cl, Cl, OMe, 3-ethyloxyoctyl, CH2CH2), (A1032, Cl, Cl, OMe, 3-ethyloxy-5,5-dimethylhexyl, CH2CH2), (A1034, Cl, Cl, OMe, 3-n-propyloxybutyl, CH2CH2), (A1035, Cl, Cl, OMe, 3-n-propyloxypentyl, CH2CH2), (A1036, Cl, Cl, OMe, 3-n-propyloxyhexyl, CH2CH2), (A1037, Cl, Cl, OMe, 3-n-propyloxy-4-methylpentyl, CH2CH2), (A1038, Cl, Cl, OMe, 3-n-propyloxyheptyl, CH2CH2), (A1039, Cl, Cl, OMe, 3-n-propyloxy-5-methylhexyl, CH2CH2), (A1040, Cl, Cl, OMe, 3-n-propyloxy-4,4-dimethylpentyl, CH2CH2), (A1041, Cl, Cl, OMe, 3-n-propyloxyoctyl, CH2CH2), (A1042, Cl, Cl, OMe, 3-n-propyloxy-5,5-dimethylhexyl, CH2CH2), (A1043, Cl, Cl, OMe, 3-isopropyloxypropyl, CH2CH2), (A1044, Cl, Cl, OMe, 3-isopropyloxybutyl, CH2CH2), (A1045, Cl, Cl, OMe, 3-isopropyloxypentyl, CH2CH2), (A1046, Cl, Cl, OMe, 3-isopropyloxyhexyl, CH2CH2), (A1047, Cl, Cl, OMe, 3-isopropyloxy-4-methylpentyl, CH2CH2), (A1048, Cl, Cl, OMe, 3-isopropyloxyheptyl, CH2CH2), (A1049, Cl, Cl, OMe, 3-isopropyloxy-5-methylhexyl, CH2CH2), (A1050, Cl, Cl, OMe, 3-isopropyloxy-4,4-dimethylpentyl, CH2CH2), (A1051, Cl, Cl, OMe, 3-isopropyloxyoctyl, CH2CH2), (A1052, Cl, Cl, OMe, 3-isopropyloxy-5,5-dimethylhexyl, CH2CH2), (A1053, Cl, Cl, OMe, 3-n-butyloxypropyl, CH2CH2), (A1054, Cl, Cl, OMe, 3-n-butyloxybutyl, CH2CH2), (A1055, Cl, Cl, OMe, 3-n-butyloxypentyl, CH2CH2), (A1056, Cl, Cl, OMe, 3-n-butyloxyhexyl, CH2CH2), (A1057, Cl, Cl, OMe, 3-n-butyloxy-4-methylpentyl, CH2CH2), (A1058, Cl, Cl, OMe, 3-n-butyloxyheptyl, CH2CH2), (A1059, Cl, Cl, OMe, 3-n-butyloxy-5-methylhexyl, CH2CH2), (A1060, Cl, Cl, OMe, 3-n-butyloxy-4,4-dimethylpentyl, CH2CH2), (A1061, Cl, Cl, OMe, 3-n-butyloxyoctyl, CH2CH2), (A1062, Cl, Cl, OMe, 3-n-butyloxy-5,5-dimethylhexyl, CH2CH2), (A1063, Cl, Cl, OMe, 3-isobutyloxypropyl, CH2CH2), (A1064, Cl, Cl, OMe, 3-isobutyloxybutyl, CH2CH2), (A1065, Cl, Cl, OMe, 3-isobutyloxypentyl, CH2CH2), (A1066, Cl, Cl, OMe, 3-isobutyloxyhexyl, CH2CH2), (A1067, Cl, Cl, OMe, 3-isobutyloxy-4-methylpentyl, CH2CH2), (A1068, Cl, Cl, OMe, 3-isobutyloxyheptyl, CH2CH2), (A1069, Cl, Cl, OMe, 3-isobutyloxy-5-methylhexyl, CH2CH2), (A1070, Cl, Cl, OMe, 3-isobutyloxy-4,4-dimethylpentyl, CH2CH2), (A1071, Cl, Cl, OMe, 3-isobutyloxyoctyl, CH2CH2), (A1072, Cl, Cl, OMe, 3-isobutyloxy-5,5-dimethylhexyl, CH2CH2), (A1073, Cl, Cl, OMe, 3-t-butyloxypropyl, CH2CH2), (A1074, Cl, Cl, OMe, 3-t-butyloxybutyl, CH2CH2), (A1075, Cl, Cl, OMe, 3-t-butyloxypentyl, CH2CH2), (A1076, Cl, Cl, OMe, 3-t-butyloxyhexyl, CH2CH2), (A1077, Cl, Cl, OMe, 3-t-butyloxy-4-methylpentyl, CH2CH2), (A1078, Cl, Cl, OMe, 3-t-butyloxyheptyl, CH2CH2), (A1079, Cl, Cl, OMe, 3-t-butyloxy-5-methylhexyl, CH2CH2), (A1080, Cl, Cl, OMe, 3-t-butyloxy-4,4-dimethylpentyl, CH2CH2), (A1081, Cl, Cl, OMe, 3-t-butyloxyoctyl, CH2CH2), (A1082, Cl, Cl, OMe, 3-t-butyloxy-5,5-dimethylhexyl, CH2CH2), (A1083, Cl, Cl, OMe, 3-n-pentyloxypropyl, CH2CH2), (A1084, Cl, Cl, OMe, 3-n-pentyloxybutyl, CH2CH2), (A1085, Cl, Cl, OMe, 3-n-pentyloxypentyl, CH2CH2), (A1086, Cl, Cl, OMe, 3-n-pentyloxyhexyl, CH2CH2), (A1087, Cl, Cl, OMe, 3-n-pentyloxy-4-methylpentyl, CH2CH2), (A1088, Cl, Cl, OMe, 3-n-pentyloxyheptyl, CH2CH2), (A1089, Cl, Cl, OMe, 3-n-pentyloxy-5-methylhexyl, CH2CH2), (A1090, Cl, Cl, OMe, 3-n-pentyloxy-4,4-dimethylpentyl, CH2CH2), (A1091, Cl, Cl, OMe, 3-n-pentyloxyoctyl, CH2CH2), (A1092, Cl, Cl, OMe, 3-n-pentyloxy-5,5-dimethylhexyl, CH2CH2), (A1093, Cl, Cl, OMe, 3-neopentyloxypropyl, CH2CH2), (A1094, Cl, Cl, OMe, 3-neopentyloxybutyl, CH2CH2), (A1095, Cl, Cl, OMe, 3-neopentyloxypentyl, CH2CH2), (A1096, Cl, Cl, OMe, 3-neopentyloxyhexyl, CH2CH2), (A1097, Cl, Cl, OMe, 3-neopentyloxy-4-methylpentyl, CH2CH2), (A1098, Cl, Cl, OMe, 3-neopentyloxyheptyl, CH2CH2), (A1099, Cl, Cl, OMe, 3-neopentyloxy-5-methylhexyl, CH2CH2), (A1100, Cl, Cl, OMe, 3-neopentyloxy-4,4-dimethylpentyl, CH2CH2), (A1101, Cl, Cl, OMe, 3-neopentyloxyoctyl, CH2CH2), (A1102, Cl, Cl, OMe, 3-neopentyloxy-5,5-dimethylhexyl, CH2CH2), (A1103, Cl, Cl, Me, 3-methyloxypropyl, OCH2), (A1104, Cl, Cl, Me, 3-methyloxybutyl, OCH2), (A1105, Cl, Cl, Me, 3-methyloxypentyl, OCH2), (A1106, Cl, Cl, Me, 3-methyloxyhexyl, OCH2), (A1107, Cl, Cl, Me, 3-methyloxy-4-methylpentyl, OCH2), (A1108, Cl, Cl, Me, 3-methyloxyheptyl, OCH2), (A1109, Cl, Cl, Me, 3-methyloxy-5-methylhexyl, OCH2), (A1110, Cl, Cl, Me, 3-metoxy-4,4-dimethylpentyl, OCH2), (A1111, Cl, Cl, Me, 3-methyloxyoctyl, OCH2), (A1112, Cl, Cl, Me, 3-methyloxy-5,5-dimethylhexyl, OCH2), (A1113, Cl, Cl, Me, 3-ethyloxypropyl, OCH2), (A1114, Cl, Cl, Me, 3-ethyloxybutyl, OCH2), (A1115, Cl, Cl, Me, 3-ethyloxypentyl, OCH2), (A1116, Cl, Cl, Me, 3-ethyloxyhexyl, OCH2), (A1117, Cl, Cl, Me, 3-ethyloxy-4-methylpentyl, OCH2), (A1118, Cl, Cl, Me, 3-ethyloxyheptyl, OCH2), (A1119, Cl, Cl, Me, 3-ethyloxy-5-methylhexyl, OCH2), (A1120, Cl, Cl, Me, 3-etoxy-4,4-dimethylpentyl, OCH2), (A1121, Cl, Cl, Me, 3-ethyloxyoctyl, OCH2), (A1122, Cl, Cl, Me, 3-ethyloxy-5,5-dimethylhexyl, OCH2), (A1124, Cl, Cl, Me, 3-n-propyloxybutyl, OCH2), (A1125, Cl, Cl, Me, 3-n-propyloxypentyl, OCH2), (A1126, Cl, Cl, Me, 3-n-propyloxyhexyl, OCH2), (A1127, Cl, Cl, Me, 3-n-propyloxy-4-methylpentyl, OCH2), (A1128, Cl, Cl, Me, 3-n-propyloxyheptyl, OCH2), (A1129, Cl, Cl, Me, 3-n-propyloxy-5-methylhexyl, OCH2), (A1130, Cl, Cl, Me, 3-n-propyloxy-4,4-dimethylpentyl, OCH2), (A1131, Cl, Cl, Me, 3-n-propyloxyoctyl, OCH2), (A1132, Cl, Cl, Me, 3-n-propyloxy-5,5-dimethylhexyl, OCH2), (A1133, Cl, Cl, Me, 3-isopropyloxypropyl, OCH2), (A1134, Cl, Cl, Me, 3-isopropyloxybutyl, OCH2), (A1135, Cl, Cl, Me, 3-isopropyloxypentyl, OCH2), (A1136, Cl, Cl, Me, 3-isopropyloxyhexyl, OCH2), (A1137, Cl, Cl, Me, 3-isopropyloxy-4-methylpentyl, OCH2), (A1138, Cl, Cl, Me, 3-isopropyloxyheptyl, OCH2), (A1139, Cl, Cl, Me, 3-isopropyloxy-5-methylhexyl, OCH2), (A1140, Cl, Cl, Me, 3-isopropyloxy-4,4-dimethylpentyl, OCH2), (A1141, Cl, Cl, Me, 3-isopropyloxyoctyl, OCH2), (A1142, Cl, Cl, Me, 3-isopropyloxy-5,5-dimethylhexyl, OCH2), (A1143, Cl, Cl, Me, 3-n-butyloxypropyl, OCH2), (A1144, Cl, Cl, Me, 3-n-butyloxybutyl, OCH2), (A1145, Cl, Cl, Me, 3-n-butyloxypentyl, OCH2), (A1146, Cl, Cl, Me, 3-n-butyloxyhexyl, OCH2), (A1147, Cl, Cl, Me, 3-n-butyloxy-4-methylpentyl, OCH2), (A1148, Cl, Cl, Me, 3-n-butyloxyheptyl, OCH2), (A1149, Cl, Cl, Me, 3-n-butyloxy-5-methylhexyl, OCH2), (A1150, Cl, Cl, Me, 3-n-butyloxy-4,4-dimethylpentyl, OCH2), (A1151, Cl, Cl, Me, 3-n-butyloxyoctyl, OCH2), (A1152, Cl, Cl, Me, 3-n-butyloxy-5,5-dimethylhexyl, OCH2), (A1153, Cl, Cl, Me, 3-isobutyloxypropyl, OCH2), (A1154, Cl, Cl, Me, 3-isobutyloxybutyl, OCH2), (A1155, Cl, Cl, Me, 3-isobutyloxypentyl, OCH2), (A1156, Cl, Cl, Me, 3-isobutyloxyhexyl, OCH2), (A1157, Cl, Cl, Me, 3-isobutyloxy-4-methylpentyl, OCH2), (A1158, Cl, Cl, Me, 3-isobutyloxyheptyl, OCH2), (A1159, Cl, Cl, Me, 3-isobutyloxy-5-methylhexyl, OCH2), (A1160, Cl, Cl, Me, 3-isobutyloxy-4,4-dimethylpentyl, OCH2), (A1161, Cl, Cl, Me, 3-isobutyloxyoctyl, OCH2), (A1162, Cl, Cl, Me, 3-isobutyloxy-5,5-dimethylhexyl, OCH2), (A1163, Cl, Cl, Me, 3-t-butyloxypropyl, OCH2), (A1164, Cl, Cl, Me, 3-t-butyloxybutyl, OCH2), (A1165, Cl, Cl, Me, 3-t-butyloxypentyl, OCH2), (A1166, Cl, Cl, Me, 3-t-butyloxyhexyl, OCH2), (A1167, Cl, Cl, Me, 3-t-butyloxy-4-methylpentyl, OCH2), (A1168, Cl, Cl, Me, 3-t-butyloxyheptyl, OCH2), (A1169, Cl, Cl, Me, 3-t-butyloxy-5-methylhexyl, OCH2), (A1170, Cl, Cl, Me, 3-t-butyloxy-4,4-dimethylpentyl, OCH2), (A1171, Cl, Cl, Me, 3-t- butyloxyoctyl, OCH2), (A1172, Cl, Cl, Me, 3-t-butyloxy-5,5-dimethylhexyl, OCH2), (A1173, Cl, Cl, Me, 3-n-pentyloxypropyl, OCH2), (A1174, Cl, Cl, Me, 3-n-pentyloxybutyl, OCH2), (A1175, Cl, Cl, Me, 3-n-pentyloxypentyl, OCH2), (A1176, Cl, Cl, Me, 3-n-pentyloxyhexyl, OCH2), (A1177, Cl, Cl, Me, 3-n-pentyloxy-4-methylpentyl, OCH2), (A1178, Cl, Cl, Me, 3-n-pentyloxyheptyl, OCH2), (A1179, Cl, Cl, Me, 3-n-pentyloxy-5-methylhexyl, OCH2), (A1180, Cl, Cl, Me, 3-n-pentyloxy-4,4-dimethylpentyl, OCH2), (A1181, Cl, Cl, Me, 3-n-pentyloxyoctyl, OCH2), (A1182, Cl, Cl, Me, 3-n-pentyloxy-5,5-dimethylhexyl, OCH2), (A1183, Cl, Cl, Me, 3-neopentyloxypropyl, OCH2), (A1184, Cl, Cl, Me, 3-neopentyloxybutyl, OCH2), (A1185, Cl, Cl, Me, 3-neopentyloxypentyl, OCH2), (A1186, Cl, Cl, Me, 3-neopentyloxyhexyl, OCH2), (A1187, Cl, Cl, Me, 3-neopentyloxy-4-methylpentyl, OCH2), (A1188, Cl, Cl, Me, 3-neopentyloxyheptyl, OCH2), (A1189, Cl, Cl, Me, 3-neopentyloxy-5-methylhexyl, OCH2), (A1190, Cl, Cl, Me, 3-neopentyloxy-4,4-dimethylpentyl, OCH2), (A1191, Cl, Cl, Me, 3-neopentyloxyoctyl, OCH2), (A1192, Cl, Cl, Me, 3-neopentyloxy-5,5-dimethylhexyl, OCH2), (A1193, Cl, Cl, OMe, 3-methyloxypropyl, OCH2), (A1194, Cl, Cl, OMe, 3-methyloxybutyl, OCH2), (A1195, Cl, Cl, OMe, 3-methyloxypentyl, OCH2), (A1196, Cl, Cl, OMe, 3-methyloxyhexyl, OCH2), (A1197, Cl, Cl, OMe, 3-methyloxy-4-methylpentyl, OCH2), (A1198, Cl, Cl, OMe, 3-methyloxyheptyl, OCH2), (A1199, Cl, Cl, OMe, 3-methyloxy-5-methylhexyl, OCH2), (A1200, Cl, Cl, OMe, 3-metoxy-4,4-dimethylpentyl, OCH2), (A1201, Cl, Cl, OMe, 3-methyloxyoctyl, OCH2), (A1202, Cl, Cl, OMe, 3-methyloxy-5,5-dimethylhexyl, OCH2), (A1203, Cl, Cl, OMe, 3-ethyloxypropyl, OCH2), (A1204, Cl, Cl, OMe, 3-ethyloxybutyl, OCH2), (A1205, Cl, Cl, OMe, 3-ethyloxypentyl, OCH2), (A1206, Cl, Cl, OMe, 3-ethyloxyhexyl, OCH2), (A1207, Cl, Cl, OMe, 3-ethyloxy-4-methylpentyl, OCH2), (A1208, Cl, Cl, OMe, 3-ethyloxyheptyl, OCH2), (A1209, Cl, Cl, OMe, 3-ethyloxy-5-methylhexyl, OCH2), (A1210, Cl, Cl, OMe, 3-etoxy-4,4-dimethylpentyl, OCH2), (A1211, Cl, Cl, OMe, 3-ethyloxyoctyl, OCH2), (A1212, Cl, Cl, OMe, 3-ethyloxy-5,5-dimethylhexyl, OCH2), (A1213, Cl, Cl, OMe, 3-n-propyloxypropyl, OCH2), (A1214, Cl, Cl, OMe, 3-n-propyloxybutyl, OCH2), (A1215, Cl, Cl, OMe, 3-n-propyloxypentyl, OCH2), (A1216, Cl, Cl, OMe, 3-n-propyloxyhexyl, OCH2), (A1217, Cl, Cl, OMe, 3-n-propyloxy-4-methylpentyl, OCH2), (A1218, Cl, Cl, OMe, 3-n-propyloxyheptyl, OCH2), (A1219, Cl, Cl, OMe, 3-n-propyloxy-5-methylhexyl, OCH2), (A1220, Cl, Cl, OMe, 3-n-propyloxy-4,4-dimethylpentyl, OCH2), (A1221, Cl, Cl, OMe, 3-n-propyloxyoctyl, OCH2), (A1222, Cl, Cl, OMe, 3-n-propyloxy-5,5-dimethylhexyl, OCH2), (A1223, Cl, Cl, OMe, 3-isopropyloxypropyl, OCH2), (A1224, Cl, Cl, OMe, 3-isopropyloxybutyl, OCH2), (A1225, Cl, Cl, OMe, 3-isopropyloxypentyl, OCH2), (A1226, Cl, Cl, OMe, 3-isopropyloxyhexyl, OCH2), (A1227, Cl, Cl, OMe, 3-isopropyloxy-4-methylpentyl, OCH2), (A1228, Cl, Cl, OMe, 3-isopropyloxyheptyl, OCH2), (A1229, Cl, Cl, OMe, 3-isopropyloxy-5-methylhexyl, OCH2), (A1230, Cl, Cl, OMe, 3-isopropyloxy-4,4-dimethylpentyl, OCH2), (A1231, Cl, Cl, OMe, 3-isopropyloxyoctyl, OCH2), (A1232, Cl, Cl, OMe, 3-isopropyloxy-5,5-dimethylhexyl, OCH2), (A1233, Cl, Cl, OMe, 3-n-butyloxypropyl, OCH2), (A1234, Cl, Cl, OMe, 3-n-butyloxybutyl, OCH2), (A1235, Cl, Cl, OMe, 3-n-butyloxypentyl, OCH2), (A1236, Cl, Cl, OMe, 3-n-butyloxyhexyl, OCH2), (A1237, Cl, Cl, OMe, 3-n-butyloxy-4-methylpentyl, OCH2), (A1238, Cl, Cl, OMe, 3-n-butyloxyheptyl, OCH2), (A1239, Cl, Cl, OMe, 3-n-butyloxy-5-methylhexyl, OCH2), (A1240, Cl, Cl, OMe, 3-n-butyloxy-4,4-dimethylpentyl, OCH2), (A1241, Cl, Cl, OMe, 3-n-butyloxyoctyl, OCH2), (A1242, Cl, Cl, OMe, 3-n-butyloxy-5,5-dimethylhexyl, OCH2), (A1243, Cl, Cl, OMe, 3-isobutyloxypropyl, OCH2), (A1244, Cl, Cl, OMe, 3-isobutyloxybutyl, OCH2), (A1245, Cl, Cl, OMe, 3-isobutyloxypentyl, OCH2), (A1246, Cl, Cl, OMe, 3-isobutyloxyhexyl, OCH2), (A1247, Cl, Cl, OMe, 3-isobutyloxy-4-methylpentyl, OCH2), (A1248, Cl, Cl, OMe, 3-isobutyloxyheptyl, OCH2), (A1249, Cl, Cl, OMe, 3-isobutyloxy-5-methylhexyl, OCH2), (A1250, Cl, Cl, OMe, 3-isobutyloxy-4,4-dimethylpentyl, OCH2), (A1251, Cl, Cl, OMe, 3-isobutyloxyoctyl, OCH2), (A1252, Cl, Cl, OMe, 3-isobutyloxy-5,5-dimethylhexyl, OCH2), (A1253, Cl, Cl, OMe, 3-t-butyloxypropyl, OCH2), (A1254, Cl, Cl, OMe, 3-t-butyloxybutyl, OCH2), (A1255, Cl, Cl, OMe, 3-t-butyloxypentyl, OCH2), (A1256, Cl, Cl, OMe, 3-t-butyloxyhexyl, OCH2), (A1257, Cl, Cl, OMe, 3-t-butyloxy-4-methylpentyl, OCH2), (A1258, Cl, Cl, OMe, 3-t-butyloxyheptyl, OCH2), (A1259, Cl, Cl, OMe, 3-t-butyloxy-5-methylhexyl, OCH2), (A1260, Cl, Cl, OMe, 3-t-butyloxy-4,4-dimethylpentyl, OCH2), (A1261, Cl, Cl, OMe, 3-t-butyloxyoctyl, OCH2), (A1262, Cl, Cl, OMe, 3-t-butyloxy-5,5-dimethylhexyl, OCH2), (A1263, Cl, Cl, OMe, 3-n-pentyloxypropyl, OCH2), (A1264, Cl, Cl, OMe, 3-n-pentyloxybutyl, OCH2), (A1265, Cl, Cl, OMe, 3-n-pentyloxypentyl, OCH2), (A1266, Cl, Cl, OMe, 3-n-pentyloxyhexyl, OCH2), (A1267, Cl, Cl, OMe, 3-n-pentyloxy-4-methylpentyl, OCH2), (A1268, Cl, Cl, OMe, 3-n-pentyloxyheptyl, OCH2), (A1269, Cl, Cl, OMe, 3-n-pentyloxy-5-methylhexyl, OCH2), (A1270, Cl, Cl, OMe, 3-n-pentyloxy-4,4-dimethylpentyl, OCH2), (A1271, Cl, Cl, OMe, 3-n-pentyloxyoctyl, OCH2), (A1272, Cl, Cl, OMe, 3-n-pentyloxy-5,5-dimethylhexyl, OCH2), (A1273, Cl, Cl, OMe, 3-neopentyloxypropyl, OCH2), (A1274, Cl, Cl, OMe, 3-neopentyloxybutyl, OCH2), (A1275, Cl, Cl, OMe, 3-neopentyloxypentyl, OCH2), (A1276, Cl, Cl, OMe, 3-neopentyloxyhexyl, OCH2), (A1277, Cl, Cl, OMe, 3-neopentyloxy-4-methylpentyl, OCH2), (A1278, Cl, Cl, OMe, 3-neopentyloxyheptyl, OCH2), (A1279, Cl, Cl, OMe, 3-neopentyloxy-5-methylhexyl, OCH2), (A1280, Cl, Cl, OMe, 3-neopentyloxy-4,4-dimethylpentyl, OCH2), (A1281, Cl, Cl, OMe, 3-neopentyloxyoctyl, OCH2), (A1282, Cl, Cl, OMe, 3-neopentyloxy-5,5-dimethylhexyl, OCH2), (A1283, F, F, F, 3-neopentyloxypropyl, CH2CH2), (A1284, F, F, Cl, 3-neopentyloxypropyl, CH2CH2), (A1285, Cl, Cl, F, 3-methyloxyhexyl, CH2CH2), (A1286, Cl, Cl, Cl, 3-methyloxyhexyl, CH2CH2), (A1287, Cl, Cl, F, 3-ethyloxypropyl, CH2CH2), (A1288, Cl, Cl, Cl, 3-ethyloxypropyl, CH2CH2), (A1289, Cl, Cl, F, 3-n-butyloxypropyl, CH2CH2), (A1290, Cl, Cl, Cl, 3-n-butyloxypropyl, CH2CH2), (A1291, Me, Me, Me, 3-methyloxyhexyl, CH2CH2), (A1292, Me, Me, Me, 3-ethyloxypropyl, CH2CH2), (A1293, Me, Me, Me, 3-n-butyloxypropyl, CH2CH2), (A1294, Me, Me, Me, 3-neopentyloxypropyl, CH2CH2)

Example 79

Synthesis of Compound (B1)

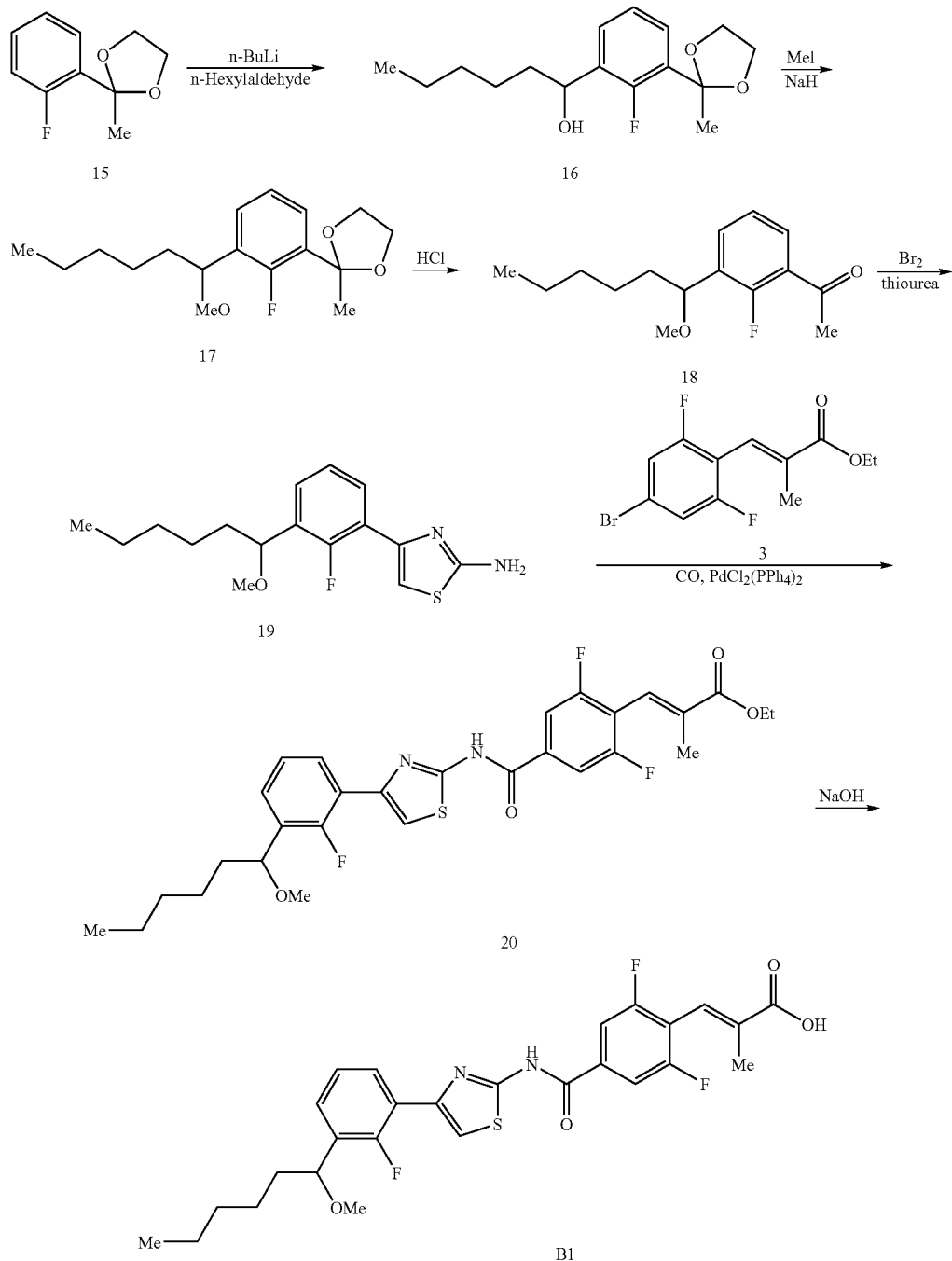

1) Synthesis of 2-[2-fluoro-3-(1-hydoxyhexyl)phenyl]-2-methyl-1,3-dioxolane (16)

To a THF (48 mL) solution of 2-(2-fluorophenyl)-2-methyl-1,3-dioxolane (6.0 g) and N,N,N',N'',N''-pentamethyldiethylenetriamine (8.0 mL) was added 1.58 M hexane solution of n-butyl lithium (25.3 mL) dropwise at −78° C. After the reaction mixture was stirred for 1 h, n-hexylaldehyde (5.88 mL) was added into the reaction mixture. After the reaction mixture was stirred for additional 1 h at −78° C., a saturated ammonium chloride aqueous solution was added into the reaction mixture. The reaction mixture was extracted with ethyl acetate, and the organic layer was washed with water, and brine, dried over magnesium sulfate, and evaporated. The obtained residue was purified by Colum chromatography (hexane:ethyl acetate=4:1) to obtain the compound (16) 6.9 g.

¹H-NMR(CDCl₃) 7.39-7.46 (m, 2H), 7.11 (t, 1H, J=7.6 Hz), 5.02-5.07 (m, 1H), 4.02-4.11 (m, 2H), 3.82-3.91 (m, 2H), 1.73-1.81 (m, 5H), 1.24-1.70 (m, 6H), 0.86-0.86-0.89 (m, 3H).

2) Synthesis of 2-[2-fluoro-3-(1-methyloxyhexyl)phenyl]-2-methyl-1,3-dioxolane (17)

To a DMF (35 mL) solution of 2-[2-fluoro-3-(1-hydroxyhexyl)phenyl]-2-methyl-1,3-dioxolane e (6.9 g) and methyl iodide (6.1 mL) was added sodium hydride (1.96 g) under ice-cooling. After the reaction mixture was stirred at room temperature for 1 h, a saturated ammonium chloride aqueous solution was added into the reaction mixture. The reaction mixture was extracted with ethyl acetate, and the organic layer was washed with water, and brine, dried over magnesium sulfate, and evaporated. The obtained residue was purified by column chromatography (hexane:ethyl acetate=20:1) to obtain the compound (17) 6.99 g.

¹H-NMR(CDCl₃) 7.33-7.44 (m, 2H), 7.12 (t, 1H, J=7.6 Hz), 4.56 (dd, 1H, J=7.6 Hz, 2.1 Hz), 4.02-4.14 (m, 2H), 3.85-3.92 (m, 2H), 3.25 (s, 3H), 1.58-1.77 (m, 5H), 1.21-1.46 (m, 6H), 0.86 (t, 3H, J=6.7 Hz).

3) Synthesis of 2-fluoro-3-(1-methyloxyhexyl)acetophenone (18)

To a methanol (10 mL) solution of 2-[2-fluoro-3-(1-methyloxyhexyl)phenyl]-2-methyl-1,3-dioxolane (6.98 g) was added 35% hydrochloric acid (0.5 mL) at room temperature. A saturated sodium hydrogencarbonate aqueous solution was added into the reaction mixture. The reaction mixture was extracted with ethyl acetate, and the organic layer was dried over magnesium sulfate, and evaporated to obtain the compound (18).

¹H-NMR(CDCl₃) 7.40-7.80 (m, 1H), 7.56-7.62 (m, 1H), 7.21-7.26 (t, 1H, J=7.6 Hz), 4.54-4.58 (m, 1H), 3.26 (s, 3H), 2.66 (d, 3H, J=4.9 Hz), 1.62-1.77 (m, 2H), 1.29-1.44 (m, 6H), 0.85-0.90 (m, 3H).

4) Synthesis of 4-[2-fluoro-3-(1-methyloxyhexyl)phenyl]thiazol-2-ylamine (19)

To a 10% methanol-chloroform (60 mL) solution of 2-fluoro-3-(1-methyloxyhexyl)acetophenone was added bromine (1.21 mL), and the reaction mixture was stirred for 1 h. After the solvent was evaporated, the residue was dissolved in ethanol (60 mL), and thiourea (1.8 g) was added into the reaction mixture. The reaction mixture was heated at reflux for 7 h, and evaporated. A saturated sodium hydrogencarbonate aqueous solution was added into the residue, and the mixture was extracted with ethyl acetate, dried over magnesium sulfate, and evaporated. The obtained residue was purified by colum chromatography (hexane:ethyl acetate=4:1) to obtain the compound (19) 5.0 g.

¹H-NMR(CDCl₃) 7.92 (dt, 1H, J=7.6 Hz, 1.8 Hz), 7.28-7.34 (m, 1H), 7.20 (t, 1H, J=7.6 Hz), 7.02 (d, 1H, J=2.4 Hz), 4.56-4.60 (m, 1H), 3.25 (s, 3H), 1.63-1.83 (m, 2H), 1.24-1.47 (m, 6H), 0.81-0.89 (m, 3H).

5) Synthesis of ethyl 3-(2,6-difluoro-4-{4-[2-fluoro-3-(1-methyloxyhexyl)phenyl]thiazol-2-ylcarbamoyl}phenyl)-2-methylacrylate (20)

To a DMF (6 mL) solution of 4-[2-fluoro-3-(1-methyloxyhexyl)phenyl]thiazol-2-ylamine (318 mg), 3-(4-bromo-2,6-difluoropheny)-2-methylacrylic acid ethyl ester (300 mg), and dichlorobistriphenylphosphinepalladium (36 mg) was added triethylamine (0.43 mL). The reaction mixture was stirred under carbon monoxide atomosphere at 85° C. for 16 h. Water was poured into the reaction mixture, and the reaction mixture extracted with ethyl acetate, and the organic layer was washed with water, and brine, dried over magnesium sulfate, and evaporated. The obtained residue was purified by Colum chromatography (hexane:ethyl acetate=4:1) to obtain the compound (20) 500 mg.

6) Synthesis of 3-(2,6-difluoro-4-{4-[2-fluoro-3-(1-methyloxyhexyl)phenyl]thiazol-2-ylcarbamoyl}phenyl)-2-methylacrylic acid (B1)

To a mixture of THF (2 mL), methanol (2 mL), and 2N sodium hydroxide aqueous solution of 3-(2,6-difluoro-4-{4-[2-fluoro-3-(1-methyloxyhexyl)phenyl]thiazol-2-ylcarbamoyl}phenyl}-2-methylacrylic acid ethyl ester (500 mg) was stirred at room temperature for 3 h. The reaction mixture was acidified with hydrochloric acid, and extracted with ethyl acetate. The organic layer was washed with water, and brine, dried over magnesium sulfate, and evaporated. The residue was recrystallized from ethyl acetate to obtain the compoumd (B1) 370 mg.

1H-NMR(DMSO-d6) 13.02 (bs, 2H), 7.94-8.08 (m, 3H), 7.66 (d, 1H, J=2.1Hz), 7.30-7.42 (m, 3H), 4.57 (t, 1H, J=6.4 Hz), 3.18 (s, 3H), 1.81 (s, 3H), 1.60-1.81 (m, 2H), 1.20-1.50 (m, 6H), 0.80-0.90 (m, 3H).

Example 80

Synthesis of Compound (B533)

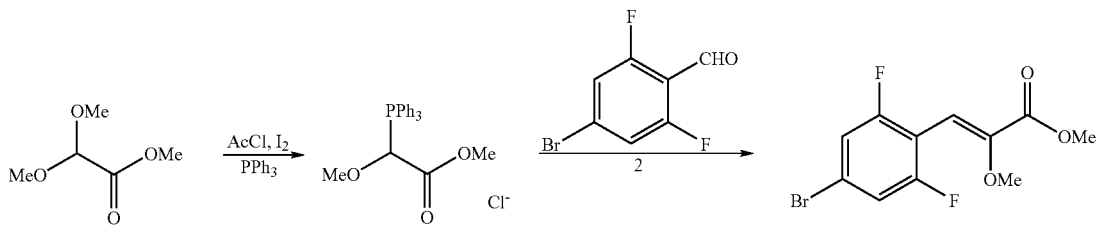

-continued

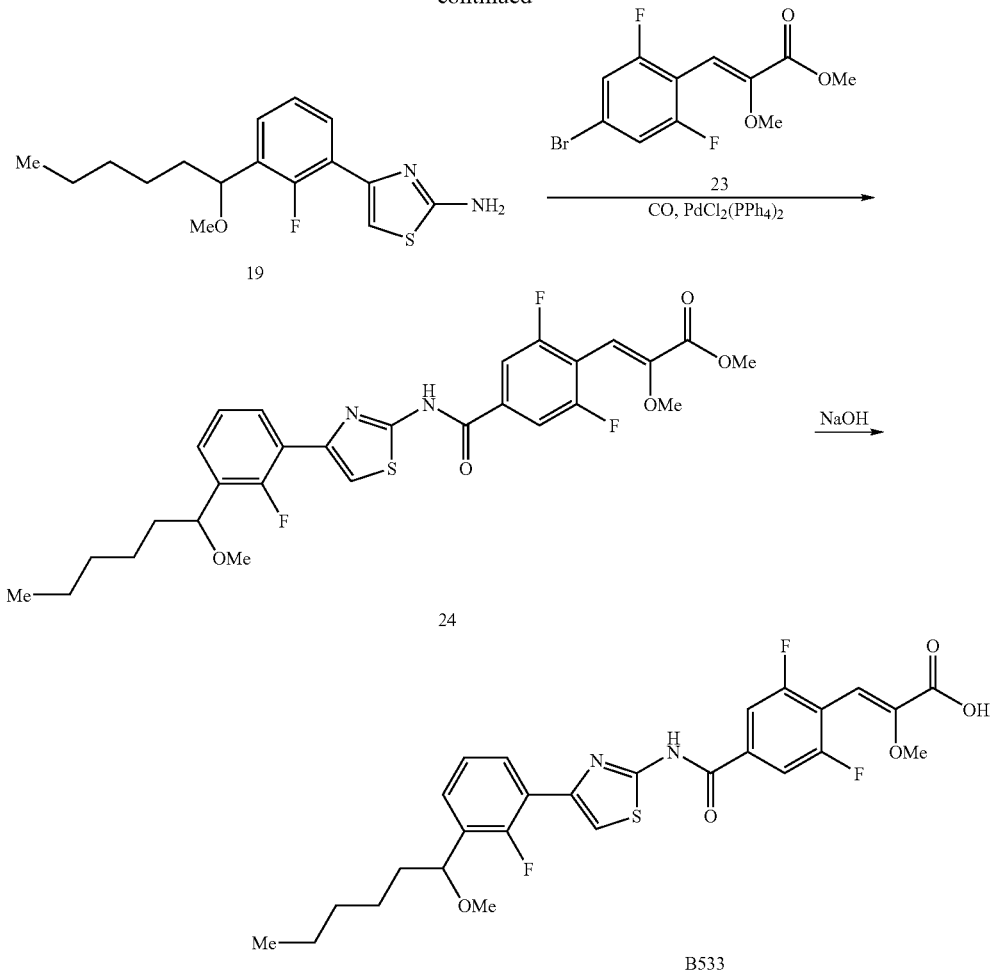

1) Synthesis of (methyloxymethyloxycarbonylmethyl)triphenylphosphonium chloride (22)

Methyl dimethyloxyacetate (15 g) was dissolved in acetyl chloride (9.7 g), and iodine (0.09 g) was added into the mixture. The reaction mixture was stirred for 3 h, and evaporated. The residue was dissolved again in dichloromethane (200 mL), and triphenylphospkine (29.5 g) was added into the reaction mixture. The reaction mixture was stirred for 3 h, and evaporated to obtain the compound (22) 44 g.

$^1$H-NMR(CDCl$_3$) 7.96-8.03 (m, 6H), 7.63-7.78 (m, 9H), 3.90 (s, 3H), 3.60 (s, 1H).

2) Syntehsis of Methyl (Z)-3-(4-bromo-2,6-difluorophenyl)-2-methyloxyacrylate (23)

4-Bromo-2,6-difluorobenzaldehyde (31.2 g) was dissolved in dichloromethane (300 mL), and (methyloxymethyloxycarbonylmethyl)triphenylphosphonium chloride (113.3 g) was added into the mixture. To the reaction mixture was added triethylamine (59 mL) dropwise, and the reaction mixture was stirred for 3 h. To the reaction mixture were added ice-water and 2N hydrochloric acid, and the reaction mixture was extracted with ethyl acetate. The organic layer was washed with water, and brine, dried over magnesium sulfate, evaporated. The obtained residue was purified by Colum chromatography (hexane:ethyl acetate=10:1) to obtain the compound (23) 32.1 g.

$^1$H-NMR(CDCl$_3$) 7.08-7.14 (m, 2H), 6.67-6.68 (m, 1H), 3.87 (s, 3H), 3.76 (s, 3 h).

3) Syntehsis of methyl (Z)-3-(2,6-difluoro-4-{4-[2-fluoro-3-(1-methyloxyhexyl)phenyl]thiazol-2-ylcarbamoyl}phenyl)-2-methyloxyacrylate (24)

4-[2-Fluoro-3-(1-methyloxyhexyl)phenyl]thiazol-2-ylamine (460 mg) and methyl (Z)-3-(4-bromo-2,6-difluorophenyl)-2-methyloxyacrylate (462 mg), and dichlorobistriphenylphosphinepalladium (150 mg) were dissolved in DMF (6 mL). Triethylamine (0.84 mL) was added into the mixture, and the reaction mixture was stirred under carbon monoxide atomosphere at 85° C. for 16 h. Water added into the reaction mixture, and the reaction mixture was extracted with ethyl acetate. The organic layer was washed with water, and brine, dried over magnesium sulfate, evaporated. The obtained residue was purified by Colum chromatography (hexane:ethyl acetate=4:1) to obtain the compound (24) 630 mg.

1H-NMR(DMSO-d6) 12.98 (bs, 2H), 8.01-8.05 (m, 1H), 7.89-7.95 (m, 2H), 7.65 (d, 1H, J=2.4 Hz), 7.31-7.39 (m, 2H), 6.66 (s, 1H), 4.55-4.60 (m, 1H), 3.80 (s, 3H), 3.18 (s, 3H), 1.64-1.76 (m, 2H), 1.26-1.41 (m, 6H), 0.81-0.86 (m, 3H).

4) Syntehsis of (Z)-3-(2,6-difluoro-4-{4-[2-fluoro-3-(1-methyloxyhexyl)phenyl]thiazol-2-ylcarbamoyl}phenyl)-2-methyloxyacrylic acid (B533)

Methyl (Z)-3-(2,6-difluoro-4-{4-[2-fluoro-3-(1-methyloxyhexyl)phenyl]thiazol-2-ylcarbamoyl}phenyl)-2-methyloxyacrylate (630 mg) was dissolved in a mixture of THF (2 mL), methanol (2 mL), and 2N sodium hydroxide aqueous solution (2 mL), and the mixture was stirred at room temperature for 3 h. The reaction mixture was acidified with hydrochloric acid, and the reaction mixture was extracted with ethyl acetate. The organic layer was washed with water, and brine, dried over magnesium sulfate, evaporated. The obtained residue was recrystallized from ethyl acetate to obtain the compound (B533) 590 mg.

1H-NMR(DMSO-d6) 12.98 (bs, 2H), 8.00-8.05 (m, 1H), 7.89-7.95 (m, 2H), 7.65 (d, 1H, J=2.4 Hz), 7.31-7.39 (m, 2H), 6.67 (s, 1H), 4.55-4.59 (m, 1H), 3.72 (s, 3H), 1.64-1.76 (m, 2H), 1.26-1.41 (m, 6H), 0.81-0.86 (m, 3H).

B2 to B101, B121, B122, B134, B169, B170, B195, B216, B233, B255, B264, B347 to B349, B354, B355, B380, B397, B418, B419, B425, B488, B505, B519, B521, B790, B896, B897, B899, B905, B927, B936, B958, B967, B1053, B1054, B1059, B1060, B1102, B1122, B1124, B1238, B1250, B1429, B1432, B1438, B1728 to B1739, B1742, B1744, B1746 to B1757, B1762 to B2047, B2049, B2051 to B2090, and B2097 to B2100 were synthsized by similar method mentioned above.

Example 81

Syntehsis of 3-(2,6-difluoro-4-{4-[3-(3,3-dimethyl-butyl)-2-fluorophenyl]thiazol-2-ylcarbamoyl}phenyl)-2-methylacrylic acid (B2)

1H-NMR(DMSO-d6) 13.01(bs, 2H), 7.88-8.02 (m, 3H), 7.64 (d, 1H, J=2.4 Hz), 7.34 (s, 1H), 7.28 (dt, 1H, J=7.0 Hz, 1.5 Hz), 7.22 (t, 1H, J=7.6 Hz), 2.60-2.70 (m, 2H), 1.81 (d, 3H, J=1.5 Hz), 1.42-1.55 (m, 2H), 0.97 (s, 9H).

Example 82

Syntehsis of 3-(4-{4-[3-(1-cyclohexyl-1-methyloxymethyl)-2-fluorophenyl]thiazol-2-ylcarbamoyl}-2,6-difluorophenyl)-2-methylacrylic acid (B3)

1H-NMR(DMSO-d6) 13.02 (bs, 2H), 7.93-8.08 (m, 3H), 7.65 (d, 1H, J=2.4 Hz), 7.28-7.48 (m, 3H), 4.32 (d, 1H, J=7.0 Hz), 3.15 (s, 3H), 1.90 (m, 1H), 1.81 (d, 3H, J=1.5 Hz), 0.90-1.80 (m, 10H).

Example 83

Syntehsis of 3-{2,6-difluoro-4-[4-(2-fluoro-3-pentylphenyl)thiazol-2-ylcarbamoyl]phenyl}-2-methylacrylic acid (B4)

1H-NMR(DMSO-d6) 13.01 (bs, 2H), 7.90-8.02 (m, 3H), 7.64 (d, 1H J=2.1 Hz), 7.34 (s, 1H), 7.18-7.32 (m, 2H), 2.68 (t, 2H, J=7.6 Hz), 1.81 (s, 3H), 1.61 (t, 2H, J=6.9 Hz), 1.20-1.40 (m, 4H), 0.88 (t, 3H, J=6.0 Hz).

Example 84

Syntehsis of 3-(2,6-difluoro-4-{4-[2-fluoro-3-(4-methylpentyl)phenyl]thiazol-2-ylcarbamoyl}phenyl)-2-methylacrylic acid (B5)

1H-NMR(DMSO-d6) 13.01 (bs, 2H), 7.90-8.02 (m, 3H), 7.64 (s, 1H), 7.34 (s, 1H), 7.18-7.33 (m, 2H), 2.67 (t, 2H, J=7.2 Hz), 1.81 (s,3H), 1.50-1.70 (m, 3H), 1.19-1.36 (m, 2H), 0.86 (d, 6H, J=6.7 Hz).

Example 85

Syntehsis of 3-(4-{4-[3-(1-cyclohexyl-1-ethyloxymethyl)-2-fluorophenyl]thiazol-2-ylcarbamoyl}-2,6-difluorophenyl)-2-methylacrylic acid (B6)

1H-NMR(DMSO-d6) 13.02 (bs, 2H), 8.00-8.06 (m, 2H), 7.97 (d, 1H, J=8.5 Hz), 7.64 (d, 1H, J=2.7 Hz), 7.30-7.38 (m, 3H), 4.41 (d, 1H, J=7.3 Hz), 3.23-3.40 (m, 2H), 1.94 (m, 1H), 1.81(d, 3H, J=1.5 Hz), 0.90-1.75 (m, 10H), 1.10 (t, 3H, J=7.0 Hz).

Example 86

Syntehsis of 3-(2,6-difluoro-4-{4-[2-fluoro-3-(2,4-dimethyl-3-methyloxy-3-pentyl)phenyl]thiazol-2-ylcarbamoyl}phenyl)-2-methylacrylic acid (B7)

1H-NMR(DMSO-d6) 13.00 (bs, 2H), 7.91-8.08 (m, 3H), 7.57 (d, 1H, J=3.1 Hz), 7.30-7.42 (m, 3H), 3.32 (s, 3H), 2.50-2.70 (m, 2H), 1.81 (s, 3H), 0.90 (d, 12H, J=6.7 Hz).

Example 87

Syntehsis of 3-(2,6-difluoro-4-{4-[2-fluoro-3-(4-methyloxy-4-pentyl)phenyl]thiazol-2-ylcarbamoyl}phenyl)-2-methylacrylic acid (B8)

1H-NMR(DMSO-d6) 13.00 (bs, 2H), 7.93-8.04 (m, 3H), 7.62 (d, 1H, J=2.7 Hz), 7.51 (dt, 1H, J=1.8, 7.8 Hz), 7.35 (s, 1H), 7.27 (t, 1H, J=7.8 Hz), 3.17 (s, 3H), 1.82-2.02 (m, 4H), 1.81 (d, 3H, J=1.5 Hz), 0.75-1.35 (m, 10H).

Example 88

Syntehsis of 3-(2,6-difluoro-4-{4-[2-fluoro-3-(1-methyloxydecyl)phenyl]thiazol-2-ylcarbamoyl}phenyl)-2-methylacrylic acid (B9)

1H-NMR(DMSO-d6) 13.01 (bs, 2H), 7.92-8.08 (m, 3H), 7.65 (d, 1H, J=2.4 Hz), 7.30-7.41 (m, 3H), 4.57 (t, 1H, J=6.4 Hz), 3.18 (s, 3H), 1.81 (d, 3H, J=1.8 Hz), 1.60-1.80 (m, 2H), 1.15-1.40 (m, 14H), 0.84 (t, 3H, J=6.5 Hz).

Example 89

Syntehsis of 3-(2,6-difluoro-4-{4-[3-(1-ethyloxy-2,2-dimethylpropyl)-2-fluorophenyl]thiazol-2-ylcarbamoyl}phenyl)-2-methylacrylic acid (B10)

1H-NMR(DMSO-d6) 13.01 (bs, 2H), 7.93-8.08 (m, 3H), 7.62 (d, 1H, J=2.7 Hz), 7.30-7.40 (m, 3H), 4.42 (s, 1H), 3.20-3.40 (m, 2H), 1.81 (d, 3H, J=1.5 Hz), 1.11 (t, 3H, J=7.0 Hz), 0.91 (s, 9H).

Example 90

Syntehsis of 3-(2,6-difluoro-4-{4-[2-fluoro-3-(1-methyloxy-4-methylpentyl)phenyl]thiazol-2-ylcarbamoyl}phenyl)-2-methylacrylic acid (B11)

1H-NMR(DMSO-d6) 13.03 (bs, 2H), 7.93-8.08 (m, 3H), 7.66 (d, 1H, J=2.7 Hz), 7.30-7.43 (m, 3H), 4.55 (t, 1H, J=6.6 Hz), 3.18 (s, 3H), 1.81 (s, 3H), 1.10-1.85 (m, 5H), 0.84 (d, 6H, J=6.7 Hz).

Example 91

Syntehsis of 3-(2,6-difluoro-4-{4-[2-fluoro-3-(4-methyloxyhexyl)phenyl]thiazol-2-ylcarbamoyl}phenyl)-2-methylacrylic acid (B12)

1H-NMR(DMSO-d6) 13.00 (bs, 2H), 7.93-7.98 (m, 3H), 7.64 (d, 1H, J=2.3 Hz), 7.20-7.34 (m, 3H), 3.20 (s, 3H), 3.10 (qint, 1H, J=5.6 Hz), 2.69 (t, 2H, J=7.7 Hz), 3.18 (s, 3H), 1.81 (d, 3H, J=1.6 Hz), 1.57-1.67 (m, 2H), 1.39-1.50 (m, 4H), 0.81 (t, 3H, J=7.5 Hz).

Example 92

Syntehsis of 3-(2,6-difluoro-4-{4-[2-fluoro-3-(1-methyloxy-2,2-dimethylpropyl)phenyl]thiazol-2-ylcarbamoyl}phenyl)-2-methylacrylic acid (B13)

1H-NMR(DMSO-d6) 13.00 (bs, 2H), 7.94-8.06 (m, 3H), 7.63 (d, 1H, J=2.7 Hz), 7.28-8.38 (m, 3H), 4.32 (s, 1H), 3.14 (s, 3H), 1.81 (d, 3H, J=1.6 Hz), 0.91 (2, 9H).

Example 93

Syntehsis of 3-(4-{4-[3-(1-cyclohexyl-1-n-pentyloxymethyl)-2-fluorophenyl]thiazol-2-ylcarbamoyl}-2,6-difluorophenyl)-2-methylacrylic acid (B14)

1H-NMR(DMSO-d6) 13.01 (bs, 2H), 7.99 (m, 1H), 7.98 (s, 1H), 7.95 (s, 1H), 7.64 (d, 1H, J=2.4 Hz), 7.28-7.36 (m, 3H), 4.39 (d, 1H, J=6.9 Hz), 3.24 (t, 2H, J=5.7 Hz), 1.93 (m, 1H), 1.81 (d, 3H, J=1.8 Hz), 0.94-1.76 (m, 16H), 0.84 (t, 3H, J=7.2 Hz).

Example 94

Syntehsis of 3-(2,6-difluoro-4-{4-[3-(2,2-dimethyl-1-n-pentyloxypropyl)-2-fluorophenyl]thiazol-2-ylcarbamoyl}phenyl)-2-methylacrylic acid (B15)

1H-NMR(DMSO-d6) 13.02 (bs, 2H), 7.96-8.05 (m, 3H), 7.62 (s, 1H), 7.26-7.37 (m, 3H), 4.39 (s, 1H), 3.22 (t, 2H, J=6.6 Hz), 1.81 (s, 3H), 1.44-1.57 (m, 2H), 1.19-1.38 (m, 4H), 0.91 (2, 9H), 0.84-0.88 (m, 3H).

Example 95

Syntehsis of 3-(2,6-difluoro-4-{4-[2-fluoro-3-(3-methylthio-1-n-pentyloxypropyl)phenyl]thiazol-2-ylcarbamoyl}phenyl)-2-methylacrylic acid (B16)

1H-NMR(DMSO-d6) 13.00 (bs, 2H), 7.94-8.05 (m, 3H), 7.66 (d, 1H, J=2.4 Hz), 7.32-7.42 (m, 3H), 4.82 (m, 1H), 3.28-3.50 (m, 2H), 2.58 (t, 2H, J=7.8 Hz), 2.06 (s, 3H), 1.87-2.02 (m, 2H), 1.81 (d, 3H, J=1.5 Hz), 1.44-1.58 (m, 2H), 1.20-1.35 (m, 4H), 0.85 (t, 3H, J=6.9 Hz).

Example 96

Syntehsis of 3-(2,6-difluoro-4-{4-[2-fluoro-3-(3-methyloxy-3-methylbutyl)phenyl]thiazol-2-ylcarbamoyl}phenyl)-2-methylacrylic acid (B17)

1H-NMR(DMSO-d6) 13.01 (bs, 2H), 7.90-8.00 (m, 3H), 7.64 (d, 1H, J=2.4 Hz), 7.12-7.34 (m, 3H), 3.14 (s, 3H), 2.64-2.70 (m, 2H), 1.81 (d, 3H, J=1.5 Hz), 1.69-1.75 (m, 2H), 1.17 (s, 6H).

Example 97

Syntehsis of 3-[2,6-difluoro-4-(4-{2-fluoro-3-{1-(3-methylbutyloxypropyl)phenyl]thiazol-2-ylcarbamoyl}phenyl]-2-methylacrylic acid (B18)

1H-NMR(DMSO-d6) 13.02 (bs, 2H), 7.95-8.04 (m, 3H), 7.64 (d, 1H, J=2.7 Hz), 7.31-7.40 (m, 3H), 4.59 (t, 1H, J=6.6 Hz), 3.08-3.50 (m, 2H), 1.81 (d, 3H, J=1.5 Hz), 1.65-1.76 (m, 3H), 1.41 (q, 2H, J=6.6 Hz), 0.81-0.91 (m, 9H).

Example 98

Syntehsis of 3-(2,6-difluoro-4-{4-[2-fluoro-3-(1-n-pentyloxypropyl)phenyl]thiazol-2-ylcarbamoyl}phenyl)-2-methylacrylic acid (B19)

1H-NMR(DMSO-d6) 13.01 (bs, 2H), 7.91-8.06 (m, 3H), 7.65.(d, 1H, J=2.4 Hz), 7.31-7.41 (m, 3H), 4.59 (t, 1H, J=6.6 Hz), 3.25-3.38 (m, 2H), 1.81 (d, 3H, J=1.8 Hz), 1.64-1.77 (m, 2H), 1.46-1.57 (m, 2H), 1.20-1.35 (m, 4H), 0.89 (t, 3H, J=7.2 Hz), 0.85 (t, 3H, J=7.2 Hz).

Example 99

Syntehsis of 3-[4-(4-{3-(2,2-dimetylpropyloxy)propyl}-2-fluorophenyl]thiazol-2-ylcarbamoyl}-2,6-difluorophenyl)-2-methylacrylic acid (B20)

1H-NMR(DMSO-d6) 13.00 (bs, 2H), 7.92-8.02 (m, 3H), 7.63 (s, 1H), 7.34 (s 1H), 7.22-7.30 (m, 2H), 3.42 (t, 2H, J=6.0 Hz), 3.04 (s, 2H), 2.76 (t, 2H, J=7.8 Hz), 1.81-1.89 (m, 5H), 0.89 (s, 9H).

Example 100

Syntehsis of 3-[4-(4-{3-[1-cyclohexyl-1-(4-ethyloxybutyloxy)methyl]-2-fluorophenyl]thiazol-2-ylcarbamoyl}-2,6-difluorophenyl)-2-methylacrylic acid (B21)

1H-NMR(DMSO-d6) 13.02 (bs, 2H), 7.95-8.04 (m, 3H), 7.64 (d, 1H, J=2.4 Hz), 7.33 (d, 3H, J=7.2 Hz), 4.39 (d, 1H, J=6.9 Hz), 3.25-3.39 (m, 6H), 1.95 (m, 1H), 1.81 (d, 3H, J=1.8 Hz), 1.45-1.76 (m, 9H), 1.36 (m, 1H), 0.98-1.23 (m, 4H), 1.07 (t, 3H, J=6.6 Hz).

Example 101

Syntehsis of 3-[2,6-difluoro-4-(4-{3-[1-(4-ethyloxybutyloxy)propyl]-2-fluorophenyl}thiazol-2-ylcarbamoyl)phenyl]-2-methylacrylic acid (B22)

1H-NMR(DMSO-d6) 13.00 (bs, 2H), 7.95-8.04 (m, 3H), 7.64 (d, 1H, J=2.4 Hz), 7.31-7.40 (m, 3H), 4.60 (t, 1H, J=5.7

Hz), 3.33-3.37 (m, 6H), 1.81 (d, 3H, J=1.5 Hz), 1.64-1.77 (m, 2H), 1.54 (s, 4H), 1.07 (t, 3H, J=6.9 Hz), 0.89 (t, 3H, J=7.2 Hz).

Example 102

Syntehsis of 3-(2,6-difluoro-4-{4-[2-fluoro-3-(1-methyloxyheptyl)phenyl]thiazol-2-ylcarbamoyl}phenyl)-2-methylacrylic acid (B23)

1H-NMR(DMSO-d6) 13.00 (bs, 1H), 7.95-8.05 (m, 3H), 7.64 (d, 1H, J=2.4 Hz), 7.23-7.33 (m, 3H), 4.54 (t, 1H, J=6.5 Hz), 3.18 (s, 3H,), 1.81 (d, 3H, J=1.3 Hz), 1.60-1.80 (m, 4H), 1.20-1.30 (m, 6H), 0.81-0.85 (m, 3H).

Example 103

Syntehsis of 3-(2,6-difluoro-4-{4-[3-(1-ethyloxybutyl)-2-fluorophenyl]thiazol-2-ylcarbamoyl}phenyl)-2-methylacrylic acid (B24)

1H-NMR(DMSO-d6) 13.00 (bs, 2H), 7.94-8.04 (m, 3H), 7.65 (d, 1H, J=2.4 Hz), 7.31-7.42 (m,3H), 4.67-4.71 (m, 1H), 3.36 (t, 2H, J=7.0 Hz), 1.81 (d, 3H, J=1.5 Hz), 1.60-1.78 (m, 2H), 1.27-1.44 (m, 2H), 1.12 (t, 3H, J=7.0 Hz), 0.89 (t, 3H, J=7.3 Hz).

Example 104

Syntehsis of 3-(2,6-difluoro-4-{4-[2-fluoro-3-(1-methyloxyoctyl)phenyl]thiazol-2-ylcarbamoyl}phenyl)-2-methylacrylic acid (B25)

1H-NMR(DMSO-d6) 13.00(bs, 2H), 7.95-8.05(m, 3H), 7.65(d, 1H, J=2.7 Hz), 7.31-8.38 (m, 3H), 4.56(t, 1H, J=6.5 Hz), 3.18(s, 3H), 1.81(d, 3H, J=1.4 Hz), 1.60-1.81 (m, 2H), 1.20-1.37 (m, 10H), 0.81-0.86 (m, 3H).

Example 105

Syntehsis of 3-(2,6-difluoro-4-{4-[2-fluoro-3-(1-n-pentyloxypentyl)phenyl]thiazol-2-ylcarbamoyl}phenyl)-2-methylacrylic acid (B26)

1H-NMR(DMSO-d6) 13.01(bs, 2H), 7.94-8.04 (m, 3H), 7.65 (d, 1H, J=2.0 Hz), 7.30-7.40 (m,3H), 4.62-4.66 (m, 1H), 3.28 (t, 2H, J=6.4 Hz), 1.80 (s, 3H), 1.60-1.75 (m, 2H), 1.45-1.54 (m, 2H), 1.22-1.33 (m, 8H), 0.83-0.87 (m, 6H).

Example 106

Syntehsis of 3-(2,6-difluoro-4-{4-[3-(1-ethyloxypentyl)-2-fluorophenyl]thiazol-2-ylcarbamoyl}phenyl)-2-methylacrylic acid (B27)

1H-NMR(DMSO-d6) 13.01 (bs, 2H), 7.95-8.04 (m, 3H), 7.64-7.65 (m, 1H), 7.30-7.41 (m, 3H), 4.67 (t, 1H, J=6.9 Hz), 3.35 (q, 2H, J=6.9 Hz), 1.81 (d, 3H, J=1.3 Hz), 1.60-1.81 (m, 2H), 1.23-1.41 (m, 4H), 1.12 (t, 3H, J=6.9 Hz), 0.83-0.87 (m, 3H).

Example 107

Syntehsis of 3-(2,6-difluoro-4-{4-[2-fluoro-3-(1-methyloxynonyl)phenyl]thiazol-2-ylcarbamoyl}phenyl)-2-methylacrylic acid (B28)

1H-NMR(DMSO-d6) 13.02 (bs, 2H), 7.95-8.05 (m, 3H), 7.65 (d, 1H, J=2.7 Hz), 7.31-7.39 (m, 3H), 4.56 (t, 1H, J=7.2 Hz), 3.18 (s, 3H), 1.81 (s, 3H), 1.55-1.85 (m, 2H), 1.17-1.45 (m, 12H), 0.83 (t, 3H, J=6.3 Hz).

Example 108

Syntehsis of 3-(2,6-difluoro-4-{4-[2-fluoro-3-(3-methyloxydecyl)phenyl]thiazol-2-ylcarbamoyl}phenyl)-2-methylacrylic acid (B29)

1H-NMR(DMSO-d6) 13.00 (bs, 1H), 7.90-7.98(m, 3H), 7.64(d, 1H, J=2.4 Hz), 7.23-7.33 (m, 3H), 3.33 (s, 3H,), 3.20-3.28 (m, 1H,), 2.65-2.70 (m, 2H,), 1.81 (d, 3H, J=1.4 Hz), 1.70-1.80 (m, 2H), 1.32-1.40 (m, 2H), 1.20-1.30 (m, 6H), 0.81-0.85 (m, 3H).

Example 109

Syntehsis of 3-(2,6-difluoro-4-{4-[2-fluoro-3-(1-n-octyloxyethyl)phenyl]thiazol-2-ylcarbamoyl}phenyl)-2-methylacrylic acid (B30)

1H-NMR(DMSO-d6) 13.00 (bs, 2H), 7.95-8.03 (m, 5H), 7.64 (d, 1H, J=2.3 Hz), 7.30-7.42 (m, 5H), 4.81 (q, 1H, J=6.4 Hz), 3.23-3.40 (m, 2H), 1.81 (s, 3H), 1.48-1.52 (m, 2H), 1.40 (d, 3H, J=6.4 Hz), 1.22-1.29 (m, 10H), 0.82-0.86 (m, 3H).

Example 110

Syntehsis of 3-(2,6-difluoro-4-{4-[2-fluoro-3-(1-n-pentyloxyethyl)phenyl]thiazol-2-ylcarbamoyl}phenyl)-2-methylacrylic acid (B31)

1H-NMR(DMSO-d6) 13.00 (bs, 2H), 7.95-8.04 (m, 3H), 7.65 (d, 1H, J=2.3 Hz), 7.30-8.43 (m, 3H), 4.80 (q, 1H, J=6.3 Hz), 3.23-3.34 (m, 2H), 1.48-1.55 (m, 2), 1.41 (d, 3H, J=6.4 Hz), 1.22-1.30 (m, 4H), 0.83-0.88 (m, 3H).

Example 111

Syntehsis of 3-(2,6-difluoro-4-{4-[2-fluoro-3-(n-decyloxymethyl)phenyl]thiazol-2-ylcarbamoyl}phenyl)-2-methylacrylic acid (B32)

1H-NMR(DMSO-d6) 13.00 (bs, 2H), 8.04 (dt, 1H, J=7.7 Hz, 1.8 Hz), 7.94-7.99 (m, 2H), 7.65 (d, 1H, J=2.5 Hz), 7.42 (t, 1H, J=7.0 Hz), 7.28-7.33 (m, 2H), 4.57 (s, 2H), 3.48 (t, 2H, 6.6 Hz), 1.81 (d, 3H, J=1.3 Hz), 1.51-1.58 (m, 2H), 1.22-1.35 (m, 14H), 0.81-0.86 (m, 3H).

Example 112

Syntehsis of 3-(2,6-difluoro-4-{4-[2-fluoro-3-(n-pentyloxymethyl)phenyl]thiazol-2-ylcarbamoyl}phenyl)-2-methylacrylic acid (B33)

1H-NMR(DMSO-d6) 13.02 (bs, 2H), 8.04 (dt, 1H, J=7.5 Hz, 1.9 Hz), 7.39-7.99 (m, 2H), 7.65 (d, 1H, J=2.7 Hz), 7.40-7.44 (m, 1H), 7.28-7.34 (m, 2H), 4.58 (s, 2H), 3.49 (t,

Example 113

Syntehsis of 3-(2,6-difluoro-4-{4-[2-fluoro-3-(1-n-propyloxybutyl)phenyl]thiazol-2-ylcarbamoyl}phenyl)-2-methylacrylic acid (B34)

1H-NMR(DMSO-d6) 13.00 (bs, 1H), 7.95-8.05(m, 3H), 7.65(d, 1H, J=2.4 Hz), 7.30-7.38 (m, 3H), 4.67 (t, 1H, J=6.4 Hz), 3.22 (t, 2H, J=6.5), 1.81 (d, 3H, J=1.3 Hz), 1.30-1.84 (m, 6H), 0.81-0.85 (m, 6H).

Example 114

Syntehsis of 3-(4-{4-[3-(1-n-butyloxybutyl)-2-fluorophenyl]thiazol-2-ylcarbamoyl}-2,6-difluorophenyl)-2-methylacrylic acid (B35)

1H-NMR(DMSO-d6) 13.00 (bs, 1H), 7.95-8.04(m, 3H), 7.64(d, 1H, J=2.4 Hz), 7.30-7.38 (m, 3H), 4.67 (t, 1H, J=6.4 Hz), 3.22 (t, 2H, J=6.5), 1.81 (d, 3H, J=1.4 Hz), 1.30-1.84 (m, 8H), 0.81-0.85 (m, 6H).

Example 115

Syntehsis of 3-(2,6-difluoro-4-{4-[2-fluoro-3-(1-n-pentyloxybutyl)phenyl]thiazol-2-ylcarbamoyl}phenyl)-2-methylacrylic acid (B36)

1H-NMR(DMSO-d6) 13.00 (bs, 1H), 7.94-8.04(m, 3H), 7.64(d, 1H, J=2.3 Hz), 7.30-7.38 (m, 3H), 4.66 (t, 1H, J=6.5 Hz), 3.22 (t, 2H, J=6.5), 1.81 (d, 3H, J=1.4 Hz), 1.26-1.70 (m, 10H), 0.81-0.85 (m, 6H).

Example 116

Syntehsis of 3-(4-{4-[3-(1-n-butyloxypropyl)-2-fluorophenyl]thiazol-2-ylcarbamoyl}-2,6-difluorophenyl)-2-methylacrylic acid (B37)

1H-NMR(DMSO-d6) 13.00 (bs, 2H), 7.94-8.03 (m, 3H), 7.64 (d, 1H, J=2.4 Hz), 7.31-7.40 (m, 3H), 4.59 (t, 1H, J=6.6 Hz), 3.25-3.33 (m, 2H), 1.81 (d, 3H, J=1.5 Hz), 1.64-1.76 (m, 2H), 1.44-1.55 (m, 2H), 1.28-1.40 (m, 2H), 0.89 (t, 3H, J=7.2 Hz), 0.86 (t, 3H, J=7.2 Hz).

Example 117

Syntehsis of 3-(2,6-difluoro-4-{4-[2-fluoro-3-(1-n-hexyloxypropyl)phenyl]thiazol-2-ylcarbamoyl}phenyl)-2-methylacrylic acid (B38)

1H-NMR(DMSO-d6) 13.01 (bs, 2H), 7.95-8.03 (m, 3H), 7.65 (s, 1H), 7.30-7.39 (m, 3H), 4.58 (t, 1H, J=6.0 Hz), 3.18-3.47 (m, 2H), 1.81 (d, 3H, J=1.5 Hz), 1.64-1.79 (m, 2H), 1.44-1.56 (m, 2H), 1.16-1.37 (m, 6H), 0.89 (t, 3H, J=7.5 Hz), 0.84 (t, 3H, J=6.6 Hz).

Example 118

Syntehsis of 3-[2,6-difluoro-4-(4-(2-fluoro-3-[3-(4-methylpentyloxy)propyl]phenyl}thiazol-2-ylcarbamoyl)phenyl]-2-methylacrylic acid (B39)

1H-NMR(DMSO-d6) 13.00 (bs, 2H), 7.91-7.95 (m, 3H), 7.63 (d, 1H, J=2.4 Hz), 7.34 (s, 1H), 7.21-7.30 (m, 2H), 3.20-3.44 (m, 4H), 2.73 (t, 2H, J=7.2 Hz), 1.76-1.90 (m, 2H), 1.80 (s, 3H), 1.44-1.56 (m, 4H), 1.14-1.25 (m, 2H), 0.86 (d, 6H, J=6.6 Hz).

Example 119

Syntehsis of 3-[2,6-difluoro-4-(4-{3-[3-(3,3-dimethylbutyloxy)propyl]-2-fluorophenyl}thiazol-2-ylcarbamoyl)phenyl]-2-methylacrylic acid (B40)

1H-NMR(DMSO-d6) 13.02 (bs, 2H), 7.91-7.98 (m, 3H), 7.63 (d, 1H, J=2.4 Hz), 7.34 (s, 1H), 7.21-7.30 (m, 2H), 3.37-3.41 (m, 4H), 2.74 (t, 2H, J=7.2 Hz), 1.81 (d, 3H, J=1.8 Hz), 1.78-1.87 (m, 2H), 1.44 (t, 2H, J=7.5 Hz), 0.90 (s, 9H).

Example 120

Syntehsis of 3-(2,6-difluoro-4-{4-[2-fluoro-3-(1-n-propyloxypentyl)phenyl]thiazol-2-ylcarbamoyl}phenyl)-2-methylacrylic acid (B41)

1H-NMR(DMSO-d6) 13.00 (bs, 2H), 7.93-8.04 (m, 3H), 7.65 (d, 1H, J=2.0 Hz), 7.31-7.41 (m, 3H), 4.63-4.67 (m, 1H), 3.25 (t, 2H, J=6.6 Hz), 1.64-1.81 (m, 5), 1.52 (q, 2H, J=6.9 Hz), 1.26-1.40 (m, 4H), 0.82-0.90 (m, 6H).

Example 121

Syntehsis of 3-(4-{4-[3-(1-n-butyloxypentyl)-2-fluorophenyl]thiazol-2-ylcarbamoyl}-2,6-difluorophenyl)-2-methylacrylic acid (B42)

1H-NMR(DMSO-d6) 13.01 (bs, 2H), 7.94-8.03 (m, 3H), 7.65 (d, 1H, J=2.3 Hz), 7.31-7.41 (m, 3H), 4.63-4.67 (m, 1H), 3.29 (t, 2H, J=6.4 Hz), 1.81 (s, 3H), 1.60-1.78 (m, 2H), 1.44-1.53 (m, 2H), 1.28-1.40 (m, 6H), 0.86 (t, 6H, J=7.2 H).

Example 122

Syntehsis of 3-[2,6-difluoro-4-(4-{3-[3-(2-ethylbutyloxy)propyl]-2-fluorophenyl}thiazol-2-ylcarbamoyl)phenyl]-2-methylacrylic acid (B43)

1H-NMR(DMSO-d6) 13.00 (bs, 2H), 7.91-7.99 (m, 3H), 7.63 (d, 1H, J=2.4 Hz), 7.34 (s, 1H), 7.21-7.30 (m, 2H), 3.25-3.42 (m, 4H), 2.74 (t, 2H, J=7.8 Hz), 1.80-1.88 (m, 2H), 1.81 (d, 3H, J=2.1 Hz), 1.25-1.42 (m, 5H), 0.85 (t, 6H, J=7.5 Hz).

Example 123

Syntehsis of 3-[4-(4-{3-[3-(2-cyclopentylethyloxy)propyl]-2-fluorophenyl}thiazol-2-ylcarbamoyl}-2,6-difluorophenyl)-2-methylacrylic acid (B44)

1H-NMR(DMSO-d6) 13.00 (bs, 2H), 7.91-7.98 (m, 3H), 7.63 (d, 1H, J=2.7 Hz), 7.34 (s, 1H), 7.20-7.30 (m, 2H), 3.24-3.44 (m, 4H), 2.74 (t, 2H, J=7.2 Hz), 1.81 Hz), (d, 3H, J=1.8 Hz), 1.66-1.89 (m, 4H), 1.40-1.64 (m, 5H), 1.00-1.14 (m, 4H).

Example 124

Syntehsis of 3-(2,6-difluoro-4-{4-[2-fluoro-3-(3-n-pentyloxypropyl)phenyl]thiazol-2-ylcarbamoyl}phenyl)-2-methylacrylic acid (B45)

1H-NMR(DMSO-d6) 13.01 (bs, 2H), 7.91-7.98 (m, 3H), 7.64 (d, 1H, J=2.4 Hz), 7.34 (s, 1H), 7.21-7.30 (m, 2H), 3.24-3.41 (m, 4H), 2.74 (t, 2H, J=7.8 Hz), 1.77-1.90 (m, 2H), 1.81 (d, 3H, J=1.8 Hz), 1.44-1.55 (m, 2H), 1.23-1.36 (m, 4H), 0.84-0.89 (m, 3H).

Example 125

Syntehsis of 3-(2,6-difluoro-4-{4-[2-fluoro-3-(3-n-hexyloxypropyl)phenyl]thiazol-2-ylcarbamoyl}phenyl)-2-methylacrylic acid (B46)

1H-NMR(DMSO-d6) 13.01 (bs, 2H), 7.91-7.99 (m, 3H), 7.64 (d, 1H, J=2.7 Hz), 7.34 (s, 1H), 7.21-7.30 (m, 2H), 3.20-3.42 (m, 4H), 2.74 (t, 2H, J=7.2 Hz), 1.77-1.87 (m, 2H), 1.81 (d, 3H, J=1.8 Hz), 1.45-1.51 (m, 2H), 1.20-1.36 (m, 6H), 0.86 (t, 3H, J=6.9 Hz).

Example 126

Syntehsis of 3-(2,6-difluoro-4-{4-[2-fluoro-3-(1-methyloxyundecyl)phenyl]thiazol-2-ylcarbamoyl}phenyl)-2-methylacrylic acid (B47)

1H-NMR(DMSO-d6) 13.01 (bs, 2H), 7.94-8.05 (m, 3H), 7.65 (d, 1H, J=2.7 Hz), 7.31-7.39 (m, 3H), 4.54-4.58 (m, 1H), 3.18 (s, 3H), 1.81 (s, 3H), 1.60-1.80 (m, 2H), 1.21-1.36 (m, 16H), 0.81-0.86 (m, 3H).

Example 127

Syntehsis of 3-(2,6-difluoro-4-{4-[2-fluoro-3-(1-methyloxydodecyl)phenyl]thiazol-2-ylcarbamoyl}phenyl)-2-methylacrylic acid (B48)

1H-NMR(DMSO-d6) 13.01 (bs, 2H), 7.94-8.05 (m, 3H), 7.64 (d, 1H, J=2.5 Hz), 7.30-7.38 (m, 3H), 4.54-4.58 (m, 1H), 3.17 (s, 3H), 1.81 (d, 3H, J=1.4 Hz), 1.61-1.81 (m, 2H), 1.21-1.36 (m, 18H), 0.81-0.85 (m, 3H).

Example 128

Syntehsis of 3-(4-{4-[3-(3-n-butyloxypropyl)-2-fluorophenyl]thiazol-2-ylcarbamoyl}-2,6-difluorophenyl)-2-methylacrylic acid (B49)

1H-NMR(DMSO-d6) 13.02 (bs, 2H), 7.91-8.00 (m, 3H), 7.64 (d, 1H, J=2.4 Hz), 7.34 (s, 1H), 7.21-7.30 (m, 2H), 3.34-3.42 (m, 4H), 2.74 (t, 2H, J=7.2 Hz), 1.78-1.88 (m, 5H), 1.44-1.53 (m, 2H), 1.25-1.39 (m, 2H), 0.88 (t, 3H, J=7.2 Hz).

Example 129

Syntehsis of 3-(4-{4-[3-(1-n-butyloxyethyl)-2-fluorophenyl]thiazol-2-ylcarbamoyl}-2,6-difluorophenyl)-2-methylacrylic acid (B50)

1H-NMR(DMSO-d6) 13.01 (bs, 2H), 7.94-8.03 (m, 3H), 7.65 (d, 1H, J=2.7 Hz), 7.31-7.43 (m, 3H), 4.77-4.84 (m, 1H), 3.24-3.41 (m, 2H), 1.81 (s, 3H), 1.45-1.55 (m, 2H), 1.41 (d, 3H, J=6.3 Hz), 1.29-1.37 (m, 2H), 0.83-0.88 (m, 3H).

Example 130

Syntehsis of 3-(4-{4-[3-(1,4-dibutyloxybutyl)-2-fluorophenyl]thiazol-2-ylcarbamoyl}-2,6-difluorophenyl)-2-methylacrylic acid (B51)

1H-NMR(DMSO-d6) 13.02 (bs, 2H), 8.00-8.04 (m, 3H), 7.64 (d, 1H, J=2.4 Hz), 7.31-7.41 (m, 3H), 4.68 (t, 1H, J=6.2 Hz), 3.28-3.33 (m, 6H), 1.81 (d, 3H, J=1.8 Hz), 1.60-1.76 (m, 4H), 1.40-1.52 (m, 4H), 1.23-1.37 (m, 4H), 0.86 (t, 3H, J=7.2 Hz).

Example 131

Syntehsis of 3-(2,6-difluoro-4-{4-[2-fluoro-3-(3-n-hexyloxy-1-methyloxyproyl)phenyl]thiazol-2-ylcarbamoyl}phenyl)-2-methylacrylic acid (B152)

1H-NMR(DMSO-d6) 13.02 (bs, 2H), 8.01-8.06 (m, 2H), 7.97 (d, 1H, J=8.7 Hz), 7.65 (d, 1H, J=2.4 Hz), 7.31-7.40 (m, 3H), 4.71 (t, 1H, J=6.6 Hz), 3.26-3.36 (m, 4H), 3.18 (s, 3H), 1.87-2.00 (m, 2H), 1.81 (s, 3H), 1.39-1.54 (m, 2H), 1.20-1.32 (m, 6H), 0.85 (t, 3H, J=6.6 Hz).

Example 132

Syntehsis of 3-(2,6-difluoro-4-{4-[2-fluoro-3-(1-methyloxy-4-n-pentyloxybutyl)phenyl]thiazol-2-ylcarbamoyl}phenyl)-2-methylacrylic acid (B53)

1H-NMR(DMSO-d6) 13.02 (bs, 2H), 8.00-8.06 (m, 2H), 7.97 (d, 1H, J=8.4 Hz), 7.65 (d, 1H, J=2.1 Hz), 7.34-7.38 (m, 3H), 4.60 (t, 1H, J=5.7 Hz), 3.22-3.40 (m, 4H), 3.19 (s, 3H), 1.81(d, 3H, J=1.5 Hz), 1.66-1.85 (m, 2H), 1.38-1.64 (m, 4H), 1.21-1.29 (m, 4H), 0.84 (t, 3H, J=6.6 Hz).

Example 133

Syntehsis of 3-(2,6-difluoro-4-{4-[2-fluoro-3-(1-methyloxy-3,3-dimethylbutyl)phenyl]thiazol-2-ylcarbamoyl}phenyl)-2-methylacrylic acid (B54)

1H-NMR(DMSO-d6) 13.01 (bs, 2H), 7.94-8.03 (m, 3H), 7.66 (d, 1H, J=2.5 Hz), 7.30-7.41 (m, 3H), 4.65 (dd, 1H, J=8.8 Hz, 3.0 Hz), 3.15 (s, 3H), 1.81 (d, 3H, J=1.6 Hz), 1.73 (dd, 1H, J=14.4 Hz, 8.6 Hz), 1.45 (dd, 1H, J=14.4 Hz, 2.8 Hz), 0.97 (s, 9H).

Example 134

Syntehsis of 3-(2,6-difluoro-4-{4-[2-fluoro-3-(1-methyloxy-3-n-butyloxypropyl)phenyl]thiazol-2-ylcarbamoyl}phenyl)-2-methylacrylic acid (B55)

1H-NMR(DMSO-d6) 13.02 (bs, 2H), 7.94-8.06 (m, 3H), 7.66 (d, 1H, J=2.7 Hz), 7.35-7.41 (m, 3H), 4.68-4.73 (m, 1H), 3.34-3.54 (m, 4H), 3.19 (s, 3H), 1.85-2.01 (m, 2H), 1.81 (d, 3H, J=1.6 Hz), 1.41-1.50 (m, 2H), 1.25-1.37 (m, 2H), 086 (t, 3H, J=7.2 Hz).

Example 135

Syntehsis of 3-(2,6-dichloro-4-{4-[3-(1-ethyloxy-2,2-dimethylpropyl)-2-fluorophenyl]thiazol-2-ylcarbamoyl}phenyl)-2-methylacrylic acid (B56)

1H-NMR(DMSO-d6) 13.02 (bs, 2H), 8.29 (s, 2H), 8.02 (m, 1H), 7.62 (d, 1H, J=2.3 Hz), 7.41 (s, 1H), 7.30-7.40 (m, 2H), 4.42 (s, 1H), 3.20-3.40 (m, 2H), 1.69 (s, 3H), 1.11 (t, 3H, J=7.0 Hz), 0.91 (s, 9H).

Example 136

Syntehsis of 3-(2,6-dichloro-4-{4-[2-fluoro-3-(4-methyloxy-4-heptyl)phenyl]thiazol-2-ylcarbamoyl}phenyl)-2-methylacrylic acid (B57)

1H-NMR(DMSO-d6) 13.02 (bs, 2H), 8.29 (s, 2H), 7.98 (t, 1H, J=7.3 Hz), 7.62 (d, 1H, J=2.4 Hz), 7.51 (t, 1H, J=7.0 Hz), 7.40 (d, 1H, J=1.2 Hz), 7.27 (t, 1H, J=7.8 Hz), 3.17 (s, 3H), 1.80-2.00 (m, 4H), 1.69 (d, 3H, J=1.2 Hz), 0.75-1.35 (m, 10H).

Example 137

Syntehsis of 3-(2,6-dichloro-4-{4-[2-fluoro-3-(1-methyloxyhexyl)phenyl]thiazol-2-ylcarbamoyl}phenyl)-2-methylacrylic acid (B58)

1H-NMR(DMSO-d6) 13.02(bs, 2H), 8.29 (s, 2H), 8.02 (m, 1H), 7.65 (d, 1H, J=2.5 Hz), 7.30-7.44 (m, 3H), 4.57 (t, 1H, J=6.8 Hz), 3.18 (s, 3H), 1.69 (d, 3H, J=1.1 Hz), 1.20-1.83 (m, 8H), 0.84 (t, 3H, J=6.1 Hz).

Example 138

Syntehsis of 3-(2,6-dichloro-4-{4-[2-fluoro-3-(3-methyloxy-2,4-dimethylpentyl)phenyl]thiazol-2-ylcarbamoyl}phenyl)-2-methylacrylic acid (B59)

1H-NMR(DMSO-d6) 13.00 (bs, 2H), 8.30 (s, 2H), 8.03 (m, 1H), 7.56 (d, 1H, J=3.1 Hz), 7.30-7.44 (m, 3H), 3.33 (s, 3H), 2.50-2.70 (m, 2H), 1.69 (d, 3H, J=1.2 Hz), 0.90 (d, 12H, J=6.7 Hz).

Example 139

Syntehsis of 3-(2,6-dichloro-4-{4-[2-fluoro-3-(1-methyloxy-4-methylpentyl)phenyl]thiazol-2-ylcarbamoyl}phenyl)-2-methylacrylic acid (B60)

1H-NMR(DMSO-d6) 13.03 (bs, 2H), 8.29 (d, 2H, J=1.2 Hz), 8.03 (m, 1H), 7.66 (d, 1H, J=0.9 Hz), 7.31-7.45 (m, 3H), 4.55 (t, 1H, J=6.3 Hz), 3.18 (d, 3H, J=1.2 Hz), 1.69 (s, 3H), 1.10-1.85 (m, 5H), 0.85 (d, 6H, J=6.7 Hz).

Example 140

Syntehsis of 3-(2,6-dichloro-4-{4-[2-fluoro-3-(1-methyloxydecyl)phenyl]thiazol-2-ylcarbamoyl}phenyl)-2-methylacrylic acid (B61)

1H-NMR(DMSO-d6) 13.03 (bs, 2H), 8.29 (s, 2H), 8.02 (m, 1H), 7.64 (d, 1H, J=1.5 Hz), 7.29-7.45 (m, 3H), 4.56 (t, 1H, J=6.4 Hz), 3.18 (s, 3H), 1.69 (s, 3H), 1.15-1.85 (m, 16H), 0.83 (t, 3H, J=6.6 Hz).

Example 141

Syntehsis of 3-(2,6-dichloro-4-{4-[2-fluoro-3-(1-ethyloxy-3,3-dimethylbutyl)phenyl]thiazol-2-ylcarbamoyl}phenyl)-2-methylacrylic acid (B62)

1H-NMR(DMSO-d6) 13.02 (bs, 2H), 8.29 (s, 2H), 8.00 (dt, 1H, J=1.8, 7.6 Hz), 7.65 (d, 1H, J=2.4 Hz), 7.29-7.45 (m, 3H), 4.77 (dd, 1H, J=2.4, 8.8 Hz), 3.25-3.40 (m, 2H), 1.69 (s, 3H), 1.68 (m, 1H), 1.43 (dd, 1H, J=2.4, 14.3 Hz), 1.12 (t, 3H, J=6.9 Hz), 0.99 (s, 9H).

Example 142

Syntehsis of 3-(2,6-dichloro-4-{4-[2-fluoro-3-(3-methyloxy-1-n-pentyloxypropyl)phenyl]thiazol-2-ylcarbamoyl}phenyl)-2-methylacrylic acid (B63)

1H-NMR(DMSO-d6) 13.01 (bs, 2H), 8.35 (s, 1H), 8.16 (d, 1H, J=9.9 Hz), 8.00-8.08 (m, 3H), 7.65 (d, 1H, J=2.4 Hz), 7.31-7.42 (m, 2H), 4.82 (q, 1H, J=4.2 Hz), 3.10-3.50 (m, 2H), 2.58 (t, 2H, J=7.5 Hz), 2.06(s, 3H), 1.82-2.02 (m, 2H), 1.46-1.58 (m, 2H), 1.20-1.36 (m, 4H), 0.85 (t, 3H, J=6.9 Hz).

Example 143

Synthesis of 3-(2,6-dichloro-4-{4-[2-fluoro-3-(1-methyloxy-2,2-dimethylpropyl)phenyl]thiazol-2-ylcarbamoyl}phenyl)-2-methylacrylic acid (B64)

1H-NMR(DMSO-d6) 13.00 (bs, 2H), 8.29 (s, 2H), 8.03 (dt, 1H, J=7.0 Hz, 2.2 Hz), 7.62 (d, 1H, J=2.5 Hz), 7.28-7.41 (m, 3H), 4.32 (s, 1H), 3.15 (s, 3H), 1.69 (d, 3H, J=1.3 Hz), 0.91 (s, 9H).

Example 144

Synthesis of 3-[2,6-dichloro-4-(4-{3-[1-(4-ethyloxy-butyloxy)propyl]-2-fluorophenyl]thiazol-2-ylcarbamoyl}phenyl)-2-methylacrylic acid (B65)

1H-NMR(DMSO-d6) 13.03 (bs, 2H), 8.29 (s, 2H), 8.01 (t, 1H, J=6.0 Hz), 7.64 (d, 1H, J=2.1 Hz), 7.40 (s, 1H), 7.30-7.37 (m, 2H), 4.59 (t, 1H, J=6.0 Hz), 3.00-3.70 (m, 6H), 1.60-1.86 (m, 2H), 1.69 (s, 3H), 1.41-1.63 (m, 4H), 1.07 (t, 3H, J=6.9 Hz), 0.89 (t, 3H, J=6.9 Hz).

Example 145

Synthesis of 3-[2,6-dichloro-4-(4-{3-[3-(2,2-dimethylpropyloxy)propyl]-2-fluorophenyl]thiazol-2-ylcarbamoyl}phenyl)-2-methylacrylic acid (B66)

1H-NMR(DMSO-d6) 13.01 (bs, 2H), 8.29 (s, 2H), 7.94 (dt, 1H, J=2.4 Hz, 7.2 Hz), 7.63 (d, 1H, J=2.7 Hz), 7.40 (d, 1H, J=1.5 Hz), 7.21-7.32 (m, 2H), 3.42 (t, 2H, J=6.0 Hz), 3.04 (s, 2H), 2.76 (t, 2H, J=7.2 Hz), 1.80-1.91 (m, 2H), 1.69 (d, 3H, J=1.2 Hz), 0.89 (s, 9H).

Example 146

Synthesis of 3-[2,6-dichloro-4-(4-{3-[1-n-pentyloxypropyl]-2-fluorophenyl}thiazol-2-ylcarbamoyl)phenyl]-2-methylacrylic acid (B67)

1H-NMR(DMSO-d6) 13.02 (bs, 2H), 8.29 (s, 2H), 8.01 (dt, 1H, J=2.4 Hz, 6.9 Hz), 7.64 (d, 1H, J=2.4 Hz), 7.31-7.40

(m, 3H), 4.59 (t, 1H, J=6.9 Hz), 3.20-3.42 (m, 2H), 1.69 (d, 3H, J=1.5 Hz), 1.64-1.81 (m, 2H), 1.46-1.56 (m, 2H), 1.23-1.34 (m, 4H), 0.89 (t, 3H, J=7.2 Hz), 0.85 (t, 3H, J=7.2 Hz).

Example 147

Synthesis of 3-(2,6-dichloro-4-{4-[2-fluoro-3-(1-methyloxyheptyl)phenyl]thiazol-2-ylcarbamoyl}phenyl)-2-methylacrylic acid (B68)

1H-NMR(DMSO-d6) 13.01 (bs, 1H), 8.29(d, 2H, J=0.9 Hz), 8.03 (t, 1H, J=7.3), 7.64 (d, 1H, J=2.3 Hz), 7.31-7.40 (m, 3H), 4.56 (t, 1H, J=6.5 Hz), 3.18 (s, 3H), 1.60-1.80 (m, 4H), 1.70 (d, 3H, J=1.3 Hz), 1.20-1.30 (m, 6H), 0.81-0.85 (m, 3H).

Example 148

Synthesis of 3-(2,6-dichloro-4-{4-[2-fluoro-3-(1-methyloxyoctyl)phenyl]thiazol-2-ylcarbamoyl}phenyl)-2-methylacrylic acid (B69)

1H-NMR(DMSO-d6) 13.00(bs, 2H), 8.29 (d, 2H, J=0.9 Hz), 7.99-8.10 (m, 1H), 7.64 (d, 1H, J=1.3 Hz), 7.31-7.40 (m, 3H), 4.56 (t, 1H, J=6.5 Hz), 3.18 (s, 3H), 1.69 (d, 3H, J=1.3 Hz), 1.58-1.84 (m, 2H), 1.16-1.40 (m, 10H), 0.81-0.85 (m, 3H).

Example 149

Synthesis of 3-(2,6-dichloro-4-{4-[2-fluoro-3-(1-n-pentyloxypentyl)phenyl]thiazol-2-ylcarbamoyl}phenyl)-2-methylacrylic acid (B70)

1H-NMR(DMSO-d6) 13.00 (bs, 2H), 8.29 (s, 2H), 8.00 (dt, 1H, J=7.4 Hz, 2.2 Hz), 7.64 (d, 1H, J=2.5 Hz), 7.30-7.40 (m, 3H), 4.64 (dt, 1H, J=1.6 Hz, 5.5 Hz), 3.28 (t, 2H, J=6.6 Hz), 1.69 (d, 3H, J=1.3 Hz), 1.62-1.73 (m, 2H), 1.45-1.52 (m, 2H), 1.22-1.33 (m, 8H), 0.82-0.87 (m, 6H).

Example 150

Synthesis of 3-(2,6-dichloro-4-{4-[3-(1-ethyloxypentyl)-2-fluorophenyl]thiazol-2-ylcarbamoyl}phenyl)-2-methylacrylic acid (B71)

1H-NMR(DMSO-d6) 13.00 (bs, 2H), 8.29 (s, 1H), 8.00 (dt, 1H, J=7.3 Hz, 2.0 Hz), 7.64 (d, 1H, J=2.5 Hz), 7.30-7.40 (m, 3H), 4.67 (t, 1H, J=6.6 Hz), 3.35 (q, 2H, J=6.9 Hz), 1.63-1.73 (m, 5H), 1.27-1.33 (m, 4H), 1.12 (t, 3H, J=6.9 Hz), 0.83-0.87 (m, 3H).

Example 151

Synthesis of 3-(2,6-dichloro-4-{4-[2-fluoro-3-(1-methyloxynonyl)phenyl]thiazol-2-ylcarbamoyl}phenyl)-2-methylacrylic acid (B72)

1H-NMR(DMSO-d6) 13.02 (bs, 2H), 8.29 (s, 2H), 8.01 (m, 1H), 7.65 (d, 1H, J=2.4 Hz), 7.41 (d, 1H, J=1.2 Hz), 7.32-7.38 (m, 2H), 4.52 (t, 1H, J=6.6 Hz), 3.20 (s, 3H), 1.68-1.84 (m, 5H), 1.18-1.40 (m, 12H), 0.87 (t, 3H, J=7.2 Hz).

Example 152

Synthesis of 3-(2,6-dichloro-4-{4-[2-fluoro-3-(3-methyloxyoctyl)phenyl]thiazol-2-ylcarbamoyl}phenyl)-2-methylacrylic acid (B73)

1H-NMR(DMSO-d6) 13.02 (bs, 2H), 8.29 (s, 2H), 7.93 (dt, 1H, J=1.8 Hz, 7.5 Hz), 7.64 (d, 1H, J=2.7 Hz), 7.40 (d, 1H, J=1.2 Hz), 7.20-7.31 (m, 2H), 3.25 (s, 3H), 3.19 (m, 1H), 2.62-2.80 (m, 2H), 1.72-1.77 (m, 2H), 1.69 (d, 3H, J=1.2 Hz), 1.40-1.54 (m, 2H), 1.20-1.38 (m, 6H), 0.86 (t, 3H, J=6.6 Hz).

Example 153

Synthesis of 3-[2,6-dichloro-4-(4-{2-fluoro-3-[1-(3-methylbutyloxy)proptyl]phenyl}thiazol-2-ylcarbamoyl)phenyl]-2-methylacrylic acid (B74)

1H-NMR(DMSO-d6) 13.01 (bs, 2H), 8.29 (s, 2H), 8.01 (dt, 1H, J=2.4 Hz, 6.9 Hz), 7.64 (d, 1H, J=2.7 Hz), 7.40 (t, 1H, J=1.5 Hz), 7.31-7.38 (m, 2H), 4.59 (t, 1H, J=6.0 Hz), 3.12-3.43 (m, 2H), 1.63-1.81 (m, 3H), 1.37-1.44 (m, 2H), 0.89 (t, 3H, J=7.2 Hz), 0.86 (t, 3H, J=6.6 Hz), 0.82 (t, 3H, J=6.6 Hz).

Example 154

Synthesis of 3-(2,6-dichloro-4-{4-[2-fluoro-3-(1-n-octyloxyethyl)phenyl]thiazol-2-ylcarbamoyl}phenyl)-2-methylacrylic acid (B75)

1H-NMR(DMSO-d6) 13.00 (bs, 2H), 8.29 (s, 2H), 8.01 (dt, 1H, J=7.5 Hz, 2.0 Hz), 7.64 (d, 1H, J=2.7 Hz), 7.38-7.42 (m, 1H), 7.32 (t, 2H, J=7.7 Hz), 4.79 (q, 1H, J=6.7 Hz), 3.23-3.40 (m, 2H), 1.69 (s, 3H), 1.45-1.40 (m, 2H), 1.41 (d, 3H, 6.4 Hz), 1.22-1.30 (m, 8H), 0.81-0.86 (m, 3H).

Example 155

Synthesis of 3-{2,6-dichloro-4-[4-(3-n-decyloxymethyl-2-fluorophenyl)thiazol-2-ylcarbamoyl]phenyl}-2-methylacrylic acid (B76)

1H-NMR(DMSO-d6) 13.03 (bs, 2H), 8.29 (s, 2H), 8.04 (dt, 1H, J=7.7 Hz, 1.3 Hz), 7.64 (d, 1H, J=2.5 Hz), 7.38-7.45 (m, 2H), 7.31 (t, 1H, J=7.7 Hz), 4.58 (s, 2H), 3.48 (t, 2H, 6.5 Hz), 1.69 (s, 3H), 1.49-1.58 (m, 2H), 1.22-1.33 (m, 14H), 0.82-0.86 (m, 3H).

Example 156

Synthesis of 3-{2,6-dichloro-4-[4-(2-fluoro-3-{n-pentyloxymethyl}phenyl)thiazol-2-ylcarbamoyl]phenyl}-2-methylacrylic acid (B77)

1H-NMR(DMSO-d6) 13.02 (bs, 2H), 8.29 (s, 2H), 8.04 (dt, 1H, J=7.5 Hz, 1.8 Hz), 7.66 (d, 1H, J=2.4 Hz), 7.40-7.46 (m, 2H), 7.31 (t, 1H, J=7.6 Hz), 4.58 (s, 2H), 3.49 (t, 2H, 6.4 Hz), 1.69 (d, 3H, J=1.5 Hz), 1.52-1.60 (m, 2H), 1.28-1.33 (m, 4H), 0.84-0.89 (m, 3H).

Example 157

Synthesis of 3-(2,6-dichloro-4-{4-[2-fluoro-3-(1-n-propyloxybutyl)phenyl]thiazol-2-ylcarbamoyl}phenyl)-2-methylacrylic acid (B78)

1H-NMR(DMSO-d6) 13.01 (bs, 1H), 8.29 (d, 2H, J=0.9 Hz), 8.03 (t, 1H, J=7.3), 7.64 (d, 1H, J=2.3 Hz), 7.31-7.40 (m, 3H), 4.67 (t, 1H, J=6.5 Hz), 3.21 (t, 2H, J=6.5), 1.66 (d, 3H, J=1.3 Hz), 1.30-1.84 (m, 6H), 0.81-0.85 (m, 6H).

Example 158

Synthesis of 3-(4-{4-[3-(1-n-butyloxybutyl)-2-fluorophenyl]thiazol-2-ylcarbamoyl}-2,6-dichlorophenyl)-2-methylacrylic acid (B79)

1H-NMR(DMSO-d6) 13.00 (bs, 1H), 8.27 (d, 2H, J=0.9 Hz), 8.00 (t, 1H, J=7.4), 7.63 (d, 1H, J=2.3 Hz), 7.31-7.38 (m, 3H), 4.67 (t, 1H, J=6.4 Hz), 3.21 (t, 2H, J=6.5), 1.69 (d, 3H, J=1.3 Hz), 1.20-1.84 (m, 8H), 0.81-0.85 (m, 6H).

Example 159

Synthesis of 3-(2,6-dichloro-4-{4-[2-fluoro-3-(1-n-pentyloxybutyl)phenyl]thiazol-2-ylcarbamoyl}phenyl)-2-methylacrylic acid (B80)

1H-NMR(DMSO-d6) 13.00 (bs, 1H), 8.28 (d, 2H, J=0.9 Hz), 8.00 (t, 1H, J=7.4), 7.63 (d, 1H, J=2.3 Hz), 7.31-7.38 (m, 3H), 4.65 (t, 1H, J=6.4 Hz), 3.21 (t, 2H, J=6.5), 1.70 (d, 3H, J=1.3 Hz), 1.20-1.70 (m, 10H), 0.81-0.85 (m, 6H).

Example 160

Synthesis of 3-(2,6-dichloro-4-{4-[2-fluoro-3-(1-n-propyloxypropyl)phenyl]thiazol-2-ylcarbamoyl}phenyl)-2-methylacrylic acid (B81)

1H-NMR(DMSO-d6) 13.02 (bs, 2H), 8.29 (s, 2H), 8.01 (dt, 1H, J=2.1 Hz, 7.2 Hz), 7.64 (d, 1H, J=2.4 Hz), 7.31-7.43 (m, 3H), 4.60 (t, 1H, J=6.3 Hz), 3.21-3.40 (m, 3H), 1.69 (d, 3H, J=1.2 Hz), 1.64-1.82 (m, 2H), 1.47-1.59 (m, 2H), 0.89 (t, 3H, J=7.5 Hz), 0.88 (t, 3H, J=7.2 Hz).

Example 161

Synthesis of 3-(4-{4-[3-(1-n-butyloxypropyl)-2-fluorophenyl]thiazol-2-ylcarbamoyl}-2,6-dichlorophenyl)-2-methylacrylic acid (B82)

1H-NMR(DMSO-d6) 13.02 (bs, 2H), 8.29 (s, 2H), 8.01 (dt, 1H, J=2.1 Hz, 7.2 Hz), 7.64 (d, 1H, J=2.7 Hz), 7.40 (d, 1H, J=1.5 Hz), 7.31-7.38 (m, 2H), 4.59 (t, 1H, J=6.6 Hz), 3.24-0.37 (m, 2H), 1.69 (d, 3H, J=1.2 Hz), 1.45-1.55 (m, 2H), 1.28-1.40 (m, 4H), 0.89 (t, 3H, J=7.5 Hz), 0.86 (t, 3H, J=7.2 Hz).

Example 162

Synthesis of 3-(2,6-dichloro-4-{4-[2-fluoro-3-(1-n-hexyloxypropyl)phenyl]thiazol-2-ylcarbamoyl}phenyl)-2-methylacrylic acid (B83)

1H-NMR(DMSO-d6) 13.02 (bs, 2H), 8.29 (s, 2H), 8.01 (dt, 1H, J=2.7 Hz, 6.9 Hz), 7.64 (d, 1H, J=2.7 Hz), 7.30-7.40 (m, 3H), 4.59 (t, 1H, J=6.6 Hz), 3.25-3.39 (m, 2H), 1.64-1.81 (m, 2H), 1.69 (d, 3H, J=1.2 Hz), 1.49-1.56 (m, 2H), 1.16-1.36 (m, 6H), 0.89 (t, 3H, J=7.2 Hz), 0.84 (t, 3H, J=6.6 Hz).

Example 163

Synthesis of 3-[2,6-dichloro-4-(4-[2-fluoro-3-[3-(4-methylpentyloxy)propyl]phenyl]thiazol-2-ylcarbamoyl)phenyl]-2-methylacrylic acid (B84)

1H-NMR(DMSO-d6) 13.00 (bs, 2H), 8.29 (s, 2H), 7.94 (dt, 1H, J=2.4 Hz, 7.2 Hz), 7.63 (d, 1H, J=2.4 Hz), 7.40 (d, 1H, J=1.2 Hz), 7.21-7.30 (m, 2H), 3.32-3.41 (m, 4H), 2.74 (t, 2H, J=7.8 Hz), 1.78-1.88 (m, 2H), 1.69 (d, 3H, J=1.5 Hz), 1.45-1.56 (m, 3H), 1.14-1.22 (m, 2H), 0.86 (d, 6H, J=6.6 Hz).

Example 164

Synthesis of 3-[2,6-dichloro-4-(4-[3-[3-(3,3-dimethylbutyloxy)propyl]-2-fluorophenyl]thiazol-2-ylcarbamoyl)phenyl]-2-methylacrylic acid (B85)

1H-NMR(DMSO-d6) 13.02 (bs, 2H), 8.29 (s, 2H), 7.94 (dt, 1H, J=1.8 Hz, 7.8 Hz), 7.63 (d, 1H, J=2.4 Hz), 7.41 (s, 1H), 7.21-7.30 (m, 2H), 3.25-3.48 (m, 4H), 2.74 (t, 2H, J=7.5 Hz), 1.78-1.87 (m, 2H), 1.69 (d, 3H, J=1.2 Hz), 1.44 (t, 2H, J=7.5 Hz), 0.90 (s, 9H).

Example 165

Synthesis of 3-(2,6-dichloro-4-{4-[2-fluoro-3-(1-n-propyloxypentyl)phenyl]thiazol-2-ylcarbamoyl}phenyl)-2-methylacrylic acid (B86)

1H-NMR(DMSO-d6) 13.01 (bs, 2H), 8.29 (s, 2H), 8.00 (dt, 1H, J=7.5 Hz, 2.0 Hz), 7.64 (d, 1H, J=2.5 Hz), 7.30-7.41 (m, 3H), 4.63-4.67(m, 1H), 3.25 (t, 2H, 6.4 Hz), 1.64-1.78 (m, 5H), 1.52 (q, 2H, J=6.9 Hz), 1.28-1.33 (m, 4H), 0.84-0.90 (m, 6H).

Example 166

Synthesis of 3-(4-{4-[3-(1-n-butyloxypentyl)-2-fluorophenyl]thiazol-2-ylcarbamoyl}-2,6-dichlorophenyl)-2-methylacrylic acid (B87)

1H-NMR(DMSO-d6) 13.01 (bs, 2H), 8.29 (s, 2H), 8.00 (dt, 1H, J=7.5 Hz, 2.2 Hz), 7.64-7.65 (m, 1H), 7.30-7.41 (m, 3H), 4.62-4.67(m, 1H), 3.29 (t, 2H, 6.4 Hz), 1.60-1.80 (m, 5H), 1.45-1.54 (m, 2H), 1.28-1.40 (m, 6H), 0.82-0.88 (m, 6H).

Example 167

Synthesis of 3-[2,6-dichloro-4-(4-[3-[3-(2-ethylbutyloxy)propyl]-2-fluorophenyl]thiazol-2-ylcarbamoyl)phenyl]-2-methylacrylic acid (B88)

1H-NMR(DMSO-d6) 13.01 (bs, 2H), 8.29 (s, 2H), 7.94 (dt, 1H, J=2.4 Hz, 7.5 Hz), 7.63 (d, 1H, J=2.7 Hz), 7.40 (d, 1H, J=1.5 Hz), 7.21-7.30 (m, 2H), 3.40 (t, 2H, J=6.3 Hz), 3.26 (d, 2H, J=5.4 Hz), 2.74 (t, 2H, J=7.2 Hz), 1.74-1.91 (m, 2H), 1.69 (d, 3H, J=1.5 Hz), 1.20-1.42 (m, 5H), 0.85 (t, 6H, J=7.8 Hz).

Example 168

Synthesis of 3-[2,6-dichloro-4-(4-[3-[3-(2-cyclopentylethyloxy)propyl]-2-fluorophenyl]thiazol-2-ylcarbamoyl)phenyl]-2-methylacrylic acid (B89)

1H-NMR(DMSO-d6) 13.01 (bs, 2H), 8.29 (s, 2H), 7.94 (dt, 1H, J=2.4 Hz, 7.2 Hz), 7.63 (d, 1H, J=2.7 Hz), 7.40 (d, 1H, J=1.5 Hz), 7.20-7.30 (m, 2H), 3.20-3.46 (m, 4H), 2.74 (t, 2H, J=7.8 Hz), 1.60-1.90 (m, 4H), 1.69 (d, 3H, J=1.5 Hz), 1.44-1.59 (m, 5H), 1.02-1.15 (m, 4H).

Example 169

Synthesis of 3-(2,6-dichloro-4-{4-[2-fluoro-3-(3-n-pentyloxy)propyl]phenyl]thiazol-2-ylcarbamoyl)phenyl]-2-methylacrylic acid (B90)

1H-NMR(DMSO-d6) 13.01 (bs, 2H), 8.29 (s, 2H), 7.94 (dt, 1H, J=2.1 Hz, 6.6 Hz), 7.63 (d, 1H, J=2.4 Hz), 7.40 (s, 1H), 7.21-7.30 (m, 2H), 3.33-3.42 (m, 4H), 2.74 (t, 2H, J=7.5 Hz), 1.78-1.88 (m, 2H), 1.69 (d, 3H, J=1.2 Hz), 1.44-1.57 (m, 2H), 1.26-1.31 (m, 4H), 0.87 (t, 3H, J=7.2 Hz).

Example 170

Synthesis of 3-(2,6-dichloro-4-{4-[2-fluoro-3-(1-methyloxyundecyl)phenyl]thiazol-2-ylcarbamoyl)phenyl]-2-methylacrylic acid (B91)

1H-NMR(DMSO-d6) 13.01 (bs, 2H), 8.29 (s, 2H), 7.99-8.05 (m, 1H), 7.64 (s, 1H), 7.30-7.40 (m, 3H), 4.56 (t, 1H, J=6.5 Hz), 3.18 (s, 3H), 1.60-1.80 (m, 5H), 1.14-1.36 (m, 16H), 0.81-0.85 (m, 3H).

Example 171

Synthesis of 3-(2,6-dichloro-4-{4-[2-fluoro-3-(1-methyloxydodecyl)phenyl]thiazol-2-ylcarbamoyl)phenyl]-2-methylacrylic acid (B92)

1H-NMR(DMSO-d6) 13.01 (bs, 2H), 8.29 (s, 2H), 8.00-8.05 (m, 1H), 7.64 (d, 1H, J=2.7 Hz), 7.31-7.41 (m, 3H), 4.56 (t, 1H, J=6.4 Hz), 3.18 (s, 3H), 1.60-1.80 (m, 5H), 1.20-1.36 (m, 18H), 0.81-0.85 (m, 3H).

Example 172

Synthesis of 3-(4-{4-[3-(3-n-butyloxypropyl)-2-fluorophenyl]thiazol-2-ylcarbamoyl}-2,6-dichlorophenyl]-2-methylacrylic acid (B93)

1H-NMR(DMSO-d6) 13.04 (bs, 2H), 8.29 (s, 2H), 7.94 (dt, 1H, J=2.4 Hz, 7.2 Hz), 7.64 (d, 1H, J=2.7 Hz), 7.40 (d, 1H, J=1.2 Hz), 7.21-7.32 (m, 2H), 3.20-3.42 (m, 4H), 2.74 (t, 2H, J=8.1 Hz), 1.78-1.88 (m, 2H), 1.69 (d, 3H, J=1.2 Hz), 1.44-1.53 (m, 2H), 1.27-1.39 (m, 2H), 0.88 (t, 3H, J=6.9 Hz).

Example 173

Synthesis of 3-(2,6-dichloro-4-{4-[2-fluoro-3-(3-isopropyloxypropyl)phenyl]thiazol-2-ylcarbamoyl)phenyl]-2-methylacrylic acid (B94)

1H-NMR(DMSO-d6) 13.02 (bs, 2H), 8.29 (s, 2H), 7.94 (dt, 1H, J=2.4 Hz, 7.2 Hz), 7.64 (d, 1H, J=2.7 Hz), 7.41 (d, 1H, J=1.2 Hz), 7.21-7.31 (m, 2H), 3.52 (m, 1H), 3.35-3.41 (m, 2H), 2.74 (t, 2H, J=8.1 Hz), 1.76-1.85 (m, 2H), 1.69 (d, 3H, J=1.8 Hz), 1.09 (d, 6H, J=6.3 Hz).

Example 174

Synthesis of 3-(2,6-dichloro-4-{4-[2-fluoro-3-(3-n-propyloxypropyl)phenyl]thiazol-2-ylcarbamoyl)phenyl]-2-methylacrylic acid (B95)

1H-NMR(DMSO-d6) 13.02 (bs, 2H), 8.29 (s, 2H), 7.94 (dt, 1H, J=1.8 Hz, 7.2 Hz), 7.64 (d, 1H, J=2.4 Hz), 7.41 (t, 1H), 7.21-7.31 (m, 2H), 3.30-3.42 (m, 4H), 2.74 (t, 2H, J=7.8 Hz), 1.78-1.88 (m, 2H), 1.69 (s, 3H), 1.49-1.58 (m, 2H), 0.88 (t, 3H, J=7.5 Hz).

Example 175

Synthesis of 3-(2,6-dichloro-4-{4-[2-fluoro-3-(3-n-hexyloxypropyl)phenyl]thiazol-2-ylcarbamoyl)phenyl]-2-methylacrylic acid (B96)

1H-NMR(DMSO-d6) 13.02 (bs, 2H), 8.29 (s, 2H), 7.93 (dt, 1H, J=2.7 Hz, 7.8 Hz), 7.63 (d, 1H, J=2.4 Hz), 7.41 (d, 1H, J=1.5 Hz), 7.21-7.31 (m, 2H), 3.20-3.45 (m, 4H), 2.74 (t, 2H, J=7.5 Hz), 1.78-1.87 (m, 2H), 1.69 (d, 3H, J=1.8 Hz), 1.44-1.53 (m, 2H), 1.21-1.36 (m, 6H), 0.86 (t, 3H, J=6.9 Hz).

Example 176

Synthesis of 3-(2,6-dichloro-4-{4-[2-fluoro-3-(1-n-propyloxyethyl)phenyl]thiazol-2-ylcarbamoyl)phenyl]-2-methylacrylic acid (B97)

1H-NMR(DMSO-d6) 13.01 (bs, 2H), 8.29 (s, 2H), 8.01 (dt, 1H, J=7.6 Hz, 1.8 Hz), 7.65 (d, 1H, J=2.4 Hz), 7.31-7.45 (m, 3H), 4.80 (t, 1H, J=6.4 Hz), 3.20-3.39 (m, 2H), 1.69 (d, 3H, J=1.5 Hz), 1.52 (qint, 2H, J=7.0 Hz), 1.41(d, 3H, J=6.4 Hz), 0.87 (t, 3H, J=7.3 Hz).

Example 177

Synthesis of 3-(4-{4-[3-(1-n-butyloxyethyl)-2-fluorophenyl]thiazol-2-ylcarbamoyl)-2,6-dichlorophenyl]-2-methylacrylic acid (B98)

1H-NMR(DMSO-d6) 13.01 (bs, 2H), 8.29 (s, 2H), 8.01 (dt, 1H, J=7.3 Hz, 1.8 Hz), 7.65 (d, 1H, J=2.4 Hz), 7.39-7.44 (m, 1H), 7.34 (t, 2H, J=7.6 Hz), 4.80 (q, 1H, J=6.4 Hz), 3.25-3.41 (m, 2H), 1.69 (d, 3H, J=1.2 Hz), 1.45-1.55 (m, 2H), 1.41(d, 3H, J=6.4 Hz), 1.29-1.37 (m, 2H), 0.86 (t, 3H, J=7.3 Hz).

Example 178

Synthesis of 3-(2,6-dichloro-4-{4-[2-fluoro-3-(1-n-hexyloxyethyl)phenyl]thiazol-2-ylcarbamoyl)phenyl]-2-methylacrylic acid (B99)

1H-NMR(DMSO-d6) 13.02 (bs, 2H), 8.29 (s, 2H), 8.00 (dt, 1H, J=7.5 Hz, 1.9 Hz), 7.64 (d, 1H, J=2.5 Hz), 7.31-7.43 (m, 3H), 4.80 (q, 1H, J=6.4 Hz), 3.23-3.40 (m, 2H), 1.69 (d, 3H, J=1.4 Hz), 1.46-1.53 (m, 2H), 1.41(d, 3H, J=6.4 Hz), 1.20-1.35 (m, 6H), 0.82-0.87 (m, 3H).

Example 179

Synthesis of 3-(4-{4-[3-(1,4-dibutyloxybutyl)-2-fluorophenyl]thiazol-2-ylcarbamoyl)-2,6-dichlorophenyl]-2-methylacrylic acid (B100)

1H-NMR(DMSO-d6) 13.02 (bs, 2H), 8.29 (s, 2H), 8.01 (dt, 1H, J=2.1 Hz, 6.8 Hz), 7.64 (d, 1H, J=2.4 Hz), 7.41 (d, 1H, J=1.5 Hz), 7.31-7.38 (m, 2H), 4.68 (t, 3H, J=6.2 Hz), 3.16-3.20 (m, 6H), 1.69 (d, 3H, J=1.5 Hz), 1.55-1.75 (m, 4H), 1.40-1.54 (m, 4H), 1.25-1.37 (m, 4H), 0.85 (dt, 6H, J=1.2 Hz, 6.9 Hz).

Example 180

Synthesis of 3-(2,6-dichloro-4-{4-[2-fluoro-3-(3-n-hexyloxy-1-methyloxypropyl)phenyl]thiazol-2-ylcarbamoyl)phenyl]-2-methylacrylic acid (B101)

1H-NMR(DMSO-d6) 13.02 (bs, 2H), 8.29 (s, 2H), 8.03 (dt, 1H, J=2.1 Hz, 6.6 Hz), 7.65 (d, 1H, J=2.7 Hz), 7.32-7.41 (m, 3H), 4.71 (m, 1H,), 3.25-3.40 (m, 4H), 3.18 (s, 3H), 1.83-2.01 (m, 2H), 1.69 (s, 3H), 1.40-1.50 (m, 2H), 1.18-1.32 (m, 6H), 0.85 (t, 3H, J=6.9 Hz).

Example 181

Synthesis of (Z)-3-(4-{4-[3-(4-methylpentyl)-2-fluorophenyl]thiazol-2-ylcarbamoyl)phenyl]-2-methyloxyacrylic acid (B121)

1H-NMR(DMSO-d6) 13.56 (bs, 1H), 12.96 (bs, 1H), 7.89-7.96 (m, 3H), 7.63 (d, 1H, J=2.6 Hz), 7.20-7.31 (m, 2H), 6.66 (s, 1H), 3.71 (s, 3H), 2.67 (t, 2H, J=7.6 Hz), 1.53-1.62 (m, 3H), 1.20-1.27 (m, 2H), 0.88 (d, 6H, J=6.6 Hz).

Example 182

Synthesis of (Z)-3-(4-{4-[3-(3,3-dimethylbutyl)-2-fluorophenyl]thiazol-2-ylcarbamoyl}-2,6-difluorophenyl]-2-methyloxyacrylic acid (B122)

1H-NMR(DMSO-d6) 13.01 (bs, 2H), 8.29 (s, 2H), 8.00-8.06 (m, 1H), 7.65 (d, 1H, J=2.6 Hz), 7.31-7.41 (m, 3H), 4.69-4.74 (m, 1H), 3.48-3.55 (m, 1H), 3.25-3.40 (m, 3H), 1.86-2.03 (m, 2H), 1.69(s, 3H), 1.43-1.54 (m, 2H), 0.83-0.88 (m, 3H).

Example 183

Synthesis of (E)-3-(4-{4-[3-(3,3-dimethylbutyl)-2-methyoxyphenyl]thiazol-2-ylcarbamoyl)-2,6-difluorophenyl]-2-methylacrylic acid (B134)

1H-NMR(DMSO-d6) 12.98(bs, 2H), 7.92-8.00(m, 2H), 7.84(dd, 1H, J=1.8, 6.9 Hz), 7.72(s, 1H), 7.33(s, 1H), 7.12-7.23(m, 2H), 3.62(s, 3H), 2.60-2.65(m, 2H), 1.81(s, 3H), 1.45-1.51(m, 2H), 0.98(s, 9H).

Example 184

Synthesis of (Z)-3-(2,6-dichloro-4-{4-[2-fluoro-3-(4-methylpentyl)phenyl]thiazol-2-ylcarbamoyl)phenyl]-2-methyloxyacrylic acid (B169)

1H-NMR(DMSO-d6) 13.20 (bs, 1H), 12.99 (bs, 1H), 8.25 (s, 2H), 7.90-7.96 (m, 1H), 7.62-7.63 (m, 1H), 7.20-7.30 (m, 2H), 6.73 (s, 1H), 3.61 (s, 3H), 2.67 (t, 2H, J=7.6 Hz), 1.53-1.66 (m, 3H), 1.20-1.27 (m, 2H), 0.88 (d, 6H, J=6.6 Hz).

Example 185

Synthesis of (Z)-3-(2,6-dichloro-4-{4-[3-(3,3-dimethylbutyl)-2-fluorophenyl]thiazol-2-ylcarbamoyl)phenyl]-2-methyloxyacrylic acid (B170)

1H-NMR(DMSO-d6) 13.51 (bs, 1H), 13.00 (bs, 1H), 8.25 (s, 2H), 7.89-7.95 (m, 1H), 7.63 (d, 1H, J=2.6 Hz), 7.19-7.31 (m, 2H), 6.73 (s, 1H), 3.62 (s, 3H), 2.62-2.68 (m, 2H), 1.45-1.50 (m, 2H), 0.97 (s, 9H).

Example 186

Synthesis of (E)-3-(2,6-difluoro-4-{4-[2-fluoro-3-(1-methyloxypropyl)phenyl]thiazol-2-ylcarbamoyl)phenyl]-2-methylacrylic acid (B195)

1H-NMR(DMSO-d6) 12.98(bs, 2H), 7.92-8.08(m, 3H), 7.65(d, 1H, J=2.7 Hz), 7.30-7.41(m, 3H), 4.52(t, 1H, J=6.3 Hz), 3.20(s, 3H), 1.65-1.85(m, 5H), 0.87(t, 3H, J=7.2 Hz).

Example 187

Synthesis of (E)-3-(2,6-difluoro-4-{4-[2-fluoro-3-(1-propyloxypropyl)phenyl]thiazol-2-ylcarbamoyl)phenyl]-2-methylacrylic acid (B216)

1H-NMR(DMSO-d6) 13.00(bs, 2H), 7.92-8.05(m, 3H), 7.64(d, 1H, J=2.7 Hz), 7.30-7.42(m, 3H), 4.60(t, 1H, J=6.6 Hz), 3.10-3.42(m, 2H), 1.65-1.86(m, 5H), 1.47-1.59(m, 2H), 0.85-0.92(m, 6H).

Example 188

Synthesis of (E)-3-(4-{4-[3-(cyclohexylpropyloxymethyl)-2-fluorophenyl]thiazol-2-ylcarbamoyl}-2,6-difluorophenyl)-2-methylacrylic acid (B233)

1H-NMR(DMSO-d6) 13.00 (bs, 2H), 7.95-8.04 (m, 3H), 7.64 (d, 1H, J=2.6 Hz), 7.32-7.35 (m, 3H), 4.40 (d, 1H, J=7.0 Hz), 3.17-3.23 (m, 2H), 1.93-1.97 (m, 1H), 1.04-1.64 (m, 12H), 0.86 (t, 3H, J=7.5 Hz).

Example 189

Synthesis of (E)-3-(4-{4-[3-(1-butyloxy-2,2-dimethylpropyl)-2-fluorophenyl]thiazol-2-ylcarbamoyl}-2,6-difluorophenyl)-2-methylacrylic acid (B255)

1H-NMR(DMSO-d6) 12.99 (bs, 2H), 7.95-8.05 (m, 3H), 7.61-7.62 (m, 1H), 7.32-7.34 (m, 3H), 4.39 (s, 1H), 3.22 (t, 2H, J=6.3 Hz), 1.81 (s, 3H), 1.33-1.51 (m, 4H), 0.84-0.91 (m, 12H).

Example 190

Synthesis of (E)-3-(4-{4-[3-(butyloxycyclohexylmethyl)-2-fluorophenyl]thiazol-2-ylcarbamoyl}-2,6-difluorophenyl)-2-methylacrylic acid (B264)

1H-NMR(DMSO-d6) 13.00 (bs, 2H), 7.94-8.04 (m, 3H), 7.64 (d, 1H, J=2.6 Hz), 7.32-7.34 (m, 3H), 4.39 (d, 1H, J=7.0 Hz), 3.22-3.27 (m, 2H), 1.93-1.97 (m, 1H), 1.04-1.64 (m, 14H), 0.86 (t, 3H, J=7.5 Hz).

Example 191

Synthesis of (E)-3-(2,6-difluoro-4-{4-[2-methyloxy-3-(1-methyloxyhexyl)phenyl]thiazol-2-ylcarbamoyl}phenyl)-2-methylacrylic acid (B347)

1H-NMR(DMSO-d6) 13.00(bs, 2H), 7.90-8.00(m, 3H), 7.72(s, 1H), 7.24-7.45(m, 3H), 4.56-4.60(m, 1H), 3.62(s, 3H), 3.16(s, 3H), 1.81(s, 3H), 1.20-1.78(m, 8H), 0.83-0.88 (m, 3H).

Example 192

Synthesis of (E)-3-(2,6-difluoro-4-{4-[2-methyloxy-3-(1-methyloxy-5-methylhexyl)phenyl]thiazol-2-ylcarbamoyl}phenyl)-2-methylacrylic acid (B348)

1H-NMR(DMSO-d6) 12.97 (bs, 2H), 7.89-7.97 (m, 3H), 7.72 (s, 1H), 7.24-7.34 (m, 3H), 4.53-4.57 (m, 1H), 3.61 (s, 3H), 3.16 (s, 3H), 1.81 (s, 3H), 0.87-1.72 (m, 13H).

Example 193

Synthesis of (E)-3-(2,6-difluoro-4-{4-[2-methyloxy-3-(1-methyloxy-3,3-dimethylbutyl)phenyl]thiazol-2-ylcarbamoyl}phenyl)-2-methylacrylic acid (B349)

1H-NMR(DMSO-d6) 12.98(bs, 2H), 7.92-8.00(m, 2H), 7.89(dd, 1H, J=1.8, 7.5 Hz), 7.71(s, 1H), 7.31-7.36(m, 2H), 7.25(t, 1H, J=7.8 Hz), 4.69(d, 1H, J=7.8 Hz), 3.63(s, 3H), 3.13(s, 3H), 1.81(s, 3H), 1.63-1.71(m, 1H), 1.40(d, 1H, J=14.4 Hz), 1.00(s, 9H).

Example 194

Synthesis of (E)-3-(2,6-difluoro-4-{4-[2-methyloxy-3-(1-methyloxydecyl)phenyl]thiazol-2-ylcarbamoyl}phenyl)-2-methylacrylic acid (B354)

1H-NMR(DMSO-d6) 13.00(bs, 2H), 7.90-8.00(m, 3H), 7.72(s, 1H), 7.24-7.36(m, 3H), 4.554.59(m, 1H), 3.61(s, 3H), 3.16(s, 3H), 1.81(s, 3H), 1.50-1.78(m, 2H), 1.16-1.50(m, 14H), 0.82-0.87(m, 3H).

Example 195

Synthesis of (E)-3-(2,6-difluoro-4-{4-[2-methyloxy-3-(1-methyloxyundecyl)phenyl]thiazol-2-ylcarbamoyl}phenyl)-2-methylacrylic acid (B355)

1H-NMR(DMSO-d6) 13.00(bs, 2H), 7.90-8.00(m, 3H), 7.73(s, 1H), 7.24-7.36(m, 3H), 4.56-4.59(m, 1H), 3.61(s, 3H), 3.15(s, 3H), 1.81(s, 3H), 1.50-1.78(m, 2H), 1.16-1.50 (m, 16H), 0.82-0.87(m, 3H).

Example 196

Synthesis of (E)-3-(2,6-difluoro-4-{4-[2-methyloxy-3-(3-propyloxypropyl)phenyl]thiazol-2-ylcarbamoyl}phenyl)-2-methylacrylic acid (B380)

1H-NMR(CDCl3-d6) 7.90(s, 1H), 7.87(s, 1H), 7.58(s, 1H), 7.48-7.52(m, 1H), 7.46(s, 1H), 7.25-7.30(m, 1H), 7.18(t, 1H, J=7.5 Hz), 3.58(s, 3H), 3.50(t, 2H, J=6.3 Hz), 3.41(t, 2H, J=6.6 Hz), 2.80(t, 2H, J=8.4 Hz), 1.91-2.02(m, 5H), 1.63(q, 2H, J=7.2 Hz), 0.95 (t, 3H, J=7.5 Hz).

Example 197

Synthesis of (E)-3-(4-{4-[3-(cyclohexylpropyloxymethyl-2-methyloxyphenyl]thiazol-2-ylcarbamoyl}-2,6-difluorophenyl)-2-methylacrylic acid (B397)

1H-NMR(DMSO-d6) 12.98(bs, 2H), 7.92-8.00(m, 2H), 7.89(dd, 1H, J=1.8, 6.9 Hz), 7.71(s, 1H), 7.34(s, 1H), 7.22-7.31(m, 2H), 4.40(d, 1H, J=6.9 Hz), 3.59(s, 3H), 3.06-3.25 (m, 2H), 1.90-2.00(m, 1H), 1.81(s, 3H), 1.44-1.76(m, 6H), 1.36-1.28(m, 1H), 1.00-1.20(m, 5H), 0.87(t, 3H, J=7.2 Hz).

Example 198

Synthesis of (E)-3-(4-{4-[3-(1-butyloxypropyl)-2-methyloxyphenyl]thiazol-2-ylcarbamoyl}-2,6-difluorophenyl)-2-methylacrylic acid (B418)

1H-NMR(DMSO-d6) 12.99(bs, 2H), 7.89-8.05(m, 3H), 7.72(s, 1H), 7.31-7.36(m, 2H), 7.26(t, 1H, J=7.8 Hz), 4.55-4.63(m, 1H), 3.61(s, 3H), 1.81(s, 3H), 1.62-1.76(m, 2H), 1.43-1.55(m, 2H), 1.28-1.41(m, 2H), 0.84-0.95(m, 6H).

Example 199

Synthesis of (E)-3-(4-{4-[3-(3-butyloxypropyl)-2-methyloxyphenyl]thiazol-2-ylcarbamoyl}-2,6-difluorophenyl)-2-methylacrylic acid (B419)

1H-NMR(CDCl3-d6) 7.91(s, 1H), 7.88(s, 1H), 7.58(s, 1H), 7.49(d, 1H, J=7.5 Hz), 7.46(s, 1H), 7.25-7.29(m, 1H), 7.17(t, 1H, J=7.8 Hz), 3.58(s, 3H), 3.50(t, 1H, J=6.6 Hz), 3.45(t, 1H, J=6.9 Hz), 2.80(t, 2H, J=8.4 Hz), 1.90-2.02(m, 5H), 1.53-1.64(m, 2H), 1.34-1.48(m, 2H), 0.94(t, 3H, J=7.2 Hz).

Example 200

Synthesis of (E)-3-(4-{4-[3-(1-butyloxy-2,2-dimethylpropyl)-2-methyloxyphenyl]thiazol-2-ylcarbamoyl}-2,6-difluorophenyl)-2-methylacrylic acid (B425)

1H-NMR(DMSO-d6) 12.96(bs, 2H), 7.88-8.10(m, 3H), 7.70(s, 1H), 7.34(s, 1H), 7.22-7.31(m, 2H), 4.40(s, 1H), 3.57 (s, 3H), 1.81(s, 3H), 1.32-1.55(m, 4H), 0.85-0.92(m, 12H).

Example 201

Synthesis of (E)-3-(4-{4-[3-(cyclohexylpentyloxymethyl)-2-methyloxyphenyl]thiazol-2-ylcarbamoyl}-2,6-difluorophenyl)-2-methylacrylic acid (B484)

1H-NMR(DMSO-d6) 12.98(bs, 2H), 7.92-8.00(m, 2H), 7.86-7.95(m, 1H), 7.70(s, 1H), 7.34(s, 1H), 7.22-7.30(m, 2H), 4.39(d, 1H, J=7.2 Hz), 3.59(s, 3H), 3.21-3.28(m, 2H), 1.88-2.00(m, 1H), 1.81(s, 3H), 1.44-1.78(m, 6H), 1.00-1.36 (m, 10H), 0.83-0.87(m, 3H).

Example 202

Synthesis of (E)-3-(4-{4-[3-(2,2-dimethylpropyloxy)propyl]-2-methyloxyphenyl]thiazol-2-ylcarbamoyl}-2,6-difluorophenyl)-2-methylacrylic acid (B488)

1H-NMR(DMSO-d6) 12.97(bs, 2H), 7.92-8.00(m, 2H), 7.84-7.90(m, 1H), 7.73(s, 1H), 7.34(s, 1H), 7.14-7.25(m,

2H), 3.62(s, 3H), 3.45(t, 2H, J=6.3 Hz), 3.06(s, 2H), 2.74(t, 2H, J=6.3 Hz), 1.81-1.90(m, 5H), 1.90(s, 9H).

Example 203

Synthesis of (E)-3-(2,6-difluoro-4-{4-[3-(3-hexyloxypropyl)-2-methyloxyphenyl]thiazol-2-ylcarbamoyl}phenyl)-2-methylacrylic acid (B505)

1H-NMR(DMSO-d6) 12.97(bs, 2H), 7.92-8.00(m, 2H), 7.86(dd, 1H, J=1.5, 7.5 Hz), 7.72(s, 1H), 7.34(s, 1H), 7.23(dd, 2H, J=1.5, 7.5 Hz), 7.16(t, 1H, J=7.5 Hz), 3.61(s, 3H), 3.20-3.46(m, 4H), 2.69-2.74(m, 2H), 1.76-1.88(m, 5H), 1.46-1.56 (m, 2H), 1.20-1.38(m, 6H), 1.84-0.89(m, 3H).

Example 204

Synthesis of (E)-3-(4-{4-[3-(cyclohexylhexyloxymethyl)-2-methyloxyphenyl]thiazol-2-ylcarbamoyl}-2,6-difluorophenyl)-2-methylacrylic acid (B519)

1H-NMR(DMSO-d6) 13.00(bs, 2H), 7.92-8.00(m, 2H), 7.89(dd, 1H, J=2.7, 7.5 Hz), 7.70(s, 1H), 7.34(s, 1H), 7.22-7.29(m, 2H), 4.39(d, 1H, J=7.2 Hz), 3.59(s, 3H), 1.90-2.00 (m, 1H), 1.81(s, 3H), 1.02-1.76(m, 16H), 1.32-1.55(m, 4H), 0.85(t, 3H, J=6.9 Hz).

Example 205

Synthesis of (E)-3-[4-(4-{3-[3-(3,3-dimethylbutyloxy)propyl]-2-methyloxyphenyl}thiazol-2-ylcarbamoyl}-2,6-difluorophenyl)-2-methylacrylic acid (B521)

1H-NMR(CDCl3-d6) 7.91(s, 1H), 7.88(s, 1H), 7.58(s, 1H), 7.43-7.54(m, 2H), 7.25-7.30(m, 1H), 7.17(t, 1H, J=7.5 Hz), 3.58(s, 3H), 3.46-3.52(m, 4H), 2.80(t, 2H, J=8.1 Hz), 1.90-2.30(m, 5H), 1.54(t, 2H, J=7.5 Hz), 0.94(s, 9H).

Example 206

Synthesis of (Z)-3-(2,6-difluoro-4-{4-[2-fluoro-3-(1-methyloxyhexyl)phenyl]thiazol-2-ylcarbamoyl}phenyl)-2-methyloxyacrylic acid (B533)

1H-NMR(DMSO-d6) 12.98 (bs, 2H), 8.00-8.05 (m, 1H), 7.89-7.95 (m, 2H), 7.65 (d, 1H, J=2.4 Hz), 7.31-7.39 (m, 2H), 6.67 (s, 1H), 4.55-4.59 (m, 1H), 3.72 (s, 3H), 3.18 (s, 3H), 1.64-1.76 (m, 2H), 1.26-1.41 (m, 6H), 0.81-0.86 (m, 3H).

Example 207

Synthesis of (Z)-3-(4-{4-[3-(3-butyloxypropyl)-2-methyloxyphenyl]thiazol-2-ylcarbamoyl}-2,6-difluorophenyl)-2-methyloxyacrylic acid (B790)

1H-NMR(CDCl3-d6) 7.83(s, 1H), 7.80(s, 1H), 7.48(d, 1H, J=7.8 Hz), 7.44(s, 1H), 7.26-7.30(m, 1H), 7.17(t, 1H, J=7.5 Hz), 6.91(s, 1H), 3.90(s, 3H), 3.58(s, 3H), 3.50(t, 2H, J=6.3 Hz), 3.44(t, 2H, J=6.3 Hz), 2.80(t, 2H, J=8.1 Hz), 1.91-2.05 (m, 2H), 1.53-1.63(m, 2H), 1.34-1.46(m, 2H), 0.94(t, 3H, J=7.5 Hz).

Example 208

Synthesis of (E)-3-(2,6-dichloro-4-{4-[2-fluoro-3-(1-methyloxypropyl)phenyl]thiazol-2-ylcarbamoyl}phenyl)-2-methylacrylic acid (B896)

1H-NMR(DMSO-d6) 13.02(bs, 2H), 8.29(s, 2H), 7.95-8.06(m, 1H), 7.65(d, 1H, J=2.4 Hz), 7.32-7.42(m, 3H), 4.52(t, 1H, J=6.3 Hz), 3.20(s, 3H), 1.66-1.84(m, 5H), 0.87(t, 1H, J=7.5 Hz).

Example 209

Synthesis of (E)-3-(2,6-dichloro-4-{4-[2-fluoro-3-(1-methyloxy-3-propyloxypropyl)phenyl]thiazol-2-ylcarbamoyl}phenyl)-2-methylacrylic acid (B897)

1H-NMR(DMSO-d6) 13.01 (bs, 2H), 8.29 (s, 2H), 8.00-8.06 (m, 1H), 7.65 (d, 1H, J=2.6 Hz), 7.31-7.41 (m, 3H), 4.69-4.74 (m, 1H), 3.48-3.55 (m, 1H), 3.25-3.40 (m, 3H), 1.86-2.03 (m, 2H), 1.69(s, 3H), 1.43-1.54 (m, 2H), 0.83-0.88 (m, 3H).

Example 210

Synthesis of (E)-3-(2,6-dichloro-4-{4-[2-fluoro-3-(1-methyloxy-4-pentyloxybutyl)phenyl]thiazol-2-ylcarbamoyl}phenyl)-2-methylacrylic acid (B899)

1H-NMR(DMSO-d6) 13.00(bs, 2H), 8.29(s, 2H), 7.97-8.06(m, 1H), 7.64(d, 1H, J=2.4 Hz), 7.31-7.40(m, 3H), 4.60(t, 1H, J=6.0 Hz), 3.19(s, 3H), 1.66-1.82(m, 5), 1.41-1.65(m, 4H), 1.22-1.30(m, 4H), 0.81-0.86(m, 3H).

Example 211

Synthesis of (E)-3-(2,6-dichloro-4-{4-[2-fluoro-3-(1-methyloxy-3,3-dimethylbutyl)phenyl]thiazol-2-ylcarbamoyl}phenyl)-2-methylacrylic acid (B905)

1H-NMR(DMSO-d6) 13.02 (bs, 2H), 8.29 (s, 2H), 7.97-8.03 (m, 1H), 7.65 (d, 1H, J=2.5 Hz), 7.30-7.40 (m, 3H), 4.64-4.68 (m, 1H), 3.25 (s, 3H), 1.69-1.77(m, 4), 1.42-1.48 (m, 1H), 0.97 (s, 9H).

Example 208

Synthesis of (E)-3-(2,6-dichloro-4-{4-[3-(2,2-dimethyl-1-propyloxypropyl)-2-fluorophenyl]thiazol-2-ylcarbamoyl}phenyl)-2-methylacrylic acid (B927)

1H-NMR(DMSO-d6) 13.00 (bs, 2H), 8.30 (s, 2H), 7.99-8.04 (m, 1H), 7.61-7.62 (m, 1H), 7.32-7.41 (m, 3H), 4.40 (s, 1H), 3.16-3.33 (m, 2H), 169 (s, 3H), 1.47-1.55 (m, 2H), 0.84-0.91 (m, 12H).

Example 213

Synthesis of (E)-3-(2,6-dichloro-4-{4-[3-(cyclohexylpropyloxymethyl)-2-fluorophenyl]thiazol-2-ylcarbamoyl}phenyl)-2-methylacrylic acid (B936)

1H-NMR(DMSO-d6) 13.00 (bs, 2H), 8.30 (s, 1H), 7.98-8.03 (m, 1H), 7.63 (d, 1H, J=2.3 Hz), 7.32-7.40 (m, 3H), 4.40 (d, 1H, J=7.0 Hz), 3.18-3.23 (m, 2H), 1.93-1.97 (m, 1H), 1.04-1.64 (m, 12H), 0.86 (t, 3H, J=7.5 Hz).

Example 214

Synthesis of (E)-3-(4-{4-[3-(1-butyloxy-2,2-dimethylpropyl)-2-fluorophenyl]thiazol-2-ylcarbamoyl}-2,6-dichlorophenyl)-2-methylacrylic acid (B958)

1H-NMR(DMSO-d6) 13.00 (bs, 2H), 8.29 (s, 2H), 7.99-8.04 (m, 1H), 7.61-7.62 (m, 1H), 7.32-7.41 (m, 3H), 4.40 (s, 1H), 3.32 (t, 2H, J=6.3 Hz), 169 (s, 3H), 1.29-1.53 (m, 4H), 0.84-0.91 (m, 12H).

Example 215

Synthesis of (E)-3-(4-{4-[3-(butyloxycyclohexylmethyl)-2-fluorophenyl]thiazol-2-ylcarbamoyl}-2,6-dichlorophenyl)-2-methylacrylic acid (B967)

1H-NMR(DMSO-d6) 13.00 (bs, 2H), 8.29 (s, 1H), 7.98-8.03 (m, 1H), 7.63 (d, 1H, J=2.3 Hz), 7.32-7.40 (m, 3H), 4.40 (d, 1H, J=7.0 Hz), 3.18-3.23 (m, 2H), 1.93-1.97 (m, 1H), 1.04-1.64 (m, 14H), 0.86 (t, 3H, J=7.5 Hz).

Example 216

Synthesis of (E)-3-(2,6-dichloro-4-{4-[2-methyloxy-3-(1-methyloxy-5-methylhexyl)phenyl]thiazol-2-ylcarbamoyl}phenyl)-2-methylacrylic acid (B1053)

1H-NMR(DMSO-d6) 12.98 (bs, 2H), 9.29 (s, 1H), 7.89-7.92 (m, 1H), 7.72 (s, 1H), 7.41 (s, 1H), 7.24-7.37 (m, 3H), 4.53-4.57 (m, 1H), 3.61 (s, 3H), 3.16 (s, 3H), 0.87-1.72 (m, 16H).

Example 217

Synthesis of (E)-3-(2,6-dichloro-4-{4-[2-methyloxy-3-(1-methyloxy-3,3-dimethylbutyl)phenyl]thiazol-2-ylcarbamoyl}phenyl)-2-methylacrylic acid (B1054)

1H-NMR(DMSO-d6) 12.99(bs, 2H), 8.29(s, 2H), 7.89(dd, 1H, J=1.6, 7.5 Hz), 7.71(s, 1H), 7.40(d, 1H, J=1.5 Hz), 7.34 (dd, 1H, J=2.1, 7.8 Hz), 7.25(t, 1H, J=7.8 Hz), 4.69(d, 1H, J=7.5 Hz), 3.63(s, 3H), 3.13(s, 3H), 1.63-1.71(m, 4H), 1.36-1.44(m, 1H), 1.00(s, 9H).

Example 218

Synthesis of (E)-3-(2,6-dichloro-4-{4-[2-methyloxy-3-(1-methyloxydecyl)phenyl]thiazol-2-ylcarbamoyl}phenyl)-2-methylacrylic acid (B1059)

1H-NMR(DMSO-d6) 13.00(bs, 2H), 8.29(s, 2H), 7.92(dd, 1H, J=2.4, 7.2 Hz), 7.72(s, 1H), 7.41(d, 1H, J=1.2 Hz), 7.24-7.38(m, 2H), 4.55-4.59(m, 1H), 3.62(s, 3H), 3.15(s, 3H), 1.50-1.78(m, 4H), 1.18-1.50(m, 15H), 0.82-0.87(m, 3H).

Example 219

Synthesis of (E)-3-(2,6-dichloro-4-{4-[2-methyloxy-3-(1-methyloxy-undecyl)phenyl]thiazol-2-ylcarbamoyl}phenyl)-2-methylacrylic acid (B1060)

1H-NMR(DMSO-d6) 13.00(bs, 2H), 8.29(s, 2H), 7.92(dd, 1H, J=2.4, 7.5 Hz), 7.72(s, 1H), 7.41(d, 1H, J=1.5 Hz), 7.24-7.33(m, 2H), 4.55-4.59(m, 1H), 3.62(s, 3H), 3.16(s, 3H), 1.50-1.78(m, 4H), 1.18-1.50(m, 17H), 0.82-0.87(m, 3H).

Example 220

Synthesis of (E)-3-(2,6-dichloro-4-{4-[3-(cyclohexylpropyloxymethyl)-2-methyloxyphenyl]thiazol-2-ylcarbamoyl}phenyl)-2-methylacrylic acid (B1102)

1H-NMR(DMSO-d6) 12.99(bs, 2H), 8.29(s, 2H), 7.89(dd, 1H, J=2.1, 7.5 Hz), 7.70(s, 1H), 7.41(d, 1H, J=1.5 Hz), 7.30 (dd, 1H, J=2.1, 7.5 Hz), 7.25(t, 1H, J=7.5 Hz), 4.40(d, 1H, J=6.9 Hz), 3.59(s, 3H), 3.17-3.24(m, 2H), 1.88-2.00(m, 1H), 1.69(s, 3H), 1.44-1.70(m, 4H), 1.00-1.38(m, 6H), 0.87(t, 3H, J=7.2 Hz).

Example 221

Synthesis of (E)-3-(4-{4-[3-(1-butyloxyethyl)-2-methyloxyphenyl]thiazol-2-ylcarbamoyl}-2,6-dichlorophenyl)-2-methylacrylic acid (B1122)

1H-NMR(DMSO-d6) 12.99(bs, 2H), 8.29(s, 2H), 7.91(dd, 1H, J=1.8, 7.8 Hz), 7.72(s, 1H), 7.40(d, 1H, J=1.2 Hz), 7.37 (dd, 1H, J=1.5, 7.5 Hz), 7.27(t, 1H, J=7.8 Hz), 4.80-4.86(m, 1H), 3.62(s, 3H), 1.69(s, 3H), 1.23-1.55(m, 7H), 0.85(t, 3H, J=7.2 Hz).

Example 222

Synthesis of (E)-3-(4-{4-[3-(3-butyloxypropyl)-2-methyloxyphenyl]thiazol-2-ylcarbamoyl}-2,6-dichlorophenyl)-2-methylacrylic acid (B1124)

1H-NMR(CDCl3-d6) 8.32(s, 2H), 7.65(s, 1H), 7.49(d, 1H, J=9.0 Hz), 7.46(s, 1H), 7.24-7.28(m, 1H), 7.17(t, 1H, J=7.5 Hz), 3.58(s, 3H), 3.49(t, 2H, J=6.6 Hz), 3.44(t, 2H, J=6.6 Hz), 2.79(t, 2H, J=7.8 Hz), 1.90-2.05(m, 2H), 1.86(bs, 3H), 1.53-1.63(m, 2H), 1.33-1.46(m, 2H), 0.93(t, 3H, J=7.5 Hz).

Example 223

Synthesis of (E)-3-(2,6-dichloro-4-{4-[2-fluoro-3-(1-methyloxyhexyl)phenyl]thiazol-2-ylcarbamoyl}phenyl)-2-methyloxyacrylic acid (B1238)

1H-NMR(DMSO-d6) 13.01 (bs, 2H), 8.25 (s, 2H), 7.99-8.05 (m, 1H), 7.65 (d, 1H, J=2.6 Hz), 7.31-7.39 (m, 2H), 6.73 (s, 1H), 4.55-4.59 (m, 1H), 3.62 (s, 3H), 3.18 (s, 3H), 1.61-1.79 (m, 2H), 1.26-1.41 (m, 6H), 0.80-0.86 (m, 3H).

Example 224

Synthesis of (Z)-3-(2,6-dichloro-4-{4-[2-fluoro-3-(1-methyloxydecyl)phenyl]thiazol-2-ylcarbamoyl}phenyl)-2-methyloxyacrylic acid (B1250)

1H-NMR(DMSO-d6) 12.97(bs, 1H), 8.25(s, 2H), 8.05(t, 1H, J=7.6 Hz), 7.64(s, 1H), 7.33-7.35(m, 2H), 6.73(s, 1H), 4.56(t, 1H, J=7.6 Hz), 3.61(s, 3H), 3.17(s, 3H), 1.70-1.80(m, 2H), 1.22-1.38(m, 14H), 0.87-0.90(m, 3H).

Example 225

Synthesis of (Z)-3-(2,6-dichloro-4-{4-[2-methyloxy-3-(1-methyloxydecyl)phenyl]thiazol-2-ylcarbamoyl}phenyl)-2-methyloxyacrylic acid (B1437)

1H-NMR(DMSO-d6) 12.99(bs, 1H), 8.25(s, 2H), 7.89-7.94(m, 1H), 7.72(s, 1H), 7.24-7.34(m, 2H), 6.73(s, 1H), 4.55-4.59(m, 1H), 3.62(s, 6H), 3.15(s, 3H), 1.18-1.80(m, 16H), 0.82-0.87(m, 3H).

Example 226

Synthesis of (Z)-3-(2,6-dichloro-4-{4-[2-methyloxy-3-(1-methyloxyundecyl)phenyl]thiazol-2-ylcarbamoyl}phenyl)-2-methyloxyacrylic acid (B1438)

1H-NMR(DMSO-d6) 12.99(bs, 1H), 8.25(s, 2H), 7.89-7.94(m, 1H), 7.72(s, 1H), 7.24-7.34(m, 2H), 6.73(s, 1H), 4.55-4.59(m, 1H), 3.62(s, 6H), 3.15(s, 3H), 1.18-1.80(m, 18H), 0.82-0.87(m, 3H).

Example 227

Synthesis of (E)-3-(4-{4-[3-(2-ethyloxy-1-methyloxypropyl)-2-fluorophenyl]thiazol-2-ylcarbamoyl}-2,6-difluorophenyl)-2-methylacrylic acid (B1728)

1H-NMR(DMSO-d6) 13.02(bs, 1H), 8.06(t, 1H, J=7.5 Hz), 7.96(s, 1H), 7.93(s, 1H), 7.66(s, 1H), 7.30-7.40(m, 3H), 4.72(t, 1H, J=6.5 Hz), 3.55-3.68(m, 2H), 3.47(q, 2H, J=7.0 Hz), 3.25(s, 3H), 1.79(s, 3H), 1.10(t, 3H, J=7.0 Hz).

Example 228

Synthesis of (Z)-3-(4-{4-[3-(2-ethyloxy-1-methyloxypropyl)-2-fluorophenyl]thiazol-2-ylcarbamoyl}-2,6-difluorophenyl)-2-methyloxyacrylic acid (B1729)

1H-NMR(DMSO-d6) 13.02(bs, 1H), 8.06(t, 1H, J=7.5 Hz), 7.92(s, 1H), 7.90(s, 1H), 7.66(s, 1H), 7.30-7.40(m, 2H), 6.65(s, 1H), 4.72(t, 1H, J=6.5 Hz), 3.71(s, 3H), 3.55-3.68(m, 2H), 3.47(q, 2H, J=7.0 Hz), 3.25(s, 3H), 1.10(t, 3H, J=7.0 Hz).

Example 229

Synthesis of (E)-3-(4-{4-[3-(2-butyloxy-1-methyloxyethyl)-2-fluorophenyl]thiazol-2-ylcarbamoyl}-2,6-difluorophenyl)-2-methylacrylic acid (B1730)

1H-NMR(DMSO-d6) 13.02(bs, 1H), 8.06(t, 1H, J=7.5 Hz), 7.96(s, 1H), 7.93(s, 1H), 7.66(s, 1H), 7.30-7.40(m, 3H), 4.72(t, 1H, J=6.5 Hz), 3.55-3.68(m, 2H), 3.42(t, 2H, J=7.0 Hz), 3.25(s, 3H), 1.79(s, 3H), 1.40-1.50(m, 2H), 1.22-1.34(m, 2H), 0.80(t, 3H, J=7.0 Hz).

Example 230

Synthesis of (Z)-3-(4-{4-[3-(2-butyloxy-1-methyloxyethyl)-2-fluorophenyl]thiazol-2-ylcarbamoyl}-2,6-difluorophenyl)-2-methyloxyacrylic acid (B1731)

1H-NMR(DMSO-d6) 13.02(bs, 1H), 8.06(t, 1H, J=7.5 Hz), 7.92(s, 1H), 7.90(s, 1H), 7.66(s, 1H), 7.30-7.40(m, 2H), 6.65(s, 1H), 4.72(t, 1H, J=6.5 Hz), 3.71(s, 3H), 3.55-3.68(m, 2H), 3.42(t, 2H, J=7.0 Hz), 3.25(s, 3H), 1.40-1.50(m, 2H), 1.22-1.34(m, 2H), 0.80(t, 3H, J=7.0 Hz).

Example 231

Synthesis of (E)-3-[2,6-difluoro-4-(4-{2-fluoro-3-[1-methyloxy-2-(3-methylbutyloxy)ethyl]phenyl}thiazol-2-ylcarbamoyl}phenyl)-2-methylacrylic acid (B1732)

1H-NMR(DMSO-d6) 13.02(bs, 1H), 8.06(t, 1H, J=7.5 Hz), 7.96(s, 1H), 7.93(s, 1H), 7.66(s, 1H), 7.30-7.40(m, 3H), 4.72(t, 1H, J=6.5 Hz), 3.55-3.68(m, 2H), 3.42(t, 2H, J=7.0 Hz), 3.25(s, 3H), 1.79(s, 3H), 1.50-1.60(m, 1H), 1.22-1.34(m, 2H), 0.85(d, 6H, J=6.0 Hz).

Example 232

Synthesis of (Z)-3-[2,6-difluoro-4-(4-{2-fluoro-3-[1-methyloxy-2-(3-methylbutyloxy)ethyl]phenyl}thiazol-2-ylcarbamoyl}phenyl)-2-methyloxyacrylic acid (B1733)

1H-NMR(DMSO-d6) 13.02(bs, 1H), 8.06(t, 1H, J=7.5 Hz), 7.92(s, 1H), 7.90(s, 1H), 7.66(s, 1H), 7.30-7.40(m, 2H), 6.65(s, 1H), 4.72(t, 1H, J=6.5 Hz), 3.68(s, 3H), 3.55-3.68(m, 2H), 3.42(t, 2H, J=7.0 Hz), 3.25(s, 3H), 1.50-1.60(m, 1H), 1.22-1.34(m, 2H), 0.85(d, 6H, J=6.0 Hz).

Example 233

Synthesis of (E)-3-(2,6-difluoro-4-{4-[3-(2-ethyloxy-1-methyloxyethyl)-2-fluorophenyl]thiazol-2-ylcarbamoyl}phenyl)-2-methylacrylic acid (B1734)

1H-NMR(DMSO-d6) 13.02(bs, 1H), 8.29(s, 2H), 8.06(t, 1H, J=7.5 Hz), 7.64(s, 1H), 7.30-7.40(m, 3H), 4.72(t, 1H, J=6.5 Hz), 3.55-3.68(m, 2H), 3.47(q, 2H, J=7.0 Hz), 3.25(s, 3H), 1.69(s, 3H), 1.10(t, 3H, J=7.0 Hz).

Example 234

Synthesis of (Z)-3-(2,6-dichloro-4-{4-[3-(2-ethyloxy-1-methyloxyethyl)-2-fluorophenyl]thiazol-2-ylcarbamoyl}phenyl)-2-methyloxyacrylic acid (B1735)

1H-NMR(DMSO-d6) 13.02(bs, 1H), 8.29(s, 2H), 8.06(t, 1H, J=7.5 Hz), 7.64(s, 1H), 7.30-7.40(m, 2H), 6.65(s, 1H), 4.72(t, 1H, J=6.5 Hz), 3.71(s, 3H), 3.55-3.68(m, 2H), 3.47(q, 2H, J=7.0 Hz), 3.25(s, 3H), 1.10(t, 3H, J=7.0 Hz).

Example 235

Synthesis of (E)-3-(4-{4-[3-(2-butyloxy-1-methyloxyethyl)-2-fluorophenyl]thiazol-2-ylcarbamoyl}-2,6-dichlorophenyl)-2-methylacrylic acid (B1736)

1H-NMR(DMSO-d6) 13.02(bs, 1H), 8.29(s, 2H), 8.06(t, 1H, J=7.5 Hz), 7.64(s, 1H), 7.30-7.40(m, 3H), 4.72(t, 1H, J=6.5 Hz), 3.55-3.68(m, 2H), 3.42(t, 2H, J=7.0 Hz), 3.25(s, 3H), 1.69(s, 3H), 1.40-1.50(m, 2H), 1.22-1.34(m, 2H), 0.80(t, 3H, J=7.0 Hz).

Example 236

Synthesis of (Z)-3-(4-{4-[3-(2-butyloxy-1-methyloxyethyl)-2-fluorophenyl]thiazol-2-ylcarbamoyl}-2,6-dichlorophenyl)-2-methyloxyacrylic acid (B1737)

1H-NMR(DMSO-d6) 13.02(bs, 1H), 8.29(s, 2H), 8.06(t, 1H, J=7.5 Hz), 7.64(s, 1H), 7.30-7.40(m, 2H), 6.65(s, 1H), 4.72(t, 1H, J=6.5 Hz), 3.55-3.68(m, 2H), 3.61(s, 3H), 3.42(t, 2H, J=7.0 Hz), 3.25(s, 3H), 1.40-1.50(m, 2H), 1.22-1.34(m, 2H), 0.80(t, 3H, J=7.0 Hz).

Example 237

Synthesis of (E)-3-[2,6-dichloro-4-(4-{2-fluoro-3-[1-methyloxy-2-(3-methylbutyloxy)ethyl]phenyl}thiazol-2-ylcarbamoyl)phenyl]-2-methylacrylic acid (B1738)

1H-NMR(DMSO-d6) 13.02(bs, 1H), 8.29(s, 2H), 8.06(t, 1H, J=7.5 Hz), 7.64(s, 1H), 7.30-7.40(m, 3H), 4.72(t, 1H, J=6.5 Hz), 3.55-3.68(m, 2H), 3.42(t, 2H, J=7.0 Hz), 3.25(s, 3H), 1.79(s, 3H), 1.50-1.60(m, 1H), 1.22-1.34(m, 2H), 0.85(d, 6H, J=6.0 Hz).

Example 238

Synthesis of (Z)-3-[2,6-dichloro-4-(4-{2-fluoro-3-[1-methyloxy-2-(3-methylbutyloxy)ethyl]phenyl}thiazol-2-ylcarbamoyl)phenyl]-2-methyloxyacrylic acid (B1739)

1H-NMR(DMSO-d6) 13.02(bs, 1H), 8.29(s, 2H), 8.06(t, 1H, J=7.5 Hz), 7.64(s, 1H), 7.30-7.40(m, 2H), 6.65(s, 1H), 4.72(t, 1H, J=6.5 Hz), 3.55-3.68(m, 2H), 3.61(s, 3H), 3.42(t, 2H, J=7.0 Hz), 3.25(s, 3H), 1.50-1.60(m, 1H), 1.22-1.34(m, 2H), 0.85(d, 6H, J=6.0 Hz).

Example 239

Synthesis of (E)-3-{2,6-difluoro-4-[6-(3-methyloxy-3-methylbutyl)-4,5-dihydronaphthino[1,2-d]thiazol-2-ylcarbamoyl]phenyl}-2-methylacrylic acid (B1742)

1H-NMR(DMSO-d6) 13.02(bs, 1H), 7.99(s, 1H), 7.96(s, 1H), 7.93(t, 1H, J=7.5 Hz), 7.62(d, 1H, J=2.3 Hz), 7.33(s, 1H), 7.19-7.28(m, 2H), 3.62(t, 2H, J=6.7 Hz), 2.69(t, 2H, J=6.7 Hz), 1.79(s, 3H), 1.70-1.79(m, 2H), 1.58-1.69(m, 2H), 1.30-1.49(m, 2H).

Example 240

Synthesis of (E)-3-(2,6-difluoro-4-{4-[2-fluoro-3-(1-methyloxy-3-methylsufanylpropyl)phenyl]thiazol-2-ylcarbamoyl}phenyl)-2-methylacrylic acid (B1744)

1H-NMR(DMSO-d6) 13.02(bs, 2H), 7.92-8.08(m, 3H), 7.67(d, 1H, J=2.7 Hz), 7.30-7.44(m, 3H), 4.71-4.75(m, 1H), 3.20(s, 3H), 2.56(t, 2H, J=7.5 Hz), 1.76-2.10(m, 8H).

Example 241

Synthesis of (E)-3-(4-{4-[3-(3-t-butyloxybutyl)-2-fluorophenyl]thiazol-2-ylcarbamoyl}-2,6-difluorophenyl]-2-methylacrylic acid (B1746)

1H-NMR(DMSO-d6) 13.00(bs, 2H), 7.90-8.00(m, 3H), 7.64(d, 1H, J=2.7 Hz), 7.20-7.34(m, 3H), 3.66-3.71(m, 1H), 2.64-2.77(m, 2H), 1.81(s, 3H), 1.62-1.70(m, 2H), 1.07-1.15(m, 12H).

Example 242

Synthesis of (E)-3-(2,6-difluoro-4-{4-[2-fluoro-3-(3-methyloxyheptyl)phenyl]thiazol-2-ylcarbamoyl}phenyl)-2-methylacrylic acid (B1747)

1H-NMR(DMSO-d6) 13.02(bs, 1H), 7.96(s, 1H), 7.93(s, 1H), 7.93(t, 1H, J=7.5 Hz), 7.64(s, 3H), 7.33(s, 1H), 7.20-7.30(m, 2H), 3.25(s, 3H), 3.17-3.22(m, 1H), 2.65-2.72(m, 2H), 1.78(s, 3H), 1.70-1.78(m, 2H), 1.45-1.53(m, 2H), 1.22-1.38(m, 4H), 0.87-0.90(m, 3H).

Example 243

Synthesis of (E)-3-[2,6-difluoro-4-(4-{2-fluoro-3-[3-(2-methyloxyethyloxy)propyl]phenyl}thiazol-2-ylcarbamoyl)phenyl]-2-methylacrylic acid (B1748)

1H-NMR(DMSO-d6) 13.02(bs, 1H), 7.96(s, 1H), 7.93(s, 1H), 7.93(t, 1H, J=7.5 Hz), 7.64(s, 1H), 7.33(s, 1H), 7.20-7.30(m, 2H), 3.40-3.50(m, 6H), 3.25(s, 3H), 2.74(t, 2H, J=7.4 Hz), 1.80-1.88(m, 2H), 1.80(s, 3H).

Example 244

Synthesis of (E)-3-{4-[4-(3-{1-[2-(2-ethyloxyethyloxy)ethyloxy]propyl}-2-fluorophenyl)thiazol-2-ylcarbamoyl]-2,6-difluorophenyl}-2-methylacrylic acid (B1749)

1H-NMR(DMSO-d6) 13.00(bs, 2H), 7.92-8.07(m, 3H), 7.65(d, 1H, J=2.4 Hz), 7.31-7.44(m, 3H), 4.67(t, 1H, J=6.3 Hz), 3.20-3.56(m, 10H), 1.67-1.82(m, 5H), 1.09(t, 3H, J=7.2 Hz), 0.89(t, 3H, J=7.2 Hz).

Example 245

Synthesis of (E)-3-[2,6-difluoro-4-(4-{2-fluoro-3-[3-(teterahydrofuran-2-ylmethyloxy)propyl]phenyl}thiazol-2-ylcarbamoyl)phenyl]-2-methylacrylic acid (B1750)

1H-NMR(DMSO-d6) 13.01(bs, 2H), 7.90-7.95(m, 3H), 7.64(d, 1H, J=2.4 Hz), 7.20-7.36(m, 3H), 3.89-3.97(m, 1H), 3.69-3.76(m, 1H), 3.58-3.65(m, 1H), 3.45(t, 4H, J=6.3 Hz), 2.74(t, 2H, J=7.5 Hz), 1.70-1.94(m, 8H), 1.50-1.60(m, 1H).

Example 246

Synthesis of (E)-3-(2,6-dichloro-4-{4-[2-fluoro-3-(3-methyloxyheptyl)phenyl]thiazol-2-ylcarbamoyl}phenyl)-2-methylacrylic acid (B1751)

1H-NMR(DMSO-d6) 12.97(bs, 1H), 8.29(s, 2H), 7.85(t, 1H, J=7.6 Hz), 7.64(s, 1H), 7.40(s, 1H), 7.20-7.31(m, 2H), 3.25(s, 3H), 3.17-3.22(m, 1H), 2.65-2.72(m, 2H), 1.70-1.80 (m, 2H), 1.68(s, 3H), 1.45-1.53(m, 2H), 1.22-1.38(m, 4H), 0.87-0.90(m, 3H).

Example 247

Synthesis of (E)-3-(2,6-dichloro-4-{4-[2-fluoro-3-(3-methyloxydecyl)phenyl]thiazol-2-ylcarbamoyl}phenyl)-2-methylacrylic acid (B1752)

1H-NMR(DMSO-d6) 12.97(bs, 1H), 8.28(s, 2H), 7.94(t, 1H, J=7.6 Hz), 7.64(s, 1H), 7.40 (s, 1H), 7.20-7.31(m, 2H), 3.20(s, 3H), 3.17-3.22(m, 1H), 2.65-2.72(m, 2H), 1.70-1.80 (m, 2H), 1.68(s, 3H), 1.45-1.53(m, 2H), 1.22-1.38(m, 8H), 0.87-0.90(m, 3H).

Example 248

Synthesis of (E)-3-[2,6-dichloro-4-(4-{2-fluoro-3-[3-(2-methyloxyethyloxy)propyl]phenyl}thiazol-2-ylcarbamoyl)phenyl]-2-methylacrylic acid (B1753)

1H-NMR(DMSO-d6) 12.97(bs, 1H), 8.28(s, 2H), 7.94(t, 1H, J=7.6 Hz), 7.64(s, 1H), 7.40(s, 1H), 7.20-7.31(m, 2H), 3.40-3.50(m, 6H), 3.25(s, 3H), 2.73(t, 2H, J=7.4 Hz), 1.80-1.88(m, 2H), 1.68(s, 3H).

Example 249

Synthesis of (E)-3-{2,6-dichloro-4-[4-(3-{1-[2-(2-ethyloxyethyloxy)ethyloxy]propyl]-2-fluorophenyl}thiazol-2-ylcarbamoyl)phenyl]-2-methylacrylic acid (B1754)

1H-NMR(DMSO-d6) 13.01(bs, 2H), 8.29(s, 2H), 8.02(dt, 1H, J=1.8, 7.5 Hz), 7.64(d, 1H, J=2.4 Hz), 7.38-7.44(m, 2H), 7.33(t, 1H, J=7.5 Hz), 4.67(t, 1H, J=6.0 Hz), 3.39-3.56(m, 10H), 1.67-1.78(m, 5H), 1.09(t, 3H, J=7.2 Hz), 0.89(t, 3H, J=6.9 Hz),

Example 250

Synthesis of (E)-3-[2,6-dichloro-4-(4-{2-fluoro-3-[3-(tetrahydrofuran-2-ylmethyloxy)propyl]phenyl}thiazol-2-ylcarbamoyl)phenyl]-2-methylacrylic acid (B1755)

1H-NMR(DMSO-d6) 13.02(bs, 2H), 8.29(s, 2H), 7.94(dt, 1H, J=2.1, 7.2 Hz), 7.64(d, 1H, J=2.7 Hz), 7.40(d, 1H, J=1.2 Hz), 7.20-7.32(m, 2H), 3.89-3.97(m, 1H), 3.69-3.76(m, 1H), 3.58-3.65(m, 1H), 3.45(t, 2H, J=6.6 Hz), 2.74(t, 2H, J=7.2 Hz), 1.73-1.94(m, 4H), 1.69(d, 3H, J=1.8 Hz), 1.50-1.59(m, 1H)

Example 251

Synthesis of (E)-3-(4-{4-[3-(3-ethyloxypropyl)-2-fluorophenyl]thiazol-2-ylcarbamoyl]-2,6-difluorophenyl}-2-methylacrylic acid (B1756)

1H-NMR(DMSO-d6) 13.01(bs, 2H), 7.90-8.10(m, 3H), 7.64(d, 1H, J=2.4 Hz), 7.20-7.38(m, 3H), 3.20-3.45(m, 4H), 2.73(t, 2H, J=7.8 Hz), 1.76-1.88(m, 5H), 1.12(d, 3H, J=6.9 Hz).

Example 252

Synthesis of (E)-3-(2,6-dichloro-4-{4-[3-(3-ethyloxypropyl)-2-fluorophenyl]thiazol-2-ylcarbamoyl}phenyl)-2-methylacrylic acid (B1757)

1H-NMR(DMSO-d6) 13.02(bs, 2H), 8.29(s, 2H), 7.94(dt, 1H, J=1.8, 6.9 Hz), 7.64(d, 1H, J=2.7 Hz), 7.20-7.33(m, 3H), 3.30-3.45(m, 2H), 2.70-2.78(m, 2H), 1.78-1.85(m, 2H), 1.69 (d, 3H, J=1.5 Hz), 1.12(t, 3H, J=7.2 Hz).

Example 253

Synthesis of (E)-3-[2,6-dichloro-4-(4-{3-[2-(2-ethyloxyethyloxy)ethyloxymethyl]-2-fluorophenyl}thiazol-2-ylcarbamoyl)phenyl]-2-methylacrylic acid (B1762)

1H-NMR(DMSO-d6) 13.02(bs, 2H), 8.29(s, 2H), 8.05(dt, 1H, J=1.8, 7.8 Hz), 7.40-7.48(m, 2H), 7.32(d, 1H, J=7.8 Hz), 4.64(s, 2H), 3.56-3.66(m, 4H), 3.50-3.55(m, 2H), 3.39-3.48 (m, 4H), 1.09(d, 3H, J=7.2 Hz).

Example 254

Synthesis of (E)-3-{4-[4-(3-ethyloxymethyl-2-fluorophenyl)thiazol-2-ylcarbamoyl]-2,6-difluorophenyl]-2-methylacrylic acid (B1763)

1H-NMR(DMSO-d6) 13.02(bs, 2H), 7.92-8.00(m, 3H), 7.66(d, 1H, J=2.7 Hz), 7.40-7.47(m, 1H), 7.28-7.37(m, 3H), 4.59(s, 2H), 3.52-3.59(m, 2H), 1.81(d, 3H, J=1.8 Hz), 1.14-1.20(m, 3H).

Example 255

Synthesis of (E)-3-{2,6-dichloro-4-[4-(3-ethyloxymethyl-2-fluorophenyl)thiazol-2-ylcarbamoyl]phenyl}-2-methylacrylic acid (B1764)

1H-NMR(DMSO-d6) 13.02(bs, 2H), 8.29(d, 2H, J=1.2 Hz), 8.00-8.10(m, 1H), 7.66(d, 1H, J=2.4 Hz), 7.38-7.47(m, 2H), 7.31(t, 1H, J=7.5 Hz), 4.59(s, 2H), 3.52-3.59(m, 2H), 1.69(d, 3H, J=0.9 Hz), 1.14-1.20(m, 3H).

Example 256

Synthesis of (E)-3-{2,6-difluoro-4-[4-(2-fluoro-3-propyloxymethylphenyl)thiazol-2-ylcarbamoyl]phenyl}-2-methylacrylic acid (B1765)

1H-NMR(DMSO-d6) 13.02(bs, 2H), 7.92-8.08(m, 3H), 7.66(d, 1H, J=2.4 Hz), 7.40-7.47(m, 1H), 7.28-7.38(m, 3H), 4.59(s, 2H), 3.46(t, 2H, J=6.6 Hz), 1.81(s, 3H), 1.51-1.64 (m, 2H), 0.90(t, 3H, J=7.5 Hz).

Example 257

Synthesis of (E)-3-{2,6-dichloro-4-[4-(2-fluoro-3-propyloxymethylphenyl)thiazol-2-ylcarbamoyl]phenyl}-2-methylacrylic acid (B1766)

1H-NMR(DMSO-d6) 13.01(bs, 2H), 8.29(s, 2H), 8.04(dt, 1H, J=2.1, 7.8 Hz), 7.65(d, 1H, J=2.4 Hz), 7.38-7.47(m, 2H), 7.31(t, 1H, J=6.6 Hz), 4.59(s, 2H), 3.46(t, 2H, J=6.6 Hz), 1.69(d, 3H, J=1.2 Hz), 1.52-1.63 (m, 4H), 0.90(t, 3H, J=7.5 Hz).

Example 258

Synthesis of (E)-3-(4-{4-[3-(4-ethyloxybutyloxymethyl)-2-fluorophenyl]thiazol-2-ylcarbamoyl}-2,6-dfluorophenyl}-2-methylacrylic acid (B1767)

1H-NMR(DMSO-d6) 13.02(bs, 2H), 7.92-8.08(m, 3H), 7.66(d, 1H, J=2.7 Hz), 7.40-7.46(m, 1H), 7.28-7.36(m, 3H), 4.59(s, 2H), 3.51(t, 2H, J=6.0 Hz), 3.25-3.42(m, 4H), 1.69(d, 3H, J=1.2 Hz), 1.81(d, 3H, J=1.8 Hz), 1.50-1.65 (m, 4H), 1.09(t, 3H, J=6.9 Hz).

Example 259

Synthesis of (E)-3-(2,6-dichloro-4-{4-[3-(4-ethyloxybutyloxymethyl)-2-fluorophenyl]thiazol-2-ylcarbamoyl}phenyl}-2-methylacrylic acid (B1768)

1H-NMR(DMSO-d6) 13.02(bs, 2H), 8.29(s, 2H), 8.05(dt, 1H, J=1.8, 8.1 Hz), 7.66(d, 1H, J=2.4 Hz), 7.39-7.46(m, 2H), 7.32(t, 1H, J=7.8 Hz), 4.59(s, 2H), 3.50(t, 2H, J=6.3 Hz), 3.25-3.41(m, 4H), 1.69(d, 3H, J=1.2 Hz), 1.50-1.62 (m, 4H), 1.08(t, 3H, J=6.9 Hz).

Example 260

Synthesis of (E)-3-(2,6-difluoro-4-{4-[2-fluoro-3-(3-methylbutyloxymethyl)phenyl]thiazol-2-ylcarbamoyl}phenyl}-2-methylacrylic acid (B1769)

1H-NMR(DMSO-d6) 13.02(bs, 2H), 7.92-8.08(m, 3H), 7.66(d, 1H, J=2.4 Hz), 7.39-7.46(m, 1H), 7.29-7.36(m, 3H), 4.86(s, 2H), 3.52(t, 2H, J=6.9 Hz), 1.63-1.81(d, 3H, J=1.8 Hz), 1.65-1.75(m, 1H), 1.42-1.49 (m, 2H), 0.87(d, 6H, J=6.3 Hz).

Example 261

Synthesis of (E)-3-(2,6-dichloro-4-{4-[2-fluoro-3-(3-methylbutyloxymethyl)phenyl]thiazol-2-ylcarbamoyl}phenyl}-2-methylacrylic acid (B1770)

1H-NMR(DMSO-d6) 13.02(bs, 2H), 8.29(s, 2H), 8.01-8.08(m, 1H), 7.65(d, 1H, J=2.7 Hz), 7.39-7.46(m, 2H), 7.31(t, 1H, J=7.8 Hz), 4.59(s, 2H), 3.52(t, 2H, J=6.9 Hz), 1.63-1.76 (m, 4H), 1.42-1.49 (m, 2H), 0.87(d, 6H, J=6.6 Hz).

Example 262

Synthesis of (E)-3-(4-{4-[3-(1,4-dimethyloxybutyl)-2-fluorophenyl]thiazol-2-ylcarbamoyl}-2,6-difluophenyl}-2-methylacrylic acid (B1771)

1H-NMR(DMSO-d6) 13.01(bs, 2H), 7.92-8.08(m, 3H), 7.66(d, 1H, J=2.7 Hz), 7.29-7.40(m, 3H), 4.55-4.62(m, 1H), 3.19(s, 6H), 1.48-1.90(m, 7H).

Example 263

Synthesis of (E)-3-(2,6-dichloro-4-{4-[3-(1,4-dimethyloxybutyl)-2-fluorophenyl]thiazol-2-ylcarbamoyl}phenyl}-2-methylacrylic acid (B1772)

1H-NMR(DMSO-d6) 13.02(bs, 2H), 8.29(s, 2H), 7.97-8.06(m, 1H), 7.65(d, 1H, J=2.7 Hz), 7.32-7.42(m, 3H), 4.50-4.62(m, 1H), 3.19(s, 6H), 1.40-1.85(m, 7H).

Example 264

Synthesis of (Z)-3-[2,6-dichloro-4-(4-{3-[3-(2-ethyloxybutyloxy)propyl]-2-fluorophenyl}thiazol-2-ylcarbamoyl}phenyl]-2-methyloxyacrylic acid (B1773)

1H-NMR(DMSO-d6) 12.97(bs, 1H), 8.28(s, 2H), 7.95(t, 1H, J=7.6 Hz), 7.61(s, 1H), 7.25-7.35(m, 2H), 6.73(s, 1H), 3.61(s, 3H), 3.39(s, 3H), 3.25(t, 2H, J=6.0 Hz), 2.74(t, 2H, J=7.4 Hz), 1.80-1.90(m, 2H), 1.22-1.38(m, 5H), 0.87(t, 6H, J=7.4 Hz).

Example 265

Synthesis of (E)-3-[2,6-difluoro-4-(4-{2-fluoro-3-[3-(2,2,2-trifluoroethyloxy)propyl]phenyl}thiazol-2-ylcarbamoyl}phenyl]-2-methylacrylic acid (B1774)

1H-NMR(DMSO-d6) 13.02(bs, 2H), 7.91-8.00(m, 3H), 7.64(d, 1H, J=2.4 Hz), 7.22-7.35(m, 3H), 4.01-4.11(m, 2H), 3.64(t, 2H, J=6.0 Hz), 2.75(t, 2H, J=7.5 Hz), 1.84-1.93(m, 2H), 1.69(d, 3H, J=1.5 Hz).

Example 266

Synthesis of (E)-3-[2,6-dichloro-4-(4-{2-fluoro-3-[3-(2,2,2-trifluoroethyloxy)propyl]phenyl}thiazol-2-ylcarbamoyl}phenyl]-2-methylacrylic acid (B1775)

1H-NMR(DMSO-d6) 13.02(bs, 2H), 8.29(s, 2H), 7.95(dt, 1H, J=2.1, 7.2 Hz), 7.64(d, 1H, J=2.4 Hz), 7.41(d, 1H, J=1.5 Hz), 7.22-7.33(m, 2H), 4.01-4.11(m, 2H), 3.64(t, 2H, J=6.3 Hz), 2.75(t, 2H, J=7.5 Hz), 1.84-1.93(m, 2H), 1.81(d, 3H, J=1.5 Hz).

Example 267

Synthesis of (E)-3-[2,6-difluoro-4-(4-{2-fluoro-3-[3-(3-methyloxybutyloxy)propyl]phenyl}thiazol-2-ylcarbamoyl}phenyl]-2-methylacrylic acid (B1776)

1H-NMR(DMSO-d6) 13.01(bs, 2H), 7.91-8.02(m, 3H), 7.67(d, 1H, J=2.7 Hz), 7.20-7.37(m, 3H), 3.24-3.45(m, 5H), 3.20(s, 3H), 2.70-2.78(m, 2H), 1.77-1.88(m, 5H), 1.55-1.75 (m, 2H), 1.08(d, 3H, J=6.3 Hz).

Example 268

Synthesis of (E)-3-[2,6-dichloro-4-(4-{2-fluoro-3-[3-(3-methyloxybutyloxy)propyl]phenyl}thiazol-2-ylcarbamoyl}phenyl]-2-methylacrylic acid (B1777)

1H-NMR(DMSO-d6) 13.01(bs, 2H), 8.29(s, 2H), 7.90-8.08(m, 1H), 7.63(d, 1H, J=2.7 Hz), 7.41(s, 1H), 7.21-7.32 (m, 2H), 3.36-3.45(m, 5H), 3.20(s, 3H), 2.71-2.77(m, 2H), 1.78-1.88(m, 2H), 1.55-1.75(m, 5H), 1.08(d, 3H, J=6.3 Hz).

Example 269

Synthesis of (Z)-3-[2,6-dichloro-4-(4-{2-fluoro-3-[3-(3-methyloxybutyloxy)propyl]phenyl}thiazol-2-ylcarbamoyl}phenyl]-2-methyloxyacrylic acid (B1778)

1H-NMR(DMSO-d6) 12.99(bs, 1H), 8.25(s, 2H), 7.94(dt, 1H, J=1.5, 6.6 Hz), 7.62(d, 1H, J=2.7 Hz), 7.21-7.32(m, 2H), 6.73(s, 1H), 3.61(s, 3H), 3.37-3.44(m, 5H), 3.20(s, 3H), 1.76-1.84(m, 2H), 1.52-1.75(m, 2H), 1.08(d, 3H, J=6.0 Hz).

Example 270

Synthesis of (E)-3-(4-{4-[3-(ethyloxyphenylmethyl)-2-fluorophenyl]thiazol-2-ylcarbamoyl}-2,6-difluorophenyl}-2-methylacrylic acid (B1779)

1H-NMR(DMSO-d6) 13.00 (bs, 2H), 7.93-8.02 (m, 3H), 7.62 (d, 1H, J=2.6 Hz), 7.49-7.53 (m, 1H), 7.25-7.41(m, 7H), 5.78 (s, 1H), 3.51 (q, 2H, J=7.0 Hz), 1.83 (s, 3H), 1.20 (t, 3H, J=7.0 Hz).

Example 271

Synthesis of (E)-3-(2,6-dichloro-4-{4-[3-(ethyloxypehnylmethyl)-2-fluorophenyl]thiazol-2-ylcarbamoyl}phenyl)-2-methylacrylic acid (B1780)

1H-NMR(DMSO-d6) 13.00 (bs, 2H), 8.30 (s, 2H), 7.98-8.02 (m, 1H), 7.61 (d, 1H, J=2.6 Hz), 7.49-7.53 (m, 1H), 7.25-7.41(m, 7H), 5.78 (s, 1H), 3.51 (q, 2H, J=7.0 Hz), 1.66 (s, 3H), 1.20 (t, 3H, J=7.0 Hz).

Example 272

Synthesis of (E)-3-(2,6-difluoro-4-{4-[2-fluoro-3-(1-methyloxy-3-phenylpropyl)phenyl]thiazol-2-ylcarbamoyl}phenyl)-2-methylacrylic acid (B1781)

1H-NMR(DMSO-d6) 13.00 (bs, 2H), 7.94-8.06 (m, 3H), 7.65 (d, 1H, J=2.6 Hz), 7.15-7.44 (m, 8H), 4.54-4.58 (m, 1H), 3.20 (s, 3H), 2.61-2.73 (m, 2H), 1.94-2.09 (m, 2H), 1.81(s, 3H).

Example 273

Synthesis of (E)-3-(2,6-dichloro-4-{4-[2-fluoro-3-(1-methyloxy-3-phenylpropyl)phenyl]thiazol-2-ylcarbamoyl}phenyl)-2-methylacrylic acid (B1782)

1H-NMR(DMSO-d6) 13.02 (bs, 2H), 8.30(s, 2H), 8.00-8.06 (m, 1H), 7.65 (d, 1H, J=2.6 Hz), 7.16-7.44 (m, 8H), 4.54-4.58 (m, 1H), 3.21 (s, 3H), 2.64-2.74 (m, 2H), 1.96-2.08 (m, 2H), 1.69(s, 3H).

Example 274

Synthesis of (E)-3-(4-{4-[3-(2-ethyl-1-methoxybutyl)-2-fluorophenyl]thiazol-2-ylcarbamoyl}-2,6-difluorophenyl)-2-methylacrylic acid (B1783)

1H-NMR(DMSO-d6) 13.00 (bs, 2H), 7.95-8.05 (m, 3H), 7.65 (d, 1H, J=2.6 Hz), 7.33-7.36 (m, 3H), 4.51 (d, 1H, 6.4 Hz), 3.16 (s, 3H), 1.81(d, 3H, J=1.4 Hz), 1.35-1.60 (m, 3H), 1.24-1.36 (m, 2H), 0.81-0.86 (m, 6H).

Example 275

Synthesis of (E)-3-(2,6-dichloro-4-{4-[3-(2-ethyloxy-1-methyloxybutyl)-2-fluorophenyl]thiazol-2-ylcarbamoyl}phenyl)-2-methylacrylic acid (B1784)

1H-NMR(DMSO-d6) 13.01 (bs, 2H), 8.29 (s, 2H), 7.99-8.05 (m, 1H), 7.65 (d, 1H, J=2.6 Hz), 7.40 (s, 1H), 7.34-7.36 (m, 2H), 4.521 (d, 1H, 6.1 Hz), 3.16 (s, 3H), 1.39(s, 3H), 1.38-1.60 (m, 3H), 1.18-1.38 (m, 2H), 0.81-0.86 (m, 6H).

Example 275

Synthesis of (E)-3-(4-{4-[3-(3-butyloxy-1-methyloxypropyl)-2-fluorophenyl]thiazol-2-ylcarbamoyl}-2,6-difluorophenyl)-2-methylacrylic acid (B1785)

1H-NMR(DMSO-d6) 13.00 (bs, 2H), 94-8.06 (m, 3H), 7.66 (d, 1H, J=2.5 Hz), 7.32-7.42 (m, 3H), 4.68-4.70 (m, 1H), 3.47-3.55 (m, 1H), 3.30-3.38 (m, 3H), 1.85-2.01 (m, 2H), 1.81(s, 3H), 1.42-1.50 (m, 2H), 1.27-1.37 (m, 2H), 0.84-0.89 (m, 3H).

Example 277

Synthesis of (E)-3-(4-{4-[3-(3-butyloxy-1-methyloxypropyl)-2-fluorophenyl]thiazol-2-ylcarbamoyl}-2,6-dichlorophenyl)-2-methyl acrylic acid (B1786)

1H-NMR(DMSO-d6) 13.01 (bs, 2H), 8.29 (s, 2H), 8.00-8.06 (m, 1H), 7.65 (d, 1H, J=2.6 Hz), 7.31-7.41 (m, 3H), 4.68-4.73 (m, 1H), 3.47-3.55 (m, 1H), 3.28-3.39 (m, 3H), 1.85-2.01 (m, 2H), 1.69(s, 3H), 1.43-1.50 (m, 2H), 1.29-1.34 (m, 2H), 0.84-0.89 (m, 3H).

Example 278

Synthesis of (E)-3-{4-[4-(4'-t-butyl-2-methyloxybiphenyl-3-yl)thiazol-2-ylcarbamoyl]-2,6-difluorophenyl)-2-methylacrylic acid (B1787)

1H-NMR(DMSO-d6) 12.96 (bs, 2H), 8.04-8.07 (m, 1H), 7.96-7.98 (m, 2H), 7.79 (s, 1H), 7.48-7.55 (m, 4H), 7.27-7.34 (m, 3H), 3.31 (s, 3H), 1.81 (s, 3H), 1.34 (s, 9H).

Example 279

Synthesis of (E)-3-{4-[4-(4'-t-butyl-2-methyloxybiphenyl-3-yl)thiazol-2-ylcarbamoyl]-2,6-dichlorophenyl)-2-methylacrylic acid (B1788)

1H-NMR(DMSO-d6) 12.98 (bs, 2H), 8.30 (s, 2H), 8.03-8.06 (m, 1H), 7.79 (s, 1H), 7.48-7.55 (m, 4H), 7.40 (s, 1H), 7.27-7.35 (m, 2H), 3.31 (s, 3H), 1.69 (s, 3H).

Example 280

Synthesis of (E)-3-{4-[4-(4'-t-butyl-2-fluorobiphenyl-3-yl)thiazol-2-ylcarbamoyl]-2,6-difluorophenyl)-2-methylacrylic acid (B1789)

1H-NMR(DMSO-d6) 13.01 (bs, 2H), 8.06-8.11 (m, 1H), 7.95-8.00 (m, 2H), 7.69 (d, 1H, J=2.6 Hz), 7.34-7.53 (m, 7H), 1.81 (s, 3H), 1.34 (s, 9H).

Example 281

Synthesis of (E)-3-{4-[4-(4'-t-butyl-2-fluorobiphenyl-3-yl)thiazol-2-ylcarbamoyl]-2,6-dichlorophenyl)-2-methylacrylic acid (B1790)

1H-NMR(DMSO-d6) 13.05 (bs, 2H), 8.30 (s, 2H), 8.06-8.10 (m, 1H), 7.69 (d, 1H, J=2.6 Hz), 7.37-7.53 (m, 7H), 1.69 (s, 3H), 1.34 (s, 9H).

Example 282

Synthesis of (E)-3-(4-{4-[3-(4-butyloxy-1-methyloxybutyl)-2-fluorophenyl]thiazol-2-ylcarbamoyl}-2,6-difluorophenyl)-2-methylacrylic acid (B1791)

1H-NMR(DMSO-d6) 13.00(bs, 2H), 7.93-8.06(m, 3H), 7.65(d, 1H, J=2.7 Hz), 7.32-7.39(m, 3H), 4.58-4.62(m, 1H), 3.20-3.44(m, 4H), 3.19(s, 3H), 1.22-1.88(m, 11H), 0.85(t, 3H, J=7.2 Hz).

Example 283

Synthesis of (E)-3-(2,6-difluoro-4-{4-[2-fluoro-3-(1-methyloxy-4-propyloxybutyl)phenyl]thiazol-2-ylcarbamoyl}phenyl)-2-methylacrylic acid (B1792)

1H-NMR(DMSO-d6) 13.00(bs, 2H), 7.93-8.06(m, 3H), 7.65(d, 1H, J=2.7 Hz), 7.32-7.40(m, 3H), 4.58-4.62(m, 1H), 3.25-3.37(m, 4H), 3.19(s, 3H), 1.41-1.85(m, 9H), 0.83(t, 3H, J=7.2 Hz).

Example 284

Synthesis of (E)-3-(4-{4-[3-(4-ethyloxy-1-methyloxybutyl)-2-fluorophenyl]thiazol-2-ylcarbamoyl}-2,6-difluorophenyl)-2-methylacrylic acid (B1793)

1H-NMR(DMSO-d6) 13.02(bs, 2H), 7.94-8.07(m, 3H), 7.65(d, 1H, J=2.4 Hz), 7.32-7.40(m, 3H), 4.58-4.63(m, 1H), 3.28-3.40(m, 4H), 3.19(s, 3H), 1.43-1.83(m, 7H), 1.08(t, 3H, J=7.2 Hz).

Example 285

Synthesis of (E)-3-(2,6-dichloro-4-{4-[3-(4-ethyloxy-1-methyloxybutyl)-2-fluorophenyl]thiazol-2-ylcarbamoyl}phenyl)-2-methylacrylic acid (B1794)

1H-NMR(DMSO-d6) 13.02(bs, 2H), 8.29(s, 2H), 8.00-8.05(m, 1H), 7.65(d, 1H, J=2.7 Hz), 7.32-7.41(m, 3H), 4.58-4.31(m, 1H), 3.26-3.40(m, 4H), 3.19(s, 3H), 1.40-1.88(m, 7H), 1.08(t, 3H, J=7.2 Hz).

Example 286

Synthesis of (E)-3-(4-{4-[3-(3,3-dimethylbut-1-ynyl)-2-fluorophenyl]thiazol-2-ylcarbamoyl}-2,6-difluorophenyl)-2-methylacrylic acid (B1795)

1H-NMR(DMSO-d6) 13.01 (bs, 2H), 8.03-8.08 (m, 1H), 7.95-7.98 (m, 2H), 7.72 (d, 1H, J=2.7 Hz), 7.26-7.45 (m, 3H), 1.81 (s, 3H), 1.33 (s, 9H).

Example 287

Synthesis of (E)-3-(2,6-dichloro-4-{4-[3-(3,3-dimethylbut-1-ynyl)-2-fluorophenyl]thiazol-2-ylcarbamoyl}phenyl)-2-methylacrylic acid (B1796)

1H-NMR(DMSO-d6) 13.01 (bs, 2H), 8.30 (s, 2H), 8.02-8.08 (m, 1H), 7.72 (d, 1H, J=2.6 Hz), 7.40-7.44 (m, 2H), 7.27-7.32 (m, 1H), 1.69 (s, 3H), 1.37 (s, 9H).

Example 288

Synthesis of (E)-3-{2,6-difluoro-4-[4-(2-octyloxyphenyl)thiazol-2-ylcarbamoyl]phenyl)-2-methylacrylic acid (B1797)

1H-NMR(DMSO-d6) 12.91(bs, 2H), 7.92-8.00(m, 2H), 7.38-7.51(m, 3H), 7.30-7.37(m, 2H), 7.27(s, 1H), 4.13(t, 2H, J=6.6 Hz), 1.80-1.92(m, 5H), 1.20-1.52(m, 10H), 0.83-0.88 (m, 3H).

Example 289

Synthesis of (E)-3-{2,6-dichloro-4-[4-(2-octyloxyphenyl)thiazol-2-ylcarbamoyl]phenyl)-2-methylacrylic acid (B1798)

1H-NMR(DMSO-d6) 12.97(bs, 2H), 8.28(s, 2H), 7.30-7.50(m, 5H), 7.27(s, 1H), 4.13(t, 2H, J=6.6 Hz), 1.80-1.90(m, 2H), 1.69(d, 3H, J=1.5 Hz), 1.18-1.52(m, 10H), 0.83-0.88(m, 3H).

Example 290

Synthesis of (E)-3-(2,6-difluoro-4-{4-[2-methyloxy-3-(1-methyloxy-4-propyloxybutyl)phenyl]thiazol-2-ylcarbamoyl}phenyl)-2-methylacrylic acid (B1799)

1H-NMR(DMSO-d6) 13.00(bs, 2H), 7.90-8.10(m, 3H), 7.73(s, 1H), 7.25-7.34(m, 3H), 4.59-4.63(m, 1H), 3.62(s, 3H), 3.16(s, 3H), 1.81(s, 3H), 1.42-1.76(m, 6H), 0.84(t, 3H, J=7.5 Hz).

Example 291

Synthesis of (E)-3-(2,6-dichloro-4-{4-[2-methyloxy-3-(1-methyloxy-4-propyloxybutyl)phenyl]thiazol-2-ylcarbamoyl}phenyl)-2-methylacrylic acid (B1800)

1H-NMR(DMSO-d6) 13.00(bs, 2H), 8.29(s, 2H), 7.86(dd, 1H, J=1.6, 7.5 Hz), 7.70(s, 1H), 7.41(d, 1H, J=0.9 Hz), 7.31 (dd, 1H, J=1.8, 7.8 Hz), 7.25(t, 1H, J=7.5 Hz), 4.53-4.58(m, 1H), 3.67-3.74(m, 2H), 3.15(s, 3H), 1.69(s, 3H), 1.20-1.40 (m, 19H), 0.83-0.87(m, 3H).

Example 292

Synthesis of (E)-3-{2,6-difluoro-4-[4-(2-fluoro-3-pent-1-ynylphenyl)thiazol-2-ylcarbamoyl]phenyl}-2-methylacrylic acid (B1801)

1H-NMR(DMSO-d6) 13.01(bs, 2H), 8.05(dt, 1H, J=1.8, 7.8 Hz), 7.92-8.00(m, 2H), 7.71(d, 1H, J=2.7 Hz), 7.43-7.48 (m, 1H), 7.34(s, 1H), 7.30(t, 1H, J=7.8 Hz), 1.81(s, 3H), 1.54-1.66(m, 2H), 1.03(d, 3H, J=7.5 Hz).

Example 293

Synthesis of (E)-3-{2,6-dichloro-4-[4-(2-fluoro-3-pent-1-ynylphenyl)thiazol-2-ylcarbamoyl]phenyl}-2-methylacrylic acid (B1802)

1H-NMR(DMSO-d6) 13.02(bs, 2H), 8.28(s, 2H), 8.05(dt, 1H, J=2.1, 7.8 Hz), 7.66-1.70(m, 1H), 7.38-7.48(m, 2H), 7.30(t, 1H, J=7.8 Hz), 1.69(s, 3H), 1.57-1.64(m, 2H), 1.03(d, 3H, J=7.5 Hz).

Example 294

Synthesis of (E)-3-{2,6-difluoro-4-[4-(2-fluoro-3-hert-1-ynylphenyl)thiazol-2-ylcarbamoyl]phenyl}-2-methylacrylic acid (B1803)

1H-NMR(DMSO-d6) 13.01(bs, 2H), 8.02-8.10(m, 1H), 7.90-8.00(m, 2H), 7.68(d, 1H, J=3.0 Hz), 7.41-7.48(m, 1H), 7.35(s, 1H), 7.30(t, 1H, J=7.8 Hz), 1.81(s, 3H), 1.56-1.65(m, 2H), 1.30-1.48(m, 4H), 0.91(t, 3H, J=7.2 Hz).

Example 295

Synthesis of (E)-3-{2,6-dichloro-4-[4-(2-fluoro-3-hert-1-ynylphenyl)thiazol-2-ylcarbamoyl]phenyl}-2-methylacrylic acid (B1804)

1H-NMR(DMSO-d6) 13.02(bs, 2H), 8.28(s, 2H), 8.05(dt, 1H, J=1.8, 7.8 Hz), 7.69(d, 1H, J=2.7 Hz), 7.38-7.48(m, 2H), 7.30(t, 1H, J=7.8 Hz), 1.69(s, 3H), 1.54-1.63(m, 2H), 1.31-1.48(m, 4H), 0.91(d, 3H, J=7.2 Hz).

Example 296

Synthesis of (E)-3-{4-[4-(3-dec-1-ynyl-2-fluorophenyl)thiazol-2-ylcarbamoyl]-2,6-difluorophenyl}-2-methylacrylic acid (B1805)

1H-NMR(DMSO-d6) 13.02(bs, 2H), 8.05(dt, 1H, J=1.8, 7.8 Hz), 7.92-8.00(m, 2H), 7.68(d, 1H, J=2.7 Hz), 7.42-7.47(m, 1H), 7.34(s, 1H), 7.30(t, 1H, J=7.8 Hz), 1.80(s, 1H), 1.52-1.65(m, 2H), 1.37-1.50(m, 2H), 1.23-1.34(m, 8H), 0.84-0.89(m, 3H).

Example 297

Synthesis of (E)-3-{2,6-dichloro-4-[4-(3-dec-1-ynyl-2-fluorophenyl)thiazol-2-ylcarbamoyl]phenyl}-2-methylacrylic acid (B1806)

1H-NMR(DMSO-d6) 13.02(bs, 2H), 8.28(s, 2H), 8.02-8.09(m, 1H), 7.68(d, 1H, J=2.4 Hz), 7.38-7.47(m, 2H), 7.29(t, 1H, J=7.8 Hz), 1.69(s, 3H), 1.20-1.62(m, 12H), 0.82-0.90(m, 3H).

Example 296

Synthesis of (E)-3-(2,6-difluoro-4-{4-[2-fluoro-3-(4-methylpent-1-ynyl)phenyl]thiazol-2-ylcarbamoyl}phenyl)-2-methylacrylic acid (B1807)

1H-NMR(DMSO-d6) 13.02(bs, 2H), 8.05(dt, 1H, J=2.1, 7.8 Hz), 7.92-8.00(m, 2H), 7.70(d, 1H, J=2.7 Hz), 7.42-7.49(m, 1H), 7.34(s, 1H), 7.30(t, 1H, J=7.5 Hz), 2.41(d, 2H, J=6.3 Hz), 1.86-1.94(m, 1H), 1.80(s, 3H), 1.04(d, 6H, J=6.9 Hz).

Example 299

Synthesis of (E)-3-(2,6-dichloro-4-{4-[2-fluoro-3-(4-methylpent-1-ynyl)phenyl]thiazol-2-ylcarbamoyl}phenyl)-2-methylacrylic acid (B1808)

1H-NMR(DMSO-d6) 13.04(bs, 2H), 8.29(s, 2H), 8.05(dt, 1H, J=1.5, 7.8 Hz), 7.70(d, 1H, J=2.7 Hz), 7.38-7.59(m, 2H), 7.30(t, 1H, J=7.8 Hz), 2.42(d, 2H, J=6.3 Hz), 1.83-1.96(m, 1H), 1.69(s, 3H), 1.04(d, 6H, J=6.6 Hz).

Example 300

Synthesis of (E)-3-{4-[4-(3-cyclohexy-1-enylethynyl-2-fluorophenyl)thiazol-2-ylcarbamoyl]-2,6-difluorophenyl)-2-methylacrylic acid (B1809)

1H-NMR(DMSO-d6) 13.02(bs, 2H), 8.04-8.12(m, 1H), 7.92-8.02(m, 2H), 7.72(d, 1H, J=3.0 Hz), 7.44-7.51(m, 1H), 7.27-7.35(m, 2H), 6.26-6.30(m, 1H), 2.10-2.24(m, 4H), 1.81(s, 3H), 1.46-1.69(m, 4H).

Example 301

Synthesis of (E)-3-{4-[4-(3-cyclohexy-1-enylethynyl-2-fluorophenyl)thiazol-2-ylcarbamoyl]-2,6-difluorophenyl)-2-methyloxyacrylic acid (B1810)

1H-NMR(DMSO-d6) 13.02(bs, 2H), 8.12(dt, 1H, J=1.8, 7.8 Hz), 7.92-8.00(m, 2H), 7.72(d, 1H, J=2.4 Hz), 7.51-7.57(m, 1H), 7.33-7.38(m, 2H), 4.41(s, 2H), 3.71(s, 3H), 1.81(s, 1H).

Example 302

Synthesis of (E)-3-(2,6-difluoro-4-{4-[2-fluoro-3-(3-propyloxyprop-1-ynyl)phenyl]thiazol-2-ylcarbamoyl}phenyl)-2-methylacrylic acid (B1811)

1H-NMR(DMSO-d6) 13.02(bs, 1H), 8.13(t, 1H, J=7.5 Hz), 7.96(s, 1H), 7.93(s, 1H), 7.72(s, 1H), 7.52(t, 1H, J=7.5 Hz), 7.40(s, 1H), 7.38(t, 1H, J=7.5 Hz), 4.43(s, 2H), 3.50(t, 2H, J=7.0 Hz), 1.80(s, 3H), 1.50-1.6 (m, 2H), 0.93(t, 3H, J=7.0 Hz).

Example 303

Synthesis of (E)-3-(2,6-difluoro-4-{4-[2-fluoro-3-(3-isopropyloxyprop-1-ynyl)phenyl]thiazol-2-ylcarbamoyl}phenyl)-2-methylacrylic acid (B1812)

1H-NMR(DMSO-d6) 13.02(bs, 1H), 8.11(t, 1H, J=7.5 Hz), 7.99(s, 1H), 7.96(s, 1H), 7.72(s, 1H), 7.52(t, 1H, J=7.5 Hz), 7.34(s, 1H), 7.32(t, 1H, J=7.5 Hz), 4.43(s, 2H), 3.70-3.75(m, 1H), 1.80(s, 3H), 1.13 (d, 6H, J=6.0 Hz).

Example 304

Synthesis of (E)-3-(2,6-difluoro-4-{4-[2-fluoro-3-(3-pentyloxyprop-1-ynyl)phenyl]thiazol-2-ylcarbamoyl}phenyl)-2-methylacrylic acid (B1813)

1H-NMR(DMSO-d6) 13.02(bs, 1H), 8.10(t, 1H, J=7.5 Hz), 7.99(s, 1H), 7.96(s, 1H), 7.72(s, 1H), 7.52(t, 1H, J=7.5 Hz), 7.34(s, 1H), 7.32(t, 1H, J=7.5 Hz), 4.40(s, 2H), 3.50(t, 2H, J=7.0 Hz), 1.80(s, 3H), 1.50-1.61(m, 2H), 1.20-1.31(m, 4H), 0.88-0.92(m, 3H).

Example 305

Synthesis of (E)-3-(2,6-dichloro-4-{4-[2-fluoro-3-(3-propyloxyprop-1-ynyl)phenyl]thiazol-2-ylcarbamoyl}phenyl)-2-methylacrylic acid (B1814)

1H-NMR(DMSO-d6) 13.02(bs, 1H), 8.28(s, 2H), 8.10(t, 1H, J=7.5 Hz), 7.72(s, 1H), 7.52(t, 1H, J=7.5 Hz), 7.40(s, 1H), 7.34(t, 1H, J=7.5 Hz), 4.40(s, 2H), 3.48(t, 2H, J=7.0 Hz), 1.69(s, 3H), 1.50-1.61(m, 2H), 0.93(t, 3H, J=7.0 Hz).

Example 306

Synthesis of (E)-3-(2,6-dichloro-4-{4-[2-fluoro-3-(3-isopropyloxyprop-1-ynyl)phenyl]thiazol-2-ylcarbamoyl}phenyl)-2-methylacrylic acid (B1815)

1H-NMR(DMSO-d6) 13.02(bs, 1H), 8.28(s, 2H), 8.10(t, 1H, J=7.5 Hz), 7.72(s, 1H), 7.52(t, 1H, J=7.5 Hz), 7.40(s, 1H), 7.34(t, 1H, J=7.5 Hz), 4.40(s, 2H), 3.70-3.75(m, 1H), 1.69(s, 3H), 1.13(d, 6H, J=6.0 Hz).

Example 307

Synthesis of (E)-3-(2,6-dichloro-4-{4-[2-fluoro-3-(3-pentyloxyprop-1-ynyl)phenyl]thiazol-2-ylcarbamoyl}phenyl)-2-methylacrylic acid (B1816)

1H-NMR(DMSO-d6) 13.02(bs, 1H), 8.28(s, 2H), 8.10(t, 1H, J=7.5 Hz), 7.72(s, 1H), 7.44(t, 1H, J=7.5 Hz), 7.40(s, 1H), 7.34(t, 1H, J=7.5 Hz), 4.44(s, 2H), 3.51(t, 2H, J=7.0 Hz), 1.69(s, 3H), 1.50-1.61(m, 2H), 1.20-1.31(m, 4H), 0.93(t, 3H, J=7.0 Hz).

Example 308

Synthesis of (E)-3-[2,6-dichloro-4-(4-{3-[3-(2,2-dimethylpropyloxy)prop-1-ynyl]-2-fluorophenyl}thiazol-2-ylcarbamoyl)phenyl]-2-methylacrylic acid (B1817)

1H-NMR(DMSO-d6) 13.02(bs, 1H), 8.28(s, 2H), 8.10(t, 1H, J=7.5 Hz), 7.71(s, 1H), 7.50(t, 1H, J=7.5 Hz), 7.40(s, 1H), 7.34(t, 1H, J=7.5 Hz), 4.46(s, 2H), 3.23(s, 2H), 1.69(s, 3H), 0.91(s, 9H).

Example 309

Synthesis of (E)-3-(4-{4-[3-(5-chloro-pent-1-ynyl)-2-fluorophenyl]thiazol-2-ylcarbamoyl}-2,6-difluorophenyl)-2-methylacrylic acid (B1818)

1H-NMR(DMSO-d6) 13.02(bs, 1H), 8.07(t, 1H, J=7.5 Hz), 7.92-8.00(m, 2H), 7.71(d, 1H, J=3.0 Hz), 7.49(t, 1H, J=7.2 Hz), 7.29-7.34(m, 2H), 3.81(t, 2H, J=6.6 Hz), 2.67(t, 2H, J=7.2 Hz), 1.99-2.08(m, 2H), 1.81(s, 3H).

Example 310

Synthesis of (E)-3-(2,6-dichloro-4-{4-[3-(5-chloro-pent-1-ynyl)-2-fluorophenyl]thiazol-2-ylcarbamoyl}phenyl)-2-methylacrylic acid (B1819)

1H-NMR(DMSO-d6) 13.02(bs, 2H), 8.28(s, 2H), 8.06(t, 1H, J=6.9 Hz), 7.70(d, 1H, J=2.4 Hz), 7.48(t, 1H, J=6.3 Hz), 7.40(s, 1H), 7.31(t, 1H, J=7.8. Hz), 3.81(t, 2H, J=6.3 Hz), 2.67(t, 2H, J=6.3 Hz), 1.99-2.08(m, 2H), 1.69(s, 3H).

Example 311

Synthesis of (E)-3-(4-{4-[3-(5-cyano-pent-1-ynyl)-2-fluorophenyl]thiazol-2-ylcarbamoyl}-2,6-difluorophenyl)-2-methylacrylic acid (B1820)

1H-NMR(DMSO-d6) 8.07(dt, 1H, J=1.5, 7.8 Hz), 7.91-8.00(m, 2H), 7.70(d, 1H, J=2.7 Hz), 7.50(dt, 1H, J=1.5, 6.8 Hz), 7.29-7.34(m, 2H), 2.61-2.69(m, 4H), 1.85-1.94(m, 2H), 1.81(s, 3H).

Example 312

Synthesis of (Z)-3-{4-[4-(3-dec-1-ynyl-2-fluorophenyl)thiazol-2-ylcarbamoyl]-2,6-difluorophenyl)-2-methyloxyacrylic acid (B1821)

1H-NMR(DMSO-d6) 12.99(bs, 1H), 8.04(dt, 1H, J=1.8, 7.8 Hz), 7.88-7.95(m, 2H), 7.69(d, 1H, J=2.7 Hz), 7.44(dt, 1H, J=1.8, 6.6 Hz), 7.29(t, 1H, J=7.8 Hz), 6.64(s, 1H), 3.71(s, 3H), 1.16-1.64(m, 14H), 0.84-0.88(m, 3H).

Example 313

Synthesis of (E)-3-{2,6-difluoro-4-[4-(2-fluoro-3-pyridyn-3-ylethynylphenyl)thiazol-2-ylcarbamoyl]phenyl)-2-methylacrylic acid (B1822)

1H-NMR(DMSO-d6) 13.00(bs, 2H), 8.81(s, 1H), 8.64(d, 1H, J=3.9 Hz), 8.17(t, 1H, J=7.2 Hz), 8.04(d, 1H, J=7.8 Hz), 7.92-8.10(m, 2H), 7.77(d, 1H, J=2.1 Hz), 7.67(t, 1H, J=6.6 Hz), 7.49-7.53(m, 1H), 7.42(t, 1H, J=7.2 Hz), 7.34(s, 1H), 1.81(s, 3H).

Example 314

Synthesis of (E)-3-{4-[4-(3-ethynyl-2-fluorophenyl)thiazol-2-ylcarbamoyl]-2,6-difluorophenyl)-2-methylacrylic acid (B1823)

1H-NMR(DMSO-d6) 13.02(bs, 2H), 8.12(dt, 1H, J=1.8, 7.5 Hz), 7.92-8.00(m, 2H), 7.72(d, 1H, J=2.7 Hz), 7.55(dt, 1H, J=1.5, 6.9 Hz), 7.32-7.37(m, 2H), 4.57(s, 1H), 1.81(s, 1H).

Example 315

Synthesis of (Z)-3-(2,6-difluoro-4-{4-[2-fluoro-3-(4-methylpent-1-ynyl)phenyl]thiazol-2-ylcarbamoyl}phenyl)-2-methyloxyacrylic acid (B1824)

1H-NMR(DMSO-d6) 12.99(bs, 1H), 8.04(dt, 1H, J=1.5, 7.5 Hz), 7.87-7.95(m, 2H), 7.71(d, 1H, J=2.7 Hz), 7.46(dt, 1H, J=1.8, 7.0 Hz), 7.29(t, 1H, J=7.8 Hz), 6.65(s, 1H), 3.71(s, 3H), 2.41(d, 2H, J=6.6 Hz), 1.85-1.94(m, 1H), 1.04(d, 6H, J=6.6 Hz).

Example 316

Synthesis of (E)-3-(2,6-difluoro-4-{4-[2-fluoro-3-(3-methylhexyn-1-ynyl)phenyl]thiazol-2-ylcarbamoyl}phenyl)-2-methylacrylic acid (B1825)

1H-NMR(DMSO-d6) 13.00(bs, 2H), 8.04(dt, 1H, J=1.8, 7.5 Hz), 7.92-8.00(m, 2H), 7.71(d, 1H, J=2.7 Hz), 7.43(dt, 1H, J=1.8, 7.0 Hz), 7.34(s, 1H), 7.29(t, 1H, J=7.8 Hz), 2.68-2.82(m, 1H), 1.81(s, 1H), 1.42-1.64(m, 4H), 1.24(d, 3H, J=6.9 Hz), 0.91-0.96(m, 3H).

Example 317

Synthesis of (E)-3-(4-{4-[3-(3-cyclopentylprop-1-ynyl)-2-fluorophenyl)thiazol-2-ylcarbamoyl}-2,6-difluorophenyl)-2-methylacrylic acid (B1826)

1H-NMR(DMSO-d6) 13.00(bs, 2H), 8.04(dt, 1H, J=1.8, 6.9 Hz), 7.92-8.00(m, 2H), 7.70(d, 1H, J=2.7 Hz), 7.44(dt,

1H, J=1.8, 7.0 Hz), 7.33(s, 1H), 7.30(t, 1H, J=7.8 Hz), 2.05-2.17(m, 1H), 1.76-1.87(m, 5H), 1.48-1.70(m, 4H), 1.29-1.40 (m, 2H).

Example 318

Synthesis of (Z)-3-{4-[4-(3-cyclohexy-1-enylethynyl-2-fluorophenyl)thiazol-2-ylcarbamoyl}-2,6-difluorophenyl)-2-methyloxyacrylic acid (B1827)

1H-NMR(DMSO-d6) 12.99(bs, 1H), 8.07(dt, 1H, J=1.5, 7.5 Hz), 7.87-7.95(m, 2H), 7.72(d, 1H, J=2.7 Hz), 7.48(dt, 1H, J=1.8, 6.0 Hz), 7.32(t, 1H, J=7.8 Hz), 6.65(s, 1H), 6.25-6.30(m, 1H), 3.71(s, 3H), 2.10-2.24(m, 4H), 1.54-1.70(m, 4H).

Example 319

Synthesis of (E)-3-(2,6-dichloro-4-{4-[3-(3,3-dimethylbutyl)-2-fluorophenyl]-5-morpholin-4-ylthiazol-2-ylcarbamoyl}phenyl)-2-methylacrylic acid (B1828)

1H-NMR(DMSO-d6) 12.82(bs, 1H), 8.23(s, 2H), 7.42(t, 1H, J=7.6 Hz), 7.40(s, 1H), 7.29(t, 1H, J=7.6 Hz), 7.09(d, 1H, J=7.6 Hz ), 3.66-3.72(m, 4H), 2.66-2.78(m, 4H), 2.60-2.70 (m, 2H), 1.68(s, 3H), 1.39-1.45(m, 2H), 0.95(s, 9H).

Example 320

Synthesis of (E)-3-(2,6-difluoro-4-{4-[2-fluoro-3-(1-methyloxyhexyl)phenyl]-5-morpholin-4-ylthiazol-2-ylcarbamoyl}phenyl)-2-methylacrylic acid (B1829)

1H-NMR(DMSO-d6) 13.02(bs, 1H), 7.92(s, 1H), 7.89(s, 1H), 7.50(t, 1H, J=7.5 Hz), 7.39(t, 1H, J=7.5 Hz), 7.33(s, 1H), 7.28(t, 1H, J=7.5 Hz), 4.51(t, 1H, J=6.5 Hz), 3.66-3.72(m, 4H), 3.16(s, 3H), 2.75-2.86(m, 4H), 1.78(s, 3H), 1.70-1.78 (m, 2H,), 1.12-1.38(m, 6H), 0.87-0.90(m, 3H).

Example 321

Synthesis of (E)-3-(2,6-dichloro-4-{4-[2-fluoro-3-(1-methyloxyhexyl)phenyl]-5-morpholin-4-ylthiazol-2-ylcarbamoyl}phenyl)-2-methylacrylic acid (B1830)

1H-NMR(DMSO-d6) 12.82(bs, 1H), 8.23(s, 2H), 7.50(t, 1H, J=7.6 Hz), 7.38(s, 1H), 7.36(t, 1H, J=7.6 Hz), 7.28(t, 1H, J=7.6 Hz), 4.51(t, 1H, J=6.5 Hz), 3.66-3.72(m, 4H), 3.16(s, 3H), 2.75-2.86(m, 4H), 1.70-1.78(m, 2H,), 1.68(s, 3H), 1.10-1.38(m, 6H), 0.87-0.90 (m, 3H).

Example 322

Synthesis of (E)-3-(2,6-dichloro-4-{4-[2-fluoro-3-(3-propyloxypropyl)phenyl]-5-morpholin-4-ylthiazol-2-ylcarbamoyl}phenyl)-2-methylacrylic acid (B1831)

1H-NMR(DMSO-d6) 12.82(bs, 1H), 8.28(s, 2H), 742(t, 1H, J=7.6 Hz), 7.38(s, 1H), 7.28(t, 1H, J=7.6 Hz), 7.17(t, 1H, J=7.6 Hz), 3.75-3.89(m, 4H), 3.33-3.40(m, 4H), 2.75-2.86 (m, 4H), 2.74(t, 1H, J=7.0 Hz), 1.70-1.78(m, 2H), 1.68(s, 3H), 1.20-1.30(m, 2H), 0.87(t, 3H, J=7.0 Hz).

Example 323

Synthesis of (E)-3-(4-{4-[3-(3-dimethylamino-prop-1-ynyl)-2-fluorophenyl]thiazol-2-ylcarbamoyl}-2,6-difluorophenyl)-2-methylacrylic acid (B1832)

1H-NMR(DMSO-d6) 13.01(bs, 2H), 8.08(dt, 1H, J=1.8, 7.5H), 7.72(d, 1H, J=2.4 Hz), 7.51(dt, 1H, J=1.8, 7.2H), 7.30-7.54(m, 2H), 3.56(s, 2H), 2.29(s, 6H), 1.81 (s, 3H).

Example 324

Synthesis of (E)-3-[2,6-dichloro-4-(4-{3-[3-(2,2-dimethylpropyloxy)propyl)-2-methyloxyphenyl]thiazol-2-ylcarbamoyl}phenyl)-2-methylacrylic acid (B1833)

1H-NMR(CDCl3-d6) 8.31(s, 2H), 7.66(s, 1H), 7.46-7.53 (m, 2H), 7.24-7.30(m, 1H), 7.17(t, 1H J=7.8 Hz), 3.59(s, 3H), 3.46-3.52(m, 2H), 3.08(s, 2H), 2.76-2.84(m, 2H), 1.92-1.98 (m, 2H), 1.87(s, 3H), 0.94(s, 9H).

Example 325

Synthesis of (E)-3-(4-{4-[3-(2-butyloxyethyl)-2-methyloxyphenyl]thiazol-2-ylcarbamoyl}-2,6-difluorophenyl)-2-methylacrylic acid (B1834)

1H-NMR(DMSO-d6) 12.96 (bs, 2H), 7.95-7.98 (m, 2H), 7.86-7.88 (m, 1H), 7.73 (s, 1H), 7.34 (s, 1H), 7.27-7.29 (m, 1H), 7.14-7.19 (m, 1H), 3.59-3.65 (m, 5H), 3.40 (t, 2H, J=6.6 Hz), 2.91 (t, 2H, J=6.9 Hz), 1.81 (s, 3H), 1.42-1.50 (m, 2H), 1.26-1.34 (m, 2H), 0.86 (t, 3H, J=7.0 Hz).

Example 326

Synthesis of (Z)-3-(4-{4-[3-(2-butyloxyethyl)-2-methyloxyphenyl]thiazol-2-ylcarbamoyl}-2,6-difluorophenyl)-2-methyloxyacrylic acid (B1835)

1H-NMR(DMSO-d6) 12.92 (bs, 2H), 7.85-7.93 (m, 3H), 7.72 (s, 1H), 7.26-7.29 (m, 1H), 7.13-7.18 (m, 1H), 6.66 (s, 1H), 3.71 (s, 3H), 3.59-3.65 (m, 5H), 3.41 (t, 2H, J=6.6 Hz), 2.91 (t, 2H, J=6.9 Hz), 1.43-1.50 (m, 2H), 1.27-1.34 (m, 2H), 0.87 (t, 3H, J=7.0 Hz).

Example 327

Synthesis of (E)-3-(4-{4-[3-(2-butyloxyethyl)-2-methyloxyphenyl]thiazol-2-ylcarbamoyl}-2,6-dichlorophenyl)-2-methylacrylic acid (B1836)

1H-NMR(DMSO-d6) 12.97 (bs, 2H), 8.26 (s, 2H), 7.85-7.89 (m, 1H), 7.72 (s, 1H), 7.40 (s, 1H), 7.26-7.29 (m, 1H), 7.13-7.19 (m, 1H), 3.59-3.65 (m, 5H), 3.41 (t, 2H, J=6.6 Hz), 2.91 (t, 2H, J=6.9 Hz), 1.69 (s, 3H), 1.43-1.50 (m, 2H), 1.27-1.34 (m, 2H), 0.86 (t, 3H, J=7.0 Hz).

Example 328

Synthesis of (Z)-3-(4-{4-[3-(2-butyloxyethyl)-2-methyloxyphenyl]thiazol-2-ylcarbamoyl}-2,6-dichlorophenyl)-2-methyloxyacrylic acid (B1837)

1H-NMR(DMSO-d6) 12.94 (bs, 2H), 8.24 (s, 2H), 7.85-7.87 (m, 1H), 7.71 (s, 1H), 7.26-7.29 (m, 1H), 7.13-7.18 (m, 1H), 6.73 (s, 1H), 3.59-3.65 (m, 5H), 3.41 (t, 2H, J=6.6 Hz), 3.20 (s, 3H), 2.91 (t, 2H, J=6.9 Hz), 1.43-1.50 (m, 2H), 1.27-1.34 (m, 2H), 0.87 (t, 3H, J=7.0 Hz).

Example 329

Synthesis of (E)-3-(2,6-difluoro-4-{4-[2-methyloxy-3-(2-propyloxyethyl)phenyl]thiazol-2-ylcarbamoyl}phenyl)-2-methylacrylic acid (B1838)

1H-NMR(DMSO-d6) 12.96 (bs, 2H), 7.95-7.97 (m, 2H), 7.85-7.89 (m, 1H), 7.72 (s, 1H), 7.34 (s, 1H), 7.26-7.29 (m, 1H), 7.14-7.19 (m, 1H), 3.60-3.65 (m, 5H), 3.70 (t, 2H, J=6.6 Hz), 2.91 (t, 2H, J=6.9 Hz), 1.81 (s, 3H), 1.45-1.52 (m, 2H), 0.85 (t, 3H, J=7.5 Hz).

Example 330

Synthesis of (E)-3-(2,6-dichloro-4-{4-[2-methyloxy-3-(2-propyloxyethyl)phenyl]thiazol-2-ylcarbamoyl}phenyl)-2-methylacrylic acid (B1839)

1H-NMR(DMSO-d6) 12.98 (bs, 2H), 8.29 (s, 2H), 7.85-7.88 (m, 1H), 7.72 (s, 1H), 7.41 (s, 1H), 7.27-7.30 (m, 1H), 7.14-7.19 (m, 1H), 3.60-3.66 (m, 5H), 3.37 (t, 2H, J=6.6 Hz), 2.91(t, 2H, J=7.0 Hz), 1.69 (s, 3H), 1.48-1.54 (m, 2H), 0.85 (t, 3H, J=7.5 Hz).

Example 331

Synthesis of (Z)-3-(2,6-dichloro-4-{4-[2-methyloxy-3-(2-propyloxyethyl)phenyl]thiazol-2-ylcarbamoyl}phenyl)-2-methyloxyacrylic acid (B1840)

1H-NMR(DMSO-d6) 13.52 (bs, 1H), 12.98 (bs, 1H), 8.25 (s, 2H), 7.85-7.88 (m, 1H), 7.72 (s, 1H), 7.26-7.30 (m, 1H), 7.14-7.19 (m, 1H), 6.74 (s, 1H), 3.60-3.66 (m, 8H), 3.70 (t, 2H, J=6.6 Hz), 2.91(t, 2H, J=7.0 Hz), 1.48-1.54 (m, 2H), 0.85 (t, 3H, J=7.5 Hz).

Example 332

Synthesis of (E)-3-{4-[4-(3-butyloxy-2-fluorophenyl)thiazol-2-ylcarbamoyl]-2,6-difluorophenyl}-2-methylacrylic acid (B1841)

1H-NMR(DMSO-d6) 13.00 (bs, 2H), 7.95-7.98 (m, 2H), 7.60-7.65 (m, 2H), 7.40 (s, 1H), 7.14-7.24 (m, 2H), 4.09 (t, 2H, J=6.6 Hz), 1.80 (s, 3H), 1.70-1.77 (m, 2H), 1.43-1.51 (m, 2H), 0.97 (t, 3H, J=7.5 Hz)

Example 333

Synthesis of (E)-3-(2,6-difluoro-4-{4-[2-fluoro-3-(1-methyloxybutyl)phenyl]-5-methyloxythiazol-2-ylcarbamoyl}phenyl)-2-methylacrylic acid (B1842)

1H-NMR(DMSO-d6) 13.02(bs, 1H), 7.93(s, 1H), 7.90(s, 1H), 7.50(t, 1H, J=7.5 Hz), 7.28-7.38(m, 3H), 4.53(t, 1H, J=6.5 Hz), 3.95(s, 3H), 3.17(s, 3H), 1.79(s, 3H), 1.50-1.78(m, 2H,), 1.20-1.30(m, 2H), 0.87(t, 3H, J=7.0 Hz).

Example 334

Synthesis of (E)-3-(2,6-dichloro-4-{4-[2-fluoro-3-(1-methyloxybutyl)phenyl]-5-methyloxythiazol-2-ylcarbamoyl}phenyl)-2-methylacrylic acid (B1843)

1H-NMR(DMSO-d6) 12.82(bs, 1H), 8.28(s, 2H), 746(t, 1H, J=7.6 Hz), 7.38(s, 1H), 7.34(t, 1H, J=7.6 Hz), 7.28(t, 1H, J=7.6 Hz), 4.58(t, 1H, J=6.5 Hz), 3.95(s, 3H), 3.17(s, 3H), 1.69(s, 3H), 1.50-1.78(m, 2H), 1.20-1.30(m, 2H), 0.87(t, 3H, J=7.0 Hz).

Example 335

Synthesis of (Z)-3-(2,6-dichloro-4-{4-[2-fluoro-3-(3-isopropyloxy-1-methyloxypropyl)phenyl]thiazol-2-ylcarbamoyl}phenyl)-2-methyloxyacrylic acid (B1844)

1H-NMR(DMSO-d6) 13.02(bs, 1H), 8.25(s, 2H), 8.06(t, 1H, J=7.5 Hz), 7.64(s, 1H), 7.30-7.40(m, 2H), 6.72(s, 1H), 4.72(t, 1H, J=6.5 Hz), 3.61(s, 3H), 3.50-3.58(m, 1H), 3.35-3.42(m, 2H), 3.17(s, 3H), 1.80-1.99(m, 2H), 1.05(d, 6H, J=6.0 Hz).

Example 336

Synthesis of (Z)-3-(2,6-dichloro-4-{4-[2-fluoro-3-(1-methyloxybutyl)phenyl]-5-methyloxythiazol-2-ylcarbamoyl}phenyl)-2-methyloxyacrylic acid (B1845)

1H-NMR(DMSO-d6) 12.82(bs, 1H), 8.25(s, 2H), 746(t, 1H, J=7.6 Hz), 7.34(t, 1H, J=7.6 Hz), 7.28(t, 1H, J=7.6 Hz), 6.72(s, 1H), 4.53(t, 1H, J=6.5 Hz), 3.9 (s, 3H), 3.60(s, 3H), 3.17(s, 3H), 1.50-1.7 (m, 2H), 1.20-1.30(m, 2H), 0.87(t, 3H, J=7.0 Hz).

Example 337

Synthesis of (E)-3-(4-{4-[3-(3,3-dimethylbutyl)phenyl]-5-methyloxythiazol-2-ylcarbamoyl}-2,6-difluorophenyl)-2-methylacrylic acid (B1846)

1H-NMR(DMSO-d6) 13.02(bs, 1H), 7.97(s, 1H), 7.96 (s, 1H), 7.77 (s, 1H), 7.75 (t, 1H, J=7.5), 7.38 (s, 1H), 7.12 (t, 1H, J=7.5), 3.99 (s, 3H), 2.50-2.60 (m, 2H), 1.78 (s, 3H), 1.39-1.45 (m, 2H), 0.95 (s, 9H).

Example 338

Synthesis of (E)-3-(2,6-dichloro-4-{4-[3-(3,3-dimethylbutyl)phenyl]-5-methyloxythiazol-2-ylcarbamoyl}-2,6-difluorophenyl)-2-methylacrylic acid (B1847)

1H-NMR(DMSO-d6) 12.82(bs, 1H), 8.28(s, 2H), 7.77(s, 1H), 7.74(t, 1H, J=7.6 Hz), 7.41(s, 1H), 7.32(t, 1H, J=7.6 Hz), 4.05(s, 3H), 2.50-2.60(m, 2H), 1.68(s, 3H), 1.39-1.45(m, 2H), 0.95(s, 9H).

Example 339

Synthesis of (E)-3-[4-(4-{3-[3-(2-ethylbutyloxy) propyl]-2-methyloxyphenyl}thiazol-2-ylcarbamoyl)-2,6-difluorophenyl]-2-methylacrylic acid (B1848)

1H-NMR(CDCl3-d6) 7.90(s, 1H), 7.88(s, 1H), 7.58(s, 1H), 7.45-7.50(m, 2H), 7.25-7.28(m, 1H), 7.17(t, 1H, J=7.2 Hz), 3.57(s, 3H), 3.49(t, 2H, J=6.0 Hz), 3.33(d, 2H, J=5.4 Hz), 2.76-2.84(m, 2H), 1.90-2.11(m, 5H), 1.30-1.50(m, 5H), 0.90(t, 6H, J=7.2 Hz).

Example 340

Synthesis of (E)-3-[2,6-dicholoro-4-(4-{3-[3-(2-ethylbutyloxy)propyl]-2-methyloxyphenyl}thiazol-2-ylcarbamoyl)phenyl]-2-methylacrylic acid (B1849)

1H-NMR(CDCl3-d6) 8.33(s, 2H), 7.65(s, 1H), 7.46-7.52 (m, 2H), 2.25-7.28(m, 1H), 7.17(t, 1H, J=7.8 Hz), 3.58(s, 3H), 3.47(t, 2H, J=6 Hz), 3.32(d, 2H, J=5.7 Hz), 2.76-2.82(m, 2H), 1.90-2.00(m, 2H), 1.86(bs, 3H), 1.31-1.50(m, 5H), 0.89 (t, 6H, J=7.5 Hz).

Example 341

Synthesis of (Z)-3-[4-(4-{3-[3-(2-ethylbutyloxy) propyl]-2-methyloxyphenyl}thiazol-2-ylcarbamoyl)-2,6-difluorophenyl]-2-methyloxyacrylic acid (B1850)

1H-NMR(CDCl3-d6) 7.82(s, 1H), 7.79(s, 1H), 7.40-7.50 (m, 2H), 7.25-7.26(m, 1H), 7.17(t, 1H, J=7.5 Hz), 6.92(s, 1H), 3.90(s, 3H), 3.48(t, 2H, J=6.3 Hz), 3.32(d, 2H, J=5.7 Hz), 2.76-2.83(m, 2H), 1.91-2.05(m, 2H), 1.31-1.52(m, 5H), 0.90(t, 6H, J=7.5 Hz).

Example 342

Synthesis of (E)-3-[2,6-difluoro-4-(4-{2-methyloxy-3-[3-(3-methylbutyloxy)propyl]phenyl}thiazol-2-ylcarbamoyl)phenyl]-2-methylacrylic acid (B1851)

1H-NMR(CDCl3-d6) 7.91(s, 1H), 7.88(s, 1H), 7.57(bs, 1H), 7.47-7.52(m, 1H), 7.47(s, 1H), 7.25-7.30(m, 1H), 7.18(t, 1H, J=7.5 Hz), 3.58(s, 3H), 3.44-3.52(m, 4H), 2.80(t, 2H, J=8.7 Hz), 1.91-2.00(m, 5H), 1.68-1.78(M, 1H), 1.49(q, 2H, J=13.8, 6.9 Hz), 0.92(d, 6H, J=6.3 Hz).

Example 343

Synthesis of (E)-3-[2,6-dichloro-4-(4-{2-methyloxy-3-[3-(3-methylbutyloxy)propyl]phenyl}thiazol-2-ylcarbamoyl)phenyl]-2-methylacrylic acid (B1852)

1H-NMR(CDCl3-d6) 8.31(s, 2H), 7.65(s, 1H), 7.50(dd, 1H, J=7.8, 1.5 Hz), 7.46(s, 1H), 7.24-7.28(m, 1H), 7.16(t, 1H, J=7.8 Hz), 3.58(s, 3H), 3.43-3.51(m, 4H), 2.76-2.82(m, 2H), 1.85-2.05(m, 2H), 1.86(s, 3H), 1.65-1.80(m, 1H), 1.49(t, 2H, J=13.5, 6.6 Hz), 0.92(d, 6H, J=6.9 Hz).

Example 344

Synthesis of (Z)-3-[2,6-difluoro-4-(4-{2-methyloxy-3-[3-(3-methylbutyloxy)propyl]phenyl}thiazol-2-ylcarbamoyl)phenyl]-2-methyloxyacrylic acid (B1853)

1H-NMR(CDCl3-d6) 7.84(s, 1H), 7.81(s, 1H), 7.49(d, 1H, J=8.1 Hz), 7.46(s, 1H), 7.29(d, 1H, J=7.5 Hz), 7.18(t, 1H, J=7.5 Hz), 6.91(s, 1H), 3.90(s, 3H), 3.59(s, 3H), 2.40-3.52(m, 4H), 2.80(t, 2H, J=8.1 Hz), 1.90-2.05(m, 2H), 1.65-1.78(m, 1H), 1.49(q, 2H, J=13.5, 6.6 Hz), 0.92(d, 6H, J=6.3 Hz).

Example 345

Synthesis of (E)-3-(4-{4-[3-(3-cyclobutylmethyloxypropyl)-2-methyloxyphenyl]thiazol-2-ylcarbamoyl}-2,6-difluorophenyl)-2-methylacrylic acid (B1854)

1H-NMR(CDCl3-d6) 7.91(s, 1H), 7.88(s, 1H), 7.58(s, 1H), 7.49(dd, 1H, J=7.5, 1.5 Hz), 7.46(s, 1H), 7.25-7.29(m, 1H), 7.18(t, 1H, J=7.5 Hz), 3.58(s, 3H), 3.50(t, 2H, J=6.3 Hz), 3.43(d, 2H, J=6.9 Hz), 2.76-2.82(m, 2H), 2.54-2.64(m, 1H), 1.72-1.21(m, 11H).

Example 346

Synthesis of (E)-3-(2,6-dichloro-4-{4-[3-(3-cyclobutylmethyloxypropyl)-2-methyloxyphenyl]thiazol-2-ylcarbamoyl}phenyl)-2-methylacrylic acid (B1855)

1H-NMR(CDCl3-d6) 8.32(s, 2H), 7.66(s, 1H), 7.49(d, 1H, J=6.6 Hz), 7.46(s, 1H), 7.24-7.26(m, 1H), 7.16(t, 1H, J=7.5 Hz), 3.57(s, 3H), 3.49(t, 2H, J=6.3 Hz), 3.42(d, 2H, J=6.6 Hz), 2.78(t, 2H, J=7.8 Hz), 2.52-2.64(m, 1H), 2.01-2.12(m, 2H), 1.70-2.00(m, 9H).

Example 347

Synthesis of (Z)-3-(4-{4-[3-(3-cyclobutylmethyloxypropyl)-2-methyloxyphenyl]thiazol-2-ylcarbamoyl}-2,6-difluorophenyl)-2-methyloxyacrylic acid (B1856)

1H-NMR(CDCl3-d6) 7.82(s, 1H), 7.79(s, 1H), 7.44-7.50 (m, 2H), 7.25-7.30(m, 1H), 7.17(t, 1H, J=7.5 Hz), 6.92(s, 1H), 3.91(s, 3H), 3.57(s, 3H), 3.50(t, 2H, J=6.3 Hz), 3.43(d, 2H, J=6.9 Hz), 2.79(t, 2H, J=7.8 Hz), 2.53-2.66(m, 1H), 1.72-2.13(m, 8H).

Example 348

Synthesis of (Z)-3-(2,6-dichloro-4-{4-[3-(3-cyclobutylmethyloxypropyl)-2-methyloxyphenyl]thiazol-2-ylcarbamoyl}phenyl)-2-methyloxyacrylic acid (B1857)

1H-NMR(CDCl3-d6) 8.25(s, 2H), 7.47(d, 1H, J=7.8 Hz), 7.44(s, 1H), 7.24-7.26(m, 1H), 7.16(t, 1H, J=7.5 Hz), 7.02(s, 1H), 3.73(s, 3H), 3.57(s, 3H), 3.49(t, 2H, J=6.0 Hz), 3.42(d, 2H, J=6.6 Hz), 2.78(t, 2H, J=8.1 Hz), 2.53-2.64(m, 1H), 1.71-2.14(m, 8H).

Example 349

Synthesis of (E)-3-(2,6-difluoro-4-{4-[2-fluoro-3-(1-methyloxyhexyl)phenyl]-5-methyoxythiazol-2-ylcarbamoyl}phenyl)-2-methylacrylic acid (B1858)

1H-NMR(DMSO-d6) 13.02(bs, 1H), 7.93(s, 1H), 7.90(s, 1H), 7.48(t, 1H, J=7.5 Hz), 7.28-7.38(m, 3H), 4.51(t, 1H, J=6.5 Hz), 3.95(s, 3H), 3.17(s, 3H), 1.79(s, 3H), 1.50-1.78(m, 2H), 1.20-1.30(m, 6H), 0.87-0.90(m, 3H).

Example 350

Synthesis of (E)-3-(2,6-dichloro-4-{4-[2-fluoro-3-(1-methyloxyhexyl)phenyl]-5-methyoxythiazol-2-ylcarbamoyl}phenyl)-2-methylacrylic acid (B1859)

1H-NMR(DMSO-d6) 12.82(bs, 1H), 8.28(s, 2H), 7.46(t, 1H, J=7.6 Hz), 7.38(s, 1H), 7.34(t, 1H, J=7.6 Hz), 7.28(t, 1H, J=7.6 Hz), 4.51(t, 1H, J=6.5 Hz), 3.95(s, 3H), 3.17(s, 3H), 1.50-1.78(m, 2H), 1.69(s, 3H), 1.20-1.30(m, 6H), 0.87-0.90(m, 3H).

Example 351

Synthesis of (Z)-3-(2,6-difluoro-4-{4-[2-fluoro-3-(1-methyloxyhexyl)phenyl]-5-methyoxythiazol-2-ylcarbamoyl}phenyl)-2-methyloxyacrylic acid (B1860)

1H-NMR(DMSO-d6) 13.02(bs, 1H), 7.90(s, 1H), 7.88(s, 1H), 7.48(t, 1H, J=7.5 Hz), 7.36(t, 1H, J=7.5 Hz), 7.28(t, 1H, J=7.5 Hz), 6.65(s, 1H), 4.51(t, 1H, J=6.5 Hz), 3.95(s, 3H), 3.70(s, 3H), 3.17(s, 3H), 1.50-1.78(m, 2H,), 1.20-1.30(m, 6H), 0.87-0.90(m, 3H).

Example 352

Synthesis of (Z)-3-(2,6-dichloro-4-{4-[2-fluoro-3-(1-methyloxyhexyl)phenyl]-5-methyoxythiazol-2-ylcarbamoyl}phenyl)-2-methyloxyacrylic acid (B1861)

1H-NMR(DMSO-d6) 12.82(bs, 1H), 8.20(s, 2H), 7.46(t, 1H, J=7.6 Hz), 7.34(t, 1H, J=7.6 Hz), 7.28(t, 1H, J=7.6 Hz), 6.65(s, 1H), 4.51(t, 1H, J=6.5 Hz), 3.95(s, 3H), 3.60(s, 3H), 3.17(s, 3H), 1.50-1.78(m, 2H), 1.20-1.30(m, 6H), 0.87-0.90(m, 3H).

Example 353

Synthesis of (E)-3-(2,6-difluoro-4-{5-methyloxy-4-[3-(3-propyloxypropyl)phenyl]thiazol-2-ylcarbamoyl}phenyl)-2-methylacrylic acid (B1862)

1H-NMR(DMSO-d6) 13.02(bs, 1H), 7.93(s, 1H), 7.90(s, 1H), 7.77(s, 1H), 7.76(d, 1H, J=7.5 Hz), 7.34(s, 1H), 7.33(t, 1H, J=7.6 Hz), 7.11(t, 1H, J=7.6 Hz), 4.05(s, 3H), 3.33-3.40 (m, 4H), 2.74(t, 1H, J=7.0 Hz), 1.75-1.85(m, 2H), 1.79(s, 3H), 1.45-1.55(m, 2H), 0.87(t, 3H, J=7.0 Hz).

Example 354

Synthesis of (E)-3-(2,6-dichloro-4-{5-methyloxy-4-[3-(3-propyloxypropyl)phenyl]thiazol-2-ylcarbamoyl}phenyl)-2-methylacrylic acid (B1863)

1H-NMR(DMSO-d6) 13.02(bs, 1H), 8.28(s, 2H), 7.77(s, 1H), 7.76(d, 1H, J=7.5 Hz), 7.39(s, 1H), 7.33(t, 1H, J=7.6 Hz), 7.11(t, 1H, J=7.6 Hz), 4.05(s, 3H), 3.33-3.40(m, 4H), 2.74(t, 1H, J=7.0 Hz), 1.75-1.85(m, 2H), 1.68(s, 3H), 1.45-1.55(m, 2H), 0.87(t, 3H, J=7.0 Hz).

Example 355

Synthesis of (Z)-3-(2,6-difluoro-4-{5-methyloxy-4-[3-(3-propyloxypropyl)phenyl]thiazol-2-ylcarbamoyl}phenyl)-2-methyloxyacrylic acid (B1864)

1H-NMR(DMSO-d6) 13.02(bs, 1H), 7.88(s, 1H), 7.85(s, 1H), 7.77(s, 1H), 7.76(d, 1H, J=7.5 Hz), 7.33(t, 1H, J=7.6 Hz), 7.11(t, 1H, J=7.6 Hz), 6.63(s, 1H), 4.05(s, 3H), 3.79(s, 3H), 3.33-3.40(m, 4H), 2.74(t, 1H, J=7.0 Hz), 1.75-1.85(m, 2H), 1.45-1.55 (m, 2H), 0.87(t, 3H, J=7.0 Hz).

Example 356

Synthesis of (Z)-3-(2,6-dichloro-4-{5-methyloxy-4-[3-(3-propyloxypropyl)phenyl]thiazol-2-ylcarbamoyl}phenyl)-2-methyloxyacrylic acid (B1865)

1H-NMR(DMSO-d6) 13.02(bs, 1H), 8.28(s, 2H), 7.77(s, 1H), 7.76(d, 1H, J=7.5 Hz), 7.33(t, 1H, J=7.6 Hz), 7.11(t, 1H, J=7.6 Hz), 6.63(s, 1H), 4.05(s, 3H), 3.70(s, 3H), 3.33-3.40(m, 4H), 2.64(t, 1H, J=7.0 Hz), 1.75-1.85(m, 2H), 1.45-1.55(m, 2H), 0.87(t, 3H, J=7.0 Hz).

Example 357

Synthesis of (E)-3-(4-{4-[3-(3-ethyloxy-1-methyloxypropyl)-2-fluorophenyl]thiazol-2-ylcarbamoyl}-2,6-difluorophenyl)-2-methylacrylic acid (B1866)

1H-NMR(DMSO-d6) 13.01(bs, 2H), 8.03(dt, 1H, J=2.4, 7.5 Hz), 7.93-7.99(m, 2H), 7.66(d, 1H, J=2.7 Hz), 7.32-7.41 (m, 3H), 4.68-4.73(m, 1H), 3.47-3.54(m, 1H), 3.36-3.43(m, 2H), 3.18(s, 3H), 1.85-2.02(m, 2H), 1.81(s, 3H), 1.09(t, 3H, J=6.9 Hz).

Example 358

Synthesis of (E)-3-(2,6-dichloro-4-{4-[3-(3-ethyloxy-1-methyloxypropyl)phenyl]thiazol-2-ylcarbamoyl}phenyl)-2-methylacrylic acid (B1867)

1H-NMR(DMSO-d6) 13.00(bs, 2H), 8.27(s, 2H), 8.01(dt, 1H, J=3.0, 6.6 Hz), 7.63(d, 1H, J=2.4 Hz), 7.30-7.39(m, 3H), 4.66-4.71(m, 1H), 3.45-3.53(m, 1H), 3.16(s, 3H), 1.83-2.00 (m, 2H), 1.67(s, 3H), 1.07(t, 3H, J=6.9 Hz).

Example 359

Synthesis of (E)-3-{4-[4-(3-benzyloxy-2-methyloxyphenyl)thiazol-2-ylcarbamoyl}-2,6-difluorophenyl)-2-methylacrylic acid (B11868)

1H-NMR(DMSO-d6) 12.95 (bs, 2H), 7.95-7.98 (m, 2H), 7.77 (s, 1H), 7.66-7.69 (m, 1H), 7.34-7.54 (m, 6H), 7.13-7.15 (m, 2H), 5.20 (s, 2H), 3.82 (s, 3H), 1.81 (s, 3H).

Example 360

Synthesis of (Z)-3-{4-[4-(3-benzyloxy-2-methyloxyphenyl)thiazol-2-ylcarbamoyl}-2,6-difluorophenyl)-2-methyloxyacrylic acid (B1869)

1H-NMR(DMSO-d6) 12.89 (bs, 2H), 7.89-7.92 (m, 2H), 7.76 (s, 1H), 7.66-7.69 (m, 1H), 7.34-7.53 (m, 5H), 7.13-7.15 (m, 2H), 6.66 (s, 1H), 5.19 (s, 2H), 3.82 (s, 3H), 3.71 (s, 3H).

Example 361

Synthesis of (E)-3-{4-[4-(3-benzyloxy-2-methyloxyphenyl)thiazol-2-ylcarbamoyl}-2,6-dichlorophenyl)-2-methylacrylic acid (B1870)

1H-NMR(DMSO-d6) 12.95 (bs, 2H), 8.29 (s, 2H), 7.76 (s, 1H), 7.66-7.69 (m, 1H), 7.35-7.54 (m, 6H), 7.13-7.15 (m, 2H), 5.20 (s, 2H), 3.82 (s, 3H), 1.69 (s, 3H).

Example 362

Synthesis of (Z)-3-{4-[4-(3-benzyloxy-2-methyloxyphenyl)thiazol-2-ylcarbamoyl}-2,6-dichlorophenyl)-2-methyloxyacrylic acid (B1871)

1H-NMR(DMSO-d6) 12.92 (bs, 2H), 8.24 (s, 2H), 7.76 (s, 1H), 7.66-7.69 (m, 1H), 7.35-7.54 (m, 5H), 7.13-7.15 (m, 2H), 6.74 (s, 2H), 5.20 (s, 1H), 3.82 (s, 3H), 3.61 (s, 3H).

Example 363

Synthesis of (E)-3-(4-{4-[3-(4-chlorobutyloxy)-2-methyloxyphenyl]thiazol-2-ylcarbamoyl}-2,6-difluorophenyl)-2-methylacrylic acid (B1872)

1H-NMR(DMSO-d6) 12.93 (bs, 2H), 7.95-7.97 (m, 2H), 7.75 (s, 1H), 7.64-7.67 (m, 1H), 7.33 (s, 1H), 7.11-7.16 (m, 1H), 7.03-7.06 (m, 1H), 4.06-4.10 (m, 2H,), 3.80 (s, 3H), 3.74-3.78 (m, 2H), 1.93 (bs, 4H), 1.81 (s, 3H).

Example 364

Synthesis of (E)-3-(4-{4-[3-(4-chlorobutyloxy)-2-methyloxyphenyl]thiazol-2-ylcarbamoyl}-2,6-difluorophenyl)-2-methyloxyacrylic acid (B1873)

1H-NMR(DMSO-d6) 12.89 (bs, 2H), 7.89-7.92 (m, 2H), 7.75 (s, 1H), 7.65-7.67 (m, 1H), 7.11-7.16 (m, 1H), 7.03-7.06 (m, 1H), 6.67 (s, 1H), 4.06-4.10 (m, 2H,), 3.80 (s, 3H), 3.74-3.78 (m, 2H), 3.71 (s, 3H), 1.93 (bs, 4H).

Example 365

Synthesis of (Z)-3-(2,6-dichloro-4-{4-[3-(4-chlorobutyloxy)-2-methyloxyphenyl]thiazol-2-ylcarbamoyl}phenyl)-2-methyloxyacrylic acid (B1874)

1H-NMR(DMSO-d6) 12.96 (bs, 2H), 8.29 (s, 2H), 7.75 (s, 1H), 7.65-7.67 (m, 1H), 7.40 (s, 1H), 7.11-7.16 (m, 1H), 7.03-7.06 (m, 1H), 4.06-4.10 (m, 2H,), 3.80 (s, 3H), 3.74-3.78 (m, 2H), 1.93 (bs, 4H), 1.69 (s, 3H).

Example 366

Synthesis of (E)-3-(2,6-difluoro-4-{4-[2-methyloxy-3-(3-methyloxypropylphenyl]thiazol-2-ylcarbamoyl}phenyl)-2-methylacrylic acid (B1875)

1H-NMR(CDCl3-d6) 7.90(s, 1H), 7.88(s, 1H), 7.58(s, 1H), 7.49(d, 1H, J=6.3 Hz), 7.46(s, 1H), 7.25-7.28(m, 1H), 7.18(t, 1H, J=7.5 Hz), 3.57(s, 3H), 3.47(t, 2H, J=6.3 Hz), 3.37(s, 3H), 2.79(t, 2H, J=8.1 Hz), 1.93-2.00(m, 5H).

Example 367

Synthesis of (E)-3-(2,6-dichloro-4-{4-[2-methyloxy-3-(3-methyloxypropylphenyl]thiazol-2-ylcarbamoyl}phenyl)-2-methylacrylic acid (B1876)

1H-NMR(CDCl3-d6) 8.32(s, 2H), 7.66(s, 1H), 7.45-7.51 (m, 2H), 7.24-7.27(m, 1H), 7.17(t, 1H, J=7.5 Hz), 3.57(s, 3H), 3.46(t, 2H, J=6.3 Hz), 3.37(s, 3H), 2.78(t, 2H, J=8.7 Hz), 1.90-2.04(m, 2H), 1.87(s, 3H).

Example 368

Synthesis of (E)-3-(2,6-difluoro-4-{4-[3-(3-isobuyloxypropyl)-2-methyloxyphenyl]thiazol-2-ylcarbamoyl}phenyl)-2-methylacrylic acid (B1877)

1H-NMR(CDCl3-d6) 7.90(s, 1H), 7.87(s, 1H), 7.58(s, 1H), 7.45-7.52(m, 2H), 7.24-7.30(m, 1H), 7.17(t, 1H, J=7.5 Hz), 3.57(s, 3H), 3.50(t, 2H, 6.3 Hz), 3.21(d, 2H, J=6.6 Hz), 2.80(t, 2H, 8.7 Hz), 1.84-2.03(m, 6H), 0.93(d, 6H, J=6.3 Hz).

Example 369

Synthesis of (E)-3-(2,6-dichloro-4-{4-[3-(3-isobuyloxypropyl)-2-methyloxyphenyl]thiazol-2-ylcarbamoyl}phenyl)-2-methylacrylic acid (B1878)

1H-NMR(CDCl3-d6) 8.32(s, 2H), 7.66(s, 1H), 7.45(d, 1H, J=7.2 Hz), 7.46(s, 1H), 7.24-7.28(m, 1H), 7.16(t, 1H, J=7.5 Hz), 3.57(s, 3H), 3.49(t, 2H, J=6.0 Hz), 3.20(d, 2H, J=6.6 Hz), 2.80(t, 2H, J=8.4 Hz), 1.83-2.04(m, 6H), 0.92(d, 6H, J=6.3 Hz).

Example 370

Synthesis of (Z)-3-(2,6-difluoro-4-{4-[3-(3-isobuyloxypropyl)-2-methyloxyphenyl]thiazol-2-ylcarbamoyl}phenyl)-2-methyloxyacrylic acid (B1879)

1H-NMR(CDCl3-d6) 7.80(s, 1H), 7.78(s, 1H), 7.46(dd, 1H, J=7.8, 2.1 Hz), 7.44(s, 1H), 7.25-7.32(m, 1H), 7.17(t, 1H, J=7.5 Hz), 6.92(s, 1H), 3.91(s, 3H), 3.57(s, 3H), 3.50(t, 2H,

J=6.3 Hz), 3.21(d, 2H, J=6.6 Hz), 2.80(t, 2H, J=8.7 Hz), 1.83-2.01(m, 3H), 0.93(d, 6H, J=6.3 Hz).

Example 371

Synthesis of (Z)-3-(2,6-dichloro-4-{4-[3-(3-isobuyloxypropyl)-2-methyloxyphenyl]thiazol-2-ylcarbamoyl}phenyl)-2-methyloxyacrylic acid (B1880)

1H-NMR(CDCl3-d6) 8.25(s, 2H), 7.47(dd, 1H, J=7.8, 1.8 Hz), 7.44(s, 1H), 7.24-7.28(m, 1H), 7.16(t, 1H, J=7.5 Hz), 7.03(s, 1H), 3.73(s, 3H), 3.57(s, 3H), 3.49(t, 2H, J=6.3 Hz), 3.20(d, 2H, J=6.9 Hz), 2.79(t, 2H, J=8.4 Hz), 1.83-2.00(m, 3H), 0.92(d, 6H, J=6.9 Hz).

Example 372

Synthesis of (E)-3-(2,6-difluoro-4-{4-[2-methyloxy-3-(3-propyloxymethyl)phenyl]thiazol-2-ylcarbamoyl}phenyl)-2-methylacrylic acid (B1881)

1H-NMR(DMSO-d6) 12.95(bs, 2H), 7.93-7.97(m, 3H), 7.72(s, 1H), 7.32-7.38(m, 2H), 7.22(t, 1H, J=7.5 Hz), 4.55(s, 2H), 3.64(s, 3H), 3.45(t, 2H, J=6.6 Hz), 1.79(d, 3H, J=1.5 Hz), 1.54-1.61(m, 2H), 0.89(t, 3H, J=7.2 Hz).

Example 373

Synthesis of (E)-3-(2,6-dichloro-4-{4-[2-methyloxy-3-(3-propyloxymethyl)phenyl]thiazol-2-ylcarbamoyl}phenyl)-2-methylacrylic acid (B13882)

1H-NMR(DMSO-d6) 12.95(bs, 2H), 8.27(s, 2H), 7.94-7.97(m, 1H), 7.71(s, 1H), 7.36-7.38(m, 2H), 7.22(t, 1H, J=7.5 Hz), 4.55(s, 2H), 3.64(s, 3H), 3.45(t, 2H, J=6.6 Hz), 1.67(s, 3H), 1.54-1.61(m, 2H), 0.89(t, 3H, J=7.3 Hz).

Example 374

Synthesis of (Z)-3-(2,6-dichloro-4-{4-[2-methyloxy-3-(3-propyloxymethyl)phenyl]thiazol-2-ylcarbamoyl}phenyl)-2-methyloxyacrylic acid (B1883)

1H-NMR(DMSO-d6) 12.95(bs, 2H), 8.24(s, 2H), 7.97(dd, 1H, J=3.0 Hz, 7.65 Hz), 7.73(s, 1H), 7.37-7.40(m, 1H), 7.24 (t, 1H, J=7.8 Hz), 6.72(s, 1H), 4.57(s, 2H), 3.66(s, 3H), 3.61 (s, 3H), 3.47(t, 2H, J=6.3 Hz), 1.55-1.62(m, 2H), 0.91(t, 3H, J=7.2 Hz).

Example 375

Synthesis of (E)-3-(2,6-dichloro-4-{4-[2-methyloxy-3-(3-pentyloxymethyl)phenyl]thiazol-2-ylcarbamoyl}phenyl)-2-methylacrylic acid (B1884)

1H NMR(DMSO-d6) 12.96(bs, 2H), 7.95-7.99(m, 3H), 7.74(s, 1H), 7.34-7.40(m, 2H), 7.24(t, 1H, J=7.8 Hz), 4.56(s, 2H), 3.65(s, 3H), 3.50(t, 2H, J=6.6 Hz), 1.81 (d, 3H, J=1.8 Hz), 1.55-1.59(m, 2H), 1.30-1.34(m, 4H), 0.85-0.90(m, 3H).

Example 376

Synthesis of (E)-3-(2,6-difluoro-4-{4-[2-methyloxy-3-(3-pentyloxymethyl)phenyl]thiazol-2-ylcarbamoyl}phenyl)-2-methyloxyacrylic acid (B1885)

1H NMR(DMSO-d6) 12.93(bs, 2H), 7.90-7.99(m, 3H), 7.74(s, 1H), 7.37-7.40(m, 1H), 7.24(t, 1H, J=7.5 Hz), 6.67(s, 1H), 4.56(s, 2H), 3.72(s, 3H), 3.65(s, 3H), 3.50(t, 2H, J=6.3 Hz), 1.55-1.60(m, 2H), 1.30-1.34(m, 4H), 0.87(t, 3H, J=6.9 Hz).

Example 377

Synthesis of (E)-3-(2,6-dichloro-4-{4-[2-methyloxy-3-(3-pentyloxymethyl)phenyl]thiazol-2-ylcarbamoyl}phenyl)-2-methylacrylic acid (B1886)

1H NMR(DMSO-d6) 12.98(bs, 2H), 8.29(s, 2H), 7.96-7.99(m, 1H), 7.74(s, 1H), 7.36-7.41(m, 2H), 7.24(t, 1H, J=7.8 Hz), 4.56(s, 2H), 3.65(s, 3H), 3.50(t, 2H, J=6.3 Hz), 1.69(d, 3H, J=1.5 Hz), 1.55-1.60(m, 2H), 1.30-1.34(m, 4H), 0.87(t, 3H, J=6.9 Hz).

Example 378

Synthesis of (Z)-3-(2,6-dichloro-4-{4-[2-methyloxy-3-(3-pentyloxymethyl)phenyl]thiazol-2-ylcarbamoyl}phenyl)-2-methyloxyacrylic acid (B1887)

1H NMR(DMSO-d6) 12.97(bs, 2H), 8.25(s, 2H), 7.97(dd, 1H, J=1.5 Hz, 7.8 Hz), 7.74(s, 1H), 7.37-7.40(m, 1H), 7.24(t, 1H, J=7.5 Hz), 6.72(s, 1H), 4.56(s, 2H), 3.65(s, 3H), 3.62(s, 3H), 3.50(t, 2H, J=6.3 Hz), 1.55-1.60(m, 2H), 1.30-1.34(m, 4H), 0.87(t, 3H, J=6.9 Hz).

Example 379

Synthesis of (E)-3-(2,6-difluoro-4-{4-[3-isopropyloxy-2-methyloxyphenyl]thiazol-2-ylcarbamoyl}phenyl)-2-methylacrylic acid (B1888)

1H NMR(DMSO-d6) 12.96(bs, 2H), 7.96(d, 3H, J=8.1 Hz), 7.74(s, 1H), 7.38-7.40(m, 1H), 7.34(s, 1H), 7.23(t, 1H, J=7.5 Hz), 4.56(s, 2H), 3.68-3.76(m, 1H), 3.66(s, 3H), 1.81(s, 3H), 1.19(d, 6H, J=6.3 Hz).

Example 380

Synthesis of (E)-3-(2,6-dichloro-4-{4-[3-isopropyloxy-2-methyloxyphenyl]thiazol-2-ylcarbamoyl}phenyl)-2-methylacrylic acid (B1889)

1H NMR(DMSO-d6) 12.98(bs, 2H), 8.29(s, 2H), 7.96(dd, 1H, J=1.5 Hz, 8.1 Hz), 7.74(s, 1H), 7.37-7.41(m, 2H), 7.23(t, 1H, J=7.8 Hz), 4.56(s, 2H), 3.68-3.76(m, 1H), 3.66(s, 3H), 1.69(d, 3H, J=1.5 Hz), 1.19(d, 6H, J=6.3 Hz).

Example 381

Synthesis of (E)-3-(4-{4-[3-(1-ethylpropyloxymethyl)-2-methyloxyphenyl]thiazol-2-ylcarbamoyl}-2,6-difluorophenyl)-2-methylacrylic acid (B1890)

1H NMR(DMSO-d6) 13.20(bs, 2H), 7.96(d, 3H, J=8.7 Hz), 7.73(s, 1H), 7.40-7.42(m, 1H), 7.34(s, 1H), 7.24(t, 1H, J=7.5 Hz), 4.57(s, 2H), 3.65(s, 3H), 3.10-3.46(m, 1H), 1.881 (d, 3H, J=1.5 Hz), 1.52-1.57(m, 4H), 0.89(t, 6H, J=7.5 Hz).

Example 382

Synthesis of (Z)-3-(4-{4-[3-(1-ethylpropyloxymethyl)-2-methyloxyphenyl]thiazol-2-ylcarbamoyl}-2,6-difluorophenyl)-2-methyloxyacrylic acid (B1891)

1H NMR(DMSO-d6) 12.93(bs, 2H), 7.90-7.98(m, 3H), 7.73(s, 1H), 7.41(dd, 1H, J=1.8 Hz, 7.5 Hz), 7.24(t, 1H, J=7.5 Hz), 6.64(s, 1H), 4.57(s, 2H), 3.71(s, 3H), 3.66(s, 3H), 3.20-3.45(m, 1H), 1.50-1.59(m, 4H), 0.89(t, 6H, J=7.2 Hz).

Example 383

Synthesis of (E)-3-(2,6-dichloro-4-{4-[3-(1-ethylpropyloxymethyl)-2-methyloxyphenyl]thiazol-2-ylcarbamoyl}phenyl)-2-methylacrylic acid (B1892)

1H NMR(DMSO-d6) 12.98(bs, 2H), 8.29(s, 2H), 7.96(dd, 1H, J=1.5 Hz, 7.8 Hz), 7.73(s, 1H), 7.40-7.42(m, 2H), 7.24(t, 1H, J=7.5 Hz), 4.57(s, 2H), 3.66(s, 3H), 3.26-3.38(m, 1H), 1.69(s, 3H), 1.50-1.59(m, 4H), 0.89(t, 6H, J=7.5 Hz).

Example 384

Synthesis of (Z)-3-(2,6-dichloro-4-{4-[3-(1-ethylpropyloxymethyl)-2-methyloxyphenyl]thiazol-2-ylcarbamoyl}phenyl)-2-methyloxyacrylic acid (B1893)

1H NMR(DMSO-d6) 12.95(bs, 2H), 8.24(s, 2H), 7.96(dd, 1H, J=1.8 Hz, 7.8 Hz), 7.73(s, 1H), 7.41(dd, 1H, J=1.5 Hz, 7.5 Hz), 7.24(t, 1H, J=7.5 Hz), 6.71(s, 1H), 4.57(s, 2H), 3.66(s, 3H), 3.62(s, 3H), 3.24-3.38(m, 1H), 1.50-1.59(m, 4H), 0.89(t, 6H, J=7.5 Hz).

Example 385

Synthesis of (E)-3-{4-[4-(3-cyclohexyloxymethyl)-2-methyloxyphenyl]thiazol-2-ylcarbamoyl}-2,6-difluorophenyl)-2-methylacrylic acid (B1894)

1H NMR(DMSO-d6) 12.97(bs, 2H), 7.96(d, 3H, J=8.4 Hz), 7.74(s, 1H), 7.39-7.7.41(m, 1H), 7.34(s, 1H), 7.23(t, 1H, J=7.8 Hz), 4.59(s, 2H), 3.66(s, 3H), 3.40-3.44(m, 1H), 1.91-1.94(m, 2H), 1.81(d, 3H, J=1.8 Hz), 1.69-1.71(m, 2H), 1.49-1.51(m, 1H), 1.25-1.35(m, 5H).

Example 386

Synthesis of (Z)-3-{4-[4-(3-cyclohexyloxymethyl)-2-methyloxyphenyl]thiazol-2-ylcarbamoyl}-2,6-difluorophenyl)-2-methyloxyacrylic acid (B1895)

1H NMR(DMSO-d6) 12.94(bs, 2H), 7.90-7.98(m, 3H), 7.74(s, 1H), 7.40(d, 1H, J=7.2 Hz), 7.23(t, 1H, J=7.8 Hz), 6.65(s, 1H), 4.59(s, 2H), 3.72(s, 3H), 3.66(s, 3H), 3.33-3.43(m, 1H), 1.91-1.96(m, 2H), 1.69-1.71(m, 2H), 1.49-1.51(m, 1H), 1.23-1.35(m, 5H).

Example 387

Synthesis of (E)-3-{2,6-dichloro-4-[4-(3-cyclohexyloxymethyl)-2-methyloxyphenyl]thiazol-2-ylcarbamoyl}phenyl)-2-methylacrylic acid (B1896)

1H NMR(DMSO-d6) 13.00(bs, 2H), 8.29(s, 2H), 7.97(d, 1H, J=7.5 Hz), 7.73(s, 1H), 7.38-7.40(m, 2H), 7.23(t, 1H, J=7.5 Hz), 4.59(s, 2H), 3.66(s, 3H), 3.34-3.42(m, 1H), 1.91-1.96(m, 2H), 1.69-1.74(m, 5H), 1.48-1.51(m, 1H), 1.25-1.35 (m, 5H).

Example 388

Synthesis of (Z)-3-{2,6-dichloro-4-[4-(3-cyclohexyloxymethyl)-2-methyloxyphenyl]thiazol-2-ylcarbamoyl}phenyl)-2-methyloxyacrylic acid (B1897)

1H NMR(DMSO-d6) 12.98(bs, 2H), 8.24(s, 2H), 7.96(d, 1H, J=7.8 Hz), 7.73(s, 1H), 7.39(d, 1H, J=7.2 Hz), 7.23(t, 1H, J=7.5 Hz), 6.71(s, 1H), 4.59(s, 2H), 3.66(s, 3H), 3.61(s, 3H), 3.20-3.45(m, 1H), 1.91-1.94(m, 2H), 1.69-1.70(m, 2H), 1.48-1.51(m, 1H), 1.25-1.32(m, 5H).

Example 389

Synthesis of (E)-3-[4-(4-{3-[3-(2,2-dimethylpropyloxy)propyl]phenyl}-5-methyloxythiazol-2-ylcarbamoyl)-2,6-difluorophenyl]-2-methylacrylic acid (B1898)

1H-NMR(DMSO-d6) 13.02(bs, 1H), 7.93(s, 1H), 7.90(s, 1H), 7.77(s, 1H), 7.76(d, 1H, J=7.5 Hz), 7.34(s, 1H), 7.33(t, 1H, J=7.6 Hz), 7.11(t, 1H, J=7.6 Hz), 4.03(s, 3H), 3.37(t, 2H, J=7.0 Hz), 3.03(s, 2H), 2.70(t, 2H, J=7.0 Hz), 1.80(s, 3H), 1.70-1.80(m, 2H,), 0.90(s, 9H).

Example 390

Synthesis of (E)-3-[2,6-dichloro-4-(4-{3-[3-(2,2-dimethylpropyloxy)propyl]phenyl}-5-methyloxythiazol-2-ylcarbamoyl)phenyl]-2-methylacrylic acid (B1899)

1H-NMR(DMSO-d6) 13.02(bs, 1H), 8.20(s, 2H), 7.77(s, 1H), 7.76(d, 1H, J=7.5 Hz), 7.39(s, 1H), 7.33(t, 1H, J=7.6 Hz), 7.11(t, 1H, J=7.6 Hz), 4.05(s, 3H), 3.39(t, 2H, J=7.0 Hz), 3.03(s, 2H), 2.70(t, 2H, J=7.0 Hz), 1.70-1.80(m, 2H), 1.68(s, 3H), 0.90(s, 9H).

Example 391

Synthesis of (Z)-3-[4-(4-{3-[3-(2,2-dimethylpropyloxy)propyl]phenyl}-5-methyloxythiazol-2-ylcarbamoyl)-2,6-difluorophenyl]-2-methyloxyacrylic acid (B1900)

1H-NMR(DMSO-d6) 13.02(bs, 1H), 7.88(s, 1H), 7.85(s, 1H), 7.80(s, 1H), 7.76(d, 1H, J=7.5 Hz), 7.33(t, 1H, J=7.6 Hz), 7.11(t, 1H, J=7.6 Hz), 6.63(s, 1H), 4.05(s, 3H), 3.71(s, 3H), 3.39(t, 2H, J=7.0 Hz), 3.03(s, 2H), 2.70(t, 2H, J=7.0 Hz), 1.70-1.80(m, 2H), 0.90(s, 9H).

Example 392

Synthesis of (Z)-3-[2,6-dichloro-4-(4-{3-[3-(2,2-dimethylpropyloxy)propyl]phenyl}-5-methyloxythiazol-2-ylcarbamoyl)phenyl]-2-methyloxyacrylic acid (B1901)

1H-NMR(DMSO-d6) 13.02(bs, 1H), 8.20(s, 2H), 7.77(s, 1H), 7.76(d, 1H, J=7.5 Hz), 7.33(t, 1H, J=7.6 Hz), 7.11(t, 1H, J=7.6 Hz), 6.63(s, 1H), 4.05(s, 3H), 3.61(s, 3H), 3.39(t, 2H, J=7.0 Hz), 3.03(s, 2H), 2.70(t, 2H, J=7.0 Hz), 1.70-1.80(m, 2H,), 0.90(s, 9H).

Example 393

Synthesis of (E)-3-[4-(4-{3-[3-(2,2-dimethylpropyloxy)propyl]-2-fluorophenyl}-5-methyloxythiazol-2-ylcarbamoyl)-2,6-difluorophenyl]-2-methylacrylic acid (B1902)

1H-NMR(DMSO-d6) 13.02(bs, 1H), 7.93(s, 1H), 7.90(s, 1H), 7.38(t, 1H, J=7.5 Hz), 7.35(s, 1H), 7.32(t, 1H, J=7.6 Hz), 7.11(t, 1H, J=7.6 Hz), 3.95(s, 3H), 3.37(t, 2H, J=7.0 Hz), 3.03(s, 2H), 2.70(t, 2H, J=7.0 Hz), 1.76-1.85(m, 2H), 1.80(s, 3H), 0.9(s, 9H).

Example 394

Synthesis of (E)-3-[2,6-dichloro-4-(4-{3-[3-(2,2-dimethylpropyloxy)propyl]-2-fluorophenyl}-5-methyloxythiazol-2-ylcarbamoyl)phenyl]-2-methylacrylic acid (B1903)

1H-NMR(DMSO-d6) 12.82(bs, 1H), 8.28(s, 2H), 7.40(t, 1H, J=7.6 Hz), 7.39(s, 1H), 7.25(t, 1H, J=7.6 Hz), 7.16(t, 1H, J=7.6 Hz), 3.94(s, 3H), 3.39(t, 2H, J=7.0 Hz), 3.03(s, 2H), 2.70(t, 2H, J=7.0 Hz), 1.70-1.80(m, 2H), 1.67(s, 3H), 0.90(s, 9H).

Example 395

Synthesis of (Z)-3-[4-(4-{3-[3-(2,2-dimethylpropyloxy)propyl]-2-fluorophenyl}-5-methyloxythiazol-2-ylcarbamoyl)-2,6-difluorophenyl]-2-methyloxyacrylic acid (B1904)

1H-NMR(DMSO-d6) 13.02(bs, 1H), 7.90(s, 1H), 7.88(s, 1H), 7.38(t, 1H, J=7.5 Hz), 7.29(t, 1H, J=7.5 Hz), 7.18(t, 1H, J=7.5 Hz), 6.65(s, 1H), 3.95(s, 3H), 3.71(s, 3H), 3.39(t, 2H, J=7.0 Hz), 3.03(s, 2H), 2.70(t, 2H, J=7.0 Hz), 1.70-1.80(m, 2H), 0.90(s, 9H).

Example 396

Synthesis of (Z)-3-[2,6-difluoro-4-(4-{3[3-(2,2-dimethylpropyloxy)propyl]-2-fluorophenyl}-5-methyloxythiazol-2-ylcarbamoyl)phenyl]-2-methyloxyacrylic acid (B1905)

1H-NMR(DMSO-d6) 12.82(bs, 1H), 8.20(s, 2H), 7.40(t, 1H, J=7.6 Hz), 7.29(t, 1H, J=7.6 Hz), 7.16(t, 1H, J=7.6 Hz), 6.65(s, 1H), 3.95(s, 3H), 3.61(s, 3H), 3.39(t, 2H, J=7.0 Hz), 3.03(s, 2H), 2.70(t, 2H, J=7.0 Hz), 1.70-1.80(m, 2H), 0.90(s, 9H).

Example 397

Synthesis of (E)-3-(2,6-difluoro-4-{[4-[2-fluoro-3-(1-methyloxy-2,2-dimethylpropyl)phenyl]-5-methyloxythiazol-2-ylcarbamoyl}phenyl)-2-methylacrylic acid (B1906)

1H-NMR(DMSO-d6) 13.02(bs, 1H), 7.93(s, 1H), 7.90(s, 1H), 7.50(t, 1H, J=7.5 Hz), 7.28-7.38(m, 3H), 4.27(s, 1H), 3.95(s, 3H), 3.17(s, 3H), 1.79(s, 3H), 0.90(s, 9H).

Example 398

Synthesis of (E)-3-(2,6-dichloro-4-{4-[2-fluoro-3-(1-methyloxy-2,2-dimethylpropyl)phenyl]-5-methyloxythiazol-2-ylcarbamoyl}phenyl)-2-methylacrylic acid (B1907)

1H-NMR(DMSO-d6) 12.82(bs, 1H), 8.28(s, 2H), 746-7.52(m, 1H), 7.38(s, 1H), 7.34-7.38(m, 2H), 4.27(s, 1H), 3.95(s, 3H), 3.17(s, 3H), 1.69(s, 3H), 0.90(s, 9H).

Example 399

Synthesis of (Z)-3-(2,6-difluoro-4-{4-[2-fluoro-3-(1-methyloxy-2,2-dimethylpropyl)phenyl]-5-methyloxythiazol-2-ylcarbamoyl}phenyl)-2-methyloxyacrylic acid (B1908)

1H-NMR(DMSO-d6) 13.02(bs, 1H), 7.90(s, 1H), 7.88(s, 1H), 7.50(m, 1H), 7.28-7.38(m, 2H), 6.65(s, 1H), 4.27(s, 1H), 3.95(s, 3H), 3.70(s, 3H), 3.17(s, 3H), 0.90(s, 9H).

Example 400

Synthesis of (Z)-3-(2,6-dichloro-4-{4-[2-fluoro-3-(1-methyloxy-2,2-dimethylpropyl)phenyl]-5-methyloxythiazol-2-ylcarbamoyl}phenyl)-2-methyloxyacrylic acid (B1909)

1H-NMR(DMSO-d6) 12.82(bs, 1H), 8.28(s, 2H), 746-7.52(m, 1H), 7.34-7.38(m, 2H), 6.65(s, 1H), 4.27(s, 1H), 3.95(s, 3H), 3.70(s, 3H), 3.17(s, 3H), 1.69(s, 3H), 0.90(s, 9H).

Example 401

Synthesis of (Z)-3-(2,6-dichloro-4-{4-[3-(3-ethyloxy-1-methyloxypropyl)-2-fluorophenyl]thiazol-2-ylcarbamoyl}phenyl)-2-methyloxyacrylic acid (B1910)

1H-NMR(DMSO-d6) 13.02(bs, 1H), 8.25(s, 2H), 8.03(t, 1H, J=7.2 Hz), 7.66(d, 1H, J=2.4 Hz), 7.32-7.40(m, 2H), 6.72(s, 1H), 4.68-4.72(m, 1H), 3.61(s, 3H), 3.45-3.54(m, 1H), 3.18(s, 3H), 1.85-2.01(m, 2H), 1.09(t, 3H, J=6.9 Hz).

Example 402

Synthesis of (Z)-3-{2,6-difluoro-4-[4-(2-fluoro-3-heptyloxymethylphenyl)thiazol-2-ylcarbamoyl]phenyl}-2-methyloxyacrylic acid (B1911)

1H-NMR(DMSO-d6) 13.00(bs, 1H), 8.05(t, 1H, J=7.5 Hz), 7.88-7.98(m, 2H), 7.65(d, 1H, J=2.4 Hz), 7.42(t, 1H, J=6.9 Hz), 7.32(t, 1H, J=7.5 Hz), 6.66(s, 1H), 4.58(s, 2H), 3.72(s, 3H), 3.48(t, 2H, J=6.6 Hz), 1.51-1.60(m, 2H), 1.20-1.40(m, 8H), 0.85(t, 3H, J=6.6 Hz).

Example 403

Synthesis of (Z)-3-{2,6-dichloro-4-[4-(2-fluoro-3-heptyloxymethylphenyl)thiazol-2-ylcarbamoyl]phenyl-2-methyloxyacrylic acid (B1912)

1H-NMR(DMSO-d6) 13.01(bs, 1H), 8.25(s, 2H), 8.04(dt, 1H, J=1.8, 7.2 Hz), 7.65(d, 1H, J=2.4 Hz), 7.42(t, 1H, J=6.6 Hz), 7.31(t, 1H, J=7.5 Hz), 6.73(s, 1H), 4.58(s, 2H), 3.61(s, 3H), 3.48(t, 2H, J=6.6 Hz), 1.50-1.58(m, 2H), 1.20-1.40(m, 8H), 0.85(t, 3H, J=6.9 Hz).

Example 404

Synthesis of (Z)-3-{4-[4-(3-ethyloxymethyl-2-fluorophenyl)thiazol-2-ylcarbamoyl]-2,6-difluorophenyl}-2-methyloxyacrylic acid (B1913)

1H-NMR(DMSO-d6) 13.01(bs, 1H), 8.05(t, 1H, J=7.5 Hz), 7.88-7.96(m, 2H), 7.67(d, 1H, J=2.4 Hz), 7.44(t, 1H, J=6.9 Hz), 7.32(t, 1H, J=7.5 Hz), 6.66(s, 1H), 4.59(s, 2H), 3.72(s, 3H), 3.52-3.59(m, 2H), 1.18(t, 3H, J=6.9 Hz).

Example 405

Synthesis of (Z)-3-{2,6-dichloro-4-[4-(3-ethyloxymethyl-2-fluorophenyl)thiazol-2-ylcarbamoyl]phenyl}-2-methyloxyacrylic acid (B1914)

1H-NMR(DMSO-d6) 13.02(bs, 1H), 8.25(s, 2H), 8.04(dt, 1H, J=2.1, 6.9 Hz), 7.66(d, 1H, J=2.7 Hz), 7.43(t, 1H, J=6.3 Hz), 7.31(t, 1H, J=7.8 Hz), 6.73(s, 1H), 4.59(s, 2H), 3.61(s, 3H), 3.52-3.59(m, 2H), 1.18(t, 3H, J=6.9 Hz).

Example 406

Synthesis of (E)-3-[2,6-difluoro-4-(4-{2-fluoro-3-[1-methyloxy-3-(4-methylpentyloxy)propyl]phenyl}thiazol-2-ylcarbamoyl)phenyl]-2-methylacrylic acid (B1915)

1H-NMR(DMSO-d6) 13.01(bs, 2H), 8.07-7.30(m, 3H), 7.66(d, 1H, J=2.7 Hz), 7.32-7.42(m, 3H), 4.69-4.73(m, 1H), 3.45-3.58(m, 1H), 3.18(s, 3H), 1.84-2.40(m, 2H), 1.81(s, 3H), 1.42-1.54(m, 3H), 1.12-1.20(m, 2H), 0.84(d, 6H, J=6.6 Hz).

Example 407

Synthesis of (E)-3-(4-{4-[3-(2-cyclohexylethyloxy)-2-methylphenyl]thiazol-2-ylcarbamoyl}-2,6-difluorophenyl)-2-methylacrylic acid (B1916)

1H-NMR(DMSO-d6) 12.97 (bs, 2H), 7.90-7.93 (m, 2H), 7.74 (s, 1H), 7.63-7.66 (m, 1H), 7.04-7.16 (m, 2H), 6.69 (s, 1H), 4.07 (t, 2H, J=6.7 Hz), 3.79 (s, 3H), 3.71(s, 3H), 0.94-1.80 (m, 16H).

Example 408

Synthesis of (Z)-3-(4-{4-[3-(2-cyclohexylethyloxy)-2-methylphenyl]thiazol-2-ylcarbamoyl}-2,6-difluorophenyl)-2-methyloxy acrylic acid (B1917)

1H-NMR(DMSO-d6) 12.97 (bs, 2H), 7.90-7.93 (m, 2H), 7.74 (s, 1H), 7.31 (s, 1H), 7.63-7.66 (m, 1H), 7.04-7.16 (m, 2H), 4.07 (t, 2H, J=6.7 Hz), 3.79 (s, 3H), 0.94-1.80 (m, 13H).

Example 409

Synthesis of (E)-3-(2,6-dichloro-4-{4-[3-(2-cyclohexylethyloxy)-2-methylphenyl]thiazol-2-ylcarbamoyl}phenyl)-2-methylacrylic acid (B1918)

1H-NMR(DMSO-d6) 12.97 (bs, 2H), 8.29 (s, 2H), 7.75 (s, 1H), 7.63-7.66 (m, 1H), 7.41 (s, 1H), 7.04-7.16 (m, 2H), 4.07 (t, 2H, J=6.4 Hz), 3.79 (s, 3H), 3.61(s, 3H), 0.94-1.80 (m, 16H).

Example 410

Synthesis of (Z)-3-(2,6-dichloro-4-{4-[3-(2-cyclohexylethyloxy)-2-methylphenyl]thiazol-2-ylcarbamoyl}phenyl)-2-methyloxyacrylic acid (B1919)

1H-NMR(DMSO-d6) 12.97 (bs, 2H), 8.25 (s, 2H), 7.74 (s, 1H), 7.63-7.66 (m, 1H), 7.04-7.16 (m, 2H), 6.74 (s, 1H), 4.07 (t, 2H, J=6.4 Hz), 3.79 (s, 3H), 3.61(s, 3H), 0.94-1.80 (m, 13H).

Example 411

Synthesis of (E)-3-[2,6-difluoro-4-(4-{2-methyloxy-3-[2-(4-methylpentyloxy)ethyl]phenyl}thiazol-2-ylcarbamoyl)phenyl)-2-methylacrylic acid (B1920)

1H-NMR(DMSO-d6) 12.97 (bs, 2H), 7.94-7.97 (m, 2H), 7.85-7.88 (m, 1H), 7.72 (s, 1H), 7.34 (s, 1H), 7.26-7.29 (m, 1H), 7.13-7.18 (m, 1H), 3.59-3.65 (m, 5H), 3.37-3.41 (m, 2H), 2.91 (t, 2H, J=7.0 Hz), 1.81 (s, 3H), 1.44-1.53 (m, 3H), 1.12-1.20 (m, 2H), 0.84 (d, 6H, J=6.7 Hz).

Example 412

Synthesis of (Z)-3-[2,6-difluoro-4-(4-{2-methyloxy-3-[2-(4-methylpentyloxy)ethyl]phenyl}thiazol-2-ylcarbamoyl)phenyl)-2-methyloxyacrylic acid (B1921)

1H-NMR(DMSO-d6) 13.57 (bs, 1H), 12.97 (bs, 1H), 7.85-7.92 (m, 3H), 7.72 (s, 1H), 7.26-7.29 (m, 1H), 7.13-7.18 (m, 1H), 6.66 (s, 1H), 3.71 (s, 3H), 3.59-3.65 (m, 2H), 3.37-3.41 (m, 2H), 2.91 (t, 2H, J=7.0 Hz), 1.44-1.53 (m, 3H), 1.12-1.20 (m, 2H), 0.84 (d, 6H, J=6.7 Hz).

Example 413

Synthesis of (E)-3-[2,6-dichloro-4-(4-{2-methyloxy-3-[2-(4-methylpentyloxy)ethyl]phenyl}thiazol-2-ylcarbamoyl)phenyl)-2-methylacrylic acid (B1922)

1H-NMR(DMSO-d6) 12.97 (bs, 2H), 8.29 (s, 2H), 7.86-7.88 (m, 1H), 7.72 (s, 1H), 7.40 (s, 1H), 7.27-7.29 (m, 1H), 7.13-7.18 (m, 1H), 3.60-3.64 (m, 5H), 3.36-3.41 (m, 2H), 2.91 (t, 2H, J=7.0 Hz), 1.69 (s, 3H), 1.44-1.53 (m, 3H), 1.12-1.20 (m, 2H), 0.84 (d, 6H, J=6.7 Hz).

Example 414

Synthesis of (Z)-3-[2,6-dichloro-4-(4-{2-methyloxy-3-[2-(4-methylpentyloxy)ethyl]phenyl}thiazol-2-ylcarbamoyl)phenyl)-2-methyloxyacrylic acid (B1923)

1H-NMR(DMSO-d6) 13.57 (bs, 1H), 12.97 (bs, 1H), 8.25 (s, 2H), 7.85-7.88 (m, 1H), 7.72 (s, 1H), 7.26-7.29 (m, 1H), 7.13-7.18 (m, 1H), 6.74 (s, 1H), 3.59-3.65 (m, 8H), 3.37-3.41 (m, 2H), 2.91 (t, 2H, J=7.0 Hz), 1.46-1.51 (m, 3H), 1.12-1.19 (m, 2H), 0.83 (d, 6H, J=6.6 Hz).

Example 415

Synthesis of (E)-3-(2,6-difluoro-4-{4-[2-methyloxy-3-(2-pentyloxyethyl)phenyl]thiazol-2-ylcarbamoyl)phenyl)-2-methylacrylic acid (B1924)

1H-NMR(DMSO-d6) 12.96 (bs, 2H), 7.95-7.98 (m, 2H), 7.85-7.88 (m, 1H), 7.72 (s1H), 7.34 (s, 1H), 7.27-7.29 (m, 1H), 7.14-7.19 (m, 1H), 3.59-3.65 (m, 5H), 3.36-3.41 (m, 2H), 2.91 (t, 2H, J=7.4 Hz), 1.81 (s, 3H), 1.44-1.49 (m, 2H), 1.24-1.27 (m, 4H), 0.82-0.87 (m, 3H).

Example 416

Synthesis of (E)-3-(2,6-dichloro-4-{4-[2-methyloxy-3-(2-pentyloxyethyl)phenyl]thiazol-2-ylcarbamoyl)phenyl)-2-methylacrylic acid (B1925)

1H-NMR(DMSO-d6) 12.95 (bs, 2H), 8.29 (s, 2H), 7.85-7.88 (m, 1H), 7.72 (s1H), 7.41 (s, 1H), 7.27-7.29 (m, 1H), 7.13-7.19 (m, 1H), 3.59-3.65 (m, 5H), 3.36-3.41 (m, 2H), 2.91 (t, 2H, J=7.4 Hz), 1.69 (s, 3H), 1.44-1.49 (m, 2H), 1.24-1.27 (m, 4H), 0.82-0.87 (m, 3H).

Example 417

Synthesis of (E)-3-(2,6-difluoro-4-{4-[3-(2-hexyloxyethyl)-2-methyloxyphenyl]thiazol-2-ylcarbamoyl)phenyl)-2-methylacrylic acid (B1926)

1H-NMR(DMSO-d6) 12.98 (bs, 2H), 7.95-7.98 (m, 2H), 7.85-7.89 (m, 1H), 7.72 (s, 1H), 7.40 (s, 1H), 7.26-7.29 (m, 1H), 7.13-7.19 (m, 1H), 3.59-3.64 (m, 5H), 3.37-3.41 (m, 2H), 2.91 (t, 2H, J=7.0 Hz), 1.81 (s, 3H), 1.44-1.49 (m, 2H), 1.24-1.27 (m, 6H), 0.82-0.87 (m, 3H).

Example 418

Synthesis of (Z)-3-(2,6-difluoro-4-{4-[3-(2-hexyloxyethyl)-2-methyloxyphenyl]thiazol-2-ylcarbamoyl)phenyl)-2-methyloxyacrylic acid (B1927)

1H-NMR(DMSO-d6) 13.55 (bs, 1H), 12.98 (bs, 1H), 7.85-7.92 (m, 3H), 7.72 (s, 1H), 7.26-7.29 (m, 1H), 7.13-7.19 (m, 1H), 6.66 (s, 1H), 3.71 (s, 3H), 3.59-3.64 (m, 5H), 3.37-3.41 (m, 2H), 2.91 (t, 2H, J=7.0 Hz), 1.44-1.49 (m, 2H), 1.24-1.27 (m, 6H), 0.82-0.87 (m, 3H).

Example 419

Synthesis of (E)-3-(2,6-dichloro-4-{4-[3-(2-hexyloxyethyl)-2-methyloxyphenyl]thiazol-2-ylcarbamoyl)phenyl)-2-methylacrylic acid (B1928)

1H-NMR(DMSO-d6) 12.98 (bs, 2H), 8.29 (s, 2H), 7.85-7.88 (m, 1H), 7.72 (s, 1H), 7.41 (s, 1H), 7.26-7.29 (m, 1H), 7.13-7.19 (m, 1H), 3.59-3.65 (m, 5H), 3.37-3.41 (m, 2H), 2.91 (t, 2H, J=7.0 Hz), 1.69 (s, 3H), 1.44-1.49 (m, 2H), 1.24-1.27 (m, 6H), 0.82-0.87 (m, 3H).

Example 420

Synthesis of (Z)-3-(2,6-dichloro-4-{4-[3-(2-hexyloxyethyl)-2-methyloxyphenyl]thiazol-2-ylcarbamoyl)phenyl)-2-methyloxyacrylic acid (B1929)

1H-NMR(DMSO-d6) 13.57 (bs, 1H), 12.97 (bs, 1H), 8.24 (s, 2H), 7.85-7.88 (m, 1H), 7.72 (s, 1H), 7.26-7.29 (m, 1H), 7.13-7.18 (m, 1H), 6.73 (s, 1H), 3.59-3.65 (m, 8H), 3.37-3.41 (m, 2H), 2.91 (t, 2H, J=7.4 Hz), 1.44-1.49 (m, 2H), 1.24-1.27 (m, 6H), 0.82-0.87 (m, 3H).

Example 421

Synthesis of (Z)-3-[2,6-difluoro-4-(4-{2-fluoro-3-[1-methyloxy-3-(4-methylpentyloxy)propyl]phenyl}thiazol-2-ylcarbamoyl)phenyl)-2-methyloxyacrylic acid (B1930)

1H-NMR(DMSO-d6) 12.98(bs, 1H), 8.03(dt, 1H, J=3.3, 6.6 Hz), 7.87-7.96(m, 2H), 7.65(d, 1H, J=2.1 Hz), 7.31-7.41 (m, 2H), 6.64(s, 1H), 4.68-4.73(m, 1H), 3.17(s, 3H), 3.45-3.58(m, 1H), 3.18(s, 3H), 1.86-1.93(m, 2H), 1.41-1.57(m, 3H), 1.12-1.22(m, 2H), 0.84(d, 6H, J=6.6 Hz).

Example 422

Synthesis of (E)-3-[2,6-dichloro-4-(4-{2-fluoro-3-[1-methyloxy-3-(4-methylpentyloxy)propyl]phenyl}thiazol-2-ylcarbamoyl)phenyl)-2-methylacrylic acid (B1931)

1H-NMR(DMSO-d6) 13.02(bs, 2H), 8.29(s, 2H), 8.03(dt, 1H, J=2.1, 7.5 Hz), 7.65(d, 1H, J=2.7 Hz), 7.31-7.44(m, 3H), 4.68-4.73(m, 1H), 3.18(s, 3H), 1.86-2.05(m, 2H), 1.69(s, 3H), 1.41-1.56(m, 3H), 1.12-1.29(m, 2H), 0.84(d, 6H, J=6.6 Hz).

Example 423

Synthesis of (Z)-3-[2,6-dicloro-4-(4-{2-fluoro-3-[1-methyloxy-3-(4-methylpentyloxy)propyl]phenyl}thiazol-2-ylcarbamoyl)phenyl)-2-methyloxyacrylic acid (B1932)

1H-NMR(DMSO-d6) 13.02(bs, 1H), 8.25(s, 2H), 8.03(dt, 1H, J=3.3, 6.6 Hz), 7.65(d, 1H, J=2.4 Hz), 7.31-7.40(m, 2H), 6.71(s, 1H), 4.68-4.73(m, 1H), 3.61(s, 3H), 3.45-3.54(m, 1H), 3.18(s, 3H), 1.85-2.01(m, 2H), 1.41-1.55(m, 3H), 1.12-1.20(m, 2H), 0.84(d, 6H, J=6.3 Hz).

Example 424

Synthesis of (E)-3-(4-{4-[3-(2,2-dimethylpropyloxymethyl)-2-methyloxyphenyl]thiazol-2-ylcarbamoyl}-2,6-difluorophenyl)-2-methylacrylic acid (B1933)

1H NMR(DMSO-d6) 12.93(bs, 2H), 7.93-7.97(m, 3H), 7.72(s, 1H), 7.38(dd, 1H, J=1.5 Hz, 7.5 Hz), 7.32(s, 1H), 7.23(t, 1H, J=7.5 Hz), 4.58(s, 2H), 3.64(s, 3H), 3.18(s, 2H), 1.79(d, 3H, J=1.2 Hz), 0.91(s, 9H).

Example 425

Synthesis of (E)-3-(4-{4-[3-(3,3-dimethylbutyloxymethyl)-2-methyloxyphenyl]thiazol-2-ylcarbamoyl}-2,6-difluorophenyl)-2-methylacrylic acid (B1934)

1H NMR(DMSO-d6) 12.98(bs, 2H), 7.96(d, 3H, J=7.8 Hz), 7.74(s, 1H), 7.34-7.39(m, 2H), 7.24(t, 1H, J=7.8 Hz), 4.56(s, 2H), 3.66(s, 3H), 3.57(t, 2H, J=7.2 Hz), 1.81(s, 3H), 1.53(t, 2H, J=7.2 Hz), 0.92(s, 9H).

Example 426

Synthesis of (Z)-3-(4-{4-[3-(3,3-dimethylbutyloxymethyl)-2-methyloxyphenyl]thiazol-2-ylcarbamoyl}-2,6-difluorophenyl)-2-methyloxyacrylic acid (B1935)

1H NMR(DMSO-d6) 12.93(bs, 2H), 7.88-7.98(m, 3H), 7.73(s, 1H), 7.37(dd, 1H, J=1.8 Hz, 7.5 Hz), 7.23(t, 1H, J=7.5 Hz), 6.65(s, 1H), 4.56(s, 2H), 3.71(s, 3H), 3.65(s, 3H), 3.57(t, 2H, J=7.2 Hz), 1.53(t, 2H, J=7.2 Hz), 0.92(s, 9H).

Example 427

Synthesis of (Z)-3-(2,6-dichloro-4-{4-[3-(3,3-dimethylbutyloxymethyl)-2-methyloxyphenyl]thiazol-2-ylcarbamoyl}phenyl)-2-methylacrylic acid (B1936)

1H NMR(DMSO-d6) 12.99(bs, 2H), 8.29(s, 2H), 7.97(d, 1H, 7.2 Hz), 7.73(s, 1H), 7.37-7.40(m, 2H), 7.23(t, 1H, J=7.2 Hz), 4.56(s, 2H), 3.65(s, 3H), 3.57(t, 2H, J=7.2 Hz), 1.69(s, 3H), 1.52(t, 2H, J=7.5 Hz), 0.92(s, 9H).

Example 428

Synthesis of (Z)-3-(2,6-dichloro-4-{4-[3-(3,3-dimethylbutyloxymethyl)-2-methyloxyphenyl]thiazol-2-ylcarbamoyl}phenyl)-2-methyloxyacrylic acid (B1937)

1H NMR(DMSO-d6) 12.97(bs, 2H), 8.25(s, 2H), 7.97(d, 1H, J=7.8 Hz), 7.74(s, 1H), 7.38(d, 1H, J=7.2 Hz), 7.24(t, 1H, J=7.5 Hz), 6.72(s, 1H), 4.57(s, 2H), 3.66(s, 3H), 3.63(s, 3H), 3.58(t, 2H, J=7.2 Hz), 1.53(t, 2H, J=7.5 Hz), 0.92(s, 9H).

Example 429

Synthesis of (E)-3-(2,6-difluoro-4-{4-[2-methyloxy-3-(4-pentyloxymethyl)phenyl]thiazol-2-ylcarbamoyl}phenyl)-2-methylacrylic acid (B1938)

1H NMR(DMSO-d6) 12.99(bs, 2H), 7.95-7.99(m, 3H), 7.74(s, 1H), 7.34-7.39(m, 2H), 7.24(t, 1H, J=7.8 Hz), 4.56(s, 2H), 3.65(s, 3H), 3.49(t, 2H, J=6.9 Hz), 1.81(s, 3H), 1.49-1.62(m, 3H), 1.19-1.26(m, 2H), 0.87(d, 6H, J=6.6 Hz).

Example 430

Synthesis of (Z)-3-(2,6-difluoro-4-{4-[2-methyloxy-3-(4-pentyloxymethyl)phenyl]thiazol-2-ylcarbamoyl}phenyl)-2-methyloxyacrylic acid (B1939)

1H NMR(DMSO-d6) 12.94(bs, 2H), 7.90-7.99(m, 3H), 7.74(s, 1H), 7.37-7.39(m, 1H), 7.24(t, 1H, J=7.8 Hz), 6.66(s, 1H), 4.56(s, 2H), 3.72(s, 3H), 3.65(s, 3H), 3.49(t, 2H, J=6.6 Hz), 1.49-1.62(m, 3H), 1.19-1.26(m, 2H), 0.87(d, 6H, J=6.6 Hz).

Example 431

Synthesis of (E)-3-(2,6-dichloro-4-{4-[2-methyloxy-3-(4-pentyloxymethyl)phenyl]thiazol-2-ylcarbamoyl}phenyl)-2-methylacrylic acid (B1940)

1H NMR(DMSO-d6) 12.98(bs, 2H), 8.29(s, 2H), 7.98(d, 1H, J=7.8 Hz), 7.74(s, 1H), 7.37-7.40(m, 2H), 7.24(t, 1H, J=7.5 Hz), 4.56(s, 2H), 3.66(s, 3H), 3.49(t, 2H, J=6.6 Hz), 1.69(s, 3H), 1.49-1.62(m, 3H), 1.19-1.26(m, 2H), 0.87(d, 6H, J=6.6 Hz).

Example 432

Synthesis of (Z)-3-(2,6-dichloro-4-{4-[2-methyloxy-3-(4-pentyloxymethyl)phenyl]thiazol-2-ylcarbamoyl}phenyl)-2-methyloxyacrylic acid (B1941)

1H NMR(DMSO-d6) 12.97(bs, 2H), 8.25(s, 2H), 7.97(dd, 1H, J=1.5 Hz, 7.8 Hz), 7.74(s, 1H), 7.37-7.39(m, 1H), 7.24(t, 1H, J=7.8 Hz), 6.73(s, 1H), 4.56(s, 2H), 3.65(s, 3H), 3.63(s, 3H), 3.49(t, 2H, J=6.6 Hz), 1.49-1.62(m, 3H), 1.15-1.26(m, 2H), 0.87(d, 6H, J=6.6 Hz).

Example 433

Synthesis of (E)-3-(2,6-dichloro-4-{4-[3-(3-ethyloxypropyl)-2-methyloxyphenyl]thiazol-2-ylcarbamoyl}phenyl)-2-methylacrylic acid (B1942)

1H-NMR(CDCl3-d6) 8.32(s, 2H), 7.65(d, 1H, J=1.2 Hz), 7.49(dd, 1H, J=7.8, 1.8 Hz), 7.45(s, 1H), 7.24-7.28(m, 1H), 7.16(t, 1H, J=7.8 Hz), 3.57(s, 3H), 3.46-3.53(m, 4H), 2.75-2.82(m, 2H), 1.91-2.05(m, 2H), 1.86(d, 3H, J=1.5 Hz), 1.22(t, 3H, J=6.9 Hz).

Example 434

Synthesis of (Z)-3-(2,6-dichloro-4-{4-[3-(3-ethyloxypropyl)-2-methyloxyphenyl]thiazol-2-ylcarbamoyl}phenyl)-2-methyloxyacrylic acid (B1943)

1H-NMR(DMSO-d6) 13.0(bs, 2H), 8.24(s, 2H), 7.85(dd, 1H, J=7.8, 2.1 Hz), 7.72(s, 1H), 7.13-7.24(m, 2H), 6.73(s, 1H), 3.61(s, 6H), 3.39-3.47(m, 4H), 2.68-2.75(m, 2H), 1.78-1.90(m, 2H), 1.13(t, 3H, J=6.9 Hz).

Example 435

Synthesis of (E)-3-(4-{4-[3-(3-cyclopropylmethyloxypropyl)-2-methyloxyphenyl]thiazol-2-ylcarbamoyl}-2,6-difluorophenyl)-2-methylacrylic acid (B1944)

1H-NMR(DMSO-d6) 13.0(bs, 2H), 7.98(s, 1H), 7.95(s, 1H), 7.86(d, 1H, J=7.8 Hz), 7.73(s, 1H), 7.34(bs, 1H), 7.13-7.26(m, 2H), 3.61(s, 3H), 3.44(t, 2H, J=6.0 Hz), 3.23(d, 1H, J=6.9 Hz), 2.72(t, 2H, J=8.4 Hz), 1.80-1.90(m, 5H), 0.94-1.10(m, 1H), 0.42-0.53(m, 2H), 0.16-0.21(m, 2H).

Example 436

Synthesis of (E)-3-(2,6-dichloro-4-{4-[3-(3-cyclopropylmethyloxypropyl)-2-methyloxyphenyl]thiazol-2-ylcarbamoyl}phenyl)-2-methylacrylic acid (B1945)

1H-NMR(DMSO-d6) 13.0(bs, 2H), 8.29(s, 2H), 7.86(d, 1H, J=7.8 Hz), 7.72(bs, 1H), 7.41(s, 1H), 7.13-7.26(m, 2H), 3.62(s, 3H), 3.44(t, 2H, J=6.3 Hz), 3.23(d, 2H, J=6.9 Hz), 2.72(t, 2H, J=8.4 Hz), 1.80-1.93(m, 2H), 1.69(s, 3H), 0.96-1.08(m, 1H), 0.45-0.54(m, 2H), 0.16-0.25(m, 2H).

Example 437

Synthesis of (Z)-3-(4-{4-[3-(3-cyclopropylmethyloxypropyl)-2-methyloxyphenyl]thiazol-2-ylcarbamoyl}-2,6-difluorophenyl)-2-methyloxyacrylic acid (B1946)

1H-NMR(DMSO-d6) 13.6(bs, 1H), 13.0(bs, 1H), 7.83-7.96(m, 3H), 7.72(s, 1H), 7.13-7.26(m, 2H), 6.66(s, 1H), 3.71(s, 3H), 3.61(s, 3H), 3.44(t, 2H, J=6.3 Hz), 3.23(d, 2H, J=6.9 Hz), 2.72(t, 2H, J=8.7 Hz), 1.79-1.89(m, 2H), 0.97-1.06(m, 1H), 0.43-0.50(m, 2H), 0.14-0.21(m, 2H).

Example 438

Synthesis of (Z)-3-(2,6-dichloro-4-{4-[3-(3-cyclopropylmethyloxypropyl)-2-methyloxyphenyl]thiazol-2-ylcarbamoyl}phenyl)-2-methyloxyacrylic acid (B1947)

1H-NMR(DMSO-d6) 13.0(bs, 2H), 8.25(s, 2H), 8.36(d, 1H, J=8.4 Hz), 7.73(s, 1H), 7.13-7.26(m, 2H), 6.73(s, 1H), 3.61(s, 6H), 3.44(t, 2H, J=5.7 Hz), 3.23(d, 2H, J=6.6 Hz), 2.69-2.76(m, 2H), 1.78-1.88(m, 2H), 0.97-1.15(m, 1H), 0.44-0.51(m, 2H), 0.16-0.20(m, 2H).

Example 439

Synthesis of (E)-3-(4-{4-[3-(3-cyclopentylmethyloxypropyl)-2-methyloxyphenyl]thiazol-2-ylcarbamoyl}-2,6-difluorophenyl)-2-methylacrylic acid (B1948)

1H-NMR(DMSO-d6) 13.0(bs, 2H), 7.98(s, 1H), 7.95(s, 1H), 7.85(dd, 1H, J=7.5, 1.8 Hz), 7.73(s, 1H), 7.34(bs, 1H), 7.13-7.25(m, 2H), 3.61(s, 3H), 3.43(t, 2H, J=6 Hz), 3.25(d, 2H, J=6.9 Hz), 2.72(t, 2H, J=9.0 Hz), 2.06-2.16(m, 1H), 2.48-2.54(m, 5H), 1.46-1.76(m, 6H), 1.16-1.30(m, 2H).

Example 440

Synthesis of (E)-3-(2,6-dichloro-4-{4-[3-(3-cyclopentylmethyloxypropyl)-2-methyloxyphenyl]thiazol-2-ylcarbamoyl}phenyl)-2-methylacrylic acid (B1949)

1H-NMR(DMSO-d6) 13.0(bs, 2H), 8.29(s, 2H), 7.86(d, 1H, J=7.2 Hz), 7.72(s, 1H), 7.40(s, 1H), 7.13-7.25(m, 2H), 3.61(s, 3H), 3.43(t, 2H, J=6.3 Hz), 3.25(d, 2H, J=6.9 Hz), 2.69-2.78(m, 2H), 2.06-2.16(m, 1H), 1.80-1.90(m, 2H), 1.64-1.76(m, 5H), 1.46-1.60(m, 4H), 1.08-1.12(m, 2H).

Example 441

Synthesis of (Z)-3-(4-{4-[3-(3-cyclopentylmethyloxypropyl)-2-methyloxyphenyl]thiazol-2-ylcarbamoyl}-2,6-difluorophenyl)-2-methyloxyacrylic acid (B1950)

1H-NMR(DMSO-d6) 13.6(bs, 1H), 13.0(bs, 1H), 7.83-7.96(m, 3H), 7.72(s, 1H), 7.13-7.26(m, 2H), 6.66(s, 1H), 3.71(s, 3H), 3.61(s, 3H), 3.43(t, 2H, J=6.0 Hz), 3.25(d, 2H, J=6.9 Hz), 2.72(t, 2H, J=6.3 Hz), 2.06-2.16(m, 1H), 1.78-1.90(m, 2H), 1.62-1.75(m, 2H), 1.44-1.60(m, 4H), 1.18-1.21(m, 2H).

Example 442

Synthesis of (Z)-3-(2,6-dichloro-4-{4-[3-(3-cyclopentylmethyloxypropyl)-2-methyloxyphenyl]thiazol-2-ylcarbamoyl}phenyl)-2-methyloxyacrylic acid (B1951)

1H-NMR(DMSO-d6) 13.0(bs, 2H), 8.24(s, 2H), 7.86(d, 1H, J=7.5 Hz), 7.72(s, 1H), 7.13-7.25(m, 2H), 6.73(s, 1H), 3.43(t, 2H, J=6.3 Hz), 3.25(d, 2H, J=6.9 Hz), 2.72(t, 2H, J=8.4 Hz), 2.06-2.17(m, 1H), 1.80-1.90(m, 2H), 1.62-1.76(m, 2H), 1.46-1.60(m, 4H), 1.17-1.30(m, 2H).

Example 443

Synthesis of (E)-3-(2,6-difluoro-4-{4-[3-(2-heptyloxyethyl)-2-methyloxyphenyl]thiazol-2-ylcarbamoyl}phenyl)-2-methylacrylic acid (B1952)

1H-NMR(DMSO-d6) 12.96 (bs, 2H), 7.95-7.99 (m, 2H), 7.85-7.88 (m, 1H), 7.72 (s, 1H), 7.34 (s, 1H), 7.26-7.29 (m, 1H), 7.13-7.18 (m, 1H), 3.59-3.65 (m, 5H), 3.40 (t, 2H, J=6.6 Hz), 2.91 (t, 2H, J=6.9 Hz), 1.81 (d, 3H, J=1.5 Hz), 1.48 (t, 2H, J=6.6 Hz), 1.24 (bs, 8H), 0.82-0.88 (m, 3H).

Example 444

Synthesis of (Z)-3-(2,6-difluoro-4-{4-[3-(2-heptyloxyethyl)-2-methyloxyphenyl]thiazol-2-ylcarbamoyl}phenyl)-2-methyloxyacrylic acid (B1953)

1H-NMR(DMSO-d6) 12.92 (bs, 2H), 7.85-7.92 (m, 3H), 7.72 (s, 1H), 7.26-7.29 (m, 1H), 7.13-7.18 (m, 1H), 6.66 (s, 1H), 3.71 (s, 3H), 3.59-3.64 (m, 5H), 3.40 (t, 2H, J=6.6 Hz), 2.91 (t, 2H, J=6.9 Hz), 1.46-1.51 (m, 2H), 1.24 (bs, 8H), 0.82-0.87 (m, 3H).

Example 445

Synthesis of (E)-3-[2,6-difluoro-4-(4-{2-methyloxy-3-[2-(3-methylbutyloxyethyl)phenyl}thiazol-2-ylcarbamoyl)phenyl]-2-methylacrylic acid (B1954)

1H-NMR(DMSO-d6) 12.95 (bs, 2H), 7.95-7.97 (m, 2H), 7.85-7.88(m, 1H), 7.72 (s, 1H), 7.34(s, 1H), 7.26-7.29 (m, 1H), 7.13-7.19 (m, 1H), 3.59-3.65 (m, 5H), 3.43 (t, 2H, J=6.6 Hz), 2.91 (t, 2H, J=6.9 Hz), 1.81 (s, 3H), 1.58-1651 (m, 1H), 1.36-1.42 (m, 2H), 0.85 (d, 6H, J=6.6 Hz).

Example 446

Synthesis of (E)-3-[2,6-dichloro-4-(4-{2-methyloxy-3-[2-(3-methylbutyloxy)ethyl]pheny]}thiazol-2-ylcarbamoyl)phenyl]-2-methylacrylic acid (B1955)

1H-NMR(DMSO-d6) 12.98 (bs, 2H), 8.29 (s, 2H), 7.85-7.88 (m, 1H), 7.72 (s, 1H), 7.41 (s, 1H), 7.27-7.29 (m, 1H), 7.14-7.19 (m, 1H), 3.60-3.66 (m, 5H), 3.43 (t, 2H, J=6.6 Hz), 2.91 (t, 2H, J=7.0 Hz), 1.59-1.69 (m, 4H), 1.36-1.40 (m, 2H), 0.85 (d, 6H, J=6.6 Hz).

Example 447

Synthesis of (Z)-3-[2,6-difluoro-4-(4-{2-methyloxy-3-[2-(3-methylbutyloxy)ethyl]pheny]}thiazol-2-ylcarbamoyl)phenyl]-2-methyloxyacrylic acid (B1956)

1H-NMR(DMSO-d6) 12.92 (bs, 2H), 7.86-7.93 (m, 3H), 7.72 (s, 1H), 7.27-7.29 (m, 1H), 7.13-7.19(m, 1H), 6.67 (s, 1H), 3.71 (s, 3H), 3.62-3.64 (m, 5H), 3.43 (t, 2H, J=6.9 Hz), 2.91(t, 2H, J=6.6 Hz), 1.58-1.67 (m, 1H), 1.35-1.42 (m, 2H), 0.85 (d, 6H, J=6.4 Hz).

Example 448

Synthesis of (E)-3-(4-{4-[3-(2-cyclohexylmethyloxyethyl)-2-methyloxypheny]}thiazol-2-ylcarbamoyl)-2,6-difluorophenyl)-2-methylacrylic acid (B1957)

1H-NMR(DMSO-d6) 12.98 (bs, 2H), 7.95-7.98 (m, 2H), 7.85-7.89 (m, 1H), 7.73 (s, 1H), 7.34 (s, 1H), 7.26-7.29 (m, 1H), 7.14-7.19 (m, 1H), 3.59-3.65 (m, 5H), 3.23 (d, 2H, J=6.3 Hz), 2.91 (t, 2H, J=6.9 Hz), 1.81 (d, 3H, J=1.5 Hz), 1.63-1.68 (m, 6H), 1.08-1.21(m, 2H), 0.87-0.94 (m, 1H).

Example 449

Synthesis of (E)-3-[2,6-dichloro-4-(4-{3-[2-(2-ethylbutyloxy)ethyl]-2-methyloxyphenyl}thiazol-2-ylcarbamoyl)phenyl]-2-methylacrylic acid (B1958)

1H-NMR(DMSO-d6) 12.98 (bs, 2H), 8.29 (s, 2H), 7.85-7.89 (m, 1H), 7.72 (s, 1H), 7.41 (s, 1H), 7.27-7.30 (m, 1H), 7.14-7.19 (m, 1H), 3.60-3.66 (m, 5H), 3.30-3.32 (m, 2H), 2.91(t, 2H, J=6.9 Hz), 1.69 (s, 3H), 1.22-1.40 (m, 5H), 0.82 (t, 6H, J=7.5 Hz).

Example 450

Synthesis of (E)-3-[4-(4-{3-[2-(2-ethylbutyloxy)ethyl]-2-methyloxyphenyl}thiazol-2-ylcarbamoyl)-2,6-difluorophenyl]-2-methylacrylic acid (B1959)

1H-NMR(DMSO-d6) 12.97 (bs, 2H), 7.95-7.98 (m, 2H), 7.85-7.89 (m, 1H), 7.72 (s, 1H), 7.42 (s, 1H), 7.27-7.29 (m, 1H), 7.13-7.19 (m, 1H), 3.60-3.65 (m, 5H), 3.30-3.32 (m, 2H), 2.91(t, 2H, J=6.9 Hz), 1.81 (s, 3H), 1.22-1.40 (m, 5H), 0.82 (t, 6H, J=7.3 Hz).

Example 451

Synthesis of (Z)-3-[2,6-dicholoro-4-(4-{3-[2-(2-ethylbutyloxy)ethyl]-2-methyloxyphenyl}thiazol-2-ylcarbamoyl)phenyl]-2-methyloxyacrylic acid (B1960)

1H-NMR(DMSO-d6) 12.95 (bs, 2H), 8.24 (s, 1H), 7.85-7.88 (m, 1H), 7.72(s, 1H), 7.27-7.30 (m, 1H), 7.13-7.18(m, 1H), 6.73 (s, 1H), 3.60-3.64 (m, 8H), 3.30-3.33 (m, 2H), 2.91(t, 2H, J=6.7 Hz), 1.22-1.40 (m, 5H), 0.82 (t, 6H, J=7.3 Hz).

Example 452

Synthesis of (E)-3-[4-(4-{3-[2-(4-chlorobutyloxy)ethyl]-2-methyloxyphenyl}thiazol-2-ylcarbamoyl)-2,6-difluorophenyl]-2-methylacrylic acid (B1961)

1H-NMR(DMSO-d6) 13.01 (bs, 2H), 7.95-7.98 (m, 2H), 7.86-7.88 (m, 1H), 7.72(s, 1H), 7.26-7.41 (m, 2H), 7.14-7.19 (m, 1H), 3.61-3.65 (m, 7H), 3.44(t, 2H, J=6.3 Hz), 2.91 (t, 2H, J=6.9 Hz), 1.70-1.81 (m, 5H), 1.60-1.66 (m, 2H).

Example 453

Synthesis of (Z)-3-[4-(4-{3-[2-(4-chlorobutyloxy)ethyl]-2-methyloxyphenyl}thiazol-2-ylcarbamoyl)-2,6-difluorophenyl]-2-methyloxyacrylic acid (B 1962)

1H-NMR(DMSO-d6) 12.91 (bs, 2H), 7.85-7.92 (m, 3H), 7.72 (s, 1H), 7.26-7.29 (m, 1H), 7.13-7.19(m, 1H), 6.66 (s, 1H), 3.71 (s, 3H), 3.60-3.65 (m, 7H), 2.91(t, 2H, J=6.9 Hz), 1.72-1.77 (m, 2H), 1.59-1.63 (m, 2H).

Example 454

Synthesis of (E)-3-[2,6-dichloro-4-(4-{3-[2-(4-chlorobutyloxy)ethyl]-2-methyloxyphenyl}thiazol-2-ylcarbamoyl)phenyl]-2-methylacrylic acid (B 1963)

1H-NMR(DMSO-d6) 12.98 (bs, 2H), 8.29 (s, 2H), 7.86-7.88 (m, 1H), 7.72(s, 1H), 7.41 (s, 1H), 7.27-7.29 (m, 1H), 7.14-7.19 (m, 1H), 3.61-3.66 (m, 7H), 3.46 (t, 2H, J=6.1 Hz), 2.91 (t, 2H, J=6.7 Hz), 1.59-1.77 (m, 7H).

Example 455

Synthesis of (Z)-3-[2,6-dichloro-4-(4-{3-[2-(4-chlorobutyloxy)ethyl]-2-methyloxyphenyl}thiazol-2-ylcarbamoyl)phenyl]-2-methyloxyacrylic acid (B 1964)

1H-NMR(DMSO-d6) 12.95 (bs, 2H), 8.24 (s, 2H), 7.86-7.88 (m, 1H), 7.72 (s, 1H), 7.27-7.29 (m, 1H), 7.14-7.19 (m,

1H), 6.73 (s, 1H), 3.61-3.65 (m, 10H), 3.42-3.46 (m, 2H), 2.90-2.94 (m, 2H), 1.58-1.77 (m, 5H).

Example 456

Synthesis of (E)-3-(2,6-difluoro-4-{4-[2-fluoro-3-(3-isobutyloxy-1-methyloxypropyl)phenyl]thiazol-2-ylcarbamoyl}phenyl)-2-methylacrylic acid (B 1965)

1H-NMR(DMSO-d6) 13.02(bs, 1H), 8.06(t, 1H, J=7.5 Hz), 7.96(s, 1H), 7.93(s, 1H), 7.64(s, 1H), 7.30-7.40(m, 3H), 4.72(t, 1H, J=6.5 Hz), 3.50-3.58(m, 1H), 3.35-3.42(m, 1H), 3.17(s, 3H), 3.09-3.16(m, 2H), 1.85-1.95(m, 2H), 1.79(s, 3H), 1.74-1.79(m, 1H), 0.85(d, 6H, J=6.0 Hz).

Example 457

Synthesis of (E)-3-(2,6-dichloro-4-{4-[2-fluoro-3-(3-isobutyloxy-1-methyloxypropyl)phenyl]thiazol-2-ylcarbamoyl}phenyl)-2-methylacrylic acid (B 1966)

1H-NMR(DMSO-d6) 13.02(bs, 1H), 8.29(s, 2H), 8.06(t, 1H, J=7.5 Hz), 7.64(s, 1H), 7.30-7.40(m, 3H), 4.72(t, 1H, J=6.5 Hz), 3.50-3.58(m, 1H), 3.35-3.42(m, 1H), 3.17(s, 3H), 3.09-3.16(m, 2H), 1.85-1.95(m, 2H), 1.74-1.79(m, 1H), 1.68 (s, 3H), 0.85(d, 6H, J=6.0 Hz).

Example 458

Synthesis of (Z)-3-(2,6-difluoro-4-{4-[2-fluoro-3-(3-isobutyloxy-1-methyloxypropyl)phenyl]thiazol-2-ylcarbamoyl}phenyl)-2-methyloxy acrylic acid (B1967)

1H-NMR(DMSO-d6) 13.02(bs, 1H), 8.06(t, 1H, J=7.5 Hz), 7.96(s, 1H), 7.93(s, 1H), 7.64(s, 1H), 7.30-7.40(m, 2H), 6.65(s, 1H), 4.72(t, 1H, J=6.5 Hz), 3.71(s, 3H), 3.50-3.58(m, 1H), 3.35-3.42(m, 1H), 3.17(s, 3H), 3.09-3.16(m, 2H), 1.85-1.95(m, 2H), 1.74-1.79(m, 1H), 0.85(d, 6H, J=6.0 Hz).

Example 459

Synthesis of (Z)-3-(2,6-dichloro-4-{4-[2-fluoro-3-(3-isobutyloxy-1-methyloxypropyl)phenyl]thiazol-2-ylcarbamoyl}phenyl)-2-methyloxyacrylic acid (B 1968)

1H-NMR(DMSO-d6) 13.02(bs, 1H), 8.25(s, 2H), 8.06(t, 1H, J=7.5 Hz), 7.64(s, 1H), 7.30-7.40(m, 2H), 6.72(s, 1H), 4.72(t, 1H, J=6.5 Hz), 3.61(s, 3H), 3.50-3.58(m, 1H), 3.35-3.42(m, 1H), 3.17(s, 3H), 3.09-3.16(m, 2H), 1.85-1.95(m, 2H), 1.74-1.79(m, 1H), 0.85 (d, 6H, J=6.0 Hz).

Example 460

Synthesis of (E)-3-(4-{4-[3-(2-ethylbutyloxymethyl)-2-fluorophenyl]thiazol-2-ylcarbamoyl}-2,6-difluorophenyl)-2-methylacrylic acid (B 1969)

1H-NMR(DMSO-d6) 13.01(bs, 2H), 8.04(dt, 1H, J=1.5, 7.5 Hz), 7.92-8.00(m, 2H), 7.65(d, 1H, J=2.7 Hz), 7.43(dt, 1H, J=2.1, 7.5 Hz), 7.34(s, 1H), 7.31(t, 1H, J=7.5 Hz), 4.59(s, 2H), 1.81(s, 3H), 1.25-1.49(m, 5H), 0.84(t, 6H, J=7.5 Hz).

Example 461

Synthesis of (Z)-3-(4-{4-[3-(2-ethylbutyloxymethyl)-2-fluorophenyl]thiazol-2-ylcarbamoyl}-2,6-difluorophenyl)-2-methyloxyacrylic acid (B1970)

1H-NMR(DMSO-d6) 12.98(bs, 1H), 8.04(dt, 1H, J=1.8, 7.8 Hz), 7.87-7.95(m, 2H), 7.65(d, 1H, J=2.7 Hz), 7.43(t, 1H, J=6.6 Hz), 7.31(t, 1H, J=7.5 Hz), 6.64(s, 1H), 4.59(s, 2H), 3.71(s, 3H), 3.40(d, 2H, J=5.7 Hz), 1.25-1.49(m, 5H), 0.84(t, 6H, J=7.5 Hz).

Example 462

Synthesis of (E)-3-(2,6-dichloro-4-{4-[3-(2-ethylbutyloxymethyl)-2-fluorophenyl]thiazol-2-ylcarbamoyl}phenyl)-2-methylacrylic acid (B1971)

1H-NMR(DMSO-d6) 13.01(bs, 2H), 8.29(s, 2H), 8.04(dt, 1H, J=1.5, 7.5 Hz), 7.64(d, 1H, J=2.4 Hz), 7.38-7.46(m, 2H), 7.31(t, 1H, J=7.5 Hz), 4.59(s, 2H), 3.40(d, 2H, J=5.7 Hz), 1.69(s, 3H), 1.25-1.49(m, 5H), 0.84(t, 6H, J=7.5 Hz).

Example 463

Synthesis of (Z)-3-(2,6-dichloro-4-{4-[3-(2-ethylbutyloxymethyl)-2-fluorophenyl]thiazol-2-ylcarbamoyl}phenyl)-2-methyloxyacrylic acid (B 1972)

1H-NMR(DMSO-d6) 13.00(bs, 1H), 8.24(s, 2H), 8.04(dt, 1H, J=1.8, 7.8 Hz), 7.65(d, 1H, J=2.7 Hz), 7.43(t, 1H, J=6.6 Hz), 7.31(t, 1H, J=7.5 Hz), 6.71(s, 1H), 4.59(s, 2H), 3.61(s, 3H), 3.40(d, 2H, J=5.4 Hz), 1.25-1.49(m, 5H), 0.84(t, 6H, J=7.5 Hz).

Example 464

Synthesis of (E)-3-{2,6-difluoro-4-[4-(2-fluoro-3-isobutyloxymethylphenyl)thiazol-2-ylcarbamoyl]phenyl}-2-methylacrylic acid (B 1973)

1H-NMR(DMSO-d6) 13.01(bs, 2H), 8.04(dt, 1H, J=1.8, 7.8 Hz), 7.92-8.00(m, 2H), 7.65(d, 1H, J=2.4 Hz), 7.43(t, 1H, J=6.0 Hz), 7.34(s, 1H), 7.32(t, 1H, J=7.5 Hz), 4.60(s, 2H), 1.80-1.93(m, 1H), 1.81(s, 3H), 0.89(d, 6H, J=6.6 Hz).

Example 465

Synthesis of (Z)-3-{2,6-difluoro-4-[4-(2-fluoro-3-isobutyloxymethylphenyl)thiazol-2-ylcarbamoyl]phenyl}-2-methyloxyacrylic acid (B1974)

1H-NMR(DMSO-d6) 12.98(bs, 1H), 8.04(dt, 1H, J=1.8, 7.5 Hz), 7.87-7.95(m, 2H), 7.65(d, 1H, J=2.4 Hz), 7.43(dt, 1H, J=1.8, 6.6 Hz), 7.32(t, 1H, J=7.5 Hz), 6.66(s, 1H), 4.59(s, 2H), 3.71(s, 3H), 1.80-1.93(m, 1H), 0.89(d, 6H, J=6.9 Hz).

Example 466

Synthesis of (E)-3-{2,6-dichloro-4-[4-(2-fluoro-3-isobutyloxymethylphenyl)thiazol-2-ylcarbamoyl]phenyl}-2-methylacrylic acid (B 1975)

1H-NMR(DMSO-d6) 13.01(bs, 2H), 8.29(s, 2H), 8.04(dt, 1H, J=2.1, 7.8 Hz), 7.65(d, 1H, J=2.7 Hz), 7.38-7.46(m, 2H), 7.32(t, 1H, J=7.5 Hz), 4.60(s, 2H), 1.82-1.91(m, 1H), 1.69(s, 3H), 0.89(d, 6H, J=6.6 Hz).

Example 467

Synthesis of (Z)-3-{2,6-dichloro-4-[4-(2-fluoro-3-isobutyloxymethylphenyl)thiazol-2-ylcarbamoyl]phenyl}-2-methyloxyacrylic acid (B 1976)

1H-NMR(DMSO-d6) 13.01(bs, 1H), 8.25(s, 2H), 8.04(dt, 1H, J=1.8, 7.8 Hz), 7.66(d, 1H, J=2.4 Hz), 7.44(t, 1H, J=6.6 Hz), 7.32(t, 1H, J=7.5 Hz), 6.72(s, 1H), 4.60(s, 2H), 3.62(s, 3H), 1.82-1.89(m, 1H), 0.89(d, 6H, J=6.9 Hz).

Example 468

Synthesis of (Z)-3-(2,6-difluoro-4-{4-[2-fluoro-3-(3-methylbutyloxymethyl)phenyl]thiazol-2-ylcarbamoyl}phenyl)-2-methyloxyacrylic acid (B 1977)

1H-NMR(DMSO-d6) 12.98(bs, 1H), 8.04(dt, 1H, J=1.5, 7.2 Hz), 7.86-7.96(m, 2H), 7.66(d, 1H, J=2.4 Hz), 7.43(d, 1H, J=6.0 Hz), 7.31(t, 1H, J=7.5 Hz), 6.65(s, 1H), 4.59(s, 2H), 3.72(s, 3H), 3.52(t, 2H, J=6.6 Hz), 1.63-1.76(m, 1H), 1.42-1.49 (m, 2H), 0.88(d, 6H, J=6.6 Hz).

Example 469

Synthesis of (Z)-3-(2,6-dichloro-4-{4-[2-fluoro-3-(3-methylbutyloxymethyl)phenyl]thiazol-2-ylcarbamoyl}phenyl)-2-methyloxy acrylic acid (B1978)

1H-NMR(DMSO-d6) 13.00(bs, 1H), 8.25(s, 2H), 8.04(dt, 1H, J=1.5, 7.5 Hz), 7.65(d, 1H, J=2.4 Hz), 7.42(t, 1H, J=6.9 Hz), 7.31(t, 1H, J=7.2 Hz), 6.72(s, 1H), 4.58(s, 2H), 3.61(s, 3H), 3.52(t, 2H, J=6.6 Hz), 1.62-1.76(m, 1H), 1.42-1.49 (m, 2H), 0.88(d, 6H, J=6.6 Hz).

Example 470

Synthesis of (E)-3-{4-[4-(3-cyclobutylmethyloxymethyl-2-fluorophenyl)thiazol-2-ylcarbamoyl]-2,6-difluorophenyl}-2-methylacrylic acid (B 1979)

1H-NMR(DMSO-d6) 13.00(bs, 2H), 8.04(dt, 1H, J=2.1, 7.8 Hz), 7.92-8.00(m, 2H), 7.65(d, 1H, J=2.4 Hz), 7.42(dt, 1H, J=1.8, 6.9 Hz), 7.34(s, 1H), 7.31(t, 1H, J=7.8 Hz), 4.59(s, 2H), 3.48(d, 2H, J=6.6 Hz), 2.50-2.61(m, 1H), 1.64-2.04(m, 9H).

Example 471

Synthesis of (Z)-3-{4-[4-(3-cyclobutylmethyloxymethyl-2-fluorophenyl)thiazol-2-ylcarbamoyl]-2,6-difluorophenyl}-2-methyloxyacrylic acid (B1980)

1H-NMR(DMSO-d6) 12.97(bs, 1H), 8.04(dt, 1H, J=1.8, 7.8 Hz), 7.86-7.95(m, 2H), 7.65(d, 1H, J=2.4 Hz), 7.43(dt, 1H, J=1.8, 7.5 Hz), 7.31(t, 1H, J=7.5 Hz), 6.65(s, 1H), 4.60(s, 2H), 3.71(s, 3H), 3.48(d, 2H, J=6.6 Hz), 2.50-2.61(m, 1H), 1.67-2.05(m, 6H).

Example 472

Synthesis of (E)-3-{2,6-dichloro-4-[4-(3-cyclobutylmethyloxymethyl-2-fluorophenyl)thiazol-2-ylcarbamoyl]phenyl)-2-methylacrylic acid (B1981)

1H-NMR(DMSO-d6) 13.03(bs, 2H), 8.29(s, 2H), 8.04(t, 1H, J=7.2 Hz), 7.65(d, 1H, J=2.7 Hz), 7.38-7.48(m, 2H), 7.31(t, 1H, J=7.8 Hz), 4.60(s, 2H), 3.47(d, 2H, J=6.6 Hz), 1.62-2.03(m, 6H), 1.69(s, 3H).

Example 473

Synthesis of (Z)-3-{2,6-dichloro-4-[4-(3-cyclobutylmethyloxymethyl-2-fluorophenyl)thiazol-2-ylcarbamoyl]phenyl)-2-methyloxyacrylic acid (B1982)

1H-NMR(DMSO-d6) 13.00(bs, 1H), 8.24(s, 2H), 8.04(dt, 1H, J=1.8, 7.5 Hz), 7.65(d, 1H, J=2.7 Hz), 7.43(t, 1H, J=6.3 Hz), 7.31(t, 1H, J=7.5 Hz), 6.72(s, 1H), 4.60(s, 2H), 3.61(s, 3H), 3.48(d, 2H, J=6.9 Hz), 2.48-2.52(m, 1H), 2.05-1.67 (m, 6H).

Example 474

Synthesis of (E)-3-(4-{4-[3-(2,2-dimethylpropyloxymethyl)-2-fluorophenyl]thiazol-2-ylcarbamoyl}-2,6-difluorophenyl)-2-methylacrylic acid (B 1983)

1H-NMR(DMSO-d6) 13.01(bs, 2H), 7.92-8.08(m, 2H), 7.65(d, 1H, J=2.4 Hz), 7.44(t, 1H, J=5.4 Hz), 7.34(d, 1H, J=2.4 Hz), 7.32 (t, 1H, J=7.5 Hz), 4.62(s, 2H), 3.18(s, 2H), 1.81(s, 3H), 0.91(s, 9H).

Example 475

Synthesis of (Z)-3-(4-{4-[3-(2,2-dimethylpropyloxymethyl)-2-fluorophenyl]thiazol-2-ylcarbamoyl}-2,6-difluorophenyl)-2-methyloxyacrylic acid (B 1984)

1H-NMR(DMSO-d6) 12.98(bs, 1H), 8.04(dt, 1H, J=1.8, 7.5 Hz), 7.87-7.94(m, 2H), 7.65(d, 1H, J=2.7 Hz), 7.45(dt, 1H, J=1.8, 6.6 Hz), 7.32(t, 1H, J=7.5 Hz), 6.66(s, 1H), 4.62(s, 2H), 3.61(s, 3H), 3.18(s, 2H), 0.91(s, 9H).

Example 476

Synthesis of (E)-3-(2,6-dichloro-4-{3-[3-(2,2-dimethylpropyloxymethyl)-2-fluorophenyl]thiazol-2-ylcarbamoyl}phenyl)-2-methylacrylic acid (B 1985)

1H-NMR(DMSO-d6) 13.00(bs, 2H), 8.29(s, 2H), 8.04(dt, 1H, J=1.8, 7.5 Hz), 7.63(d, 1H, J=2.4 Hz), 7.44(dt, 1H, J=2.1, 8.4 Hz), 7.40 (d, 1H, J=1.2 Hz), 7.32(t, 1H, J=7.8 Hz), 4.62(s, 2H), 3.18(s, 2H), 1.39(s, 3H), 0.91(s, 9H).

Example 477

Synthesis of (Z)-3-(2,6-dichloro-4-{4-[3-(2,2-dimethyl-propyloxymethyl)-2-fluorophenyl]thiazol-2-ylcarbamoyl}phenyl)-2-methyloxyacrylic acid (B 1986)

1H-NMR(DMSO-d6) 13.01(bs, 1H), 8.24(s, 2H), 8.04(dt, 1H, J=1.5, 7.2 Hz), 7.65(d, 1H, J=2.7 Hz), 7.43(t, 1H, J=6.6 Hz), 7.32(t, 1H, J=7.5 Hz), 6.72(s, 1H), 4.62(s, 2H), 3.61(s, 3H), 3.18(s, 2H), 0.91(s, 9H).

Example 478

Synthesis of (E)-3-(4-{4-[3-(2-cyclopentyethyloxymethyl)-2-fluorophenyl]thiazol-2-ylcarbamoyl}-2,6-difluorophenyl)-2-methylacrylic acid (B 1987)

1H-NMR(DMSO-d6) 12.99(bs, 2H), 8.04(dt, 1H, J=1.8, 7.8 Hz), 7.92-8.02(m, 2H), 7.66(d, 1H, J=2.7 Hz), 7.39-7.46 (m, 1H), 7.28-7.36(m, 2H), 4.59(s, 2H), 3.51(t, 2H, J=6.9 Hz), 1.45-1.95(m, 11H), 1.00-1.18(m, 2H).

Example 479

Synthesis of (E)-3-(2,6-dichloro-4-{4-[3-(2-cyclopentyethyloxymethyl)-2-fluorophenyl]thiazol-2-ylcarbamoyl}phenyl)-2-methylacrylic acid (B 1988)

1H-NMR(DMSO-d6) 13.04(bs, 2H), 8.29(s, 2H), 8.01-8.07(m, 1H), 7.65(d, 1H, J=2.4 Hz), 7.38-7.47(m, 2H), 7.31(t, 1H, J=7.8 Hz), 4.59(s, 2H), 3.51(t, 2H, J=6.6 Hz), 1.65-1.90 (m, 6H), 1.40-1.65(m, 5H), 1.00-1.17(m, 2H).

Example 480

Synthesis of (Z)-3-(2,6-dichloro-4-{4-[3-(2-cyclopentyethyloxymethyl)-2-fluorophenyl]thiazol-2-ylcarbamoyl}phenyl)-2-methyloxyacrylic acid (B 1989)

1H-NMR(DMSO-d6) 12.85(bs, 1H), 8.07(s, 2H), 7.87(dt, 1H, J=1.8, 7.8 Hz), 7.48(d, 1H, J=1.8 Hz), 7.22-7.30(m, 1H), 7.14(t, 1H, J=7.8 Hz), 6.55(s, 1H), 4.41(s, 2H), 3.44(s, 3H), 3.33(t, 2H, J=6.6 Hz), 1.26-1.73(m, 9H), 0.86-1.00(m, 2H).

Example 481

Synthesis of (E)-3-{2,6-difluoro-4-[4-(3-heptyloxymethyl-2-methyloxyphenyl)thiazol-2-ylcarbamoyl]phenyl}-2-methylacrylic acid (B 1990)

1H-NMR(DMSO-d6) 12.96 (bs, 2H), 7.95-7.98 (m, 3H), 7.74 (s, 1H), 7.34-7.39 (m, 2H), 7.21-7.26 (m, 1H), 4.56 (s, 2H), 3.65 (s, 3H), 3.50 (t, 2H, J=6.0 Hz), 1.81 (s, 3H), 1.54-1.56 (m, 2H), 1.25 (bs, 8H), 0.83-0.86 (m, 3H).

Example 482

Synthesis of (E)-3-{2,6-dichloro-4-[4-(3-heptyloxymethyl-2-methyloxyphenyl)thiazol-2-ylcarbamoyl]phenyl}-2-methylacrylic acid (B 1991)

1H-NMR(DMSO-d6) 12.98 (bs, 2H), 8.29 (s, 2H), 7.96-7.99 (m, 1H), 7.74 (s, 1H), 7.36-7.41 (m, 2H), 7.21-7.26 (m, 1H), 4.56 (s, 2H), 3.66 (s, 3H), 3.50 (t, 2H, J=6.0 Hz), 169 (s, 3H), 1.52-1.59 (m, 2H), 1.25 (bs, 8H), 0.83-0.88 (m, 3H).

Example 483

Synthesis of (E)-3-{2,6-difluoro-4-[4-(3-hexyloxymethyl-2-methyloxyphenyl)thiazol-2-ylcarbamoyl]phenyl}-2-methylacrylic acid (B1992)

1H-NMR(DMSO-d6) 12.96 (bs, 2H), 7.95-7.99 (m, 3H), 7.74 (s, 1H), 7.34-7.39 (m, 2H), 7.21-7.26 (m, 1H), 4.56 (s, 2H), 3.65 (s, 3H), 3.50 (t, 2H, J=6.0 Hz), 1.81 (s, 3H), 1.52-1.59 (m, 2H), 1.27-1.36 (m, 6H), 0.84-0.88 (m, 3H).

Example 484

Synthesis of (E)-3-{2,6-dichloro-4-[4-(3-hexyloxymethyl-2-methyloxyphenyl)thiazol-2-ylcarbamoyl]phenyl}-2-methylacrylic acid (B1993)

1H-NMR(DMSO-d6) 12.96 (bs, 2H), 8.29 (s, 2H), 7.96-7.98 (m, 1H), 7.73 (s, 1H), 7.36-7.40 (m, 2H), 7.21-7.26 (m, 1H), 4.56 (s, 2H), 3.65 (s, 3H), 3.50 (t, 2H, J=6.0 Hz), 1.69 (s, 3H), 1.52-1.59 (m, 2H), 1.26-1.36 (m, 6H), 0.84-0.88 (m, 3H).

Example 484

Synthesis of (Z)-3-{2,6-dichloro-4-[4-(3-hexyloxymethyl-2-methyloxyphenyl)thiazol-2-ylcarbamoyl]phenyl}-2-methyloxyacrylic acid (B 1994)

1H-NMR(DMSO-d6) 12.95 (bs, 2H), 8.25 (s, 2H), 7.96-7.99 (m, 1H), 7.73 (s, 1H), 7.36-7.39 (m, 1H), 7.21-7.27 (m, 1H), 6.73 (s, 1H), 4.56 (s, 2H), 3.65 (s, 3H), 3.62 (s, 3H), 3.50 (t, 2H, J=6.3 Hz), 1.52-1.59 (m, 2H), 1.26-1.36 (m, 6H), 0.84-0.88 (m, 3H)

Example 486

Synthesis of (E)-3-{4-[4-(3-butyloxymethyl-2-methyloxyphenyl)thiazol-2-ylcarbamoyl]-2,6-dichlorophenyl}-2-methylacrylic acid (B 1995)

1H-NMR(DMSO-d6) 12.98 (bs, 2H), 8.29 (s, 2H), 7.96-7.99 (m, 1H), 7.74 (s, 1H), 7.37-7.41 (m, 2H), 7.21-7.26 (m, 1H), 4.56 (s, 2H), 3.66 (s, 3H), 3.51 (t, 2H, J=6.3 Hz), 1.69 (s, 3H), 1.51-1.60 (m, 2H), 1.30-1.43 (m, 2H), 0.87-0.92 (m, 3H).

Example 487

Synthesis of (Z)-3-{4-[4-(3-butyloxymethyl-2-methyloxyphenyl)thiazol-2-ylcarbamoyl]-2,6-dichlorophenyl}-2-methyloxyacrylic acid (B 1996)

1H-NMR(DMSO-d6) 12.96 (bs, 2H), 8.25 (s, 2H), 7.96-7.99 (m, 1H), 7.73 (s, 1H), 7.36-7.40 (m, 1H), 7.21-7.26 (m, 1H), 6.73 (s, 1H), 4.56 (s, 2H), 3.66 (s, 3H), 3.61 (s, 3H), 3.51 (t, 2H, J=6.0 Hz), 1.51-1.60 (m, 2H), 1.31-1.43 (m, 2H), 0.87-0.92 (m, 3H).

Example 488

Synthesis of (E)-3-{4-[4-(3-butyloxymethyl-2-methyloxyphenyl)thiazol-2-ylcarbamoyl]-2,6-difluorophenyl}-2-methylacrylic acid (B 1997)

1H-NMR(DMSO-d6) 12.97 (bs, 2H), 7.96-8.00 (m, 3H), 7.75 (s, 1H), 7.34-7.39 (m, 2H), 7.22-7.27 (m, 1H), 4.56 (s, 2H), 3.66 (s, 3H), 3.51 (t, 2H, J=6.0 Hz), 1.81 (s, 3H), 1.51-1.60 (m, 2H), 1.31-1.43 (m, 2H), 0.87-0.92 (m, 3H).

Example 489

Synthesis of (E)-3-{2,6-difluoro-4-[4-(3-heptyloxy-2-methyloxyphenyl)thiazol-2-ylcarbamoyl]phenyl}-2-methylacrylic acid (B 1998)

1H-NMR(DMSO-d6) 12.95 (bs, 2H), 7.95-7.97 (m, 2H), 7.74 (s, 1H), 7.64-7.66 (m, 1H), 7.34 (s, 1H), 7.10-7.16 (m,

1H), 7.02-7.04 (m, 1H), 4.03 (t, 2H, J=6.3 Hz), 3.80 (s, 3H), 1.74-1.80 (m, 5H), 1.43-1.50 (m, 2H), 1.30-1.36 (m, 6H). 0.86-0.90 (m, 3H).

Example 490

Synthesis of (E)-3-{2,6-dichloro-4-[4-(3-heptyloxy-2-methyloxyphenyl)thiazol-2-ylcarbamoyl]phenyl}-2-methylacrylic acid (B 1999)

1H-NMR(DMSO-d6) 12.95 (bs, 2H), 8.29 (s, 2H), 7.75 (s, 1H), 7.64-7.66 (m, 1H), 7.40 (s, 1H), 7.10-7.15 (m, 1H), 7.02-7.05 (m, 1H), 4.03 (t, 2H, J=6.0 Hz), 3.80 (s, 3H), 1.76-1.81 (m, 2H), 1.69 (s, 3H), 1.45-1.50 (m, 2H), 1.30-1.36 (m, 6H). 0.86-0.90 (m, 3H).

Example 491

Synthesis of (Z)-3-{2,6-difluoro-4-[4-(3-heptyloxy-2-methyloxyphenyl)thiazol-2-ylcarbamoyl]phenyl}-2-methyloxyacrylic acid (B2000)

1H-NMR(DMSO-d6) 13.56 (bs, 1H), 12.87 (bs, 1H), 7.89-7.92 (m, 2H), 7.74 (s, 1H), 7.63-7.66 (m, 1H), 7.10-7.15 (m, 1H), 7.02-7.05 (m, 1H), 6.66(s, 1H), 4.03 (t, 2H, J=6.0 Hz), 3.80 (s, 3H), 3.71 (s, 3H), 1.76-1.83 (m, 3H), 1.45-1.50 (m, 2H), 1.30-1.39 (m, 6H). 0.86-0.90 (m, 3H).

Example 492

Synthesis of (Z)-3-{2,6-dichloro-4-[4-(3-heptyloxy-2-methyloxyphenyl)thiazol-2-ylcarbamoyl]phenyl}-2-methyloxyacrylic acid (B2001)

1H-NMR(DMSO-d6) 12.90 (bs, 2H), 8.24 (s, 2H), 7.74 (s, 1H), 7.63-7.66 (m, 1H), 7.10-7.15 (m, 1H), 7.01-7.05 (m, 1H), 6.73 (s, 1H), 4.03 (t, 2H, J=6.0 Hz), 3.80 (s, 3H), 3.61 (s, 3H), 1.76-1.83 (m, 3H), 1.45-1.50 (m, 2H), 1.30-1.39 (m, 6H). 0.86-0.90 (m, 3H).

Example 493

Synthesis of (E)-3-[2,6-difluoro-4-(4-{3-[2-(4-fluorobutyloxy)ethyl]-2-methyloxyphenyl}thiazol-2-ylcarbamoyl)phenyl]-2-methylacrylic acid (B 2002)

1H-NMR(DMSO-d6) 12.96 (bs, 2H), 7.95-7.88 (m, 2H), 7.85-7.88 (m, 1H), 7.72 (s, 1H), 7.33 (s, 1H), 7.26-7.29 (m, 1H), 7.13-7.19 (m, 1H), 4.50 (t, 1H, J=6.0 Hz), 4.34 (t, 1H, J=6.0 Hz), 3.62-3.66 (m, 5H), 3.45 (t, 2H, J=6.3 Hz), 2.91 (t, 2H, J=7.0 Hz), 1.81 (s, 3H), 1.55-1.73 (m, 4H).

Example 494

Synthesis of (E)-3-[2,6-dichloro-4-(4-{3-[2-(4-fluorobutyloxy)ethyl]-2-methyloxyphenyl}thiazol-2-ylcarbamoyl)phenyl]-2-methylacrylic acid (B2003)

1H-NMR(DMSO-d6) 12.97 (bs, 2H), 8.29 (s, 2H), 7.85-7.88 (m, 1H), 7.72 (s, 1H), 7.40 (s, 1H), 7.26-7.29 (m, 1H), 7.14-7.19 (m, 1H), 4.50 (t, 1H, J=6.0 Hz), 4.34 (t, 1H, J=6.0 Hz), 3.62-3.66 (m, 5H), 3.45 (t, 2H, J=6.3 Hz), 2.91 (t, 2H, J=7.0 Hz), 1.55-1.73 (m, 7H).

Example 495

Synthesis of (E)-3-{2,6-difluoro-4-[4-(2-methyloxy-3-octyloxyphenyl)thiazol-2-ylcarbamoyl]phenyl}-2-methylacrylic acid (B2004)

1H-NMR(DMSO-d6) 12.92 (bs, 2H), 7.95-7.97 (m, 2H), 7.75 (s, 1H), 7.64-7.66 (m, 1H), 7.34 (s, 1H), 7.10-7.15 (m, 1H), 7.02-7.04 (m, 1H), 4.03 (t, 2H, J=6.3 Hz), 3.80 (s, 3H), 1.76-1.81 (m, 5H), 1.43-1.50 (m, 2H), 1.28-1.36 (m, 8H). 0.86-0.90 (m, 3H).

Example 496

Synthesis of (E)-3-{2,6-dichloro-4-[4-(2-methyloxy-3-octyloxyphenyl)thiazol-2-ylcarbamoyl]phenyl}-2-methylacrylic acid (B2005)

1H-NMR(DMSO-d6) 12.94 (bs, 2H), 8.28 (s, 2H), 7.74 (s, 1H), 7.63-7.66 (m, 1H), 7.40 (s, 1H), 7.10-7.15 (m, 1H), 7.01-7.04 (m, 1H), 4.03 (t, 2H, J=6.0 Hz), 3.80 (s, 3H), 1.75-1.80 (m, 2H), 1.69 (s, 3H), 1.45-1.50 (m, 2H), 1.30-1.36 (m, 8H). 0.86-0.90 (m, 3H).

Example 497

Synthesis of (E)-3-[4-(4-{3-[3-(2,2-dimethylpropyloxy)-1-methyloxypropyl]-2-fluorophenyl}thiazol-2-ylcarbamoyl)-2,6-difluorophenyl]-2-methylacrylic acid (B2006)

1H-NMR(DMSO-d6) 13.02(bs, 1H), 8.06(t, 1H, J=7.5 Hz), 7.96(s, 1H), 7.93(s, 1H), 7.64(s, 1H), 7.30-7.40(m, 3H), 4.72(t, 1H, J=6.5 Hz), 3.50-3.58(m, 1H), 3.35-3.42(m, 1H), 3.17(s, 3H), 3.00-3.06(m, 2H), 1.85-1.95(m, 2H), 1.79(s, 3H), 0.90(s, 9H).

Example 498

Synthesis of (E)-3-[2,6-dichloro-4-(4-{3-[3-(2,2-dimethylpropyloxy)-1-methyloxypropyl]-2-fluorophenyl}thiazol-2-ylcarbamoyl)phenyl]-2-methylacrylic acid (B2007)

1H-NMR(DMSO-d6) 13.02(bs, 1H), 8.29(s, 2H), 8.01(t, 1H, J=7.5 Hz), 7.64(s, 1H), 7.30-7.40(m, 3H), 4.72(t, 1H, J=6.5 Hz), 3.50-3.58(m, 1H), 3.35-3.42(m, 1H), 3.17(s, 3H), 3.00-3.06(m, 2H), 1.85-1.95(m, 2H), 1.69(s, 3H), 0.90(s, 9H).

Example 499

Synthesis of (Z)-3-[4-(4-{3-[3-(2,2-dimethylpropyloxy)-1-methyloxypropyl]-2-fluorophenyl}thiazol-2-ylcarbamoyl)-2,6-difluorophenyl]-2-methyloxyacrylic acid (B2008)

1H-NMR(DMSO-d6) 13.02(bs, 1H), 8.06(t, 1H, J=7.5 Hz), 7.96(s, 1H), 7.93(s, 1H), 7.64(s, 1H), 7.30-7.40(m, 2H), 6.65(s, 1H), 4.72(t, 1H, J=6.5 Hz), 3.71(s, 3H), 3.50-3.58(m, 1H), 3.35-3.42(m, 1H), 3.17(s, 3H), 3.00-3.06(m, 2H), 1.85-1.95(m, 2H), 0.90(s, 9H).

Example 500

Synthesis of (Z)-3-[2,6-dichloro-4-(4-{3-[3-(2,2-dimethylpropyloxy)-1-methyloxypropyl]-2-fluorophenyl}thiazol-2-ylcarbamoyl)phenyl]-2-methyloxyacrylic acid (B2009)

1H-NMR(DMSO-d6) 13.02(bs, 1H), 8.29(s, 2H), 8.01(t, 1H, J=7.5 Hz), 7.64(s, 1H), 7.30-7.40(m, 2H), 6.65(s, 1H), 4.72(t, 1H, J=6.5 Hz), 3.61(s, 3H), 3.50-3.58(m, 1H), 3.35-3.42(m, 1H), 3.17(s, 3H), 3.00-3.06(m, 2H), 1.85-1.95(m, 2H), 0.90(s, 9H).

Example 501

Synthesis of (E)-3-(2,6-difluoro-4-{4-[2-fluoro-3-(3-isopropyloxy-1-methyloxypropyl)phenyl]thiazol-2-ylcarbamoyl}phenyl)-2-methylacrylic acid (B2010)

1H-NMR(DMSO-d6) 13.02(bs, 1H), 8.06(t, 1H, J=7.5 Hz), 7.96(s, 1H), 7.93(s, 1H), 7.64(s, 1H), 7.30-7.40(m, 3H), 4.72(t, 1H, J=6.5 Hz), 3.50-3.58(m, 1H), 3.35-3.42(m, 2H), 3.17(s, 3H), 1.79-1.95(m, 2H), 1.79(s, 3H), 1.05(d, 6H, J=6.0 Hz).

Example 502

Synthesis of (E)-3-(2,6-dichloro-4-{4-[2-fluoro-3-(3-isopropyloxy-1-methyloxypropyl)phenyl]thiazol-2-ylcarbamoyl}phenyl)-2-methylacrylic acid (B2011)

1H-NMR(DMSO-d6) 13.02(bs, 1H), 8.29(s, 2H), 8.06(t, 1H, J=7.5 Hz), 7.64(s, 1H), 7.30-7.40(m, 3H), 4.72(t, 1H, J=6.5 Hz), 3.50-3.58(m, 1H), 3.35-3.42(m, 2H), 3.17(s, 3H), 1.80-1.98(m, 2H), 1.68(s, 3H), 1.05(d, 6H, J=6.0 Hz).

Example 503

Synthesis of (Z)-3-(2,6-difluoro-4-{4-[2-fluoro-3-(3-isopropyloxy-1-methyloxypropyl)phenyl]thiazol-2-ylcarbamoyl}phenyl)-2-methyloxyacrylic acid (B2012)

1H-NMR(DMSO-d6) 13.02(bs, 1H), 8.06(t, 1H, J=7.5 Hz), 7.96(s, 1H), 7.93(s, 1H), 7.64(s, 1H), 7.30-7.40(m, 2H), 6.65(s, 1H), 4.72(t, 1H, J=6.5 Hz), 3.71(s, 3H), 3.50-3.58(m, 1H), 3.35-3.42(m, 2H), 3.17(s, 3H), 1.80-1.98(m, 2H), 1.05(d, 6H, J=6.0 Hz).

Example 504

Synthesis of (E)-3-(2,6-difluoro-4-{4-[2-fluoro-3-(4-methylpentyloxymethyl)phenyl]thiazol-2-ylcarbamoyl}phenyl)-2-methylacrylic acid (B2013)

1H-NMR(DMSO-d6) 13.02(bs, 2H), 8.04(dt, 1H, J=1.8, 7.5 Hz), 7.92-8.00(m, 2H), 7.65(d, 1H, J=2.4 Hz), 7.39-7.45(m, 1H), 7.28-7.36(m, 2H), 4.58(s, 2H), 3.48(t, 2H, J=6.6 Hz), 1.81(d, 3H, J=1.8 Hz), 1.46-1.60(m, 3H), 1.17-1.25(m, 2H), 0.86(d, 6H, J=6.6 Hz).

Example 505

Synthesis of (Z)-3-(2,6-difluoro-4-{4-[2-fluoro-3-(4-methylpentyloxymethyl)phenyl]thiazol-2-ylcarbamoyl}phenyl)-2-methyloxyacrylic acid (B2014)

1H-NMR(DMSO-d6) 12.97(bs, 1H), 8.04(dt, 1H, J=1.8, 7.5 Hz), 7.86-7.96(m, 2H), 7.65(d, 1H, J=2.7 Hz), 7.38-7.46(m, 1H), 7.31(t, 1H, J=7.8 Hz), 6.64(s, 1H), 4.58(s, 2H), 3.71(s, 3H), 3.48(t, 2H, J=6.6 Hz), 1.45-1.62(m, 3H), 1.17-1.20(m, 2H), 0.86(d, 6H, J=6.6 Hz).

Example 506

Synthesis of (E)-3-(2,6-dichloro-4-{4-[2-fluoro-3-(4-methylpentyloxymethyl)phenyl]thiazol-2-ylcarbamoyl}phenyl)-2-methylacrylic acid (B2015)

1H-NMR(DMSO-d6) 13.02(bs, 2H), 8.29(s, 2H), 8.04(dt, 1H, J=1.8, 7.2 Hz), 7.65(d, 1H, J=2.7 Hz), 7.38-7.46(m, 2H), 7.31(t, 1H, J=7.5 Hz), 4.58(s, 2H), 3.48(t, 2H, J=6.6 Hz), 1.69(s, 3H), 1.46-1.60(m, 3H), 1.17-1.25(m, 2H), 0.86(d, 6H, J=6.6 Hz).

Example 507

Synthesis of (Z)-3-(2,6-dichloro-4-{4-[2-fluoro-3-(4-methylpentyloxymethyl)phenyl]thiazol-2-ylcarbamoyl}phenyl)-2-methyloxyacrylic acid (B2016)

1H-NMR(DMSO-d6) 13.01(bs, 1H), 8.25(s, 2H), 8.04(dt, 1H, J=1.5, 7.5 Hz), 7.65(d, 1H, J=2.7 Hz), 7.39-7.46(m, 1H), 7.31(t, 1H, J=7.8 Hz), 6.73(s, 1H), 4.58(s, 2H), 3.61(s, 3H), 3.48(t, 2H, J=6.3 Hz), 1.46-1.60(m, 3H), 1.15-1.27(m, 2H), 0.86(d, 6H, J=6.6 Hz).

Example 508

Synthesis of (E)-3-{2,6-difluoro-4-[4-(2-fluoro-3-methyloxyphenyl)thiazol-2-ylcarbamoyl]phenyl}-2-methylacrylic acid (B2017)

1H-NMR(DMSO-d6) 13.0(bs, 2H), 7.98(s, 1H), 7.95(s, 1H), 7.60-7.68(m, 2H), 7.34(bs, 1H), 7.14-7.28(m, 2H), 3.89(s, 3H), 1.81(s, 3H).

Example 509

Synthesis of (E)-3-{2,6-dichloro-4-[4-(2-fluoro-3-methyloxyphenyl)thiazol-2-ylcarbamoyl]phenyl}-2-methylacrylic acid (B2018)

1H-NMR(DMSO-d6) 13.0(bs, 2H), 8.29(s, 2H), 7.59-7.68(m, 2H), 7.40(s, 1H), 7.14-7.28(m, 2H), 3.89(s, 3H), 1.69(s, 3H).

Example 510

Synthesis of (Z)-3-{2,6-dichloro-4-[4-(2-fluoro-3-methyloxyphenyl)thiazol-2-ylcarbamoyl]phenyl}-2-methyloxyacrylic acid (B2019)

1H-NMR(DMSO-d6) 13.6(bs, 1H), 13.0(bs, 1H), 8.25(s, 2H), 7.60-7.68(m, 2H), 7.14-7.26(m, 2H), 6.74(s, 1H), 3.89(s, 3H), 3.61(s, 3H).

Example 511

Synthesis of (E)-3-(4-{4-[3-(2,2-dimethylpropyloxymethyl)-2-methyloxyphenyl]thiazol-2-ylcarbamoyl}-2,6-difluorophenyl)-2-methyloxyacrylic acid (B2020)

1H NMR(DMSO-d6) 12.93(bs, 2H), 7.90-7.99(m, 3H), 7.74(s, 1H), 7.39-7.41(m, 1H), 7.25(t, 1H, J=7.5 Hz), 6.65(s, 1H), 4.60(s, 2H), 3.72(s, 3H), 3.3.66(s, 3H), 3.19(s, 2H), 0.92(s, 9H).

Example 512

Synthesis of (E)-3-(2,6-dichloro-4-{4-[3-(2,2-dimethylpropyloxymethyl)-2-methyloxyphenyl]thiazol-2-ylcarbamoyl}phenyl)-2-methylacrylic acid (B2021)

1H NMR(DMSO-d6) 12.98(bs, 2H), 8.29(s, 2H), 7.98(dd, 1H, J=1.5 Hz, 7.5 Hz), 7.74(s, 1H), 7.39-7.41(m, 2H), 7.25(t, 1H, J=7.5 Hz), 4.60(s, 2H), 3.66(s, 3H), 3.19(s, 2H), 1.69(d, 3H, J=1.2 Hz), 0.92(s, 9H).

Example 513

Synthesis of (Z)-3-(2,6-dichloro-4-{4-[3-(2,2-dimethylpropyloxymethyl)-2-methyloxyphenyl]thiazol-2-ylcarbamoyl}phenyl)-2-methyloxyacrylic acid (B2022)

1H NMR(DMSO-d6) 12.96(bs, 2H), 8.25(s, 2H), 7.97(dd, 1H, J=1.5 Hz, 7.5 Hz), 7.74(s, 1H), 7.40(dd, 1H, J=1.5 Hz, 7.5 Hz), 7.25(t, 1H, J=7.5 Hz), 6.73(s, 1H), 4.60(s, 2H), 3.66(s, 3H), 3.62(s, 3H), 3.19(s, 2H), 0.92(s, 9H).

Example 514

Synthesis of (E)-3-(4-{4-[3-(2-ethylbutyloxymethyl)-2-methyloxyphenyl]thiazol-2-ylcarbamoyl}-2,6-difluorophenyl)-2-methyl acrylic acid (B2023)

1H NMR(DMSO-d6) 12.98(bs, 2H), 7.95-7.99(m, 3H), 7.74(s, 1H), 7.37-7.39(dd, 1H, J=1.8 Hz, 7.8 Hz), 7.34(s, 1H), 7.24(t, 1H, J=7.5 Hz), 4.56(s, 2H), 3.65(s, 3H), 3.42(d, 2H, J=5.7 Hz), 1.81(s, 3H), 1.26-1.51(m, 5H), 0.85(t, 6H, J=7.5 Hz).

Example 515

Synthesis of (Z)-3-(4-{4-[3-(2-ethylbutyloxymethyl)-2-methyloxyphenyl]thiazol-2-ylcarbamoyl}-2,6-difluorophenyl)-2-methyloxyacrylic acid (B2024)

1H NMR(DMSO-d6) 12.93(bs, 2H), 7.90-7.99(m, 3H), 7.74(s, 1H), 7.37-7.40(m, 1H), 7.24(t, 1H, J=7.5 Hz), 6.65(s, 1H), 4.56(s, 2H), 3.72(s, 3H), 3.65(s, 3H), 3.42(d, 2H, J=5.4 Hz), 1.24-1.49(m, 5H), 0.85(t, 6H, J=7.5 Hz).

Example 516

Synthesis of (E)-3-(2,6-dichloro-4-{4-[3-(2-ethylbutyloxymethyl)-2-methyloxyphenyl]thiazol-2-ylcarbamoyl}phenyl)-2-methylacrylic acid (B2025)

1H NMR(DMSO-d6) 13.00(bs, 2H), 8.29(s, 2H), 7.97(dd, 1H, J=1.5 Hz, 7.5 Hz), 7.74(s, 1H), 7.37-7.41(m, 2H), 7.25(t, 1H, J=7.5 Hz), 4.57(s, 2H), 3.66(s, 3H), 3.42(d, 2H, J=5.7 Hz), 1.69(s, 3H), 1.25-1.49(m, 5H), 0.86(t, 6H, J=7.5 Hz).

Example 517

Synthesis of (Z)-3-(2,6-dichloro-4-{4-[3-(2-ethylbutyloxymethyl)-2-methyloxyphenyl]thiazol-2-ylcarbamoyl}phenyl)-2-methyloxyacrylic acid (B2026)

1H NMR(DMSO-d6) 12.95(bs, 2H), 8.25(s, 2H), 7.97(d, 1H, J=8.1 Hz), 7.73(s, 1H), 7.38(d, 1H, J=6.0 Hz), 7.24(t, 1H, J=7.5 Hz), 6.73(s, 1H), 4.57(s, 2H), 3.66(s, 3H), 3.62(s, 3H), 3.42(d, 2H, J=5.7 Hz), 1.24-1.49(m, 5H), 0.85(t, 6H, J=7.5 Hz).

Example 518

Synthesis of (E)-3-(2,6-difluoro-4-{4-[2-methyloxy-3-(3-methylbutyloxymethyl)phenyl]thiazol-2-ylcarbamoyl}phenyl)-2-methylacrylic acid (B2027)

1H NMR(DMSO-d6) 12.94(bs, 2H), 7.95-7.99(m, 3H), 7.74(s, 1H), 7.34-7.40(m, 2H), 7.24(t, 1H, J=7.5 Hz), 4.56(s, 2H), 3.65(s, 3H), 3.54(t, 2H, J=6.3 Hz), 1.81(s, 3H), 1.66-1.71(m, 1H), 1.47(q, 2H, 6.6 Hz), 0.89(d, 6H, J=6.6 Hz).

Example 519

Synthesis of (E)-3-(2,6-dichloro-4-{4-[2-methyloxy-3-(3-methylbutyloxymethyl)phenyl]thiazol-2-ylcarbamoyl}phenyl)-2-methylacrylic acid (B2028)

1H NMR(DMSO-d6) 12.97(bs, 2H), 8.29(s, 2H), 7.97(dd, 1H, J=9.3 Hz), 7.73(s, 1H), 7.37-7.41(m, 2H), 7.24(t, 1H, J=7.5 Hz), 4.56(s, 2H), 3.66(s, 3H), 3.54(t, 2H, J=6.6 Hz), 1.66-1.75(m, 1H), 1.69(s, 3H), 1.47(q, 2H, 6.6 Hz), 0.89(d, 6H, J=6.6 Hz).

Example 520

Synthesis of (E)-3-(4-{4-[3-(3,3-dimethylbutyloxymethyl)-2-fluorophenyl]thiazol-2-ylcarbamoyl}-2,6-difluorophenyl)-2-methylacrylic acid (B2029)

1H-NMR(DMSO-d6) 13.04(bs, 2H), 8.00-8.08(m, 1H), 7.92-8.08(m, 2H), 7.65(d, 1H, J=1.8 Hz), 7.39-7.46(m, 1 Hz), 7.28-7.36(m, 2H), 4.58(s, 2H), 3.56(t, 2H, J=7.2 Hz), 1.81(s, 3H), 1.51(t, 2H, J=7.2 Hz), 0.91(s, 9H).

Example 521

Synthesis of (Z)-3-(4-{4-[3-(3,3-dimethylbutyloxymethyl)-2-fluorophenyl]thiazol-2-ylcarbamoyl}-2,6-difluorophenyl)-2-methyloxyacrylic acid (B2030)

1H-NMR(DMSO-d6) 12.99(bs, 1H), 8.00-8.07(m, 1H), 7.86-7.96(m, 2H), 7.65(d, 1H, J=2.4 Hz), 7.39-7.46(m, 1H), 7.31(t, 1H, J=7.5 Hz), 6.65(s, 1H), 4.58(s, 2H), 3.71(s, 3H), 3.56(t, 2H, J=7.2 Hz), 1.51(t, 3H, J=7.2 Hz), 0.90(s, 9H).

Example 522

Synthesis of (E)-3-(2,6-dichloro-4-{4-[3-(3,3-dimethylbutyloxymethyl)-2-fluorophenyl]thiazol-2-ylcarbamoyl}phenyl)-2-methylacrylic acid (B2031)

1H-NMR(DMSO-d6) 13.02(bs, 2H), 8.29(s, 2H), 8.00-8.08(m, 1H), 7.65(d, 1H, J=2.1 Hz), 7.39-7.48(m, 2H), 7.31(t, 1H, J=7.5 Hz), 4.58(s, 2H), 3.56(t, 2H, J=7.2 Hz), 1.69(s, 3H), 1.51(t, 2H, J=7.2 Hz), 0.91(s, 9H).

Example 523

Synthesis of (Z)-3-(2,6-dichloro-4-{4-[3-(3,3-dimethylbutyloxymethyl)-2-fluorophenyl]thiazol-2-ylcarbamoyl}phenyl)-2-methyloxyacrylic acid (B2032)

1H-NMR(DMSO-d6) 13.02(bs, 1H), 8.25(s, 2H), 8.00-8.08(m, 1H), 7.66(d, 1H, J=2.4 Hz), 7.39-7.46(m, 1H), 7.31(t, 1H, J=7.5 Hz), 6.73(s, 1H), 4.59(s, 2H), 3.62(s, 3H), 3.56(t, 2H, J=7.2 Hz), 1.51(t, 2H, J=7.2 Hz), 0.91(s, 9H).

Example 524

Synthesis of (E)-3-{4-[4-(3-cyclohexylmethyloxymethyl-2-fluorophenyl)thiazol-2-ylcarbamoyl]-2,6-difluorophenyl}-2-methylacrylic acid (B2033)

1H-NMR(DMSO-d6) 13.04(bs, 2H), 7.92-8.08(m, 3H), 7.65(d, 1H, J=2.4 Hz), 7.39-7.46(m, 1H), 7.28-7.36(m, 2H), 4.58(s, 2H), 1.81(s, 3H), 1.54-1.79(m, 6H), 1.10-1.25(m, 3H), 0.80-1.02(m, 2H).

Example 525

Synthesis of (Z)-3-{4-[4-(3-cyclohexylmethyloxymethyl-2-fluorophenyl)thiazol-2-ylcarbamoyl]-2,6-difluorophenyl}-2-methyloxyacrylic acid (B2034)

1H-NMR(DMSO-d6) 12.98(bs, 1H), 8.04(dt, 1H, J=2.1, 7.5 Hz), 7.70-7.96(m, 2H), 7.65(d, 1H, J=2.7 Hz), 7.39-7.46(m, 1H), 7.31(t, 1H, J=7.8 Hz), 6.66(s, 1H), 4.58(s, 2H), 3.72(s, 3H), 1.52-1.79(m, 6H), 1.06-1.28(m, 3H), 0.83-1.02(m, 2H).

Example 526

Synthesis of (E)-3-{2,6-dichloro-4-[4-(3-cyclohexylmethyloxymethyl-2-fluorophenyl)thiazol-2-ylcarbamoyl]phenyl}-2-methylacrylic acid (B2035)

1H-NMR(DMSO-d6) 13.02(bs, 2H), 8.29(s, 2H), 8.04(dt, 1H, J=1.8, 7.8 Hz), 7.65(d, 1H, J=2.4 Hz), 7.38-7.46(m, 2H), 7.31(t, 1H, J=7.8 Hz), 4.58(s, 2H), 1.50-1.80(m, 6H), 1.07-1.30(m, 3H), 0.82-1.05(m, 2H).

Example 527

Synthesis of (Z)-3-{2,6-dichloro-4-[4-(3-cyclohexylmethyloxymethyl-2-fluorophenyl)thiazol-2-ylcarbamoyl]phenyl}-2-methyloxyacrylic acid (B2036)

1H-NMR(DMSO-d6) 13.02(bs, 1H), 8.25(s, 2H), 8.00-8.08(m, 1H), 7.65(d, 1H, J=2.4 Hz), 7.39-7.46(m, 1H), 7.31(t, 1H, J=8.1 Hz), 6.72(s, 1H), 4.58(s, 2H), 3.62(s, 3H), 1.50-1.78(m, 6H), 1.08-1.30(m, 3H), 0.86-1.00(m, 2H).

Example 528

Synthesis of (E)-3-(4-{4-[3-(2-ethylsufanylethyloxymethyl)-2-fluorophenyl]thiazol-2-ylcarbamoyl}-2,6-difluorophenyl)-2-methylacrylic acid (B2037)

1H-NMR(DMSO-d6) 13.02(bs, 2H), 8.05(dt, 1H, J=1.8, 7.5 Hz), 7.92-8.05(m, 2H), 7.65(d, 1H, J=2.7 Hz), 7.42-7.48(m, 1 Hz), 7.28-7.35(m, 2H), 4.64(s, 2H), 3.66(t, 2H, J=6.6 Hz), 2.73(t, 2H, J=6.9 Hz), 2.50-2.59(m, 2H), 1.81(s, 3H), 1.17(t, 3H, J=7.5 Hz).

Example 529

Synthesis of (Z)-3-(4-{4-[3-(2-ethylsufanylethyloxymethyl)-2-fluorophenyl]thiazol-2-ylcarbamoyl}-2,6-difluorophenyl)-2-methyloxyacrylic acid (B2038)

1H-NMR(DMSO-d6) 12.98(bs, 1H), 8.05(dt, 1H, J=1.8, 7.8 Hz), 7.70-7.95(m, 2H), 7.66(d, 1H, J=2.7 Hz), 7.42-7.49(m, 1H), 7.32(t, 1H, J=7.8 Hz), 6.66(s, 1H), 4.64(s, 2H), 3.71(s, 3H), 3.66(t, 2H, J=6.6 Hz), 2.73(t, 2H, J=6.6 Hz), 2.50-2.59(m, 2H), 1.17(t, 3H, J=7.5 Hz).

Example 530

Synthesis of (E)-3-(2,6-dichloro-4-{4-[3-(2-ethylsufanylethyloxymethyl)-2-fluorophenyl]thiazol-2-ylcarbamoyl}phenyl)-2-methylacrylic acid (B2039)

1H-NMR(DMSO-d6) 13.02(bs, 2H), 8.29(s, 2H), 8.05(dt, 1H, J=1.8, 7.8 Hz), 7.65(d, 1H, J=2.7 Hz), 7.42-7.48(m, 1H), 7.40(d, 1H, J=1.2 Hz), 7.31(t, 1H, J=7.5 Hz), 4.64(s, 2H), 3.66(t, 2H, J=6.6 Hz), 2.73(t, 2H, J=6.9 Hz), 2.50-2.59(m, 2H), 1.69(s, 3H), 1.17(t, 3H, J=7.5 Hz).

Example 531

Synthesis of (Z)-3-(2,6-dichloro-4-{4-[3-(2-ethylsufanylethyloxymethyl)-2-fluorophenyl]thiazol-2-ylcarbamoyl}phenyl)-2-methyloxyacrylic acid (B2040)

1H-NMR(DMSO-d6) 13.01(bs, 1H), 8.24(s, 2H), 8.05(dt, 1H, J=1.8, 7.5 Hz), 7.65(d, 1H, J=2.4 Hz), 7.42-7.49(m, 1H), 7.32(t, 1H, J=7.5 Hz), 6.73(s, 1H), 4.64(s, 2H), 3.66(t, 2H, J=6.6 Hz), 3.61(s, 3H), 2.73(t, 2H, J=6.9 Hz), 2.50-2.59(m, 2H), 1.17(t, 3H, J=7.5 Hz).

Example 532

Synthesis of (E)-3-{2,6-difluoro-4-[4-(2-methyloxy-3-nonyloxyphenyl)thiazol-2-ylcarbamoyl]phenyl}-2-methylacrylic acid (B2041)

1H-NMR(DMSO-d6) 12.92 (bs, 2H), 7.93-7.97 (m, 2H), 7.75 (s, 1H), 7.63-7.66 (m, 1H), 7.34 (s, 1H), 7.08-7.15 (m, 1H), 7.02-7.04 (m, 1H), 4.02 (t, 1H, J=6.3 Hz), 3.80 (s, 3H), 1.73-1.81 (m, 5H), 1.43-1.50 (m, 2H), 1.26-1.38 (m, 10H), 0.84-0.88 (m, 3H).

Example 533

Synthesis of (E)-3-{2,6-dichloro-4-[4-(2-methyloxy-3-nonyloxyphenyl)thiazol-2-ylcarbamoyl]phenyl}-2-methylacrylic acid (B2042)

1H-NMR(DMSO-d6) 12.94 (bs, 2H), 8.28 (s, 2H), 7.74 (s, 1H), 7.63-7.66 (m, 1H), 7.40 (s, 1H), 7.10-7.15 (m, 1H), 7.02-7.04 (m, 1H), 4.03 (t, 1H, J=6.3 Hz), 3.80 (s, 3H), 1.73-1.81 (m, 2H), 1.69 (s, 3H), 1.43-1.50 (m, 2H), 1.26-1.38 (m, 10H), 0.84-0.88 (m, 3H).

Example 534

Synthesis of (E)-3-(2,6-difluoro-4-{4-[2-methyloxy-3-(4-methylpentyloxy)phenyl]thiazol-2-ylcarbamoyl}phenyl)-2-methylacrylic acid (B2043)

1H-NMR(DMSO-d6) 12.93 (bs, 2H), 7.95-7.97 (m, 2H), 7.75 (s, 1H), 7.63-7.66 (m, 1H), 7.34 (s, 1H), 7.10-7.15 (m, 1H), 7.02-7.04 (m, 1H), 4.02 (t, 1H, J=6.3 Hz), 3.80 (s, 3H), 1.74-1.81 (m, 5H), 1.58-1.67 (m, 1H), 1.33-1.41 (m, 2H), 0.91 (d, 6H, J=5.5 Hz).

Example 535

Synthesis of (E)-3-(2,6-dichloro-4-{4-[2-methyloxy-3-(4-methylpentyloxy)phenyl]thiazol-2-ylcarbamoyl}phenyl)-2-methylacrylic acid (B2044)

1H-NMR(DMSO-d6) 12.93 (bs, 2H), 8.28 (s, 2H), 7.74 (s, 1H), 7.63-7.66 (m, 1H), 7.40 (s, 1H), 7.10-7.15 (m, 1H), 7.01-7.04 (m, 1H), 4.02 (t, 1H, J=6.3 Hz), 3.80 (s, 3H), 1.74-1.82 (m, 2H), 1.69 (s, 3H), 1.58-1.67 (m, 1H), 1.33-1.41 (m, 2H), 0.91 (d, 6H, J=5.5 Hz).

Example 536

Synthesis of (E)-3-{2,6-difluoro-4-[4-(3-hexyloxy-2-methyloxyphenyl)thiazol-2-ylcarbamoyl]phenyl}-2-methylacrylic acid (B2045)

1H-NMR(DMSO-d6) 12.96 (bs, 2H), 7.93-7.97 (m, 2H), 7.75 (s, 1H), 7.63-7.66 (m, 1H), 7.34 (s, 1H), 7.10-7.15 (m, 1H), 7.01-7.04 (m, 1H), 4.03 (t, 1H, J=6.3 Hz), 3.80 (s, 3H), 1.74-1.81 (m, 5H), 1.44-1.53 (m, 2H), 1.32-1.37 (m, 4H), 0.87-0.92 (m, 3H).

Example 537

Synthesis of (E)-3-{2,6-dichloro-4-[4-(3-hexyloxy-2-methyloxyphenyl)thiazol-2-ylcarbamoyl]phenyl}-2-methylacrylic acid (B2046)

1H-NMR(DMSO-d6) 12.93 (bs, 2H), 8.27 (s, 2H), 7.72 (s, 1H), 7.62-7.64 (m, 1H), 7.38 (s, 1H), 7.08-7.13 (m, 1H), 7.00-7.03 (m, 1H), 4.02 (t, 1H, J=6.3 Hz), 3.78 (s, 3H), 1.72-1.81 (m, 2H), 1.67 (s, 3H), 1.42-1.51 (m, 2H), 1.32-1.37 (m, 4H), 0.87-0.92 (m, 3H).

Example 538

Synthesis of (E)-3-(2,6-difluoro-4-{4-[2-methyloxy-3-(1-methyloxy-4-methylpentyl)phenyl]thiazol-2-ylcarbamoyl}phenyl)-2-methylacrylic acid (B2047)

1H-NMR(DMSO-d6) 12.97 (bs, 2H), 7.89-7.97 (m, 3H), 7.72 (s, 1H), 7.24-7.34 (m, 3H), 4.53-4.57 (m, 1H), 3.61 (s, 3H), 3.16 (s, 3H), 1.81 (s, 3H), 0.87-1.72 (m, 11H).

Example 539

Synthesis of (E)-3-(2,6-dichloro-4-{4-[2-methyloxy-3-(1-methyloxy-4-methylpentyl)phenyl]thiazol-2-ylcarbamoyl}phenyl)-2-methylacrylic acid (B2049)

1H-NMR(DMSO-d6) 12.98 (bs, 2H), 9.29 (s, 1H), 7.89-7.92 (m, 1H), 7.72 (s, 1H), 7.41 (s, 1H), 7.24-7.37 (m, 3H), 4.53-4.57 (m, 1H), 3.61 (s, 3H), 3.16 (s, 3H), 0.87-1.72 (m, 14H).

Example 540

Synthesis of (E)-3-{2,6-dichloro-4-[4-(2-fluoro-3-propyloxyphenyl)thiazol-2-ylcarbamoyl]phenyl}-2-methylacrylic acid (B2051)

1H-NMR(DMSO-d6) 13.0(bs, 2H), 7.98(s, 1H), 7.95(s, 1H), 7.59-7.67(m, 2H), 7.34(bs, 1H), 7.12-7.25(m, 2H), 4.05 (t, 2H, J=6.6 Hz), 1.74-1.84(m, 5H), 1.01(t, 3H, J=7.2 Hz).

Example 541

Synthesis of (E)-3-{2,6-dichloro-4-[4-(2-fluoro-3-propyloxyphenyl)thiazol-2-ylcarbamoyl]phenyl}-2-methylacrylic acid (B2052)

1H-NMR(DMSO-d6) 13.0(bs, 2H), 8.29(s, 2H), 7.60-7.66 (m, 2H), 7.41(s, 1H), 7.13-7.26(m, 2H), 4.06(t, 2H, J=6.6 Hz), 1.79(q, 2H, J=6.9 Hz), 1.70(s, 3H), 1.02(t, 3H, J=7.5 Hz).

Example 542

Synthesis of (Z)-3-{2,6-difluoro-4-[4-(2-fluoro-3-propyloxyphenyl)thiazol-2-ylcarbamoyl]phenyl}-2-methyloxyacrylic acid (B2053)

1H-NMR(DMSO-d6) 13.0(bs, 2H), 7.92(s, 1H), 7.89(s, 1H), 7.60-7.67(m, 2H), 7.14-7.25(m, 2H), 6.62-6.70(m, 1H), 4.05(t, 2H, J=6.3 Hz), 3.71(s, 3H), 1.78(q, 2H, J=6.3 Hz), 1.01(t, 3H, J=7.2 Hz).

Example 543

Synthesis of (Z)-3-{2,6-dichloro-4-[4-(2-fluoro-3-propyloxyphenyl)thiazol-2-ylcarbamoyl]phenyl}-2-methyloxyacrylic acid (B2054)

1H-NMR(DMSO-d6) 13.0(bs, 2H), 8.25(s, 2H), 7.59-7.66 (m, 2H), 7.13-7.26(m, 2H), 6.73(s, 2H), 4.05(t, 2H, J=6.6 Hz), 3.61(s, 3H), 1.78(q, 2H, J=6.9 Hz), 1.01(t, 3H, J=7.2 Hz).

Example 544

Synthesis of (E)-3-{2,6-difluoro-4-[4-(2-fluoro-3-pentyloxyphenyl)thiazol-2-ylcarbamoyl]phenyl}-2-methylacrylic acid (B2055)

1H-NMR(DMSO-d6) 13.0(bs, 2H), 7.97(s, 1H), 7.95(s, 1H), 7.59-7.67(m, 2H), 7.34(bs, 1H), 7.13-7.25(m, 2H), 4.08 (t, 2H, J=6.6 Hz), 1.72-1.82(m, 5H), 1.33-1.50(m, 4H), 0.91 (t, 3H, J=7.2 Hz).

Example 545

Synthesis of (E)-3-{2,6-dichloro-4-[4-(2-fluoro-3-pentyloxyphenyl)thiazol-2-ylcarbamoyl]phenyl}-2-methylacrylic acid (B2056)

1H-NMR(DMSO-d6) 13.0(bs, 2H), 8.28(s, 2H), 7.59-7.66 (m, 2H), 7.40(bs, 1H), 7.12-7.25(m, 2H), 4.08(t, 2H, J=6.6 Hz), 1.71-1.82(m, 2H), 1.69(s, 3H), 1.30-1.51(m, 4H), 0.91(t, 3H, J=7.2 Hz).

Example 546

Synthesis of (Z)-3-{2,6-difluoro-4-[4-(2-fluoro-3-pentyloxyphenyl)thiazol-2-ylcarbamoyl]phenyl}-2-methyloxyacrylic acid (B 2057)

1H-NMR(DMSO-d6) 13.0(bs, 2H), 7.93(s, 1H), 7.89(s, 1H), 7.59-7.65(m, 2H), 7.12-7.24(m, 2H), 6.65(s, 1H), 4.08(t, 2H, J=6.6 Hz), 3.71(s, 3H), 1.71-1.80(m, 2H), 1.35-1.50(m, 4H), 0.91(t, 3H, J=7.2 Hz).

Example 547

Synthesis of (Z)-3-{2,6-dichloro-4-[4-(2-fluoro-3-pentyloxyphenyl)thiazol-2-ylcarbamoyl]phenyl}-2-methylacrylic acid (B2058)

1H-NMR(DMSO-d6) 13.0(bs, 2H), 8.24(s, 2H), 7.58-7.65 (m, 2H), 7.12-7.25(m, 2H), 6.73(s, 1H), 4.08(t, 2H, J=6.6 Hz), 3.61(s, 3H), 1.72-1.82(m, 2H), 1.33-1.48(m, 4H), 0.91(t, 3H, J=6.9 Hz).

Example 548

Synthesis of (E)-3-{2,6-difluoro-4-[4-(2-fluoro-3-hexyloxyphenyl)thiazol-2-ylcarbamoyl]phenyl}-2-methylacrylic acid (B2059)

1H-NMR(DMSO-d6) 13.0(bs, 2H), 7.98(s, 1H), 7.95(s, 1H), 7.59-7.66(m, 2H), 7.34(s, 1H), 7.13-7.24(m, 2H), 4.08(t, 2H, J=6.6 Hz), 1.71-1.84(m, 5H), 1.30-1.51(m, 6H), 0.89(t, 3H, J=7.2 Hz).

Example 549

Synthesis of (E)-3-{2,6-dichloro-4-[4-(2-fluoro-3-hexyloxyphenyl)thiazol-2-ylcarbamoyl]phenyl}-2-methylacrylic acid (B2060)

1H-NMR(DMSO-d6) 13.0(bs, 2H), 8.29(s, 2H), 7.59-7.65 (m, 2H), 7.41(s, 1H), 7.13-7.25(m, 2H), 4.08(t, 2H, J=6.6 Hz), 1.70-1.80(m, 2H), 1.69(s, 3H), 1.30-1.50(m, 6H), 0.89(t, 3H, J=6.9 Hz).

Example 550

Synthesis of (Z)-3-{2,6-difluoro-4-[4-(2-fluoro-3-hexyloxyphenyl)thiazol-2-ylcarbamoyl]phenyl}-2-methyloxyacrylic acid (B2061)

1H-NMR(DMSO-d6) 13.6(bs, 1H), 13.0(bs, 1H), 7.93(s, 1H), 7.90(s, 1H), 7.59-7.66(m, 2H), 7.12-7.25(m, 2H), 6.66 (s, 1H), 4.08(t, 2H, J=6.6 Hz), 3.71(s, 3H), 1.71-1.80(m, 2H), 1.29-1.50(m, 6H), 0.89(t, 3H, J=7.2 Hz).

Example 551

Synthesis of (Z)-3-{2,6-dichloro-4-[4-(2-fluoro-3-hexyloxyphenyl)thiazol-2-ylcarbamoyl]phenyl}-2-methyloxyacrylic acid (B2062)

1H-NMR(DMSO-d6) 13.6(bs, 1H), 13.0(bs, 1H), 8.25(s, 2H), 7.59-7.66(m, 2H), 7.12-7.25(m, 2H), 6.74(s, 1H), 4.08(t, 2H, J=6.6 Hz), 3.61(s, 3H), 1.70-1.81(m, 2H), 1.30-1.50(m, 6H), 0.89(t, 3H, J=6.9 Hz).

Example 552

Synthesis of (E)-3-{2,6-difluoro-4-[4-(2-fluoro-3-heptyloxyphenyl)thiazol-2-ylcarbamoyl]phenyl}-2-methylacrylic acid (B2063)

1H-NMR(DMSO-d6) 13.0(bs, 2H), 7.98(s, 1H), 7.95(s, 1H), 7.59-7.66(m, 2H), 7.34(bs, 1H), 7.13-7.25(m, 2H), 4.08 (t, 2H, J=6.3 Hz), 1.73-1.82(m, 5H), 1.28-1.50(m, 8H), 0.88 (t, 3H, J=7.5 Hz).

Example 553

Synthesis of (E)-3-{2,6-dichloro-4-[4-(2-fluoro-3-heptyloxyphenyl)thiazol-2-ylcarbamoyl]phenyl]-2-methylacrylic acid (B2064)

1H-NMR(DMSO-d6) 13.0(bs, 2H), 8.29(s, 2H), 7.59-7.67 (m, 2H), 7.40(s, 1H), 7.13-7.24(m, 2H), 4.08(t, 2H, J=6.3 Hz), 1.70-1.80(m, 2H), 1.69(s, 3H), 1.23-1.50(m, 8H), 0.88(t, 3H, J=6.9 Hz).

Example 554

Synthesis of (Z)-3-{2,6-difluoro-4-[4-(2-fluoro-(3-heptyloxyphenyl)thiazol-2-ylcarbamoyl)phenyl]-2-methyloxyacrylic acid (B2065)

1H-NMR(DMSO-d6) 13.0(bs, 2H), 7.92(s, 1H), 7.89(s, 1H), 7.60-7.65(m, 2H), 7.13-7.25(m, 2H), 6.61(s, 1H), 4.08(t, 2H, J=6.0 Hz), 3.72(s, 3H), 1.71-1.80(m, 2H), 1.27-1.50(m, 8H), 0.88(t, 3H, J=6.9 Hz).

Example 555

Synthesis of (Z)-3-{2,6-dichloro-4-[4-(2-fluoro-3-heptyloxyphenyl)thiazol-2-ylcarbamoyl]phenyl}-2-methyloxyacrylic acid (B 2066)

1H-NMR(DMSO-d6) 13.6(bs, 1H), 13.0(bs, 1H), 8.25(s, 2H), 7.59-7.66(m, 2H), 7.12-7.24(m, 2H), 6.74(s, 1H), 4.08(t, 2H, J=6.6 Hz), 3.62(s, 3H), 1.70-1.81(m, 2H), 1.26-1.50(m, 8H), 0.88 (t, 3H, J=6.6 Hz).

Example 556

Synthesis of (E)-3-(2,6-difluoro-4-{4-[2-fluoro-(3-methylbutyloxy)phenyl]thiazol-2-ylcarbamoyl}phenyl)-2-methylacrylic acid (B2067)

1H-NMR(DMSO-d6) 13.0(bs, 2H), 7.98(s, 1H), 7.95(s, 1H), 7.60-7.67(m, 2H), 7.34(s, 1H), 7.15-7.25(m, 2H), 4.12(t, 2H, J=6.6 Hz), 1.63-1.87(m, 6H), 0.96(d, 6H, J=6.6 Hz).

Example 557

Synthesis of (Z)-3-(2,6-difluoro-4-{4-[2-fluoro-(3-methylbutyloxy)phenyl]thiazol-2-ylcarbamoyl}phenyl)-2-methyloxyacrylic acid (B2068)

1H-NMR(DMSO-d6) 13.6(bs, 1H), 13.0(bs, 1H), 7.93(s, 1H), 7.90(s, 1H), 7.60-7.68(m, 2H), 7.15-7.26(m, 2H), 6.66(s, 1H), 4.12(t, 2H, J=6.6 Hz), 3.71(s, 3H), 1.76-1.80(m, 1H), 1.63-1.71(m, 2H), 0.96(d, 6H, J=6.6 Hz).

Example 558

Synthesis of (Z)-3-(2,6-dichloro-4-{4-[2-fluoro-3-(3-methylbutyloxy)phenyl]thiazol-2-ylcarbamoyl}phenyl)-2-methyloxyacrylic acid (B2069)

1H-NMR(DMSO-d6) 13.6(bs, 1H), 13.0(bs, 1H), 8.25(s, 2H), 7.60-7.66(m, 2H), 7.15-7.26(m, 2H), 6.74(s, 1H), 4.12(t, 2H, J=6.6 Hz), 3.62(s, 3H), 1.76-1.90(m, 1H), 1.63-1.71(m, 2H), 0.97(d, 6H, J=6.6 Hz).

Example 559

Synthesis of (E)-3-(4-{4-[3-(2-cyclohexylethyloxy)-2-fluorophenyl]thiazol-2-ylcarbamoyl}-2,6-difluorophenyl)-2-methylacrylic acid (B2070)

1H-NMR(DMSO-d6) 13.0(bs, 2H), 7.98(s, 1H), 7.95(s, 1H), 7.59-7.66(m, 2H), 7.34(s, 1H), 7.14-7.24(m, 2H), 4.12(t, 2H, J=6.6 Hz), 1.41-1.83(m, 11H), 0.88-1.31(m, 5H).

Example 560

Synthesis of (E)-3-(2,6-dichloro-4-{4-[3-(2-cyclohexylethyloxy)-2-fluorophenyl]thiazol-2-ylcarbamoyl}phenyl)-2-methylacrylic acid (B 2071)

1H-NMR(DMSO-d6) 13.0(bs, 2H), 8.29(s, 2H), 7.59-7.67(m, 2H), 7.40(s, 1H), 7.14-7.25(m, 2H), 4.12(t, 2H, J=6.6 Hz), 1.46-1.70(m, 11H), 0.91-1.30(m, 5H).

Example 561

Synthesis of (Z)-3-(4-{4-[3-(2-cyclohexylethyloxy)-2-fluorophenyl]thiazol-2-ylcarbamoyl)-2,6-difluorophenyl)-2-methyloxyacrylic acid (B2072)

1H-NMR(DMSO-d6) 13.0(bs, 2H), 7.92(s, 1H), 7.89(s, 1H), 7.59-7.66(m, 2H), 7.13-7.25(m, 2H), 6.61(s, 1H), 4.12(t, 2H, J=6.6 Hz), 3.72(s, 3H), 1.46-1.80(m, 8H,), 0.91-1.30(m, 5H).

Example 562

Synthesis of (Z)-3-{2,6-dichloro-4-[4-(3-cyclohexylmethyloxy-2-fluorophenyl)thiazol-2-ylcarbamoyl]phenyl}-2-methyloxyacrylic acid (B2073)

1H-NMR(DMSO-d6) 13.0(bs, 2H), 8.25(s, 2H), 7.59-7.66(m, 2H), 7.14-7.24(m, 2H), 6.73(s, 1H), 4.12(t, 2H, J=6.6 Hz), 3.61(s, 3H), 1.46-1.71(m, 8H), 0.95-1.30(m, 5H).

Example 563

Synthesis of (E)-3-{4-[4-(3-cyclohexylmethyloxy-2-fluorophenyl)thiazol-2-ylcarbamoyl]-2,6-difluorophenyl}-2-methylacrylic acid (B2074)

1H-NMR(DMSO-d6) 13.0(bs, 2H), 7.98(s, 1H), 7.95(s, 1H), 7.59-7.66(m, 2H), 7.34(s, 1H), 7.12-7.24(m, 2H), 3.90(d, 2H, J=5.7 Hz), 1.61-1.89(m, 9H), 1.03-1.55(m, 5H).

Example 564

Synthesis of (E)-3-{2,6-dichloro-4-[4-(3-cyclohexylmethyloxy-2-fluorophenyl)thiazol-2-ylcarbamoyl]phenyl}-2-methylacrylic acid (B2075)

1H-NMR(DMSO-d6) 13.0(bs, 2H), 8.29(s, 2H), 7.59-7.66(m, 2H), 7.41(s, 1H), 7.12-7.24(m, 2H), 3.90(d, 2H, J=6.0 Hz), 1.62-1.88(m, 9H), 1.02-1.37(m, 5H).

Example 565

Synthesis of (Z)-3-{4-[4-(3-cyclohexylmethyloxy-2-fluorophenyl)thiazol-2-ylcarbamoyl]-2,6-difluorophenyl}-2-methyloxyacrylic acid (B2076)

1H-NMR(DMSO-d6) 13.0(bs, 2H), 7.93(s, 1H), 7.90(s, 1H), 7.60-7.67(m, 2H), 7.12-7.25(m, 2H), 6.66(s, 1H), 3.90(d, 2H, J=5.4 Hz), 3.71(s, 3H), 1.62-1.89(m, 6H), 1.02-1.37(m, 5H).

Example 566

Synthesis of (Z)-3-{2,6-dichloro-4-[4-(3-cyclohexylmethyloxy-2-fluorophenyl)thiazol-2-ylcarbamoyl]phenyl}-2-methyloxyacrylic acid (B2077)

1H-NMR(DMSO-d6) 13.0(bs, 2H), 8.25(s, 2H), 7.59-7.66(m, 2H), 7.13-7.24(m, 2H), 6.73(s, 1H), 3.90(d, 2H, J=5.7 Hz), 3.61(s, 3H), 1.62-1.89(m, 6H), 1.03-1.35(m, 5H).

Example 567

Synthesis of (E)-3-{2,6-difluoro-4-[4-(3-isobutyloxymethyl-2-methyloxyphenyl)thiazol-2-ylcarbamoyl]phenyl}-2-methylacrylic acid (B2078)

1H NMR(DMSO-d6) 13.01(bs, 2H), 7.95-7.99(m, 3H), 7.74(s, 1H), 7.38-7.41(m, 1H), 7.34(s, 1H), 7.25(t, 1H, J=7.5 Hz), 4.57(s, 2H), 3.66(s, 3H), 3.29(d, 2H, J=6.9 Hz), 1.81-1.91(m, 1H), 1.81(s, 3H), 0.91(d, 6H, J=6.6 Hz).

Example 568

Synthesis of (E)-3-{2,6-difluoro-4-[4-(3-isobutyloxymethyl-2-methyloxyphenyl)thiazol-2-ylcarbamoyl]phenyl}-2-methyloxyacrylic acid (B2079)

1H NMR(DMSO-d6) 12.92(bs, 2H), 7.90-7.99(m, 3H), 7.74(s, 1H), 7.39(d, 1H, J=7.5 Hz), 7.25(t, 1H, J=7.5 Hz), 6.65(s, 1H), 4.57(s, 2H), 3.72(s, 3H), 3.65(s, 3H), 3.29(d, 2H, J=6.6 Hz), 1.83-1.91(m, 1H), 0.91(d, 6H, J=6.6 Hz).

Example 569

Synthesis of (E)-3-{2,6-dichloro-4-[4-(3-isobutyloxymethyl-2-methyloxyphenyl)thiazol-2-ylcarbamoyl]phenyl}-2-methylacrylic acid (B2080)

1H NMR(DMSO-d6) 12.99(bs, 2H), 8.29(s, 2H), 7.96-7.99(m, 1H), 7.74(s, 1H), 7.38-7.41(m, 2H), 7.25(t, 1H, J=7.5 Hz), 4.57(s, 2H), 3.66(s, 3H), 3.29(d, 2H, J=6.6 Hz), 1.83-1.92(m, 1H), 1.69(s, 3H), 0.91(d, 6H, J=6.6 Hz).

Example 570

Synthesis of (Z)-3-{2,6-dichloro-4-[4-(3-isobutyloxymethyl-2-methyloxyphenyl)thiazol-2-ylcarbamoyl]phenyl}-2-methyloxyacrylic acid (B2081)

1H NMR(DMSO-d6) 12.97(bs, 2H), 8.25(s, 2H), 7.97(dd, 1H, J=1.5 Hz, 7.8 Hz), 7.74(s, 1H), 7.39(dd, 1H, J=1.5 Hz, 7.5 Hz), 7.25(t, 1H, J=7.8 Hz), 6.72(s, 1H), 4.57(s, 2H), 3.66(s, 3H), 3.62(s, 3H), 3.29(d, 2H, J=6.6 Hz), 1.83-1.92(m, 1H), 0.91(d, 6H, J=6.6 Hz).

Example 571

Synthesis of (E)-3-{4-[4-(3-cyclohexylmethyloxymethyl-2-methyloxyphenyl)thiazol-2-ylcarbamoyl]-2,6-difluorophenyl}-2-methylacrylic acid (B2082)

1H NMR(DMSO-d6) 12.93(bs, 2H), 7.95-7.99(m, 3H), 7.74(s, 1H), 7.39(dd, 1H, J=1.8 Hz, 7.5 Hz), 7.34(s, 1H), 7.24(t, 1H, J=7.5 Hz), 4.57(s, 2H), 3.66(s, 3H), 3.39(d, 2H, J=6.9 Hz), 2.12-2.21(m, 1H), 1.81(s, 3H), 1.65-1.73(m, 2H), 1.47-1.58(m, 4H), 1.21-1.27(m, 2H).

Example 572

Synthesis of (Z)-3-{4-[4-(3-cyclohexylmethyloxymethyl-2-methyloxyphenyl)thiazol-2-ylcarbamoyl]-2,6-difluorophenyl}-2-methyloxyacrylic acid (B2083)

1H NMR(DMSO-d6) 12.93(bs, 2H), 7.90-7.99(m, 3H), 7.74(s, 1H), 7.39(dd, 1H, J=1.8 Hz, 7.5 Hz), 7.24(t, 1H, J=7.5 Hz), 6.65(s, 1H), 4.57(s, 2H), 3.72(s, 3H), 3.66(s, 3H), 3.39(d, 2H, J=6.9 Hz), 2.11-2.21(m, 1H), 1.66-1.73(m, 2H), 1.47-1.58(m, 4H), 1.23-1.30(m, 2H).

Example 573

Synthesis of (E)-3-{2,6-dichloro-4-[4-(3-cyclopentylmethyloxymethyl-2-methyloxyphenyl)thiazol-2-ylcarbamoyl]phenyl}-2-methylacrylic acid (B 2084)

1H NMR(DMSO-d6) 12.99(bs, 2H), 8.29(s, 2H), 7.97(dd, 1H, J=1.8 Hz, 7.8 Hz), 7.73(s, 1H), 7.38-7.41(m, 2H), 7.24(t, 1H, J=7.5 Hz), 4.57(s, 2H), 3.66(s, 3H), 3.39(d, 2H, J=7.2 Hz), 2.11-2.19(m, 1H), 1.69(s, 3H), 1.65-1.73(m, 2H), 1.49-1.58(m, 4H), 1.21-1.27(m, 2H).

Example 574

Synthesis of (Z)-3-{2,6-dichloro-4-[4-(3-cyclopentylmethyloxymethyl-2-methylphenyl)thiazol-2-ylcarbamoyl]phenyl}-2-methyloxyacrylic acid (B2085)

1H NMR(DMSO-d6) 12.95(bs, 2H), 8.25(s, 2H), 7.97(dd, 1H, J=1.8 Hz, 7.8 Hz), 7.73(s, 1H), 7.39(dd, 1H, J=1.8 Hz, 7.5 Hz), 7.24(t, 1H, J=7.8 Hz), 6.73(s, 1H), 4.57(s, 2H), 3.66(s, 3H), 3.62(s, 3H), 3.39(d, 2H, J=7.2 Hz), 2.11-2.21(m, 1H), 1.65-1.71(m, 2H), 1.51-1.58(m, 4H), 1.21-1.27(m, 2H).

Example 575

Synthesis of (E)-3-{2,6-difluoro-4-[4-(2-fluoro-3-isobutyloxyphenyl)thiazol-2-ylcarbamoyl]phenyl}-2-methylacrylic acid (B 2086)

1H NMR(DMSO-d6) 12.85(bs, 2H), 7.79(d, 2H, J=8.4 Hz), 7.43-7.48(m, 2H), 7.16(s, 1H), 6.96-7.07(m, 2H), 3.70 (d, 2H, J=6.6 Hz), 1.86-1.92(m, 1H), 1.63(s, 3H), 0.84(d, 6H, J=6.6 Hz).

Example 576

Synthesis of (E)-3-{2,6-dichloro-4-[4-(2-fluoro-3-isobutyloxyphenyl)thiazol-2-ylcarbamoyl}phenyl)-2-methylacrylic acid (B 2087)

1H NMR(DMSO-d6) 12.77(bs, 2H), 8.11(s, 2H), 7.43-7.48(m, 2H), 7.23(d, 1H, J=1.2 Hz), 6.98-7.07(m, 2H), 3.70 (d, 2H, J=6.3 Hz), 1.86-1.95(m, 1H), 1.52(s, 3H), 0.84(d, 6H, J=6.6 Hz).

Example 577

Synthesis of (E)-3-{2,6-difluoro-4-[4-(2-fluoro-3-(2-methylbutyloxyphenyl)thiazol-2-ylcarbamoyl)phenyl]-2-methylacrylic acid (B2088)

1H NMR(DMSO-d6) 12.84(bs, 2H), 7.79(d, 2H, J=8.4 Hz), 7.43-7.48(m, 2H), 7.16(s, 1H), 6.97-7.07(m, 2H), 3.68-3.81(m, 2H), 1.68-1.73(m, 1H), 1.64(s, 3H), 1.34-1.41(m, 1H), 1.05-1.14(m, 1H), 0.83(d, 3H, J=6.6 Hz), 0.76(t, 3H, J=7.5 Hz).

Example 578

(E)-3-{4-[6-(3,3-dimethylbutyn-1yl)-4,5-dihydronaphtho[1,2-d]thiazol-2-ylcarbamoyl]-2,6-difluorophenyl}-2-methylacrylic acid (B2089)

1H-NMR(DMSO-d6) 12.87 (bs, 2H), 7.93-7.96 (m, 2H), 7.69-7.72 (m, 1H), 7.32 (s 1H), 7.22-7.29 (m, 2H), 3.13-3.18 (m, 2H), 2.99-3.04 (m, 2H), 1.33 (s, 9H).

Example 579

Synthesis of (Z)-3-(2,6-difluoro-4-{4-[2-methyloxy-3-(2-propyloxyethyl)phenyl]thiazol-2-ylcarbamoyl}phenyl)-2-methyloxyacrylic acid (B2090)

1H-NMR(DMSO-d6) 13.57 (bs, 1H), 12.93 (bs, 1H), 7.86-7.92 (m, 3H), 7.72 (s, 1H), 7.27-7.30 (m, 1H), 7.14-7.19 (m,

1H), 6.66 (s, 1H), 3.71 (s, 3H), 3.60-3.65 (m, 5H), 3.70 (t, 2H, J=6.6 Hz), 2.91 (t, 2H, J=6.9 Hz), 1.47-1.54 (m, 2H), 0.85 (t, 3H, J=7.5 Hz).

Example 580

Synthesis of (E)-3-{2,6-dichloro-4-[4-(2-fluoro-3-(3-methylbutyloxyphenyl)thiazol-2-ylcarbamoyl]phenyl}-2-methylacrylic acid (B2097)

1H-NMR(DMSO-d6) 13.0(bs, 2H), 8.29(s, 2H), 7.59-7.66 (m, 2H), 7.40(s, 1H), 7.15-7.25(m, 2H), 4.11(t, 2H, J=6.6 Hz), 1.76-1.87(m, 1H), 1.63-1.72(m, 5H), 0.96(d, 6H, J=6.6 Hz).

Example 581

Synthesis of (E)-3-{2,6-dichloro-4-[4-(2-fluoro-3-(2-methylbutyloxyphenyl)thiazol-2-ylcarbamoyl]phenyl}-2-methylacrylic acid (B2098)

1H NMR(DMSO-d6) 12.82(bs, 2H), 8.12(s, 2H), 7.43-7.48(m, 2H), 7.23(s, 1H), 6.96-7.07(m, 2H), 3.68-3.81(m, 2H), 1.68-1.70(m, 1H), 1.52(s, 3H), 1.36-1.43(m, 1H), 1.07-1.14(m, 1H), 0.83(d, 3H, J=6.9 Hz), 0.76(t, 3H, J=6.9 Hz).

Example 582

(E)-3-(4-{4-[2-ethyloxy-3-(1-methyloxydecyl)phenyl]thiazol-2-ylcarbamoyl}-2,6-difluorophenyl)-2-methylacrylic acid (B2099)

1H-NMR(DMSO-d6) 13.00(bs, 2H), 7.93-8.00(m, 2H), 7.86(dd, 1H, J=2.1, 7.8 Hz), 7.70(s, 1H), 7.34(s, 1H), 7.31(dd, 3H, J=2.1, 7.5 Hz), 7.25(t, 1H, J=7.5 Hz), 4.53-4.57(m, 1H), 3.66-3.74(m, 2H), 3.15(s, 3H), 1.81(s, 3H), 1.52-1.78(m, 2H), 1.18-1.50(m, 17H), 0.83-0.87(m, 3H).

Example 583

Synthesis of (Z)-3-{2,6-difluoro-4-[4-(2-fluoro-3-methyloxyphenyl)thiazol-2-ylcarbamoyl]phenyl}-2-methyloxyacrylic acid (B2100)

1H-NMR(DMSO-d6) 13.0(bs, 2H), 7.92(s, 1H), 7.90(s, 1H), 7.60-7.67(m, 2H), 7.13-7.28(m, 2H), 6.66(s, 1H), 3.89 (s, 3H), 3.71(s, 3H).

The following compounds can be synthesized by similar reaction to above-mentioned method.

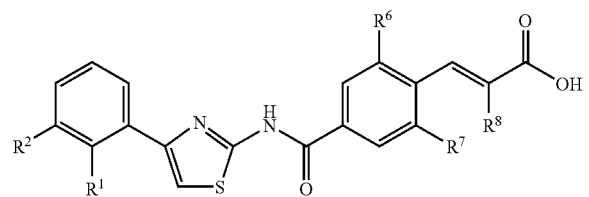

wherein $R^6$, $R^7$, and $R^8$ are each independently fluoro, chloro, or methyl;

$R^1$ is fluoro or methyl;

$R^1$ is methyl, ethyl, n-propyl, isopropyl, n-butyl, isobutyl, tert-butyl, n-pentyl, neopentyl, n-hexyl, isohexyl, 3,3-dimethylbutyl, 1-methyloxyethyl, 1-methyloxypropyl, 1-methyloxy-3-n-propyloxypropyl, 1-methyloxy-3-n-hexyloxypropyl, 1-methyloxybutyl, 1-methyloxy-4-n-pentyloxypropyl, 1-methyloxy-2-methylpropyl, 1-methyloxypentyl, 1-methyloxy-3-methylbutyl, 3-methyloxy-3-methylbutyl, 1-methyloxy-2,2-dimethylpropyl, 1-methyloxyhexyl, 4-methyloxyhexyl, 1-methyloxy-4-methylpentyl, 1-methyloxy-3,3-dimethylbutyl, 1-methyloxyheptyl, 4-methyloxy-4-heptyl, 3-methyloxy-2,4-dimethyl-3-pentyl, 1-methyloxyoctyl, 3-methyloxyoctyl, 1-methyloxynonyl, 1-methyloxydecyl, 3-methyloxydecyl, 1-methyloxyundecyl, 1-methyloxydoecyl, 1-methyloxy-1-cyclohexylmethyl, 1-(4-ethyloxybutyloxy)-1-cyclohexylmethyl, 1-ethyloxyethyl, 1-ethyloxypropyl, 1-ethyloxy-3-n-hexyloxypropyl, 1-(4-ethyloxybutyloxy)propyl, 1-ethyloxybutyl, 1-ethyloxy-4-n-pentyloxybutyl, 1-ethyloxy-2-methylproyl, 1-ethyloxypentyl, 1-ethyloxy-3-methylbutyl, 1-ethyloxy-2,2-dimethylpropyl, 1-ethyloxyhexyl, 1-ethyloxy-3,3-dimethylbutyl, 1-ethyloxyheptyl, 1-ethyloxyoctyl, 1-ethyloxynonyl, 1-ethyloxydecyl, 1-ethyloxyundecyl, 1-ethyloxydodecyl, 1-ethyloxy-1-cyclohexylmethyl, 1-n-propyloxyethyl, 1-n-propyloxypropyl, 3-n-propyloxypropyl, 1-n-propyloxy-3-n-hexyloxypropyl, 1-n-propyloxybutyl, 1-n-propyloxy-4-n-pentyloxybutyl, 1-n-propyloxy-2-methylpropyl, 1-n-propyloxypentyl, 1-n-propyloxy-3-methylbutyl, 1-n-propyloxy-2,2-dimethylpropyl, 1-n-propyloxyhexyl, 1-n-propyloxy-3,3-dimethylbutyl, 1-n-propyloxyheptyl, 1-n-propyloxyoctyl, 1-n-propyloxynonyl, 1-n-propyloxydecyl, 1-n-propyloxyundecyl, 1-n-propyloxydodecyl, 1-n-propyloxy-1-cyclohexylmethyl, 1-isopropyloxyethyl, 1-isopropyloxypropyl, 3-isopropyloxypropyl, 1-isopropyloxy-3-n-hexyloxypropyl, 1-isopropyloxybutyl, 1-iso-propyloxy-4-n-pentyloxybutyl, 1-isopropyloxy-2-methylpropyl, 1-isopropyloxypentyl, 1-isopropyloxy-3-methylbutyl, 1-isopropyloxy-2,2-dimethylpropyl, 1-isopropyloxyhexyl, 1-isopropyloxy-3,3-dimethylbutyl, 1-isopropyloxyheptyl, 1-isopropyloxyoctyl, 1-isopropyloxynonyl, 1-isopropyloxydecyl, 1-isopropyloxyundecyl, 1-isopropyloxydodecyl, 1-isopropyloxy-1-cyclohexylmethyl, 1-n-butyloxyethyl, 1-n-butyloxypropyl, 3-n-butyloxypropyl, 1-n-butyloxybutyl, 1,4-di(n-butyloxy)butyl, 1-n-butyloxy-2-methylpropyl, 1-n-butyloxypentyl, 1-n-butyloxy-3-methylbutyl, 1-n-butyloxy-2,2-dimethylpropyl, 1-n-butyloxyhexyl, 1-n-butyloxy-3,3-dimethylbutyl, 1-n-butyloxyheptyl, 1-n-butyloxyoctyl, 1-n-butylxynonyl, 1-n-butyloxydecyl, 1-n-butyloxyundecyl, 1-n-butyloxydodecyl, 1-n-butyloxy-1-cyclohexylmethyl, 1-isobutyloxyethyl, 1-isobutyloxypropyl, 1-isobutyloxybutyl, 1-isobutyloxy-2-methylpropyl, 1-isobutyloxypentyl, 1-isobutyloxy-3-methylbutyl, 1-isobutyloxy-2,2-dimethylpropyl, 1-isobutyloxyhexyl, 1-isobutyloxy-3,3-dimethylbutyl, 1-isobutyloxyheptyl, 1-isobutyloxyoctyl, 1-isobutylxynonyl, 1-isobutyloxydecyl, 1-isobutyloxyundecyl, 1-isobutyloxydodecyl, 1-isobutyloxy-1-cyclohexylmethyl, 1-t-butyloxyethyl, 1-t-butyloxypropyl, 1-t-butyloxybutyl, 1-t-butyloxy-2-methylpropyl, 1-t-butyloxypentyl, 1-t-butyloxy-3-methylbutyl, 1-t-butyloxy-2,2-dimethylpropyl, 1-t-butyloxyhexyl, 1-t-butyloxy-3,3-dimethylbutyl, 1-t-butyloxyheptyl, 1-t-butyloxyoctyl, 1-t-butyloxynonyl, 1-t-butyloxydecyl, 1-t-butyloxyundecyl, 1-t-butyloxydodecyl, 1-t-butyloxy-1-cyclohexylmethyl, n-pentyloxymethyl, 1-n-pentyloxyethyl, 1-n-pentyloxypropyl, 3-n-pentyloxypropyl, 1-n-pentyloxy-3-methylthiopropyl, 1-n-pentyloxybutyl, 1-n-pentyloxy-2-methylpropyl, 1-n-pentyloxypentyl, 1-n-pentyloxy-3-methylbutyl, 1-n-p entyloxy-2,2-dimethylpropyl, 1-n-pentyloxyhexyl, 1-n-pentyloxy-3,3-dimethylbutyl, 1-n-pentyloxyheptyl, 1-n-pentyloxyoctyl, 1-n-pentyloxynonyl, 1-n-pentyloxydecyl, 1-n-pentyloxyundecyl, 1-n-pentyloxydodecyl, 1-n-pentyloxy-1-cyclohexylmethyl, 1-neopentyloxyethyl, 1-neopentyloxypropyl, 3-neopentyloxypropyl, 1-neopentyloxy-3-methylthiopropyl, 1-neopentyloxybutyl, 1-neopentyloxy-2-methylpropyl, 1-neopentyloxypentyl, 1-neopentyloxy-3-methylbutyl, 1-neopentyloxy-2,2-dimethylpropyl, 1-neopentyloxyhexyl, 1-neopentyloxy-3,3-dimethylbutyl, 1-neopentyloxyheptyl, 1-neopentyloxyoctyl, 1-neopentyloxynonyl, 1-neopentyloxydecyl, 1-neopentyloxyundecyl, 1-neopentyloxydodecyl, 1-neopentyloxy-1-cyclohexylmethyl, 1-n-hexyloxyethyl, 1-n-hexyloxypropyl, 3-n-hexyloxypropyl, 1-n-hexyloxy-3-methylthiopropyl, 1-n-hexyloxybutyl, 1-n-hexyloxy-2-methylpropyl, 1-n-hexyloxypentyl, 1-n-hexyloxy-3-methylbutyl, 1-n-hexyloxy-2,2-dimethylpropyl, 1-n-hexyloxyhexyl, 1-n-hexyloxy-3,3-dimethylbutyl, 1-n-hexyloxyheptyl, 1-n-hexyloxyoctyl, 1-n-hexyloxynonyl, 1-n-hexyloxydecyl, 1-n-hexylloxyundecyl, 1-n-hexyloxydodecyl, 1-n-hexyloxy-1-cyclohexylmethyl, 3-isohexyloxypropyl, 3-(2-ethylbutyloxy)propyl, 3-(3,3-dimethylbutyloxy)propyl, 3-(2-cyclopentylethyloxy)propyl, 1-n-octyloxyethyl, or n-dodecyloxymethyl (Compound No., $R^6$, $R^7$, $R^8$, $R^1$, $R^2$)=(B102, F, F, Me, F, methyl), (B103, F, F, Me, F, ethyl), (B104, F, F, Me, F, n-propyl), (B105, F, F, Me, F, isopropyl), (B106, F, F, Me, F, n-butyl), (B107, F, F, Me, F, isobutyl), (B108, F, F, Me, F, t-butyl), (B109, F, F, Me, F, neopentyl), (B110, F, F, Me, F, n-hexyl), (B111, F, F, OMe, F, methyl), (B112, F, F, OMe, F, ethyl), (B113, F, F, OMe, F, n-propyl), (B114, F, F, OMe, F, isopropyl), (B115, F, F, OMe, F, n-butyl), (B116, F, F, OMe, F, isobutyl), (B117, F, F, OMe, F, t-butyl), (B118, F, F, OMe, F, n-pentyl), (B119, F, F, OMe, F, neopentyl), (B120, F, F, OMe, F, n-hexyl), (B123, F, F, Me, OMe, methyl), (B124, F, F, Me, OMe, ethyl), (B125, F, F, Me, OMe, n-propyl), (B126, F, F, Me, OMe, isopropyl), (B127, F, F, Me, OMe, n-butyl), (B128, F, F, Me, OMe, isobutyl), (B129, F, F, Me, OMe, t-butyl), (B130, F, F, Me, OMe, n-pentyl), (B131, F, F, Me, OMe, neopentyl), (B132, F, F, Me, OMe, n-hexyl), (B133, F, F, Me, OMe, isohexyl), (B135, F, F, OMe, OMe, methyl), (B136, F, F, OMe, OMe, ethyl), (B137, F, F, OMe, OMe, n-propyl), (B138, F, F, OMe, OMe, isopropyl), (B139, F, F, OMe, OMe, n-butyl), (B140, F, F, OMe, OMe, isobutyl), (B141, F, F, OMe, OMe, t-butyl), (B142, F, F, OMe, OMe, n-pentyl), (B143, F, F, OMe, OMe, neopentyl), (B144, F, F, OMe, OMe, n-hexyl), (B145, F, F, OMe, OMe, isohexyl), (B146, F, F, OMe, OMe, 3,3-dimethylbutyl), (B147, Cl, Cl, Me, F, methyl), (B148, Cl, Cl, Me, F, ethyl), (B149, Cl, Cl, Me, F, n-propyl), (B150, Cl, Cl, Me, F, isopropyl), (B151, Cl, Cl, Me, F, n-butyl), (B152, Cl, Cl, Me, F, isobutyl), (B153, Cl, Cl, Me, F, t-butyl), (B154, Cl, Cl, Me, F, n-pentyl), (B155, Cl, Cl, Me, F, neopentyl), (B156, Cl, Cl, Me, F, n-hexyl), (B157, Cl, Cl, Me, F, isohexyl), (B158, Cl, Cl, Me, F, 3,3-dimethylbutyl), (B159, Cl, Cl, OMe, F, methyl), (B160, Cl, Cl, OMe, F, ethyl), (B161, Cl, Cl, OMe, F, n-propyl), (B162, Cl, Cl, OMe, F, isopropyl), (B163, Cl, Cl, OMe, F, n-butyl), (B164, Cl, Cl, OMe, F, isobutyl), (B165, Cl, Cl, OMe, F, t-butyl), (B166, Cl, Cl, OMe, F, n-pentyl), (B167, Cl, Cl, OMe, F, neopentyl), (B168, Cl, Cl, OMe, F, n-hexyl), (B171, Cl, Cl, Me, OMe, methyl), (B172, Cl, Cl, Me, OMe, ethyl), (B173, Cl, Cl, Me, OMe, n-propyl), (B174, Cl, Cl, Me, OMe, isopropyl), (B175, Cl, Cl, Me, OMe, n-butyl), (B176, Cl, Cl, Me, OMe, isobutyl), (B177, Cl, Cl, Me, OMe, t-butyl), (B178, Cl, Cl, Me, OMe, n-pentyl), (B179, Cl, Cl, Me, OMe, neopentyl), (B180, Cl, Cl, Me, OMe, n-hexyl), (B181, Cl, Cl, Me, OMe, isohexyl), (B182, Cl, Cl, Me, OMe, 3,3-dimethylbutyl), (B183, Cl, Cl, OMe, OMe, methyl), (B184, Cl, Cl, OMe, OMe, ethyl), (B185, Cl, Cl, OMe, OMe, n-propyl), (B186, Cl, Cl, OMe, OMe, isopropyl), (B187, Cl, Cl, OMe, OMe, n-butyl), (B188, Cl, Cl, OMe, OMe, isobutyl), (B189, Cl, Cl, OMe, OMe, t-butyl), (B190, Cl, Cl, OMe, OMe, n-pentyl), (B191, Cl, Cl, OMe, OMe, neopentyl), (B192, Cl, Cl, OMe, OMe, n-hexyl), (B193, Cl, Cl, OMe, OMe, isohexyl), (B194, Cl, Cl, OMe, OMe, 3,3-dimethylbutyl), (B196, F, F, Me, F, 1-methyloxypropyl), (B197, F, F, Me, F, 1-methyloxybutyl), (B198, F, F, Me, F, 1-methyloxy-2-methylpropyl), (B199, F, F, Me, F, 1-methyloxypentyl), (B200, F, F, Me, F, 1-methyloxy-3-methylbutyl), (B201, F, F, Me, F, 3-methyloxyoctyl), (B202, F, F, Me, F, 1-ethyloxyethyl), (B203, F, F, Me, F, 1-ethyloxy-3-n-hexyloxypropyl), (B204, F, F, Me, F, 1-ethyloxy-4-n-pentyloxybutyl), (B205, F, F, Me, F, 1-ethyloxybutyl), (B206, F, F, Me, F, 1-ethyloxy-2-methylpropyl), (B207, F, F, Me, F, 1-ethyloxy-3-methylbutyl), (B208, F, F, Me, F, 1-ethyloxyhexyl), (B209, F, F, Me, F, 1-ethyloxy-3,3-dimethylbutyl), (B210, F, F, Me, F, 1-ethyloxyheptyl), (B211, F, F, Me, F, 1-ethyloxyoctyl), (B212, F, F, Me, F, 1-ethyloxynonyl), (B213, F, F, Me, F, 1-ethyloxydecyl), (B214, F, F, Me, F, 1-ethyloxyundecyl), (B215, F, F, Me, F, 1-ethyloxydodecyl), (B217, F, F, Me, F, 1-n-propyloxypropyl), (B218, F, F, Me, F, 3-n-propyloxypropyl), (B219, F, F, Me, F, 1-n-propyloxy-3-n-hexyloxypropyl), (B220, F, F, Me, F, 1-n-propyloxy-4-n-pentyloxybutyl), (B221, F, F, Me, F, 1,4-di(n-propyloxy)butyl), (B222, F, F, Me, F, 1-n-propyloxy-2-methylpropyl), (B223, F, F, Me, F, 1-n-propyloxy-3-methylbutyl), (B224, F, F, Me, F, 1-n-propyloxy-2,2-dimethylpropyl), (B225, F, F, Me, F, 1-n-propyloxyhexyl), (B226, F, F, Me, F, 1-n-propyloxy-3,3-dimethylbutyl), (B227, F, F, Me, F, 1-n-propyloxyheptyl), (B228, F, F, Me, F, 1-n-propyloxyoctyl), (B229, F, F, Me, F, 1-n-propyloxynonyl), (B230, F, F, Me, F, 1-n-propyloxydecyl), (B231, F, F, Me, F, 1-n-propyloxyundecyl), (B232, F, F, Me, F, 1-n-propyloxydodecyl), (B234, F, F, Me, F, 1-isopropyloxyethyl), (B235, F, F, Me, F, 1-isopropyloxypropyl), (B236, F, F, Me, F, 3-isopropyloxypropyl), (B237, F, F, Me, F, 1-isopropyloxy-3-n-hexyloxypropyl), (B238, F, F, Me, F, 1-isopropyloxybutyl), (B239, F, F, Me, F, 1-isopropyloxy-4-n-pentyloxybutyl), (B240, F, F, Me, F, 1-isopropyloxy-2-methylpropyl), (B241, F, F, Me, F, 1-isopropyloxypentyl), (B242, F, F, Me, F, 1-isopropyloxy-3-methylbutyl), (B243, F, F, Me, F, 1-isopropyloxy-2,2-dimethylpropyl), (B244, F, F, Me, F, 1-isopropyloxyhexyl), (B245, F, F, Me, F, 1-isopropyloxy-3,3-dimethylbutyl), (B246, F, F, Me, F, 1-isopropyloxyheptyl), (B247, F, F, Me, F, 1-isopropyloxyoctyl), (B248, F, F, Me, F, 1-isopropyloxynonyl), (B249, F, F, Me, F, 1-isopropyloxydecyl), (B250, F, F, Me, F, 1-isopropyloxyundecyl), (B251, F, F, Me, F, 1-isopropyloxydodecyl), (B252, F, F, Me, F, 1-isopropyloxy-1-cyclohexylmethyl), (B253, F, F, Me, F, 1-n-butyloxy-2-methylpropyl), (B254, F, F, Me, F, 1-n-butyloxy-3-methylbutyl), (B256, F, F, Me, F, 1-n-butyloxyhexyl), (B257, F, F, Me, F, 1-n-butyloxy-3,3-dimethylbutyl), (B258, F, F, Me, F, 1-n-butyloxyheptyl), (B259, F, F, Me, F, 1-n-butyloxyoctyl), (B260, F, F, Me, F, 1-n-butyloxynonyl), (B261, F, F, Me, F, 1-n-butyloxydecyl), (B262, F, F, Me, F, 1-n-butyloxyundecyl), (B263, F, F, Me, F, 1-n-butyloxydodecyl), (B265, F, F, Me, F, 1-isobutyloxyethyl), (B266, F, F, Me, F, 1-isobutyloxypropyl), (B267, F, F, Me, F, 1-isobutyloxybutyl), (B268, F, F, Me, F, 1-isobutyloxy-2-methylpropyl), (B269, F, F, Me, F, 1-isobutyloxypentyl), (B270, F, F, Me, F, 1-isobutyloxy-3-methylbutyl), (B271, F, F, Me, F, 1-isobutyloxy-2,2-dimethylpropyl), (B272, F, F, Me, F, 1-isobutyloxyhexyl), (B273, F, F, Me, F, 1-isobutyloxy-3,3-dimethylbutyl), (B274, F, F, Me, F, 1-isobutyloxyheptyl), (B275, F, F, Me, F, 1-isobutyloxyoctyl), (B276, F, F, Me, F, 1-isobutyloxyynonyl), (B277, F, F, Me, F, 1-isobutyloxydecyl), (B278, F, F, Me, F, 1-isobutyloxyundecyl), (B279, F, F, Me, F, 1-isobutyloxydodecyl), (B280, F, F, Me, F, 1-isobutyloxy-1-cyclohexylmethyl), (B281, F, F, Me, F, 1-t-butyloxyethyl), (B282, F, F, Me, F, 1-t-butyloxypropyl), (B283, F, F, Me, F, 1-t-butyloxybutyl), (B284, F, F, Me, F, 1-t-butyloxy-2-methylpropyl), (B285, F, F, Me, F, 1-t-butyloxypentyl), (B286, F, F, Me, F, 1-t-butyloxy-3-methylbutyl), (B287, F, F, Me, F, 1-t-butyloxy-2,2-dimethylpropyl), (B288, F, F, Me, F, 1-t-butyloxyhexyl), (B289, F, F, Me, F, 1-t-butyloxy-3,3-dimethylbutyl), (B290, F, F, Me, F, 1-t-butyloxyheptyl), (B291, F, F, Me, F, 1-t-butyloxyoctyl), (B292, F, F, Me, F, 1-t-butyloxynonyl), (B293, F, F, Me, F, 1-t-butyloxydecyl), (B294, F, F, Me, F, 1-t-butyloxyundecyl), (B295, F, F, Me, F, 1-t-butyloxyydodecyl), (B296, F, F, Me, F, 1-t-butyloxy-1-cyclohexylmethyl), (B297, F, F, Me, F, 1-n-pentyloxy-2-methylpropyl), (B298, F, F, Me, F, 1-n-pentyloxy-3-methylbutyl), (B299, F, F, Me, F, 1-n-pentyloxyhexyl), (B300, F, F, Me, F, 1-n-pentyloxy-3,3-dimethylbutyl), (B301, F, F, Me, F, 1-n-pentyloxyheptyl), (B302, F, F, Me, F, 1-n-pentyloxyoctyl), (B303, F, F, Me, F, 1-n-pentyloxynonyl), (B304, F, F, Me, F, 1-n-pentyloxydecyl), (B305, F, F, Me, F, 1-n-pentyloxyundecyl), (B306, F, F, Me, F, 1-n-pentyloxydodecyl), (B307, F, F, Me, F, 1-neopentyloxyethyl), (B308, F, F, Me, F, 1-neopentyloxypropyl), (B309, F, F, Me, F, 1-neopentyloxybutyl), (B310, F, F, Me, F, 1-neopentyloxy-2-methylpropyl), (B311, F, F, Me, F, 1-neopentyloxypentyl), (B312, F, F, Me, F, 1-neopentyloxy-3-methylbutyl), (B313, F, F, Me, F, 1-neopentyloxy-2,2-dimethylpropyl), (B314, F, F, Me, F, 1-neopentyloxyhexyl), (B315, F, F, Me, F, 1-neopentyloxy-3,3-dimethylbutyl), (B316, F, F, Me, F, 1-neopentyloxyheptyl), (B317, F, F, Me, F, 1-neopentyloxyoctyl), (B318, F, F, Me, F, 1-neopentyloxynonyl), (B319, F, F, Me, F, 1-neopentyloxydecyl), (B320, F, F, Me, F, 1-neopentyloxyundecyl), (B321, F, F, Me, F, 1-neopentyloxydodecyl), (B322, F, F, Me, F, 1-neopentyloxy-1-cyclohexylmethyl), (B323, F, F, Me, F, 1-n-hexyloxyethyl), (B324, F, F, Me, F, 1-n-hexyloxybutyl), (B325, F, F, Me, F, 1-n-hexyloxy-2-methylpropyl), (B326, F, F, Me, F, 1-n-hexyloxypentyl), (B327, F, F, Me, F, 1-n-hexyloxy-3-methylbutyl), (B328, F, F, Me, F, 1-n-hexyloxy-2,2-dimethylpropyl), (B329, F, F, Me, F, 1-n-hexyloxyhexyl), (B330, F, F, Me, F, 1-n-hexyloxy-3,3-dimethylbutyl), (B331, F, F, Me, F, 1-n-hexyloxyheptyl), (B332, F, F, Me, F, 1-n-hexyloxyoctyl), (B333, F, F, Me, F, 1-n-hexyloxynonyl), (B334, F, F, Me, F, 1-n-hexyloxydecyl), (B335, F, F, Me, F, 1-n-hexyloxyundecyl), (B336, F, F, Me, F, 1-n-hexyloxydodecyl), (B337, F, F, Me, F, 1-n-hexyloxy-1-cyclohexylmethyl), (B338, F, F, Me, OMe, 1-methyloxyethyl), (B339, F, F, Me, OMe, 1-methyloxypropyl), (B340, F, F, Me, OMe, 1-methyloxy-3-n-hexyloxypropyl), (B341, F, F, Me, OMe, 1-methyloxybutyl), (B342, F, F, Me, OMe, 1-methyloxy-4-n-pentyloxybutyl), (B343, F, F, Me, OMe, 1-methyloxy-2-methylpropyl), (B344, F, F, Me, OMe, 1-methyloxypentyl), (B345, F, F, Me, OMe, 1-methyloxy-3-methylbutyl), (B346, F, F, Me, OMe, 1-methyloxy-2,2-dimethylpropyl), (B350, F, F, Me, OMe, 1-methyloxyheptyl), (B351, F, F, Me, OMe, 1-methyloxyoctyl), (B352, F, F, Me, OMe, 3-methyloxyoctyl), (B353, F, F, Me, OMe, 1-methyloxynonyl), (B356, F, F, Me, OMe, 1-methyloxydodecyl), (B357, F, F, Me, OMe, 1-methyloxy-1-cyclohexylmethyl), (B358, F, F, Me, OMe, 1-(4-ethyloxybutyloxy)-1-cyclohexylmethyl), (B359, F, F, Me, OMe, 1-ethyloxyethyl), (B360, F, F, Me, OMe, 1-(4-ethyloxybutyloxy)propyl), (B361, F, F, Me, OMe, 1-ethyloxypropyl), (B362, F, F, Me, OMe, 1-ethyloxy-3-n-hexyloxypropyl), (B363, F, F, Me, OMe, 1-ethyloxybutyl), (B364, F, F, Me, OMe, 1-ethyloxy-3-n-pentylbutyl), (B365, F, F, Me, OMe, 1-ethyloxy-2-methylpropyl), (B366, F, F, Me, OMe, 1-ethyloxypentyl), (B367, F, F, Me, OMe, 1-ethyloxy-3-methylbutyl), (B368, F, F, Me, OMe, 1-ethyloxy-2,2-dimethylpropyl), (B369, F, F, Me, OMe, 1-ethyloxyhexyl), (B370, F, F, Me, OMe, 1-ethyloxy-3,3-dimethylbutyl), (B371, F, F, Me, OMe, 1-ethyloxyheptyl), (B372, F, F, Me, OMe, 1-ethyloxyoctyl), (B 373, F, F, Me, OMe, 1-ethyloxynonyl), (B374, F, F, Me, OMe, 1-ethyloxydecyl), (B375, F, F, Me, OMe, 1-ethyloxyundecyl), (B376, F, F, Me, OMe, 1-ethyloxydodecyl), (B377, F, F, Me, OMe, 1-ethyloxy-1-cyclohexylmethyl), (B378, F, F, Me, OMe, 1-n-propyloxyethyl), (B379, F, F, Me, OMe, 1-n-propyloxypropyl), (B381, F, F, Me, OMe, 1-n-propyloxy-3-n-hexyloxypropyl), (B382, F, F, Me, OMe, 1-n-propyloxybutyl), (B383, F, F, Me, OMe, 1-n-propyloxy-4-n-pentyloxybutyl), (B384, F, F, Me, OMe, 1,4-di(n-propyloxy)butyl), (B385, F, F, Me, OMe, 1-n-propyloxy-2-methylpropyl), (B386, F, F, Me, OMe, 1-n-propyloxypentyl), (B387, F, F, Me, OMe, 1-n-propyloxy-3-methylbutyl), (B388, F, F, Me, OMe, 1-n-propyloxy-2,2-dimethylpropyl), (B389, F, F, Me, OMe, 1-n-propyloxyhexyl), (B390, F, F, Me, OMe, 1-n-propyloxy-3,3-dimethylbutyl), (B391, F, F, Me, OMe, 1-n-propyloxyheptyl), (B392, F, F, Me, OMe, 1-n-propyloxyoctyl), (B393, F, F, Me, OMe, 1-n-propyloxynonyl), (B394, F, F, Me, OMe, 1-n-propyloxydecyl), (B395, F, F, Me, OMe, 1-n-propyloxyundecyl), (B396, F, F, Me, OMe, 1-n-propyloxydodecyl), (B398, F, F, Me, OMe, 1-isopropyloxyethyl), (B399, F, F, Me, OMe, 1-isopropyloxypropyl), (B400, F, F, Me, OMe, 3-isopropyloxypropyl), (B401, F, F, Me, OMe, 1-isopropyloxy-3-n-hexyloxypropyl), (B402, F, F, Me, OMe, 1-isopropyloxybutyl), (B403, F, F, Me, OMe, 1-isopropyloxy-4-n-pentyloxybutyl), (B404, F, F, Me, OMe, 1-isopropyloxy-2-methylpropyl), (B405, F, F, Me, OMe, 1-isopropyloxypentyl), (B406, F, F, Me, OMe, 1-isopropyloxy-3-methylbutyl), (B407, F, F, Me, OMe, 1-isopropyloxy-2,2-dimethylpropyl), (B408, F, F, Me, OMe, 1-isopropyloxyhexyl), (B409, F, F, Me, OMe, 1-isopropyloxy-3,3-dimethylbutyl), (B410, F, F, Me, OMe, 1-isopropyloxyheptyl), (B411, F, F, Me, OMe, 1-isopropyloxyoctyl), (B412, F, F, Me, OMe, 1-isopropyloxynonyl), (B413, F, F, Me, OMe, 1-isopropyloxydecyl), (B414, F, F, Me, OMe, 1-isopropyloxyundecyl), (B415, F, F, Me, OMe, 1-isopropyloxydodecyl), (B416, F, F, Me, OMe, 1-isopropyloxy-1-cyclohexylmethyl), (B417, F, F, Me, OMe, 1-n-butyloxyethyl), (B420, F, F, Me, OMe, 1-n-butyloxybutyl), (B421, F, F, Me, OMe, 1,4-di(n-butyloxy)butyl), (B422, F, F, Me, OMe, 1-n-butyloxy-2-methylpropyl), (B423, F, F, Me, OMe, 1-n-butyloxypentyl), (B424, F, F, Me, OMe, 1-n-butyloxy-3-methylbutyl), (B426, F, F, Me, OMe, 1-n-butyloxyhexyl), (B427, F, F, Me, OMe, 1-n-butyloxy-3,3-dimethylbutyl), (B428, F, F, Me, OMe, 1-n-butyloxyheptyl), (B429, F, F, Me, OMe, 1-n-butyloxyoctyl), (B430, F, F, Me, OMe, 1-n-butyloxynonyl), (B431, F, F, Me, OMe, 1-n-butyloxydecyl), (B432, F, F, Me, OMe, 1-n-butyloxyundecyl), (B433, F, F, Me, OMe, 1-n-butyloxydodecyl), (B434, F, F, Me, OMe, 1-n-butyloxy-l-cyclohexylmethyl), (B435, F, F, Me, OMe, 1-isobutyloxyethyl), (B436, F, F, Me, OMe, 1-isobutyloxypropyl), (B437, F, F, Me, OMe, 1-isobutyloxybutyl), (B438, F, F, Me, OMe, 1-isobutyloxy-2-methylpropyl), (B439, F, F, Me, OMe, 1-isobutyloxypentyl), (B440, F, F, Me, OMe, 1-isobutyloxy-3-methylbutyl), (B441, F, F, Me, OMe, 1-isobutyloxy-2,2-dimethylpropyl), (B442, F, F, Me, OMe, 1-isobutyloxyhexyl), (B443, F, F, Me, OMe, 1-isobutyloxy-3,3-dimethylbutyl), (B444, F, F, Me, OMe, 1-isobutyloxyheptyl), (B445, F, F, Me, OMe, 1-isobutyloxyoctyl), (B446, F, F, Me, OMe, 1-isobutyloxyynonyl), (B447, F, F, Me, OMe, 1-isobutyloxydecyl), (B448, F, F, Me, OMe, 1-isobutyloxyundecyl), (B449, F, F, Me, OMe, 1-isobutyloxydodecyl), (B450, F, F, Me, OMe, 1-isobutyloxy-1-cyclohexylmethyl), (B451, F, F, Me, OMe, 1-t-butyloxyethyl), (B452, F, F, Me, OMe, 1-t-butyloxypropyl), (B453, F, F, Me, OMe, 1-t-butyloxybutyl), (B454, F, F, Me, OMe, 1-t-butyloxy-2-methylpropyl), (B455, F, F, Me, OMe, 1-t-butyloxypentyl), (B456, F, F, Me, OMe, 1-t-butyloxy-3-methylbutyl), (B457, F, F, Me, OMe, 1-t-butyloxy-2,2-dimethylpropyl), (B458, F, F, Me, OMe, 1-t-butyloxyhexyl), (B459, F, F, Me, OMe, 1-t-butyloxy-3,3-dimethylbutyl), (B460, F, F, Me, OMe, 1-t-butyloxyheptyl), (B461, F, F, Me, OMe, 1-t-butyloxyoctyl), (B462, F, F, Me, OMe, 1-t-butyloxynonyl), (B463, F, F, Me, OMe, 1-t-butyloxydecyl), (B464, F, F, Me, OMe, 1-t-butyloxyundecyl), (B465, F, F, Me, OMe, 1-t-butyloxydodecyl), (B466, F, F, Me, OMe, 1-t-butyloxy-1-cyclohexylmethyl), (B467, F, F, Me, OMe, 1-n-pentyloxyethyl), (B468, F, F, Me, OMe, 1-n-pentyloxypropyl), (B469, F, F, Me, OMe, 3-n-pentyloxypropyl), (B470, F, F, Me, OMe, 1-n-pentyloxy-3-methylthiopropyl), (B471, F, F, Me, OMe, 1-n-pentyloxybutyl), (B472, F, F, Me, OMe, 1-n-pentyloxy-2-methylpropyl), (B473, F, F, Me, OMe, 1-n-pentyloxypentyl), (B474, F, F, Me, OMe, 1-n-pentyloxy-3-methylbutyl), (B475, F, F, Me, OMe, 1-n-pentyloxy-2,2-dimethylpropyl), (B476, F, F, Me, OMe, 1-n-pentyloxyhexyl), (B477, F, F, Me, OMe, 1-n-pentyloxy-3,3-dimethylbutyl), (B478, F, F, Me, OMe, 1-n-pentyloxyheptyl), (B479, F, F, Me, OMe, 1-n-pentyloxyoctyl), (B480, F, F, Me, OMe, 1-n-pentyloxynonyl), (B481, F, F, Me, OMe, 1-n-pentyloxydecyl), (B482, F, F, Me, OMe, 1-n-pentyloxyundecyl), (B483, F, F, Me, OMe, 1-n-pentyloxydodecyl), (B484, F, F, Me, OMe, 1-n-pentyloxy1-cyclohexylmethyl), (B485, F, F, Me, OMe, 1-isopentyloxypropyl), (B486, F, F, Me, OMe, 1-neopentyloxyethyl), (B487, F, F, Me, OMe, 1-neopentyloxypropyl), (B489, F, F, Me, OMe, 1-neopentyloxybutyl), (B490, F, F, Me, OMe, 1-neopentyloxy-2-methylpropyl), (B491, F, F, Me, OMe, 1-neopentyloxypentyl), (B492, F, F, Me, OMe, 1-neopentyloxy-3-methylbutyl), (B493, F, F, Me, OMe, 1-neopentyloxy-2,2-dimethylpropyl), (B494, F, F, Me, OMe, 1-neopentyloxyhexyl), (B495, F, F, Me, OMe, 1-neopentyloxy-3,3-dimethylbutyl), (B496, F, F, Me, OMe, 1-neopentyloxyheptyl), (B497, F, F, Me, OMe, 1-neopentyloxyoctyl), (B498, F, F, Me, OMe, 1-neopentyloxynonyl), (B499, F, F, Me, OMe, 1-neopentyloxydecyl), (B500, F, F, Me, OMe, 1-neopentyloxyundecyl), (B501, F, F, Me, OMe, 1-neopentyloxydodecyl), (B502, F, F, Me, OMe, 1-neopentyloxy-1-cyclohexylmethyl), (B503, F, F, Me, OMe, 1-n-hexyloxyethyl), (B504, F, F, Me, OMe, 1-n-hexyloxypropyl), (B506, F, F, Me, OMe, 1-n-hexyloxybutyl), (B507, F, F, Me, OMe, 1-n-hexyloxy-2-methylpropyl), (B508, F, F, Me, OMe, 1-n-hexyloxypentyl), (B509, F, F, Me, OMe, 1-n-hexyloxy-3-methylbutyl), (B510, F, F, Me, OMe, 1-n-hexyloxy-2,2-dimethylpropyl), (B511, F, F, Me, OMe, 1-n-hexyloxyhexyl), (B512, F, F, Me, OMe, 1-n-hexyloxy-3,3-dimethylbutyl), (B513, F, F, Me, OMe, 1-n-hexyloxyheptyl), (B514, F, F, Me, OMe, 1-n-hexyloxyoctyl), (B515, F, F, Me, OMe, 1-n-hexyloxynonyl), (B516, F, F, Me, OMe, 1-n-hexyloxydecyl), (B517, F, F, Me, OMe, 1-n-hexyloxyundecyl), (B518, F, F, Me, OMe, 1-n-hexyloxydodecyl), (B520, F, F, Me, OMe, 3-isohexyloxydodecyl), (B522, F, F, Me, OMe, 3-(2-cyclopentylethyloxy)propyl), (B523, F, F, Me, OMe, 1-n-octyloxydodecyl), (B524, F, F, OMe, F, 1-methyloxyethyl), (B525, F, F, OMe, F, 1-methyloxypropyl), (B526, F, F, OMe, F, 1-methyloxy-3-n-hexyloxypropyl), (B527, F, F, OMe, F, 1-methyloxybutyl), (B528, F, F, OMe, F, 1-methyloxy-4-n-pentyloxybutyl), (B529, F, F, OMe, F, 1-methyloxy-2-methylpropyl), (B530, F, F, OMe, F, 1-methyloxypentyl), (B531, F, F, OMe, F, 1-methyloxy-3-methylbutyl), (B532, F, F, OMe, F, 1-methyloxy-2,2-dimethylpropyl), (B534, F, F, OMe, F, 4-methyloxyhexyl), (B535, F, F, OMe, F, 1-methyloxy-4-methylpentyl), (B536, F, F, OMe, F, 1-methyloxy-3,3-dimethylbutyl), (B537, F, F, OMe, F, 3-methyloxy-2,4-dimethyl-3-pentyl), (B538, F, F, OMe, F, 1-methyloxyheptyl), (B539, F, F, OMe, F, 4-methyloxy-4-heptyl), (B540, F, F, OMe, F, 1-methyloxyoctyl), (B541, F, F, OMe, F, 3-methyloxyoctyl), (B542, F, F, OMe, F, 1-methyloxynonyl), (B543, F, F, OMe, F, 1-methyloxydecyl), (B544, F, F, OMe, F, 1-methyloxyundecyl), (B545, F, F, OMe, F, 1-methyloxydodecyl), (B546, F, F, OMe, F, 1-methyloxy-1-cyclohexylmethyl), (B547, F, F, OMe, F, 1-(4-ethyloxybutyloxy)-1-cyclohexylmethyl), (B548, F, F, OMe, F, 1-ethyloxyethyl), (B549, F, F, OMe, F, 1-ethyloxypropyl), (B550, F, F, OMe, F, 1-ethyloxy-3-n-hexyloxypropyl), (B551, F, F, OMe, F, 1-(4-ethyloxybutyloxy)propyl), (B552, F, F, OMe, F, 1-ethyloxybutyl), (B553, F, F, OMe, F, 1-ethyloxy-4-n-pentyloxybutyl), (B554, F, F, OMe, F, 1-ethyloxy-2-methylpropyl), (B555, F, F, OMe, F, 1-ethyloxypentyl), (B556, F, F, OMe, F, 1-ethyloxy-3-methylbutyl), (B557, F, F, OMe, F, 1-ethyloxy-2,2-dimethylpropyl), (B558, F, F, OMe, F, 1-ethyloxyhexyl), (B559, F, F, OMe, F, 1-ethyloxy-3,3-dimethylbutyl), (B560, F, F, OMe, F, 1-ethyloxyheptyl), (B561, F, F, OMe, F, 1-ethyloxyoctyl), (B562, F, F, OMe, F, 1-ethyloxynonyl), (B563, F, F, OMe, F, 1-ethyloxydecyl), (B564, F, F, OMe, F, 1-ethyloxyundecyl), (B565, F, F, OMe, F, 1-ethyloxydodecyl), (B566, F, F, OMe, F, 1-ethyloxy-1-cyclohexylmethyl), (B567, F, F, OMe, F, 1-n-propyloxyethyl), (B568, F, F, OMe, F, 1-n-propyloxypropyl), (B569, F, F, OMe, F, 3-n-propyloxypropyl), (B570, F, F, OMe, F, 1-n-propyloxy-3-n-hexyloxypropyl), (B571, F, F, OMe, F, 1-n-propyloxybutyl), (B572, F, F, OMe, F, 1-n-propyloxy-4-n-pentyloxybutyl), (B573, F, F, OMe, F, 1,4-di(n-propyloxy)butyl), (B574, F, F, OMe, F, 1-n-propyloxy-2-methylpropyl), (B575, F, F, OMe, F, 1-n-propyloxypentyl), (B576, F, F, OMe, F, 1-n-propyloxy-3-methylbutyl), (B577, F, F, OMe, F, 1-n-propyloxy-2,2-dimethylpropyl), (B578, F, F, OMe, F, 1-n-propyloxyhexyl), (B579, F, F, OMe, F, 1-n-propyloxy-3,3-dimethylbutyl), (B580, F, F, OMe, F, 1-n-propyloxyheptyl), (B581, F, F, OMe, F, 1-n-propyloxyoctyl), (B582, F, F, OMe, F, 1-n-propyloxynonyl), (B583, F, F, OMe, F, 1-n-propyloxydecyl), (B584, F, F, OMe, F, 1-n-propyloxyundecyl), (B585, F, F, OMe, F, 1-n-propyloxydodecyl), (B586, F, F, OMe, F, 1-n-propyloxy-1-cyclohexylmethyl), (B587, F, F, OMe, F, 1-isopropyloxyethyl), (B588, F, F, OMe, F, 1-isopropyloxypropyl), (B589, F, F, OMe, F, 3-isopropyloxypropyl), (B590, F, F, OMe, F, 1-isopropyloxy-3-n-hexyloxypropyl), (B591, F, F, OMe, F, 1-isopropyloxybutyl), (B592, F, F, OMe, F, 1-isopropyloxy-4-n-pentyloxybutyl), (B593, F, F, OMe, F, 1-isopropyloxy-2-methylpropyl), (B594, F, F, OMe, F, 1-isopropyloxypentyl), (B595, F, F, OMe, F, 1-isopropyloxy-3-methylbutyl), (B596, F, F, OMe, F, 1-isopropyloxy-2,2-dimethylpropyl), (B597, F, F, OMe, F, 1-isopropyloxyhexyl), (B598, F, F, OMe, F, 1-isopropyloxy-3,3-dimethylbutyl), (B599, F, F, OMe, F, 1-isopropyloxyheptyl), (B600, F, F, OMe, F, 1-isopropyloxyoctyl), (B601, F, F, OMe, F, 1-isopropyloxynonyl), (B602, F, F, OMe, F, 1-isopropyloxydecyl), (B603, F, F, OMe, F, 1-isopropyloxyundecyl), (B604, F, F, OMe, F, 1-isopropyloxydodecyl), (B605, F, F, OMe, F, 1-isopropyloxy-1-cyclohexylmethyl), (B606, F, F, OMe, F, 1-n-butyloxyethyl), (B607, F, F, OMe, F, 1-n-butyloxypropyl), (B608, F, F, OMe, F, 3-n-butyloxypropyl), (B609, F, F, OMe, F, 1-n-butyloxybutyl), (B610, F, F, OMe, F, 1,4-di(n-butyloxy)butyl), (B611, F, F, OMe, F, 1-n-butyloxy-2-methylpropyl), (B612, F, F, OMe, F, 1-n-butyloxypentyl), (B613, F, F, OMe, F, 1-n-butyloxy-3-methylbutyl), (B614, F, F, OMe, F, 1-n-butyloxy-2,2-dimethylpropyl), (B615, F, F, OMe, F, 1-n-butyloxyhexyl), (B616, F, F, OMe, F, 1-n-butyloxy-3,3-dimethylbutyl), (B617, F, F, OMe, F, 1-n-butyloxyheptyl), (B618, F, F, OMe, F, 1-n-butyloxyoctyl), (B619, F, F, OMe, F, 1-n-butyloxynonyl), (B620, F, F, OMe, F, 1-n-butyloxydecyl), (B621, F, F, OMe, F, 1-n-butyloxyundecyl), (B622, F, F, OMe, F, 1-n-butyloxydodecyl), (B623, F, F, OMe, F, 1-n-butyloxy-1-cyclohexylmethyl), (B624, F, F, OMe, F, 1-isobutyloxyethyl), (B625, F, F, OMe, F, 1-isobutyloxypropyl), (B626, F, F, OMe, F, 1-isobutyloxybutyl), (B627, F, F, OMe, F, 1-isobutyloxy-2-methylpropyl), (B628, F, F, OMe, F, 1-isobutyloxypentyl), (B629, F, F, OMe, F, 1-isobutyloxy-3-methylbutyl), (B630, F, F, OMe, F, 1-isobutyloxy-2,2-dimethylpropyl), (B631, F, F, OMe, F, 1-isobutyloxyhexyl), (B632, F, F, OMe, F, 1-isobutyloxy-3,3-dimethylbutyl), (B633, F, F, OMe, F, 1-isobutyloxyheptyl), (B634, F, F, OMe, F, 1-isobutyloxyoctyl), (B635, F, F, OMe, F, 1-isobutyloxyynonyl), (B636, F, F, OMe, F, 1-isobutyloxydecyl), (B637, F, F, OMe, F, 1-isobutyloxyundecyl), (B638, F, F, OMe, F, 1-isobutyloxydodecyl), (B639, F, F, OMe, F, 1-isobutyloxy-1-cyclohexylmethyl), (B640, F, F, OMe, F, 1-t-butyloxyethyl), (B641, F, F, OMe, F, 1-t-butyloxypropyl), (B642, F, F, OMe, F, 1-t-butyloxybutyl), (B643, F, F, OMe, F, 1-t-butyloxy-2-methylpropyl), (B644, F, F, OMe, F, 1-t-butyloxypentyl), (B645, F, F, OMe, F, 1-t-butyloxy-3-methylbutyl), (B646, F, F, OMe, F, 1-t-butyloxy-2,2-dimethylpropyl), (B647, F, F, OMe, F, 1-t-butyloxyhexyl), (B648, F, F, OMe, F, 1-t-butyloxy-3,3-dimethylbutyl), (B649, F, F, OMe, F, 1-t-butyloxyheptyl), (B650, F, F, OMe, F, 1-t-butyloxyoctyl), (B651, F, F, OMe, F, 1-t-butyloxynonyl), (B652, F, F, OMe, F, 1-t-butyloxydecyl), (B653, F, F, OMe, F, 1-t-butyloxyundecyl), (B654, F, F, OMe, F, 1-t-butyloxydodecyl), (B655, F, F, OMe, F, 1-t-butyloxy-1-cyclohexylmethyl), (B656, F, F, OMe, F, 1-n-pentyloxyethyl), (B657, F, F, OMe, F, 1-n-pentyloxypropyl), (B658, F, F, OMe, F, 3-n-pentyloxypropyl), (B659, F, F, OMe, F, 1-n-pentyloxy-3-methylthiopropyl), (B660, F, F, OMe, F, 1-n-pentyloxybutyl), (B661, F, F, OMe, F, 1-n-pentyloxy-2-methylpropyl), (B662, F, F, OMe, F, 1-n-pentyloxypentyl), (B663, F, F, OMe, F, 1-n-pentyloxy-3-methylbutyl), (B664, F, F, OMe, F, 1-n-pentyloxy-2,2-dimethylpropyl), (B665, F, F, OMe, F, 1-n-pentyloxyhexyl), (B666, F, F, OMe, F, 1-n-pentyloxy-3,3-dimethylbutyl), (B667, F, F, OMe, F, 1-n-pentyloxyheptyl), (B668, F, F, OMe, F, 1-n-pentyloxyoctyl), (B669, F, F, OMe, F, 1-n-pentyloxynonyl), (B670, F, F, OMe, F, 1-n-pentyloxydecyl), (B671, F, F, OMe, F, 1-n-pentyloxyundecyl), (B672, F, F, OMe, F, 1-n-pentyloxydodecyl), (B673, F, F, OMe, F, 1-n-pentyloxy-1-cyclohexylmethyl), (B674, F, F, OMe, F, 1-isopentyloxyproyl), (B675, F, F, OMe, F, 1-neopentyloxyethyl), (B676, F, F, OMe, F, 1-neopentyloxypropyl), (B677, F, F, OMe, F, 1-neopentyloxybutyl), (B678, F, F, OMe, F, 1-neopentyloxy-2-methylpropyl), (B679, F, F, OMe, F, 1-neopentyloxypentyl), (B680, F, F, OMe, F, 1-neopentyloxy-3-methylbutyl), (B681, F, F, OMe, F, 1-neopentyloxy-2,2-dimethylpropyl), (B682, F, F, OMe, F, 1-neopentyloxyhexyl), (B683, F, F, OMe, F, 1-neopentyloxy-3,3-dimethylbutyl), (B684, F, F, OMe, F, 1-neopentyloxyheptyl), (B685, F, F, OMe, F, 1-neopentyloxyoctyl), (B686, F, F, OMe, F, 1-neopentyloxynonyl), (B687, F, F, OMe, F, 1-neopentyloxydecyl), (B688, F, F, OMe, F, 1-neopentyloxyundecyl), (B689, F, F, OMe, F, 1-neopentyloxydodecyl), (B690, F, F, OMe, F, 1-neopentyloxy-1-cyclohexylmethyl), (B691, F, F, OMe, F, 1-n-hexyloxyethyl), (B692, F, F, OMe, F, 1-n-hexyloxypropyl), (B693, F, F, OMe, F, 3-n-hexyloxypropyl), (B694, F, F, OMe, F, 1-n-hexyloxybutyl), (B695, F, F, OMe, F, 1-n-hexyloxy-2-methylpropyl), (B696, F, F, OMe, F, 1-n-hexyloxypentyl), (B697, F, F, OMe, F, 1-n-hexyloxy-3-methylbutyl), (B698, F, F, OMe, F, 1-n-hexyloxy-2,2-dimethylpropyl), (B699, F, F, OMe, F, 1-n-hexyloxyhexyl), (B700, F, F, OMe, F, 1-n-hexyloxy-3,3-dimethylbutyl), (B701, F, F, OMe, F, 1-n-hexyloxyheptyl), (B702, F, F, OMe, F, 1-n-hexyloxyoctyl), (B703, F, F, OMe, F, 1-n-hexyloxynonyl), (B704, F, F, OMe, F, 1-n-hexyloxydecyl), (B705, F, F, OMe, F, 1-n-hexyloxyundecyl), (B706, F, F, OMe, F, 1-n-hexyloxydecyl), (B707, F, F, OMe, F, 1-n-hexyloxy-1-cyclohexylmethyl), (B708, F, F, OMe, F, 3-iso-hexyloxyproyl), (B709, F, F, OMe, F, 3-(3,3-dimethylbutyloxy)propyl), (B710, F, F, OMe, F, 3-(2-cyclopentylethyloxy)propyl), (B711, F, F, OMe, F, 1-n-octyloxydodecyl), (B712, F, F, OMe, OMe, 1-methyloxyethyl), (B713, F, F, OMe, OMe, 1-methyloxypropyl), (B714, F, F, OMe, OMe, 1-methyloxy-3-n-hexyloxypropyl), (B715, F, F, OMe, OMe, 1-methyloxybutyl), (B716, F, F, OMe, OMe, 1-methyloxy-4-n-pentyloxybutyl), (B717, F, F, OMe, OMe, 1-methyloxy-2-methylpropyl), (B718, F, F, OMe, OMe, 1-methyloxypentyl), (B719, F, F, OMe, OMe, 1-methyloxy-3-methylbutyl), (B720, F, F, OMe, OMe, 1-methyloxy-2,2-dimethylpropyl), (B721, F, F, OMe,. OMe, 1-methyloxyhexyl), (B722, F, F, OMe, OMe, 4-methyloxyhexyl), (B723, F, F, OMe, OMe, 1-methyloxy-4-methylpentyl), (B724, F, F, OMe, OMe, 1-methyloxy-3,3-dimethylbutyl), (B725, F, F, OMe, OMe, 3-methyloxy-2,4-dimethyl-3-pentyl), (B726, F, F, OMe, OMe, 1-methyloxyheptyl), (B727, F, F, OMe, OMe, 4-methyloxy-4-heptyl), (B728, F, F, OMe, OMe, 1-methyloxyoctyl), (B729, F, F, OMe, OMe, 3-methyloxyoctyl), (B730, F, F, OMe, OMe, 1-methyloxynonyl), (B731, F, F, OMe, OMe, 1-methyloxydecyl), (B732, F, F, OMe, OMe, 1-methyloxyundecyl), (B733, F, F, OMe, OMe, 1-methyloxydodecyl), (B734, F, F, OMe, OMe, 1-methyloxy-1-cyclohexylmethyl), (B735, F, F, OMe, OMe, 1-(4-ethyloxybutyloxy)-1-cyclohexylmethyl), (B736, F, F, OMe, OMe, 1-ethyloxyethyl), (B737, F, F, OMe, OMe, 1-ethyloxypropyl), (B738, F, F, OMe, OMe, 1-(4-ethyloxybutyloxy)propyl), (B739, F, F, OMe, OMe, 1-ethyloxybutyl), (B740, F, F, OMe, OMe, 1-ethyloxy-2-methylpropyl), (B741, F, F, OMe, OMe, 1-ethyloxypentyl), (B742, F, F, OMe, OMe, 1-ethyloxy-3-methylbutyl), (B743, F, F, OMe, OMe, 1-ethyloxy-2,2-dimethylpropyl), (B744, F, F, OMe, OMe, 1-ethyloxyhexyl), (B745, F, F, OMe, OMe, 1-ethyloxy-3,3-dimethylbutyl), (B746, F, F, OMe, OMe, 1-ethyloxyheptyl), (B747, F, F, OMe, OMe, 1-ethyloxyoctyl), (B748, F, F, OMe, OMe, 1-ethyloxynonyl), (B749, F, F, OMe, OMe, 1-ethyloxydecyl), (B750, F, F, OMe, OMe, 1-ethyloxyundecyl), (B751, F, F, OMe, OMe, 1-ethyloxydodecyl), (B752, F, F, OMe, OMe, 1-ethyloxy-1-cyclohexylmethyl), (B753, F, F, OMe, OMe, 1-n-propyloxyethyl), (B754, F, F, OMe, OMe, 1-n-propyloxypropyl), (B755, F, F, OMe, OMe, 3-n-propyloxypropyl), (B756, F, F, OMe, OMe, 1-n-propyloxybutyl), (B757, F, F, OMe, OMe, 1,4-di(n-propyloxy)butyl), (B758, F, F, OMe, OMe, 1-n-propyloxy-2-methylpropyl), (B759, F, F, OMe, OMe, 1-n-propyloxypentyl), (B760, F, F, OMe, OMe, 1-n-propyloxy-3-methylbutyl), (B761, F, F, OMe, OMe, 1-n-propyloxy-2,2-dimethylpropyl), (B762, F, F, OMe, OMe, 1-n-propyloxyhexyl), (B763, F, F, OMe, OMe, 1-n-propyloxy-3,3-dimethylbutyl), (B764, F, F, OMe, OMe, 1-n-propyloxyheptyl), (B765, F, F, OMe, OMe, 1-n-propyloxyoctyl), (B766, F, F, OMe, OMe, 1-n-propyloxynonyl), (B767, F, F, OMe, OMe, 1-n-propyloxydecyl), (B768, F, F, OMe, OMe, 1-n-propyloxyundecyl), (B769, F, F, OMe, OMe, 1-n-propyloxydodecyl), (B770, F, F, OMe, OMe, 1-n-propyloxy-1-cyclohexylmethyl), (B771, F, F, OMe, OMe, 1-isopropyloxyethyl), (B772, F, F, OMe, OMe, 1-isopropyloxypropyl), (B773, F, F, OMe, OMe, 3-isopropyloxypropyl), (B774, F, F, OMe, OMe, 1-isopropyloxybutyl), (B775, F, F, OMe, OMe, 1-isopropyloxy-2-methylpropyl), (B776, F, F, OMe, OMe, 1-isopropyloxypentyl), (B777, F, F, OMe, OMe, 1-isopropyloxy-3-methylbutyl), (B778, F, F, OMe, OMe, 1-isopropyloxy-2,2-dimethylpropyl), (B779, F, F, OMe, OMe, 1-isopropyloxyhexyl), (B780, F, F, OMe, OMe, 1-isopropyloxy-3,3-dimethylbutyl), (B781, F, F, OMe, OMe, 1-isopropyloxyheptyl), (B782, F, F, OMe, OMe, 1-isopropyloxyoctyl), (B783, F, F, OMe, OMe, 1-isopropyloxynonyl), (B784, F, F, OMe, OMe, 1-isopropyloxydecyl), (B785, F, F, OMe, OMe, 1-isopropyloxyundecyl), (B786, F, F, OMe, OMe, 1-isopropyloxydodecyl), (B787, F, F, OMe, OMe, 1-isopropyloxy-1-cyclohexylmethyl), (B788, F, F, OMe, OMe, 1-n-butyloxyethyl), (B789, F, F, OMe, OMe, 1-n-butyloxypropyl), (B791, F, F, OMe, OMe, 1-n-butyloxybutyl), (B792, F, F, OMe, OMe, 1,4-di(n-butyloxy)butyl), (B793, F, F, OMe, OMe, 1-n-butyloxy-2-methylpropyl), (B794, F, F, OMe, OMe, 1-n-butyloxypentyl), (B795, F, F, OMe, OMe, 1-n-butyloxy-3-methylbutyl), (B796, F, F, OMe, OMe, 1-n-butyloxy-2,2-dimethylpropyl), (B797, F, F, OMe, OMe, 1-n-butyloxyhexyl), (B798, F, F, OMe, OMe, 1-n-butyloxy-3,3-dimethylbutyl), (B799, F, F, OMe, OMe, 1-n-butyloxyheptyl), (B800, F, F, OMe, OMe, 1-n-butyloxyoctyl), (B801, F, F, OMe, OMe, 1-n-butyloxynonyl), (B802, F, F, OMe, OMe, 1-n-butyloxydecyl), (B803, F, F, OMe, OMe, 1-n-butyloxyundecyl), (B804, F, F, OMe, OMe, 1-n-butyloxydodecyl), (B805, F, F, OMe, OMe, 1-n-butyloxy-1-cyclohexylmethyl), (B806, F, F, OMe, OMe, 1-isobutyloxyethyl), (B807, F, F, OMe, OMe, 1-isobutyloxypropyl), (B808, F, F, OMe, OMe, 1-isobutyloxybutyl), (B809, F, F, OMe, OMe, 1-isobutyloxy-2-methylpropyl), (B810, F, F, OMe, OMe, 1-isobutyloxypentyl), (B811, F, F, OMe, OMe, 1-isobutyloxy-3-methylbutyl), (B812, F, F, OMe, OMe, 1-isobutyloxy-2,2-dimethylpropyl), (B813, F, F, OMe, OMe, 1-isobutyloxyhexyl), (B814, F, F, OMe, OMe, 1-isobutyloxy-3,3-dimethylbutyl),. (B815, F, F, OMe, OMe, 1-isobutyloxyheptyl), (B816, F, F, OMe, OMe, 1-isobutyloxyoctyl), (B817, F, F, OMe, OMe, 1-isobutyloxyynonyl), (B818, F, F, OMe, OMe, 1-isobutyloxydecyl), (B819, F, F, OMe, OMe, 1-isobutyloxyundecyl), (B820, F, F, OMe, OMe, 1-isobutyloxydodecyl), (B821, F, F, OMe, OMe, 1-isobutyloxy-1-cyclohexylmethyl), (B822, F, F, OMe, OMe, 1-t-butyloxyethyl), (B823, F, F, OMe, OMe, 1-t-butyloxypropyl), (B824, F, F, OMe, OMe, 1-t-butyloxybutyl), (B825, F, F, OMe, OMe, 1-t-butyloxy-2-methylpropyl), (B826, F, F, OMe, OMe, 1-t-butyloxypentyl), (B827, F, F, OMe, OMe, 1-t-butyloxy-3-methylbutyl), (B828, F, F, OMe, OMe, 1-t-butyloxy-2,2-dimethylpropyl), (B829, F, F, OMe, OMe, 1-t-butyloxyhexyl), (B830, F, F, OMe, OMe, 1-t-butyloxy-3,3-dimethylbutyl), (B831, F, F, OMe, OMe, 1-t-butyloxyheptyl), (B832, F, F, OMe, OMe, 1-t-butyloxyoctyl), (B833, F, F, OMe, OMe, 1-t-butyloxynonyl), (B834, F, F, OMe, OMe, 1-t-butyloxydecyl), (B835, F, F, OMe, OMe, 1-t-butyloxyundecyl), (B836, F, F, OMe, OMe, 1-t-butyloxydodecyl), (B837, F, F, OMe, OMe, 1-t-butyloxy-1-cyclohexylmethyl), (B838, F, F, OMe, OMe, 1-n-pentyloxyethyl), (B839, F, F, OMe, OMe, 1-n-pentyloxypropyl), (B840, F, F, OMe, OMe, 3-n-pentyloxypropyl), (B841, F, F, OMe, OMe, 1-n-pentyloxy-3-methylthiopropyl), (B842, F, F, OMe, OMe, 1-n-pentyloxybutyl), (B843, F, F, OMe, OMe, 1-n-pentyloxy-2-methylpropyl), (B844, F, F, OMe, OMe, 1-n-pentyloxypentyl), (B845, F, F, OMe, OMe, 1-n-pentyloxy-3-methylbutyl), (B846, F, F, OMe, OMe, 1-n-pentyloxy-2,2-dimethylpropyl), (B847, F, F, OMe, OMe, 1-n-pentyloxyhexyl), (B848, F, F, OMe, OMe, 1-n-pentyloxy-3,3-dimethylbutyl), (B849, F, F, OMe, OMe, 1-n-pentyloxyheptyl), (B850, F, F, OMe, OMe, 1-n-pentyloxyoctyl), (B851, F, F, OMe, OMe, 1-n-pentyloxynonyl), (B852, F, F, OMe, OMe, 1-n-pentyloxydecyl), (B853, F, F, OMe, OMe, 1-n-pentyloxyundecyl), (B854, F, F, OMe, OMe, 1-n-pentyloxydodecyl), (B855, F, F, OMe, OMe, 1-n-pentyloxy-1-cyclohexylmethyl), (B856, F, F, OMe, OMe, 1-isopentyloxypropyl), (B857, F, F, OMe, OMe, 1-neopentyloxyethyl), (B858, F, F, OMe, OMe, 1-neopentyloxypropyl), (B859, F, F, OMe, OMe, 3-neopentyloxyethyl), (B860, F, F, OMe, OMe, 1-neopentyloxybutyl), (B861, F, F, OMe, OMe, 1-neopentyloxy-2-methylpropyl), (B862, F, F, OMe, OMe, 1-neopentyloxypentyl), (B863, F, F, OMe, OMe, 1-neopentyloxy-3-methylbutyl), (B864, F, F, OMe, OMe, 1-neopentyloxy-2,2-dimethylpropyl), (B865, F, F, OMe, OMe, 1-neopentyloxyhexyl), (B866, F, F, OMe, OMe, 1-neopentyloxy-3,3-dimethylbutyl), (B867, F, F, OMe, OMe, 1-neopentyloxyheptyl), (B868, F, F, OMe, OMe, 1-neopentyloxyoctyl), (B869, F, F, OMe, OMe, 1-neopentyloxynonyl), (B870, F, F, OMe, OMe, 1-neopentyloxydecyl), (B871, F, F, OMe, OMe, 1-neopentyloxyundecyl), (B872, F, F, OMe, OMe, 1-neopentyloxydodecyl), (B873, F, F, OMe, OMe, 1-neopentyloxy-1-cyclohexylmethyl), (B874, F, F, OMe, OMe, 1-n-hexyloxyethyl), (B875, F, F, OMe, OMe, 1-n-hexyloxypropyl), (B876, F, F, OMe, OMe, 3-n-hexyloxypropyl), (B877, F, F, OMe, OMe, 1-n-hexyloxybutyl), (B878, F, F, OMe, OMe, 1-n-hexyloxy-2-methylpropyl), (B879, F, F, OMe, OMe, 1-n-hexyloxypentyl), (B880, F, F, OMe, OMe, 1-n-hexyloxy-3-methylbutyl), (B881, F, F, OMe, OMe, 1-n-hexyloxy-2,2-dimethylpropyl), (B882, F, F, OMe, OMe, 1-n-hexyloxyhexyl), (B883, F, F, OMe, OMe, 1-n-hexyloxy-3,3-dimethylbutyl), (B884, F, F, OMe, OMe, 1-n-hexyloxyheptyl), (B885, F, F, OMe, OMe, 1-n-hexyloxyoctyl), (B886, F, F, OMe, OMe, 1-n-hexyloxynonyl), (B887, F, F, OMe, OMe, 1-n-hexyloxydecyl), (B888, F, F, OMe, OMe, 1-n-hexyloxyundecyl), (B889, F, F, OMe, OMe, 1-n-hexyloxydodecyl), (B890, F, F, OMe, OMe, 1-n-hexyloxy-1-cyclohexylmethyl), (B891, F, F, OMe, OMe, 3-isohexyloxypropyl), (B892, F, F, OMe, OMe, 3-(3,3-dimethylbutyloxy)propyl), (B893, F, F, OMe, OMe, 3-(2-cyclopentylethyloxy)propyl), (B894, F, F, OMe, OMe, 1-n-octyloxyethyl), (B895, Cl, Cl, Me, F, 1-methyloxyethyl), (B898, Cl, Cl, Me, F, 1-methyloxybutyl), (B900, Cl, Cl, Me, F, 1-methyloxy-2-methylpropyl), (B901, Cl, Cl, Me, F, 1-methyloxypentyl), (B902, Cl, Cl, Me, F, 1-methyloxy-3-methylbutyl), (B903, Cl, Cl, Me, F, 3-methyloxy-3-methylbutyl), (B904, Cl, Cl, Me, F, 4-methyloxyhexyl), (B906, Cl, Cl, Me, F, 1-methyloxy-1-cyclohexylmethyl), (B907, Cl, Cl, Me, F, 1-(4-ethyloxybutyloxy)-1-cyclohexylmethyl), (B908, Cl, Cl, Me, F, 1-ethyloxyethyl), (B909, Cl, Cl, Me, F, 1-ethyloxypropyl), (B910, Cl, Cl, Me, F, 1-ethyloxy-3-n-hexyloxypropyl), (B911, Cl, Cl, Me, F, 1-ethyloxybutyl), (B912, Cl, Cl, Me, F, 1-ethyloxy-4-n-pentyloxybutyl), (B913, Cl, Cl, Me, F, 1-ethyloxy-2-methylpropyl), (B914, Cl, Cl, Me, F, 1-ethyloxy-3-methylbutyl), (B915, Cl, Cl, Me, F, 1-ethyloxyhexyl), (B916, Cl, Cl, Me, F, 1-ethyloxyheptyl), (B917, Cl, Cl, Me, F, 1-ethyloxyoctyl), (B918, Cl, Cl, Me, F, 1-ethyloxynonyl), (B919, Cl, Cl, Me, F, 1-ethyloxydecyl), (B920, Cl, Cl, Me, F, 1-ethyloxyundecyl), (B921, Cl, Cl, Me, F, 1-ethyloxydodecyl), (B922, Cl, Cl, Me, F, 1-ethyloxy-1-cyclohexylmethyl), (B923, Cl, Cl, Me, F, 1-n-propyloxy-3-n-hexyloxypropyl), (B924, Cl, Cl, Me, F, 1-n-propyloxy-4-n-pentyloxybutyl), (B925, Cl, Cl, Me, F, 1-n-propyloxy-2-methylpropyl), (B926, Cl, Cl, Me, F, 1-n-propyloxy-3-methylbutyl), (B928, Cl, Cl, Me, F, 1-n-propyloxyhexyl), (B929, Cl, Cl, Me, F, 1-n-propyloxy-3,3-dimethylbutyl), (B930, Cl, Cl, Me, F, 1-n-propyloxyheptyl), (B931, Cl, Cl, Me, F, 1-n-propyloxyoctyl), (B932, Cl, Cl, Me, F, 1-n-propyloxynonyl), (B933, Cl, Cl, Me, F, 1-n-propyloxydecyl), (B934, Cl, Cl, Me, F, 1-n-propyloxyundecyl), (B935, Cl, Cl, Me, F, 1-n-propyloxydodecyl), (B937, Cl, Cl, Me, F, 1-isopropyloxyethyl), (B938, Cl, Cl, Me, F, 1-isopropyloxypropyl), (B939, Cl, Cl, Me, F, 1-isopropyloxy-3-n-hexyloxypropyl), (B940, Cl, Cl, Me, F, 1-isopropyloxybutyl), (B941, Cl, Cl, Me, F, 1-isopropyloxy-4-n-pentyloxybutyl), (B942, Cl, Cl, Me, F, 1-isopropyloxy-2-methylpropyl), (B943, Cl, Cl, Me, F, 1-isopropyloxypentyl), (B944, Cl, Cl, Me, F, 1-isopropyloxy-3-methylbutyl), (B945, Cl, Cl, Me, F, 1-isopropyloxy-2,2-dimethylpropyl), (B946, Cl, Cl, Me, F, 1-isopropyloxyhexyl), (B947, Cl, Cl, Me, F, 1-isopropyloxy-3,3-dimethylbutyl), (B948, Cl, Cl, Me, F, 1-isopropyloxyheptyl), (B949, Cl, Cl, Me, F, 1-isopropyloxyoctyl), (B950, Cl, Cl, Me, F, 1-isopropyloxynonyl), (B951, Cl, Cl, Me, F, 1-isopropyloxydecyl), (B952, Cl, Cl, Me, F, 1-isopropyloxyundecyl), (B953, Cl, Cl, Me, F, 1-isopropyloxydodecyl), (B954, Cl, Cl, Me, F, 1-isopropyloxy-1-cyclohexylmethyl), (B955, Cl, Cl, Me, F, 1,4-di(n-butyloxy)butyl), (B956, Cl, Cl, . Me, F, 1-n-butyloxy-2-methylpropyl), (B957, Cl, Cl, Me, F, 1-n-butyloxy-3-methylbutyl), (B959, Cl, Cl, Me, F, 1-n-butyloxyhexyl), (B960, Cl, Cl, Me, F, 1-n-butyloxy-3,3-dimethylbutyl), (B961, Cl, Cl, Me, F, 1-n-butyloxyheptyl), (B962, Cl, Cl, Me, F, 1-n-butyloxyoctyl), (B963, Cl, Cl, Me, F, 1-n-butyloxynonyl), (B964, Cl, Cl, Me, F, 1-n-butyloxydecyl), (B965, Cl, Cl, Me, F, 1-n-butyloxyundecyl), (B966, Cl, Cl, Me, F, 1-n-butyloxydodecyl), (B968, Cl, Cl, Me, F, 1-isobutyloxyethyl), (B969, Cl, Cl, Me, F, 1-isobutyloxypropyl), (B970, Cl, Cl, Me, F, 1-isobutyloxybutyl), (B971, Cl, Cl, Me, F, 1-isobutyloxy-2-methylpropyl), (B972, Cl, Cl, Me, F, 1-isobutyloxypentyl), (B973, Cl, Cl, Me, F, 1-isobutyloxy-3-methylbutyl), (B974, Cl, Cl, Me, F, 1-isobutyloxy-2,2-dimethylpropyl), (B975, Cl, Cl, Me, F, 1-isobutyloxyhexyl), (B976, Cl, Cl, Me, F, 1-isobutyloxy-3,3-dimethylbutyl), (B977, Cl, Cl, Me, F, 1-isobutyloxyheptyl), (B978, Cl, Cl, Me, F, 1-isobutyloxyoctyl), (B979, Cl, Cl, Me, F, 1-isobutyloxyynonyl), (B980, Cl, Cl, Me, F, 1-isobutyloxydecyl), (B981, Cl, Cl, Me, F, 1-isobutyloxyundecyl), (B982, Cl, Cl, Me, F, 1-isobutyloxydodecyl), (B983, Cl, Cl, Me, F, 1-isobutox-1-cyclohexylymethyl), (B984, Cl, Cl, Me, F, 1-t-butyloxyethyl), (B985, Cl, Cl, Me, F, 1-t-butyloxypropyl), (B986, Cl, Cl, Me, F, 1-t-butyloxybutyl), (B987, Cl, Cl, Me, F, 1-t-butyloxy-2-methylpropyl), (B988, Cl, Cl, Me, F, 1-t-butyloxypentyl), (B989, Cl, Cl, Me, F, 1-t-butyloxy-3-methylbutyl), (B990, Cl, Cl, Me, F, 1-t-butyloxy-2,2-dimethylpropyl), (B991, Cl, Cl, Me, F, 1-t-butyloxyhexyl), (B992, Cl, Cl, Me, F, 1-t-butyloxy-3,3-dimethylbutyl), (B993, Cl, Cl, Me, F, 1-t-butyloxyheptyl), (B994, Cl, Cl, Me, F, 1-t-butyloxyoctyl), (B995, Cl, Cl, Me, F, 1-t-butyloxynonyl), (B996, Cl, Cl, Me, F, 1-t-butyloxydecyl), (B997, Cl, Cl, Me, F, 1-t-butyloxyundecyl), (B998, Cl, Cl, Me, F, 1-t-butyloxydodecyl), (B999, Cl, Cl, Me, F, 1-t-butyloxy-1-cyclohexylmethyl), (B1000, Cl, Cl, Me, F, 1-n-pentyloxyethyl), (B1001, Cl, Cl, Me, F, 1-n-pentyloxy-2-methylpropyl), (B1002, Cl, Cl, Me, F, 1-n-pentyloxy-3-methylbutyl), (B1003, Cl, Cl, Me, F, 1-n-pentyloxy-2,2-dimethylpropyl), (B1004, Cl, Cl, Me, F, 1-n-pentyloxyhexyl), (B1005, Cl, Cl, Me, F, 1-n-pentyloxy-3,3-dimethylbutyl), (B1006, Cl, Cl, Me, F, 1-n-pentyloxyheptyl), (B1007, Cl, Cl, Me, F, 1-n-pentyloxyoctyl), (B1008, Cl, Cl, Me, F, 1-n-pentyloxynonyl), (B 1009, Cl, Cl, Me, F, 1-n-pentyloxydecyl), (B1010, Cl, Cl, Me, F, 1-n-pentyloxyundecyl), (B1011, Cl, Cl, Me, F, 1-n-pentyloxydodecyl), (B1012, Cl, Cl, Me, F, 1-n-pentyloxy-1-cyclohexylmethyl), (B1013, Cl, Cl, Me, F, 1-neopentyloxyethyl), (B1014, Cl, Cl, Me, F, 1-neopentyloxypropyl), (B1015, Cl, Cl, Me, F, 1-neopentyloxybutyl), (B1016, Cl, Cl, Me, F, 1-neopentyloxy-2-methylpropyl), (B1017, Cl, Cl, Me, F, 1-neopentyloxypentyl), (B1018, Cl, Cl, Me, F, 1-neopentyloxy-3-methylbutyl), (B1019, Cl, Cl, Me, F, 1-neopentyloxy-2,2-dimethylpropyl), (B1020, Cl, Cl, Me, F, 1-neopentyloxyhexyl), (B1021, Cl, Cl, Me, F, 1-neopentyloxy-3,3-dimethylbutyl), (B1022, Cl, Cl, Me, F, 1-neopentyloxyheptyl), (B 1023, Cl, Cl, Me, F, 1-neopentyloxyoctyl), (B1024, Cl, Cl, Me, F, 1-neopentyloxynonyl), (B1025, Cl, Cl, Me, F, 1-neopentyloxydecyl), (B 1026, Cl, Cl, Me, F, 1-neopentyloxyundecyl), (B1027, Cl, Cl, Me, F, 1-neopentyloxydodecyl), (B1028, Cl, Cl, Me, F, 1-neopentyloxy-1-cyclohexylmethyl), (B1029, Cl, Cl, Me, F, 1-n-hexyloxybutyl), (B1030, Cl, Cl, Me, F, 1-n-hexyloxy-2-methylpropyl), (B1031, Cl, Cl, Me, F, 1-n-hexyloxypentyl), (B1032, Cl, Cl, Me, F, 1-n-hexyloxy-3-methylbutyl), (B1033, Cl, Cl, Me, F, 1-n-hexyloxy-2,2-dimethylpropyl), (B 1034, Cl, Cl, Me, F, 1-n-hexyloxyhexyl), (B1035, Cl, Cl, Me, F, 1-n-hexyloxy-3,3-dimethylbutyl), (B1036, Cl, Cl, Me, F, 1-n-hexyloxyheptyl), (B1037, Cl, Cl, Me, F, 1-n-hexyloxyoctyl), (B1038, Cl, Cl, Me, F, 1-n-hexyloxynonyl), (B1039, Cl, Cl, Me, F, 1-n-hexyloxydecyl), (B1040, Cl, Cl, Me, F, 1-n-hexyloxyundecyl), (B1041, Cl, Cl, Me, F, 1-n-hexyloxydodecyl), (B1042, Cl, Cl, Me, F, 1-n-hexyloxy-1-cyclohexylmethyl), (B1043, Cl, Cl, Me, OMe, 1-methyloxyethyl), (B1044, Cl, Cl, Me, OMe, 1-methyloxypropyl), (B1045, Cl, Cl, Me, OMe, 1-methyloxy-3-n-hexyloxypropyl), (B1046, Cl, Cl, Me, OMe, 1-methyloxybutyl), (B1047, Cl, Cl, Me, OMe, 1-methyloxy-4-n-pentyloxybutyl), (B1048, Cl, Cl, Me, OMe, 1-methyloxy-2-methylpropyl), (B1049, Cl, Cl, Me, OMe, 1-methyloxypentyl), (B1050, Cl, Cl, Me, OMe, 1-methyloxy-3-methylbutyl), (B1051, Cl, Cl, Me, OMe, 1-methyloxy-2,2-dimethylpropyl), (B1052, Cl, Cl, Me, OMe, 1-methyloxyhexyl), (B1055, Cl, Cl, Me, OMe, 1-methyloxyheptyl), (B1056, Cl, Cl, Me, OMe, 1-methyloxyoctyl), (B1057, Cl, Cl, Me, OMe, 3-methyloxyoctyl), (B1058, Cl, Cl, Me, OMe, 1-methyloxynonyl), (B1061, Cl, Cl, Me, OMe, 1-methyloxydodecyl), (B1062, Cl, Cl, Me, OMe, 1-methyloxy-1-cyclohexylmethyl), (B1063, Cl, Cl, Me, OMe, 1-(4-ethyloxybutyloxy)-1-cyclohexylmethyl), (B1064, Cl, Cl, Me, OMe, 1-ethyloxyethyl), (B1065, Cl, Cl, Me, OMe, 1-ethyloxypropyl), (B1066, Cl, Cl, Me, OMe, 1-ethyloxy-3-n-hexyloxypropyl), (B1067, Cl, Cl, Me, OMe, 1-(4-ethyloxybutyloxy)propyl), (B1068, Cl, Cl, Me, OMe, 1-ethyloxybutyl), (B1069, Cl, Cl, Me, OMe, 1-ethyloxy-4-n-pentyloxybutyl), (B1070, Cl, Cl, Me, OMe, 1-ethyloxy-2-methylpropyl), (B1071, Cl, Cl, Me, OMe, 1-ethyloxypentyl), (B1072, Cl, Cl, Me, OMe, 1-ethyloxy-3-methylbutyl), (B 1073, Cl, Cl, Me, OMe, 1-ethyloxy-2,2-dimethylpropyl), (B1074, Cl, Cl, Me, OMe, 1-ethyloxyhexyl), (B1075, Cl, Cl, Me, OMe, 1-ethyloxy-3,3-dimethylbutyl), (B1076, Cl, Cl, Me, OMe, 1-ethyloxyheptyl), (B1077, Cl, Cl, Me, OMe, 1-ethyloxyoctyl), (B1078, Cl, Cl, Me, OMe, 1-ethyloxynonyl), (B1079, Cl, Cl, Me, OMe, 1-ethyloxydecyl), (B1080, Cl, Cl, Me, OMe, 1-ethyloxyundecyl), (B1081, Cl, Cl, Me, OMe, 1-ethyloxydodecyl), (B1082, Cl, Cl, Me, OMe, 1-ethyloxy-1-cyclohexylmethyl), (B1083, Cl, Cl, Me, OMe, 1-n-propyloxyethyl), (B1084, Cl, Cl, Me, OMe, 1-n-propyloxypropyl), (B1085, Cl, Cl, Me, OMe, 3-n-propyloxypropyl), (B1086, Cl, Cl, Me, OMe, 1-n-propyloxy-3-n-hexyloxypropyl), (B1087, Cl, Cl, Me, OMe, 1-n-propyloxybutyl), (B1088, Cl, Cl, Me, OMe, 1-n-propyloxy-4-n-pentyloxybutyl), (B1089, Cl, Cl, Me, OMe, 1,4-di(n-propyloxy)butyl), (B1090, Cl, Cl, Me, OMe, 1-n-propyloxy-2-methylpropyl), (B1091, Cl, Cl, Me, OMe, 1-n-propyloxypentyl), (B1092, Cl, Cl, Me, OMe, 1-n-propyloxy-3-methylbutyl), (B1093, Cl, Cl, Me, OMe, 1-n-propyloxy-2,2-dimethylpropyl), (B1094, Cl, Cl, Me, OMe, 1-n-propyloxyhexyl), (B1095, Cl, Cl, Me, OMe, 1-n-propyloxy-3,3-dimethylbutyl), (B1096, Cl, Cl, Me, OMe, 1-n-propyloxyheptyl), (B1097, Cl, Cl, Me, OMe, 1-n-propyloxyoctyl), (B1098, Cl, Cl, Me, OMe, 1-n-propyloxynonyl), (B1099, Cl, Cl, Me, OMe, 1-n-propyloxydecyl), (B1100, Cl, Cl, Me, OMe, 1-n-propyloxyundecyl), (B1101, Cl, Cl, Me, OMe, 1-n-propyloxydodecyl), (B1103, Cl, Cl, Me, OMe, 1-isopropyloxyethyl), (B1104, Cl, Cl, Me, OMe, 1-isopropyloxypropyl), (B1105, Cl, Cl, Me, OMe, 3-isopropyloxypropyl), (B 1106, Cl, Cl, Me, OMe, 1-isopropyloxy-3-n-hexyloxypropyl), (B1107, Cl, Cl, Me, OMe, 1-isopropyloxybutyl), (B1108, Cl, Cl, Me, OMe, 1-isopropyloxy-4-n-pentyloxybutyl), (B 1109, Cl, Cl, Me, OMe, 1-isopropyloxy-2-methylpropyl), (B1110, Cl, Cl, Me, OMe, 1-isopropyloxypentyl), (B111, Cl, Cl, Me, OMe, 1-isopropyloxy-3-methylbutyl), (B 1112, Cl, Cl, Me, OMe, 1-isopropyloxy-2,2-dimethylpropyl), (B1113, Cl, Cl, Me, OMe, 1-isopropyloxyhexyl), (B1114, Cl, Cl, Me, OMe, 1-isopropyloxy- 3,3-dimethylbutyl), (B1115, Cl, Cl, Me, OMe, 1-isopropyloxyheptyl), (B1116, Cl, Cl, Me, OMe, 1-isopropyloxyoctyl), (B1117, Cl, Cl, Me, OMe, 1-isopropyloxynonyl), (B1118, Cl, Cl, Me, OMe, 1-isopropyloxydecyl), (B1119, Cl, Cl, Me, OMe, 1-isopropyloxyundecyl), (B1120, Cl, Cl, Me, OMe, 1-isopropyloxydodecyl), (B1121, Cl, Cl, Me, OMe, 1-isopropyloxy-1-cyclohexylmethyl), (B1123, Cl, Cl, Me, OMe, 1-n-butyloxypropyl), (B1125, Cl, Cl, Me, OMe, 1,4-di(n-butyloxy)butyl), (B1126, Cl, Cl, Me, OMe, 1-n-butyloxybutyl), (B1127, Cl, Cl, Me, OMe, 1-n-butyloxy-2-methylpropyl), (B1128, Cl, Cl, Me, OMe, 1-n-butyloxypentyl), (B1129, Cl, Cl, Me, OMe, 1-n-butyloxy-3-methylbutyl), (B1130, Cl, Cl, Me, OMe, 1-n-butyloxy-2,2-dimethylpropyl), (B1131, Cl, Cl, Me, OMe, 1-n-butyloxyhexyl), (B1132, Cl, Cl, Me, OMe, 1-n-butyloxy-3,3-dimethylbutyl), (B1133, Cl, Cl, Me, OMe, 1-n-butyloxyheptyl), (B1134, Cl, Cl, Me, OMe, 1-n-butyloxyoctyl), (B1135, Cl, Cl, Me, OMe, 1-n-butyloxynonyl), (B1136, Cl, Cl, Me, OMe, 1-n-butyloxydecyl), (B1137, Cl, Cl, Me, OMe, 1-n-butyloxyundecyl), (B1138, Cl, Cl, Me, OMe, 1-n-butyloxydodecyl), (B1139, Cl, Cl, Me, OMe, 1-n-butyloxy-1-cyclohexylmethyl), (B1140, Cl, Cl, Me, OMe, 1-isobutyloxyethyl), (B1141, Cl, Cl, Me, OMe, 1-isobutyloxypropyl), (B1142, Cl, Cl, Me, OMe, 1-isobutyloxybutyl), (B1143, Cl, Cl, Me, OMe, 1-isobutyloxy-2-methylpropyl), (B1144, Cl, Cl, Me, OMe, 1-isobutyloxypentyl), (B1145, Cl, Cl, Me, OMe, 1-isobutyloxy-3-methylbutyl), (B1146, Cl, Cl, Me, OMe, 1-isobutyloxy-2,2-dimethylpropyl), (B1147, Cl, Cl, Me, OMe, 1-isobutyloxyhexyl), (B1148, Cl, Cl, Me, OMe, 1-isobutyloxy-3,3-dimethylbutyl), (B1149, Cl, Cl, Me, OMe, 1-isobutyloxyheptyl), (B1150, Cl, Cl, Me, OMe, 1-isobutyloxyoctyl), (B1151, Cl, Cl, Me, OMe, 1-isobutyloxyynonyl), (B1152, Cl, Cl, Me, OMe, 1-isobutyloxydecyl), (B1153, Cl, Cl, Me, OMe, 1-isobutyloxyundecyl), (B1154, Cl, Cl, Me, OMe, 1-isobutyloxydodecyl), (B1155, Cl, Cl, Me, OMe, 1-isobutyloxy-1-cyclohexylmethyl), (B1156, Cl, Cl, Me, OMe, 1-t-butyloxyethyl), (B1157, Cl, Cl, Me, OMe, 1-t-butyloxypropyl), (B1158, Cl, Cl, Me, OMe, 1-t-butyloxybutyl), (B1159, Cl, Cl, Me, OMe, 1-t-butyloxy-2-methylpropyl), (B1160, Cl, Cl, Me, OMe, 1-t-butyloxypentyl), (B1161, Cl, Cl, Me, OMe, 1-t-butyloxy-3-methylbutyl), (B1162, Cl, Cl, Me, OMe, 1-t-butyloxy-2,2-dimethylpropyl), (B1163, Cl, Cl, Me, OMe, 1-t-butyloxyhexyl), (B1164, Cl, Cl, Me, OMe, 1-t-butyloxy-3,3-dimethylbutyl), (B1165, Cl, Cl, Me, OMe, 1-t-butyloxyheptyl), (B1166, Cl, Cl, Me, OMe, 1-t-butyloxyoctyl), (B1167, Cl, Cl, Me, OMe, 1-t-butyloxynonyl), (B1168, Cl, Cl, Me, OMe, 1-t-butyloxydecyl), (B1169, Cl, Cl, Me, OMe, 1-t-butyloxyundecyl), (B1170, Cl, Cl, Me, OMe, 1-t-butyloxydodecyl), (B1171, Cl, Cl, Me, OMe, 1-t-butyloxy-1-cyclohexylmethyl), (B1172, Cl, Cl, Me, OMe, 1-n-pentyloxyethyl), (B1173, Cl, Cl, Me, OMe, 1-n-pentyloxypropyl), (B1174, Cl, Cl, Me, OMe, 3-n-pentyloxypropyl), (B1175, Cl, Cl, Me, OMe, 1-n-pentyloxy-3-methylthiopropyl), (B1176, Cl, Cl, Me, OMe, 1-n-pentyloxybutyl), (B1177, Cl, Cl, Me, OMe, 1-n-pentyloxy-2-methylpropyl), (B1178, Cl, Cl, Me, OMe, 1-n-pentyloxypentyl), (B1179, Cl, Cl, Me, OMe, 1-n-pentyloxy-3-methylbutyl), (B1180, Cl, Cl, Me, OMe, 1-n-pentyloxy-2,2-dimethylpropyl), (B1181, Cl, Cl, Me, OMe, 1-n-pentyloxyhexyl), (B1182, Cl, Cl, Me, OMe, 1-n-pentyloxy-3,3-dimethylbutyl), (B1183, Cl, Cl, Me, OMe, 1-n-pentyloxyheptyl), (B1184, Cl, Cl, Me, OMe, 1-n-pentyloxyoctyl), (B1185, Cl, Cl, Me, OMe, 1-n-pentyloxynonyl), (B1186, Cl, Cl, Me, OMe, 1-n-pentyloxydecyl), (B1187, Cl, Cl, Me, OMe, 1-n-pentyloxyundecyl), (B1188, Cl, Cl, Me, OMe, 1-n-pentyloxydodecyl), (B1189, Cl, Cl, Me, OMe, 1-n-pentyloxy-1-cyclohexylmethyl), (B1190, Cl, Me, OMe, 1-isopentyloxypropyl), (B1191, Cl, Cl, Me, OMe, 1-neopentyloxyethyl), (B1192, Cl, Cl, Me, OMe, 1-neopentyloxypropyl), (B1193, Cl, Cl, Me, OMe, 3-neopentyloxypropyl), (B1194, Cl, Cl, Me, OMe, 1-neopentyloxybutyl), (B1195, Cl, Cl, Me, OMe, 1-neopentyloxy-2-methylpropyl), (B1196, Cl, Cl, Me, OMe, 1-neopentyloxypentyl), (B1197, Cl, Cl, Me, OMe, 1-neopentyloxy-3-methylbutyl), (B1198, Cl, Cl, Me, OMe, 1-neopentyloxy-2,2-dimethylpropyl), (B1199, Cl, Cl, Me, OMe, 1-neopentyloxyhexyl), (B1200, Cl, Cl, Me, OMe, 1-neopentyloxy-3,3-dimethylbutyl), (B1201, Cl, Cl, Me, OMe, 1-neopentyloxyheptyl), (B1202, Cl, Cl, Me, OMe, 1-neopentyloxyoctyl), (B1203, Cl, Cl, Me, OMe, 1-neopentyloxynonyl), (B1204, Cl, Cl, Me, OMe, 1-neopentyloxydecyl), (B1205, Cl, Cl, Me, OMe, 1-neopentyloxyundecyl), (B1206, Cl, Cl, Me, OMe, 1-neopentyloxydodecyl), (B1207, Cl, Cl, Me, OMe, 1-neopentyloxy-1-cyclohexylmethyl), (B1208, Cl, Cl, Me, OMe, 1-n-hexyloxyethyl), (B1209, Cl, Cl, Me, OMe, 1-n-hexyloxypropyl), (B1210, Cl, Cl, Me, OMe, 3-n-hexyloxypropyl), (B1211, Cl, Cl, Me, OMe, 1-n-hexyloxybutyl), (B1212, Cl, Cl, Me, OMe, 1-n-hexyloxy-2-methylpropyl), (B1213, Cl, Cl, Me, OMe, 1-n-hexyloxypentyl), (B1214, Cl, Cl, Me, OMe, 1-n-hexyloxy-3-methylbutyl), (B1215, Cl, Cl, Me, OMe, 1-n-hexyloxy-2,2-dimethylpropyl), (B1216, Cl, Cl, Me, OMe, 1-n-hexyloxyhexyl), (B1217, Cl, Cl, Me, OMe, 1-n-hexyloxy-3,3-dimethylbutyl), (B 1218, Cl, Cl, Me, OMe, 1-n-hexyloxyheptyl), (B 1219, Cl, Cl, Me, OMe, 1-n-hexyloxyoctyl), (B1220, Cl, Cl, Me, OMe, 1-n-hexyloxynonyl), (B1221, Cl, Cl, Me, OMe, 1-n-hexyloxydecyl), (B1222, Cl, Cl, Me, OMe, 1-n-hexyloxyundecyl), (B1223, Cl, Cl, Me, OMe, 1-n-hexyloxydodecyl), (B1224, Cl, Cl, Me, OMe, 1-n-hexyloxy-1-cyclohexylmethyl), (B1225, Cl, Cl, Me, OMe, 3-isohexyloxydodecyl), (B1226, Cl, Cl, Me, OMe, 3-(3,3-dimethylbutyloxy)propyl), (B1227, Cl, Cl, Me, OMe, 3-(2-cyclopentylethyloxy)propyl), (B1228, Cl, Cl, Me, OMe, 1-n-octyloxydodecyl), (B1229, Cl, Cl, OMe, F, 1-methyloxyethyl), (B1230, Cl, Cl, OMe, F, 1-methyloxypropyl), (B1231, Cl, Cl, OMe, F, 1-methyloxy-3-n-hexyloxypropyl), (B1232, Cl, Cl, OMe, F, 1-methyloxybutyl), (B1233, Cl, Cl, OMe, F, 1-methyloxy-4-n-pentyloxybutyl), (B1234, Cl, Cl, OMe, F, 1-methyloxy-2-methylpropyl), (B1235, Cl, Cl, OMe, F, 1-methyloxypentyl), (B1236, Cl, Cl, OMe, F, 1-methyloxy-3-methylbutyl), (B1237, Cl, Cl, OMe, F, 1-methyloxy-2,2-dimethylpropyl), (B1239, Cl, Cl, OMe, F, 4-methyloxyhexyl), (B1240, Cl, Cl, OMe, F, 1-methyloxy-4-methylpentyl), (B1241, Cl, Cl, OMe, F, 1-methyloxy-3,3-dimethylbutyl), (B1242, Cl, Cl, OMe, F, 3-methyloxy-2,4-dimethyl-3-pentyl), (B1243, Cl, Cl, OMe, F, 1-methyloxyheptyl), (B1244, Cl, Cl, OMe, F, 4-methyloxy-4-heptyl), (B1245, Cl, Cl, OMe, F, 1-methyloxyoctyl), (B1246, Cl, Cl, OMe, F, 3-methyloxyoctyl), (B1247, Cl, Cl, OMe, F, 1-methyloxynonyl), (B1248, Cl, Cl, OMe, F, 1-methyloxydecyl), (B1249, Cl, Cl, OMe, F, 1-methyloxyundecyl), (B1251, Cl, Cl, OMe, F, 1-methyloxy-1-cyclohexylmethyl), (B1252, Cl, Cl, OMe, F, 1-(4-ethyloxybutyloxy)-1-cyclohexylmethyl), (B1253, Cl, Cl, OMe, F, 1-ethyloxyethyl), (B1254, Cl, Cl, OMe, F, 1-ethyloxypropyl), (B1255, Cl, Cl, OMe, F, 1-ethyloxy-3-n-hexyloxypropyl), (B1256, Cl, Cl, OMe, F, 1-(4-ethyloxybutyloxy)propyl), (B1257, Cl, Cl, OMe, F, 1-ethyloxybutyl), (B1258, Cl, Cl, OMe, F, 1-ethyloxy-4-n-pentyloxybutyl), (B1259, Cl, Cl, OMe, F, 1-ethyloxy-2-methylpropyl), (B1260, Cl, Cl, OMe, F, 1-ethyloxypentyl), (B1261, Cl, Cl, OMe, F, 1-ethyloxy-3-methylbutyl), (B1262, Cl, Cl, OMe, F, 1-ethyloxy-2,2-dimethylpropyl), (B1263, Cl, Cl, OMe, F, 1-ethyloxyhexyl), (B1264, Cl, Cl, OMe, F, 1-ethyloxy-3,3-dimethylbutyl), (B1265, Cl, Cl, OMe, F, 1-ethyloxyheptyl), (B1266, Cl, Cl, OMe, F, 1-ethyloxyoctyl), (B1267, Cl, Cl, OMe, F, 1-ethyloxynonyl), (B1268, Cl, Cl, OMe, F, 1-ethyloxydecyl), (B1269, Cl, Cl, OMe, F, 1-ethyloxyundecyl), (B1270, Cl, Cl, OMe, F, 1-ethyloxydodecyl), (B1271, Cl, Cl, OMe, F, 1-ethyloxy-1-cyclohexylmethyl), (B1272, Cl, Cl, OMe, F, 1-n-propyloxyethyl), (B1273, Cl, Cl, OMe, F, 1-n-propyloxypropyl), (B1274, Cl, Cl, OMe, F, 3-n-propyloxypropyl), (B1275, Cl, Cl, OMe, F, 1-n-propyloxy-3-n-hexyloxypropyl), (B1276, Cl, Cl, OMe, F, 1-n-propyloxybutyl), (B1277, Cl, Cl, OMe, F, 1-n-propyloxy-4-n-pentyloxybutyl), (B1278, Cl, Cl, OMe, F, 1,4-di(n-propyloxy)butyl), (B1279, Cl, Cl, OMe, F, 1-n-propyloxy-2-methylpropyl), (B1280, Cl, Cl, OMe, F, 1-n-propyloxypentyl), (B1281, Cl, Cl, OMe, F, 1-n-propyloxy-3-methylbutyl), (B1282, Cl, Cl, OMe, F, 1-n-propyloxy-2,2-dimethylpropyl), (B1283, Cl, Cl, OMe, F, 1-n-propyloxyhexyl), (B1284, Cl, Cl, OMe, F, 1-n-propyloxy-3,3-dimethylbutyl), (B1285, Cl, Cl, OMe, F, 1-n-propyloxyheptyl), (B1286, Cl, Cl, OMe, F, 1-n-propyloxyoctyl), (B1287, Cl, Cl, OMe, F, 1-n-propyloxynonyl), (B1288, Cl, Cl, OMe, F, 1-n-propyloxydecyl), (B1289, Cl, Cl, OMe, F, 1-n-propyloxyundecyl), (B1290, Cl, Cl, OMe, F, 1-n-propyloxydodecyl), (B1291, Cl, Cl, OMe, F, 1-n-propyloxy-1-cyclohexylmethyl), (B1292, Cl, Cl, OMe, F, 1-isopropyloxyethyl), (B1293, Cl, Cl, OMe, F, 1-isopropyloxypropyl), (B1294, Cl, Cl, OMe, F, 3-isopropyloxypropyl), (B1295, Cl, Cl, OMe, F, 1-isopropyloxy-3-n-hexyloxypropyl), (B1296, Cl, Cl, OMe, F, 1-isopropyloxybutyl), (B1297, Cl, Cl, OMe, F, 1-isopropyloxy-4-n-pentyloxybutyl), (B1298, Cl, Cl, OMe, F, 1-isopropyloxy-2-methylpropyl), (B1299, Cl, Cl, OMe, F, 1-isopropyloxypentyl), (B1300, Cl, Cl, OMe, F, 1-isopropyloxy-3-methylbutyl), (B1301, Cl, Cl, OMe, F, 1-isopropyloxy-2,2-dimethylpropyl), (B1302, Cl, Cl, OMe, F, 1-isopropyloxyhexyl), (B1303, Cl, Cl, OMe, F, 1-isopropyloxy-3,3-dimethylbutyl), (B1304, Cl, Cl, OMe, F, 1-isopropyloxyheptyl), (B1305, Cl, Cl, OMe, F, 1-isopropyloxyoctyl), (B1306, Cl, Cl, OMe, F, 1-isopropyloxynonyl), (B1307, Cl, Cl, OMe, F, 1-isopropyloxydecyl), (B1308, Cl, Cl, OMe, F, 1-isopropyloxyundecyl), (B1309, Cl, Cl, OMe, F, 1-isopropyloxydodecyl), (B1310, Cl, Cl, OMe, F, 1-isopropyloxy-1-cyclohexylmethyl), (B1311, Cl, Cl, OMe, F, 1-n-butyloxyethyl), (B1312, Cl, Cl, OMe, F, 1-n-butyloxypropyl), (B1313, Cl, Cl, OMe, F, 3-n-butyloxypropyl), (B1314, Cl, Cl, OMe, F, 1-n-butyloxybutyl), (B1315, Cl, Cl, OMe, F, 1,4-di(n-butyloxy)butyl), (B1316, Cl, Cl, OMe, F, 1-n-butyloxy-2-methylpropyl), (B1317, Cl, Cl, OMe, F, 1-n-butyloxypentyl), (B1318, Cl, Cl, OMe, F, 1-n-butyloxy-3-methylbutyl), (B1319, Cl, Cl, OMe, F, 1-n-butyloxy-2,2-dimethylpropyl), (B1320, Cl, Cl, OMe, F, 1-n-butyloxyhexyl), (B1321, Cl, Cl, OMe, F, 1-n-butyloxy-3,3-dimethylbutyl), (B1322, Cl, Cl, OMe, F, 1-n-butyloxyheptyl), (B1323, Cl, Cl, OMe, F, 1-n-butyloxyoctyl), (B1324, Cl, Cl, OMe, F, 1-n-butyloxynonyl), (B1325, Cl, Cl, OMe, F, 1-n-butyloxydecyl), (B1326, Cl, Cl, OMe, F, 1-n-butyloxyundecyl), (B1327, Cl, Cl, OMe, F, 1-n-butyloxydodecyl), (B1328, Cl, Cl, OMe, F, 1-n-butyloxy-1-cyclohexylmethyl), (B1329, Cl, Cl, OMe, F, 1-isobutyloxyethyl), (B1330, Cl, Cl, OMe, F, 1-isobutyloxypropyl), (B1331, Cl, Cl, OMe, F, 1-isobutyloxybutyl), (B1332, Cl, Cl, OMe, F, 1-isobutyloxy-2-methylpropyl), (B1333, Cl, Cl, OMe, F, 1-isobutyloxypentyl), (B1334, Cl, Cl, OMe, F, 1-isobutyloxy-3-methylbutyl), (B1335, Cl, Cl, OMe, F, 1-isobutyloxy-2,2-dimethylpropyl), (B1336, Cl, Cl, OMe, F, 1-isobutyloxyhexyl), (B1337, Cl, Cl, OMe, F, 1-isobutyloxy-3,3-dimethylbutyl), (B1338, Cl, Cl, OMe, F, 1-isobutyloxyheptyl), (B1339, Cl, Cl, OMe, F, 1-isobutyloxyoctyl), (B1340, Cl, Cl, OMe, F, 1-isobutyloxyynonyl), (B1341, Cl, Cl, OMe, F, 1-isobutyloxydecyl), (B1342, Cl, Cl, OMe, F, 1-isobutyloxyundecyl), (B1343, Cl, Cl, OMe, F, 1-isobutyloxydodecyl), (B1344, Cl, Cl, OMe, F, 1-isobutyloxy-1-cyclohexylmethyl), (B1345, Cl, Cl, OMe, F, 1-t-butyloxyethyl), (B1346, Cl, Cl, OMe, F, 1-t-butyloxypropyl), (B1347, Cl, Cl, OMe, F, 1-t-butyloxybutyl), (B1348, Cl, Cl, OMe, F, 1-t-butyloxy-2-methylpropyl), (B1349, Cl, Cl, OMe, F, 1-t-butyloxypentyl), (B1350, Cl, Cl, OMe, F, 1-t-butyloxy-3-methylbutyl), (B1351, Cl, Cl, OMe, F, 1-t-butyloxy-2,2-dimethylpropyl), (B1352, Cl, Cl, OMe, F, 1-t-butyloxyhexyl), (B1353, Cl, Cl, OMe, F, 1-t-butyloxy-3,3-dimethylbutyl), (B1354, Cl, Cl, OMe, F, 1-t-butyloxyheptyl), (B1355, Cl, Cl, OMe, F, 1-t-butyloxyoctyl), (B1356, Cl, Cl, OMe, F, 1-t-butyloxynonyl), (B1357, Cl, Cl, OMe, F, 1-t-butyloxydecyl), (B1358, Cl, Cl, OMe, F, 1-t-butyloxyundecyl), (B1359, Cl, Cl, OMe, F, 1-t-butyloxydodecyl), (B1360, Cl, Cl, OMe, F, 1-t-butyloxy-1-cyclohexylmethyl), (B1361, Cl, Cl, OMe, F, 1-n-pentyloxyethyl), (B1362, Cl, Cl, OMe, F, 1-n-pentyloxypropyl), (B1363, Cl, Cl, OMe, F, 3-n-pentyloxypropyl), (B1364, Cl, Cl, OMe, F, 1-n-pentyloxy-3-methylthiopropyl), (B1365, Cl, Cl, OMe, F, 1-n-pentyloxybutyl), (B1366, Cl, Cl, OMe, F, 1-n-pentyloxy-2-methylpropyl), (B1367, Cl, Cl, OMe, F, 1-n-pentyloxypentyl), (B1368, Cl, Cl, OMe, F, 1-n-pentyloxy-3-methylbutyl), (B1369, Cl, Cl, OMe, F, 1-n-pentyloxy-2,2-dimethylpropyl), (B1370, Cl, Cl, OMe, F, 1-n-pentyloxyhexyl), (B1371, Cl, Cl, OMe, F, 1-n-pentyloxy-3,3-dimethylbutyl), (B1372, Cl, Cl, OMe, F, 1-n-pentyloxyheptyl), (B1373, Cl, Cl, OMe, F, 1-n-pentyloxyoctyl), (B1374, Cl, Cl, OMe, F, 1-n-pentyloxynonyl), (B1375, Cl, Cl, OMe, F, 1-n-pentyloxydecyl), (B1376, Cl, Cl, OMe, F, 1-n-pentyloxyundecyl), (B1377, Cl, Cl, OMe, F, 1-n-pentyloxydodecyl), (B1378, Cl, Cl, OMe, F, 1-n-pentyloxy-1-cyclohexylmethyl), (B1379, Cl, Cl, OMe, F, 1-isopentyloxypropyl), (B1380, Cl, Cl, OMe, F, 1-neopentyloxyethyl), (B1381, Cl, Cl, OMe, F, 1-neopentyloxypropyl), (B1382, Cl, Cl, OMe, F, 3-neopentyloxypropyl), (B1383, Cl, Cl, OMe, F, 1-neopentyloxybutyl), (B1384, Cl, Cl, OMe, F, 1-neopentyloxy-2-methylpropyl), (B1385, Cl, Cl, OMe, F, 1-neopentyloxypentyl), (B1386, Cl, Cl, OMe, F, 1-neopentyloxy-3-methylbutyl), (B1387, Cl, Cl, OMe, F, 1-neopentyloxy-2,2-dimethylpropyl), (B1388, Cl, Cl, OMe, F, 1-neopentyloxyhexyl), (B1389, Cl, Cl, OMe, F, 1-neopentyloxy-3,3-dimethylbutyl), (B1390, Cl, Cl, OMe, F, 1-neopentyloxyheptyl), (B1391, Cl, Cl, OMe, F, 1-neopentyloxyoctyl), (B1392, Cl, Cl, OMe, F, 1-neopentyloxynonyl), (B1393, Cl, Cl, OMe, F, 1-neopentyloxydecyl), (B1394, Cl, Cl, OMe, F, 1-neopentyloxyundecyl), (B1395, Cl, Cl, OMe, F, 1-neopentyloxydodecyl), (B1396, Cl, Cl, OMe, F, 1-neopentyloxy-1-cyclohexylmethyl), (B1397, Cl, Cl, OMe, F, 1-n-hexyloxyethyl), (B1398, Cl, Cl, OMe, F, 1-n-hexyloxypropyl), (B1399, Cl, Cl, OMe, F, 3-n-hexyloxypropyl), (B1400, Cl, Cl, OMe, F, 1-n-hexyloxybutyl), (B1401, Cl, Cl, OMe, F, 1-n-hexyloxy-2-methylpropyl), (B1402, Cl, Cl, OMe, F, 1-n-hexyloxypentyl), (B1403, Cl, Cl, OMe, F, 1-n-hexyloxy-3-methylbutyl), (B1404, Cl, Cl, OMe, F, 1-n-hexyloxy-2,2-dimethylpropyl), (B1405, Cl, Cl, OMe, F, 1-n-hexyloxyhexyl), (B1406, Cl, Cl, OMe, F, 1-n-hexyloxy-3,3-dimethylbutyl), (B1407, Cl, Cl, OMe, F, 1-n-hexyloxyheptyl), (B1408, Cl, Cl, OMe, F, 1-n-hexyloxyoctyl), (B1409, Cl, Cl, OMe, F, 1-n-hexyloxynonyl), (B1410, Cl, Cl, OMe, F, 1-n-hexyloxydecyl), (B1411, Cl, Cl, OMe, F, 1-n-hexyloxyundecyl), (B1412, Cl, Cl, OMe, F, 1-n-hexyloxydodecyl), (B1413, Cl, Cl, OMe, F, 1-n-hexyloxy-1-cyclohexylmethyl), (B1414, Cl, Cl, OMe, F, 3-isohexyloxypropyl), (B1415, Cl, Cl, OMe, F, 3-(3,3-dimethylbutyloxy)propyl), (B1416, Cl, Cl, OMe, F, 3-(2-cyclopentyletoxy)propyl), (B1417, Cl, Cl, OMe, F, 1-n-octyloxyethyl), (B1418, Cl, Cl, OMe, OMe, 1-methyloxyethyl), (B1419, Cl, Cl, OMe, OMe, 1-methyloxypropyl), (B1420, Cl, Cl, OMe, OMe, 1-methyloxy-3-n-hexyloxypropyl), (B1421, Cl, Cl, OMe, OMe, 1-methyloxybutyl), (B1422, Cl, Cl, OMe, OMe, 1-methyloxy-4-n-pentyloxybutyl), (B 1423, Cl, Cl, OMe, OMe, 1-methyloxy-2-methylpropyl), (B 1424, Cl, Cl, OMe, OMe, 1-methyloxypentyl), (B1425, Cl, Cl, OMe, OMe, 1-methyloxy-3-methylbutyl), (B1426, Cl, Cl, OMe, OMe, 1-methyloxy-2,2-dimethylpropyl), (B1427, Cl, Cl, OMe, OMe, 1-methyloxyhexyl), (B1428, Cl, Cl, OMe, OMe, 4-methyloxyhexyl), (B1429, Cl, Cl, OMe, OMe, 1-methyloxy-4-methylpentyl), (B1430, Cl, Cl, OMe, OMe, 1-methyloxy-3,3-dimethylbutyl), (B1431, Cl, Cl, OMe, OMe, 3-methyloxy-2,4-dimethyl-3-pentyl), (B1432, Cl, Cl, OMe, OMe, 1-methyloxyheptyl), (B1433, Cl, Cl, OMe, OMe, 4-methyloxy-4-heptyl), (B1434, Cl, Cl, OMe, OMe, 1-methyloxyoctyl), (B1435, Cl, Cl, OMe, OMe, 3-methyloxyoctyl), (B1436, Cl, Cl, OMe, OMe, 1-methyloxynonyl), (B1437, Cl, Cl, OMe, OMe, 1-methyloxydecyl), (B1439, Cl, Cl, OMe, OMe, 1-methyloxydodecyl), (B1440, Cl, Cl, OMe, OMe, 1-methyloxy-1-cyclohexylmethyl), (B1441, Cl, Cl, OMe, OMe, 1-(4-ethyloxybutyloxy)-1-cyclohexylmethyl), (B 1442, Cl, Cl, OMe, OMe, 1-ethyloxyethyl), (B1443, Cl, Cl, OMe, OMe, 1-ethyloxypropyl), (B1444, Cl, Cl, OMe, OMe, 1-(4-ethyloxybutyloxy)propyl), (B1445, Cl, Cl, OMe, OMe, 1-ethyloxybutyl), (B1446, Cl, Cl, OMe, OMe, 1-ethyloxy-2-methylpropyl), (B1447, Cl, Cl, OMe, OMe, 1-ethyloxypentyl), (B1448, Cl, Cl, OMe, OMe, 1-ethyloxy-3-methylbutyl), (B1449, Cl, Cl, OMe, OMe, 1-ethyloxy-2,2-dimethylpropyl), (B1450, Cl, Cl, OMe, OMe, 1-ethyloxyhexyl), (B1451, Cl, Cl, OMe, OMe, 1-ethyloxy-3,3-dimethylbutyl), (B1452, Cl, Cl, OMe, OMe, 1-ethyloxyheptyl), (B1453, Cl, Cl, OMe, OMe, 1-ethyloxyoctyl), (B1454, Cl, Cl, OMe, OMe, 1-ethyloxynonyl), (B1455, Cl, Cl, OMe, OMe, 1-ethyloxydecyl), (B1456, Cl, Cl, OMe, OMe, 1-ethyloxyundecyl), (B1457, Cl, Cl, OMe, OMe, 1-ethyloxydodecyl), (B 1458, Cl, Cl, OMe, OMe, 1-ethyloxy-1-cyclohexylmethyl), (B1459, Cl, Cl, OMe, OMe, 1-n-propyloxyethyl), (B1460, Cl, Cl, OMe, OMe, 1-n-propyloxypropyl), (B1461, Cl, Cl, OMe, OMe, 3-n-propyloxypropyl), (B1462, Cl, Cl, OMe, OMe, 1-n-propyloxybutyl), (B1463, Cl, Cl, OMe, OMe, 1,4-di(n-propyloxy)butyl), (B1464, Cl, Cl, OMe, OMe, 1-n-propyloxy-2-methylpropyl), (B1465, Cl, Cl, OMe, OMe, 1-n-propyloxypentyl), (B1466, Cl, Cl, OMe, OMe, 1-n-propyloxy-3-methylbutyl), (B1467, Cl, Cl, OMe, OMe, 1-n-propyloxy-2,2-dimethylpropyl), (B1468, Cl, Cl, OMe, OMe, 1-n-propyloxyhexyl), (B1469, Cl, Cl, OMe, OMe, 1-n-propyloxy-3,3-dimethylbutyl), (B1470, Cl, Cl, OMe, OMe, 1-n-propyloxyheptyl), (B1471, Cl, Cl, OMe, OMe, 1-n-propyloxyoctyl), (B1472, Cl, Cl, OMe, OMe, 1-n-propyloxynonyl), (B1473, Cl, Cl, OMe, OMe, 1-n-propyloxydecyl), (B1474, Cl, Cl, OMe, OMe, 1-n-propyloxyundecyl), (B 1475, Cl, Cl, OMe, OMe, 1-n-propyloxydodecyl), (B1476, Cl, Cl, OMe, OMe, 1-n-propyloxy-1-cyclohexylmethyl), (B1477, Cl, Cl, OMe, OMe, 1-isopropyloxyethyl), (B1478, Cl, Cl, OMe, OMe, 1-isopropyloxypropyl), (B1479, Cl, Cl, OMe, OMe, 3-isopropyloxypropyl), (B1480, Cl, Cl, OMe, OMe, 1-isopropyloxybutyl), (B1481, Cl, Cl, OMe, OMe, 1-isopropyloxy-2-methylpropyl), (B1482, Cl, Cl, OMe, OMe, 1-isopropyloxypentyl), (B1483, Cl, Cl, OMe, OMe, 1-isopropyloxy-3-methylbutyl), (B 1484, Cl, Cl, OMe, OMe, 1-isopropyloxy-2,2-dimethylpropyl), (B1485, Cl, Cl, OMe, OMe, 1-isopropyloxyhexyl), (B1486, Cl, Cl, OMe, OMe, 1-isopropyloxy-3,3-dimethylbutyl), (B1487, Cl, Cl, OMe, OMe, 1-isopropyloxyheptyl), (B1488, Cl, Cl, OMe, OMe, 1-isopropyloxyoctyl), (B1489, Cl, Cl, OMe, OMe, 1-isopropyloxynonyl), (B1490, Cl, Cl, OMe, OMe, 1-isopropyloxydecyl), (B1491, Cl, Cl, OMe, OMe, 1-isopropyloxyundecyl), (B1492, Cl, Cl, OMe, OMe, 1-isopropyloxydodecyl), (B1493, Cl, Cl, OMe, OMe, 1-isopropyloxy-1-cyclohexylmethyl), (B1494, Cl, Cl, OMe, OMe, 1-n-butyloxyethyl), (B1495, Cl, Cl, OMe, OMe, 1-n-butyloxypropyl), (B1496, Cl, Cl, OMe, OMe, 3-n-butyloxypropyl), (B1497, Cl, Cl, OMe, OMe, 1-n-butyloxybutyl), (B1498, Cl, Cl, OMe, OMe, 1,4-di(n-butyloxy)butyl), (B1499, Cl, Cl, OMe, OMe, 1-n-butyloxy-2-methylpropyl), (B1500, Cl, Cl, OMe, OMe, 1-n-butyloxypentyl), (B1501, Cl, Cl, OMe, OMe, 1-n-butyloxy-3-methylbutyl), (B1502, Cl, Cl, OMe, OMe, 1-n-butyloxy-2,2-dimethylpropyl), (B1503, Cl, Cl, OMe, OMe, 1-n-butyloxyhexyl), (B1504, Cl, Cl, OMe, OMe, 1-n-butyloxy-3,3-dimethylbutyl), (B1505, Cl, Cl, OMe, OMe, 1-n-butyloxyheptyl), (B1506, Cl, Cl, OMe, OMe, 1-n-butyloxyoctyl), (B1507, Cl, Cl, OMe, OMe, 1-n-butyloxynonyl), (B1508, Cl, Cl, OMe, OMe, 1-n-butyloxydecyl), (B1509, Cl, Cl, OMe, OMe, 1-n-butyloxyundecyl), (B1510, Cl, Cl, OMe, OMe, 1-n-butyloxydodecyl), (B1511, Cl, Cl, OMe, OMe, 1-n-butyloxy-1-cyclohexylmethyl), (B1512, Cl, Cl, OMe, OMe, 1-isobutyloxyethyl), (B1513, Cl, Cl, OMe, OMe, 1-isobutyloxypropyl), (B1514, Cl, Cl, OMe, OMe, 1-isobutyloxybutyl), (B1515, Cl, Cl, OMe, OMe, 1-isobutyloxy-2-methylpropyl), (B1516, Cl, Cl, OMe, OMe, 1-isobutyloxypentyl), (B 1517, Cl, Cl, OMe, OMe, 1-isobutyloxy-3-methylbutyl), (B 1518, Cl, Cl, OMe, OMe, 1-isobutyloxy-2,2-dimethylpropyl), (B1519, Cl, Cl, OMe, OMe, 1-isobutyloxyhexyl), (B1520, Cl, Cl, OMe, OMe, 1-isobutyloxy-3,3-dimethylbutyl), (B1521, Cl, Cl, OMe, OMe, 1-isobutyloxyheptyl), (B1522, Cl, Cl, OMe, OMe, 1-isobutyloxyoctyl), (B1523, Cl, Cl, OMe, OMe, 1-isobutyloxyynonyl), (B1524, Cl, Cl, OMe, OMe, 1-isobutyloxydecyl), (B1525, Cl, Cl, OMe, OMe, 1-isobutyloxyundecyl), (B1526, Cl, Cl, OMe, OMe, 1-isobutyloxydodecyl), (B1527, Cl, Cl, OMe, OMe, 1-isobutyloxy-1-cyclohexylmethyl), (B1528, Cl, Cl, OMe, OMe, 1-t-butyloxyethyl), (B1529, Cl, Cl, OMe, OMe, 1-t-butyloxypropyl), (B1530, Cl, Cl, OMe, OMe, 1-t-butyloxybutyl), (B1531, Cl, Cl, OMe, OMe, 1-t-butyloxy-2-methylpropyl), (B1532, Cl, Cl, OMe, OMe, 1-t-butyloxypentyl), (B1533, Cl, Cl, OMe, OMe, 1-t-butyloxy-3-methylbutyl), (B1534, Cl, Cl, OMe, OMe, 1-t-butyloxy-2,2-dimethylpropyl), (B1535, Cl, Cl, OMe, OMe, 1-t-butyloxyhexyl), (B1536, Cl, Cl, OMe, OMe, 1-t-butyloxy-3,3-dimethylbutyl), (B1537, Cl, Cl, OMe, OMe, 1-t-butyloxyheptyl), (B1538, Cl, Cl, OMe, OMe, 1-t-butyloxyoctyl), (B1539, Cl, Cl, OMe, OMe, 1-t-butyloxynonyl), (B1540, Cl, Cl, OMe, OMe, 1-t-butyloxydecyl), (B1541, Cl, Cl, OMe, OMe, 1-t-butyloxyundecyl), (B1542, Cl, Cl, OMe, OMe, 1-t-butyloxydodecyl), (B1543, Cl, Cl, OMe, OMe, 1-t-butyloxy-1-cyclohexylmethyl), (B1544, Cl, Cl, OMe, OMe, 1-n-pentyloxyethyl), (B1545, Cl, Cl, OMe, OMe, 1-n-pentyloxypropyl), (B1546, Cl, Cl, OMe, OMe, 3-n-pentyloxypropyl), (B1547, Cl, Cl, OMe, OMe, 1-n-pentyloxy-3-methylthiopropyl), (B1548, Cl, Cl, OMe, OMe, 1-n-pentyloxybutyl), (B1549, Cl, Cl, OMe, OMe, 1-n-pentyloxy-2-methylpropyl), (B1550, Cl, Cl, OMe, OMe, 1-n-pentyloxypentyl), (B1551, Cl, Cl, OMe, OMe, 1-n-pentyloxy-3-methylbutyl), (B1552, Cl, Cl, OMe, OMe, 1-n-pentyloxy-2,2-dimethylpropyl), (B1553, Cl, Cl, OMe, OMe, 1-n-pentyloxyhexyl), (B1554, Cl, Cl, OMe, OMe, 1-n-pentyloxy-3,3-dimethylbutyl), (B1555, Cl, Cl, OMe, OMe, 1-n-pentyloxyheptyl), (B1556, Cl, Cl, OMe, OMe, 1-n-pentyloxyoctyl), (B1557, Cl, Cl, OMe, OMe, 1-n- pentyloxynonyl), (B1558, Cl, Cl, OMe, OMe, 1-n-pentyloxydecyl), (B1559, Cl, Cl, OMe, OMe, 1-n-pentyloxyundecyl), (B1560, Cl, Cl, OMe, OMe, 1-n-pentyloxydodecyl), (B1561, Cl, Cl, OMe, OMe, 1-n-pentyloxy-1-cyclohexylmethyl), (B1562, Cl, Cl, OMe, OMe, 1-isopentyloxypropyl), (B1563, Cl, Cl, OMe, OMe, 1-neopentyloxyethyl), (B1564, Cl, Cl, OMe, OMe, 1-neopentyloxypropyl), (B1565, Cl, Cl, OMe, OMe, 3-neopentyloxypropyl), (B1566, Cl, Cl, OMe, OMe, 1-neopentyloxybutyl), (B1567, Cl, Cl, OMe, OMe, 1-neopentyloxy-2-methylpropyl), (B1568, Cl, Cl, OMe, OMe, 1-neopentyloxypentyl), (B1569, Cl, Cl, OMe, OMe, 1-neopentyloxy-3-methylbutyl), (B1570, Cl, Cl, OMe, OMe, 1-neopentyloxy-2,2-dimethylpropyl), (B1571, Cl, Cl, OMe, OMe, 1-neopentyloxyhexyl), (B1572, Cl, Cl, OMe, OMe, 1-neopentyloxy-3,3-dimethylbutyl), (B1573, Cl, Cl, OMe, OMe, 1-neopentyloxyheptyl), (B1574, Cl, Cl, OMe, OMe, 1-neopentyloxyoctyl), (B1575, Cl, Cl, OMe, OMe, 1-neopentyloxynonyl), (B1576, Cl, Cl, OMe, OMe, 1-neopentyloxydecyl), (B1577, Cl, Cl, OMe, OMe, 1-neopentyloxyundecyl), (B1578, Cl, Cl, OMe, OMe, 1-neopentyloxydodecyl), (B1579, Cl, Cl, OMe, OMe, 1-neopentyloxy-1-cyclohexylmethyl), (B1580, Cl, Cl, OMe, OMe, 1-n-hexyloxyethyl), (B1581, Cl, Cl, OMe, OMe, 1-n-hexyloxypropyl), (B1582, Cl, Cl, OMe, OMe, 3-n-hexyloxypropyl), (B1583, Cl, Cl, OMe, OMe, 1-n-hexyloxybutyl), (B1584, Cl, Cl, OMe, OMe, 1-n-hexyloxy-2-methylpropyl), (B1585, Cl, Cl, OMe, OMe, 1-n-hexyloxypentyl), (B1586, Cl, Cl, OMe, OMe, 1-n-hexyloxy-3-methylbutyl), (B1587, Cl, Cl, OMe, OMe, 1-n-hexyloxy-2,2-dimethylpropyl), (B1588, Cl, Cl, OMe, OMe, 1-n-hexyloxyhexyl), (B1589, Cl, Cl, OMe, OMe, 1-n-hexyloxy-3,3-dimethylbutyl), (B1590, Cl, Cl, OMe, OMe, 1-n-hexyloxyheptyl), (B1591, Cl, Cl, OMe, OMe, 1-n-hexyloxyoctyl), (B1592, Cl, Cl, OMe, OMe, 1-n-hexyloxynonyl), (B1593, Cl, Cl, OMe, OMe, 1-n-hexyloxydecyl), (B1594, Cl, Cl, OMe, OMe, 1-n-hexyloxyundecyl), (B1595, Cl, Cl, OMe, OMe, 1-n-hexyloxydodecyl), (B1596, Cl, Cl, OMe, OMe, 1-n-hexyloxy-1-cyclohexylmethyl), (B1597, Cl, Cl, OMe, OMe, 3-isohexyloxypropyl), (B1598, Cl, Cl, OMe, OMe, 3-(3,3-dimethylbutyloxy)propyl), (B1599, Cl, Cl, OMe, OMe, 3-(2-cyclopentylethyloxy)propyl), (B1600, Cl, Cl, OMe, OMe, 1-n-octyloxyethyl), (B1601, F, F, F, F, 1-methyloxy-3-n-hexyloxypropyl), (B1602, F, F, Cl, F, 1-methyloxy-3-n-hexyloxypropyl), (B1603, F, F, F, F, 1-methyloxy-4-n-pentyloxybutyl), (B1604, F, F, Cl, F, 1-methyloxy-4-n-pentyloxybutyl), (B1605, F, F, Me, F, 1-methyloxy-2,2-dimethylpropyl), (B1606, F, F, Me, F, 1-methyloxy-4-methylpentyl), (B1607, F, F, Me, F, 1-methyloxyheptyl), (B1608, F, F, Me, F, 1-methyloxyoctyl), (B1609, F, F, Me, F, 1-methyloxynonyl), (B1610, F, F, Me, F, 1-methyloxydecyl), (B1611, F, F, Me, F, 1-(4-ethyloxybutyloxy)-1-cyclohexylmethyl), (B 1612, F, F, Me, F, 1-(4-ethyloxybutyloxy)propyl), (B1613, F, F, Me, F, 1-ethyloxypentyl), (B1614, F, F, Me, F, 1-n-propyloxybutyl), (B1615, F, F, Me, F, 1-n-propyloxypentyl), (B1616, F, F, Me, F, 1-n-butyloxyethyl), (B1617, F, F, Me, F, 1-n-butyloxypropyl), (B1618, F, F, Me, F, 3-n-butyloxypropyl), (B1619, F, F, Me, F, 1-n-butyloxybutyl), (B1620, F, F, Me, F, 1,4-di(n-butyloxy)butyl), (B1621, F, F, Me, F, 1-n-butyloxypentyl), (B1622, F, F, Me, F, 1-n-pentyloxyethyl), (B1623, F, F, Me, F, 1-n-pentyloxypropyl), (B1624, F, F, Me, F, 3-n-pentyloxypropyl), (B1625, F, F, Me, F, 1-n-pentyloxy-3-methylthiopropyl), (B1626, F, F, Me, F, 1-n-pentyloxybutyl), (B1627, F, F, Me, F, 1-n-pentyloxypentyl), (B1628, F, F, Me, F, 1-n-pentyloxy-2,2-dimethylpropyl), (B1629, F, F, Me, F, 1-n-pentyloxy-1-cyclohexylmethyl), (B1630, F, F, Me, F, 1-isopentyloxypropyl), (B1631, F, F, Me, F, 3-neopentyloxypropyl), (B1632, F, F, Me, F, 1-n-hexyloxypropyl), (B1633, F, F, Me, F, 3-n-hexyloxypropyl), (B1634, F, F, Me, F, 3-isohexyloxypropyl), (B1635, F, F, Me, F, 3-(3,3-dimethylbutyloxy)propyl), (B1636, F, F, Me, F, 3-(2-cyclopentylethyloxy)propyl), (B1637, F, F, Me, F, 1-n-octyloxyethyl), (B1638, Cl, Cl, Me, F, 1-methyloxy-2,2-dimethylpropyl), (B1639, Cl, Cl, Me, F, 1-methyloxyhexyl), (B1640, Cl, Cl, Me, F, 1-methyloxy-4-methylpentyl), (B1641, Cl, Cl, Me, F, 1-methyloxyheptyl), (B1642, Cl, Cl, Me, F, 1-methyloxyoctyl), (B1643, Cl, Cl, Me, F, 3-methyloxyoctyl), (B1644, Cl, Cl, Me, F, 1-methyloxynonyl), (B1645, Cl, Cl, Me, F, 1-methyloxydecyl), (B1646, Cl, Cl, Me, F, 1-methyloxyundecyl), (B1647, Cl, Cl, Me, F, 1-(4-ethyloxybutyloxy)propyl), (B1648, Cl, Cl, Me, F, 1-ethyloxypentyl), (B1649, Cl, Cl, Me, F, 1-ethyloxy-3,3-dimethylbutyl), (B1650, Cl, Cl, Me, F, 1-n-propyloxyethyl), (B1651, Cl, Cl, Me, F, 1-n-propyloxypropyl), (B1652, Cl, Cl, Me, F, 3-n-propyloxypropyl), (B1653, Cl, Cl, Me, F, 1-n-propyloxybutyl), (B1654, Cl, Cl, Me, F, 1,4-di(n-propyloxy)butyl), (B1655, Cl, Cl, Me, F, 1-n-propyloxypentyl), (B1656, Cl, Cl, Me, F, 3-isopropyloxypropyl), (B1657, Cl, Cl, Me, F, 1-n-butyloxyethyl), (B1658, Cl, Cl, Me, F, 1-n-butyloxypropyl), (B1659, Cl, Cl, Me, F, 3-n-butyloxypropyl), (B1660, Cl, Cl, Me, F, 1-n-butyloxybutyl), (B1661, Cl, Cl, Me, F, 1-n-butyloxypentyl), (B1662, Cl, Cl, Me, F, 1-n-pentyloxypropyl), (B1663, Cl, Cl, Me, F, 3-n-pentyloxypropyl), (B1664, Cl, Cl, Me, F, 1-n-pentyloxy-3-methylthiopropyl), (B1665, Cl, Cl, Me, F, 1-n-pentyloxybutyl), (B1666, Cl, Cl, Me, F, 1-n-pentyloxypentyl), (B1667, Cl, Cl, Me, F, 1-isopentyloxypropyl), (B1668, Cl, Cl, Me, F, 3-neopentyloxypropyl), (B1669, Cl, Cl, Me, F, 1-n-hexyloxypropyl), (B1670, Cl, Cl, Me, F, 3-n-hexyloxypropyl), (B1671, Cl, Cl, Me, F, 3-isohexyloxypropyl), (B1672, Cl, Cl, Me, F, 3-(3,3-dimethylbutyloxy)propyl), (B1673, Cl, Cl, Me, F, 3-(2-cyclopentylethyloxy)propyl), (B1674, Cl, Cl, Me, F, 1-n-octyloxyethyl), (B1675, Me, Me, Me, F, 1-methyloxy-3-n-hexyloxypropyl), (B1676, Me, Me, Me, F, 1-methyloxy-4-n-pentyloxybutyl), (B1677, Me, Me, Me, F, 1-methyloxy-2,2-dimethylpropyl), (B1678, Me, Me, Me, F, 1-methyloxyhexyl), (B1679, Me, Me, Me, F, 1-methyloxy-4-methylpentyl), (B1680, Me, Me, Me, F, 1-methyloxyheptyl), (B1681, Me, Me, Me, F, 1-methyloxyoctyl), (B1682, Me, Me, Me, F, 3-methyloxyoctyl), (B1683, Me, Me, Me, F, 1-methyloxynonyl), (B1684, Me, Me, Me, F, 1-methyloxydecyl), (B1685, Me, Me, Me, F, 1-methyloxyundecyl), (B1686, Me, Me, Me, F, 1-(4-ethyloxybutyloxy)-1-cyclohexylmethyl), (B1687, Me, Me, Me, F, 1-(4-ethyloxybutyloxy)propyl), (B1688, Me, Me, Me, F, 1-ethyloxypentyl), (B1689, Me, Me, Me, F, 1-ethyloxy-3,3-dimethylbutyl), (B1690, Me, Me, Me, F, 1-n-propyloxyethyl), (B1691, Me, Me, Me, F, 1-n-propyloxypropyl), (B1692, Me, Me, Me, F, 3-n-propyloxypropyl), (B1693, Me, Me, Me, F, 1-n-propyloxybutyl), (B1694, Me, Me, Me, F, 1,4-di(n-propyloxy)butyl), (B1695, Me, Me, Me, F, 1-n-propyloxypentyl), (B1696, Me, Me, Me, F, 3-isopropyloxypropyl), (B1697, Me, Me, Me, F, 1-n-butyloxyethyl), (B1698, Me, Me, Me, F, 1-n-butyloxypropyl), (B1699, Me, Me, Me, F, 3-n-butyloxypropyl), (B1700, Me, Me, Me, F, 1-n-butyloxybutyl), (B1701, Me, Me, Me, F, 1,4-di(n-butyloxy)butyl), (B1702, Me, Me, Me, F, 1-n-butyloxypentyl), (B1703, Me, Me, Me, F, 1-n-pentyloxyethyl), (B1704, Me, Me, Me, F, 1-n-pentyloxypropyl), (B1705, Me, Me, Me, F, 3-n-pentyloxypropyl), (B1706, Me, Me, Me, F, 1-n-pentyloxy-3-methylthiopropyl), (B1707, Me, Me, Me, F, 1-n-pentyloxybutyl), (B1708, Me, Me, Me, F, 1-n-pentyloxypentyl), (B1709, Me, Me, Me, F, 1-n-pentyloxy-2,2-dimethylpropyl), (B1710, Me, Me, Me, F, 1-n-pentyloxy-1-cyclohexylmethyl), (B1711, Me, Me, Me, F, 1-isopentyloxypropyl), (B1712, Me, Me, Me, F, 3-neopentyloxypropyl), (B1713, Me, Me, Me, F, 1-n-hexyloxypropyl), (B1714, Me, Me, Me, F, 3-n-hexyloxypropyl), (B1715, Me, Me, Me, F, 3-isohexyloxypropyl), (B1716, Me, Me, Me, F, 3-(3,3-dimethylbutyloxy)propyl), (B1717, Me, Me, Me, F, 3-(2-cyclopentylethyloxy)propyl), (B1718, Me, Me, Me, F, 1-n-octyloxyethyl), (B1719, Me, Me, Me, F, 1-methyloxyhexyl), (B1720, Me, Me, Me, F, 3-methyloxyoctyl), (B1721, Me, Me, Me, F, 1-methyloxyundecyl), (B1722, Me, Me, Me, F, 1-ethyloxy-3,3-dimethylbutyl), (B1723, Me, Me, Me, F, 1-n-propyloxyethyl), (B1724, Me, Me, Me, F, 1-n-propyloxypropyl), (B1725, Me, Me, Me, F, 3-n-propyloxypropyl), (B1726, Me, Me, Me, F, 1,4-di(n-propyloxy)butyl), (B1727, Me, Me, Me, F, 3-isopropyloxypropyl)

Example 584

Synthesis of 3-(4-{4-[3-(1-n-butyloxypropyl)-2-fluorophenyl]thiazol-2-ylcarbonyl}-2,6-difluorophenyl)-2-methylacrylic acid disodium salt (C1)

To a suspension of methanol (100 mL) solution of 3-(4-{4-[3-(1-n-butyloxypropyl)-2-fluorophenyl]thiazol-2-ylcarbonyl}-2,6-difluorophenyl)-2-methylacrylic acid (3.22 mg) was added 2M sodium hydroxide aqueous solution (6.06 mL). After stirring for 1 h, n-hexylaldehyde (5.88 mL) was added to the reaction mixture. After methanol was evaporated under reduced pressure, the obtained residue was redissolved by adding water (40 mL). The water solution was freeze drying to obtain the compound (C1) 3.40 g.

$^1$H-NMR(DMSO-d6) 8.05-8.11 (m, 1H), 7.69-7.75 (m, 1H), 7.22-7.29 (m, 2H), 7.15 (d, 1H, J=3.1 Hz), 7.03 (s, 1H), 4.56-4.60 (m, 1H), 3.31 (t, 2H, J=6.3 Hz), 1.65-1.80 (m, 5H), 1.45-1.55 (m, 2H), 1.30-1.40 (m, 2H), 0.83-0.91 (m, 6H).

C2 to C6 were synthesized by similar method described above.

Example 585

Synthesis of 3-[2,6-dichloro-4-(4-{3-[3-(2-ethylbutyloxy)propyl]-2-fluorophenyl}thiazol-2-ylcarbonyl)phenyl]-2-methylacrylic acid disodium salt (C2)

1H-NMR(DMSO-d6) 8.11 (s, 2H), 7.97-8.03 (m, 2H), 7.11-7.18 (m, 1H), 3.26-3.41 (m, 4H), 2.72 (t, 2H, J=7.3 Hz), 1.78-1.87 (m, 2H), 1.62 (s, 3H), 1.24-1.62 (m, 5H), 0.86 (t, 6H, J=7.3 Hz).

Example 586

Synthesis of 3-(2,6-dichloro-4-{4-[2-fluoro-3-(1-methyloxydecyl)phenyl]thiazol-2-ylcarbonyl}phenyl)-2-methylacrylic acid disodium salt (C3)

1H-NMR(DMSO-d6) 8.06-8.17 (m, 3H), 7.20-7.28 (m, 2H), 7.13 (d, 1H, J=3.2 Hz), 7.06 (s, 1H), 4.53-4.58 (m, 1H), 3.17 (s, 3H), 1.60-1.82 (m, 5H), 1.23 (m, 14H), 0.86 (t, 3H, J=7.0 Hz).

Example 587

Synthesis of 3-(2,6-dichloro-4-{4-[2-fluoro-3-(1-methyloxyoctyl)phenyl]thiazol-2-ylcarbonyl}phenyl)-2-methylacrylic acid disodium salt (C4)

1H-NMR(DMSO-d6) 8.06-8.12 (m, 3H), 7.23-7.29 (m, 2H), 7.16 (d, 1H, J=3.1 Hz), 7.12 (s, 1H), 4.53-4.57 (m, 1H), 3.17 (s, 3H), 1.60-1.82 (m, 5H), 1.23-1.37 (m, 10H), 0.84 (t, 3H, J=6.6 Hz).

Example 588

Synthesis of 3-(2,6-dichloro-4-{4-[2-fluoro-3-(3-n-propyloxypropyl)phenyl]thiazol-2-ylcarbonyl}phenyl)-2-methylacrylic acid disodium salt (C5)

1H-NMR(DMSO-d6) 8.13 (s, 2H), 7.98-8.04 (m, 1H), 7.12-7.17 (m, 4H), 3.40 (t, 2H, J=6.3 Hz), 3.30 (t, 2H, J=6.6 Hz), 7.20 (t, 2H, J=7.5 Hz), 1.78-1.88 (m, 2H), 1.64 (s, 3H), 1.47-1.64 (m, 2H), 0.88 (t, 3H, J=7.5 Hz).

Example 589

Synthesis of 3-(4-{4-[3-(3-ethyloxypropyl)-2-fluorophenyl]thiazol-2-ylcarbonyl}-2,6-difluorophenyl)-2-methylacrylic acid disodium salt (C6)

1H-NMR(DMSO-d6) 7.99-8.05 (m, 1H), 7.72-7.78 (m, 2H), 7.12-7.19 (m, 3H), 7.07 (s, 1H), 3.38-3.47 (m, 4H), 2.69-2.74 (m, 2H), 1.76-1.87 (m, 5H), 1.13 (t, 3H, J=7.0 Hz).

TEST EXAMPLES

Test Example 1

Isolation and Purification of Thrombopoietin (TPO)

Human TPO (hTPO) and murine TPO (mTPO) were purchased from R&D Systems.

Test Example 2

The Thrombopoietic Activity

The TPO dependent BaF/hTPOR cell line which was established by introducing human TPO receptor (hTPOR) into BaF-B03 cells according to Collins et al (J. Cell. Physiol., 137:293-298 (1988)) was used to test the thrombopoietic activity of the present compound. The DNA sequences and encoded peptide sequences for human hTPOR have been described by Vigon et al (Proc. Natl. Acad. Sci. USA, 89:5640-5644 (1992)). TPO dose not have any ability to support proliferation of interlukin-3 dependent parental cell line BaF-B03. BAF/hTPOR cells were maintained in RPMI medium and WEHI-3B conditioned medium as a source of murine interleukin-3 (IL-3). These cells were washed and resuspended in RPMI medium without a source of murine IL-3 and seeded into each well of 96-well microtiter plates at a density of $5 \times 10^4$ cells per well in the absence or presence of various concentration of hTPO or the present compound. After incubation at 37° C. for 20 hours in the 5% $CO_2$ incubator, 10% WST-1 reagent (Takara Biomedicals, Japan) was added to each wells and the cells were further incubated for 4 hours. The absorbance at 450 nm was measured. Tables 1 and 2 exemplify the $ED_{50}$ for tested compounds of the present invention, wherein the $ED_{50}$ is the half concentration of the concentration showing the maximum thrombopoietic activity.

TABLE 1

| No. | ED50(μM) |
|---|---|
| A1 | 0.00227 |
| A2 | 0.004 |
| A3 | 0.004 |

TABLE 1-continued

| No. | ED50(μM) |
|---|---|
| A4 | 0.00180 |
| A5 | 0.00191 |
| A6 | 0.00104 |
| A7 | 0.00226 |
| A8 | 0.0029 |
| A9 | 0.0030 |
| A10 | 0.0012 |
| A11 | 0.00087 |
| A12 | 0.0008 |
| A1123 | 0.00727 |
| A1308 | 0.0129 |
| A1309 | 0.01278 |
| A1310 | 0.0123 |
| A1311 | 0.00886 |
| A1312 | 0.01083 |
| A1314 | 0.01251 |
| A1315 | 0.01247 |
| A1316 | 0.00529 |
| A1317 | 0.01506 |
| B1 | 0.0022 |
| B2 | 0.004 |
| B6 | 0.0024 |
| B7 | 0.0036 |
| B8 | 0.0040 |
| B9 | 0.0016 |
| B10 | 0.0019 |
| B11 | 0.00081 |
| B12 | 0.0021 |
| B13 | 0.0010 |
| B14 | 0.00073 |
| B15 | 0.00073 |
| B16 | 0.00077 |
| B18 | 0.00057 |
| B19 | 0.00073 |
| B20 | 0.00081 |
| B21 | 0.00067 |
| B22 | 0.00114 |
| B23 | 0.00123 |
| B24 | 0.00197 |
| B25 | 0.00093 |
| B26 | 0.00039 |
| B27 | 0.00075 |
| B28 | 0.00079 |
| B29 | 0.00203 |
| B30 | 0.00078 |
| B31 | 0.00085 |
| B32 | 0.00303 |
| B33 | 0.00333 |
| B34 | 0.00099 |
| B35 | 0.00077 |
| B36 | 0.00063 |
| B37 | 0.00088 |
| B38 | 0.00062 |
| B39 | 0.00101 |
| B40 | 0.00088 |
| B41 | 0.00067 |
| B42 | 0.00034 |
| B43 | 0.00165 |
| B44 | 0.00127 |
| B45 | 0.00136 |
| B46 | 0.00128 |
| B47 | 0.00280 |
| B48 | 0.00223 |
| B49 | 0.0013 |
| B50 | 0.00080 |
| B51 | 0.00068 |
| B52 | 0.0017 |
| B53 | 0.0014 |
| B56 | 0.0027 |
| B58 | 0.0015 |
| B60 | 0.00075 |
| B61 | 0.00076 |
| B62 | 0.00076 |
| B63 | 0.00020 |
| B64 | 0.00119 |
| B65 | 0.00104 |
| B66 | 0.00091 |

TABLE 1-continued

| No. | ED50(μM) |
|---|---|
| B67 | 0.00048 |
| B68 | 0.00082 |
| B69 | 0.00078 |
| B70 | 0.00043 |
| B71 | 0.00100 |
| B72 | 0.00078 |
| B73 | 0.00135 |
| B74 | 0.00080 |
| B75 | 0.00077 |
| B76 | 0.00298 |
| B77 | 0.00306 |
| B78 | 0.00097 |
| B79 | 0.00077 |
| B80 | 0.00070 |
| B81 | 0.00139 |
| B82 | 0.00107 |
| B83 | 0.00072 |
| B84 | 0.00102 |
| B85 | 0.00088 |
| B86 | 0.00063 |
| B87 | 0.00062 |
| B88 | 0.00311 |
| B89 | 0.00151 |
| B90 | 0.00115 |
| B91 | 0.00102 |
| B93 | 0.00091 |
| B94 | 0.00097 |
| B95 | 0.00082 |
| B96 | 0.00078 |
| B97 | 0.00094 |
| B98 | 0.00073 |
| B99 | 0.00059 |
| B100 | 0.00068 |
| B101 | 0.0019 |
| B347 | 0.01872 |
| B349 | 0.01679 |
| B354 | 0.0032 |
| B355 | 0.0033 |
| B380 | 0.02325 |
| B397 | 0.00252 |
| B418 | 0.0063 |
| B419 | 0.01455 |
| B425 | 0.00201 |
| B484 | 0.00129 |
| B488 | 0.01588 |
| B505 | 0.012 |
| B519 | 0.00103 |
| B521 | 0.01688 |
| B1054 | 0.01994 |
| B1059 | 0.0032 |
| B1060 | 0.0039 |
| B1102 | 0.00286 |
| B1122 | 0.00825 |
| B1124 | 0.01584 |
| B1437 | 0.0065 |
| B1438 | 0.0063 |
| B1799 | 0.01732 |
| B1800 | 0.00304 |
| B1833 | 0.01899 |
| B1848 | 0.01594 |
| B1851 | 0.01684 |
| B1852 | 0.01648 |
| B1877 | 0.01304 |
| B1884 | 0.01685 |
| B1890 | 0.01815 |
| B1892 | 0.01164 |
| B1916 | 0.01286 |
| B1920 | 0.01452 |
| B1922 | 0.01359 |
| B1925 | 0.01841 |
| B1926 | 0.01556 |
| B1927 | 0.01944 |
| B1928 | 0.01257 |
| B1933 | 0.00788 |
| B1934 | 0.01304 |
| B1936 | 0.01711 |
| B1938 | 0.01268 |

TABLE 1-continued

| No. | ED50(μM) |
|---|---|
| B1940 | 0.01883 |
| B1945 | 0.01927 |
| B1948 | 0.01091 |
| B1949 | 0.01316 |
| B1952 | 0.01013 |
| B1953 | 0.01007 |
| B1954 | 0.01294 |
| B1955 | 0.01165 |
| B1956 | 0.01507 |
| B1957 | 0.01275 |
| B1958 | 0.00757 |
| B1959 | 0.01126 |
| B1960 | 0.01014 |
| B1990 | 0.01214 |
| B1991 | 0.01323 |
| B1992 | 0.01305 |
| B1993 | 0.01392 |
| B1994 | 0.01424 |
| B1995 | 0.01093 |
| B1997 | 0.01553 |
| B1998 | 0.00835 |
| B1999 | 0.01324 |
| B2001 | 0.01942 |
| B2004 | 0.01394 |
| B2005 | 0.01033 |
| B2020 | 0.01094 |
| B2021 | 0.00609 |
| B2022 | 0.01563 |
| B2023 | 0.00645 |
| B2024 | 0.00996 |
| B2025 | 0.0032 |
| B2026 | 0.01259 |
| B2027 | 0.01259 |
| B2028 | 0.01143 |
| B2099 | 0.00291 |

TABLE 2

| No. | ED50(μM) |
|---|---|
| B380 | 0.02325 |
| B1836 | 0.02102 |
| B1849 | 0.02245 |
| B1854 | 0.02443 |
| B1855 | 0.02133 |
| B1861 | 0.02282 |
| B1863 | 0.02276 |
| B1878 | 0.02119 |
| B1886 | 0.02208 |
| B1900 | 0.02316 |
| B1901 | 0.02425 |
| B1904 | 0.02457 |
| B1905 | 0.02665 |
| B1908 | 0.02628 |
| B1909 | 0.02586 |
| B1918 | 0.02102 |
| B1919 | 0.02793 |
| B1923 | 0.02017 |
| B1924 | 0.02058 |
| B1929 | 0.02584 |
| B1935 | 0.0254 |
| B1937 | 0.02308 |
| B1941 | 0.02413 |
| B1951 | 0.02226 |
| B1963 | 0.02858 |
| B2000 | 0.0205 |
| B2003 | 0.02271 |
| B2012 | 0.02419 |
| B2018 | 0.02351 |

FORUMLATION EXAMPLE

Formulation Example 1

Granules are prepared using the following ingredients.

| Ingredients | The compound represented by the formula (I) | 10 mg |
|---|---|---|
| | Lactose | 700 mg |
| | Corn starch | 274 mg |
| | HPC-L | 16 mg |
| | | 1000 mg |

The compound represented by the formula (I) and lactose are made pass through a 60 mesh sieve. Corn starch is made pass through a 120 mesh sieve. They are mixed by a twin shell blender. An aqueous solution of HPC-L (low mucosity hydroxypropylcellulose) is added to the mixture and the resulting mixture is kneaded, granulated (by the extrusion with pore size 0.5 to 1 mm mesh), and dried. The dried granules thus obtained are sieved by a swing sieve (12/60 mesh) to yield the granules.

Formulation 2

Powders for filling capsules are prepared using the following ingredients.

| Ingredients | The compound represented by the formula (I) | 10 mg |
|---|---|---|
| | Lactose | 79 mg |
| | Corn starch | 10 mg |
| | Magnesium stearate | 1 mg |
| | | 100 mg |

The compound represented by the formula (I) and lactose are made pass through a 60 mesh sieve. Corn starch is made pass through a 120 mesh sieve. These ingredients and magnesium stearate are mixed by a twin shell blender. 100 mg of the 10-fold trituration is filled into a No. 5 hard gelatin capsule.

Formulation 3

Granules for filling capsules are prepared using the following ingredients.

| Ingredients | The compound represented by the formula (I) | 15 mg |
|---|---|---|
| | Lactose | 90 mg |
| | Corn starch | 42 mg |
| | HPC-L | 3 mg |
| | | 150 mg |

The compound represented by the formula (I) and lactose are made pass through a 60 mesh sieve. Corn starch is made pass through a 120 mesh sieve. After mixing them, an aqueous solution of HPC-L is added to the mixture and the resulting mixture is kneaded, granulated, and dried. After the dried granules are lubricated, 150 mg of that are filled into a No. 4 hard gelatin capsule.

185

Formulation 4

Tablets are prepared using the following ingredients.

| Ingredients | The compound represented by the formula (I) | 10 mg |
|---|---|---|
| | Lactose | 90 mg |
| | Microcrystal cellulose | 30 mg |
| | CMC-Na | 15 mg |
| | Magnesium stearate | 5 mg |
| | | 150 mg |

The compound represented by the formula (I), lactose, microcrystal cellulose, and CMC—Na (carboxymethylcellulose sodium salt) are made pass through a 60 mesh sieve and then mixed. The resulting mixture is mixed with magnesium stearate to obtain the mixed powder for the tablet formulation. The mixed powder is compressed to yield tablets of 150 mg.

Formulation 5

Intravenous formulations are prepared using the following ingredients.

| Ingredients | The compound represented by the formula (I) | 100 mg |
|---|---|---|
| | Saturated fattyacid glyceride | 1000 ml |

Usually a solution of ingredients above described is administered intravenously to a patient by the speed of 1 ml/min.

INDUSTRIAL APPLICABILITY

The compounds of the present invention have thrombopoietin receptor agonism and are useful as the treating or preventing agent for hemopathy accompanied with unusual count of platelet, for example, thrombocytopenia and the like.

What is claimed is:

1. A compound represented by the general formula (I):

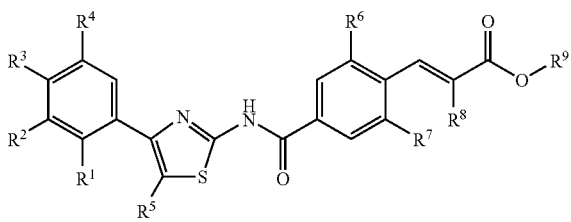

wherein $R^1$ is a hydrogen atom, halogen atom, C1-C6 alkyl, or C1-C12 alkyloxy;

$R^2$, $R^3$, and $R^4$ are each independently a hydrogen atom, a halogen atom, C1-C15 alkyl optionally substituted with one or two substituent(s) selected from substituent group A, C2-C15 alkenyl optionally substituted with one or two substituent(s) selected from substituent group A, C2-C15 alkynyl optionally substituted with one or two substituent(s) selected from substituent group A, C3-C8 cycloalkyl, C1-C15 alkyloxy optionally substituted with one or two substituent(s) selected from substituent group A, or phenyl optionally substituted with one or two substituent(s) selected from substituent group A;

$R^5$ is a hydrogen atom, a halogen atom, C1-C3 alkyl, or C1-C3 alkyloxy;

$R^6$ is a hydrogen atom, a halogen atom, or C1-C3 alkyl;

$R^7$ is a halogen atom or C1-C3 alkyl;

$R^8$ is a halogen atom, C1-C3 alkyl, or C1-C3 alkyloxy;

$R^9$ is a hydrogen atom or C1-C6 alkyl; or $R^1$ and $R^5$ are taken together with the adjacent carbon atoms may form a 5 to 8 membered ring which may contain a heteroatom and/or an unsaturated bond, wherein the ring may be substituted with one or two C1-C8 alkyl;

provided that when $R^2$ and $R^3$ are a chlorine atom, $R^6$ is not a hydrogen atom;

substituent group A consists of halogen atom, C3-C8 cycloalkyl, C3-C8 cycloalkenyl, phenyl, naphthyl, pyridyl, oxolanyl, cyano, C1-C12 alkyloxy, C2-C12 alkenyloxy, C2-C12 alkynyloxy, C3-C8 cycloalkyl-C1-C8 alkyloxy, phenyl-C1-C8 alkyloxy, naphthyl-C1-C8 alkyloxy, C1-C8 alkyloxy-C1-C8 alkyloxy, (C1-C8 alkyloxy-C1-C8 alkyloxy)C1-C8 alkyloxy, di(C1-C8 alkyloxy)C1-C8 alkyloxy, oxolanyl-C1-C8 alkyloxy, haloC1-C8 alkyloxy, C3-C8 cycloalkyloxy, amino optionally substituted with C1-C8 alkyl, C1-C8 alkylthio, and C1-C8 alkylthio-C1-C8 alkyloxy;

a pharmaceutically acceptable salt, or solvate thereof.

2. A compound of claim 1, wherein both of $R^6$ and $R^7$ are fluorine atom or chlorine atom, a pharmaceutically acceptable salt, or solvate thereof.

3. A compound of claim 1, wherein $R^5$ is a hydrogen atom or C1-C3 alkyloxy, a pharmaceutically acceptable salt, or solvate thereof.

4. A compound of claim 1, wherein $R^8$ is methyl or methyloxy, a pharmaceutically acceptable salt, or solvate thereof.

5. A compound of any one of claims 1 to 4, wherein $R^2$ is C1-C15 alkyl optionally substituted with one or two substituent(s) selected from substituent group A, C2-C15 alkynyl optionally substituted with one or two substituent(s) selected from substituent group A, or C1-C15 alkyloxy optionally substituted with one or two substituent(s) selected from substituent group A, a pharmaceutically acceptable salt, or solvate thereof.

6. A compound of any one of claims 1 to 4, wherein $R^2$ is C1-C12 alkyl optionally substituted with one or two C1-C8 alkyloxy, and both of $R^3$ and $R^4$ are a hydrogen atom, a pharmaceutically acceptable salt, or solvate thereof.

7. A compound represented by the general formula (II):

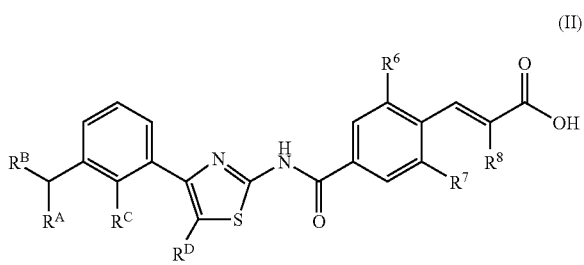

wherein $R^A$ is a hydrogen atom, C1-C12 alkyloxy, C1-C8 alkyloxy-C1-C8 alkyloxy or (C1-C8 alkyloxy-C1-C8 alkyloxy)C1-C8 alkyloxy;

$R^B$ is C1-C14 alkyl optionally substituted with one or two substituent(s) selected from substituent group B, C2-C14 alkynyl optionally substituted with one or two substituent(s) selected from substituent group B, C3-C8 cycloalkyl, C1-C14 alkyloxy optionally substituted with one or two substituent(s) selected from substituent group B, phenyl, or naphthyl;

$R^C$ is a hydrogen atom, halogen atom, C1-C6 alkyl, or C1-C12 alkyloxy;

$R^D$ is a hydrogen atom, halogen atom, C1-C3 alkyl, or C1-C3 alkyloxy;

$R^6$ and $R^7$ are each independently halogen atom or C1-C3 alkyl;

$R^8$ is halogen atom, C1-C3 alkyl, or C1-C3 alkyloxy;

substituent group B consists of halogen atom, C3-C8 cycloalkyl, C3-C8 cycloalkenyl, phenyl, naphthyl, pyridyl, oxolanyl, cyano, C1-C8 alkyloxy, C2-C8 alkenyloxy, C2-C8 alkynyloxy, C3-C8 cycloalkyl-C1-C8 alkyloxy, phenyl-C1-C8 alkyloxy, naphthyl-C1-C8 alkyloxy, C1-C8 alkyloxy-C1-C8 alkyloxy, (C1-C8 alkyloxy-C1-C8 alkyloxy)C1-C8 alkyloxy, di(C1-C8 alkyloxy)C1-C8 alkyloxy, oxolanyl-C1-C8 alkyloxy, haloC1-C8 alkyloxy, C3-C8 cycloalkyloxy, amino optionally substituted with C1-C8 alkyl, C1-C8 alkylthio, and C1-C8 alkylthio-C1-C8 alkyloxy; a pharmaceutically acceptable salt, or solvate thereof.

8. A compound of claim 7, wherein both of $R^6$ and $R^7$ are fluorine atom or chlorine atom, a pharmaceutically acceptable salt, or solvate thereof.

9. A compound of claim 7, wherein $R^8$ is methyl or methyloxy, a pharmaceutically acceptable salt, or solvate thereof.

10. A compound of claim 7, wherein $R^C$ is fluorine atom or C1-C3 alkyloxy, a pharmaceutically acceptable salt, or solvate thereof.

11. A compound of any one of claims 7 to 10, wherein $R^A$ is C1-C8 alkyloxy; $R^B$ is C1-C11 alkyl optionally substituted with one or two substituent(s) selected from substituent group B, or C2-C11 alkynyl optionally substituted with one or two substituent(s) selected from substituent group B, a pharmaceutically acceptable salt, or solvate thereof.

12. A compound of claim 7, wherein $R^C$ is fluorine atom or C1-C3 alkyloxy, $R^D$ is a hydrogen atom or C1-C3 alkyloxy, both of $R^6$ and $R^7$ are fluorine atom or chlorine atom, $R^8$ is methyl or methyloxy, $R^A$ is C1-C3 alkyloxy, $R^B$ is C8-C12 alkyl optionally substituted with one or two substituent(s) selected from substituent group B, a pharmaceutically acceptable salt, or solvate thereof.

13. A compound represented by the general formula (II-A):

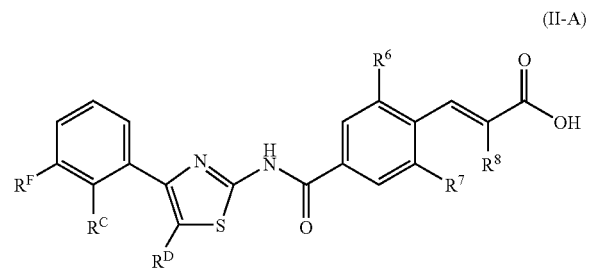

(II-A)

wherein $R^C$ is a hydrogen atom, a halogen atom, C1-C6 alkyl, or C1-C12 alkyloxy;

$R^D$ is a hydrogen atom, a halogen atom, C1-C3 alkyl, or C1-C3 alkyloxy;

$R^F$ is C1-C14 alkyl optionally substituted with one or two substituent(s) selected from substituent group D, C2-C14 alkenyl optionally substituted with one or two substituent(s) selected from substituent group D, C2-C14 alkynyl optionally substituted with one or two substituent(s) selected from substituent group D, C1-C14 alkyloxy optionally substituted with one or two substituent(s) selected from substituent group C, C3-C8 cycloalkyl, or phenyl optionally substituted with one or two substituent(s) selected from substituent group D;

$R^6$ and $R^7$ are each independently halogen atom or C1-C3 alkyl;

$R^8$ is halogen atom, C1-C3 alkyl, or C1-C3 alkyloxy;

substituent group D consists of halogen atom, C3-C8 cycloalkyl, C3-C8 cycloalkenyl, phenyl, naphthyl, pyridyl, oxolanyl, cyano, C1-C8 alkyloxy, C2-C8 alkenyloxy, C2-C8 alkynyloxy, C3-C8 cycloalkyl-C1-C8 alkyloxy, phenyl-C1-C8 alkyloxy, naphthyl-C1-C8 alkyloxy, C1-C8 alkyloxy-C1-C8 alkyloxy, (C1-C8 alkyloxy-C1-C8 alkyloxy)C1-C8 alkyloxy, di(C1-C8 alkyloxy)C1-C8 alkyloxy, oxolanyl-C1-C8 alkyloxy, haloC1-C8 alkyloxy, C3-C8 cycloalkyloxy, amino optionally substituted with C1-C8 alkyl, C1-C8 alkylthio, and C1-C8 alkylthio-C1-C8 alkyloxy;

a pharmaceutically acceptable salt, or solvate thereof.

14. A compound of claim 13, wherein both of $R^6$ and $R^7$ are fluorine atom or chlorine atom, a pharmaceutically acceptable salt, or solvate thereof.

15. A compound of claim 13, wherein $R^8$ is methyl or methyloxy, a pharmaceutically acceptable salt, or solvate thereof.

16. A compound of claim 13, wherein $R^C$ is fluorine atom or C1-C3 alkyloxy, a pharmaceutically acceptable salt, or solvate thereof.

17. A compound of any one of claims 13 to 16, wherein $R^F$ is C1-C14 alkyl optionally substituted with one or two substituent(s) selected from substituent group D, C2-C14 alkynyl optionally substituted with one or two substituent(s) selected from substituent group D, or C1-C14 alkyloxy optionally substituted with one or two substituent(s) selected from substituent group D, a pharmaceutically acceptable salt, or solvate thereof.

18. A pharmaceutical composition containing a compound as an active ingredient, a pharmaceutically acceptable salt, or solvate thereof of any one of claims 1 to 4, 7 to 10, or 13 to 16.

19. A pharmaceutical composition containing a compound as an active ingredient, a pharmaceutically acceptable salt, or solvate thereof of any one of claims 1 to 4, 7 to 10, or 13 to 16 in an amount effective for exhibiting thrombopoietin receptor agonism.

20. A pharmaceutical composition containing a compound as an active ingredient, a pharmaceutically acceptable salt, or solvate thereof of any one of claims 1 to 4, 7 to 10, or 13 to 16 in an amount effective for modifying platelet production.

21. A method for treating or preventing hemopathy in a mammal, including a human, in need thereof, comprising administering to said mammal a compound, a pharmaceutically acceptable salt, or solvate thereof of any one of claims 1 to 4, 7 to 10, or 13 to 16 in an amount effective amount for modifying platelet production.

22. A compound of claim 1, wherein the compound is

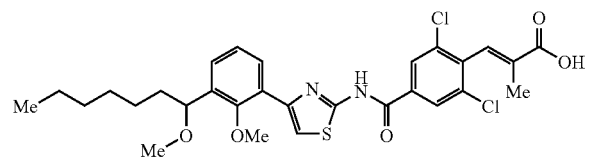

or a pharmaceutically acceptable salt thereof.

23. A compound of claim 1, wherein the compound is
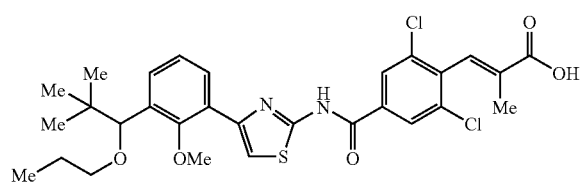
or a pharmaceutically acceptable salt thereof.
24. A compound of claim 1, wherein the compound is
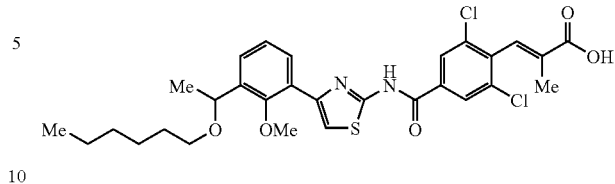
or a pharmaceutically acceptable salt thereof.
* * * * *